(12) United States Patent
Anthes et al.

(10) Patent No.: US 8,524,697 B2
(45) Date of Patent: Sep. 3, 2013

(54) C20-C21 SUBSTITUTED GLUCOCORTICOID RECEPTOR AGONISTS

(75) Inventors: John C. Anthes, Cranford, NJ (US); Kevin D. McCormick, Basking Ridge, NJ (US); John A. Hey, Edmond, OK (US); Robert G. Aslanian, Rockaway, NJ (US); Purakkattle J. Biju, Piscataway, NJ (US); Michael Y. Berlin, Flemington, NJ (US); Daniel M. Solomon, Edison, NJ (US); Phillippa H. Solomon, legal representative, Edison, NJ (US); Hongwu Yang, Westfield, NJ (US); Yeon-Hee Lim, Woodbridge, NJ (US); Yoon Joo Lee, Scotch Plains, NJ (US); Rema Danielle Bitar, Clifton, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 266 days.

(21) Appl. No.: 12/736,063

(22) PCT Filed: Dec. 18, 2008
(Under 37 CFR 1.47)

(86) PCT No.: PCT/US2008/087300
§ 371 (c)(1),
(2), (4) Date: Jan. 11, 2011

(87) PCT Pub. No.: WO2009/085879
PCT Pub. Date: Jul. 9, 2009

(65) Prior Publication Data
US 2011/0182828 A1    Jul. 28, 2011

Related U.S. Application Data

(60) Provisional application No. 61/016,135, filed on Dec. 21, 2007.

(51) Int. Cl.
*A01N 43/00* (2006.01)
*A61K 31/33* (2006.01)
*C07D 215/00* (2006.01)
*C07D 277/62* (2006.01)

(52) U.S. Cl.
USPC ............................ 514/183; 546/157; 548/160

(58) Field of Classification Search
USPC ......................... 514/183; 546/157; 548/160
See application file for complete search history.

(56) References Cited

U.S. PATENT DOCUMENTS

| | | | |
|---|---|---|---|
| 1,119,082 A | 1/1967 | Nathansohn et al. | |
| 5,420,120 A | 5/1995 | Boltralik et al. | |
| 2011/0262368 A1 | 10/2011 | Anthes et al. | |

FOREIGN PATENT DOCUMENTS

| | | |
|---|---|---|
| EP | 0208202 B1 | 4/1989 |
| WO | WO02/12266 A1 | 2/2002 |
| WO | WO2006/138212 A1 | 12/2006 |

OTHER PUBLICATIONS

Mitsukuchi et. al. (Chem. Pharm. Bull (1989) 37:1795-1801).*
Simons et al., "Fluorescent Chemoaffinity Labeling. Potential Application of a New Affinity Labeling Technique to Glucocorticoid Receptors", Biochemistry, 1979, vol. 18, No. 22, pp. 4915-4922.
Mitsukuchi et al., "Studies on Topical Antiinflammatory Agents. II.1) Synthesis and Vasoconstrictive Activity of 21-Substituted Corticosteroids with Sulfur-Containing Moieties", Chem. Pharm. Bull, 37(7) 1989, pp. 1795-1801.
Mitsukuchi et al., "Studies on Topical Antiinflammatory Agents. III. 1,2) Synthesis of 17x-Acyloxy-9x-fluro-11β-hydroxy-16β-methyl-1,4-pregnadiene-3,20-dione 21-Thio Derivatives and Related Compounds", Chem. Phar. Bull, 37 (12), 1989, pp. 3286-3293.

* cited by examiner

*Primary Examiner* — Marcos Sznaidman
(74) *Attorney, Agent, or Firm* — Patricia A. Shatynski; Valerie J. Camara

(57) ABSTRACT

The present invention provides compounds of Formula (I), and pharmaceutically acceptable salts, solvates, esters, prodrugs, tautomers, or isomers of said compounds), having the general structure:

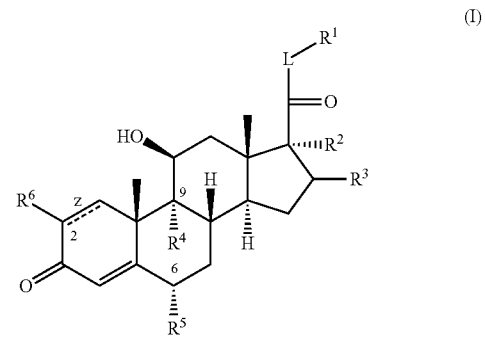

wherein L, $R^1$, $R^2$, $R^3$, $R^4$, $R^5$, and $R^6$ are selected independently of each other and as defined herein. The present invention also provides compounds (and salts, solvates, esters, prodrugs, tautomers, and isomers) of Formulas II, III, IV, V, and VI, as defined herein. Also provided are pharmaceutical compositions, methods of preparing, and methods of using such compounds in the treatment and prophylaxis of a wide range of immune, autoimmune, and inflammatory diseases and conditions.

7 Claims, No Drawings

C20-C21 SUBSTITUTED GLUCOCORTICOID RECEPTOR AGONISTS

CROSS REFERENCE TO RELATED APPLICATIONS

This application is a U.S. National Phase application under 35 U.S.C. §371 of PCT Application No. PCT/US2008/087300, filed Dec. 18, 2008, which claims priority under 35 U.S.C. §119(e) from U.S. Provisional Application Ser. No. 61/016,135, filed Dec. 21, 2007.

RELATED APPLICATION

This application is related to, and claims the benefit of priority to, U.S. provisional patent application No. 61/016,135, filed Dec. 21, 2007, the contents of which are incorporated herein by reference in their entirety.

FIELD OF THE INVENTION

This invention relates to novel C-21 steroid derivatives that are agonists of the glucocorticoid receptor and methods for their preparation. The present invention also relates to pharmaceutical formulations comprising the inventive C-21 steroid derivatives as well as to their use in the treatment of disease states involving inflammation and allergic conditions. The inventive C-21 steroid derivatives exhibit "dissociated" properties; i.e., the metabolic effects, which are associated with adverse side effects, are dissociated from the anti-inflammatory and anti-allergic effects, thereby providing glucocorticoid receptor agonists that exhibit better therapeutic profiles than the agonists currently commercially available.

BACKGROUND OF THE INVENTION

The glucocorticoid receptor is part of the family of nuclear receptors. The receptor is a nuclear transcription factor that when bound to a ligand promotes or suppresses the transcription of genes. Glucocorticoid receptor agonists occur naturally or may be prepared synthetically. Examples of synthetic glucocorticoid receptor agonists include prednisolone and dexamethasone. Glucocorticoid receptor agonists possess valuable anti-inflammatory properties and have found widespread use in the art in controlling wide range of allergic and inflammatory conditions, such as asthma, rheumatoid arthritis, eczema, psoriasis and others (see, for example, Barnes, P. "Corticosteroids: The drugs to beat" *European Journal of Pharmacology* 2006, 533, p. 2-14). Unfortunately, the therapeutic potential of this class of compounds has not been fully maximized because of the existence of adverse side effects, which limit the dose of drug that may be administered to the patient or the time period for which the agonist may be administered to the patient. Side effects include suppression of hypothalamic-pituitary-adrenal axis, bone demineralization and osteoporosis, ocular side effects (e.g., glaucoma, cataracts), growth retardation in children, disruption of carbohydrate metabolism.

Hence, a goal in the art has been the development of glucocorticoid receptor agonists that exhibit reduced side effects. One approach has been the development of glucocorticoids that can be administered by inhalation. Agents administered in this manner exhibit a higher safety profile because they posses low systemic bioavailability; this due to the combination of inhaled administration, slow pulmonary absorption and rapid clearance (see, for example, Flogger, P. "Current Concepts for Optimizing the Therapeutic Index of Glucocorticoid Receptor Ligands for Oral and Inhalative Use: Basic Considerations and Clinical Reality", *Current Medicinal Chemistry -Anti-Inflammatory &Anti-Allergy Agents* 2003, 2, p. 395-408). Examples of compounds developed following this approach include fluticasone propionate and its structurally related analogues (see, e.g., U.S. Pat. No. 4,335,121), mometasone furoate and its structurally related analogues (see, e.g., U.S. Pat. No. 4,472,393), or more recently, analogues disclosed in WO 2002/12265.

A problem associated with inhaled glucocorticoids is that while they exhibit improved safety profiles at low therapeutic doses, their safety profile decreases at higher doses or when these agents are administered for a long period of time. Hence, while this approach has advantages over earlier-developed glucocorticoids, there remains a need in the art for glucocorticoids that can be administered at higher doses, for longer periods of time or both, thereby permitting one to expand the scope of disease states that can be treated or allowing one to reduce the undesired side effects.

Another approach is to discover compounds where the metabolic effects, which cause the undesired side effects, are dissociated from the anti-inflammatory effects. The discovery of steroids in which anti-inflamatory activity has been separated from the metabolic activity would be an advance in this art.

Steroid-based and nonsteroidal-based glucocorticoids analogues are well known in this art. For example, WO 1999/041256 describes glucocorticoids selective anti-inflammatory agents of nonsteroidal nature. GB 2,018,256, U.S. Pat. No. 3,989,686, U.S. Pat. No. 4,263,289, and EP 0 004 773 describe 17 thiocarboxylic acid steroid derivatives. WO 1997/23565 describes lactone derivatives of 17-β-carboxy, carboxythio, and amide andronstane derivative with anti-inflammatory or anti-allergic properties. WO 2006/043015 reports that the 6α,9α-difluoro-11β-hydroxy-16α-methyl-3-oxo-17α-pro-pionyloxy-androsta-1,4-diene-17β-carbothioic acid S-(2-oxo-tetrahydro-furan-3-yl)ester of the formula:

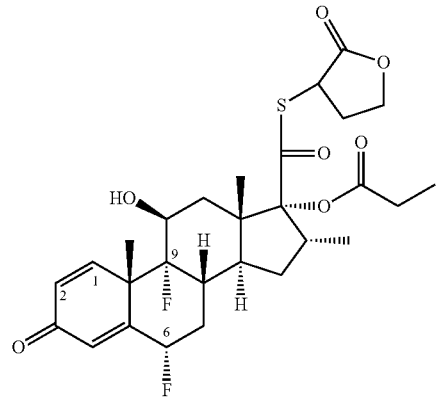

possesses useful anti-inflammatory activity, while having little or no systemic activity. Other derivatives are disclosed in WO 1997/24368, WO 2000/64882, WO 2003/035668, CN1414008, U.S. Pat. No. 3,598,816 and U.S. Pat. No. 5,645,404.

U.S. Pat. No. 4,861,765, discloses 21-substituted thioether glucocorticoid steroid derivatives of the formula:

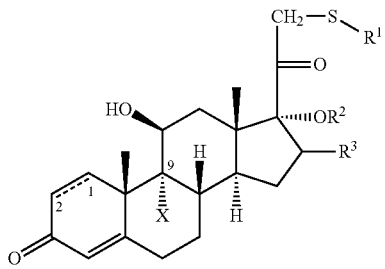

that are reported to have reduced systemic side effect and excellent anti-inflammatory properties. U.S. Pat. No. 5,420,120, also discloses 21-substituted thioether glucocorticoid steroid derivatives similar to those disclosed in U.S. Pat. No. 4,861,767; these compounds are said to be effective topical anti-inflammatory agents for the treatment of ophthalmic inflammatory disorders. Other C21-substituted thioether derivatives are disclosed in WO 1997/24367, U.S. Pat. No. 3,687,942 and S. Wu et al., *Ann. Chim. Acta*, vol 268, pp. 255-260 (1992).

DE20211718 discloses C21-substituted phenyl ether steroid derivatives. And WO95/18621 discloses steroids, including 6alpha,9alpha-fluoro-11beta,17-dihydroxy-16alpha-methyl-pregna-1,4-diene-3-one-17-carboxylic acid and related compounds. According to the description, the steroids disclosed in WO95/18621 have angiostatic activity and reduced glucocorticoid activity. One such compound exemplified (in example 23) in WO95/18621 has the following structure:

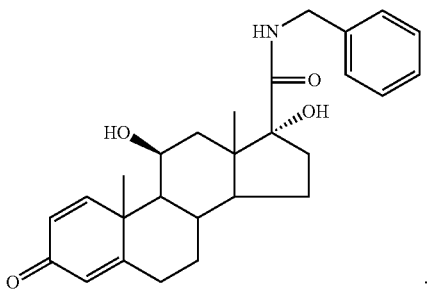 [SMILES: CC12C=CC(=O)C=C1CCC1C2[C@@H](O)CC2(C)C1CC[C@]2(O)C(=O)NCc1ccccc1]

SUMMARY OF THE INVENTION

The present invention provides novel steroid compounds, as described herein, which exhibit good pharmacological (e.g., glucocorticoid) activity. Such compounds may be referred to herein as "compound(s) of the invention." In some embodiments, the compounds of the invention exhibit desirable pharmacological activity, such as anti-inflammatory activity and antiallergenic activity. In some preferred embodiments, the compounds of the invention exhibit desirable pharmacological activity, such as anti-inflammatory activity and antiallergenic activity and reduced side effect activity.

In one embodiment, the present invention provides a compound, or a pharmaceutically acceptable salt, solvate, ester, prodrug, tautomer, or isomer of said compound, said compound having the general structure shown in Formula (I):

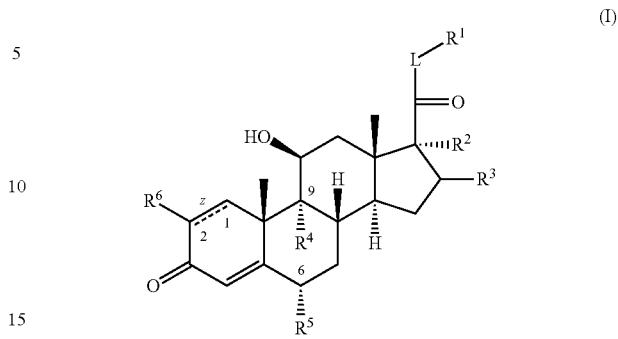

wherein L, $R^1$, $R^2$, $R^3$, $R^4$, $R^5$, $R^6$, and z are selected independently of each other and wherein:

L is a divalent moiety selected from

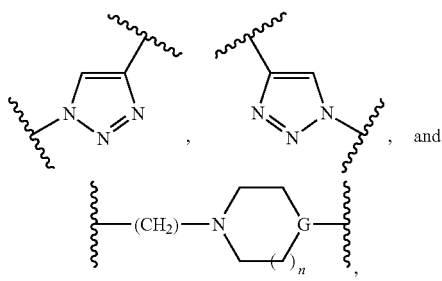

wherein G is N or CH and n is an integer from 0 to 2, with the proviso that when n is 0, G is CH, or, alternatively, L is a divalent moiety selected from —CH$_2$—S—CH$_2$—C(O)—NH—, —CH$_2$O—, —CH$_2$—OC(O)—NH—, —CH$_2$S(O)—, —CH$_2$S(O)$_2$—, —NR$^{11}$—, —N(R$^{11}$)—C(O)—, —N(R$^{11}$)—S(O)—, —N(R$^{11}$)—S(O)$_2$—, —NR$^{11}$O—, —CH$_2$N(R$^{11}$)—, —CH$_2$—N(R$^{11}$)—C(O)—, —CH$_2$—N(R$^{11}$)—C(O)—N(R$^{11}$)—, —CH$_2$—N(R$^{11}$)—C(O)O—, —CH$_2$—N(R$^{11}$)—OC(O)—, —CH$_2$N(R$^{11}$)C(=NH)NR$^{11}$—, —CH$_2$—N(R$^{11}$)—S(O)—, and —CH$_2$—N(R$^{11}$)—S(O)$_2$—, with the proviso that when L is —CH$_2$—N(R$^{11}$)—C(O)—, —CH$_2$—N(R$^{11}$)—C(O)—N(R$^{11}$)—, —CH$_2$N(R$^{11}$)C(=NH)NR$^{11}$—, —CH$_2$—N(R$^{11}$)—S(O)—, or —CH$_2$—N(R$^{11}$)—S(O)$_2$—, then $R^3$ is —OH or $R^2$ and $R^3$ are taken together to form a moiety of formula 2 or formula 3, and with the further proviso that when L is —NH—, $R^1$ is not

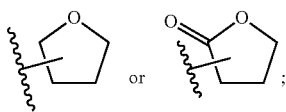

$R^1$ is selected from alkyl, aryl, arylalkyl-, heteroarylfused aryl-, heteroarylfused arylalkyl-, cycloalkylfused aryl-, cycloalkylfused arylalkyl-, heteroaryl, heteroarylalkyl-, benzofused heteroaryl-, benzofused heteroarylalkyl-, heteroarylfused heteroaryl-, heteroarylfused heteroarylalkyl-, cycloalkyl, cycloalkenyl, cycloalkylalkyl-, cycloalkenylalkyl-, heterocycloalkyl, heterocycloalkenyl, heterocycloalkylalkyl-, heterocycloalkenylalkyl-, benzofused heterocycloalkyl-, benzofused heterocycloalkenyl-, benzofused heterocycloalkylalkyl-, benzofused heterocycloalkenylalkyl-, heteroarylfused heterocycloalkenyl-, and heteroarylfused heterocycloalkenylalkyl-, wherein each said $R^1$ group is unsubstituted or optionally substituted with from 1 to 5 substituents, which may be the same or different, each independently selected from halogen, hydroxy, —CN, oxo, oxide, alkyl, alkenyl, alkynyl, haloalkyl, haloalkoxy-, hydroxyalkyl-, heteroalkyl, cyanoalkyl-, alkoxy, optionally substituted aryl, optionally substituted —O-aryl, optionally substituted —O-alkyl-aryl, optionally substituted heteroaryl, optionally substituted arylalkyl-, optionally substituted arylalkoxy, optionally substituted heterocycloalkyl, optionally substituted heterocycloalkylalkyl-, optionally substituted —O-heterocycloalkyl, —N($R^7$)$_2$, -alkylN($R^7$)$_2$, —NC(O)$R^7$, —C(O)$R^7$, —CO$_2R^7$, —SO$_2R^7$, and —SO$_2$N($R^7$)$_2$, wherein said optional substituents are present from 1 to 4 times and may be the same or different, each independently selected from alkyl, halogen, haloalkyl, hydroxyl, —CN, and —N($R^{11}$)$_2$;

and wherein the benzo portion of each said benzofused $R^1$ group is optionally further fused to another ring selected from heteroaryl, cycloalkyl, cycloalkenyl, heterocycloalkyl, and heterocycloalkenyl, and wherein the alkyl-portion of said arylalkyl-, heteroarylfused cycloalkylfused arylalkyl-, heteroarylalkyl-, benzofused heteroarylalkyl-, heteroarylfused heteroarylalkyl-, cycloalkylalkyl-, cycloalkenylalkyl-, heterocycloalkylalkyl-, heterocycloalkenylalkyl-, benzofused heterocycloalkylalkyl-, benzofused heterocycloalkenylalkyl-, and heteroarylfused heterocycloalkenylalkyl- of $R^1$ is optionally substituted with one or more substituents independently selected from alkyl, haloalkyl, and spirocycloalkyl;

$R^2$ is —O$R^8$;
$R^3$ is selected from hydrogen, hydroxy, and straight or branched alkyl,
or $R^2$ and $R^3$ taken together form a moiety of formula 2:

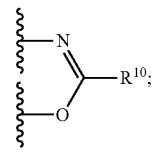

wherein X and Y are each independently selected from hydrogen, alkyl, haloalkyl, cycloalkyl, heterocycloalkyl, aryl, and heteroaryl,
wherein each of said alkyl, haloalkyl, cycloalkyl, heterocycloalkyl, aryl and heteroaryl of X and Y is optionally independently unsubstituted or substituted with from 1 to 4 substituents independently selected from alkyl, halogen, haloalkyl, hydroxy, —N($R^7$)$_2$, and —CN,
or X and Y of formula 2 are taken together with the carbon atom to which they are attached to form a 3 to 7-membered cycloalkyl or heterocycloalkyl ring, which ring is optionally substituted with from 1 to 4 substituents independently selected from alkyl, halogen, haloalkyl, hydroxy, —N($R^7$)$_2$ and —CN, or $R^2$ and $R^3$ taken together form a moiety of formula 3:

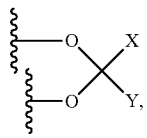

$R^4$ is selected from H and halogen;
$R^5$ is selected from H, halogen, and alkyl;
z (the dotted line) represents a single or double bond, with the proviso that when z is a single bond, then $R^6$ is H;
$R^6$ is selected from H and halogen;
each $R^7$ is independently selected from hydrogen, alkyl, haloalkyl, aryl, and heteroaryl,
or, when two groups $R^7$ are attached to the same nitrogen atom, two groups $R^7$ are taken together with the nitrogen atom to which they are attached to form a 3- to 7-membered heterocycloalkyl group;
$R^8$ selected from hydrogen, alkyl, haloalkyl, aryl, heteroaryl, arylalkyl, heteroarylalkyl, —C(O)$R^9$, and —C(O)NH$R^9$;
$R^9$ is selected from alkyl, haloalkyl, aryl, heteroaryl, cycloalkyl, and heterocycloalkyl, each optionally substituted with 1 to 4 substituents independently selected from the group consisting of alkyl, halogen, haloalkyl, hydroxy, —N($R^7$), and —CN;
$R^{10}$ is selected from hydrogen and alkyl; and
$R^{11}$ is selected from hydrogen and alkyl,
with the proviso that when -L- is —NH—, $R^2$ is —OH, $R^3$, $R^4$, and $R^5$ are each H, and z is a double bond and $R^6$ is H, then $R^1$ is not benzyl,
and with the further proviso that when -L- is —CH$_2$—O—, then $R^1$ is not unsubstituted or substituted phenyl.

In another embodiment, the present invention provides a compound, or a pharmaceutically acceptable salt, solvate, ester, prodrug, tautomer, or isomer of said compound, said compound having the general structure shown in Formula (II):

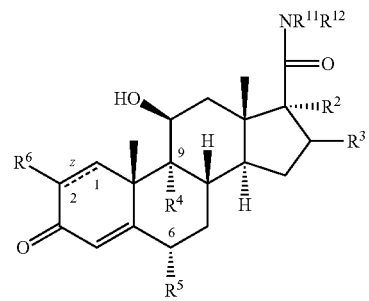

wherein $R^{11}$, $R^{12}$, $R^2$, $R^3$, $R^4$, $R^5$, $R^6$, and z are selected independently of each other and wherein:
$R^{11}$ and $R^{12}$ are taken together with the nitrogen to which they are shown attached to form a 3- to 7-membered heterocycloalkyl ring, a 3- to 7-membered heterocycloalkenyl ring, a 3- to 7-membered benzofused heterocycloalkyl-ring, or a 3- to 7-membered benzofused heterocycloalkenyl-ring,
wherein each said 3- to 7-membered heterocycloalkyl ring, 3- to 7-membered heterocycloalkenyl ring, 3- to 7-membered benzofused heterocycloalkyl ring, and said 3- to 7-membered benzofused heterocycloalkenyl ring is unsubstituted or substituted with from 1 to 4 substituents, which may be the same or different, independently selected from halogen, hydroxy, —CN, oxo, oxide, alkyl, haloalkyl, -alkyl-CN, alkoxy, aryl, halo-substituted aryl, —O-aryl, —O-alkyl-aryl, heteroaryl, arylalkyl-, arylalkoxy, haloalkoxy, —N(R$^7$)$_2$, -alkylN(R)$_2$, —NC(O)R$^7$, —CO$_2$R$^7$, —SO$_2$R$^7$, and —SO$_2$N(R$^7$)$_2$;

R$^2$ is —OR$^8$;

R$^3$ is selected from hydrogen, hydroxy, and straight or branched alkyl, or R$^2$ and R$^3$ taken together form a moiety of formula 2:

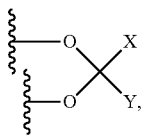

2 wherein X and Y are each independently selected from hydrogen, alkyl, haloalkyl, cycloalkyl, heterocycloalkyl, aryl, and heteroaryl, wherein each of said alkyl, haloalkyl, cycloalkyl, heterocycloalkyl, aryl and heteroaryl of X and Y is optionally independently unsubstituted or substituted with from 1 to 4 substituents independently selected from alkyl, halogen, haloalkyl, hydroxy, —N(R$^7$), and —CN, or X and Y of formula 2 are taken together with the carbon atom to which they are attached to form a 3 to 7-membered cycloalkyl or heterocycloalkyl ring, which ring is optionally substituted with from 1 to 4 substituents independently selected from alkyl, halogen, haloalkyl, hydroxy, —N(R$^7$) and —CN, or R$^2$ and R$^3$ taken together form a moiety of formula 3:

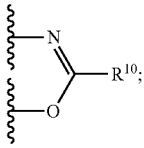

3

R$^4$ is selected from H and halogen;

R$^5$ is selected from H, halogen, and alkyl;

z (the dotted line) represents a single or double bond, with the proviso that when z is a single bond, then R$^6$ is H;

R$^6$ is selected from H and halogen;

each R$^7$ is independently selected from hydrogen, alkyl, haloalkyl, aryl, and heteroaryl, or, when two groups R$^7$ are attached to the same nitrogen atom, two groups R$^7$ are taken together with the nitrogen atom to which they are attached to form a 3- to 7-membered heterocycloalkyl group;

R$^8$ selected from hydrogen, alkyl, haloalkyl, aryl, heteroaryl, arylalkyl, heteroarylalkyl, —C(O)R$^9$, and —C(O)NHR$^9$;

R$^9$ is selected from alkyl, haloalkyl, aryl, heteroaryl, cycloalkyl, and heterocycloalkyl, each optionally substituted with 1 to 4 substituents independently selected from the group consisting of alkyl, halogen, haloalkyl, hydroxy, —N(R$^7$), and —CN; and R$^{10}$ is selected from hydrogen and alkyl.

In another embodiment, the present invention provides a compound, or a pharmaceutically acceptable salt, solvate, ester, prodrug, tautomer, or isomer of said compound, said compound having the general structure shown in Formula (III);

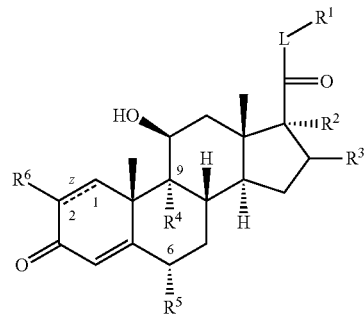

(III)

wherein L, R$^1$, R$^2$, R$^3$, R$^4$, R$^5$, R$^6$, and z are selected independently of each other and wherein:

L is —CH$_2$O—N=;

R$^1$ is cycloalkyl which is unsubstituted or optionally substituted with from 1 to 5 groups, which may be the same or different, each independently selected from halogen, hydroxy, —CN, oxo, oxide, alkyl, haloalkyl, -alkyl-CN, alkoxy, spirocycloalkyl, aryl, halo-substituted aryl, —O-aryl, —O-alkyl-aryl, heteroaryl, arylalkyl-, arylalkoxy, haloalkoxy, —N(R$^7$)$_2$, -alkylN(R$^7$)$_2$, —NC(O)R$^7$, —CO$_2$R$^7$, —SO$_2$R$^7$, and —SO$_2$N(R$^7$)$_2$;

R$^2$ is —OR$^8$,

R$^3$ is selected from hydrogen, hydroxy, and straight or branched alkyl, or R$^2$ and R$^3$ taken together form a moiety of formula 2:

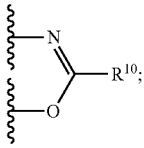

2 wherein X and Y are each independently selected from hydrogen, alkyl, haloalkyl, cycloalkyl, heterocycloalkyl, aryl, and heteroaryl, wherein each of said alkyl, haloalkyl, cycloalkyl, heterocycloalkyl, aryl and heteroaryl of X and Y is optionally independently unsubstituted or substituted with from 1 to 4 substituents independently selected from alkyl, halogen, haloalkyl, hydroxy, —N(R$^7$), and —CN, or X and Y of formula 2 are taken together with the carbon atom to which they are attached to form a 3 to 7-membered cycloalkyl or heterocycloalkyl ring, which ring is optionally substituted with from 1 to 4 substituents independently selected from alkyl, halogen, haloalkyl, hydroxy, —N(R$^7$) and —CN, or $R^2$ and $R^3$ taken together form a moiety of formula 3:

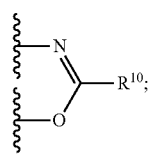

$R^4$ is selected from H and halogen;
$R^5$ is selected from H, halogen, and alkyl;
z (the dotted line) represents a single or double bond, with the proviso that when z is a single bond, $R^6$ is H;
$R^6$ is selected from H and halogen;
each $R^7$ is independently selected from hydrogen, alkyl, haloalkyl, aryl, and heteroaryl,
or, when two groups $R^7$ are attached to the same nitrogen atom, two groups $R^7$ are taken together with the nitrogen atom to which they are attached to form a 3- to 7-membered heterocycloalkyl group;
$R^8$ selected from hydrogen, alkyl, haloalkyl, aryl, heteroaryl, arylalkyl, heteroarylalkyl, —C(O)$R^9$, and —C(O)NH$R^9$;
$R^9$ is selected from alkyl, haloalkyl, aryl, heteroaryl, cycloalkyl, and heterocycloalkyl, each optionally substituted with 1 to 4 substituents independently selected from the group consisting of alkyl, halogen, haloalkyl, hydroxy, —N($R^7$), and —CN; and
$R^{10}$ is selected from hydrogen and alkyl.

In another embodiment, the present invention provides a compound, or a pharmaceutically acceptable salt, solvate, ester, prodrug, tautomer, or isomer of said compound, said compound having the general structure shown in Formula (IV):

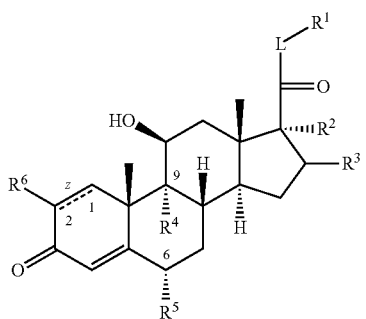

wherein L, $R^1$, $R^2$, $R^3$, $R^4$, $R^6$, and $R^6$ are selected independently of each other and wherein:
L is —CH$_2$—S—;
$R^1$ is selected from alkyl, aryl, arylalkyl-, heteroarylfused aryl-, heteroarylfused arylalkyl-, cycloalkylfused aryl, cycloalkylfused arylalkyl-, heteroaryl, heteroarylalkyl-, benzofused heteroaryl-, benzofused heteroarylalkyl-, heteroarylfused heteroaryl-, heteroarylfused heteroarylalkyl-, cycloalkyl, cycloalkenyl, cycloalkylalkyl-, cycloalkylalkenyl-, heterocycloalkyl, heterocycloalkenyl, heterocycloalkylalkyl-, heterocycloalkenylalkyl-, benzofused heterocycloalkyl-, benzofused heterocycloalkenyl-, benzofused heterocycloalkylalkyl-, benzofused heterocycloalkenylalkyl-, heteroarylfused heterocycloalkenyl-, and heteroarylfused heterocycloalkenylalkyl-, wherein each said $R^1$ group is unsubstituted or optionally substituted with from 1 to 5 substituents, which may be the same or different, each independently selected from halogen, hydroxy, —CN, oxo, oxide, alkyl, haloalkyl, haloalkoxy-, hydroxyalkyl-, heteroalkyl, cyanoalkyl-, alkoxy, optionally substituted aryl, optionally substituted —O-aryl, optionally substituted —O-alkyl-aryl, optionally substituted heteroaryl, optionally substituted arylalkyl-, optionally substituted arylalkoxy, —N($R^7$)$_2$, -alkylN($R^7$)$_2$, —NC(O)$R^7$, —CO$_2R^7$, —SO$_2R^7$, and —SO$_2$N($R^7$)$_2$, wherein said optional substituents are present from 1 to 4 times and may be the same or different, each independently selected from alkyl, halogen, haloalkyl, hydroxyl, —CN, and —N($R^{11}$)$_2$;
and wherein the benzo portion of each said benzofused $R^1$ group is optionally further fused to another ring selected from heteroaryl, cycloalkyl, cycloalkenyl, heterocycloalkyl, and heterocycloalkenyl,
and wherein the alkyl-portion of said arylalkyl-, heteroarylfused arylalkyl-, cycloalkylfused arylalkyl-, heteroarylalkyl-, benzofused heteroarylalkyl-, heteroarylfused heteroarylalkyl-, cycloalkylalkyl-, cycloalkylalkenyl-, heterocycloalkylalkyl-, heterocycloalkenylalkyl-, benzofused heterocycloalkylalkyl-, benzofused heterocycloalkenylalkyl-, and said heteroarylfused heterocycloalkenylalkyl- of $R^1$ is optionally substituted with one or more substituents independently selected from alkyl, haloalkyl, and spirocycloalkyl;

$R^2$ is —O$R^8$;
$R^3$ is selected from hydrogen, hydroxy, and straight or branched alkyl,
or $R^2$ and $R^3$ taken together form a moiety of formula 2:

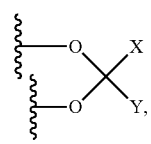

wherein X and Y are each independently selected from hydrogen, alkyl, haloalkyl, cycloalkyl, heterocycloalkyl, aryl, and heteroaryl,
wherein each of said haloalkyl, cycloalkyl, heterocycloalkyl, aryl and heteroaryl of X and Y is optionally independently unsubstituted or substituted with from 1 to 4 substituents independently selected from alkyl, halogen, haloalkyl, hydroxy, —N($R^7$)$_2$, and —CN, with the proviso that at least one of X or Y is selected from haloalkyl, cycloalkyl, heterocycloalkyl, heteroaryl, and halo-substituted aryl,
or X and Y of formula 2 are taken together with the carbon atom to which they are attached to form a 3 to 7-membered cycloalkyl or heterocycloalkyl ring, which ring is optionally substituted with from 1 to 4 substituents independently selected from alkyl, halogen, haloalkyl, hydroxy, —N($R^7$)$_2$ and —CN, or $R^2$ and $R^3$ taken together form a moiety of formula 3:

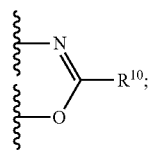

$R^4$ is selected from H and halogen;
$R^5$ is selected from H, halogen, and alkyl;
z (the dotted line) represents a single or double bond, with the proviso that when z is a single bond, $R^6$ is H;
$R^6$ is selected from H and halogen;
each $R^7$ is independently selected from hydrogen, alkyl, haloalkyl, aryl, and heteroaryl,
or, when two groups $R^7$ are attached to the same nitrogen atom, two groups $R^7$ are taken together with the nitrogen atom to which they are attached to form a 3- to 7-membered heterocycloalkyl group;
$R^8$ selected from haloalkyl, aryl, heteroaryl, arylalkyl, heteroarylalkyl, —C(O)NHR$^9$, and —C(O)R$^{11}$;
$R^9$ is selected from alkyl, haloalkyl, aryl, heteroaryl, cycloalkyl, and heterocycloalkyl, each unsubstituted or optionally substituted with from 1 to 4 substituents independently selected from the group consisting of alkyl, halogen, haloalkyl, hydroxy, —N(R$^7$)$_2$, and —CN;
$R^{10}$ is selected from hydrogen and alkyl; and
$R^{11}$ is selected from haloalkyl, aryl, heteroaryl, cycloalkyl, heterocycloalkyl, and heterocycloalkenyl, each unsubstituted or optionally substituted with from 1 to 4 substituents independently selected from the group consisting of alkyl, halogen, haloalkyl, hydroxy, —N(R$^7$)$_2$, and —CN.

In another embodiment, the present invention provides a compound, or a pharmaceutically acceptable salt, solvate, ester, prodrug, tautomer, or isomer of said compound, said compound having the general structure shown in Formula (V):

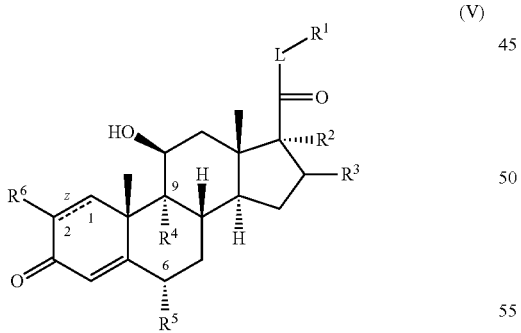

wherein L, $R^1$, $R^2$, $R^3$, $R^4$, $R^5$, and $R^6$ are selected independently of each other and wherein:
L is —CH$_2$—S—;
$R^1$ is selected from heteroarylfused aryl-, heteroarylfused arylalkyl-, cycloalkylfused aryl-, cycloalkylfused arylalkyl-, benzofused 6-membered heteroaryl-, heteroarylalkyl-, benzofused heteroarylalkyl-, heteroarylfused heteroaryl-, heteroarylfused heteroarylalkyl-, cycloalkylalkyl-, cycloalkylalkenyl-, 5-membered heterocycloalkyl-, benzofused 5-membered heterocycloalkyl-, 6-membered heterocycloalkyl-, benzofused 6-membered heterocycloalkyl-, heterocycloalkylalkyl-, benzofused heterocycloalkylalkyl-, benzofused 6-membered heterocycloalkenyl-, heterocycloalkylalkenyl-, benzofused heterocycloalkenylalkyl-, heteroarylfused heterocycloalkenyl-, and heteroarylfused heterocycloalkenylalkyl-,
wherein each said $R^1$ group is unsubstituted or optionally substituted with from 1 to 5 substituents, which may be the same or different, each independently selected from halogen, hydroxy, —CN, oxo, oxide, alkyl, haloalkyl, haloalkoxy-, hydroxyalkyl-, heteroalkyl, cyanoalkyl-, alkoxy, optionally substituted aryl, optionally substituted —O-aryl, optionally substituted —O-alkyl-aryl, optionally substituted heteroaryl, optionally substituted arylalkyl-, optionally substituted arylalkoxy, —N(R$^7$)$_2$, -alkylN(R$^7$)$_2$, —NC(O)R$^7$, —CO$_2$R$^7$, —SO$_2$R$^7$, and —SO$_2$N(R$^7$)$_2$,
wherein said optional substituents are present from 1 to 4 times and may be the same or different, each independently selected from alkyl, halogen, haloalkyl, hydroxyl, —CN, and —N(R$^{11}$)$_2$;
and wherein the benzo portion of each said benzofused $R^1$ group is optionally further fused to another ring selected from heteroaryl, cycloalkyl, cycloalkenyl, heterocycloalkyl, and heterocycloalkenyl,
and wherein the alkyl-portion of said heteroarylfused arylalkyl-, cycloalkylfused arylalkyl-, heteroarylalkyl-, benzofused heteroarylalkyl-, heteroarylfused heteroarylalkyl-, cycloalkylalkyl-, cycloalkylalkenyl-, heterocycloalkylalkyl-, benzofused heterocycloalkylalkyl-, heterocycloalkylalkenyl-, benzofused heterocycloalkenylalkyl-, and heteroarylfused heterocycloalkenylalkyl- of $R^1$ is optionally substituted with one or more substituents independently selected from alkyl, haloalkyl, and spirocycloalkyl;
$R^2$ is —OR$^8$;
$R^3$ is selected from hydrogen, hydroxy, and straight or branched alkyl,
or $R^2$ and $R^3$ taken together form a moiety of formula 2:

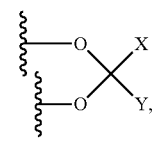

wherein X and Y are each independently selected from hydrogen, alkyl, and aryl,
wherein each of said alkyl and said aryl of X and Y is optionally independently unsubstituted or substituted with from 1 to 4 substituents independently selected from alkyl, halogen, haloalkyl, hydroxy, —N(R$^7$), and —CN;
$R^4$ is selected from H and halogen;
$R^6$ is selected from H, halogen, and alkyl;
z (the dotted line) represents a single or double bond, with the proviso that when z is a single bond, $R^6$ is H;
$R^6$ is selected from H and halogen;
each $R^7$ is independently selected from hydrogen, alkyl, haloalkyl, aryl, and heteroaryl,
or, when two groups $R^7$ are attached to the same nitrogen atom, two groups $R^7$ are taken together with the nitrogen atom to which they are attached to form a 3- to 7-membered heterocycloalkyl group;
$R^8$ selected from hydrogen, alkyl, and —C(O)R$^9$; and $R^9$ is selected from alkyl, optionally substituted with 1 to 4 substituents independently selected from the group consisting of alkyl, halogen, haloalkyl, hydroxy, —N($R^7$), and —CN, with the proviso that $R^1$ is not

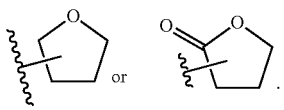

In another embodiment, the present invention provides a compound, or a pharmaceutically acceptable salt, solvate, ester, prodrug, tautomer, or isomer of said compound, said compound having the general structure shown in Formula (VI):

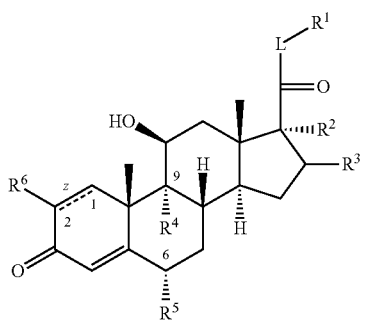

(VI)

wherein L, $R^1$, $R^2$, $R^3$, $R^4$, $R^6$, and $R^6$ are selected independently of each other and wherein:

L is —CH$_2$—S—;

$R^1$ is selected from aryl, arylalkyl-, cycloalkyl, 5-membered heterocycloalkenyl, benzofused 5-membered heterocycloalkenyl-, 5-membered heteroaryl, benzofused 5-membered heteroaryl-, 6-membered heterocycloalkenyl-, and 6-membered heteroaryl, wherein each said $R^1$ group is substituted with from 1 to 5 substituents, which may be the same or different, each independently selected from hydroxy, —CN, oxo, oxide, haloalkyl, haloalkoxy-, hydroxyalkyl-, heteroalkyl, cyanoalkyl-, optionally substituted aryl, optionally substituted —O-aryl, optionally substituted —O-alkyl-aryl, optionally substituted heteroaryl, optionally substituted arylalkyl-, optionally substituted arylalkoxy, -alkylN($R^7$)$_2$, —NC(O)$R^7$, —SO$_2R^7$, and —SO$_2$N($R^7$)$_2$, wherein said optional substituents are present from 1 to 4 times and may be the same or different, each independently selected from alkyl, halogen, haloalkyl, hydroxyl, —CN, and —N($R^{11}$)$_2$;

and wherein the alkyl-portion of said arylalkyl- of $R^1$ is optionally substituted with one or more substituents independently selected from alkyl, haloalkyl, and spirocycloalkyl;

$R^2$ is —O$R^8$;

$R^3$ is selected from hydrogen, hydroxy, and straight or branched alkyl, or $R^2$ and $R^3$ taken together form a moiety of formula 2:

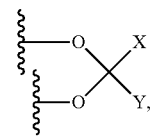

2 wherein X and Y are each independently selected from hydrogen, alkyl, and aryl,
  wherein each of said alkyl and said aryl of X and Y is optionally independently unsubstituted or substituted with from 1 to 4 substituents independently selected from alkyl, halogen, haloalkyl, hydroxy, —N($R^7$), and —CN;

$R^4$ is selected from H and halogen;

$R^5$ is selected from H, halogen, and alkyl;

z (the dotted line) represents a single or double bond, with the proviso that when z is a single bond, $R^6$ is H;

$R^6$ is selected from H and halogen;

each $R^7$ is independently selected from hydrogen, alkyl, haloalkyl, aryl, and heteroaryl, or two groups $R^7$ are taken together with the nitrogen atom to which they are attached (when present) to form a 3- to 7-membered heterocycloalkyl group;

$R^8$ selected from hydrogen, alkyl, and —C(O)$R^9$; and $R^9$ is selected from alkyl, optionally substituted with 1 to 4 substituents independently selected from the group consisting of alkyl, halogen, haloalkyl, hydroxy, —N($R^7$), and —CN, with the proviso that $R^1$ is not

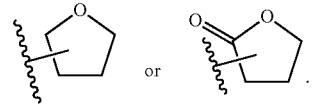

In one embodiment, the present invention provides a compound, or a pharmaceutically acceptable salt, solvate, ester, prodrug, tautomer, or isomer of said compound, said compound having the general structure shown in Formula (VIII):

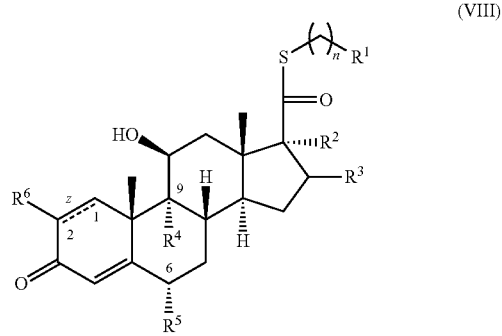

(VIII)

wherein n, $R^1$, $R^2$, $R^3$, $R^4$, $R^5$, $R^6$, and z are selected independently of each other and wherein:

n is 0 or 1;

$R^1$ is selected from phenyl, naphthyl, benzyl, heteroarylfused aryl-, heteroarylfused arylalkyl-, cycloalkylfused aryl-, cycloalkylfused arylalkyl-, heteroaryl, heteroarylalkyl-, benzofused heteroaryl-, benzofused heteroarylalkyl-, heteroarylfused heteroaryl-, heteroarylfused heteroarylalkyl-, cycloalkyl, cycloalkenyl, cycloalkylalkyl-, cycloalkenylalkyl-, heterocycloalkenyl, heterocycloalkylalkyl-, heterocycloalkenylalkyl-, benzofused heterocycloalkyl-, benzofused heterocycloalkenyl-, benzofused heterocycloalkylalkyl-, benzofused heterocycloalkenylalkyl-, heteroarylfused heterocycloalkenyl-, and heteroarylfused heterocycloalkenylalkyl-, wherein each said $R^1$ group is unsubstituted or optionally substituted with from 1 to 5 substituents, which may be the same or different, each independently selected from halogen, hydroxy, —CN, oxo, oxide, alkyl, alkenyl, alkynyl, haloalkyl, haloalkoxy-, hydroxyalkyl-, heteroalkyl, cyanoalkyl-, alkoxy, optionally substituted aryl, optionally substituted —O-aryl, optionally substituted —O-alkyl-aryl, optionally substituted heteroaryl, optionally substituted arylalkyl-, optionally substituted arylalkoxy, optionally substituted heterocycloalkyl, optionally substituted heterocycloalkylalkyl-, optionally substituted —O-heterocycloalkyl, —N($R^7$)$_2$, -alkylN($R^7$)$_2$, —NC(O)$R^7$, —C(O)$R^7$, —CO$_2$$R^7$, —SO$_2$$R^7$, and —SO$_2$N($R^7$)$_2$, wherein said optional substituents are present from 1 to 4 times and may be the same or different, each independently selected from alkyl, halogen, haloalkyl, hydroxyl, —CN, and —N($R^{11}$)$_2$;

and wherein the benzo portion of each said benzofused $R^1$ group is optionally further fused to another ring selected from heteroaryl, cycloalkyl, cycloalkenyl, heterocycloalkyl, and heterocycloalkenyl, and wherein the alkyl-portion of said benzyl-, heteroarylfused arylalkyl-, cycloalkylfused arylalkyl-, heteroarylalkyl-, benzofused heteroarylalkyl-, heteroarylfused heteroarylalkyl-, cycloalkylalkyl-, cycloalkenylalkyl-, heterocycloalkylalkyl-, heterocycloalkylalkyl-, benzofused heterocycloalkylalkyl-, benzofused heterocycloalkenylalkyl-, and heteroarylfused heterocycloalkenylalkyl- of $R^1$ is optionally substituted with one or more substituents independently selected from alkyl, haloalkyl, and spirocycloalkyl;

$R^2$ is —O$R^8$;

$R^3$ is selected from hydrogen, hydroxy, and straight or branched alkyl, or $R^2$ and $R^3$ taken together form a moiety of formula 2:

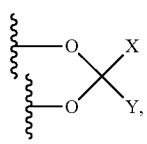

2 wherein X and Y are each independently selected from hydrogen, alkyl, haloalkyl, cycloalkyl, heterocycloalkyl, aryl, and heteroaryl, wherein each of said alkyl, haloalkyl, cycloalkyl, heterocycloalkyl, aryl and heteroaryl of X and Y is optionally independently unsubstituted or substituted with from 1 to 4 substituents independently selected from alkyl, halogen, haloalkyl, hydroxy, —N($R^7$)$_2$, and —CN, or X and Y of formula 2 are taken together with the carbon atom to which they are attached to form a 3 to 7-membered cycloalkyl or heterocycloalkyl ring, which ring is optionally substituted with from 1 to 4 substituents independently selected from alkyl, halogen, haloalkyl, hydroxy, —N($R^7$)$_2$ and —CN, or $R^2$ and $R^3$ taken together form a moiety of formula 3:

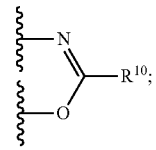

3

$R^4$ is selected from H and halogen;
$R^6$ is selected from H, halogen, and alkyl;
z (the dotted line) represents a single or double bond, with the proviso that when z is a single bond, then $R^6$ is H;
$R^6$ is selected from H and halogen;
each $R^7$ is independently selected from hydrogen, alkyl, haloalkyl, aryl, and heteroaryl,
or, when two groups $R^7$ are attached to the same nitrogen atom, two groups $R^7$ are taken together with the nitrogen atom to which they are attached to form a 3- to 7-membered heterocycloalkyl group;
$R^8$ selected from hydrogen, alkyl, haloalkyl, aryl, heteroaryl, arylalkyl, heteroarylalkyl, —C(O)$R^9$, and —C(O)NHR$^9$;
$R^9$ is selected from alkyl, haloalkyl, aryl, heteroaryl, cycloalkyl, and heterocycloalkyl, each optionally substituted with 1 to 4 substituents independently selected from the group consisting of alkyl, halogen, haloalkyl, hydroxy, —N($R^7$), and —CN;
$R^{10}$ is selected from hydrogen and alkyl; and
$R^{11}$ is selected from hydrogen and alkyl,
with the proviso that when $R^2$ is —O$R^8$, $R^8$ is —C(O)$R^9$, and $R^9$ is selected from alkyl, haloalkyl, aryl, and cycloalkyl, each optionally substituted with 1 to 4 substituents independently selected from the group consisting of alkyl, halogen, haloalkyl, hydroxy, —N($R^7$), and —CN, then $R^1$ is not optionally substituted phenyl or optionally substituted benzyl.

In another embodiment, pharmaceutical formulations or compositions comprising a therapeutically effective amount of at least one of the inventive compounds, and/or a pharmaceutically acceptable salt, solvate, ester, prodrug, or isomer thereof, and a pharmaceutically acceptable carrier also are provided. In another embodiment, pharmaceutical formulations or compositions comprising a therapeutically effective amount of at least one of the inventive compounds (and/or a pharmaceutically acceptable salt, solvate, ester, prodrug, or isomer thereof) and a pharmaceutically acceptable carrier together with one or more additional active ingredients are also contemplated.

In another embodiment, the present invention provides methods of treating inflammatory diseases and conditions, such methods comprising administering at least one compound or composition of the invention to a patient in need thereof.

In another embodiment, the present invention provides methods for the treatment of inflammatory diseases and conditions in a patient in need thereof, wherein the anti-inflammatory properties are dissociated from the systemic side-effects which comprises administering to said patient a dissociated steroid compound of the invention.

DETAILED DESCRIPTION

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

As will be appreciated by those of ordinary skill in the art, conventions for depicting the stereoconfiguration of steroidal compounds have developed, The present disclosure conforms to such convention. Thus, for example, the C8, C14, 10-CH$_3$, and 18-CH$_3$ positions of the steroid core, when depicted herein as:

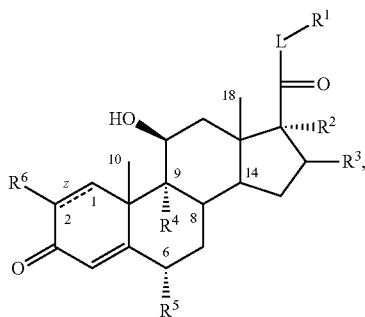

are for purposes of this disclosure and the appended claims considered equivalent to the stereoconfiguration shown as follows:

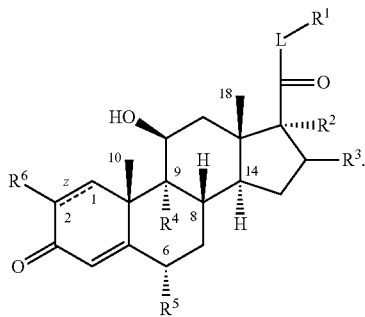

As described herein, the variable "-L-", when present in the various generic formulas depicting compounds of the invention, is shown as a divalent moiety. It shall be understood that the various moieties within the definitions of L, throughout the description and claims, are to be read from left to right as written, such that the point of attachment of the left-most bond of L is to the rest of the compound, and the point of attachment of the right-most bond of L as written is understood to be R$^1$. Thus, as a non-limiting example, when -L- is written as CH$_2$—S—, the points of attachment of -L- are understood to be as follows: "rest of molecule"—CH$_2$—S—R$^1$.

"Patient" includes both human and animals.

"Mammal" means humans and other mammalian animals.

"Halogen" means fluorine, chlorine, bromine, or iodine. Preferred are fluorine, chlorine and bromine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being as described herein or independently selected from the group consisting of halo, alkyl, haloalkyl, spirocycloalkyl, aryl, cycloalkyl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Haloalkyl" means an alkyl as defined above wherein one or more hydrogen atoms on the alkyl is replaced by a halo group defined above.

"Heteroalkyl" means an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical. Suitable such heteroatoms include O, S, and N. Non-limiting examples include ethers, thioethers, amines, hydroxymethyl, 3-hydroxypropyl, 1,2-dihydroxyethyl, 2-methoxyethyl, 2-aminoethyl, 2-dimethylaminoethyl, and the like.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched, "Alkenyl" may be unsubstituted or optionally substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. More generally, the suffix "ene" on alkyl, aryl, heterocycloalkyl, etc. indicates a divalent moiety, e.g., —CH$_2$CH$_2$— is ethylene, and

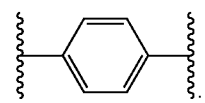

is para-phenylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Alkenylene" means a difunctional group obtained by removal of a hydrogen from an alkenyl group that is defined above. Non-limiting examples of alkenylene include —CH═CH—, —C(CH$_3$)═CH—, and —CH═CHCH$_2$—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like. Further non-limiting examples of cycloalkyl include the following:

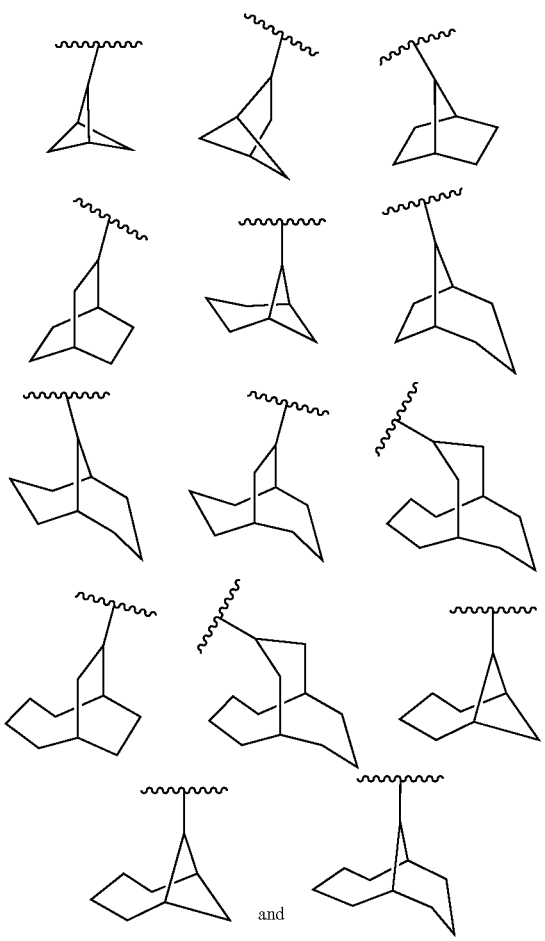

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl, as well as unsaturated moieties of the examples shown above for cycloalkyl.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes rings wherein =O replaces two available hydrogens on the same carbon atom (i.e., heterocyclyl includes rings having a carbonyl group in the ring). Such =O groups may be referred to herein as "oxo." Example of such moiety is pyrrolidone:

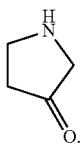

"Heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom (i.e., heterocyclyl includes rings having a carbonyl group in the ring). Example of such moiety is pyrrolidinone:

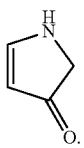

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

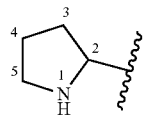

there is no —OH attached directly to carbons marked 2 and 5.

It should also be noted that tautomeric forms such as, for example, the moieties:

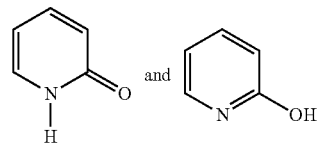 [SMILES: O=c1cccc[nH]1 ; Oc1ccccn1]

are considered equivalent in certain embodiments of this invention.

"Arylcycloalkyl" (or "arylfused cycloalkyl") means a group derived from a fused aryl and cycloalkyl as defined herein. Preferred arylcycloalkyls are those wherein aryl is phenyl (which may be referred to as "benzofused") and cycloalkyl consists of about 5 to about 6 ring atoms. The arylcycloalkyl can be optionally substituted as described herein. Non-limiting examples of suitable arylcycloalkyls include indanyl (a benzofused cycloalkyl) and 1,2,3,4-tetrahydronaphthyl and the like. The bond to the parent moiety is through a non-aromatic carbon atom.

"Arylheterocycloalkyl" (or "arylfused heterocycloalkyl") means a group derived from a fused aryl and heterocycloalkyl as defined herein. Preferred arylcycloalkyls are those wherein aryl is phenyl (which may be referred to as "benzofused") and heterocycloalkyl consists of about 5 to about 6 ring atoms. The arylheterocycloalkyl can be optionally substituted, and/or contain the oxide or oxo, as described herein. Non-limiting examples of suitable arylfused heterocycloalkyls include:

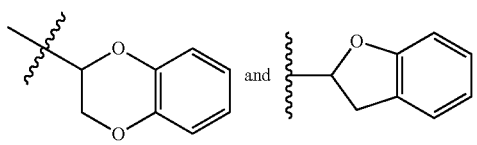

The bond to the parent moiety is through a non-aromatic carbon atom.

It is also understood that the terms "arylfused aryl-", "arylfused cycloalkyl-", "arylfused cycloalkenyl-", "arylfused heterocycloalkyl-", arylfused heterocycloalkenyl-", "arylfused heteroaryl-", "cycloalkylfused aryl-", "cycloalkylfused cycloalkyl-", "cycloalkylfused cycloalkenyl-", "cycloalkylfused heterocycloalkyl-", "cycloalkylfused heterocycloalkenyl-", "cycloalkylfused heteroaryl-, "cycloalkenylfused aryl-", "cycloalkenylfused cycloalkyl-", "cycloalkenylfused cycloalkenyl-", "cycloalkenylfused heterocycloalkyl-", "cycloalkenylfused heterocycloalkenyl-", "cycloalkenylfused heteroaryl-", "heterocycloalkylfused aryl-", "heterocycloalkylfused cycloalkyl-", "heterocycloalkylfused cycloalkenyl-", "heterocycloalkylfused heterocycloalkyl-", "heterocycloalkylfused heterocycloalkenyl-", "heterocycloalkylfused heteroaryl-", "heterocycloalkenylfused aryl-", "heterocycloalkenylfused cycloalkyl-", "heterocycloalkenylfused cycloalkenyl-", "heterocycloalkenylfused heterocycloalkyl-", "heterocycloalkenylfused heterocycloalkenyl-", "heterocycloalkenylfused heteroaryl-", "heteroarylfused aryl-", "heteroarylfused cycloalkyl-", "heteroarylfused cycloalkenyl-", "heteroarylfused heterocycloalkyl-", "heteroarylfused heterocycloalkenyl-", and "heteroarylfused heteroaryl-" are similarly represented by the combination of the groups aryl, cycloalkyl, cycloalkenyl, heterocycloalkyl, heterocycloalkenyl, and heteroaryl, as previously described. Any such groups may be unsubstituted or substituted with one or more ring system substituents at any available position as described herein. The point of attachment to the parent moiety, which may be indicated by a "-", is to the non-fused moiety.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl. The term (and similar terms) may be written as "arylalkyl-" to indicate the point of attachment to the parent moiety.

Similarly, "heteroarylalkyl", "cycloalkylalkyl", "cycloalkenylalkyl", "heterocycloalkylalkyl", "heterocycloalkenylalkyl", etc., mean a heteroaryl, cycloalkyl, cycloalkenyl, heterocycloalkyl, heterocycloalkenyl, etc. as described herein bound to a parent moiety through an alkyl group. Preferred groups contain a lower alkyl group. Such alkyl groups may be straight or branched, unsubstituted and/or substituted as described herein.

Similarly, "arylfused arylalkyl-", arylfused cycloalkylalkyl-, etc., means an arylfused aryl group, arylfused cycloalkyl group, etc. linked to a parent moiety through an alkyl group. Preferred groups contain a lower alkyl group. Such alkyl groups may be straight or branched, unsubstituted and/or substituted as described herein.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkylether" means a non-aromatic ring of 3 to 7 members comprising an oxygen atom and 2 to 7 carbon atoms. Ring carbon atoms can be substituted, provided that substituents adjacent to the ring oxygen do not include halo or substituents joined to the ring through an oxygen, nitrogen or sulfur atom.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl, adamantylpropyl, and the like.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclylalkyl" (or "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenylalkyl" means a heterocyclenyl moiety as defined above linked via an alkyl moiety (defined above) to a parent core.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl, "Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Cyanoalkyl" means a CN-alkyl- group in which alkyl is as previously defined. Preferred cyanalkyls contain lower alkyl. Non-limiting examples of suitable cyanoalkyl groups include cyanomethyl and 2-cyanoethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkyoxyalkyl" means a group derived from an alkoxy and alkyl as defined herein. The bond to the parent moiety is through the alkyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" (or "arylalkyloxy") means an aralkyl-O— group (an arylaklyl-O— group) in which the aralkyl group is as previously described. Non-limiting examples of suitable aralkyloxy groups include benzyloxy and 1- or 2-naphthalenemethoxy. The bond to the parent moiety is through the ether oxygen.

"Arylalkenyl" means a group derived from an aryl and alkenyl as defined herein. Preferred arylalkenyls are those wherein aryl is phenyl and the alkenyl consists of about 3 to about 6 atoms. The arylalkenyl can be optionally substituted by one or more $R^{27}$ substituents. The bond to the parent moiety is through a non-aromatic carbon atom.

"Arylalkynyl" means a group derived from a aryl and alkenyl as defined herein. Preferred arylalkynyls are those wherein aryl is phenyl and the alkynyl consists of about 3 to about 6 atoms. The arylalkynyl can be optionally substituted by one or more $R^{27}$ substituents. The bond to the parent moiety is through a non-aromatic carbon atom.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

"Spirocycloalkyl" means a cycloalkyl group attached to a parent moiety at a single carbon atom. Non-limiting examples of spirocycloalkyl wherein the parent moiety is a cycloalkyl include Spiro[2.5]octane, Spiro[2.4]heptane, etc. Non-limiting examples of spirocycloalkyl wherein the parent moiety is an The alkyl moiety linking fused ring systems (such as the alkyl moiety in heteroarylfused heteroarylalkyl-) may optionally be substituted with spirocycloalkyl or other groups as described herein. Non-limiting spirocycloalkyl groups include spirocyclopropyl, spriorcyclobutyl, spirocycloheptyl, and spirocyclohexyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" it is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., R$^7$ in —N(R$^7$)$_2$, or a variable appears more than once in a structure presented herein such as Formula (I), the variables can be the same or different.

"Compound(s) of the invention" (or "inventive compound(s)") refers, individually and/or collectively, to the inventive compounds encompassed by the general Formulas (I)-(VI) and (VIII), and the various embodiments described therein or the individual compounds encompassed thereby.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. With respect to the compositions and methods comprising the use of "at least one compound of the invention, e.g., of Formula (I)," one to three compounds of the invention, e.g., of Formula (I), can be administered at the same time.

Compounds of the invention may contain one or more rings having one or more ring system substituents. "Ring system substituent" means a substituent attached to an aromatic or non-aromatic ring system which, for example, replaces an available hydrogen on the ring system. Ring system substituents may be the same or different, each being as described herein or independently selected from the group consisting of alkyl, alkenyl, alkynyl, haloalkyl, heteroalkyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl, "Ring system substituent" may also mean a single moiety which simultaneously replaces two available hydrogens on two adjacent carbon atoms (one H on each carbon) on a ring system. Examples of such moieties are rings such as heteroaryl, cycloalkyl, cycloalkenyl, heterocycloalkyl, and heterocycloalkenyl rings. Additional non-limiting examples include methylene dioxy, ethylenedioxy, —C(CH$_3$)$_2$— and the like which form moieties such as, for example:

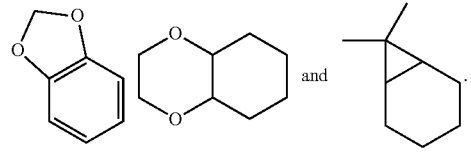

As used herein, the term "composition" is intended to encompass a product comprising the specified ingredients in the specified amounts, as well as any product which results, directly or indirectly, from combination of the specified ingredients in the specified amounts.

The line ----, as a bond generally indicates a mixture of, or either of, the possible isomers, e.g., containing (R)- and (S)-stereochemistry. For example:

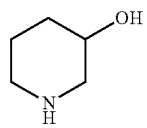

means containing both

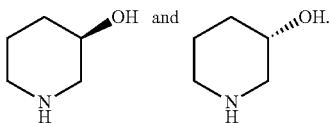

The wavy line ~~~, as used herein, indicates a point of attachment to the rest of the compound. For example, each wavy line in the following structure:

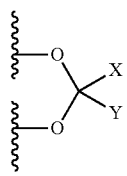

indicates a point of attachment to the core structure, as described herein.

Lines drawn into the ring systems, such as, for example:

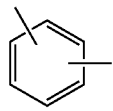

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

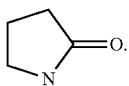

In this specification, where there are multiple oxygen and/or sulfur atoms in a ring system, there cannot be any adjacent oxygen and/or sulfur present in said ring system.

It is noted that the carbon atoms for compounds of the invention may be replaced with 1 to 3 silicon atoms so long as all valency requirements are satisfied.

As well known in the art, a bond drawn from a particular atom wherein no moiety is depicted at the terminal end of the bond indicates a methyl group bound through that bond to the atom, unless stated otherwise. For example:

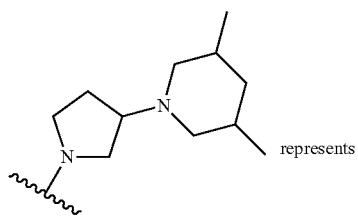 represents

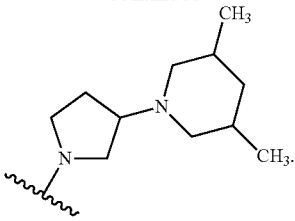

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like) in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood, in the gastrointestinal tract, or in the lungs. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$ alkyl, and the like.

Similarly, if a compound of the invention contains an alcohol functional group, a prodrug can be formed by the replacement of the hydrogen atom of the alcohol group with a group such as, for example, $(C_1-C_6)$alkanoyloxymethyl, 1-(($C_1-C_6$) alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

Compounds of the invention contain a hydroxyl group at the C-11 position. 11-keto prodrugs of any of the compounds of the invention may be obtained by conversion of the starting core moiety from the C-11 hydroxy to the corresponding C-11 keto compound, then following the procedures described herein. Examples of prodrugs of the compounds of the invention are shown in Table 5 below.

If a compound of the invention incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$ alkyl and $Y^3$ is $(C_1-C_6)$alkyl, carboxy$(C_1-C_6)$alkyl, amino $(C_1-C_4)$alkyl or mono-N— or di-N,N—$(C_1-C_6)$alkylaminoalkyl, —$C(Y^4)Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira at al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of the invention can form salts which are also within the scope of this invention. Reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the invention may be formed, for example, by reacting a compound of the invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of the invention, and salts, solvates, esters and prodrugs thereof, may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of the invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of the invention can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of the invention, and of the salts, solvates, esters and prodrugs of the compounds of the invention, are intended to be included in the present invention.

The term "pharmaceutical composition" is also intended to encompass both the bulk composition and individual dosage units comprised of more than one (e.g., two or more) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills, aerosols and other forms suitable for inhalation, and the like. Similarly, the herein-described method of treating a patient by administering a pharmaceutical composition of the present invention is also intended to encompass the administration of the afore-said bulk composition and individual dosage units.

The following embodiments (stated as "In one embodiment" or as "In another embodiment" or "In other embodiments" and the like) are independent of each other; different such embodiments can be independently selected and combined in various combinations. Such combinations should be considered as part of the invention.

In all the embodiments shown below, where moieties for more than one variable are listed for the same embodiment, each variable should be considered as being selected independently of one another.

In the various embodiments described herein, unless otherwise stated, variables of each of the general formulas not explicitly defined in the context of the respective formula are as defined in the formula to which they refer.

In one embodiment, the present invention provides a compound, or a pharmaceutically acceptable salt, solvate, ester, prodrug, or isomer of said compound, having the general structure shown in Formula (I) as described above.

In one embodiment, in Formula (I), is a compound having the structural formula:

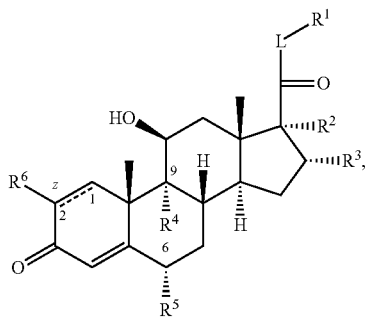

or a pharmaceutically acceptable salt, solvate, ester, prodrug, tautomer, or isomer thereof, wherein L, $R^1$, $R^2$, $R^3$, $R^4$, $R^5$, $R^6$, and z are selected independently and as defined in Formula (I).

In one embodiment, in Formula (I), L is selected from —CH$_2$—S—CH$_2$—C(O)—NH—, —CH$_2$O—, —CH$_2$—OC(O)—NH—, —CH$_2$S(O)—, —CH$_2$S(O)$_2$—, —NR$^{11}$—, —N(R$^{11}$)—C(O)—, —N(R$^{11}$)—S(O)—, —N(R$^{11}$)—S(O)$_2$—, —NR$^{11}$O—, —CH$_2$N(R$^{11}$)—, —CH$_2$—N(R$^{11}$)—C(O)—, —CH$_2$—N(R$^{11}$)—C(O)—N(R$^{11}$)—, —CH$_2$—N(R$^{11}$)—C(O)O—, —CH$_2$—N(R$^{11}$)—OC(O)—, —CH$_2$N(R$^{11}$)C(=NH)NR$^{11}$—, —CH$_2$—N(R$^{11}$)—S(O)—, and —CH$_2$—N(R$^{11}$)—S(O)$_2$—, with the proviso that when L is —CH$_2$—N(R$^{11}$)—C(O)—, —CH$_2$—N(R$^{11}$)—C(O)—N(R$^{11}$)—, —CH$_2$N(R$^{11}$)C(=NH)NR$^{11}$—, —CH$_2$—N(R$^{11}$)—S(O)—, or —CH$_2$—N(R$^{11}$)—S(O)$_2$—, then $R^3$ is —OH or $R^2$ and $R^3$ are taken together to form a moiety of formula 2 or formula 3, and with the further proviso that when L is —NH—, $R^1$ is not heterocycloalkyl or substituted heterocycloalkyl.

In one embodiment, in Formula (I), L is selected from —CH$_2$—S—CH$_2$—C(O)—NH—, —CH$_2$O—, —CH$_2$—OC(O)—NH—, —CH$_2$S(O)—, —CH$_2$S(O)$_2$—, —NR$^{11}$—, —N(R$^{11}$)—C(O)—, —N(R$^{11}$)—S(O)—, —N(R$^{11}$)—S(O)$_2$—, —NR$^{11}$O—, —CH$_2$N(R$^{11}$)—, —CH$_2$—N(R$^{11}$)—C(O)—, —CH$_2$—N(R$^{11}$)—C(O)—N(R$^{11}$)—, —CH$_2$—N(R$^{11}$)—C(O)O—, —CH$_2$—N(R$^{11}$)—OC(O)—, —CH$_2$N(R$^{11}$)C(=NH)NR$^{11}$—, —CH$_2$—N(R$^{11}$)—S(O)—, and —CH$_2$—N(R$^{11}$)—S(O)$_2$—, with the proviso that when L is —CH$_2$—N(R$^{11}$)—C(O)—, —CH$_2$—N(R$^{11}$)—C(O)—N(R$^{11}$)—, —CH$_2$N(R$^{11}$)C(=NH)NR$^{11}$—, —CH$_2$—N(R$^{11}$)—S(O)—, or —CH$_2$—N(R$^{11}$)—S(O)$_2$—, then $R^3$ is —OH or $R^2$ and $R^3$ are taken together to form a moiety of formula 2 or formula 3, and with the further proviso that when L is —NH—, $R^1$ is not

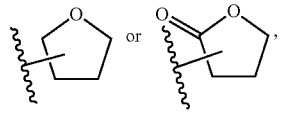

and with the further proviso that when L is —CH$_2$—O—, $R^1$ is not aryl or substituted aryl.

In one embodiment, in Formula (I), L is selected from —CH$_2$O— and —NH—.

In one embodiment, in Formula (I), $R^1$ is selected from optionally substituted aryl, optionally substituted heteroaryl, optionally substituted heterocycloalkenyl, optionally substituted benzofused heteroaryl, optionally substituted heteroarylfused heteroaryl, optionally substituted benzofused heterocycloalkenyl, and optionally substituted heteroarylfused heterocycloalkenyl.

In one embodiment, in Formula (I), $R^1$ is selected from alkyl, phenyl, naphthyl, phenylalkyl-, naphthylalkyl-, 4- to 6-membered heteroarylfused phenyl, 4- to 6-membered heteroarylfused phenylalkyl-, 4- to 6-membered cycloalkylfused phenyl, 4- to 6-membered cycloalkylfused phenyl alkyl-, 4- to 6-membered heteroaryl, 4- to 6-membered heteroarylalkyl-, benzofused 4- to 6-membered heteroaryl, benzofused 4- to 6-membered heteroarylalkyl-, 4- to 6-membered heteroarylfused 4- to 6-membered heteroaryl, 4- to 6-membered heteroarylfused 4- to 6-membered heteroarylalkyl-, 3- to 7-membered cycloalkyl, 3- to 7-membered cycloalkenyl, 3- to 7-membered cycloalkylalkyl-, 3- to 7-membered cycloalkenylalkyl-, 4- to 6-membered heterocycloalkyl, 4- to 6-membered heterocycloalkenyl, 4- to 6-membered heterocycloalkylalkyl-, 4- to 6-membered heterocycloalkenylalkyl-, benzofused 4- to 6-membered heterocycloalkyl, benzofused 4- to 6-membered heterocycloalkenyl, benzofused 4- to 6-membered heterocycloalkylalkyl-, benzofused 4- to 6-membered heterocycloalkenylalkyl-, 4- to 6-membered heteroarylfused 4- to 6-membered heterocycloalkenyl, and 4- to 6-membered heteroarylfused 4- to 6-membered heterocycloalkenylalkyl-, wherein each said hetero ring-containing moiety of $R^1$ and each said heterofused containing moiety of $R^1$ independently contains 1, 2, or 3 ring heteroatoms independently selected from any combination of N, O, and S, wherein each said $R^1$ group is unsubstituted or optionally substituted with from 1 to 5 substituents, which may be the same or different, each independently selected from halogen, hydroxy, —CN, oxo, oxide, alkyl, haloalkyl, haloalkoxy-, hydroxyalkyl-, heteroalkyl, cyanoalkyl-, alkoxy, optionally substituted aryl, optionally substituted —O-aryl, optionally substituted —O-alkyl-aryl, optionally substituted heteroaryl, optionally substituted arylalkyl-, optionally substituted arylalkoxy, —N(R$^7$)$_2$, -alkylN(R$^7$)$_2$, —NC(O)R$^7$, —CO$_2$R$^7$, —SO$_2$R$^7$, and —SO$_2$N(R$^7$)$_2$, wherein said optional substituents are present from 1 to 4 times and may be the same or different, each independently selected from alkyl, halogen, haloalkyl, hydroxyl, —CN, and —N(R$^{11}$)$_2$;

and wherein the benzo portion of each said benzofused $R^1$ group is optionally further fused to another ring selected from heteroaryl, cycloalkyl, cycloalkenyl, heterocycloalkyl, and heterocycloalkenyl, and wherein the alkyl-portion of said phenylalkyl-, naphthylalkyl-, 4- to 6-membered heteroarylfused phenylalkyl-, 4- to 6-membered cycloalkylfused phenylalkyl-, 4- to 6-membered heteroarylalkyl-, benzofused 4- to 6-membered heteroarylalkyl-, 4- to 6-membered heteroarylfused 4- to 6-membered heteroarylalkyl-, 3- to 7-membered cycloalkylalkyl-, 4- to 6-membered heterocycloalkylalkyl-, 4- to 6-membered heterocycloalkenylalkyl-, benzofused 4- to 6-membered heterocycloalkenyl, benzofused 4- to 6-membered heterocycloalkylalkyl-, benzofused 4- to 6-membered heterocycloalkenylalkyl-, and 4- to 6-membered heteroarylfused 4- to 6-membered heterocycloalkenylalkyl-, of $R^1$ is optionally substituted with one or more substituents independently selected from alkyl, haloalkyl, and spirocycloalkyl.

In one embodiment, in Formula (I), $R^1$ is selected from aryl, arylalkyl-, heteroarylfused aryl, heteroarylfused arylalkyl-, heteroaryl, heteroarylalkyl-, benzofused heteroaryl-, benzofused heteroarylalkyl-, heteroarylfused heteroaryl-, and heteroarylfused heteroarylalkyl-, wherein each said $R^1$ group is unsubstituted or optionally substituted with 1 to 2 substituents, which may be the same or different, each substituent being independently selected from halogen, hydroxy, —CN, alkyl, haloalkyl, alkoxy, aryl, —O-aryl and heteroaryl.

In one embodiment, in Formula (I), the alkyl-portion of said phenylalkyl-, naphthylalkyl-, 4- to 6-membered heteroarylfused phenylalkyl-, 4- to 6-membered cycloalkylfused phenylalkyl-, 4- to 6-membered heteroarylalkyl-, benzofused 4- to 6-membered heteroarylalkyl-, 4- to 6-membered heteroarylfused 4- to 6-membered heteroarylalkyl-, 3- to 7-membered cycloalkylalkyl-, 4- to 6-membered heterocycloalkylalkyl-, 4- to 6-membered heterocycloalkenylalkyl-, benzofused 4- to 6-membered heterocycloalkenyl, benzofused 4- to 6-membered heterocycloalkylalkyl-, benzofused 4- to 6-membered heterocycloalkenylalkyl-, and 4- to 6-membered heteroarylfused 4- to 6-membered heterocycloalkenylalkyl-, of $R^1$ is substituted with spirocyclopropyl.

In one embodiment, in Formula (I), the alkyl-portion of said phenylalkyl-, naphthylalkyl-, 4- to 6-membered heteroarylfused phenylalkyl-, 4- to 6-membered cycloalkylfused phenylalkyl-, 4- to 6-membered heteroarylalkyl-, benzofused 4- to 6-membered heteroarylalkyl-, 4- to 6-membered heteroarylfused 4- to 6-membered heteroarylalkyl-, 3- to 7-membered cycloalkylalkyl-, 4- to 6-membered heterocycloalkylalkyl-, 4- to 6-membered heterocycloalkenylalkyl-, benzofused 4- to 6-membered heterocycloalkenyl, benzofused 4- to 6-membered heterocycloalkylalkyl-, benzofused 4- to 6-membered heterocycloalkenylalkyl-, and 4- to 6-membered heteroarylfused 4- to 6-membered heterocycloalkenylalkyl-, of $R^1$ is a moiety of the formula:

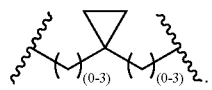

In one embodiment, in Formula (I), the alkyl-portion of said phenylalkyl-, naphthylalkyl-, 4- to 6-membered heteroarylfused phenylalkyl-, 4- to 6-membered cycloalkylfused phenylalkyl-, 4- to 6-membered heteroarylalkyl-, benzofused 4- to 6-membered heteroarylalkyl-, 4- to 6-membered heteroarylfused 4- to 6-membered heteroarylalkyl-, 3- to 7-membered cycloalkylalkyl-, 4- to 6-membered heterocycloalkylalkyl-, 4- to 6-membered heterocycloalkenylalkyl-, benzofused 4- to 6-membered heterocycloalkenyl, benzofused 4- to 6-membered heterocycloalkylalkyl-, benzofused 4- to 6-membered heterocycloalkenylalkyl-, and 4- to 6-membered heteroarylfused 4- to 6-membered heterocycloalkenylalkyl-, of $R^1$ is a moiety of the formula:

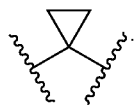 [SMILES: *C1(*)CC1]

In one embodiment, in Formula (I), the alkyl-portion of said phenylalkyl-, naphthylalkyl-, 4- to 6-membered heteroarylfused phenylalkyl-, 4- to 6-membered cycloalkylfused phenylalkyl-, 4- to 6-membered heteroarylalkyl-, benzofused 4- to 6-membered heteroarylalkyl-, 4- to 6-membered heteroarylfused 4- to 6-membered heteroarylalkyl-, 3- to 7-membered cycloalkylalkyl-, 4- to 6-membered heterocycloalkylalkyl-, 4- to 6-membered heterocycloalkenylalkyl-, benzofused 4- to 6-membered heterocycloalkenyl, benzofused 4- to 6-membered heterocycloalkylalkyl-, benzofused 4- to 6-membered heterocycloalkenylalkyl-, and 4- to 6-membered heteroarylfused 4- to 6-membered heterocycloalkenylalkyl-, of $R^1$ is a moiety of the formula:

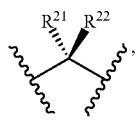

wherein one of $R^{21}$ and $R^{22}$ is hydrogen and the other is selected from $C_1$-$C_2$ alkyl, $C_1$-$C_2$ haloalkyl, fluorine, and hydroxyl. In one such embodiment, one of $R^{21}$ and $R^{22}$ is hydrogen and the other is selected from methyl and —$CF_3$.

in one embodiment, in Formula (I), $R^1$ is unsubstituted.

In one embodiment, in Formula (I), $R^1$ is substituted with from 1 to 4 substituents.

In one embodiment, in Formula (I), $R^1$ is substituted with from 1 to 3 substituents.

In one embodiment, in Formula (I), $R^1$ is substituted with from 1 to 2 substituents.

In one embodiment, in Formula (I), $R^1$ is substituted with 1 substituent.

In one embodiment, in Formula (I), $R^1$ is substituted with from 1 to 2 substituents, which may be the same or different, each independently selected from halogen, hydroxy, —CN, alkyl, haloalkyl, optionally substituted aryl, optionally substituted heteroaryl, and optionally substituted arylalkoxy.

In one embodiment, in Formula (I), $R^1$ is selected from aryl, arylalkyl-, heteroarylfused aryl, heteroarylfused arylalkyl-, heteroaryl, heteroarylalkyl-, benzofused heteroaryl-, benzofused heteroarylalkyl-, heteroarylfused heteroaryl-, and heteroarylfused heteroarylalkyl-, wherein each said $R^1$ group is unsubstituted or optionally substituted with from 1 to 2 substituents, which may be the same or different, each substituent being independently selected from halogen, hydroxy, —CN, alkyl, haloalkyl, alkoxy, aryl, —O-aryl and heteroaryl.

Non-limiting examples of $R^1$, in Formula (I), include:

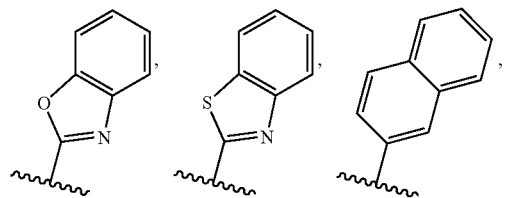

-continued

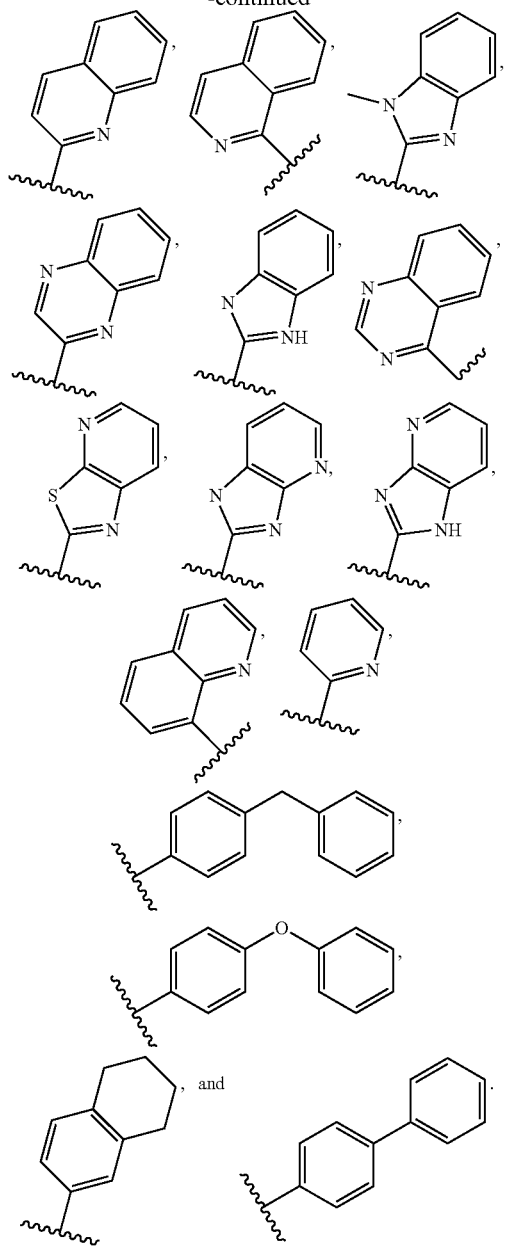

In one embodiment, in Formula (I), $R^2$ is selected from —OH and —OC(O)$R^9$.

In one embodiment, in Formula (I), $R^9$ is unsubstituted.

In one embodiment, in Formula (I), $R^9$ is substituted with from 1 to 3 substituents.

In one embodiment, in Formula (I), $R^9$ is substituted with from 1 to 2 substituents.

In one embodiment, in Formula (I), $R^9$ is substituted with 1 substituent.

In one embodiment, in Formula (I), $R^9$ is substituted with from 1 to 2 substituents, which may be the same or different, each independently selected from alkyl, halogen, and haloalkyl.

In one embodiment, in Formula (I), $R^9$ is unsubstituted or substituted heterocycloalkyl, In one embodiment, in Formula (I), $R^9$ is unsubstituted or substituted heterocycloalkenyl.

In one embodiment, in Formula (I), $R^9$ is unsubstituted or substituted heteroaryl.

In one embodiment, in Formula (I), $R^2$ is

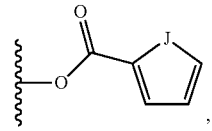

wherein J is selected from O, S, and N, or the oxides thereof.

In one embodiment, in Formula (I), $R^2$ is

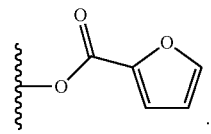

In one embodiment, in Formula (I), $R^2$ is a moiety selected from

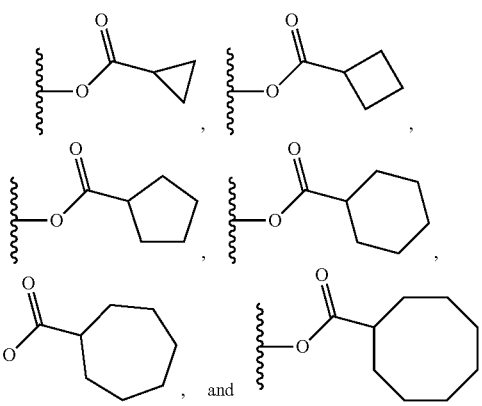

, and wherein the cycloalkyl portion of said moiety is unsubstituted or substituted with from 1 to 4 substituents independently selected from alkyl, halogen, haloalkyl, hydroxyl, —N($R^7$)$_2$, and CN.

In one embodiment, in Formula (I), $R^2$ is

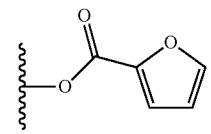 [SMILES: *OC(=O)c1ccco1]

and $R^3$ is H.

In one embodiment, in Formula (I), $R^2$ is

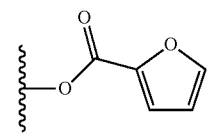 [SMILES: *OC(=O)c1ccco1]

and $R^3$ is methyl.

In one embodiment, in Formula (I), $R^3$ is selected from hydrogen, hydroxyl, and methyl.

In one embodiment, in Formula (I), $R^3$ is selected from hydrogen and methyl.

In one embodiment, in Formula (I), $R^3$ is hydrogen.

In one embodiment, in Formula (I), $R^3$ is hydroxy.

In one embodiment, in Formula (I), $R^3$ is alkyl.

In one embodiment, in Formula (I), $R^3$ is methyl.

In one embodiment, in Formula (I), $R^3$ is ethyl.

In one embodiment, in Formula (I), $R^3$ is straight or branched propyl.

In one embodiment, in Formula (I), $R^2$ is —$OR^8$, wherein $R^8$ is hydrogen, and $R^3$ is methyl.

In one embodiment, in Formula (I), $R^2$ is —$OR^8$, wherein $R^8$ is hydrogen, and $R^3$ is hydrogen.

In one embodiment, in Formula (I), $R^2$ and $R^3$ are taken together form a moiety of formula 2:

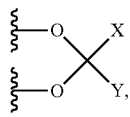

2 wherein X and Y are each alkyl. In one such embodiment, X and Y are each methyl. In another such embodiment, X and Y are each ethyl. In another such embodiment, X is methyl and Y is ethyl. In another such embodiment, X is hydrogen and Y is selected from alkyl, haloalkyl, and cycloalkyl. In another such embodiment, X is hydrogen and Y is selected from methyl. In another such embodiment, X is hydrogen and Y is selected from ethyl. In another such embodiment, X is hydrogen and Y is selected from straight or branched propyl. In another such embodiment, X is hydrogen and Y is selected from straight or branched butyl. In another such embodiment, X is hydrogen and Y is selected from haloalkyl. In another such embodiment, X is hydrogen and Y is selected from cyclopropyl.

In one embodiment, in Formula (I), $R^2$ and $R^3$ are taken together form a moiety of formula:

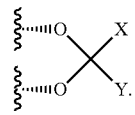

In one embodiment, in Formula (I), $R^2$ and $R^3$ are taken together form a moiety of formula:

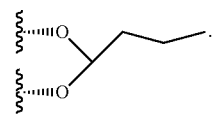

In one embodiment, in Formula (I), $R^2$ and $R^3$ are taken together form a moiety of formula:

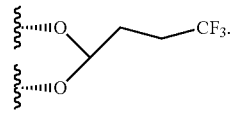

In one embodiment, in Formula (I), $R^2$ and $R^3$ are taken together form a moiety selected from:

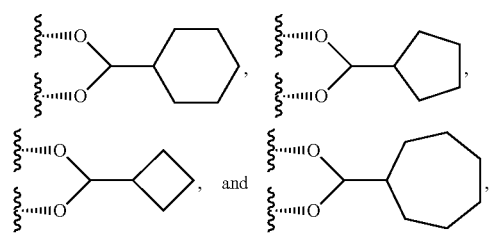

wherein said cycloalkyl ring is unsubstituted or substituted with from 1 to 4 substituents independently selected from alkyl, halogen, haloalkyl, hydroxyl, —$N(R^7)_2$, and CN.

In one embodiment, in Formula (I), $R^2$ and $R^3$ are taken together form a moiety of the formula:

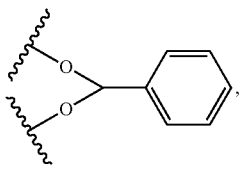

wherein the phenyl group of said moiety is unsubstituted or substituted with from 1 to 4 substituents independently selected from alkyl, halogen, haloalkyl, hydroxyl, —$N(R^7)_2$, and CN.

In one embodiment, in Formula (I), $R^2$ and $R^3$ are taken together form a moiety of formula 3:

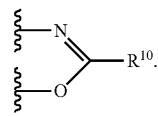

3

In one such embodiment, $R^{10}$ is H. In another such embodiment, $R^{10}$ is alkyl. In another such embodiment, $R^{10}$ is methyl. In another such embodiment, $R^{10}$ is ethyl. In another such embodiment, $R^{10}$ is straight or branched propyl.

In another embodiment, in Formula (I), $R^4$ is hydrogen.

In another embodiment, in Formula (I), $R^4$ is halogen.

In another embodiment, in Formula (I), $R^4$ is fluoro.

In another embodiment, in Formula (I), $R^4$ is chloro.

In another embodiment, in Formula (I), $R^5$ is selected from hydrogen and alkyl.

In another embodiment, in Formula (I), $R^5$ is methyl.

In another embodiment, in Formula (I), $R^5$ is ethyl.

In another embodiment, in Formula (I), $R^5$ is straight or branched propyl.

In another embodiment, in Formula (I), $R^5$ is halogen.

In another embodiment, in Formula (I), $R^5$ is fluoro.

In another embodiment, in Formula (I), $R^5$ is chloro.

In another embodiment, in Formula (I), $R^4$ is hydrogen and $R^5$ is hydrogen.

In another embodiment, in Formula (I), $R^4$ is hydrogen and $R^5$ is halogen.

In another embodiment, in Formula (I), $R^4$ is hydrogen and $R^5$ is fluoro.

In another embodiment, in Formula (I), $R^4$ is hydrogen and $R^5$ is chloro.

In another embodiment, in Formula (I), $R^4$ is hydrogen and $R^5$ is alkyl.

In another embodiment, in Formula (I), $R^4$ is hydrogen and $R^5$ is methyl.

In another embodiment, in Formula (I), $R^4$ is hydrogen and $R^5$ is ethyl.

In another embodiment, in Formula (I), $R^4$ is hydrogen and $R^5$ is straight or branched propyl.

In another embodiment, in Formula (I), $R^4$ is halogen and $R^5$ is hydrogen.

In another embodiment, in Formula (I), $R^4$ is halogen and $R^5$ is halogen.

In another embodiment, in Formula (I), $R^4$ is fluoro and $R^5$ is fluoro.

In another embodiment, in Formula (I), $R^4$ is chloro and $R^5$ is chloro.

In another embodiment, in Formula (I), $R^4$ is halogen and $R^5$ is alkyl.

In another embodiment, in Formula (I), $R^4$ is halogen and $R^5$ is methyl.

In another embodiment, in Formula (I), $R^4$ is halogen and $R^5$ is ethyl.

In another embodiment, in Formula (I), $R^4$ is halogen and $R^5$ is straight or branched propyl.

In another embodiment, in Formula (I), $R^4$ is fluoro or chloro and $R^5$ is methyl.

In another embodiment, in Formula (I), z is a double bond and $R^6$ is H or halogen.

In another embodiment, in Formula (I), z is a single bond and $R^6$ is H.

In another embodiment, in Formula (I), $R^6$ is fluoro or chloro.

In one embodiment, in Formula (I), $R^2$ is —$OR^8$, wherein $R^8$ is hydrogen, $R^3$ is hydrogen or methyl, $R^4$ and $R^5$ are both hydrogen, L is —$NR^{11}$—, and z is a double bond.

In one embodiment, the present invention provides a pharmaceutical composition formulated for oral administration, which composition comprises a compound of Formula (I), wherein $R^2$ is —$OR^8$, wherein $R^8$ is hydrogen, $R^3$ is hydrogen or methyl, $R^4$ and $R^5$ are both hydrogen, L is —$NR^{11}$—, and z is a double bond.

In one embodiment, in Formula (I), $R^1$ is selected from benzofused 5- or 6-membered heteroaryl, benzofused 5- or 6-membered heterocycloalkenyl, heteroarylfused 5- or 6-membered heteroaryl, and heteroarylfused 5- or 6-membered heterocycloalkenyl, $R^2$ is —$OR^8$, wherein $R^8$ is hydrogen, $R^3$ is hydrogen or methyl, $R^4$ and $R^5$ are both hydrogen, L is —$NR^{11}$—, and z is a double bond.

In one embodiment, the present invention provides a pharmaceutical composition formulated for oral administration, which composition comprises a compound of Formula (I), wherein $R^1$ is selected from benzofused 5- or 6-membered heteroaryl, benzofused 5- or 6-membered heterocycloalkenyl, heteroarylfused 5- or 6-membered heteroaryl, and heteroarylfused 5- or 6-membered heterocycloalkenyl, $R^2$ is —$OR^8$, wherein $R^8$ is hydrogen, $R^3$ is hydrogen or methyl, $R^4$ and $R^5$ are both hydrogen, L is —$NR^{11}$—, and z is a double bond.

In one embodiment, the present invention provides a pharmaceutical composition formulated for inhaled administration, which composition comprises a compound of Formula (I), wherein $R^4$, $R^6$, and $R^8$ are hydrogen, $R^2$ and $R^3$ are joined to form a moiety having the formula

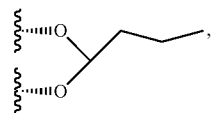

L is —$CH_2O$—, and z is a double bond. In one such embodiment, $R^1$ is benzofused aryl.

In one embodiment, in Formula (I), is a compound, or a pharmaceutically acceptable salt, solvate, ester, tautomer, or isomer thereof, said compound having a general structure shown in Formula (Ia):

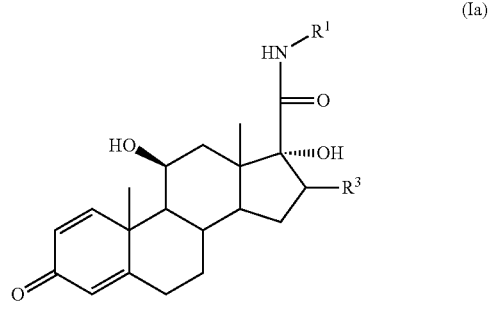

wherein each of $R^1$ and $R^3$ is selected independently and wherein:

$R^1$ is selected from aryl, arylalkyl-, heteroarylfused aryl, heteroarylfused arylalkyl-, heteroaryl, heteroarylalkyl-, benzofused heteroaryl-, benzofused heteroarylalkyl-, heteroarylfused heteroaryl-, and heteroarylfused heteroarylalkyl-, wherein each said $R^1$ group is unsubstituted or optionally substituted with 1 to 2 substituents, which may be the same or different, each independently selected from halogen, hydroxy, —CN, alkyl, haloalkyl, alkoxy, aryl, —O-aryl and heteroaryl; and $R^3$ is selected from hydrogen or methyl, and with the proviso that when $R^3$ is each H, then $R^1$ is not benzyl.

In one embodiment, in Formula (Ia), is a compound, or a pharmaceutically acceptable salt, solvate, ester, tautomer, or isomer thereof, said compound having a general structure shown in Formula (Ia.1):

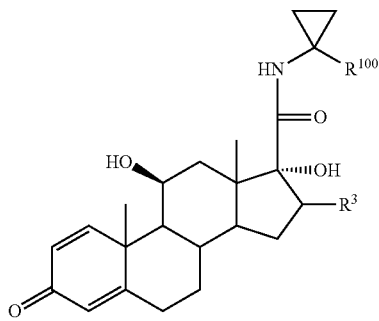

(Ia.1)

wherein each of $R^{100}$ and $R^3$ is selected independently and wherein:
$R^{100}$ is selected from aryl, heteroarylfused aryl, heteroaryl, benzofused heteroaryl-, and heteroarylfused heteroaryl-,
  wherein each said $R^{100}$ group is unsubstituted or optionally substituted with 1 to 2 substituents, which may be the same or different, each independently selected from halogen, hydroxy, —CN, alkyl, haloalkyl, alkoxy, aryl, —O-aryl and heteroaryl; and
$R^3$ is selected from hydrogen or methyl.

In one embodiment, in Formula (Ia.1), is a compound, or a pharmaceutically acceptable salt, solvate, ester, tautomer, or isomer thereof, having the general structure:

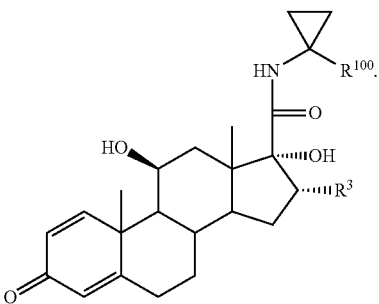

(I.a.1)

In one embodiment, in Formula (Ia), is a compound, or a pharmaceutically acceptable salt, solvate, ester, tautomer, or isomer thereof, said compound having a general structure shown in Formula (Ia.2):

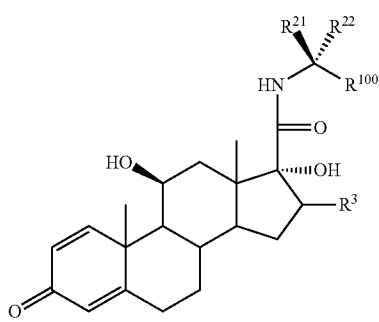

(Ia.2)

wherein each of $R^{100}$, $R^3$, $R^{21}$, and $R^{22}$ is selected independently and wherein:
$R^{100}$ is selected from aryl, heteroarylfused aryl, heteroaryl, benzofused heteroaryl-, and heteroarylfused heteroaryl-,
  wherein each said $R^{100}$ group is unsubstituted or optionally substituted with 1 to 2 substituents, which may be the same or different, each independently selected from halogen, hydroxy, —CN, alkyl, haloalkyl, alkoxy, aryl, —O-aryl and heteroaryl; one of $R^{21}$ and $R^{22}$ is hydrogen and the other is selected from $C_1$-$C_2$ alkyl, $C_1$-$C_2$ haloalkyl, fluorine, and hydroxyl; and
$R^3$ is selected from hydrogen or methyl.

In one embodiment, in Formula (I.a.2), one of $R^{21}$ and $R^{22}$ is hydrogen and the other is selected from methyl and —CF$_3$.

In one embodiment, in Formula (Ia.2), is a compound, or a pharmaceutically acceptable salt, solvate, ester, tautomer, or isomer thereof, having the general structure:

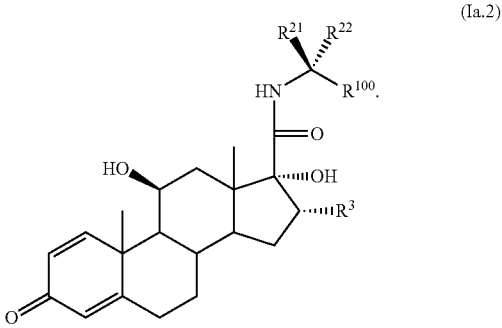

(Ia.2)

In one embodiment, in Formula (Ia), is a compound, or a pharmaceutically acceptable salt, solvate, ester, tautomer, or isomer thereof, said compound having a general structure shown in Formula (Ia.3):

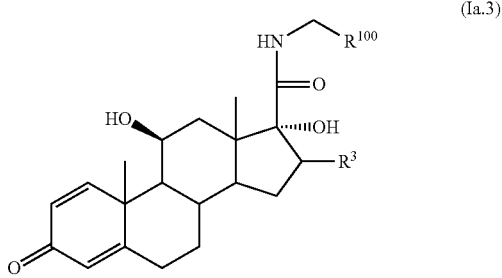

(Ia.3)

wherein each of $R^{100}$ and $R^3$ is selected independently and wherein:
$R^{100}$ is selected from aryl, heteroarylfused aryl, heteroaryl, benzofused heteroaryl-, and heteroarylfused heteroaryl-,
  wherein each said $R^{100}$ group is unsubstituted or optionally substituted with 1 to 2 substituents, which may be the same or different, each independently selected from halogen, hydroxy, —CN, alkyl, haloalkyl, alkoxy, aryl, —O-aryl and heteroaryl; and
$R^3$ is selected from hydrogen or methyl.

In one embodiment, in Formula (Ia.3), is a compound, or a pharmaceutically acceptable salt, solvate, ester, tautomer, or isomer thereof, having the general structure:

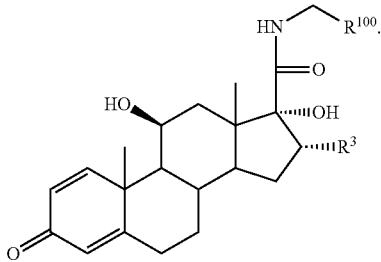

In one embodiment, in Formula (I), is a compound, or a pharmaceutically acceptable salt, solvate, ester, tautomer, or isomer thereof, said compound having a general structure shown in Formula (Ib):

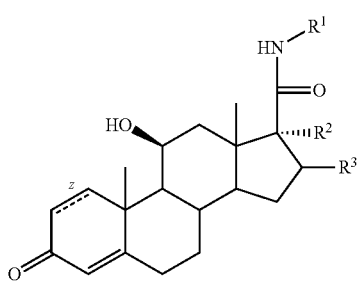

wherein each of $R^1$, $R^2$, $R^3$, and z is selected independently and wherein:

$R^1$ is selected from aryl, arylalkyl-, heteroarylfused aryl, heteroarylfused arylalkyl-, heteroaryl, heteroarylalkyl-, benzofused heteroaryl-, benzofused heteroarylalkyl-, heteroarylfused heteroaryl-, heteroarylfused heteroarylalkyl-, wherein each said $R^1$ group is unsubstituted or optionally substituted with 1 to 2 substituents, which may be the same or different, each independently selected from halogen, hydroxy, —CN, alkyl, haloalkyl, alkoxy, aryl, —O-aryl and heteroaryl;

$R^2$ is —OC(O)$R^{11}$;

$R^3$ is selected from hydrogen and methyl;

$R^{11}$ is selected from aryl and heteroaryl each unsubstituted or optionally substituted with from 1 to 2 substituents independently selected from the group consisting of alkyl, halogen, haloalkyl, hydroxy and —CN; and z (the dotted line) represents a single or double bond.

In one embodiment, in Formula (Ib), is a compound, or a pharmaceutically acceptable salt, solvate, ester, tautomer, or isomer thereof, said compound having a general structure shown in Formula (Ib.1):

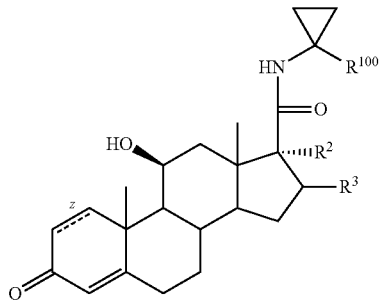

wherein each of $R^{100}$, $R^2$, $R^3$, and z is selected independently and wherein:

$R^{100}$ is selected from aryl, heteroarylfused aryl, heteroaryl, benzofused heteroaryl-, and heteroarylfused heteroaryl-, wherein each said $R^1$ group is unsubstituted or optionally substituted with 1 to 2 substituents, which may be the same or different, each independently selected from halogen, hydroxy, —CN, alkyl, haloalkyl, alkoxy, aryl, —O-aryl and heteroaryl;

$R^2$ is —OC(O)$R^{11}$;

$R^3$ is selected from hydrogen and methyl;

$R^{11}$ is selected from aryl and heteroaryl each unsubstituted or optionally substituted with from 1 to 2 substituents independently selected from the group consisting of alkyl, halogen, haloalkyl, hydroxy and —CN; and z (the dotted line) represents a single or double bond.

In one embodiment, in Formula (Ib.1), is a compound, or a pharmaceutically acceptable salt, solvate, ester, tautomer, or isomer thereof, said compound having a general structure:

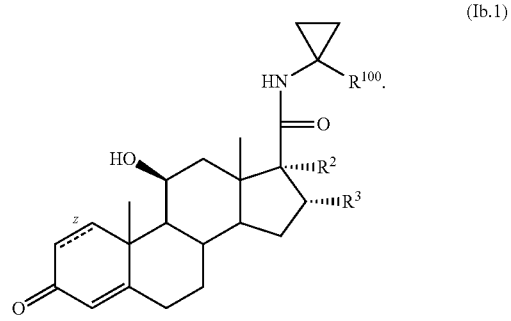

In one embodiment, in Formula (Ib), is a compound, or a pharmaceutically acceptable salt, solvate, ester, tautomer, or isomer thereof, said compound having a general structure shown in Formula (Ib.2):

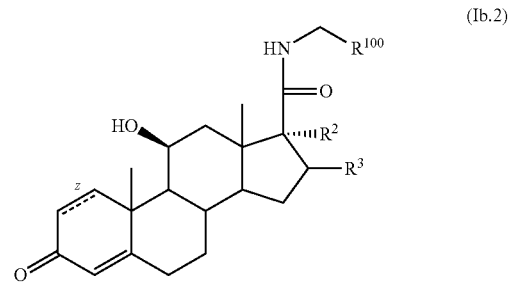

wherein each of $R^{100}$, $R^2$, $R^3$, and z is selected independently and wherein:

$R^{100}$ is selected from aryl, heteroarylfused aryl, heteroaryl, benzofused heteroaryl-, and heteroarylfused heteroaryl-, wherein each said $R^1$ group is unsubstituted or optionally substituted with 1 to 2 substituents, which may be the same or different, each independently selected from halogen, hydroxy, —CN, alkyl, haloalkyl, alkoxy, aryl, —O-aryl and heteroaryl;

$R^2$ is —OC(O)$R^{11}$;

$R^3$ is selected from hydrogen and methyl;

$R^{11}$ is selected from aryl and heteroaryl each unsubstituted or optionally substituted with from 1 to 2 substituents independently selected from the group consisting of alkyl, halogen, haloalkyl, hydroxy and —CN; and z (the dotted line) represents a single or double bond.

In one embodiment, in Formula (Ib.2), is a compound, or a pharmaceutically acceptable salt, solvate, ester, tautomer, or isomer thereof, said compound having a general structure:

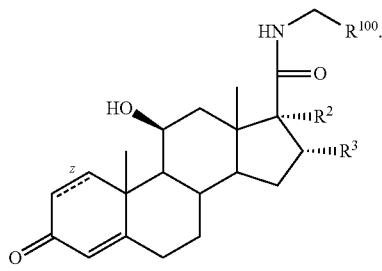

(Ib.2)

In one embodiment, in Formula (Ib), is a compound, or a pharmaceutically acceptable salt, solvate, ester, tautomer, or isomer thereof, said compound having a general structure shown in Formula (Ib.3):

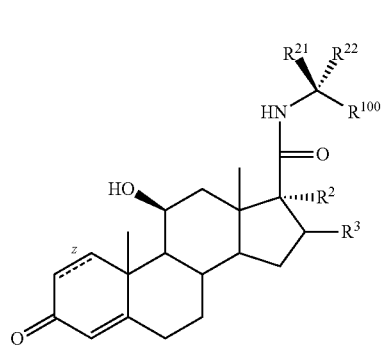

(Ib.3)

wherein each of $R^{100}$, $R^{22}$, $R^{23}$, $R^2$, $R^3$, and z is selected independently and wherein:

$R^{100}$ is selected from aryl, heteroarylfused aryl, heteroaryl, benzofused heteroaryl-, and heteroarylfused heteroaryl-, wherein each said $R^1$ group is unsubstituted or optionally substituted with 1 to 2 substituents, which may be the same or different, each independently selected from halogen, hydroxy, —CN, alkyl, haloalkyl, alkoxy, aryl, —O-aryl and heteroaryl;

one of $R^{21}$ and $R^{22}$ is hydrogen and the other is selected from $C_1$-$C_2$ alkyl, $C_4$-$C_2$ haloalkyl, fluorine, and hydroxyl;

$R^2$ is —OC(O)$R^{11}$;

$R^3$ is selected from hydrogen and methyl;

$R^{11}$ is selected from aryl and heteroaryl each unsubstituted or optionally substituted with from 1 to 2 substituents independently selected from the group consisting of alkyl, halogen, haloalkyl, hydroxy and —CN; and z (the dotted line) represents a single or double bond.

In one embodiment, in Formula (Ib.3), one of $R^{21}$ and $R^{22}$ is hydrogen and the other is selected from methyl and —CF$_3$.

In one embodiment, in Formula (Ib.3), is a compound, or a pharmaceutically acceptable salt, solvate, ester, tautomer, or isomer thereof, said compound having a general structure:

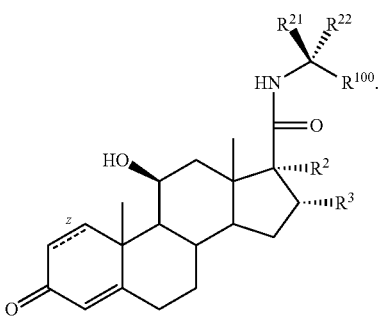

(Ib.3)

In one embodiment, in Formula (I), is a compound, or a pharmaceutically acceptable salt, solvate, ester, tautomer, or isomer thereof, said compound having a general structure shown in Formula (Ic):

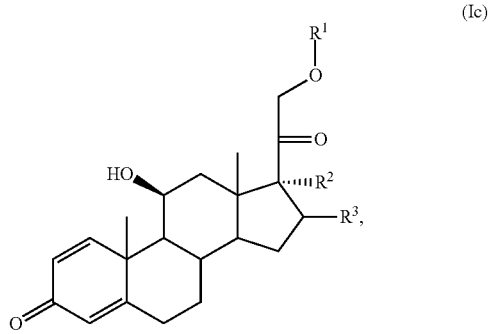

(Ic)

wherein each of $R^1$, $R^2$, and $R^3$ is selected independently and wherein:

$R^1$ is selected from heteroarylfused aryl-, heteroaryl, benzofused heteroaryl-, and heteroarylfused heteroaryl-, wherein each said $R^1$ group is unsubstituted or optionally substituted with 1 to 2 substituents, which may be the same or different, each substituent being independently selected from halogen, hydroxy, —CN, alkyl, haloalkyl, alkoxy, aryl, —O-aryl and heteroaryl;

$R^2$ is —OC(O)$R^{11}$;

$R^3$ is selected from hydrogen and methyl; and $R^{11}$ is selected from aryl, heteroaryl and cycloalkyl each unsubstituted or optionally substituted with from 1 to 2 substituents independently selected from the group consisting of alkyl, halogen, haloalkyl, hydroxy and —CN.

In one embodiment, in Formula (I), is a compound, or a pharmaceutically acceptable salt, solvate, ester, tautomer, or isomer thereof, said compound having a general structure shown in Formula (Id):

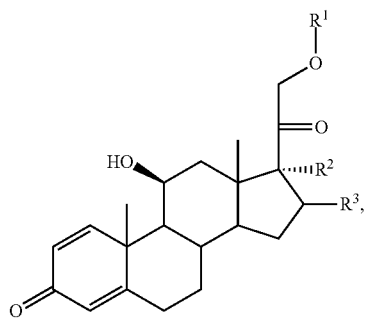

wherein each of $R^1$, $R^2$, and $R^3$ is selected independently and wherein:

$R^1$ is selected from heteroarylfused aryl-, heteroaryl, benzofused heteroaryl-, and heteroarylfused heteroaryl-,
  wherein each said $R^1$ group is unsubstituted or optionally substituted with 1 to 2 substituents, which may be the same or different, each substituent being independently selected from halogen, hydroxy, —CN, alkyl, haloalkyl, alkoxy, aryl, —O-aryl and heteroaryl;

$R^2$ and $R^3$ taken together form a moiety of formula 2:

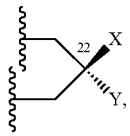

wherein X and Y are each methyl; and
$R^{11}$ is selected from aryl, heteroaryl and cycloalkyl each unsubstituted or optionally substituted with from 1 to 2 substituents independently selected from the group consisting of alkyl, halogen, haloalkyl, hydroxy and In one embodiment, in Formula (I), is a compound, or a pharmaceutically acceptable salt, solvate, ester, tautomer, or isomer thereof, said compound having a general structure shown in Formula (Ie):

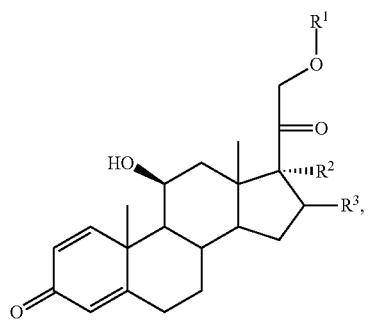

wherein each of $R^1$, $R^2$, and $R^3$ is selected independently and wherein:

$R^1$ is selected from heteroarylfused aryl-, heteroaryl, benzofused heteroaryl-, and heteroarylfused heteroaryl-,
  wherein each said $R^1$ group is unsubstituted or optionally substituted with 1 to 2 substituents, which may be the same or different, each substituent being independently selected from halogen, hydroxy, —CN, alkyl, haloalkyl, alkoxy, aryl, —O-aryl and heteroaryl;

$R^2$ and $R^3$ taken together form a moiety of formula 2:

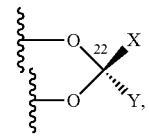

wherein X is hydrogen and Y is —CH$_2$CH$_2$CH$_3$; and
$R^{11}$ is selected from aryl, heteroaryl and cycloalkyl each unsubstituted or optionally substituted with from 1 to 2 substituents independently selected from the group consisting of alkyl, halogen, haloalkyl, hydroxy and —CN.

In one such embodiment, in Formula (Ie), the absolute stereoconfiguration of C22 in formula 2 is R.

In one embodiment is an 11-keto analog of compounds of Formula (I), or a pharmaceutically acceptable salt, solvate, ester, tautomer, or isomer thereof, said 11-keto analog having the general formula:

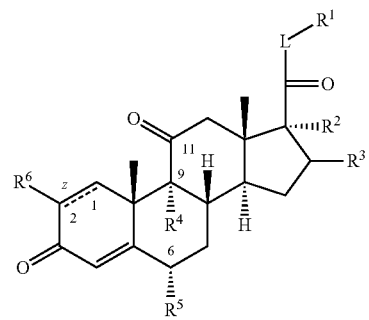

wherein L, $R^1$, $R^2$, $R^3$, $R^4$, $R^5$, $R^6$, and z are selected independently of each other and as defined in Formula (I) or any of the various embodiments of Formula (I), Formula (Ia), Formula (Ia.1), Formula (Ia.2), Formula (Ia.3), Formula (Ib), Formula (Ib.1), Formula (Ib.2), Formula (Ib.3), Formula (Ic), Formula (Id), and/or Formula (Ie), described herein.

In one embodiment, the present invention provides a compound, or a pharmaceutically acceptable salt, solvate, ester, prodrug, or isomer of said compound, having the general structure shown in Formula (II) as described above.

In one embodiment, in Formula (II), is a compound having the structural formula:

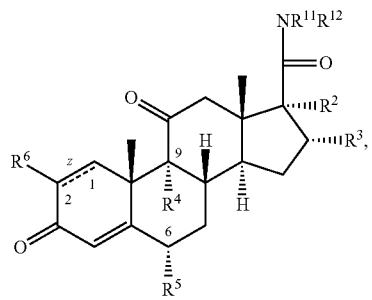

or a pharmaceutically acceptable salt, solvate, ester, prodrug, tautomer, or isomer thereof, wherein $R^{11}$, $R^{12}$, $R^2$, $R^3$, $R^4$, $R^5$, $R^6$, and z are selected independently and as defined in Formula (II).

In one embodiment, in Formula (II), $R^{11}$ and $R^{12}$ are taken together with the nitrogen to which they are shown attached to form a 5- to 6-membered heterocycloalkyl ring, a 5- to 6-membered heterocycloalkenyl ring, a 5- to 6-membered benzofused heterocycloalkyl ring, or a 5- to 6-membered benzofused heterocycloalkenyl ring, wherein each said hetero ring contains, in addition to the nitrogen of —$NR^{11}R^{12}$, from 0 to 3 ring heteroatoms each independently selected from N, O, and S and the oxides thereof, wherein each said rings is unsubstituted or substituted with from 1 to 4 substituents, which may be the same or different, each independently selected from halogen, hydroxy, —CN, oxo, oxide, alkyl, haloalkyl, -alkyl-CN, alkoxy, aryl, halo-substituted aryl, —O-aryl, —O-alkyl-aryl, heteroaryl, arylalkyl-, arylalkoxy, haloalkoxy, —$N(R^7)_2$, -alkyl$N(R^7)_2$, —$NC(O)R^7$, —$CO_2R^7$, —$SO_2R^7$, and —$SO_2N(R^7)_2$;

Non-limiting examples of rings represented by —$NR^{11}R^{12}$ include:

In one embodiment, in Formula (II), $R^2$ is selected from —OH and —$OC(O)R^9$.

In one embodiment, in Formula (II), $R^9$ is unsubstituted.

In one embodiment, in Formula (II), $R^9$ is substituted with from 1 to 3 substituents.

In one embodiment, in Formula (II), $R^9$ is substituted with from 1 to 2 substituents.

In one embodiment, in Formula (II), $R^9$ is substituted with 1 substituent.

In one embodiment, in Formula (II), $R^9$ is substituted with from 1 to 2 substituents, which may be the same or different, each independently selected from alkyl, halogen, and haloalkyl.

In one embodiment, in Formula (II), $R^9$ is unsubstituted or substituted heterocycloalkyl.

In one embodiment, in Formula (II), $R^9$ is unsubstituted or substituted heterocycloalkenyl.

In one embodiment, in Formula (II), $R^9$ is unsubstituted or substituted heteroaryl.

In one embodiment, in Formula (II), $R^2$ is wherein J is selected from O, S, and N, or the oxides thereof.

In one embodiment, in Formula (II), $R^2$ is

In one embodiment, in Formula (II), $R^2$ is a moiety selected from wherein the cycloalkyl portion of said moiety is unsubstituted or substituted with from 1 to 4 substituents independently selected from alkyl, halogen, haloalkyl, hydroxyl, —$N(R^7)_2$, and CN.

In one embodiment, in Formula (II), $R^2$ is and $R^3$ is H.

In one embodiment, in Formula (II), $R^2$ is and $R^3$ is methyl.

In one embodiment, in Formula (II), $R^3$ is hydrogen.

In one embodiment, in Formula (II), $R^3$ is hydroxy.

In one embodiment, in Formula (II), $R^3$ is alkyl.
In one embodiment, in Formula (II), $R^3$ is methyl.
In one embodiment, in Formula (II), $R^3$ is ethyl.
In one embodiment, in Formula (II), $R^3$ is straight or branched propyl.
In one embodiment, in Formula (II), $R^2$—$OR^8$, wherein $R^8$ is hydrogen, and $R^3$ is methyl.
In one embodiment, in Formula (II), $R^2$ is —$OR^B$, wherein $R^8$ is hydrogen, and $R^3$ is hydrogen.
In one embodiment, in Formula (II), $R^2$ and $R^3$ are taken together form a moiety of formula 2:

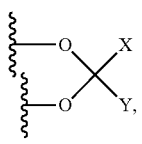

2 wherein X and Y are each alkyl. In one such embodiment, X and Y are each methyl. In another such embodiment, X and Y are each ethyl. In another such embodiment, X is methyl and Y is ethyl. In another such embodiment, X is hydrogen and Y is selected from alkyl, haloalkyl, and cycloalkyl. In another such embodiment, X is hydrogen and Y is selected from methyl. In another such embodiment, X is hydrogen and Y is selected from ethyl. In another such embodiment, X is hydrogen and Y is selected from straight or branched propyl. In another such embodiment, X is hydrogen and Y is selected from straight or branched butyl. In another such embodiment, X is hydrogen and Y is selected from haloalkyl. In another such embodiment, X is hydrogen and Y is selected from cyclopropyl.

In one embodiment, in Formula (II), $R^2$ and $R^3$ are taken together form a moiety of formula:

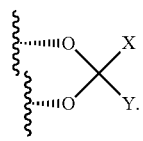

In one embodiment, in Formula (II), $R^2$ and $R^3$ are taken together form a moiety of formula:

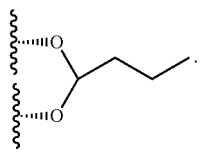

In one embodiment, in Formula (II), $R^2$ and $R^3$ are taken together form a moiety of formula:

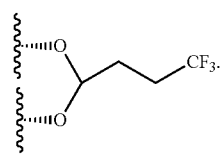

In one embodiment, in Formula (II), $R^2$ and $R^3$ are taken together form a moiety selected from:

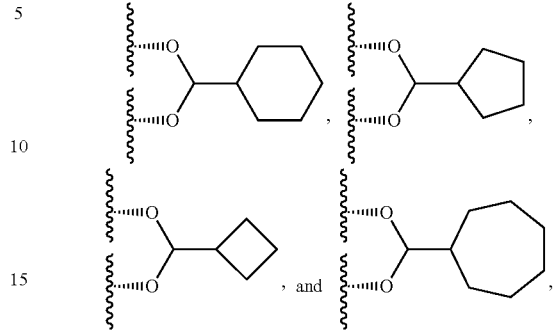

wherein said cycloalkyl ring is unsubstituted or substituted with from 1 to 4 substituents independently selected from alkyl, halogen, haloalkyl, hydroxyl, —$N(R^7)_2$, and CN.

In one embodiment, in Formula (II), $R^2$ and $R^3$ are taken together form a moiety of the formula:

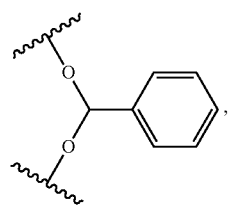 [SMILES: *OC(O*)c1ccccc1]

wherein the phenyl group of said moiety is unsubstituted or substituted with from 1 to 4 substituents independently selected from alkyl, halogen, haloalkyl, hydroxyl, —$N(R^7)_2$, and CN.

In one embodiment, in Formula (II), $R^2$ and $R^3$ are taken together form a moiety of formula 3:

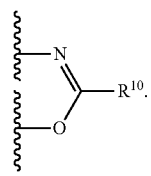

3

In one such embodiment, $R^{10}$ is H. In another such embodiment, $R^{10}$ is alkyl. In another such embodiment, $R^{10}$ is methyl. In another such embodiment, $R^{10}$ is ethyl. In another such embodiment, $R^{10}$ is straight or branched propyl.

In another embodiment, in Formula (II), $R^4$ is hydrogen.
In another embodiment, in Formula (II), $R^4$ is halogen.
In another embodiment, in Formula (II), $R^4$ is fluoro.
In another embodiment, in Formula (II), $R^4$ is chloro.
In another embodiment, in Formula (II), $R^5$ is selected from hydrogen and alkyl.
In another embodiment, in Formula (II), $R^5$ is methyl.
In another embodiment, in Formula (II), $R^5$ is ethyl.
In another embodiment, in Formula (II), $R^5$ is straight or branched propyl.
In another embodiment, in Formula (II), $R^5$ is halogen.
In another embodiment, in Formula (II), $R^5$ is fluoro.

In another embodiment, in Formula (II), $R^5$ is chloro.

In another embodiment, in Formula (II), $R^4$ and $R^5$ are hydrogen.

In another embodiment, in Formula (II), $R^4$ is hydrogen and $R^5$ is hydrogen.

In another embodiment, in Formula (II), $R^4$ is hydrogen and $R^5$ is halogen.

In another embodiment, in Formula (II), $R^4$ is hydrogen and $R^5$ is fluoro.

In another embodiment, in Formula (II), $R^4$ is hydrogen and $R^5$ is chloro.

In another embodiment, in Formula (II), $R^4$ is hydrogen and $R^5$ is alkyl.

In another embodiment, in Formula (II), $R^4$ is hydrogen and $R^5$ is methyl.

In another embodiment, in Formula (II), $R^4$ is hydrogen and $R^5$ is ethyl.

In another embodiment, in Formula (II), $R^4$ is hydrogen and $R^5$ is straight or branched propyl.

In another embodiment, in Formula (II), $R^4$ is halogen and $R^5$ is hydrogen.

In another embodiment, in Formula (II), $R^4$ is halogen and $R^5$ is halogen.

In another embodiment, in Formula (II), $R^4$ is fluoro and $R^5$ is fluoro.

In another embodiment, in Formula (II), $R^4$ is chloro and $R^5$ is chloro.

In another embodiment, in Formula (II), $R^4$ is halogen and $R^5$ is alkyl.

In another embodiment, in Formula (II), $R^4$ is halogen and $R^5$ is methyl.

In another embodiment, in Formula (II), $R^4$ is halogen and $R^5$ is ethyl.

In another embodiment, in Formula (II), $R^4$ is halogen and $R^6$ is straight or branched propyl.

In another embodiment, in Formula (II), $R^4$ is fluoro or chloro and $R^5$ is methyl.

In another embodiment, in Formula (II), z is a single bond and $R^6$ is H.

In another embodiment, in Formula (II), z is a double bond and $R^6$ is H or halogen.

In another embodiment, in Formula (II), $R^6$ is fluoro or chloro.

In one embodiment is an 1'-keto analog of compounds of Formula (II), or a pharmaceutically acceptable salt, solvate, ester, tautomer, or isomer thereof, said 11-keto analog having the general formula:

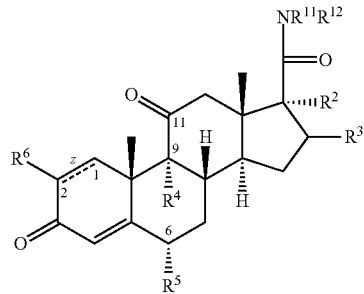

wherein $R^{11}$, $R^{12}$, $R^2$, $R^3$, $R^4$, $R^5$, $R^6$, and z are selected independently of each other and as defined in Formula (II) or any of the various embodiments of Formula (II) described herein.

In one embodiment, the present invention provides a compound, or a pharmaceutically acceptable salt, solvate, ester, prodrug, or isomer of said compound, having the general structure shown in Formula (III) as described above.

In one embodiment, in Formula (III), is a compound having the structural formula:

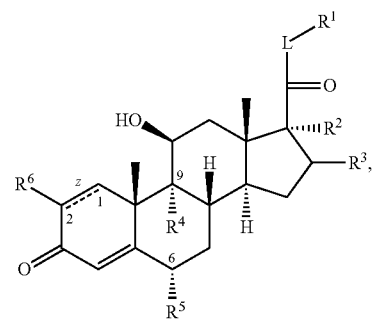

or a pharmaceutically acceptable salt, solvate, ester, prodrug, tautomer, or isomer thereof, wherein L, $R^1$, $R^2$, $R^3$, $R^4$, $R^5$, $R^6$, and z are selected independently of each other and are as defined in Formula (III).

In one embodiment, in Formula (III), $R^1$ is cycloalkyl which is unsubstituted.

In one embodiment, in Formula (III), $R^1$ is cycloalkyl which is substituted with from 1 to 5 groups, which may be the same or different, each independently selected from halogen, hydroxy, —CN, oxo, oxide, alkyl, haloalkyl, -alkyl-CN, alkoxy, spirocycloalkyl, aryl, halo-substituted aryl, —O-aryl, —O-alkyl-aryl, heteroaryl, arylalkyl-, arylalkoxy, haloalkoxy, —N($R^7$)$_2$, -alkylN($R^7$)$_2$, —NC(O)$R^7$, —CO$_2R^7$, —SO$_2R^7$, and —SO$_2$N($R^7$)$_2$;

Non-limiting examples of -L-$R^1$ in Formula (III) include:

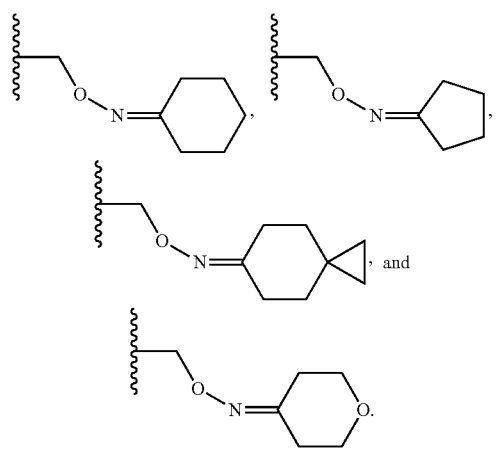

In one embodiment, in Formula (III), $R^2$ is selected from —OH and —OC(O)$R^9$.

In one embodiment, in Formula (III), $R^9$ is unsubstituted.

In one embodiment, in Formula (III), $R^9$ is substituted with from 1 to 3 substituents.

In one embodiment, in Formula (III), $R^9$ is substituted with from 1 to 2 substituents.

In one embodiment, in Formula (III), $R^9$ is substituted with 1 substituent.

In one embodiment, in Formula (III), $R^9$ is substituted with from 1 to 2 substituents, which may be the same or different, each independently selected from alkyl, halogen, and haloalkyl.

In one embodiment, in Formula (III), $R^9$ is unsubstituted or substituted heterocycloalkyl.

In one embodiment, in Formula (III), $R^9$ is unsubstituted or substituted heterocycloalkenyl.

In one embodiment, in Formula (III), $R^9$ is unsubstituted or substituted heteroaryl.

In one embodiment, in Formula (III), $R^2$ is

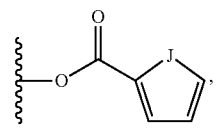

wherein J is selected from O, S, and N, or the oxides thereof.

In one embodiment, in Formula (III), $R^2$ is

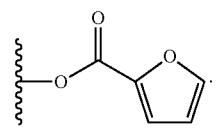 [SMILES: *OC(=O)c1ccco1 ; "."]

In one embodiment, in Formula (III), $R^2$ is a moiety selected from

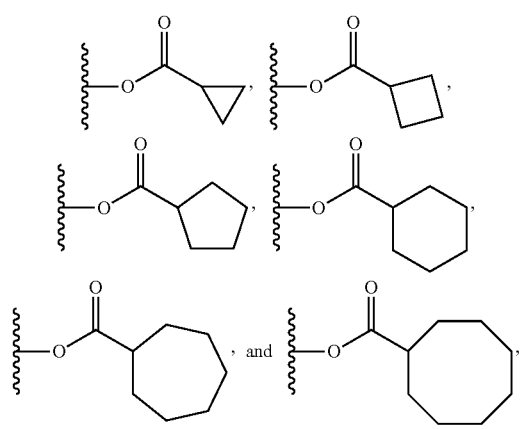

wherein the cycloalkyl portion of said moiety is unsubstituted or substituted with from 1 to 4 substituents independently selected from alkyl, halogen, haloalkyl, hydroxyl, —N($R^7$)$_2$, and CN.

In one embodiment, in Formula (III), $R^2$ is

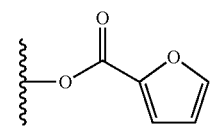

and $R^3$ is H.

In one embodiment, in Formula (III), $R^2$ is

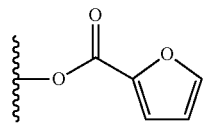 [SMILES: *OC(=O)c1ccco1]

and $R^3$ is methyl.

In one embodiment, in Formula (IV), $R^3$ is hydrogen.

In one embodiment, in Formula (III), $R^3$ is hydroxy.

In one embodiment, in Formula (III), $R^3$ is alkyl.

In one embodiment, in Formula (III), $R^3$ is methyl.

In one embodiment, in Formula (III), $R^3$ is ethyl.

In one embodiment, in Formula (III), $R^3$ is straight or branched propyl.

In one embodiment, in Formula (Ill), $R^2$—$OR^8$, wherein $R^8$ is hydrogen, and $R^3$ is methyl.

In one embodiment, in Formula (III), $R^2$ is —$OR^8$, wherein $R^8$ is hydrogen, and $R^3$ is hydrogen.

In one embodiment, in Formula (III), $R^2$ and $R^3$ are taken together form a moiety of formula 2:

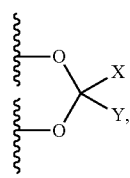

2 wherein X and Y are each alkyl. In one such embodiment, X and Y are each methyl. In another such embodiment, X and Y are each ethyl. In another such embodiment, X is methyl and Y is ethyl. In another such embodiment, X is hydrogen and Y is selected from alkyl, haloalkyl, and cycloalkyl. In another such embodiment, X is hydrogen and Y is selected from methyl. In another such embodiment, X is hydrogen and Y is selected from ethyl. In another such embodiment, X is hydrogen and Y is selected from straight or branched propyl. In another such embodiment, X is hydrogen and Y is selected from straight or branched butyl. In another such embodiment, X is hydrogen and Y is selected from haloalkyl. In another such embodiment, X is hydrogen and Y is selected from cyclopropyl.

In one embodiment, in Formula (III), $R^2$ and $R^3$ are taken together form a moiety of formula:

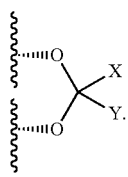

In one embodiment, in Formula (III), $R^2$ and $R^3$ are taken together form a moiety of formula:

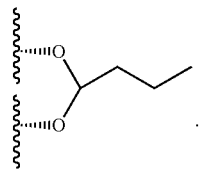

In one embodiment, in Formula (III), $R^2$ and $R^3$ are taken together form a moiety of formula:

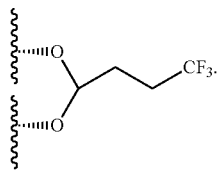

In one embodiment, in Formula (III), $R^2$ and $R^3$ are taken together form a moiety selected from:

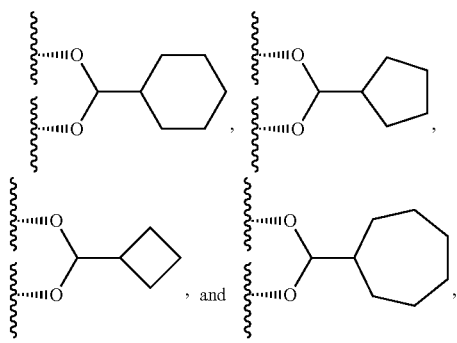

wherein said cycloalkyl ring is unsubstituted or substituted with from 1 to 4 substituents independently selected from alkyl, halogen, haloalkyl, hydroxyl, —N($R^7$)$_2$, and CN.

In one embodiment, in Formula (III), $R^2$ and $R^3$ are taken together form a moiety of the formula

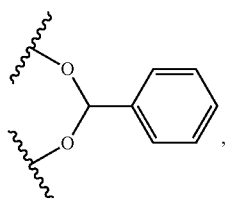 [SMILES: *OC(O*)c1ccccc1 ; ","]

wherein the phenyl group of said moiety is unsubstituted or substituted with from 1 to 4 substituents independently selected from alkyl, halogen, haloalkyl, hydroxyl, —N($R^7$)$_2$, and CN.

In one embodiment, in Formula (III), $R^2$ and $R^3$ are taken together form a moiety of formula 3:

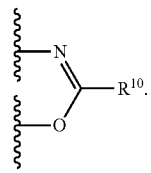

In one such embodiment, $R^{10}$ is H. In another such embodiment, $R^{10}$ is alkyl. In another such embodiment, $R^{10}$ is methyl. In another such embodiment, $R^{10}$ is ethyl. In another such embodiment, $R^{10}$ is straight or branched propyl.

In another embodiment, in Formula (III), $R^4$ is hydrogen.
In another embodiment, in Formula (III), $R^4$ is halogen.
In another embodiment, in Formula (III), $R^4$ is fluoro.
In another embodiment, in Formula (III), $R^4$ is chloro.
In another embodiment, in Formula (III), $R^5$ is selected from hydrogen and alkyl.
In another embodiment, in Formula (III), $R^5$ is methyl.
In another embodiment, in Formula (III), $R^5$ is ethyl.
In another embodiment, in Formula (III), $R^5$ is straight or branched propyl.
In another embodiment, in Formula (III), $R^5$ is halogen.
In another embodiment, in Formula (III), $R^5$ is fluoro.
In another embodiment, in Formula (III), $R^5$ is chloro.
In another embodiment, in Formula (III), $R^4$ and $R^5$ are hydrogen.
In another embodiment, in Formula (III), $R^4$ is hydrogen and $R^5$ is hydrogen.
In another embodiment, in Formula (III), $R^4$ is hydrogen and $R^5$ is halogen.
In another embodiment, in Formula (III), $R^4$ is hydrogen and $R^5$ is fluoro.
In another embodiment, in Formula (III), $R^4$ is hydrogen and $R^5$ is chloro.
In another embodiment, in Formula (III), $R^4$ is hydrogen and $R^5$ is alkyl.
In another embodiment, in Formula (III), $R^4$ is hydrogen and $R^5$ is methyl.
In another embodiment, in Formula (III), $R^4$ is hydrogen and $R^5$ is ethyl.
In another embodiment, in Formula (III), $R^4$ is hydrogen and $R^5$ is straight or branched propyl.
In another embodiment, in Formula (III), $R^4$ is halogen and $R^5$ is hydrogen.
In another embodiment, in Formula (III), $R^4$ is halogen and $R^5$ is halogen.
In another embodiment, in Formula (III), $R^4$ is fluoro and $R^5$ is fluoro.
In another embodiment, in Formula (III), $R^4$ is chloro and $R^5$ is chloro.
In another embodiment, in Formula (III), $R^4$ is halogen and $R^5$ is alkyl.
In another embodiment, in Formula (III), $R^4$ is halogen and $R^5$ is methyl.
In another embodiment, in Formula (III), $R^4$ is halogen and $R^5$ is ethyl.
In another embodiment, in Formula (III), $R^4$ is halogen and $R^5$ is straight or branched propyl.
In another embodiment, in Formula (III), $R^4$ is fluoro or chloro and $R^5$ is methyl.
In another embodiment, in Formula (III), z is a single bond and $R^6$ is H.
In another embodiment, in Formula (III), z is a double bond and $R^6$ is H or halogen.

In another embodiment, in Formula (III), $R^6$ is fluoro or chloro.

In one embodiment is an 11-keto analog of compounds of Formula (III), or a pharmaceutically acceptable salt, solvate, ester, tautomer, or isomer thereof, said 11-keto analog having the general formula:

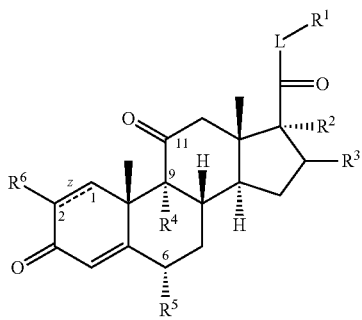

wherein L, $R^1$, $R^2$, $R^3$, $R^4$, $R^5$, $R^6$, and z are selected independently of each other and as defined in Formula (III) or any of the various embodiments of Formula (III) described herein.

In one embodiment, the present invention provides a compound, or a pharmaceutically acceptable salt, solvate, ester, prodrug, or isomer of said compound, having the general structure shown in Formula (IV) as described above.

In one embodiment, in Formula (IV), is a compound having the structural formula:

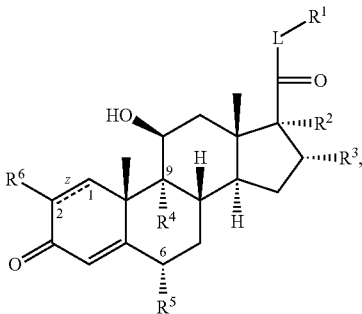

or a pharmaceutically acceptable salt, solvate, ester, prodrug, tautomer, or isomer thereof, wherein L, $R^1$, $R^2$, $R^3$, $R^4$, $R^5$, $R^6$, and z are selected independently and as defined in Formula (IV).

In one embodiment, in Formula (IV), $R^1$ is selected from optionally substituted aryl, optionally substituted heteroaryl, optionally substituted heterocycloalkenyl, optionally substituted benzofused heteroaryl, optionally substituted heteroarylfused heteroaryl, optionally substituted benzofused heterocycloalkenyl, and optionally substituted heteroarylfused heterocycloalkenyl.

In one embodiment, in Formula (IV), $R^1$ is selected from alkyl, phenyl, naphthyl, phenylalkyl-, naphthylalkyl-, 4- to 6-membered heteroarylfused phenyl, 4- to 6-membered heteroarylfused phenylalkyl-, 4- to 6-membered cycloalkylfused phenyl, 4- to 6-membered cycloalkylfused phenyl alkyl-, 4- to 6-membered heteroaryl, 4- to 6-membered heteroarylalkyl-, benzofused 4- to 6-membered heteroaryl, benzofused 4- to 6-membered heteroarylalkyl-, 4- to 6-membered heteroarylfused 4- to 6-membered heteroaryl, 4- to 6-membered heteroarylfused 4- to 6-membered heteroarylalkyl-, 3- to 7-membered cycloalkyl, 3- to 7-membered cycloalkenyl, 3- to 7-membered cycloalkylalkyl-, 3- to 7-membered cycloalkenylalkyl-, 4- to 6-membered heterocycloalkyl, 4- to 6-membered heterocycloalkenyl, 4- to 6-membered heterocycloalkylalkyl-, 4- to 6-membered heterocycloalkenylalkyl-, benzofused 4- to 6-membered heterocycloalkyl, benzofused 4- to 6-membered heterocycloalkenyl, benzofused 4- to 6-membered heterocycloalkylalkyl-, benzofused 4- to 6-membered heterocycloalkenylalkyl-, 4- to 6-membered heteroarylfused 4- to 6-membered heterocycloalkenyl, and 4- to 6-membered heteroarylfused 4- to 6-membered heterocycloalkenylalkyl-, wherein each said hetero ring-containing moiety of $R^1$ and each said heterofused containing moiety of $R^1$ independently contains 1, 2, or 3 ring heteroatoms independently selected from any combination of N, O, and S, wherein each said $R^1$ group is unsubstituted or optionally substituted with from 1 to 5 substituents, which may be the same or different, each independently selected from halogen, hydroxy, —CN, oxo, oxide, alkyl, haloalkyl, haloalkoxy-, hydroxyalkyl-, heteroalkyl, cyanoalkyl-, alkoxy, optionally substituted aryl, optionally substituted —O-aryl, optionally substituted —O-alkyl-aryl, optionally substituted heteroaryl, optionally substituted arylalkyl-, optionally substituted arylalkoxy, —N($R^7$)$_2$, -alkylN($R^7$)$_2$, —NC(O)$R^7$, —CO$_2R^7$, —SO$_2R^7$, and —SO$_2$N($R^7$)$_2$, wherein said optional substituents are present from 1 to 4 times and may be the same or different, each independently selected from alkyl, halogen, haloalkyl, hydroxyl, —CN, and —N($R^{11}$)$_2$;

and wherein the benzo portion of each said benzofused $R^1$ group is optionally further fused to another ring selected from heteroaryl, cycloalkyl, cycloalkenyl, heterocycloalkyl, and heterocycloalkenyl, and wherein the alkyl-portion of said phenylalkyl-, naphthylalkyl-, 4- to 6-membered heteroarylfused phenylalkyl-, 4- to 6-membered cycloalkylfused phenylalkyl-, 4- to 6-membered heteroarylalkyl-, benzofused 4- to 6-membered heteroarylalkyl-, 4- to 6-membered heteroarylfused 4- to 6-membered heteroarylalkyl-, 3- to 7-membered cycloalkylalkyl-, 4- to 6-membered heterocycloalkylalkyl-, 4- to 6-membered heterocycloalkenylalkyl-, benzofused 4- to 6-membered heterocycloalkenyl, benzofused 4- to 6-membered heterocycloalkylalkyl-, benzofused 4- to 6-membered heterocycloalkenylalkyl-, and 4- to 6-membered heteroarylfused 4- to 6-membered heterocycloalkenylalkyl-, of $R^1$ is optionally substituted with one or more substituents independently selected from alkyl, haloalkyl, and spirocycloalkyl.

In one embodiment, in Formula (IV), the alkyl-portion of said phenylalkyl-, naphthylalkyl-, 4- to 6-membered heteroarylfused phenylalkyl-, 4- to 6-membered cycloalkylfused phenylalkyl-, 4- to 6-membered heteroarylalkyl-, benzofused 4- to 6-membered heteroarylalkyl-, 4- to 6-membered heteroarylfused 4- to 6-membered heteroarylalkyl-, 3- to 7-membered cycloalkylalkyl-, 4- to 6-membered heterocycloalkylalkyl-, 4- to 6-membered heterocycloalkenylalkyl-, benzofused 4- to 6-membered heterocycloalkenyl, benzofused 4- to 6-membered heterocycloalkylalkyl-, benzofused 4- to 6-membered heterocycloalkenylalkyl-, and 4- to 6-membered heteroarylfused 4- to 6-membered heterocycloalkenylalkyl-, of $R^1$ is spirocyclopropyl.

In one embodiment, in Formula (IV), the alkyl-portion of said phenylalkyl-, naphthylalkyl-, 4- to 6-membered heteroarylfused phenylalkyl-, 4- to 6-membered cycloalkylfused phenylalkyl-, 4- to 6-membered heteroarylalkyl-, benzofused 4- to 6-membered heteroarylalkyl-, 4- to 6-membered heteroarylfused 4- to 6-membered heteroarylalkyl-, 3- to 7-membered cycloalkylalkyl-, 4- to 6-membered heterocycloalkylalkyl-, 4- to 6-membered heterocycloalkenylalkyl-, benzofused 4- to 6-membered heterocycloalkenyl, benzofused 4- to 6-membered heterocycloalkylalkyl-, benzofused 4- to 6-membered heterocycloalkenylalkyl-, and 4- to 6-membered heteroarylfused 4- to 6-membered heterocycloalkenylalkyl-, of $R^1$ is a moiety of the formula:

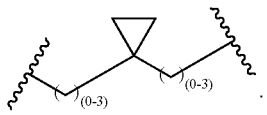

In one embodiment, in Formula (IV), $R^1$ is unsubstituted.
In one embodiment, in Formula (IV), $R^1$ is substituted with from 1 to 4 substituents.
In one embodiment, in Formula (IV), $R^1$ is substituted with from 1 to 3 substituents.
In one embodiment, in Formula (IV), $R^1$ is substituted with from 1 to 2 substituents.
In one embodiment, in Formula (IV), $R^1$ is substituted with 1 substituent.
In one embodiment, in Formula (IV), $R^1$ is substituted with from 1 to 2 substituents, which may be the same or different, each independently selected from halogen, hydroxy, —CN, alkyl, haloalkyl, optionally substituted aryl, optionally substituted heteroaryl, and optionally substituted arylalkoxy,
In one embodiment, in Formula (IV), $R^1$ is selected from aryl, heteroarylfused aryl-, heteroaryl, benzofused heteroaryl-, and heteroarylfused heteroaryl-,
wherein each said $R^1$ group is unsubstituted or optionally substituted with 1 to 2 substituents, which may be the same or different, each independently selected from halogen, hydroxy, —CN, alkyl, haloalkyl, alkoxy, aryl, —O-aryl and heteroaryl.
Non-limiting examples of $R^1$, in Formula (IV), include:

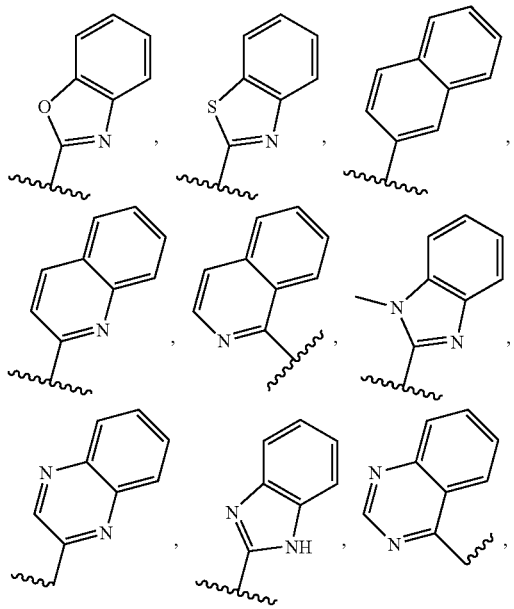

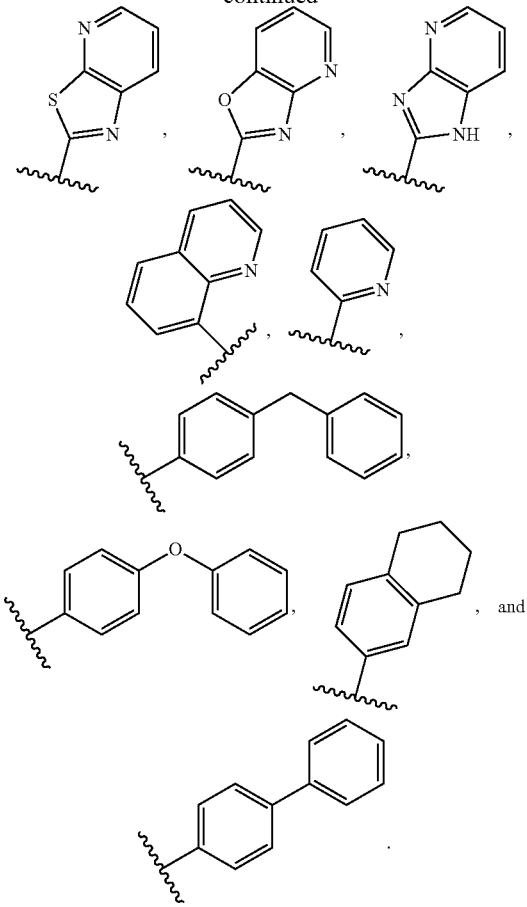

In one embodiment, in Formula (IV), $R^2$ is —OC(O)$R^{11}$.
In one embodiment, in Formula (IV), $R^{11}$ is unsubstituted.
In one embodiment, in Formula (IV), $R^{11}$ is substituted with from 1 to 3 substituents.
In one embodiment, in Formula (IV), $R^2$ is —OC(O)$R^2$ and $R^{11}$ is substituted with from 1 to 2 substituents.
In one embodiment, in Formula (IV), $R^2$ is —OC(O)$R^{11}$ and $R^{11}$ is substituted with 1 substituent.
In one embodiment, in Formula (IV), $R^2$ is —OC(O)$R^{11}$ and $R^{11}$ is substituted with from 1 to 2 substituents, which may be the same or different, each independently selected from alkyl, halogen, and haloalkyl.
In one embodiment, in Formula (IV), $R^2$ is —OC(O)$R^{11}$ and is unsubstituted or substituted heterocycloalkyl.
In one embodiment, in Formula (IV), $R^2$ is —OC(O)$R^{11}$ and $R^{11}$ is unsubstituted or substituted heterocycloalkenyl.
In one embodiment, in Formula (IV), $R^2$ is —OC(O)$R^{11}$ and $R^{11}$ is unsubstituted or substituted heteroaryl.
In one embodiment, in Formula (IV), $R^2$ is —OC(O)$R^{11}$ and $R^{11}$ is unsubstituted.
In one embodiment, in Formula (IV), $R^2$ is —OC(O)$R^{11}$ and $R^{11}$ is substituted with from 1 to 3 substituents.
In one embodiment, in Formula (IV), $R^2$ is —OC(O)$R^{11}$ and $R^{11}$ is substituted with from 1 to 2 substituents.
In one embodiment, in Formula (IV), $R^2$ is —OC(O)$R^{11}$ and $R^{11}$ is substituted with 1 substituent.
In one embodiment, in Formula (IV), $R^2$ is —OC(O)$R^{11}$ and $R^{11}$ is substituted with from 1 to 2 substituents, which may be the same or different, each independently selected from alkyl, halogen, and haloalkyl.

In one embodiment, in Formula (IV), $R^2$ is —OC(O)$R^{11}$ and $R^{11}$ is unsubstituted or substituted heterocycloalkyl.

In one embodiment, in Formula (IV), $R^2$ is —OC(O)$R^{11}$ and $R^{11}$ is unsubstituted or substituted heterocycloalkenyl.

In one embodiment, in Formula (IV), $R^2$ is —OC(O)$R^{11}$ and $R^{11}$ is unsubstituted or substituted heteroaryl.

In one embodiment, in Formula (IV), $R^2$ is —OC(O)$R^{11}$ and $R^{11}$ is selected from aryl, heteroaryl and cycloalkyl, wherein each of said aryl, said heteroaryl, and said cycloalkyl is optionally unsubstituted or substituted with from 1 to 2 substituents, each substituent being independently selected from the group consisting of alkyl, halogen, haloalkyl, hydroxy and —CN.

In one embodiment, in Formula (IV), $R^2$ is

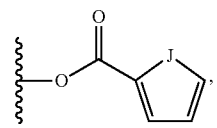

wherein J is selected from O, S, and N, or the oxides thereof.

In one embodiment, in Formula (IV), $R^2$ is

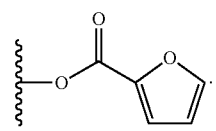

In one embodiment, in Formula (IV), $R^2$ is a moiety selected from

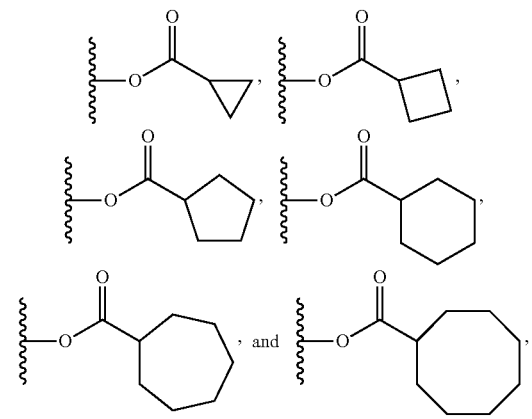

wherein the cycloalkyl portion of said moiety is unsubstituted or substituted with from 1 to 4 substituents independently selected from alkyl, halogen, haloalkyl, hydroxyl, —N($R^7$)$_2$, and CN.

In one embodiment, in Formula (IV), $R^2$ is

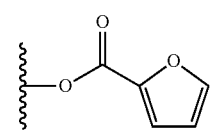

and $R^3$ is H.

In one embodiment, in Formula (IV), $R^2$ is

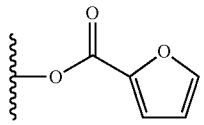 [SMILES: *OC(=O)c1ccco1]

and $R^3$ is methyl.

In one embodiment, in Formula (IV), $R^3$ is selected from hydrogen, hydroxyl, and methyl.

In one embodiment, in Formula (IV), $R^3$ is selected from hydrogen and methyl.

In one embodiment, in Formula (IV), $R^3$ is hydrogen.
In one embodiment, in Formula (IV), $R^3$ is hydroxy.
In one embodiment, in Formula (IV), $R^3$ is alkyl.
In one embodiment, in Formula (IV), $R^3$ is methyl.
In one embodiment, in Formula (IV), $R^3$ is ethyl.
In one embodiment, in Formula (IV), $R^3$ is straight or branched propyl.

In one embodiment, in Formula (IV), $R^2$ and $R^3$ are taken together form a moiety of formula 2:

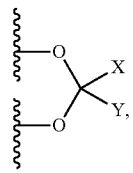

wherein one of X or Y is hydrogen, unsubstituted alkyl, or unsubstituted aryl and the other is selected from haloalkyl, cycloalkyl, heterocycloalkyl, heteroaryl, and halo-substituted aryl.

In one embodiment, in Formula (IV), $R^2$ and $R^3$ are taken together form a moiety of formula:

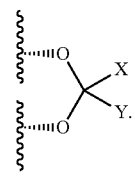

In one embodiment, in Formula (IV), $R^2$ and $R^3$ are taken together to form a moiety of formula 2a:

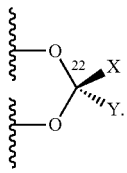

In one such embodiment, in formula 2a, X and Y are each haloalkyl.

In another such embodiment, in formula 2a, one of X and Y is hydrogen and the other is haloalkyl.

In another such embodiment, in formula 2a, X is hydrogen and Y is haloalkyl, and the absolute stereoconfiguration of the $C_{2-2}$ carbon of formula 2a is R.

In another such embodiment, in formula 2a, X is hydrogen and Y is a cyclohexyl moiety of the formula:

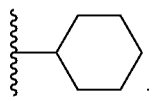 [SMILES: *C1CCCCC1 ; ","]

In another such embodiment, in formula 2a, X is hydrogen and Y is a cyclohexyl moiety of the formula

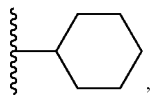

and the absolute stereoconfiguration of the $C_{2-2}$ carbon of formula 2a is R.

In one embodiment, in Formula (IV), $R^2$ and $R^3$ are taken together form a moiety of formula:

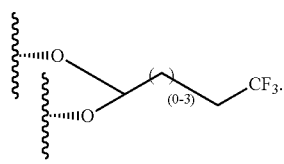

In one embodiment, in Formula (IV), $R^2$ and $R^3$ are taken together form a moiety selected from:

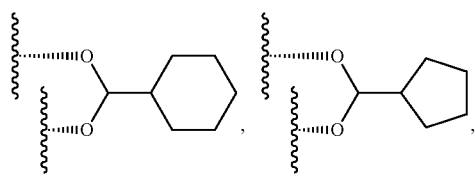

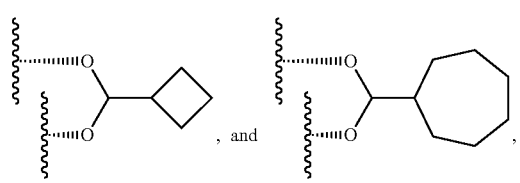

wherein said cycloalkyl ring is unsubstituted or substituted with from 1 to 4 substituents independently selected from alkyl, halogen, haloalkyl, hydroxyl, —N($R^7$)$_2$, and CN.

In one embodiment, in Formula (IV), $R^2$ and $R^3$ are taken together form a moiety of the formula:

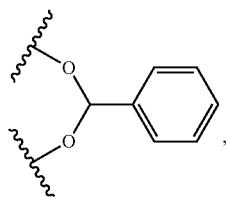 [SMILES: *OC(O*)c1ccccc1 ; ","]

wherein the phenyl group of said moiety is unsubstituted or substituted with from 1 to 4 substituents independently selected from alkyl, halogen, haloalkyl, hydroxyl, —N($R^7$)$_2$, and CN.

In one embodiment, in Formula (IV). $R^2$ and $R^3$ are taken together form a moiety of the formula:

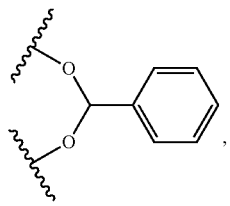 [SMILES: *OC(O*)c1ccccc1 ; ","]

wherein the phenyl group of said moiety is substituted with from 1 to 4 substituents independently selected from halo.

In one embodiment, in Formula (IV), $R^2$ and $R^3$ are taken together form a moiety of formula 3:

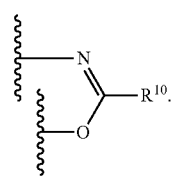

In one such embodiment, $R^{10}$ is H. In another such embodiment, $R^{10}$ is alkyl. In another such embodiment, $R^{10}$ is methyl. In another such embodiment, $R^{10}$ is ethyl. In another such embodiment, $R^{10}$ is straight or branched propyl.

In another embodiment, in Formula (IV), $R^4$ is hydrogen.
In another embodiment, in Formula (IV), $R^4$ is halogen.
In another embodiment, in Formula (IV), $R^4$ is fluoro.
In another embodiment, in Formula (IV), $R^4$ is chloro.
In another embodiment, in Formula (IV), $R^5$ is selected from hydrogen and alkyl.
In another embodiment, in Formula (IV), $R^5$ is methyl.
In another embodiment, in Formula (IV), $R^5$ is ethyl.
In another embodiment, in Formula (IV), $R^5$ is straight or branched propyl,
In another embodiment, in Formula (IV), $R^5$ is halogen.
In another embodiment, in Formula (IV), $R^5$ is fluoro.
In another embodiment, in Formula (IV), $R^5$ is chloro.
in another embodiment, in Formula (IV), $R^4$ is hydrogen and $R^5$ is hydrogen.
In another embodiment, in Formula (IV), $R^4$ is hydrogen and $R^5$ is halogen.
In another embodiment, in Formula (IV), $R^4$ is hydrogen and $R^5$ is fluoro.
In another embodiment, in Formula (IV), $R^4$ is hydrogen and $R^5$ is chloro.

In another embodiment, in Formula (IV), $R^4$ is hydrogen and $R^5$ is alkyl.

In another embodiment, in Formula (IV), $R^4$ is hydrogen and $R^5$ is methyl.

In another embodiment, in Formula (IV), $R^4$ is hydrogen and $R^5$ is ethyl.

In another embodiment, in Formula (IV), $R^4$ is hydrogen and $R^5$ is straight or branched propyl.

In another embodiment, in Formula (IV), $R^4$ is halogen and $R^5$ is hydrogen.

In another embodiment, in Formula (IV), $R^4$ is halogen and $R^5$ is halogen.

In another embodiment, in Formula (IV), $R^4$ is fluoro and $R^5$ is fluoro.

In another embodiment, in Formula (IV), $R^4$ is chloro and $R^5$ is chloro.

In another embodiment, in Formula (IV), $R^4$ is halogen and $R^5$ is alkyl.

In another embodiment, in Formula (IV), $R^4$ is halogen and $R^5$ is methyl.

In another embodiment, in Formula (IV), $R^4$ is halogen and $R^5$ is ethyl.

In another embodiment, in Formula (IV), $R^4$ is halogen and $R^5$ is straight or branched propyl.

In another embodiment, in Formula (IV), $R^4$ is fluoro or chloro and $R^5$ is methyl.

In another embodiment, in Formula (IV), z is a double bond and $R^6$ is H or halogen.

In another embodiment, in Formula (IV), z is a single bond and $R^6$ is H.

In another embodiment, in Formula (IV), $R^6$ is fluoro or chloro.

In one embodiment, in Formula (IV), $R^2$ is —$OR^8$, wherein $R^8$ is hydrogen, $R^3$ is hydrogen or methyl, $R^4$ and $R^5$ are both hydrogen, L is —$CH_2S$—, and z is a double bond.

In one embodiment, the present invention provides a pharmaceutical composition formulated for oral administration, which composition comprises a compound of Formula (IV), wherein $R^2$ is —$OR^8$, wherein $R^8$ is hydrogen, $R^3$ is hydrogen or methyl, $R^4$ and $R^5$ are both hydrogen, L is —$CH_2S$—, and z is a double bond.

In one embodiment, the present invention provides a pharmaceutical composition formulated for oral administration, which composition comprises a compound of any of Formulas (I), (II), (III), (V), and/or (VI), wherein $R^2$ is —$OR^8$, wherein $R^8$ is hydrogen, $R^3$ is hydrogen or methyl, and $R^4$ and $R^5$ are both hydrogen.

In one embodiment, in Formula (IV), $R^1$ is selected from benzofused 5- or 6-membered heteroaryl, benzofused 5- or 6-membered heterocycloalkenyl, heteroarylfused 5- or 6-membered heteroaryl, and heteroarylfused 5- or 6-membered heterocycloalkenyl, $R^2$ is —$OR^8$, wherein $R^8$ is hydrogen, $R^3$ is hydrogen or methyl, $R^4$ and $R^5$ are both hydrogen, L is —$CH_2S$—, and z is a double bond.

In one embodiment, the present invention provides a pharmaceutical composition formulated for oral administration, which composition comprises a compound of Formula (IV), wherein $R^1$ is selected from benzofused 5- or 6-membered heteroaryl, benzofused 5- or 6-membered heterocycloalkenyl, heteroarylfused 5- or 6-membered heteroaryl, and heteroarylfused 5- or 6-membered heterocycloalkenyl, $R^2$ is —$OR^8$, wherein $R^8$ is hydrogen, $R^3$ is hydrogen or methyl, $R^4$ and $R^5$ are both hydrogen, L is —$CH_2S$—, and z is a double bond.

In one embodiment, the present invention provides a pharmaceutical composition formulated for oral administration, which composition comprises a compound of any of Formulas (I), (II), (III), (V), and (VI), wherein $R^1$ is selected from benzofused 5- or 6-membered heteroaryl, benzofused 5- or 6-membered heterocycloalkenyl, heteroarylfused 5- or 6-membered heteroaryl, and heteroarylfused 5- or 6-membered heterocycloalkenyl, $R^2$ is —$OR^8$, wherein $R^8$ is hydrogen, $R^3$ is hydrogen or methyl, and $R^4$ and $R^5$ are both hydrogen.

In one embodiment, the present invention provides a pharmaceutical composition formulated for inhaled administration, which composition comprises a compound of Formula (IV), wherein $R^4$, $R^5$, and $R^6$ are hydrogen, $R^2$ and $R^3$ are joined to form a moiety having the formula

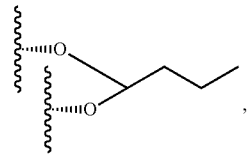

L is —$CH_2S$—, and z is a double bond. In one such embodiment, $R^1$ is selected from benzofused aryl and benzofused heteroaryl.

In one embodiment, the present invention provides a pharmaceutical composition formulated for inhaled administration, which composition comprises a compound any of Formulas (I), (II), (III), (V), (VI) and/or (VIII), wherein $R^4$, $R^6$, and $R^6$ are hydrogen, and $R^2$ and $R^3$ are joined to form a moiety having the formula

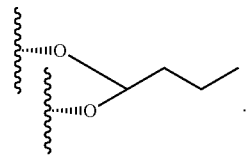

In one such embodiment, $R^1$ is selected from benzofused aryl and benzofused heteroaryl.

In one embodiment, the present invention provides a pharmaceutical composition formulated for inhaled administration, which composition comprises a compound of Formula (IV), wherein $R^4$, $R^5$, and $R^6$ are hydrogen, $R^2$ is —$OR^8$, $R^8$ is furooate, $R^3$ is H, L is —$CH_2S$—, and z is a single bond. In one such embodiment, $R^1$ is a 5- or 6-membered benzofused aryl.

In one embodiment, the present invention provides a pharmaceutical composition formulated for inhaled administration, which composition comprises a compound any of Formulas (I), (II), (III), (V), and/or (VI), wherein $R^4$, $R^5$, and $R^6$ are hydrogen, $R^2$ is —$OR^8$, $R^8$ is furoate, and $R^3$ is H. In one such embodiment, $R^1$ is selected from a benzofused aryl and a benzofused 5- or 6-membered heteroaryl.

In one embodiment, in Formula (IV), is a compound, or a pharmaceutically acceptable salt, solvate, ester, prodrug, tautomer, or isomer of said compound, said compound having the general structure shown in Formula (IVa):

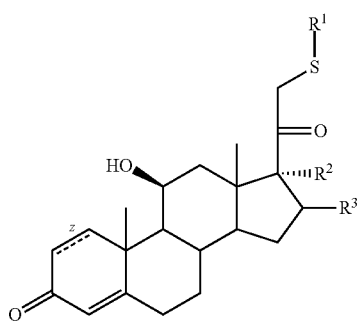

(IVa)

wherein $R^1$, $R^2$, $R^3$, and z are selected independently of each other and wherein:

$R^1$ is selected from aryl, heteroaryl, heteroarylfused aryl-, benzofused heteroaryl-, and heteroarylfused heteroaryl-,
  wherein each said $R^1$ group is unsubstituted or optionally substituted with from 1 to 2 substituents, which may be the same or different, each substituent being independently selected from halogen, hydroxy, —CN, alkyl, haloalkyl, alkoxy, aryl, —O-aryl and heteroaryl;

$R^2$ is —OC(O)$R^{11}$ and $R^{11}$ is selected from aryl, heteroaryl, and cycloalkyl, wherein each said aryl, said heteroaryl, and said cycloalkyl is unsubstituted or optionally substituted with from 1 to 2 substituents, each substitutent being independently selected from the group consisting of alkyl, halogen, haloalkyl, hydroxy and —CN;

$R^3$ is selected from hydrogen and methyl; and z is a single or double bond.

In one embodiment, in Formula (IVa), $R^1$ is benzofused 5-membered heteroaryl-; $R^2$ is —OC(O)— heteroaryl, $R^3$ is hydrogen; and z is a single bond.

In one embodiment, in Formula (IV), is a compound, or a pharmaceutically acceptable salt, solvate, ester, prodrug, tautomer, or isomer of said compound, said compound having the general structure shown in Formula (IVb):

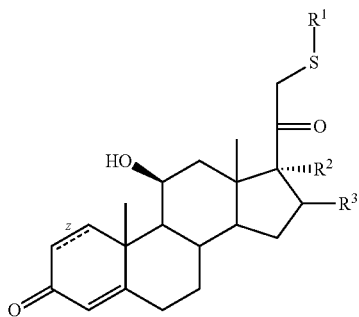

(IVb)

wherein $R^1$, $R^2$, $R^3$, and z are selected independently of each other and wherein:

$R^1$ is selected from aryl, heteroaryl, heteroarylfused aryl-, benzofused heteroaryl-, and heteroarylfused heteroaryl-,
  wherein each said $R^1$ group is unsubstituted or optionally substituted with from 1 to 2 substituents, which may be the same or different, each substituent being independently selected from halogen, hydroxy, —CN, alkyl, haloalkyl, alkoxy, aryl, —O-aryl and heteroaryl;

$R^2$ and $R^3$ are taken together form a moiety of formula 2:

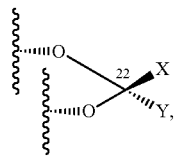

2 z is a single or double bond; and
X and Y are each independently as defined in Formula (IV).

In one embodiment, in Formula (IVb), z is a double bond.

In one embodiment, in Formula (IVb), one of X and Y is hydrogen and the other is haloalkyl.

In one embodiment, in Formula (IVb), X is hydrogen and Y is a cyclohexyl moiety of the formula:

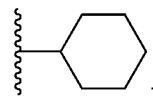 [SMILES: *C1CCCCC1 ; ","]

In one embodiment, in Formula (IVb), X is hydrogen and Y is a cyclohexyl moiety of the formula

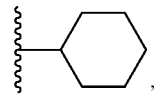

and the absolute stereoconfiguration of the $C_{2\text{-}2}$ carbon of formula 2a is R.

In one embodiment, in Formula (IV), is a compound, or a pharmaceutically acceptable salt, solvate, ester, prodrug, tautomer, or isomer of said compound, said compound having the general structure shown in Formula (IVc):

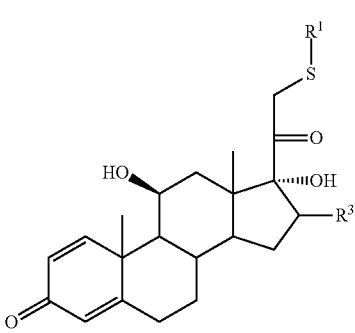

(IVc)

wherein $R^1$ and $R^3$ are selected independently of each other and wherein:

$R^1$ is selected from heteroarylfused aryl, benzofused 6-membered heteroaryl-, and heteroarylfused heteroaryl-,
  wherein each said $R^1$ group is unsubstituted or optionally substituted with 1 to 2 substituents, which may be the same or different, each substituent being independently selected from halogen, hydroxy, —CN, alkyl, haloalkyl, alkoxy, aryl, —O-aryl and heteroaryl; and $R^3$ is selected from hydrogen and methyl.

In one embodiment, in Formula (IV), is a compound, or a pharmaceutically acceptable salt, solvate, ester, prodrug, tautomer, or isomer of said compound, said compound having the general structure shown in Formula (IVd)

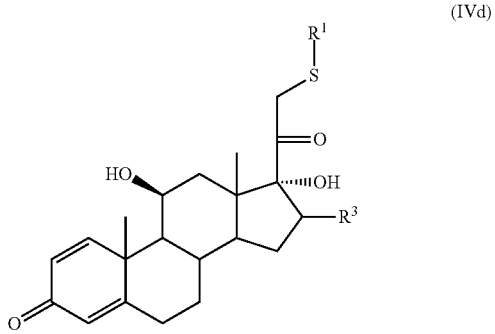

(IVd)

wherein $R^1$ and $R^3$ are selected independently of each other and wherein:

$R^1$ is selected from aryl, heteroaryl, heteroarylfused aryl, benzofused heteroaryl-, and heteroarylfused heteroaryl-,
wherein each said $R^1$ group is unsubstituted or optionally substituted with 1 to 2 substituents, which may be the same or different, each substituent being independently selected from hydroxy, —CN, haloalkyl, aryl, —O-aryl and heteroaryl; and $R^3$ is selected from hydrogen and methyl.

In one embodiment, in Formula (IV), is a compound, or a pharmaceutically acceptable salt, solvate, ester, prodrug, tautomer, or isomer of said compound, said compound having the general structure shown in Formula (IVe):

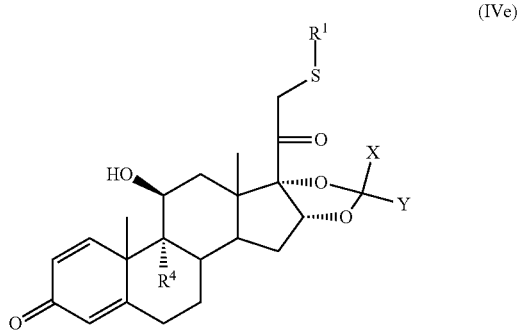

(IVe)

wherein $R^1$, $R^4$, X and Y are selected independently of each other and wherein:

$R^1$ is selected from aryl, heteroarylfused aryl- and heteroaryl, benzofused heteroaryl-, heteroarylfused heteroaryl-,
wherein each said $R^1$ group is unsubstituted or optionally substituted with 1 to 2 substituents, which may be the same or different, each independently selected from halogen, hydroxy, —CN, alkyl, haloalkyl, alkoxy, aryl, —O-aryl and heteroaryl;

$R^4$ is a halogen; and

X and Y taken together with the carbon atom to which they are attached to form a 4 to 7-membered cycloalkyl or heterocycloalkyl ring, which ring is optionally substituted with from 1 to 2 substituents independently selected from alkyl, halogen, haloalkyl, hydroxy, —N($R^7$)$_2$ and —CN, wherein each $R^7$ is independently selected and as defined in Formula (IV).

In one embodiment is an 11-keto analog of compounds of Formula (IV), or a pharmaceutically acceptable salt, solvate, ester, tautomer, or isomer thereof, said 11-keto analog having the general formula:

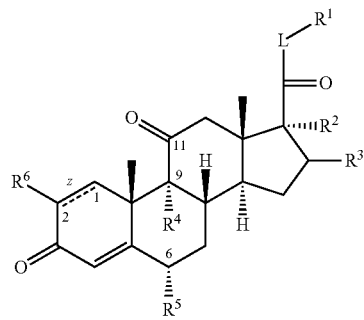

wherein L, $R^1$, $R^2$, $R^3$, $R^4$, $R^5$, $R^6$, and z are selected independently of each other and as defined in Formula (IV) or any of the various embodiments of Formula (IV), Formula (IVa), Formula (IVb), Formula (IVc), Formula (IVd), and/or Formula (IVe), described herein.

In one embodiment, the present invention provides a compound, or a pharmaceutically acceptable salt, solvate, ester, prodrug, or isomer of said compound, having the general structure shown in Formula (V) as described above.

In one embodiment, in Formula (V), is a compound having the structural formula:

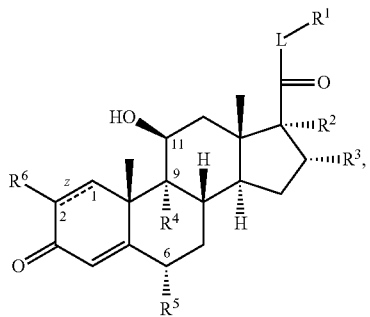

or a pharmaceutically acceptable salt, solvate, ester, prodrug, tautomer, or isomer thereof, wherein L, $R^1$, $R^2$, $R^3$, $R^4$, $R^5$, $R^6$, and z are selected independently and as defined in Formula (V).

In one embodiment, in Formula (V), $R^1$ is not heterocycloalkyl.

In one embodiment, in Formula (V), $R^1$ is not substituted heterocycloalkyl.

In one embodiment, in Formula (V), $R^1$ is selected from 4- to 6-membered heteroarylfused phenyl, 4- to 6-membered heteroarylfused napthyl, 4- to 6-membered heteroarylfused phenylalkyl-, 4- to 6-membered cycloalkylfused phenyl, 4- to 6-membered cycloalkylfused naphthyl, 4- to 6-membered cycloalkylfused phenylalkyl-, benzofused 6-membered heteroaryl, 4- to 6-membered heteroarylalkyl-, benzofused 4- to 6-membered heteroarylalkyl-, 4- to 6-membered heteroarylfused 4- to 6-membered heteroaryl, 4- to 6-membered heteroarylfused 4- to 6-membered heteroarylalkyl-, 4- to 6-membered cycloalkylalkyl-, 4- to 6-membered cycloalkylalkenyl-, 5-membered heterocycloalkyl, benzofused 5-membered heterocycloalkyl, 6-membered heterocycloalkyl, benzofused 6-membered heterocycloalkyl, 4 to 6-membered heterocycloalkylalkyl-, benzofused 4- to 6-membered heterocycloalkylalkyl-, benzofused 6-membered heterocycloalkenyl, 4- to 6-membered heterocycloalkylalkenyl-, benzofused 4- to 6-membered heterocycloalkenylalkyl-, 4- to 6-membered heteroarylfused 4- to 6-membered heterocycloalkenyl, and O-5 to 6-membered heteroarylfused 4- to 6-membered heterocycloalkenylalkyl-, wherein each said hetero ring-containing moiety of R¹ and each said heterofused containing moiety of R¹ independently comprises 1, 2, or 3 ring heteroatoms independently selected from O, N, and S, wherein each said R¹ group is unsubstituted or optionally substituted with from 1 to 5 substituents, which may be the same or different, each independently selected from halogen, hydroxy, —CN, oxo, oxide, alkyl, haloalkyl, haloalkoxy-, hydroxyalkyl-, heteroalkyl, cyanoalkyl-, alkoxy, optionally substituted aryl, optionally substituted —O-aryl, optionally substituted —O-alkyl-aryl, optionally substituted heteroaryl, optionally substituted arylalkyl-, optionally substituted arylalkoxy, —N(R⁷)₂, -alkylN(R⁷)₂, —NC(O)R⁷, —CO₂R⁷, —SO₂R⁷, and —SO₂N(R⁷)₂, wherein said optional substituents are present from 1 to 4 times and may be the same or different, each independently selected from alkyl, halogen, haloalkyl, hydroxyl, —CN, and —N(R¹¹)₂; and wherein the benzo portion of each said benzofused R¹ group is optionally further fused to another ring selected from heteroaryl, cycloalkyl, cycloalkenyl, heterocycloalkyl, and heterocycloalkenyl, and wherein the alkyl-portion of said 4- to 6-membered heteroarylfused phenylalkyl-, 4- to 6-membered cycloalkylfused phenylalkyl-, 4- to 6-membered heteroarylalkyl-, benzofused 4- to 6-membered heteroarylalkyl-, O-5 to 6-membered heteroarylfused 4- to 6-membered heteroarylalkyl-, 4- to 6-membered cycloalkylalkyl-, 4- to 6-membered cycloalkylalkenyl-, 4 to 6-membered heterocycloalkylalkyl-, benzofused 4- to 6-membered heterocycloalkylalkyl-, 4- to 6-membered heterocycloalkylalkenyl-, benzofused 4- to 6-membered heterocycloalkenylalkyl-, and 4- to 6-membered heteroarylfused 4- to 6-membered heterocycloalkenylalkyl-, of R¹ is optionally substituted with from 1 to 3 substituents independently selected from alkyl, haloalkyl, and spirocycloalkyl.

In one embodiment, in Formula (V), R¹ is selected from 5- to 6-membered heteroarylfused phenyl, 5- to 6-membered heteroarylfused napthyl, 5- to 6-membered heteroarylfused phenylalkyl-, 4- to 6-membered cycloalkylfused phenyl, 4- to 6-membered cycloalkylfused naphthyl, 4- to 6-membered cycloalkylfused phenylalkyl-, benzofused 6-membered heteroaryl, 5- to 6-membered heteroarylalkyl-, benzofused 5 to 6-membered heteroarylalkyl-, 5- to 6-membered heteroarylfused 5- to 6-membered heteroaryl, 5- to 6-membered heteroarylfused 5- to 6-membered heteroarylalkyl-, 4 to 6-membered cycloalkylalkyl-, 4- to 6-membered cycloalkylalkenyl-, 5-membered heterocycloalkyl, benzofused 5-membered heterocycloalkyl, 6-membered heterocycloalkyl, benzofused 6-membered heterocycloalkyl, 4 to 6-membered heterocycloalkylalkyl-, benzofused 4- to 6-membered heterocycloalkylalkyl-, benzofused 6-membered heterocycloalkenyl, 4- to 6-membered heterocycloalkylalkenyl-, benzofused 4- to 6-membered heterocycloalkenylalkyl-, 5- to 6-membered heteroarylfused 4- to 6-membered heterocycloalkenyl, and 5- to 6-membered heteroarylfused 4- to 6-membered heterocycloalkenylalkyl-, wherein each said hetero ring-containing moiety of R¹ and each said heterofused containing moiety of R¹ independently comprises 1, 2, or 3 ring heteroatoms independently selected from O, N, and S, wherein each said R¹ group is unsubstituted or optionally substituted with from 1 to 5 substituents, which may be the same or different, each independently selected from halogen, hydroxy, oxo, oxide, alkyl, haloalkyl, haloalkoxy-, hydroxyalkyl-, heteroalkyl, cyanoalkyl-, alkoxy, optionally substituted aryl, optionally substituted —O-aryl, optionally substituted —O-alkyl-aryl, optionally substituted heteroaryl, optionally substituted arylalkyl-, optionally substituted arylalkoxy, —N(R⁷)₂, -alkylN(R⁷)₂, —NC(O)R⁷, —CO₂R⁷, —SO₂R⁷, and —SO₂N(R⁷)₂, wherein said optional substituents are present from 1 to 4 times and may be the same or different, each independently selected from alkyl, halogen, haloalkyl, hydroxyl, —CN, and —N(R¹¹)₂;

and wherein the benzo portion of each said benzofused R¹ group is optionally further fused to another ring selected from heteroaryl, cycloalkyl, cycloalkenyl, heterocycloalkyl, and heterocycloalkenyl, and wherein the alkyl-portion of said 5- to 6-membered heteroarylfused phenylalkyl-, 4- to 6-membered cycloalkylfused phenylalkyl-, 5- to 6-membered heteroarylalkyl-, benzofused 5- to 6-membered heteroarylalkyl-, 5- to 6-membered heteroarylfused 5- to 6-membered heteroarylalkyl-, 4- to 6-membered cycloalkylalkyl-, 4- to 6-membered cycloalkylalkenyl-, 4 to 6-membered heterocycloalkylalkyl-, benzofused 4- to 6-membered heterocycloalkylalkyl-, 4- to 6-membered heterocycloalkylalkenyl-, benzofused 4- to 6-membered heterocycloalkenylalkyl-, and 5- to 6-membered heteroarylfused 4- to 6-membered heterocycloalkenylalkyl-, of R¹ is optionally substituted with from 1 to 3 substituents independently selected from alkyl, haloalkyl, and spirocycloalkyl.

In one embodiment, in Formula (V), said alkyl-portion of R¹ is substituted with spirocyclopropyl.

In one embodiment, in Formula (V), said alkyl-portion of R¹ is a moiety of the formula:

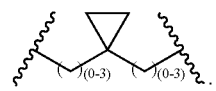

In one embodiment, in Formula (V), R¹ is selected from heteroarylfused aryl, benzofused 6-membered heteroaryl-, and heteroarylfused heteroaryl-, wherein each said R¹ group is unsubstituted or optionally substituted with 1 to 2 substituents, which may be the same or different, each independently selected from halogen, hydroxy, —CN, alkyl, haloalkyl, alkoxy, aryl, —O-aryl and heteroaryl.

In one embodiment, in Formula (V), said alkyl-portion of R¹ is substituted with haloalkyl.

In one embodiment, in Formula (V), the benzo portion of each said benzofused R¹ group is further fused with another ring selected from heteroaryl, cycloalkyl, cycloalkenyl, heterocycloalkyl, and heterocycloalkenyl. Non-limiting examples of such R¹ groups include:

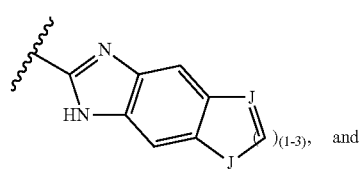
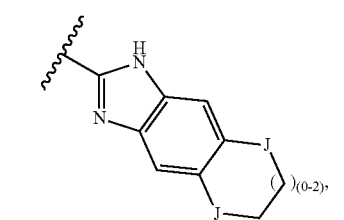
wherein each J is independently selected from N, O, and S (or oxides thereof). Further non-limiting examples of such groups R¹ include
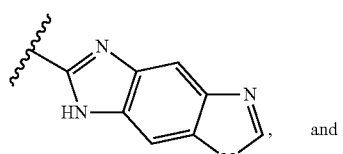
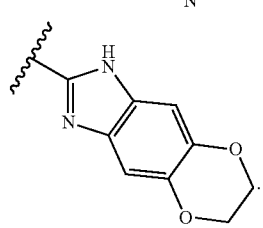
Additional non-limiting examples of R¹, in Formula (V), include:
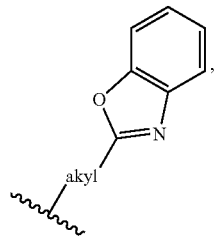 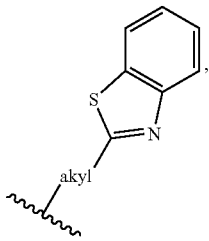
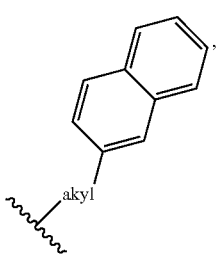 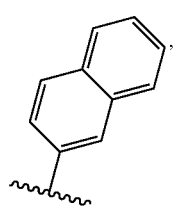
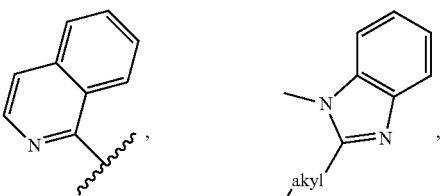
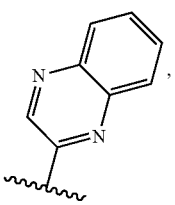 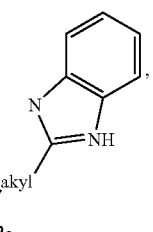
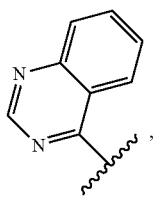 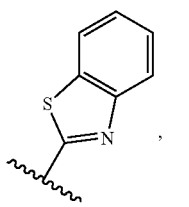
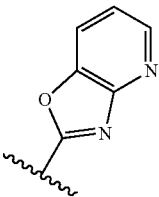 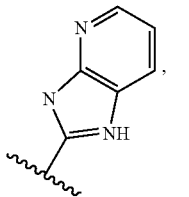
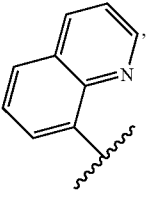 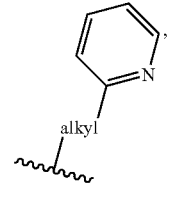
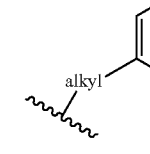 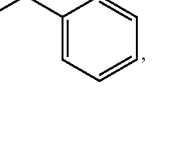
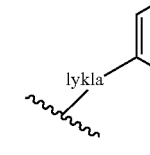 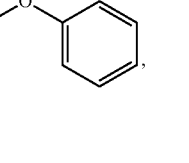
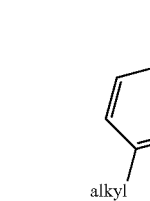 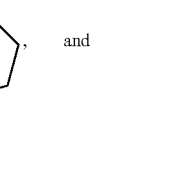

-continued

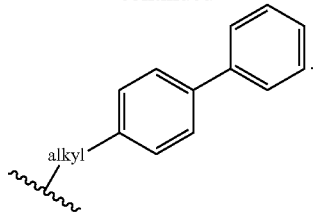

In one embodiment, in Formula (V), $R^2$ is —OH.
In one embodiment, in Formula (V), $R^2$ is —Oalkyl.
In one embodiment, in Formula (V), $R^2$ is —Omethyl.
In one embodiment, in Formula (V), $R^2$ is —Oethyl.
In one embodiment, in Formula (V), $R^2$ is —Opropyl.
In one embodiment, in Formula (V), $R^2$ is —OC(O)$R^9$.
In one embodiment, in Formula (V), $R^9$ is unsubstituted.
In one embodiment, in Formula (V), $R^9$ is substituted with from 1 to 3 substituents.
In one embodiment, in Formula (V), $R^9$ is substituted with from 1 to 2 substituents.
In one embodiment, in Formula (V), $R^9$ is substituted with 1 substituent.
In one embodiment, in Formula (V), $R^9$ is substituted with from 1 to 2 substituents, which may be the same or different, each independently selected from alkyl, halogen, and haloalkyl.
In one embodiment, in Formula (V), $R^3$ is selected from hydrogen, hydroxyl, and methyl.
In one embodiment, in Formula (V), $R^3$ is selected from hydrogen and methyl.
In one embodiment, in Formula (V), $R^3$ is hydrogen.
In one embodiment, in Formula (V), $R^3$ is hydroxy.
In one embodiment, in Formula (V), $R^3$ is alkyl.
In one embodiment, in Formula (V), $R^3$ is methyl.
In one embodiment, in Formula (V), $R^3$ is ethyl.
In one embodiment, in Formula (V), $R^3$ is straight or branched propyl.
In one embodiment, in Formula (V), $R^2$ is —$OR^8$, wherein $R^8$ is hydrogen, and $R^3$ is methyl.
In one embodiment, in Formula (V), $R^2$ is —$OR^8$, wherein $R^8$ is hydrogen, and $R^3$ is hydrogen.
In one embodiment, in Formula (V), $R^2$ and $R^3$ are taken together form a moiety of formula 2:

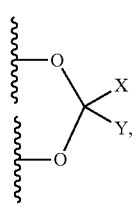

wherein X and Y are each independently selected from hydrogen, hydroxyl, and straight or branched alkyl.

In one embodiment, in formula 2, X is hydrogen and Y is straight or branched alkyl.

In one embodiment, in Formula (V), $R^2$ and $R^3$ are taken together form a moiety of formula:

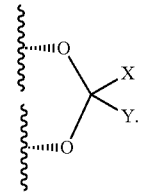

In one embodiment, in Formula (V), $R^2$ and $R^3$ are taken together form a moiety of formula:

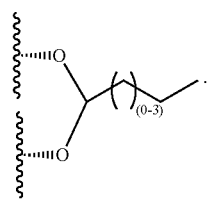

In one embodiment, in Formula (V), $R^2$ and $R^3$ are taken together form a moiety of formula:

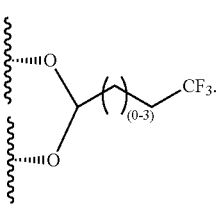

In one embodiment, in Formula (V), $R^2$ and $R^3$ are taken together form a moiety of the formula:

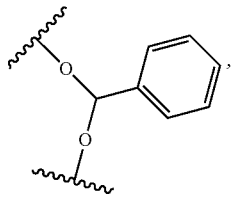 [SMILES: *OC(O*)c1ccccc1]

wherein the phenyl group of said moiety is unsubstituted or substituted with from 1 to 4 substituents independently selected from alkyl, halogen, haloalkyl, hydroxyl, —N($R^7$)$_2$, and CN.

In another embodiment, in Formula (V), $R^4$ is hydrogen.
In another embodiment, in Formula (V), $R^4$ is halogen.
In another embodiment, in Formula (V), $R^4$ is fluoro.
In another embodiment, in Formula (V), $R^4$ is chloro.
In another embodiment, in Formula (V), $R^5$ is selected from hydrogen and alkyl.
In another embodiment, in Formula (V), $R^5$ is methyl.
In another embodiment, in Formula (V), $R^5$ is ethyl.
In another embodiment, in Formula (V), $R^5$ is straight or branched propyl.
In another embodiment, in Formula (V), $R^5$ is halogen.
In another embodiment, in Formula (V), $R^5$ is fluoro.
In another embodiment, in Formula (V), $R^5$ is chloro.
In another embodiment, in Formula (V), $R^4$ is hydrogen and $R^5$ is hydrogen.

In another embodiment, in Formula (V), R⁴ is hydrogen and R⁵ is halogen.

In another embodiment, in Formula (V), R⁴ is hydrogen and R⁵ is fluoro.

In another embodiment, in Formula (V), R⁴ is hydrogen and R⁵ is chloro.

In another embodiment, in Formula (V), R⁴ is hydrogen and R⁵ is alkyl.

In another embodiment, in Formula (V), R⁴ is hydrogen and R⁵ is methyl.

In another embodiment, in Formula (V), R⁴ is hydrogen and R⁵ is ethyl.

In another embodiment, in Formula (V), R⁴ is hydrogen and R⁵ is straight or branched propyl.

In another embodiment, in Formula (V), R⁴ is halogen and R⁶ is hydrogen.

In another embodiment, in Formula (V), R⁴ is halogen and R⁵ is halogen.

In another embodiment, in Formula (V), R⁴ is fluoro and R⁵ is fluoro.

In another embodiment, in Formula (V), R⁴ is chloro and R⁵ is chloro.

In another embodiment, in Formula (V), R⁴ is halogen and R⁵ is alkyl.

In another embodiment, in Formula (V), R⁴ is halogen and R⁵ is methyl.

In another embodiment, in Formula (V), R⁴ is halogen and R⁵ is ethyl.

In another embodiment, in Formula (V), R⁴ is halogen and R⁵ is straight or branched propyl.

In another embodiment, in Formula (V), R⁴ is fluoro or chloro and R⁵ is methyl.

In another embodiment, in Formula (V), z is a double bond and R⁶ is H or halogen.

In another embodiment, in Formula (V), R⁶ is fluoro or chloro.

In another embodiment, in Formula (V), z is a single bond and R⁶ is H.

In one embodiment, in Formula (V), R² is —OR⁸, wherein R⁸ is hydrogen, R³ is hydrogen or methyl, R⁴ and R⁵ are both hydrogen, L is —CH₂S—, and z is a double bond.

In one embodiment, the present invention provides a pharmaceutical composition formulated for oral administration, which composition comprises a compound of Formula (V), wherein R² is —OR⁸, wherein R⁸ is hydrogen, R³ is hydrogen or methyl, R⁴ and R⁵ are both hydrogen, L is —CH₂S—, and z is a double bond.

In one embodiment, in Formula (V), R¹ is selected from benzofused 6-membered heteroaryl, and benzofused 6-membered heterocycloalkenyl, R² is —OR⁸, wherein R⁸ is hydrogen, R³ is hydrogen or methyl, R⁴ and R⁵ are both hydrogen, L is —CH₂S—, and z is a double bond.

In one embodiment, the present invention provides a pharmaceutical composition formulated for oral administration, which composition comprises a compound of Formula (V), wherein R¹ is selected from benzofused 5-membered heteroaryl, benzofused 5- or 6-membered heterocycloalkenyl, heteroarylfused 5- or 6-membered heteroaryl, and heteroarylfused 5- or 6-membered heterocycloalkenyl, R² is —OR⁸, wherein R⁸ is hydrogen, R³ is hydrogen or methyl, R⁴ and R⁵ are both hydrogen, L is —CH₂S—, and z is a double bond.

In one embodiment, the present invention provides a pharmaceutical composition formulated for inhaled administration, which composition comprises a compound of Formula (V), wherein R⁴, R⁵, and R⁶ are hydrogen, R² and R³ are joined to form a moiety having the formula

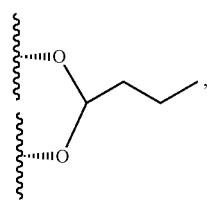

L is —CH₂S—, and z is a double bond.

In one embodiment, in Formula (V), is a compound, or a pharmaceutically acceptable salt, solvate, ester, prodrug, tautomer, or isomer of said compound, said compound having the general structure shown in Formula (Va):

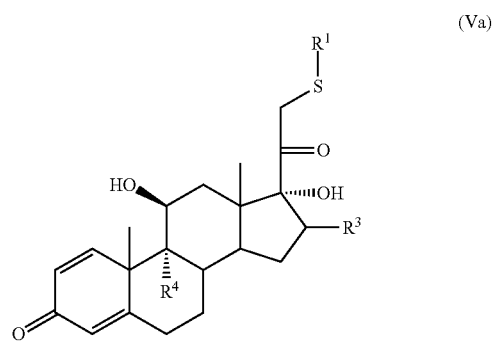

wherein R¹, R³, and R⁴ are selected independently of each other and wherein:

R¹ is selected from heteroarylfused aryl, benzofused 6-membered heteroaryl-, and heteroarylfused heteroaryl-,
  wherein each said R¹ group is unsubstituted or optionally substituted with 1 to 2 substituents, which may be the same or different, each independently selected from halogen, hydroxy, —CN, alkyl, haloalkyl, alkoxy, aryl, —O-aryl and heteroaryl;

R³ is selected from hydrogen or methyl; and

R⁴ is a hydrogen.

In one embodiment, in Formula (V), is a compound, or a pharmaceutically acceptable salt, solvate, ester, prodrug, tautomer, or isomer of said compound, said compound having the general structure shown in Formula (Vb):

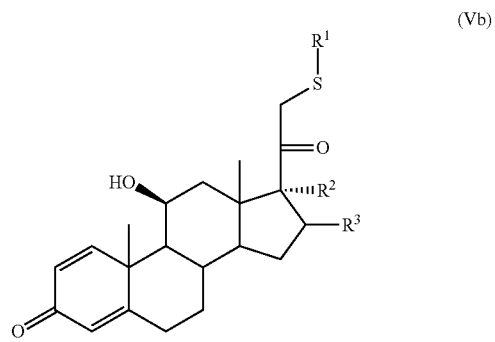

wherein R¹, R², and R³ are selected independently of each other and wherein:

$R^1$ is selected from heteroarylfused aryl-, benzofused 6-membered heteroaryl-, and heteroarylfused heteroaryl-,
  wherein each said $R^1$ group is unsubstituted or optionally substituted with 1 to 2 substituents, which may be the same or different, each independently selected from halogen, hydroxy, —CN, alkyl, haloalkyl, alkoxy, aryl, —O-aryl and heteroaryl;

$R^2$ and $R^3$ taken together form a moiety of formula 2:

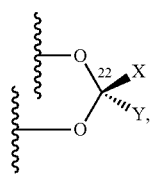

2 wherein one of X and Y is hydrogen and the other is —CH$_2$CH$_2$CH$_3$ and the absolute stereoconfiguration on C22 is R.

In one embodiment is an 11-keto analog of compounds of Formula (V), or a pharmaceutically acceptable salt, solvate, ester, tautomer, or isomer thereof, said 11-keto analog having the general formula:

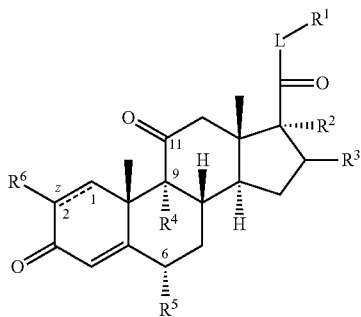

wherein L, $R^1$, $R^2$, $R^3$, $R^4$, $R^5$, $R^6$, and z are selected independently of each other and as defined in Formula (V) or any of the various embodiments of Formula (V) and/or Formula (Va), described herein.

In one embodiment, the present invention provides a compound, or a pharmaceutically acceptable salt, solvate, ester, prodrug, or isomer of said compound, having the general structure shown in Formula (VI) as described above.

In one embodiment, in Formula (VI), $R^1$ is not heterocycloalkyl.

In one embodiment, in Formula (VI), $R^1$ is not substituted heterocycloalkyl.

In one embodiment, in Formula (VI), is a compound having the structural formula:

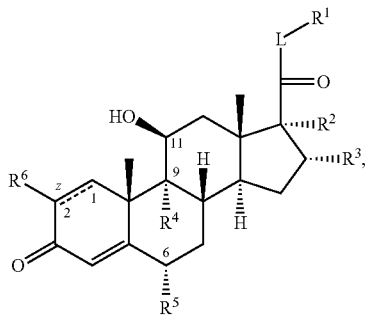

or a pharmaceutically acceptable salt, solvate, ester, prodrug, tautomer, or isomer thereof, wherein L, $R^1$, $R^2$, $R^3$, $R^4$, $R^5$, $R^6$, and z are selected independently and as defined in Formula (VI).

In one embodiment, in Formula (VI), $R^1$ is selected from aryl, arylalkyl-, cycloalkyl, 5-membered heterocycloalkenyl, benzofused 5-membered heterocycloalkenyl, 5-membered heteroaryl, benzofused 5-membered heteroaryl, 6-membered heterocycloalkenyl, and 6-membered heteroaryl,
  wherein each said 5-membered hetero ring of $R^1$ comprises from 1 to 3 ring heteroatoms, each independently selected from N, O, and S (and oxides thereof),
  wherein each said 6-membered hetero ring of $R^1$ comprises from 1 to 4 ring heteroatoms, each independently selected from N, O, and S (and oxides thereof),
  wherein each said $R^1$ group is substituted with from 1 to 5 substituents, which may be the same or different, each independently selected from hydroxy, —CN, oxo, oxide, haloalkyl, haloalkoxy-, hydroxyalkyl-, heteroalkyl, cyanoalkyl-, optionally substituted aryl, optionally substituted —O-aryl, optionally substituted —O-alkyl-aryl, optionally substituted heteroaryl, optionally substituted arylalkyl-, optionally substituted arylalkoxy, -alkylN($R^7$)$_2$, —NC(O)$R^7$, —SO$_2$R$^7$, and —SO$_2$N($R^7$)$_2$, wherein said optional substituents are present from 1 to 4 times and may be the same or different, each independently selected from alkyl, halogen, haloalkyl, hydroxyl, —CN, and —N($R^{11}$)$_2$;
  and wherein the alkyl-portion of said arylalkyl- of $R^1$ is optionally substituted with one or more substituents independently selected from alkyl, haloalkyl, and spirocycloalkyl;

In one embodiment, in Formula (VI), $R^1$ is selected from aryl, 5-membered heteroaryl, and benzofused 5-membered heteroaryl-, wherein each said $R^1$ group is unsubstituted or optionally substituted with 1 to 2 substituents, which may be the same or different, each independently selected from halogen, hydroxy, —CN, alkyl, haloalkyl, alkoxy, aryl, —O-aryl and heteroaryl.

In one embodiment, in Formula (VI), said alkyl-portion of $R^1$ is substituted with spirocyclopropyl.

In one embodiment, in Formula (VI), said alkyl-portion of $R^1$ is a moiety of the formula:

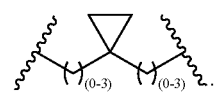

In one embodiment, in Formula (VI), said alkyl-portion of $R^1$ is substituted with haloalkyl.

Additional non-limiting examples of $R^1$, in Formula (VI), include:

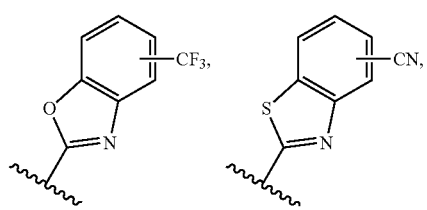

-continued

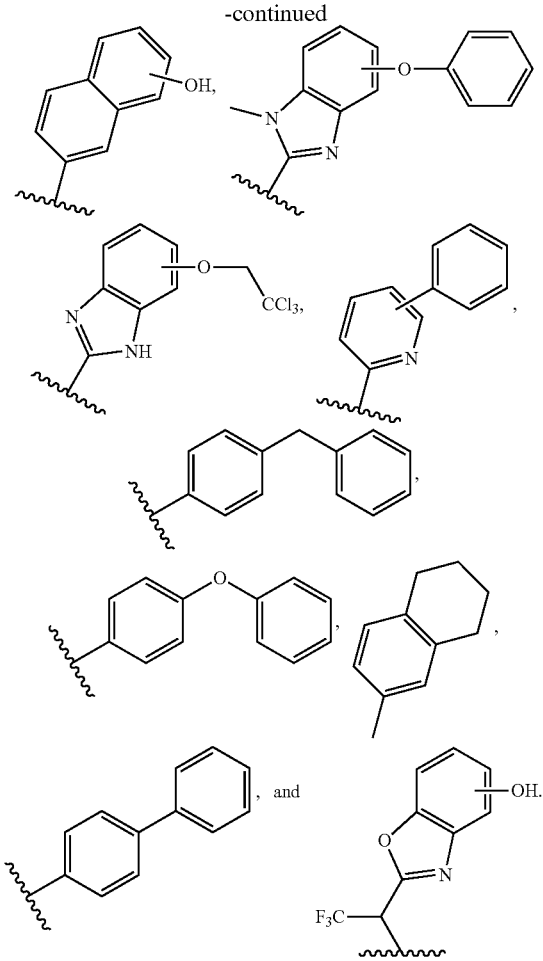

In one embodiment, in Formula (VI), $R^2$ is —OH.
In one embodiment, in Formula (VI), $R^2$ is —Oalkyl.
In one embodiment, in Formula (VI), $R^2$ is —Omethyl.
In one embodiment, in Formula (VI), $R^2$ is —Oethyl.
In one embodiment, in Formula (VI), $R^2$ is —Opropyl.
In one embodiment, in Formula (VI), $R^2$ is —OC(O)$R^9$.
In one embodiment, in Formula (VI), $R^9$ is unsubstituted.
In one embodiment, in Formula (VI), $R^9$ is substituted with from 1 to 3 substituents,
In one embodiment, in Formula (VI), $R^9$ is substituted with from 1 to 2 substituents.
In one embodiment, in Formula (VI), $R^9$ is substituted with 1 substituent.
In one embodiment, in Formula (VI), $R^9$ is substituted with from 1 to 2 substituents, which may be the same or different, each independently selected from alkyl, hydroxyl, halogen, and haloalkyl.
In one embodiment, in Formula (VI), $R^3$ is selected from hydrogen, hydroxyl, and methyl.
In one embodiment, in Formula (VI), $R^3$ is selected from hydrogen and methyl.
In one embodiment, in Formula (VI), $R^3$ is hydrogen.
In one embodiment, in Formula (VI), $R^3$ is hydroxy.
In one embodiment, in Formula (VI), $R^3$ is alkyl.
In one embodiment, in Formula (VI), $R^3$ is methyl.
In one embodiment, in Formula (VI), $R^3$ is ethyl.
In one embodiment, in Formula (VI), $R^3$ is straight or branched propyl.
In one embodiment, in Formula (VI), $R^2$ is —$OR^8$, wherein $R^8$ is hydrogen, and $R^3$ is methyl.
In one embodiment, in Formula (VI), $R^2$ is —$OR^8$, wherein $R^8$ is hydrogen, and $R^3$ is hydrogen.
In one embodiment, in Formula (VI), $R^2$ and $R^3$ are taken together form a moiety of formula 2:

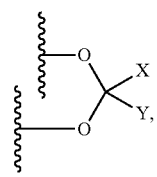

wherein X and Y are each independently selected from hydrogen, hydroxyl, and straight or branched alkyl.
In one embodiment, in formula 2, X is hydrogen and Y is straight or branched alkyl.
In one embodiment, in Formula (VI), $R^2$ and $R^3$ are taken together form a moiety of formula:

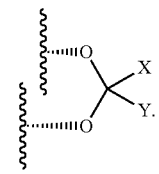

In one embodiment, in Formula (VI), $R^2$ and $R^3$ are taken together form a moiety of formula:

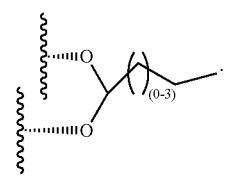

In one embodiment, in Formula (VI), $R^2$ and $R^3$ are taken together form a moiety of formula:

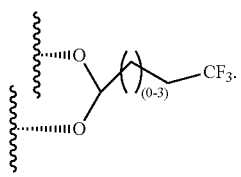

In one embodiment, in Formula (VI), $R^2$ and $R^3$ are taken together form a moiety of the formula:

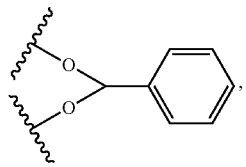 [SMILES: *OC(O*)c1ccccc1]

wherein the phenyl group of said moiety is unsubstituted or substituted with from 1 to 4 substituents independently selected from alkyl, halogen, haloalkyl, hydroxyl, —N($R^7$)$_2$, and CN.

In another embodiment, in Formula (VI), $R^4$ is hydrogen.
In another embodiment, in Formula (VI), $R^4$ is halogen.
In another embodiment, in Formula (VI), $R^4$ is fluoro.
In another embodiment, in Formula (VI), $R^4$ is chloro.
In another embodiment, in Formula (VI), $R^5$ is selected from hydrogen and alkyl.
In another embodiment, in Formula (VI), $R^5$ is methyl.
In another embodiment, in Formula (VI), $R^5$ is ethyl.
In another embodiment, in Formula (VI), $R^5$ is straight or branched propyl.
In another embodiment, in Formula (VI), $R^5$ is halogen.
In another embodiment, in Formula (VI), $R^5$ is fluoro.
In another embodiment, in Formula (VI), $R^5$ is chloro.
In another embodiment, in Formula (VI), $R^4$ is hydrogen and $R^5$ is hydrogen.
In another embodiment, in Formula (VI), $R^4$ is hydrogen and $R^5$ is halogen.
In another embodiment, in Formula (VI), $R^4$ is hydrogen and $R^5$ is fluoro.
In another embodiment, in Formula (VI), $R^4$ is hydrogen and $R^5$ is chloro.
In another embodiment, in Formula (VI), $R^4$ is hydrogen and $R^5$ is alkyl.
In another embodiment, in Formula (VI), $R^4$ is hydrogen and $R^5$ is methyl.
In another embodiment, in Formula (VI), $R^4$ is hydrogen and $R^5$ is ethyl.
In another embodiment, in Formula (VI), $R^4$ is hydrogen and $R^5$ is straight or branched propyl.
In another embodiment, in Formula (VI), $R^4$ is halogen and $R^5$ is hydrogen.
In another embodiment, in Formula (VI), $R^4$ is halogen and $R^5$ is halogen.
In another embodiment, in Formula (VI), $R^4$ is fluoro and $R^5$ is fluoro.
In another embodiment, in Formula (VI), $R^4$ is chloro and $R^5$ is chloro.
In another embodiment, in Formula (VI), $R^4$ is halogen and $R^5$ is alkyl.
In another embodiment, in Formula (VI), $R^4$ is halogen and $R^5$ is methyl.
In another embodiment, in Formula (VI), $R^4$ is halogen and $R^5$ is ethyl.
In another embodiment, in Formula (VI), $R^4$ is halogen and $R^5$ is straight or branched propyl.
In another embodiment, in Formula (VI), $R^4$ is fluoro or chloro and $R^5$ is methyl.

In another embodiment, in Formula (VI), z is a double bond and $R^6$ is H or halogen.
In another embodiment, in Formula (VI), $R^6$ is fluoro or chloro.
In another embodiment, in Formula (VI), z is a single bond and $R^6$ is H.
In one embodiment, in Formula (VI), is a compound, or a pharmaceutically acceptable salt, solvate, ester, prodrug, tautomer, or isomer of said compound, said compound having the general structure shown in Formula (VIa):

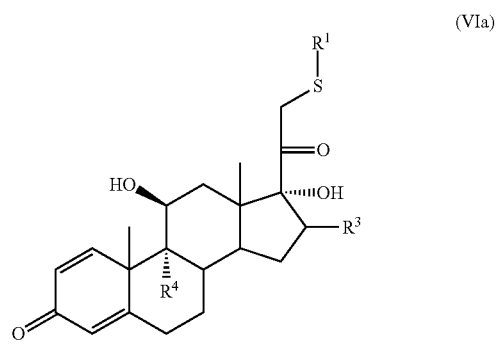

wherein $R^1$, $R^3$, and $R^4$ are selected independently of each other and wherein:
$R^1$ is selected from aryl, 5- or 6-membered heteroaryl, and benzofused 5-membered heteroaryl-,
wherein each said $R^1$ group is unsubstituted or optionally substituted with 1 to 2 substituents, which may be the same or different, each independently selected from halogen, hydroxy, —CN, alkyl, haloalkyl, alkoxy, aryl, —O-aryl and heteroaryl;
$R^3$ is selected from hydrogen and methyl; and
$R^4$ is a hydrogen.

In one embodiment is an 11-keto analog of compounds of Formula (VI), or a pharmaceutically acceptable salt, solvate, ester, tautomer, or isomer thereof, said 11-keto analog having the general formula:

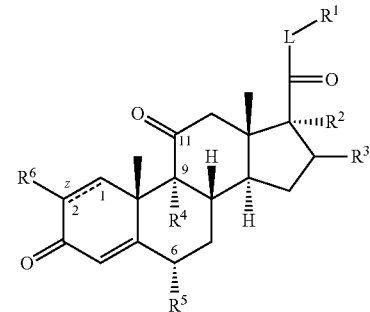

wherein L, $R^1$, $R^2$, $R^3$, $R^4$, $R^5$, $R^6$, and z are selected independently of each other and as defined in Formula (VI) or any of the various embodiments of Formula (VI) and/or Formula (VIa), described herein.

In one embodiment, the present invention provides a compound, or a pharmaceutically acceptable salt, solvate, ester, prodrug, or isomer of said compound, having the general structure shown in Formula (VIII) as described above.

In one embodiment, in Formula (VIII), is a compound having the structural formula:

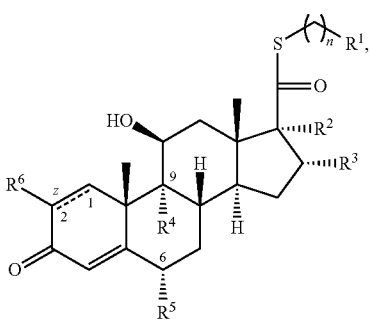

or a pharmaceutically acceptable salt, solvate, ester, prodrug, tautomer, or isomer thereof, wherein L, R¹, R², R³, R⁴, R⁵, R⁶, and z are selected independently and as defined in Formula (VIII).

In one embodiment, in Formula (VIII), R¹ is selected from optionally substituted phenyl, optionally substituted naphthyl, optionally substituted benzyl, optionally substituted heteroaryl, optionally substituted heterocycloalkenyl, optionally substituted benzofused heteroaryl, optionally substituted heteroarylfused heteroaryl, optionally substituted benzofused heterocycloalkenyl, and optionally substituted heteroarylfused heterocycloalkenyl.

In one embodiment, in Formula (VIII), R¹ is selected from phenyl, naphthyl, benzyl-, naphthylalkyl-, 4- to 6-membered heteroarylfused phenyl, 4- to 6-membered heteroarylfused benzyl-, 4- to 6-membered cycloalkylfused phenyl, 4- to 6-membered cycloalkylfused phenyl alkyl-, 4- to 6-membered heteroaryl, 4- to 6-membered heteroarylalkyl-, benzofused 4- to 6-membered heteroaryl, benzofused 4- to 6-membered heteroarylalkyl-, 4- to 6-membered heteroarylfused 4- to 6-membered heteroaryl, 4- to 6-membered heteroarylfused 4- to 6-membered heteroarylalkyl-, 3- to 7-membered cycloalkyl, 3- to 7-membered cycloalkenyl, 3- to 7-membered cycloalkylalkyl-, 3- to 7-membered cycloalkenylalkyl-, 4- to 6-membered heterocycloalkyl, 4- to 6-membered heterocycloalkenyl, 4- to 6-membered heterocycloalkylalkyl-, 4- to 6-membered heterocycloalkenylalkyl-, benzofused 4- to 6-membered heterocycloalkyl, benzofused 4- to 6-membered heterocycloalkenyl, benzofused 4- to 6-membered heterocycloalkylalkyl-, benzofused 4- to 6-membered heterocycloalkenylalkyl-, 4- to 6-membered heteroarylfused 4- to 6-membered heterocycloalkenyl, and 4- to 6-membered heteroarylfused 4- to 6-membered heterocycloalkenylalkyl-, wherein each said hetero ring-containing moiety of R¹ and each said heterofused containing moiety of R¹ independently contains 1, 2, or 3 ring heteroatoms independently selected from any combination of N, O, and S, wherein each said R¹ group is unsubstituted or optionally substituted with from 1 to 5 substituents, which may be the same or different, each independently selected from halogen, hydroxy, —CN, oxo, oxide, alkyl, haloalkyl, haloalkoxy-, hydroxyalkyl-, heteroalkyl, cyanoalkyl-, alkoxy, optionally substituted aryl, optionally substituted —O-aryl, optionally substituted —O-alkyl-aryl, optionally substituted heteroaryl, optionally substituted arylalkyl-, optionally substituted arylalkoxy, —N(R⁷)₂, -alkylN(R⁷)₂, —NC(O)R⁷, —CO₂R⁷, —SO₂R⁷, and —SO₂N(R⁷)₂, wherein said optional substituents are present from 1 to 4 times and may be the same or different, each independently selected from alkyl, halogen, haloalkyl, hydroxyl, —CN, and —N(R¹¹)₂, and wherein the benzo portion of each said benzofused R¹ group is optionally further fused to another ring selected from heteroaryl, cycloalkyl, cycloalkenyl, heterocycloalkyl, and heterocycloalkenyl, and wherein the alkyl-portion of said benzyl-, naphthylalkyl-, 4- to 6-membered heteroarylfused benzyl-, 4- to 6-membered cycloalkylfused benzyl-, 4- to 6-membered heteroarylalkyl-, benzofused 4- to 6-membered heteroarylalkyl-, 4- to 6-membered heteroarylfused 4- to 6-membered heteroarylalkyl-, 3- to 7-membered cycloalkylalkyl-, 4- to 6-membered heterocycloalkylalkyl-, 4- to 6-membered heterocycloalkenylalkyl-, benzofused 4- to 6-membered heterocycloalkenyl, benzofused 4- to 6-membered heterocycloalkylalkyl-, benzofused 4- to 6-membered heterocycloalkenylalkyl-, and 4- to 6-membered heteroarylfused 4- to 6-membered heterocycloalkenylalkyl-, of R¹ is optionally substituted with one or more substituents independently selected from alkyl, haloalkyl, and spirocycloalkyl.

In one embodiment, in Formula (VIII), R¹ is selected from phenyl, naphthyl, benzyl-, heteroarylfused aryl, heteroarylfused arylalkyl-, heteroaryl, heteroarylalkyl-, benzofused heteroaryl-, benzofused heteroarylalkyl-, heteroarylfused heteroaryl-, and heteroarylfused heteroarylalkyl-, wherein each said R¹ group is unsubstituted or optionally substituted with 1 to 2 substituents, which may be the same or different, each substituent being independently selected from halogen, hydroxy, —ON, alkyl, haloalkyl, alkoxy, aryl, —O-aryl and heteroaryl.

In one embodiment, in Formula (VIII), the alkyl-portion of said benzyl-, 4- to 6-membered heteroarylfused benzyl-, 4- to 6-membered cycloalkylfused benzyl-, 4- to 6-membered heteroarylalkyl-, benzofused 4- to 6-membered heteroarylalkyl-, 4- to 6-membered heteroarylfused 4- to 6-membered heteroarylalkyl-, 3- to 7-membered cycloalkylalkyl-, 4- to 6-membered heterocycloalkylalkyl-, 4- to 6-membered heterocycloalkenylalkyl-, benzofused O-5 to 6-membered heterocycloalkenyl, benzofused 4- to 6-membered heterocycloalkylalkyl-, benzofused 4- to 6-membered heterocycloalkenylalkyl-, and 4- to 6-membered heteroarylfused 4- to 6-membered heterocycloalkenylalkyl-, of R¹ is substituted with spirocyclopropyl.

In one embodiment, in Formula (VIII), the alkyl-portion of said benzyl-, naphthylalkyl-, 4- to 6-membered heteroarylfused benzyl-, 4- to 6-membered cycloalkylfused benzyl-, 4- to 6-membered heteroarylalkyl-, benzofused 4- to 6-membered heteroarylalkyl-, 4- to 6-membered heteroarylfused 4- to 6-membered heteroarylalkyl-, 3- to 7-membered cycloalkylalkyl-, 4- to 6-membered heterocycloalkylalkyl-, 4- to 6-membered heterocycloalkenylalkyl-, benzofused 4- to 6-membered heterocycloalkenyl, benzofused 4- to 6-membered heterocycloalkylalkyl-, benzofused 4- to 6-membered heterocycloalkenylalkyl-, and 4- to 6-membered heteroarylfused 4- to 6-membered heterocycloalkenylalkyl-, of R¹ is a moiety of the formula:

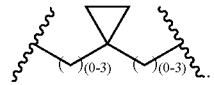

In one embodiment, in Formula (VIII), the alkyl-portion of said benzyl-, naphthylalkyl-, 4- to 6-membered heteroarylfused benzyl-, 4- to 6-membered cycloalkylfused benzyl-, 4- to 6-membered heteroarylalkyl-, benzofused 4- to 6-membered heteroarylalkyl-, 4- to 6-membered heteroarylfused 4- to 6-membered heteroarylalkyl-, 3- to 7-membered cycloalkylalkyl-, 4- to 6-membered heterocycloalkylalkyl-, 4- to 6-membered heterocycloalkenylalkyl-, benzofused 4- to 6-membered heterocycloalkenyl, benzofused 4- to 6-membered heterocycloalkylalkyl-, benzofused 4- to 6-membered heterocycloalkenylalkyl-, and 4- to 6-membered heteroarylfused 4- to 6-membered heterocycloalkenylalkyl-, of $R^1$ is a moiety of the formula:

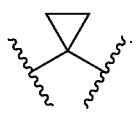 [SMILES: *C1(*)CC1]

In one embodiment, in Formula (VIII), the alkyl-portion of said benzyl-, naphthylalkyl-, 4- to 6-membered heteroarylfused benzyl-, 4- to 6-membered cycloalkylfused benzyl-, 4- to 6-membered heteroarylalkyl-, benzofused 4- to 6-membered heteroarylalkyl-, 4- to 6-membered heteroarylfused 4- to 6-membered heteroarylalkyl-, 3- to 7-membered cycloalkylalkyl-, 4- to 6-membered heterocycloalkylalkyl-, 4- to 6-membered heterocycloalkenylalkyl-, benzofused 4- to 6-membered heterocycloalkenyl, benzofused 4- to 6-membered heterocycloalkylalkyl-, benzofused 4- to 6-membered heterocycloalkenylalkyl-, and 4- to 6-membered heteroarylfused 4- to 6-membered heterocycloalkenylalkyl-, of $R^1$ is a moiety of the formula:

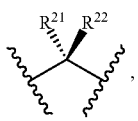

wherein one of $R^{21}$ and $R^{22}$ is hydrogen and the other is selected from $C_1$-$C_2$ alkyl, $C_1$-$C_2$ haloalkyl, fluorine, and hydroxyl. In one such embodiment, one of $R^{21}$ and $R^{22}$ is hydrogen and the other is selected from methyl and —$CF_3$.

In one embodiment, in Formula (VIII), $R^1$ is unsubstituted.

In one embodiment, in Formula (VIII), $R^1$ is substituted with from 1 to 4 substituents.

In one embodiment, in Formula (VIII), $R^1$ is substituted with from 1 to 3 substituents.

In one embodiment, in Formula (VIII), $R^1$ is substituted with from 1 to 2 substituents.

In one embodiment, in Formula (VIII), $R^1$ is substituted with 1 substituent.

In one embodiment, in Formula (VIII), $R^1$ is substituted with from 1 to 2 substituents, which may be the same or different, each independently selected from halogen, hydroxy, —CN, alkyl, haloalkyl, optionally substituted aryl, optionally substituted heteroaryl, and optionally substituted arylalkoxy.

In one embodiment, in Formula (VIII), $R^1$ is selected from phenyl, naphthyl, benzyl, heteroarylfused aryl, heteroarylfused arylalkyl-, heteroaryl, heteroarylalkyl-, benzofused heteroaryl-, benzofused heteroarylalkyl-, heteroarylfused heteroaryl-, and heteroarylfused heteroarylalkyl-, wherein each said $R^1$ group is unsubstituted or optionally substituted with from 1 to 2 substituents, which may be the same or different, each substituent being independently selected from halogen, hydroxy, —CN, alkyl, haloalkyl, alkoxy, aryl, —O-aryl and heteroaryl.

Non-limiting examples of $R^1$, in Formula (VIII), include:

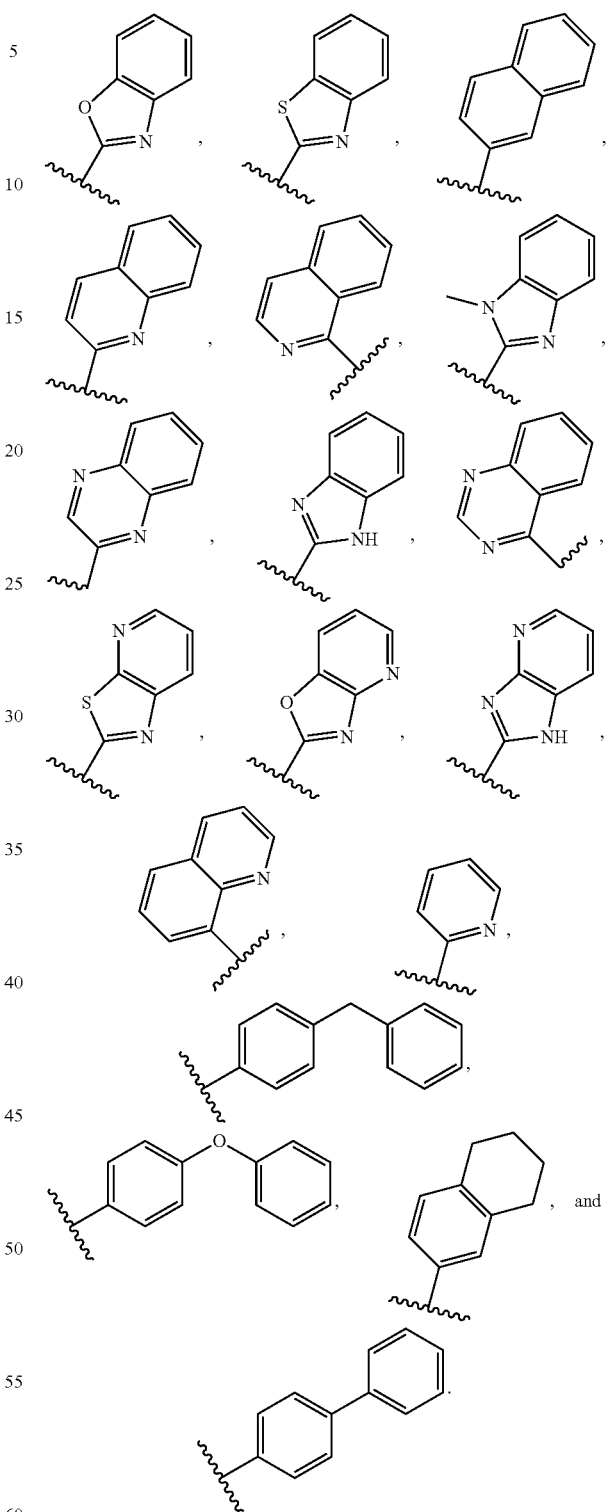

In one embodiment, in Formula (VIII), $R^2$ is selected from —OH and —OC(O)$R^9$.

In one embodiment, in Formula (VIII), $R^9$ is unsubstituted.

In one embodiment, in Formula (VIII), $R^9$ is substituted with from 1 to 3 substituents.

In one embodiment, in Formula (VIII), $R^9$ is substituted with from 1 to 2 substituents.

In one embodiment, in Formula (VIII), $R^9$ is substituted with 1 substituent.

In one embodiment, in Formula (VIII), $R^9$ is substituted with from 1 to 2 substituents, which may be the same or different, each independently selected from alkyl, halogen, and haloalkyl.

In one embodiment, in Formula (VIII), $R^9$ is unsubstituted or substituted heterocycloalkyl.

In one embodiment, in Formula (VIII), $R^9$ is unsubstituted or substituted heterocycloalkenyl.

In one embodiment, in Formula (VIII), $R^9$ is unsubstituted or substituted heteroaryl.

In one embodiment, in Formula (VIII), $R^2$ is

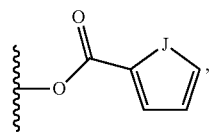

wherein J is selected from O, S, and N, or the oxides thereof.

In one embodiment, in Formula (VIII), $R^2$ is

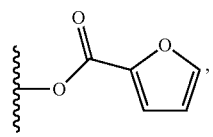

In one embodiment, in Formula (VIII), $R^2$ is a moiety selected from

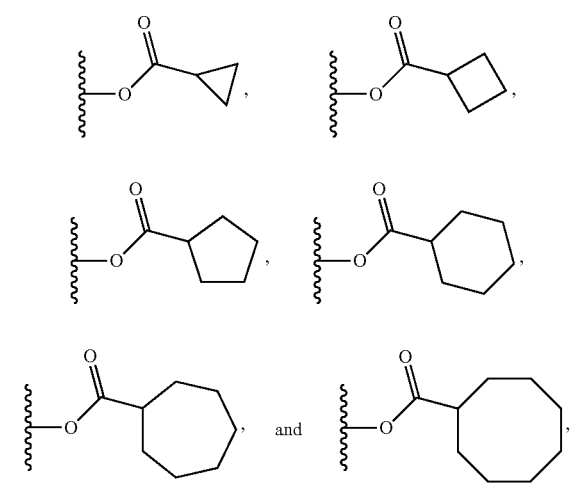

wherein the cycloalkyl portion of said moiety is unsubstituted or substituted with from 1 to 4 substituents independently selected from alkyl, halogen, haloalkyl, hydroxyl, —N($R^7$)$_2$, and CN.

In one embodiment, in Formula (VIII), $R^2$ is

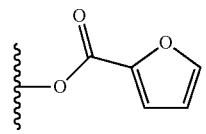 [SMILES: *OC(=O)c1ccco1]

and $R^3$ is H.

In one embodiment, in Formula (VIII), $R^2$ is

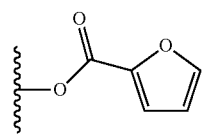

and $R^3$ is methyl.

In one embodiment, in Formula (VIII), $R^3$ is selected from hydrogen, hydroxyl, and methyl.

In one embodiment, in Formula (VIII), $R^3$ is selected from hydrogen and methyl.

In one embodiment, in Formula (VIII), $R^3$ is hydrogen.

In one embodiment, in Formula (VIII), $R^3$ is hydroxy.

In one embodiment, in Formula (VIII), $R^3$ is alkyl.

In one embodiment, in Formula (VIII), $R^3$ is methyl.

In one embodiment, in Formula (VIII), $R^3$ is ethyl.

In one embodiment, in Formula (VIII), $R^3$ is straight or branched propyl.

In one embodiment, in Formula (VIII), $R^2$ is $-OR^8$, wherein $R^8$ is hydrogen, and $R^3$ is methyl.

In one embodiment, in Formula (VIII), $R^2$ is —$OR^8$, wherein $R^8$ is hydrogen, and $R^3$ is hydrogen.

In one embodiment, in Formula (VIII), $R^2$ and $R^3$ are taken together form a moiety of formula 2:

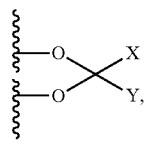

2 wherein X and Y are each alkyl. In one such embodiment, X and Y are each methyl. In another such embodiment, X and Y are each ethyl. In another such embodiment, X is methyl and Y is ethyl. In another such embodiment, X is hydrogen and Y is selected from alkyl, haloalkyl, and cycloalkyl. In another such embodiment, X is hydrogen and Y is selected from methyl. In another such embodiment, X is hydrogen and Y is selected from ethyl. In another such embodiment, X is hydrogen and Y is selected from straight or branched propyl. In another such embodiment, X is hydrogen and Y is selected from straight or branched butyl. In another such embodiment, X is hydrogen and Y is selected from haloalkyl. In another such embodiment, X is hydrogen and Y is selected from cyclopropyl.

In one embodiment, in Formula (VIII), $R^2$ and $R^3$ are taken together form a moiety of formula:

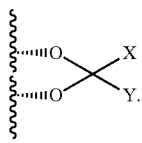

In one embodiment, in Formula (VIII), $R^2$ and $R^3$ are taken together form a moiety of formula:

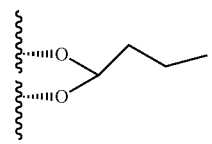

In one embodiment, in Formula (VIII), $R^2$ and $R^3$ are taken together form a moiety of formula:

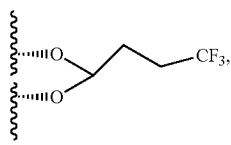

In one embodiment, in Formula (VIII), $R^2$ and $R^3$ are taken together form a moiety selected from:

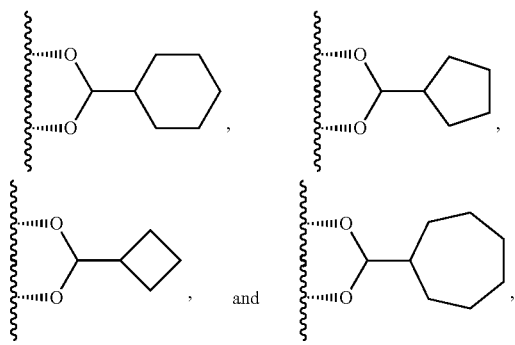

wherein said cycloalkyl ring is unsubstituted or substituted with from 1 to 4 substituents independently selected from alkyl, halogen, haloalkyl, hydroxyl, —N($R^7$)$_2$, and CN.

In one embodiment, in Formula (VIII), $R^2$ and $R^3$ are taken together form a moiety of the formula:

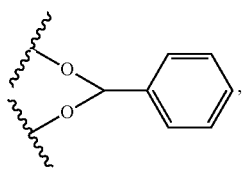

wherein the phenyl group of said moiety is unsubstituted or substituted with from 1 to 4 substituents independently selected from alkyl, halogen, haloalkyl, hydroxyl, —N($R^7$)$_2$, and CN.

In one embodiment, in Formula (VIII), $R^2$ and $R^3$ are taken together form a moiety of formula 3:

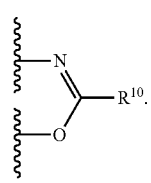

In one such embodiment, $R^{10}$ is H. In another such embodiment, $R^{10}$ is alkyl. In another such embodiment, $R^{10}$ is methyl. In another such embodiment, $R^{10}$ is ethyl. In another such embodiment, $R^{10}$ is straight or branched propyl.

In another embodiment, in Formula (VIII), $R^4$ is hydrogen.
In another embodiment, in Formula (VIII), $R^4$ is halogen.
In another embodiment, in Formula (VIII), $R^4$ is fluoro.
In another embodiment, in Formula (VIII), $R^4$ is chloro.
In another embodiment, in Formula (VIII), $R^5$ is selected from hydrogen and alkyl.
In another embodiment, in Formula (VIII), $R^5$ is methyl.
In another embodiment, in Formula (VIII), $R^5$ is ethyl.
In another embodiment, in Formula (VIII), $R^5$ is straight or branched propyl.
In another embodiment, in Formula (VIII), $R^5$ is halogen.
In another embodiment, in Formula (VIII), $R^5$ is fluoro.
In another embodiment, in Formula (VIII), $R^5$ is chloro.
In another embodiment, in Formula (VIII), $R^4$ is hydrogen and $R^5$ is hydrogen.
In another embodiment, in Formula (VIII), $R^4$ is hydrogen and $R^5$ is halogen.
In another embodiment, in Formula (VIII), $R^4$ is hydrogen and $R^5$ is fluoro.
In another embodiment, in Formula (VIII), $R^4$ is hydrogen and $R^5$ is chloro.
In another embodiment, in Formula (VIII), $R^4$ is hydrogen and $R^5$ is alkyl.
In another embodiment, in Formula (VIII), $R^4$ is hydrogen and $R^5$ is methyl.
In another embodiment, in Formula (VIII), $R^4$ is hydrogen and $R^5$ is ethyl.
In another embodiment, in Formula (VIII), $R^4$ is hydrogen and $R^5$ is straight or branched propyl.
In another embodiment, in Formula (VIII), $R^4$ is halogen and $R^5$ is hydrogen.
In another embodiment, in Formula (VIII), $R^4$ is halogen and $R^5$ is halogen.
In another embodiment, in Formula (VIII), $R^4$ is fluoro and $R^5$ is fluoro.
In another embodiment, in Formula (VIII), $R^4$ is chloro and $R^5$ is chloro.
In another embodiment, in Formula (VIII), $R^4$ is halogen and $R^5$ is alkyl.
In another embodiment, in Formula (VIII), $R^4$ is halogen and $R^5$ is methyl.
In another embodiment, in Formula (VIII), $R^4$ is halogen and $R^5$ is ethyl.
In another embodiment, in Formula (VIII), $R^4$ is halogen and $R^5$ is straight or branched propyl.

In another embodiment, in Formula (VIII), R⁴ is fluoro or chloro and R⁵ is methyl.

In another embodiment, in Formula (VIII), z is a double bond and R⁶ is H or halogen.

In another embodiment, in Formula (VIII), z is a single bond and R⁶ is H.

In another embodiment, in Formula (VIII), R⁶ is fluoro or chloro.

In one embodiment, the present invention provides a pharmaceutical composition formulated for oral administration, which composition comprises a compound of Formula (VIII), wherein R¹ is selected from benzofused 5- or 6-membered heteroaryl, benzofused 5- or 6-membered heterocycloalkenyl, heteroarylfused 5- or 6-membered heteroaryl, and heteroarylfused 5- or 6-membered heterocycloalkenyl, R² is —OR⁸, wherein R⁸ is hydrogen, R³ is hydrogen or methyl, R⁴ and R⁵ are both hydrogen, L is —NR¹¹—, and z is a double bond.

In one embodiment, the present invention provides a pharmaceutical composition formulated for inhaled administration, which composition comprises a compound of Formula (VIII), wherein R⁴, R⁵, and R⁶ are hydrogen, R² and R³ are joined to form a moiety having the formula

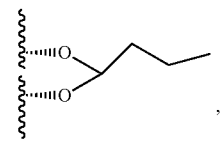

L is —CH₂O—, and z is a double bond. In one such embodiment, R¹ is benzofused aryl.

In one embodiment, in Formula (VIII), the present invention provides a compound, or a pharmaceutically acceptable salt, solvate, ester, prodrug, tautomer, or isomer of said compound, said compound having the general structure shown in Formula (VIIIa):

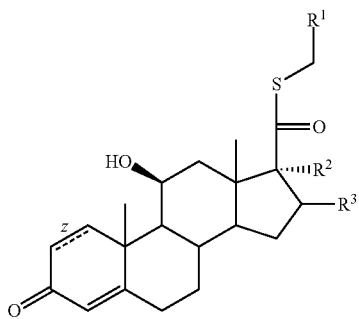

(VIIIa)

wherein R¹, R², R³, and z are selected independently of each other and wherein:

R¹ is selected from phenyl, naphthyl, heteroarylfused aryl-, heteroaryl, benzofused heteroaryl-, and heteroarylfused heteroaryl-, wherein each said R¹ group is unsubstituted or optionally substituted with 1 to 3 substituents, which may be the same or different, each substituent being independently selected from halogen, hydroxy, —CN, alkyl, haloalkyl, alkoxy, aryl, —O-aryl and heteroaryl;

R² is —OC(O)R¹¹;

R³ is selected from hydrogen or methyl;

R¹¹ is selected from aryl, heteroaryl and cycloalkyl, wherein each said aryl, said heteroaryl, and said cycloalkyl is unsubstituted or optionally substituted with from 1 to 2 substituents independently selected from the group consisting of alkyl, halogen, haloalkyl, hydroxy and —CN; and z (the dotted line) represents a single or double bond.

In one embodiment, in Formula (VIIIa), the present invention provides a compound, or a pharmaceutically acceptable salt, solvate, ester, prodrug, tautomer, or isomer of said compound, said compound having the general structure shown in Formula (VIIIa.1):

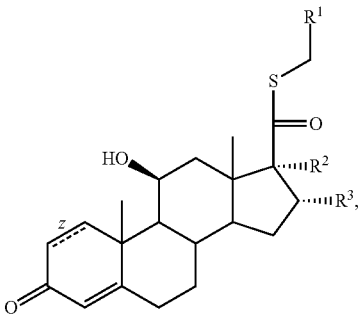

(VIIIa.1)

wherein each of R¹, R², and R³ is selected independently and wherein:

R¹ is selected from heteroarylfused aryl-, heteroaryl, benzofused heteroaryl-, and heteroarylfused heteroaryl-, wherein each said R¹ group is unsubstituted or optionally substituted with 1 to 2 substituents, which may be the same or different, each substituent being independently selected from halogen, hydroxy, —CN, alkyl, haloalkyl, alkoxy, aryl, —O-aryl and heteroaryl; and R² is —OC(O)R¹¹;

R³ is selected from hydrogen or methyl;

R¹¹ is heteroaryl; and z (the dotted line) represents a single or double bond.

In one embodiment, in Formula (VIII), is a compound, or a pharmaceutically acceptable salt, solvate, ester, tautomer, or isomer thereof, said compound having a general structure shown in Formula (VIIIb):

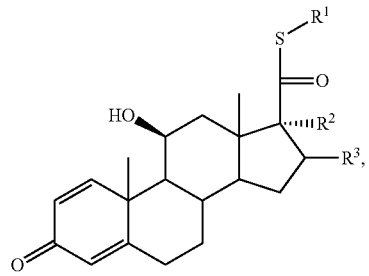

(VIIIb)

wherein each of R¹, R², and R³ is selected independently and wherein:

R¹ is selected from heteroarylfused aryl-, heteroaryl, benzofused heteroaryl-, and heteroarylfused heteroaryl-, wherein each said R¹ group is unsubstituted or optionally substituted with 1 to 2 substituents, which may be the same or different, each substituent being independently selected from halogen, hydroxy, —CN, alkyl, haloalkyl, alkoxy, aryl, —O-aryl and heteroaryl;

R² and R³ taken together form a moiety of formula 2:

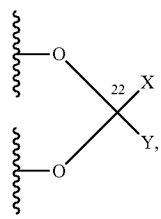

2 wherein each of X and Y is independently as defined in the various embodiments described for Formula I.

In one embodiment is an 1'-keto analog of compounds of Formula (VIII), or a pharmaceutically acceptable salt, solvate, ester, tautomer, or isomer thereof, said 11-keto analog having the general formula:

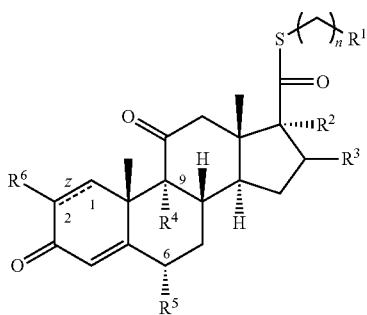

wherein n, R¹, R², R³, R⁴, R⁵, R⁶, and z are selected independently of each other and as defined in Formula (VIII) or any of the various embodiments of Formula (VIII) and/or Formulas (VIIIa) and (VIIIb), described herein.

PREPARATIVE EXAMPLES

Generally, the compounds of the invention can be prepared by a variety of methods well known to those skilled in the art, for example, by the methods as outlined below. The examples should not be construed to limit the scope of the disclosure. Alternative mechanistic pathways and analogous structures will be apparent to those skilled in the art.

Compounds of the current invention are, most commonly, prepared through the conversion of C-21 hydroxy group on commercially available steroid cores into a leaving group (e.g., methanesulfonate, trifluoromethanesulfonate), followed by reaction with appropriate nucleophile (e.g., thiol, alcohol or amine) (see Scheme 1). In cases where L is —NH— or —NR¹⁴R¹⁵ the amide is accessed through the corresponding C-20 carboxylic acid, which, in turn, is obtained through the oxidation of the corresponding C-21 alcohol, either directly (e.g., periodic acid) or through the C-20, C-21 diol (see Scheme 2). Subsequent conversion into amides is accomplished through standard amidation methods known to those skilled in the art. In addition, conversion of C-20 carboxylic acids into the corresponding C-20 thioacids (see Scheme 2a) is well precedented, as, for example, in the case of fluticasone furoate, preparation of which has been described in much detail (WO 200212265 and WO 2007144363). The thioacid function can then be alkylated with alkyl, arylalkyl or heteroarylalkyl halides to provide various thioesters. Replacement of hydrogen sulfide with the anion of mercaptothiol in the first step could produce an analog without the alkylene group between sulfur and aryl or heteroaryl group. C-21 amine and its derivatives can be accessed via C-21 aldehyde and C-21 oxime as shown in Scheme 3. Alternatively, C-21 mesylate group of the intermediate depicted in Scheme 1 can be displaced with azide anion, followed by reduction of the azido group into amino group, similarly to the sequence described in Chinese patent No. CN 1414008, incorporated herein by reference. Commercially available steroid cores can be modified as needed, as described in the examples below.

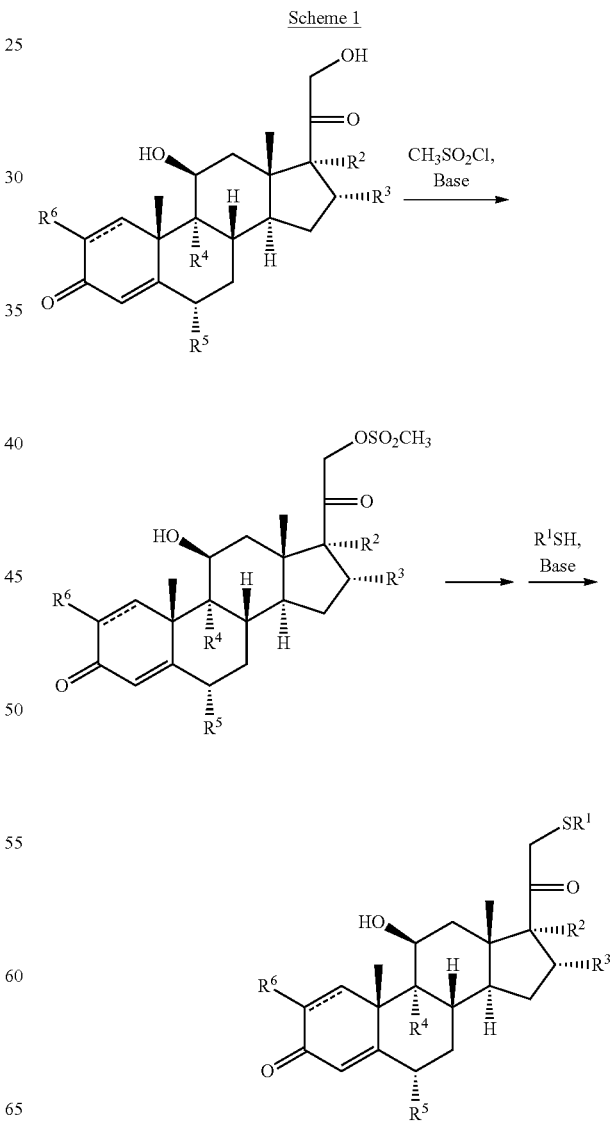

Scheme 1

Scheme 2
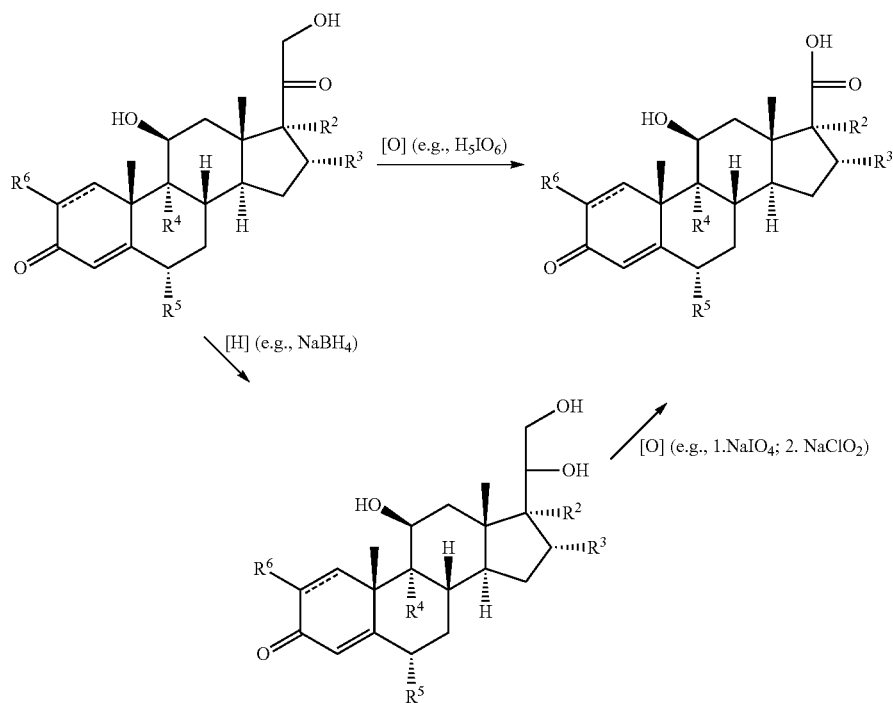
Scheme 2a
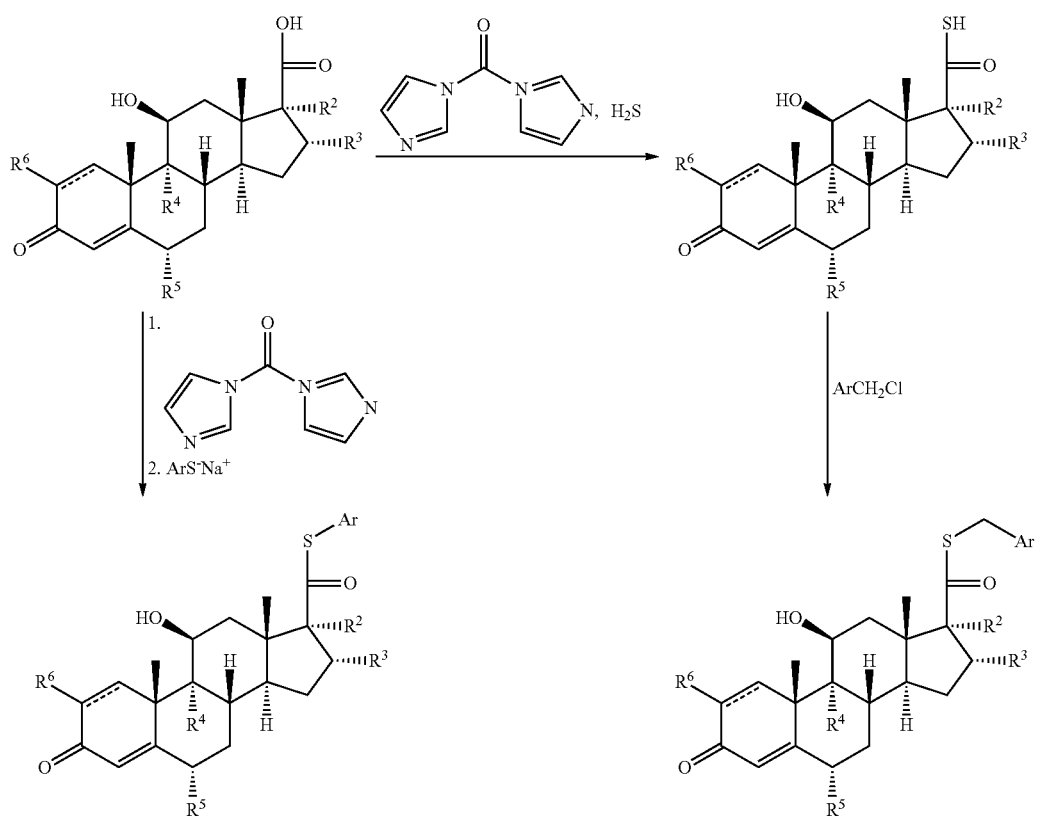

103

Scheme 3

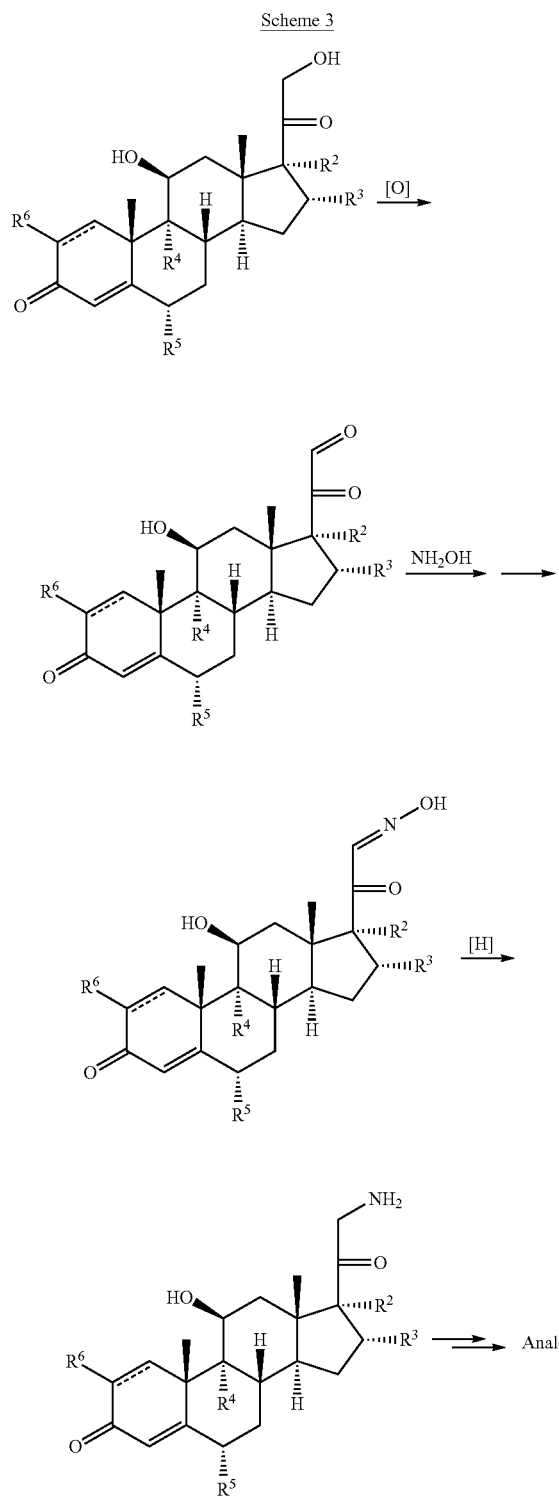

For purposes of these preparative schemes only, a simplified nomenclature is used to depict the structures of compounds. The stereochemistry of methyl groups at the C-10 and C-13 positions of the glucocorticoid core is not shown explicitly, but is understood to mean "β", identical to hydrocortisone (see FIG. 1). Similarly, stereochemistry of hydrogen atoms at the C-8 and C-14 positions is understood to depict "β" and "α" respectively.

104

FIG. 1

Hydrocortisone

Example 1

Step 1

A solution of the hydrocortisone 11 (5 g, 0.0138 mol) in dichloromethane (100 mL) was treated with diisopropylethylamine (8.9 g, 0.0691 mol) at 0° C. The reaction mixture was allowed to stir for 5 minutes; methane sulfonyl chloride (2.9 g, 0.02486 mol) was added drop wise at 0° C. and allowed to stir for 4-6 hours. The reaction mixture was diluted with dichloromethane, taken in to a separatory funnel and washed with dilute HCl, water, brine and dried over anhydrous sodium sulfate. Removal of the solvent gave the crude mesylate, which was purified by using column chromatography using dichloromethane and methanol (20:1) to afford the mesylate 12 as a crystalline solid. Yield=5.5 g (82%).

Step 2

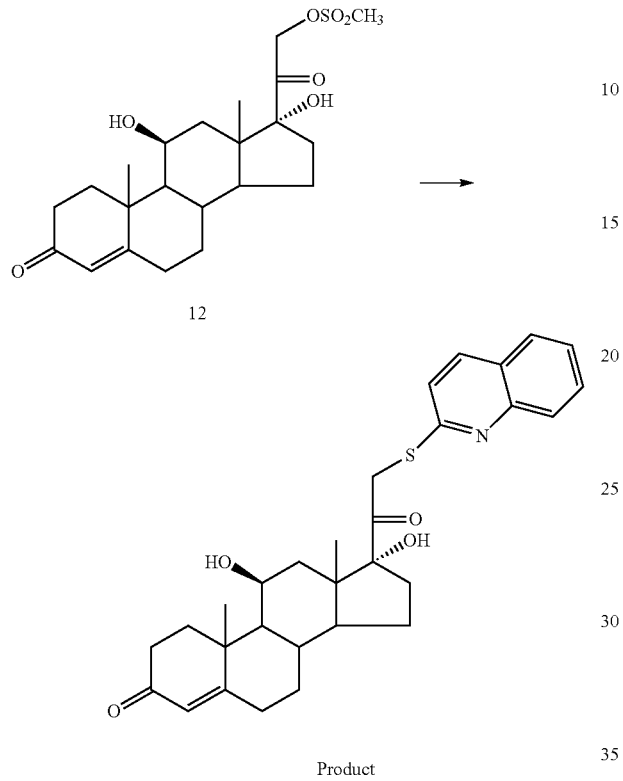

12

Product

A solution of the hydrocortisone-21-mesylate 12 (0.25 g, 0.000568 mol), 2-mercaptoquinoline (0.132 g, 0.000909 mol) and potassium carbonate (0.392 g, 0.00284 mmol) in acetone (10 ml) was refluxed for 12 hours. The reaction mixture was cooled to room temperature, filtered and the filtrate was concentrated to give the crude product. The crude Product was purified by column chromatography or preparative thin layer chromatography using dichloromethane and methanol (10:1). Yield=0.28 g (97%). MH+ 506

Example 2

Step 1

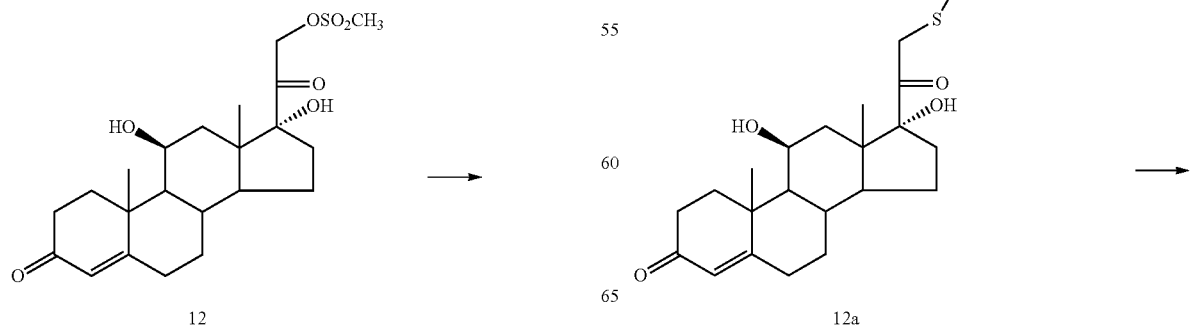

12            12a

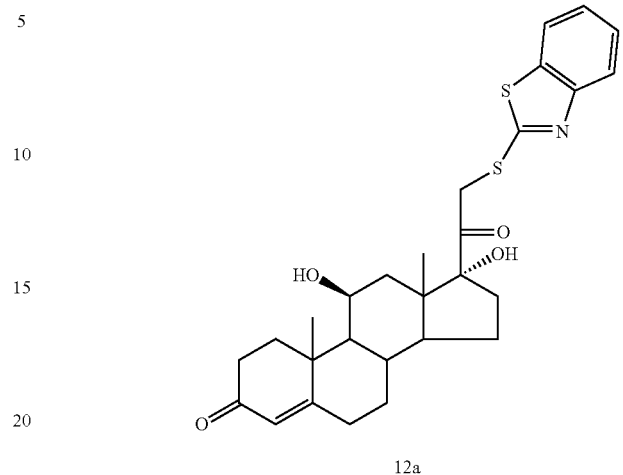

12a

To a solution of the hydrocortisone-21-mesylate 12 (10 g, 0.0227 mol) in dichloromethane was added diisopropylethyamine (14.65 g, 0.114 mol) dropwise at 0° C. The reaction mixture was then treated with the 2-mercaptobenzothiazole (5.69 g, 0.0343 mol) and stirring was continued for 6-12 hours at room temperature. The reaction mixture was diluted with dichloromethane, washed with dilute hydrochloric acid, water, and brine, dried over anhydrous sodium sulfate. Filtration and removal of solvent afforded the crude product, which was purified by using column chromatography or preparative thin layer chromatography using dichloromethane and methanol solvent system (20:1) to afford compound 12a as a white crystalline solid. Yield=8.6 g (73%).

Step 2

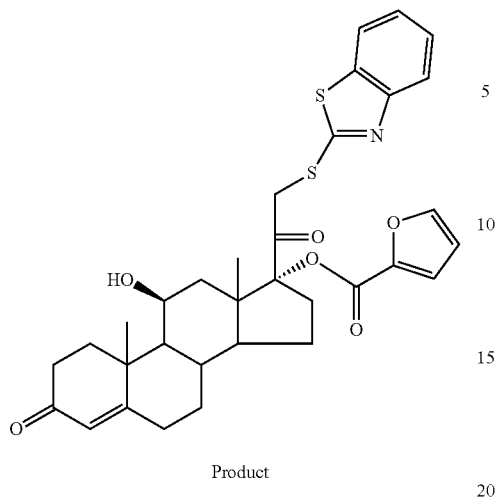

Product

To a solution of the DMAP (4.58 g, 0.0375 mol) in methylene chloride (20 ml) was added dropwise furoyl chloride (0.67 g, 0.00516 mol) at 0° C. The mixture was then treated with a solution of compound 12a (2.4 g, 0.00469 mmol) in dichloromethane (5 ml) dropwise. The reaction mixture was stirred for 12 hours, solvent was removed and the crude product was purified by either column chromatography or preparative thin layer chromatography using dichloromethane and methanol (20:1) to afford the furoate Product as a white crystalline solid. Yield=1.65 g (58%) MH+ 606

Example 3

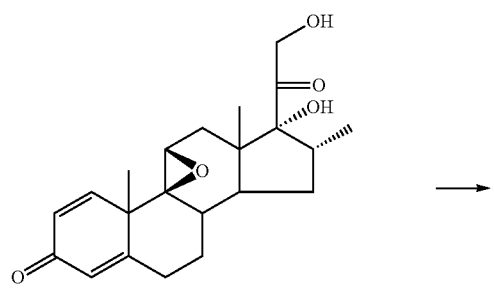

13

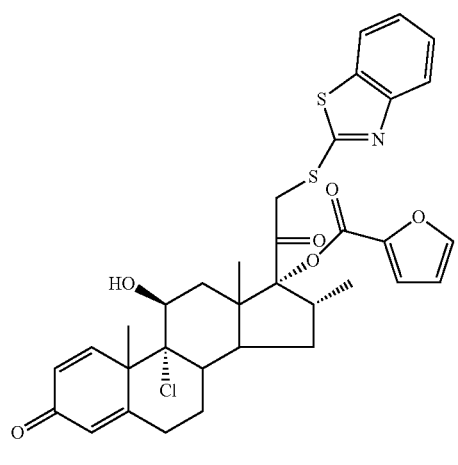

Product

Compound 13 has been described in the literature (e.g., Fu, X. et al., *Organic Process Research and Development* 2001, 5, 376-382) and is commercially available.

Compound 13 was converted to benzothiazole 14 using procedures of step 1 of Example 1, followed by the procedures of steps 1 and 2 of Example 2.

To a solution of the epoxy compound 14 (5.0 g, 0.00813 mol) while stirring in acetic acid (15 mL) was added at 0° C. a solution of HCl in acetic acid (1M, 16.26 mL) and stirred for 3-5 hours while warming to room temperature. Water was added to the reaction mixture; the precipitate was collected by filtration, dried and recrystallized from dichloromethane and methanol to afford the compound Product. Yield=4.6 g (87%) MH+ 652

Example 4

Step 1

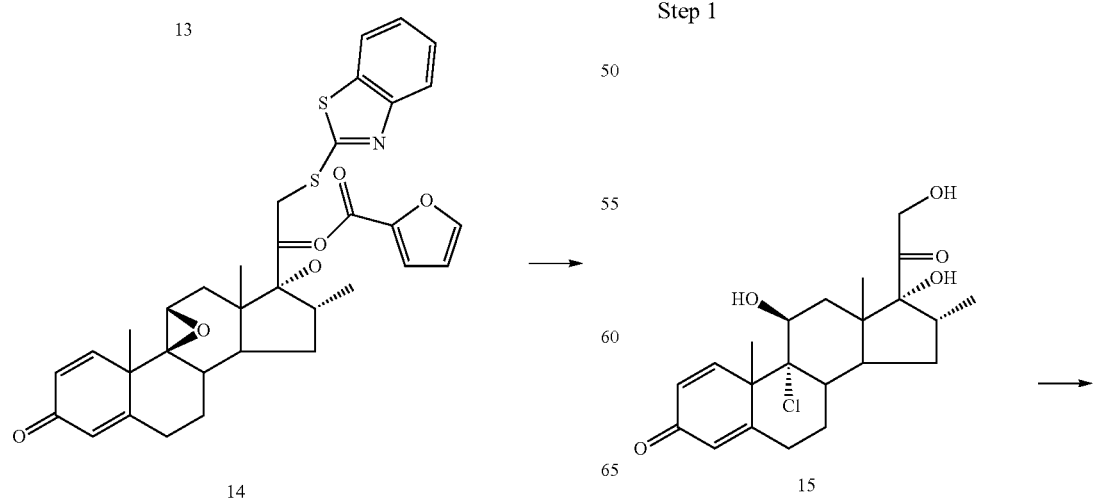

14

15

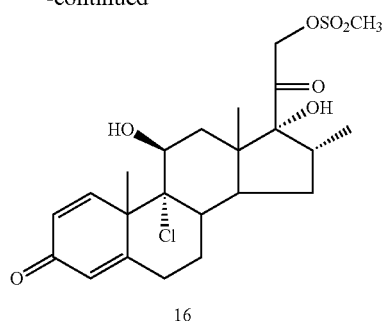

16

Compound 15 (i.e., icomethasone) has been described in the literature (e.g., WO 2001055171).

Compound 15 was converted to mesylate 16 using the same procedure as in step 1 of Example 1.

Step 2

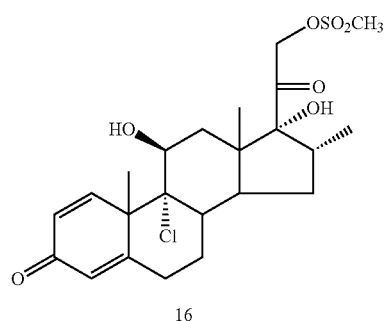

16

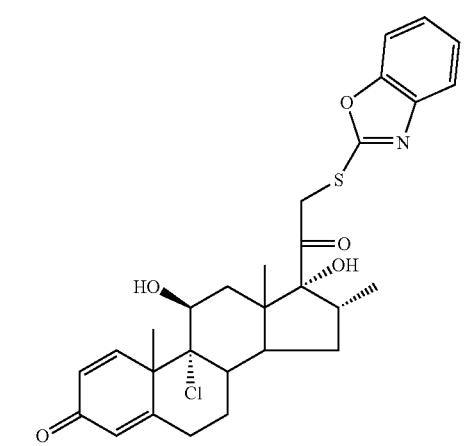

17

A solution of the mesylate 16 (0.3 g, 0.0006172 mol), 2-mercaptobenzoxazole (0.15 g, 0.000987 mol) and potassium carbonate (0.426 g, 0.00308 mol) in acetone (20 ml) was refluxed for 12 hours. The reaction mixture was cooled to room temperature, filtered and the filtrate was concentrated to give the crude product. The crude product was purified by column chromatography or preparative thin layer chromatography using dichloromethane and methanol (20:1), afforded 17 as a white crystalline solid. Yield=0.15 g (45%) MH$^+$ 636

Step 3

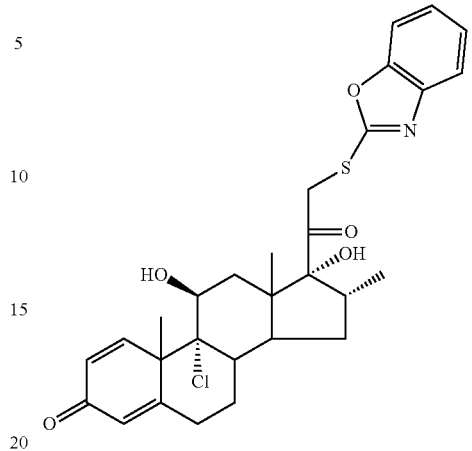

17

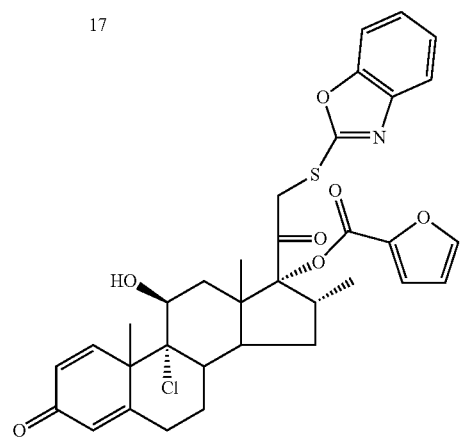

Product

To a solution of the DMAP (0.233 g, 0.00191 mol) in methylene chloride (10 ml) was added dropwise furoyl chloride (0.034 g, 0.0002638 mol) at 0° C. The mixture was then treated with a solution of the compound 17 (130 g, 0.0002398 mmol) in dichloromethane (5 ml) dropwise. The reaction mixture was stirred for 12 hours, solvent was removed and the crude product was purified by preparative thin layer chromatography using dichloromethane and methanol (20:1) to afford the furoate Product as a white crystalline solid. Yield=0.095 g (62%) MH$^+$ 636

Example 5

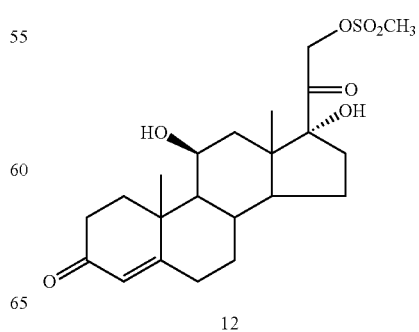

12

-continued

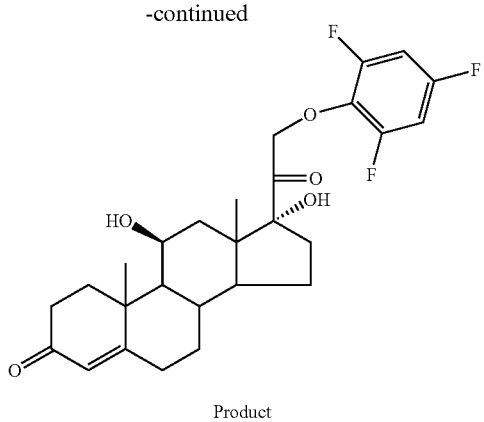

Product

Compound 12 was prepared as described in step 1 of Example 1.

To the solution of 12 (0.05 g, 0.11 mmol) and 2,4,6-trifluorophenol (0.016 g, 0.11 mmol) in 5 ml of acetone was added $K_2CO_3$ (0.06 g, 0.44 mmol). After stirring at 60° C. under $N_2$ for 20 h, the solvent was removed, the products were extracted with EtOAc and $H_2O$, washed with brine, dried over $Na_2SO_4$, and filtered. The filtrate was concentrated and purified by flash chromatography (30% EtOAc/Hexane) to give the Product compound. Yield: 92%. $MH^+$ 493

Example 6

Step 1

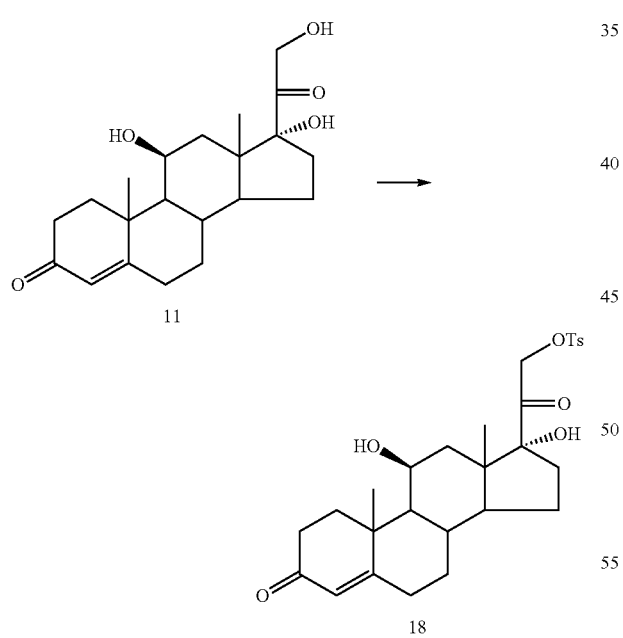

To the solution of 11 (1.01 g, 2.91 mmol) in 20 ml of $CH_2Cl_2$ was added $Et_3N$ (12 ml, 8.73 mmol), TsCl (0.83 g, 4.36 mmol) and DMAP (0.01 g). After stirring at room temperature under $N_2$ for 2 h, the reaction was quenched by adding $H_2O$, the mixture was extracted with $CH_2Cl_2$, washed with brine, dried over $Na_2SO_4$, filtered. The filtrate was concentrated and purified by flash chromatography (25% EtOAc/Hexane) to give 18. Yield: 61%.

Step 2

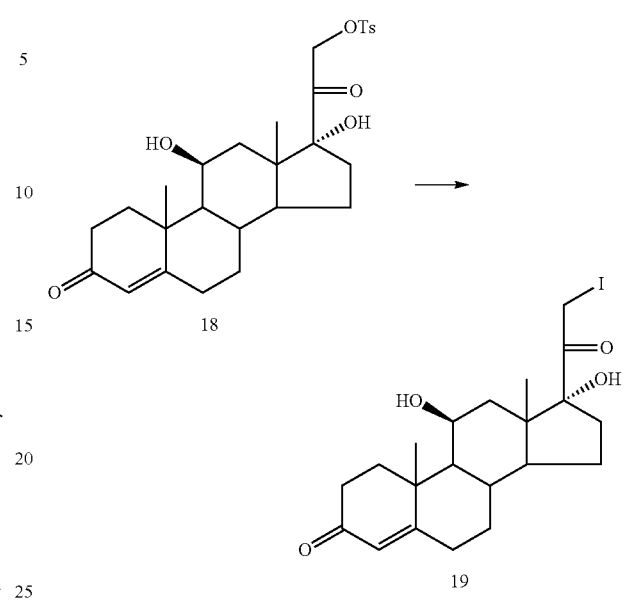

To the solution of 18 (0.53 g, 1.03 mmol) in 20 ml of acetone was added NaI (0.77 g, 5.15 mmol). After refluxing under $N_2$ for 20 h, the mixture was cooled to room temperature and filtered. The filtrate was concentrated and dissolved in EtOAc, washed with $H_2O$, brine, dried over $Na_2SO_4$, filtered to give 19. Yield: 88%.

Step 3

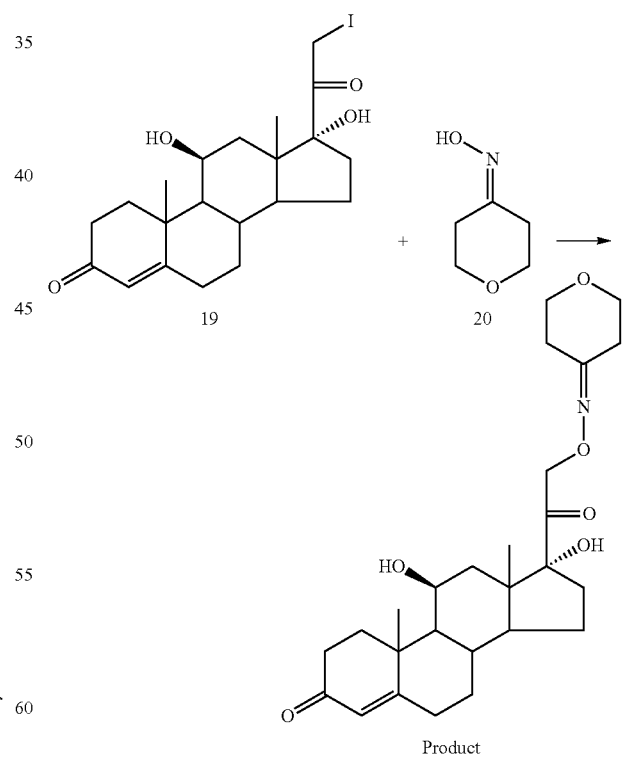

Compound 20 was prepared by adding pyridine (0.75 mL, 9.27 mmol) to the suspension of tetrahydropyran-4-one (0.50 g, 5.00 mmol) and hydroxylamine hydrochloride salt (282 mg, 5.49 mmol) in EtOH (5 mL). The resulting mixture was stirred at room temperature overnight. The volatile was removed and the crude mixture was purified by silica gel column chromatography, eluted first with 10% EtOAc/DCM then 30% EtOAc/DCM, to give compound 20 (0.45 g, 78%) as a white solid.

To the solution of 20 (0.037 g, 0.32 mmol) in 1 ml of DMF was added Cs$_2$CO$_3$ (0.21 g, 0.64 mmol). After stirring at 60° C. under N$_2$ for 2 h, the mixture was cooled to 0° C. by ice-H$_2$O bath, 19 (0.075 g, 0.16 mmol) was added. After stirring at 0° C. under N$_2$ for 0.5 h, the mixture was filtered, the filtrate was purified by reverse phase HPLC to give the Product compound. Yield: 27%. MH$^+$ 460

Example 7

Steps 1-2

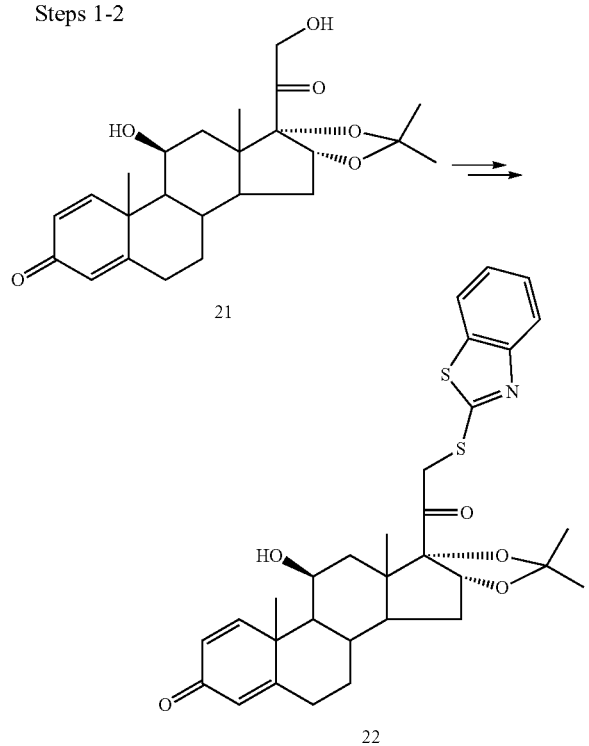

Compound 22 was prepared from desonide 21 in two steps using procedures of step 1 and 2 of Example 1.

Step 3

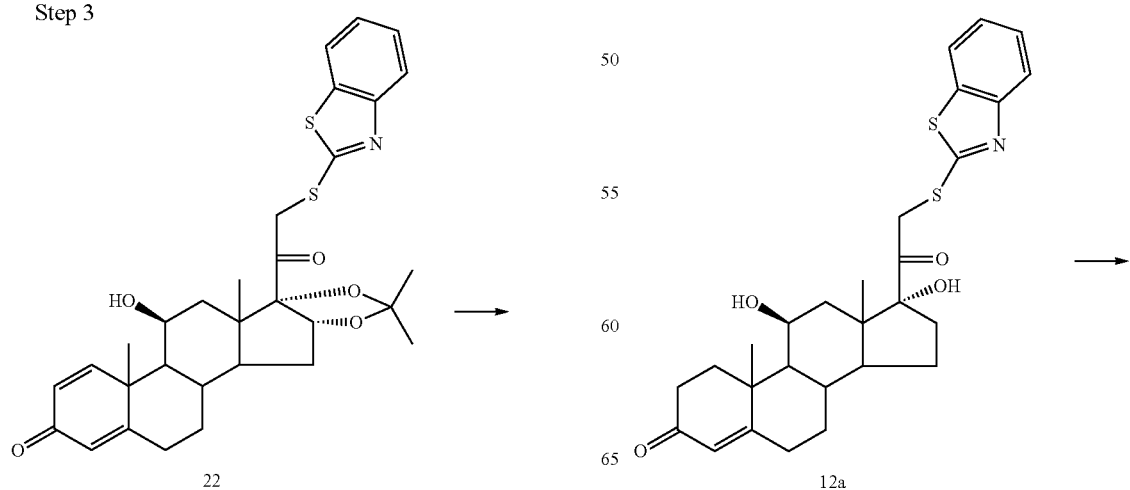

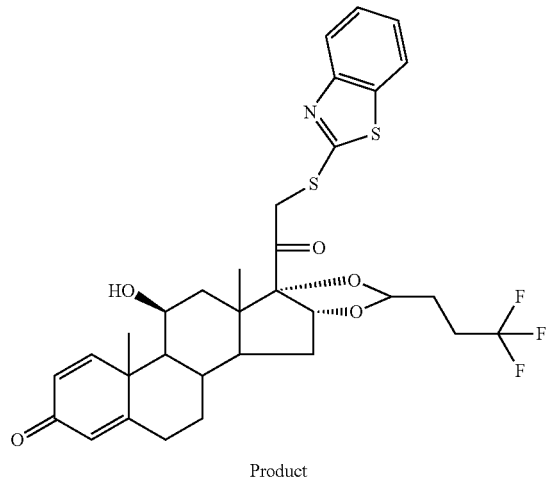

Product

To a 0° C. solution of 22 (300 mg; 0.53 mmol) in 7 mL of chloroform was added 4,4,4-trifluorobutyraldehyde (134 mg; 1.06 mmol) and HClO$_4$ (0.21 mL of 70 wt. % aqueous solution; 2.39 mmol). The reaction mixture was stirred at 0° C. for 3 h and slowly warmed to room temperature. Aqueous NaHCO$_3$ was added, followed by K$_2$CO$_3$ to adjust pH to 10. The product was extracted with CH$_2$Cl$_2$. Organic phase was concentrated, and the residue was flash chromatographed (0.5-1% MeOH/CH$_2$Cl$_2$) to produce 121 mg of the Product compound as a yellowish foam. MH$^+$ 634

Example 8

115

-continued

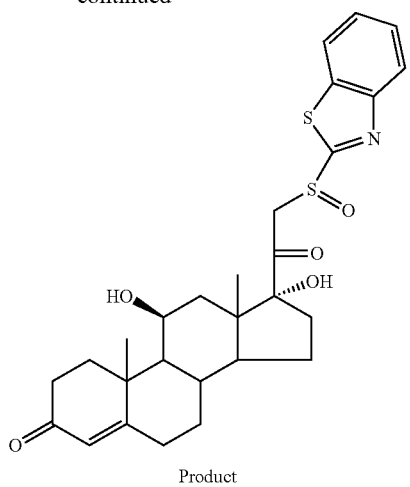

Product

To a 0° C. solution of 12a (100 mg; 0.20 mmol) in 3 mL of CH$_2$Cl$_2$ was added m-chloroperbenzoic acid (51 mg; 0.29 mmol), and reaction mixture was stirred at 0° C. for 2 h. Water was added, and the product was extracted with CH$_2$Cl$_2$ (partial precipitation in the organic phase). Organic phase was concentrated, and the residue was purified by flash chromatography (1% MeOH/CH$_2$Cl$_2$) to produce 75 mg of the Product compound as a yellowish solid. MH$^+$ 528

Example 9

Step 1

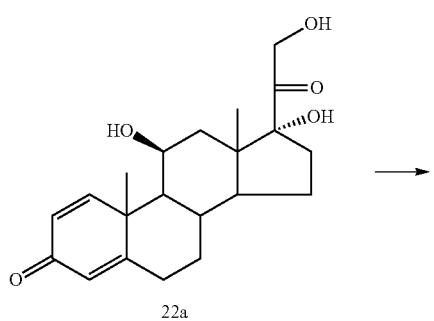

22a

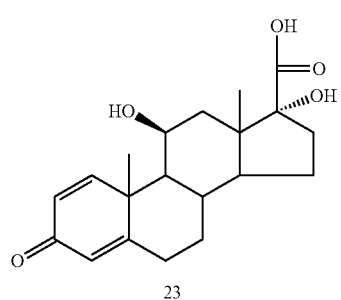

23

To the solution of prednisolone 22a (1.0 g; 2.77 mmol) in 13 mL of THF was added solution of periodic acid H$_5$IO$_6$ in 4 mL of water. Reaction mixture was stirred at room temperature overnight. Reaction mixture was concentrated, and 5 mL of water was added. The resulting white precipitate was filtered to provide 884 mg of acid 23 as a white solid.

116

Step 2

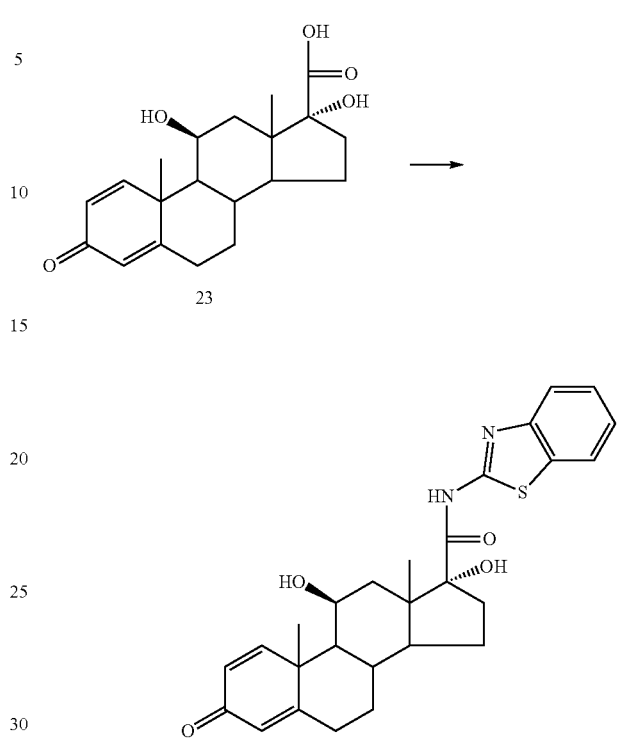

23

Product

To the solution of acid 23 (200 mg; 0.58 mmol) in 10 mL of DMF was added 2-aminobenzothiazole (104 mg; 0.69 mmol), EDC (166 mg; 0.87 mmol), HOBT (117 mg; 0.87 mmol) and Et$_3$N (0.16 mL; 1.15 mmol). Reaction mixture was stirred at room temperature overnight. DMF was removed under vacuum. The residue was dissolved in CH$_2$Cl$_2$, washed with aqueous NaHCO$_3$ and brine. Organic phase was concentrated, and the residue was flash chromatographed (0.5-1.5% MeOH/CH$_2$Cl$_2$) to produce 57 mg of the Product amide as a yellow solid. MH$^+$ 479

Example 10

Step 1

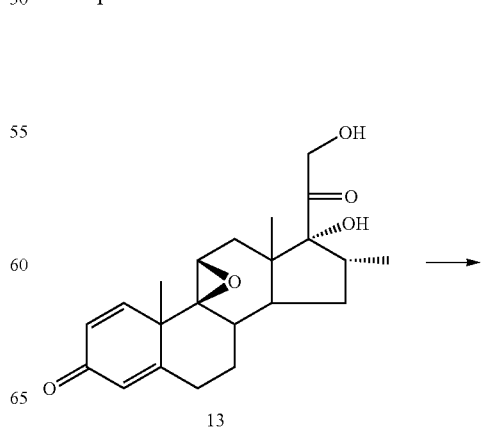

13

117
-continued

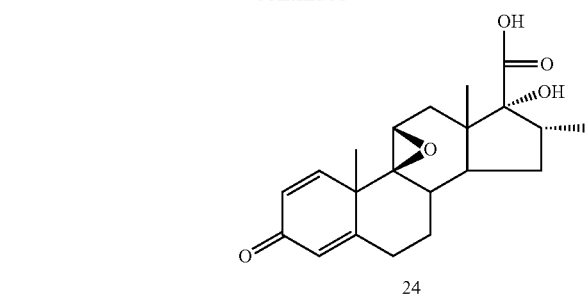

24

Compound 13 was converted to acid 24 using the procedure of step 1 of Example 9.

Step 2

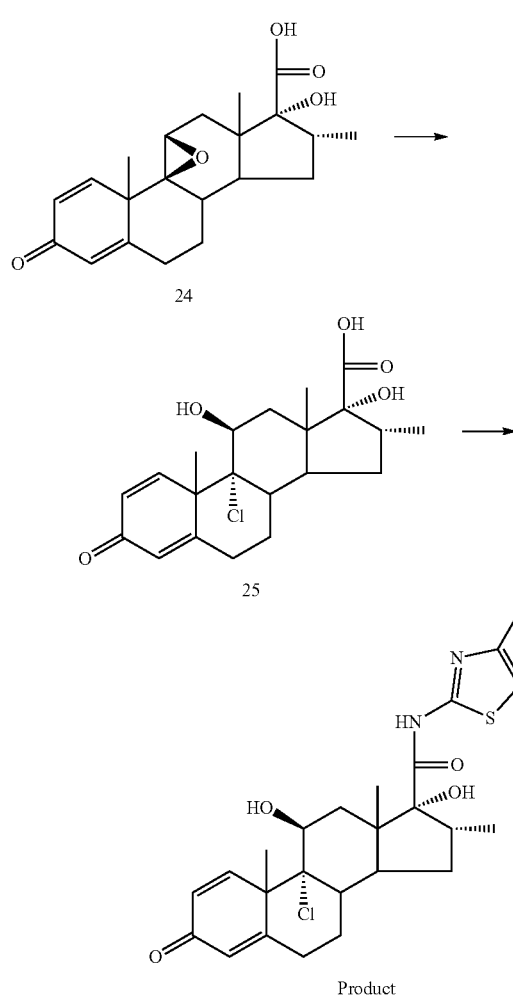

The epoxide 24 (1.54 g; 4.30 mmol) was stirred in 20 of 4N HCl solution in dioxane at room temperature overnight. An off-white precipitate formed and was filtered off. Reaction mixture was concentrated and triturated with EtOAc to produce 1.33 g of acid 25 as an off-white solid. Compound 25 was converted to the Product compound using procedure of step 2 of Example 9. MH+ 527

118
Example 11

Step 1

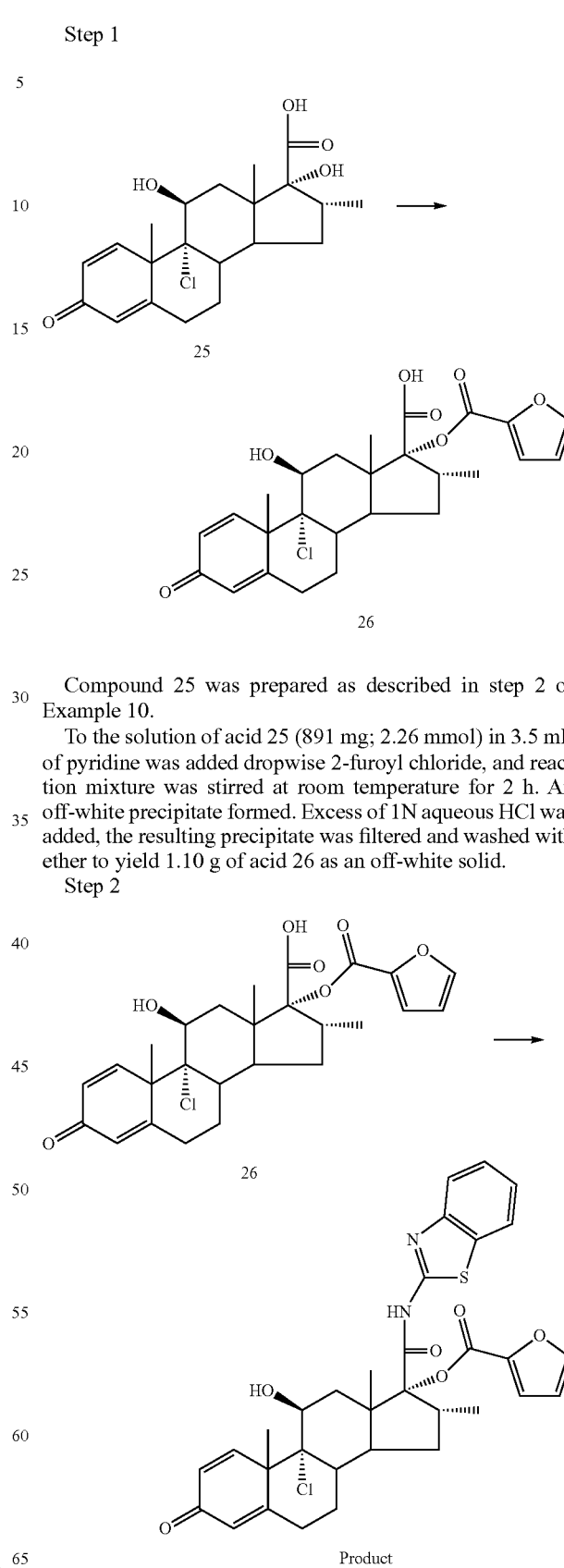

Compound 25 was prepared as described in step 2 of Example 10.

To the solution of acid 25 (891 mg; 2.26 mmol) in 3.5 mL of pyridine was added dropwise 2-furoyl chloride, and reaction mixture was stirred at room temperature for 2 h. An off-white precipitate formed. Excess of 1N aqueous HCl was added, the resulting precipitate was filtered and washed with ether to yield 1.10 g of acid 26 as an off-white solid.

Step 2

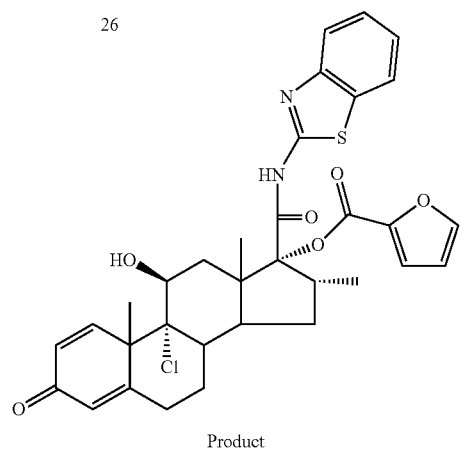

To a −20° C. suspension of acid 26 (208 mg; 0.43 mmol) in CH$_2$Cl$_2$ was added 140 µL (0.85 mmol) of trifluoromethanesulfonic anhydride, and the mixture was warmed to room temperature for 1 h. The resulting brown solution was cooled back to −20° C., and 2-aminobenzothiazole (384 mg; 2.56 mmol) and NaH (46 mg; 1.92 mmol) were added. Reaction mixture was stirred at room temperature overnight, diluted with CH$_2$Cl$_2$ and neutralized with aqueous NH$_4$Cl (pH 7-8). Extraction with CH$_2$Cl$_2$ and purification by flash chromatography (0.5% MeOH/CH$_2$Cl$_2$), followed by HPLC purification, produced 86 mg of the Product compound as a yellowish solid. MH$^+$ 621

Example 11

Step 1

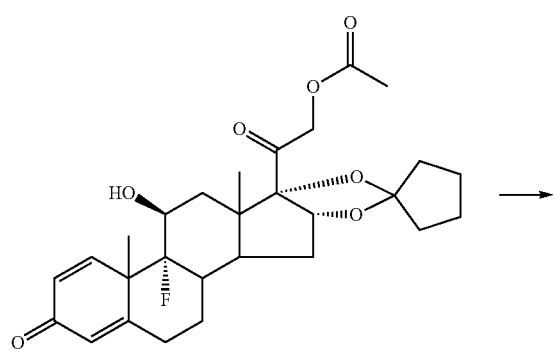

27

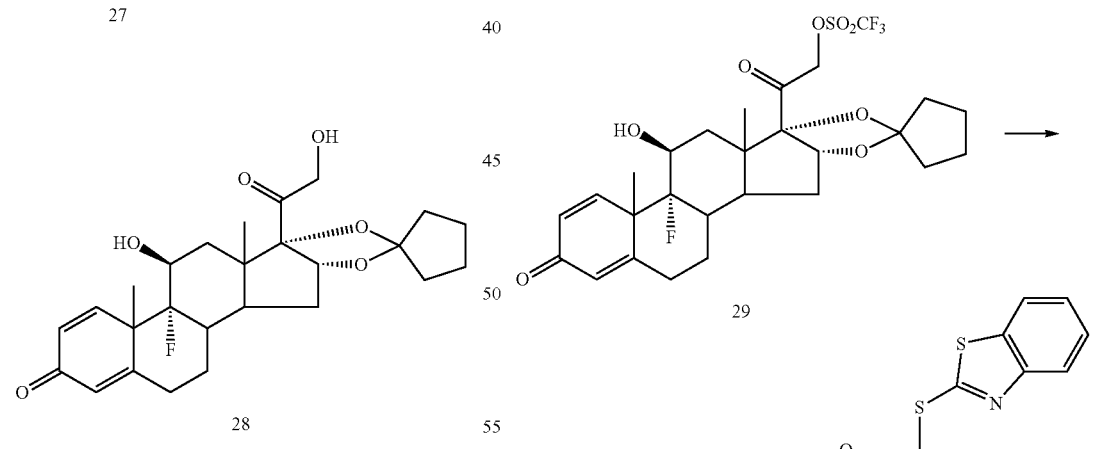

To the solution of amcinonide 27 (commercially available from Sigma) (2.0 g; 3.98 mmol) in a mixture of 25 mL MeOH and 25 mL CH$_2$Cl$_2$ was added K$_2$CO$_3$ (826 mg; 5.97 mmol), and the mixture was stirred at room temperature for 3 h. The solvent was removed under vacuum, and water was added. The product was extracted with CH$_2$Cl$_2$. Organic phase was dries and concentrated, and the residue was flash chromatographed (0.5% MeOH/CH$_2$Cl$_2$) to produce 1.30 g of compound 28 as a white solid.

Step 2

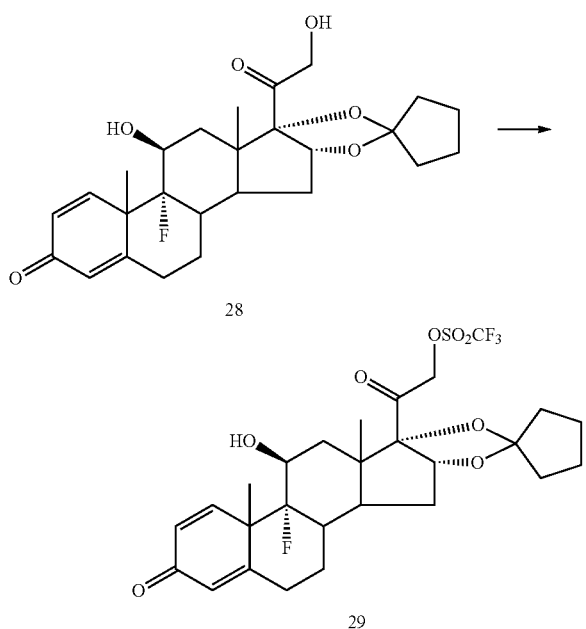

To a 0° C. solution of alcohol 28 (200 mg; 0.43 mmol) in 5 mL of CH$_2$Cl$_2$ was added pyridine (42 µL; 0.52 mmol), followed by trifluoromethanesulfonic anhydride (87 g; 0.52 mmol). Reaction mixture was stirred at 0° C. for 1.5 h. Reaction mixture was then diluted with water, organic phase was washed with aqueous NaHCO$_3$ and dried over Na$_2$SO$_4$. The pale yellow solution of crude 29 was used directly in the next step.

Step 3

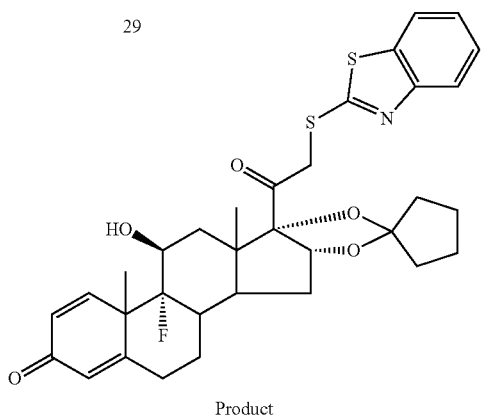

Product

To a suspension of NaH (47 mg; 1.95 mmol) in 3 mL, THF was added 2-mercaptobenzothiazole (436 mg; 2.61 mmol), and the mixture was stirred at room temperature for 10 min. CH$_2$Cl$_2$ solution of crude 29 from step 2 was then added, and reaction mixture was stirred at room temperature overnight. Reaction mixture was diluted with EtOAc and washed with aqueous NH$_4$Cl. Organic phase was dried and concentrated, and the residue was flash chromatographed (0.5% MeOH/CH$_2$Cl$_2$) to produce 181 mg of the Product compound as a yellow solid. MH$^+$ 610

Example 12

Step 1

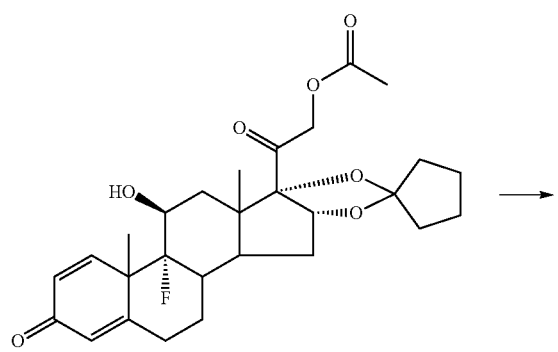

27

To the solution of amcinonide 27 (commercially available from Sigma) (2.0 g; 3.98 mmol) in a mixture of 25 MeOH and 25 mL CH$_2$Cl$_2$ was added K$_2$CO$_3$ (826 mg; 5.97 mmol), and the mixture was stirred at room temperature for 3 h. The solvent was removed under vacuum, and water was added. The product was extracted with CH$_2$Cl$_2$. Organic phase was dries and concentrated, and the residue was flash chromatographed (0.5% MeOH/CH$_2$Cl$_2$) to produce 1.30 g of compound 28 as a white solid.

Step 2

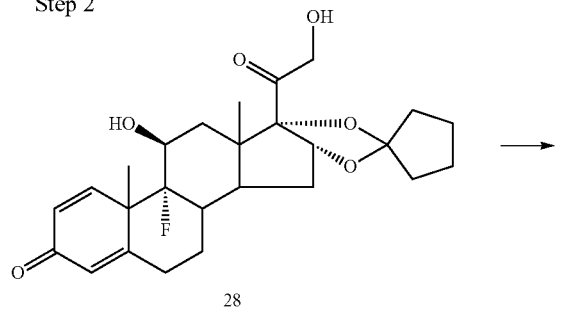

28

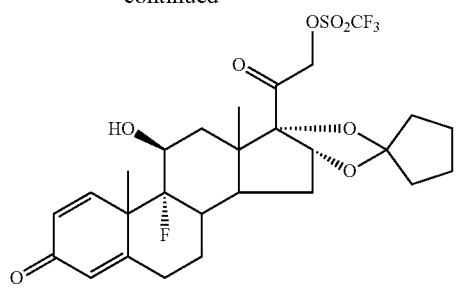

29

To a 0° C. solution of alcohol 28 (200 mg; 0.43 mmol) in 5 mL of CH$_2$Cl$_2$ was added pyridine (42 µL; 0.52 mmol), followed by trifluoromethanesulfonic anhydride (87 µL; 0.52 mmol). Reaction mixture was stirred at 0° C. for 1.5 h. Reaction mixture was then diluted with water, organic phase was washed with aqueous NaHCO$_3$ and dried over Na$_2$SO$_4$. The pale yellow solution of crude 29 was used directly in the next step.

Step 3

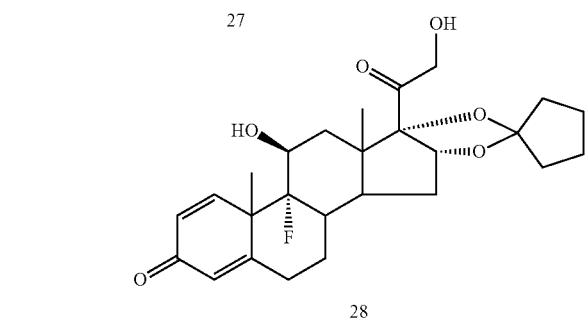

29

Product

To a suspension of NaH (47 mg; 1.95 mmol) in 3 mL THF was added 2-mercaptobenzothiazole (436 mg; 2.61 mmol), and the mixture was stirred at room temperature for 10 min. CH$_2$Cl$_2$ solution of crude 29 from step 2 was then added, and reaction mixture was stirred at room temperature overnight. Reaction mixture was diluted with EtOAc and washed with aqueous NH$_4$Cl. Organic phase was dried and concentrated, and the residue was flash chromatographed (0.5% MeOH/CH$_2$Cl$_2$) to produce 181 mg of the Product compound as a yellow solid. MH$^+$ 610

Example 13

Step 1

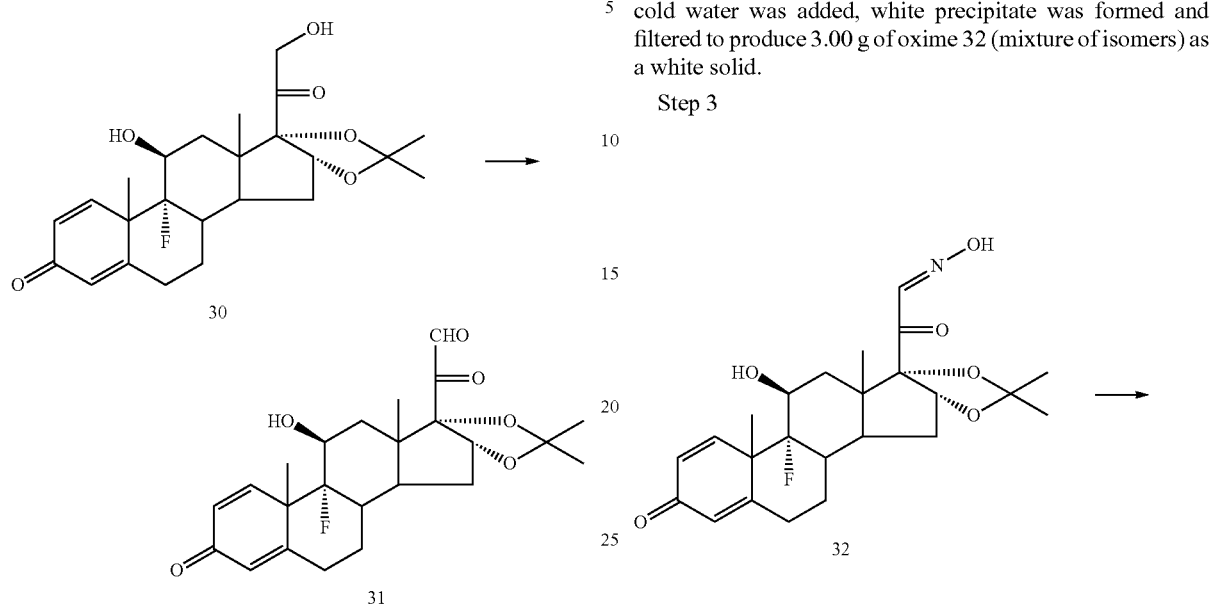

To a suspension of 3.0 g (6.90 mmol) of triamcinolone acetonide 30 in 440 mL of methanol was added solution of 0.63 g (3.45 mmol) of Cu(OAc)$_2$ in 120 mL of methanol. The mixture was stirred at room temp for 4 h, followed by the addition of saturated aqueous NaHCO$_3$ and evaporation of methanol under vacuum. The mixture was then extracted with methylene chloride, organic phase was dried (Na$_2$SO$_4$) and concentrated to produce 2.99 g of aldehyde 31 as a white solid.

Step 2

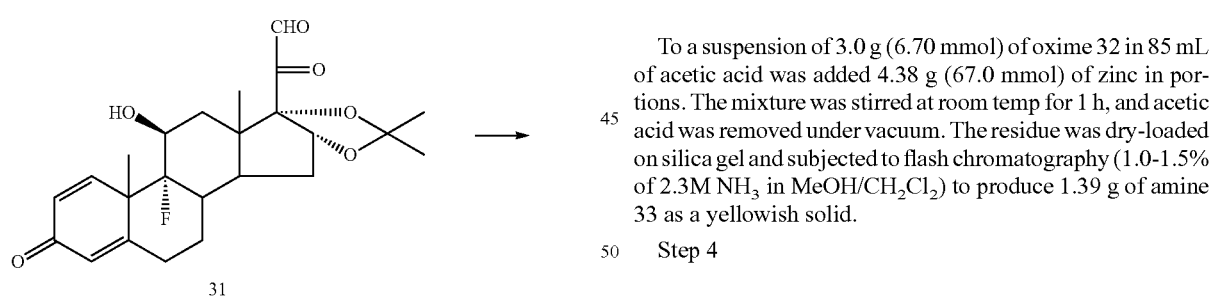

To a suspension of 2.99 g (6.90 mmol) of aldehyde 31 in 95 mL of 75% aqueous ethanol was added 0.55 g (7.94 mmol) of hydroxylamine hydrochloride and 0.48 g (345 mmol) of K$_2$CO$_3$. The mixture was stirred for 7 h at room temp. Ice-cold water was added, white precipitate was formed and filtered to produce 3.00 g of oxime 32 (mixture of isomers) as a white solid.

Step 3

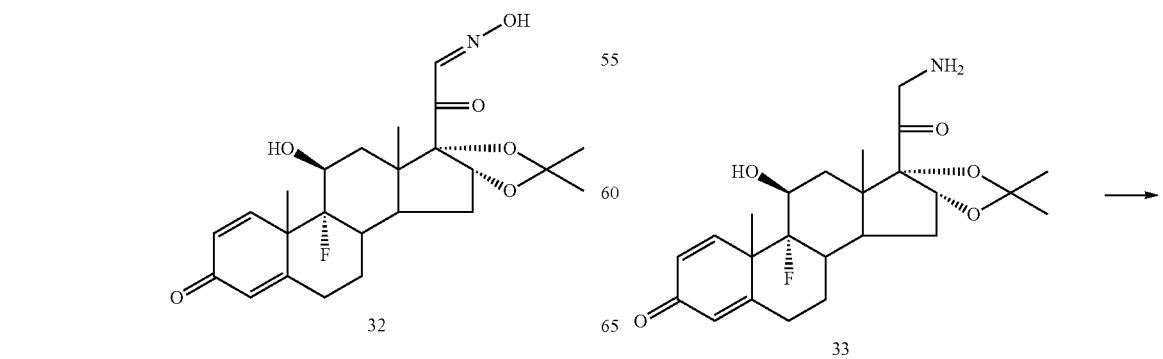

To a suspension of 3.0 g (6.70 mmol) of oxime 32 in 85 mL of acetic acid was added 4.38 g (67.0 mmol) of zinc in portions. The mixture was stirred at room temp for 1 h, and acetic acid was removed under vacuum. The residue was dry-loaded on silica gel and subjected to flash chromatography (1.0-1.5% of 2.3M NH$_3$ in MeOH/CH$_2$Cl$_2$) to produce 1.39 g of amine 33 as a yellowish solid.

Step 4

Example 15

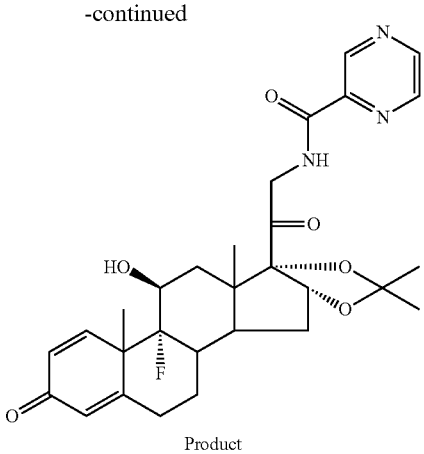

Product

Compound 33 was converted into the Product compound using procedure of step 2 of example 9. MH$^+$ 540

Example 14

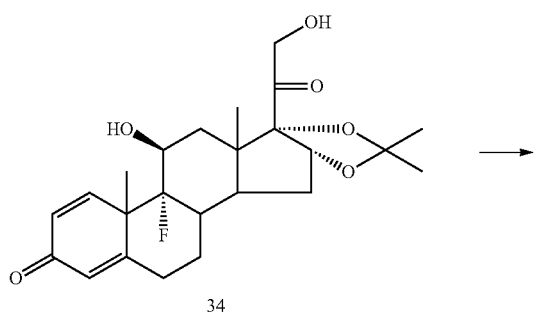

34

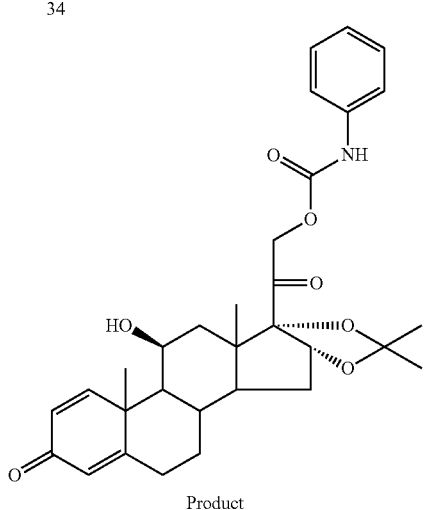

Product

To a solution of 200 mg (0.48 mmol) of desonide 34 in 5 mL of THF was added 260 μL (2.40 mmol) of phenyl isocyanate and 330 μL (2.40 mmol) of Et$_3$N. The mixture was stirred overnight at room temp. Water was added, and the product was extracted with CH$_2$Cl$_2$. Flash chromatography provided 265 mg of the Product compound as a white solid. MH$^+$ 536

Example 15

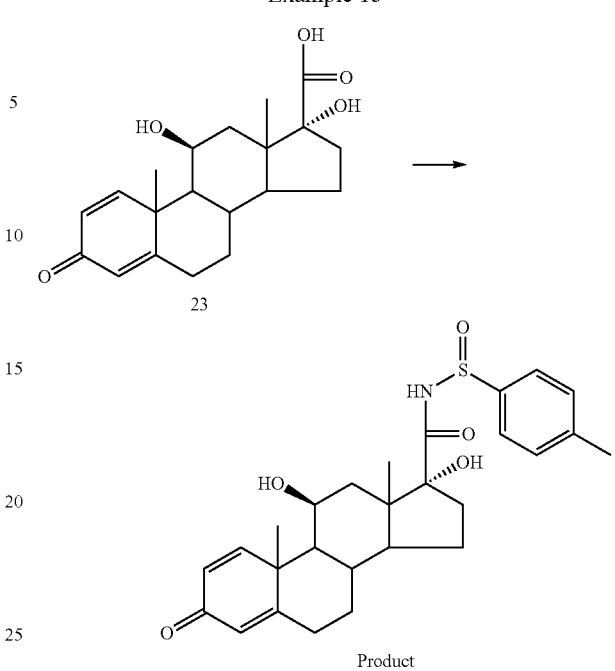

23

Product

Compound 23 was prepared as described in step 1 of example 9.

To a suspension of 200 mg (0.58 mmol) of acid 23 in 5 mL of THF was added 112 mg (0.69 mmol) of carbonyl diimidazole. The mixture was stirred for 1 h at room temp and then cannulated into a 0° C. solution of preformed lithium anion of (R)-(−)-p-toluenesulfinamide [obtained by adding 510 μL of 2.5M BuLi solution in hexanes (1.27 mmol) to a −78° C. solution of 197 mg (1.27 mmol) of sulfinamide in 5 mL of THF and warming the resulting mixture up to 0° C. over 30 min]. The mixture was stirred at 0° C. for 1 h, subjected to aqueous NH$_4$Cl work-up and extraction with ethyl acetate. Organic phase was dried over Na$_2$SO$_4$ and concentrated, and the residue was subjected to flash chromatography (1.0-1.5% MeOH/CH$_2$Cl$_2$) to produce 20 mg of the Product compound as a white solid. MH$^+$ 484

Example 16

Step 1

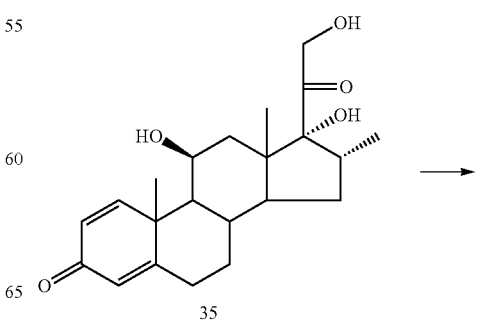

35

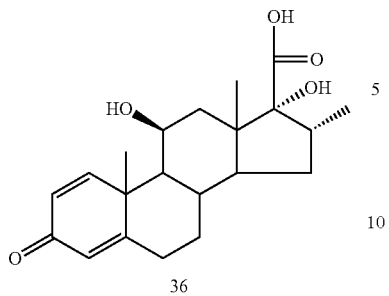

16-Methylprednisolone 35 (see U.S. Pat. No. 4,353,985, U.S. Pat. No. 3,054,725) was converted into the corresponding carboxylic acid 36 using procedure of step 1 of example 9.

Step 2

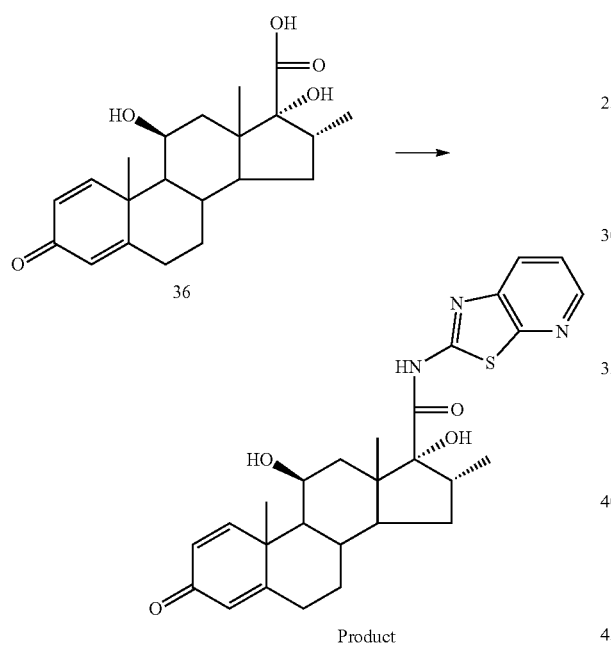

Compound 36 was converted into the Product compound using anion of 2-aminothiazolo[5,4-b]pyridine in a procedure analogous to the one described in example 15.

Example 17

Step 1

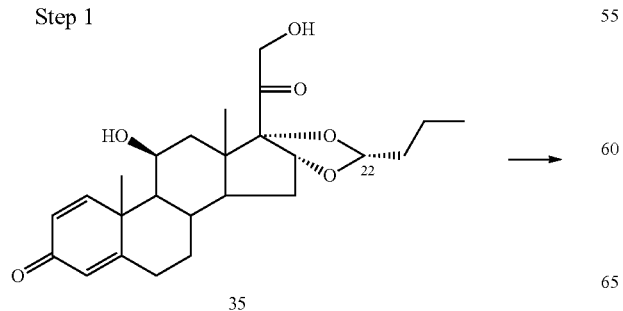

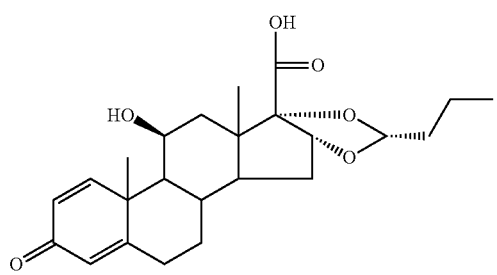

Budesonide C-22 single R-isomer (obtained from SFC separation of commercial budesonide C-22 mixture of isomers) was converted into mesylate 39 using procedure of step 1 of example 1.

Step 2

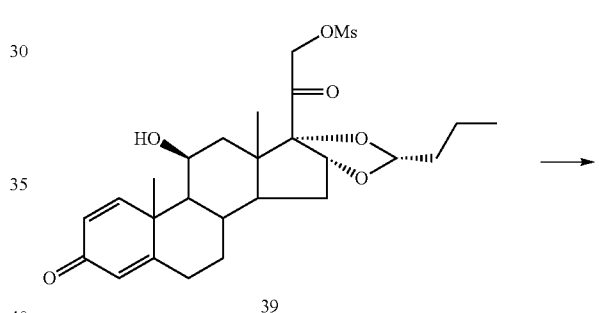

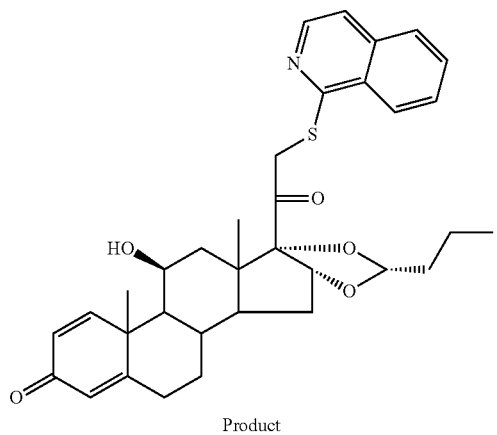

Compound 39 was converted into the Product compound through reaction with 1-mercaptoisoquinoline (see *Phosphorus and Sulfur* 1983, 14, 131-138) using procedure of step 2 of example 1. MH+ 574

Example 18

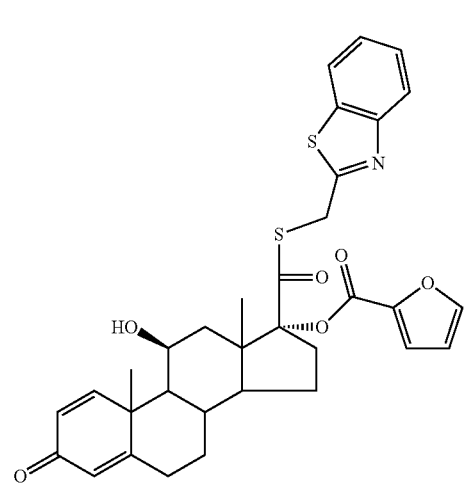 [SMILES: CC12C=CC(=O)C=C1CCC1C2[C@@H](O)CC2(C)C1CC[C@]2(OC(=O)c1ccco1)C(=O)SCc1nc2ccccc2s1]

Example 18

Step 1

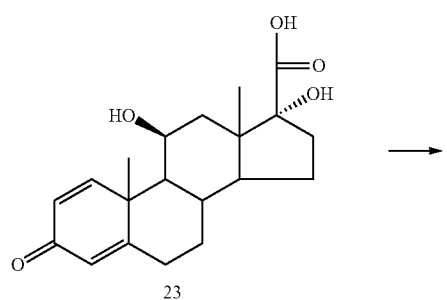

To a solution of acid 23 (1.96 g; 5.65 mmol) [prepared as described in Example 15] in 50 mL of DMF was added carbonyl diimidazole (1.83 g; 11.3 mmol), and the mixture was stirred at room temperature for 4 h. $H_2S$ gas was then passed through the solution for 30 min, and the mixture was stirred for an additional 30 min, during which time the color changed from yellow to green. The reaction mixture was poured into 2M HCl—ice mixture, and the resulting white precipitate was collected to yield 1.91 g of thioacid 101.

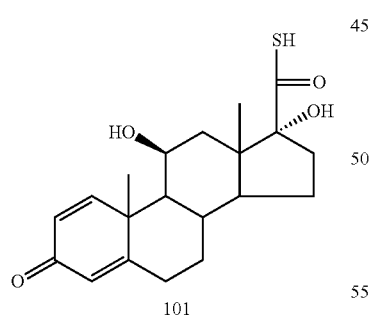

Step 2

To a suspension of thioacid 101 (954 mg; 2.63 mmol) in 10 mL of acetone at 0° C. was added dropwise over 10 min $Et_3N$ (0.77 mL; 5.53 mmol), followed by dropwise addition of 2-furoyl chloride (0.53 mL; 5.40 mmol) over 30 min. Reaction mixture was stirred at 0° C. for 2 h. The resulting precipitate was filtered off, washed with acetone and water and dried under vacuum to yield 1.36 g of difuroate 102 as a white solid.

Step 3

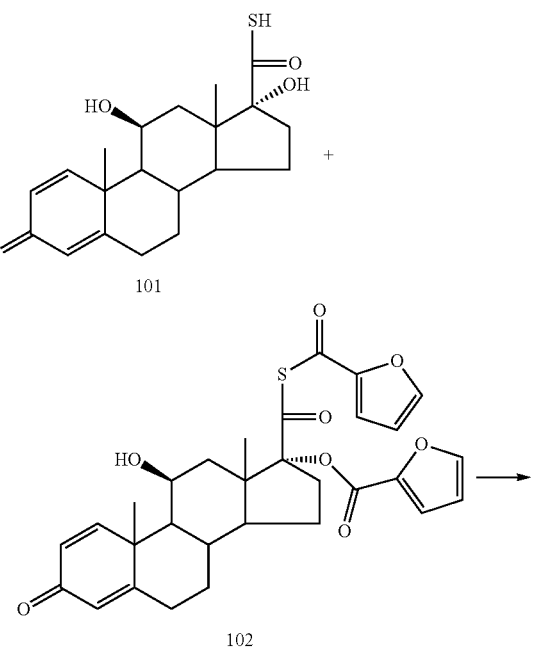

-continued

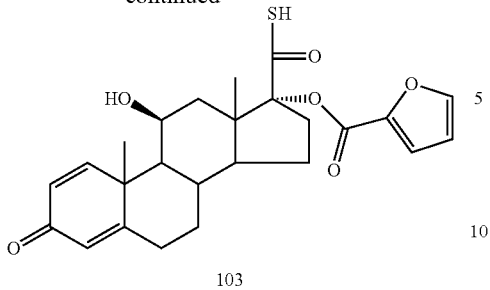

103

A 1:1 mixture of difuroate 102 (1.36 g; 2.46 mmol) and thioacid 101 (0.89 g; 2.46 mmol) with Et$_3$N (0.72 mL; 5.17 mmol) in 20 mL of DMF was stirred at room temperature for 7 h. The mixture was diluted with 70 mL of ice cold 1% aqueous HCl, and the resulting white precipitate was collected by filtration, washed with cold water and dried under vacuum to produce 2.09 g of thioacid 103.

Step 4

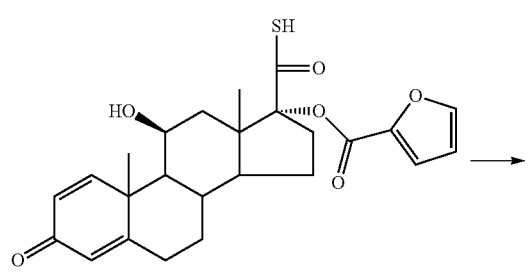

103

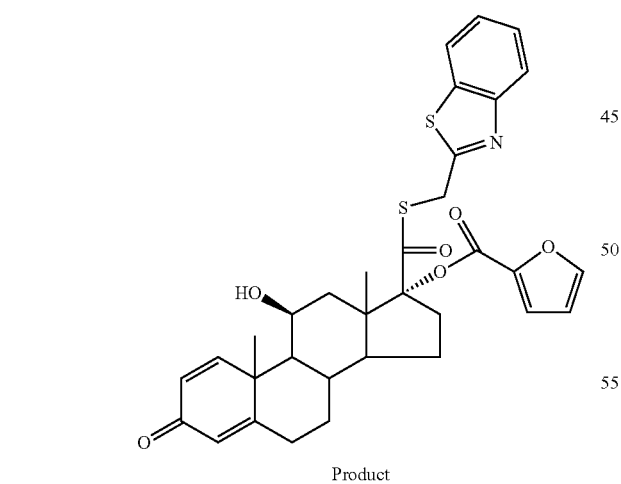

Product

To a 0° C. suspension of thioacid 103 (200 mg; 0.44 mmol) and tributylbenzylammonium chloride (14 mg; 0.044 mmol) in a mixture of 5 mL of ethyl acetate and 1 mL of water was added 2-(bromomethyl)-1,3-benzothiazole (120 mg; 0.53 mmol), and the mixture was stirred at room temperature overnight. The orange emulsion was diluted with water and CH$_2$Cl$_2$, organic phase was separated, washed with aq. ammonium chloride, sodium bicarbonate and brine solutions. Concentration of the organic phase, followed by flash chromatography (0-1% MeOH/CH$_2$Cl$_2$) produced 172 mg of the title compound as a white solid. MH$^+$ 604

Example 19

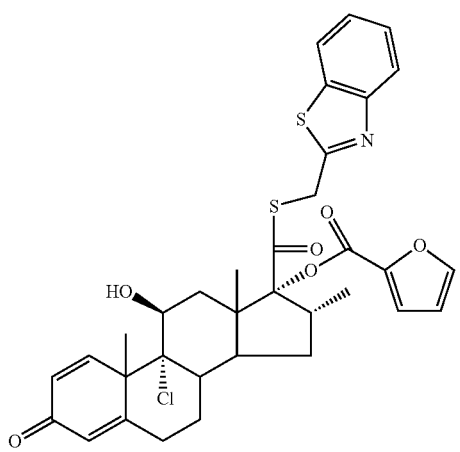

Example 19

The title compound was synthesized from acid 26 (see example 11, step 1) using procedures identical to steps 1-4 of example 18. NH$^+$ 652

Example 20

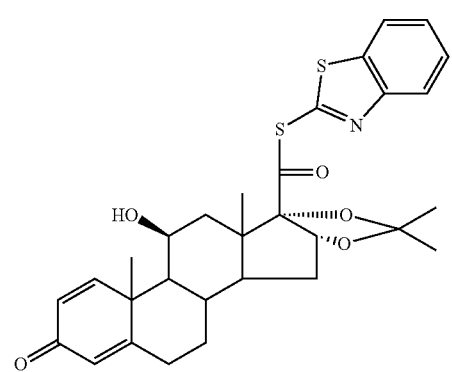 [SMILES: CC1(C)O[C@@H]2CC3C4CCC5=CC(=O)C=CC5(C)C4[C@@H](O)CC3(C)[C@]2(C(=O)Sc2nc3ccccc3s2)O1]

Example 20

Step 1

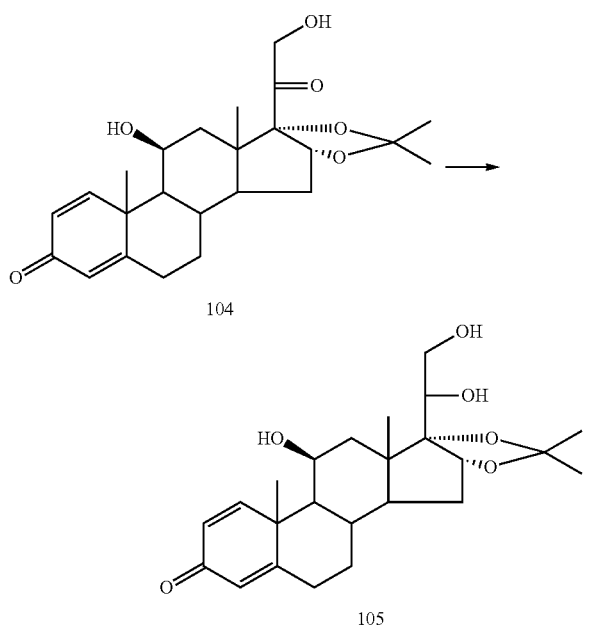

To a suspension of desonide 104 (2.0 g; 4.8 mmol) in 25 mL of THF was added NaBH₄ (182 mg; 4.8 mmol), and the reaction mixture was stirred at room temperature overnight, and quenched with aq. ammonium chloride. The resulting white precipitate was isolated by filtration to yield 1.94 g of compound 105 as a white powder.

Step 2

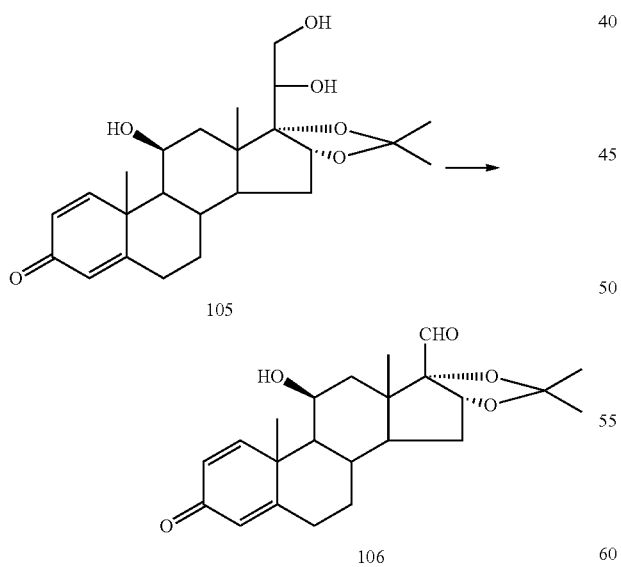

To a solution of diol 105 (714 mg; 1.71 mmol) in ethanol (30 mL) was added NaIO₄ (658 mg; 3.08 mmol) and water (3 mL), Reaction mixture was stirred at room temperature for 6 h. The white solid was isolated by filtration and washed with EtOAc. The combined filtrate and washings were evaporated, and white residue was dissolved in CH₂Cl₂. Organic phase was washed with water, brine, and concentrated to produce 680 mg of aldehyde 106 as an off-white solid.

Step 3

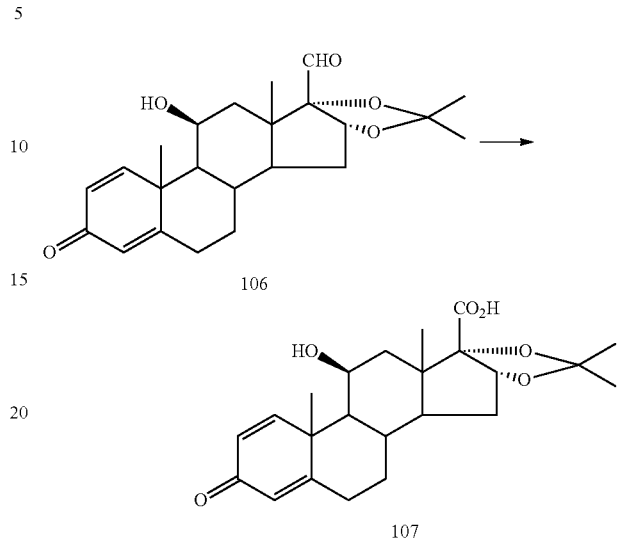

To a solution of aldehyde 106 (2.0 g; 5.17 mmol) in 40 mL of tert-butanol was added saturated aqueous solution of KH₂PO₄ (3.52 g; 25.9 mmol), followed by 2-methyl-2-butene (3.29 mL; 31.0 mmol) and NaClO₂ (1.87 g; 201 mmol). Reaction mixture was stirred at room temperature overnight, concentrated-dry loaded on silica gel and flash chromatographed (25-30% 2.5M NH₃ in MeOH/CH₂Cl₂) to produce 1.46 g of acid 107 as a yellowish solid.

Step 4

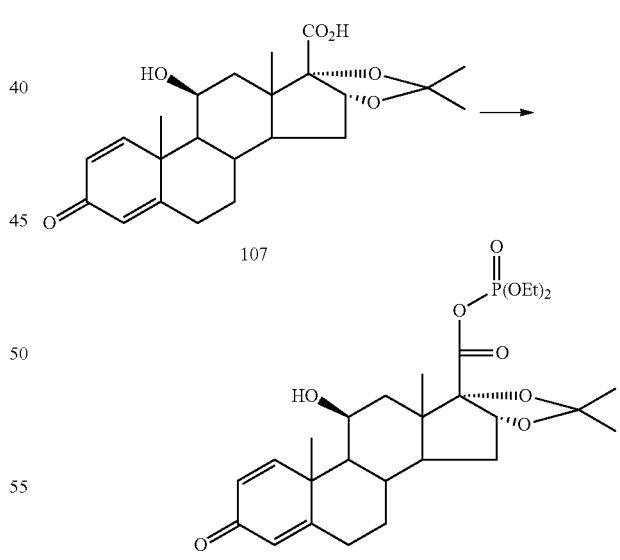

To a solution of acid 107 (353 mg; 0.88 mmol) in 10 mL of THF was added dropwise Et₃N (0.244 mL; 1.75 mmol), followed after 20 min by the addition of diethyl chlorophosphate (0.25 mL; 1.75 mmol) over 20 min. Reaction mixture was stirred for 2 h at room temperature, diluted with water and extracted with CH₂Cl₂. Evaporation of solvent produced 473 mg of compound 108 as a beige solid.

Step 5

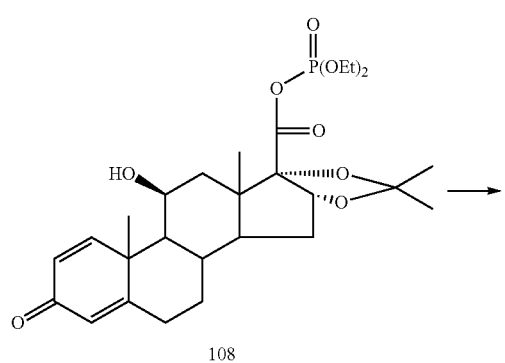

108

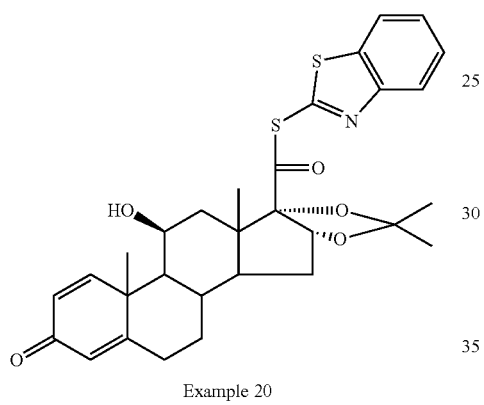

Example 20

To a stirred solution of 2-mercaptobenzothiazole (117 mg; 0.70 mmol) and NaH (18 mg; 0.77 mmol) in 5 mL of THF was added compound 108 (150 mg; 0.28 mmol), and reaction mixture was stirred at room temperature for 24 h. Flash chromatography (0.5-1.0% MeOH/CH$_2$Cl$_2$) produced 150 mg of the title compound as a white solid. MH$^+$ 552

Example 21

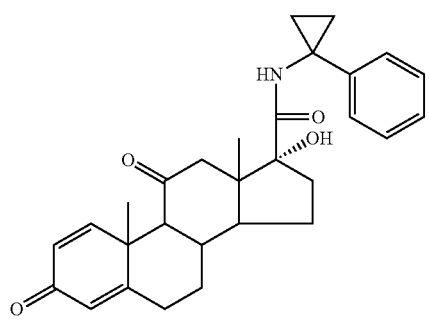 [SMILES: CC12C=CC(=O)C=C1CCC1C2C(=O)CC2(C)C1CC[C@]2(O)C(=O)NC1(c2ccccc2)CC1]

Example 21

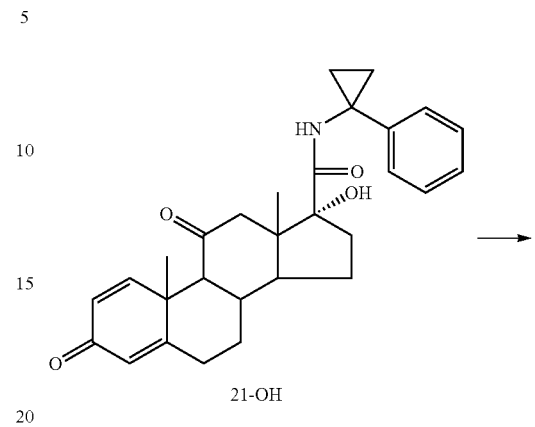

21-OH

Example 21

To a suspension of compound 21-OH (127 mg; 0.27 mmol) [prepared using procedures similar to those of example 9] in 4 mL of CH$_2$Cl$_2$ was added pyridinium chlorochromate (95 mg; 0.44 mmol), and reaction mixture was stirred at room temperature overnight, and filtered through Celite. The filtrate was concentrated, and the residue was purified by flash chromatography (1-1.5% MeOH/CH$_2$Cl$_2$) to produce 90 mg of the title compound as a white foam. MH$^+$ 460

Example 22

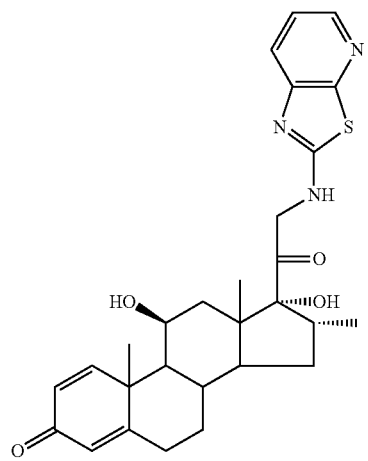 [SMILES: C[C@@H]1CC2C3CCC4=CC(=O)C=CC4(C)C3[C@@H](O)CC2(C)[C@@]1(O)C(=O)CNc1nc2cccnc2s1]

Example 22

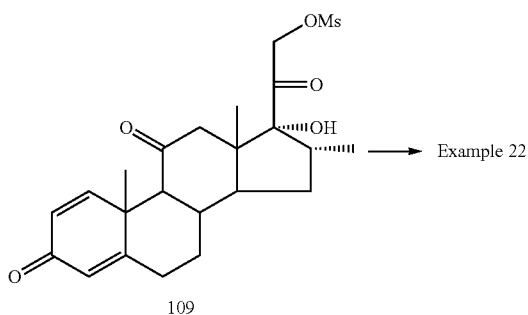 [SMILES: C[C@@H]1CC2C3CCC4=CC(=O)C=CC4(C)C3C(=O)CC2(C)[C@@]1(O)C(=O)COS(C)(=O)=O]

109

Mesylate 109 was prepared from alcohol 35 (see example 16) using procedure of example 1, step 1.

To a stirred solution of 2-aminothiazolo[5,4-b]pyridine (217.4 mg, 1.43 mmol) in DMF (5 mL) was added NaH (60% in mineral oil, 57.4 mg, 1.43 mmol) at 0° C. After 30 min, a solution of 109 (217 mg, 0.479 mmol) in DMF (0.5 mL) was added. The reaction mixture was stirred at room temperature overnight and then quenched by 1N HCl (aq) and acidified. The aqueous solution was extracted with dichloromethane (40 mL×2). The combined organic layer was washed with H$_2$O and brine solution, dried over MgSO$_4$, filtered and concentrated. The crude product was purified by flash chromatography (10% MeOH/CH$_2$Cl$_2$) to give 131 mg of the title compound. MH$^+$ 506

Example 23

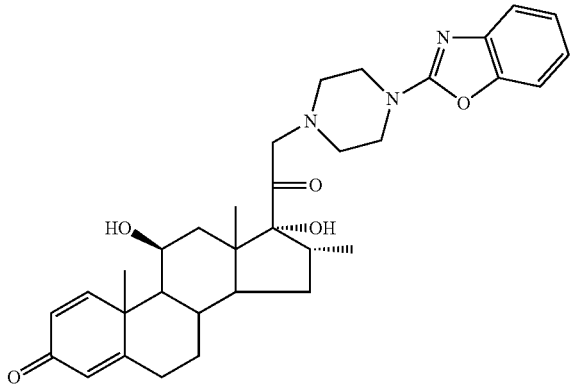 [SMILES: C[C@@H]1CC2C3CCC4=CC(=O)C=CC4(C)C3[C@@H](O)CC2(C)[C@@]1(O)C(=O)CN1CCN(c2nc3ccccc3o2)CC1]

Example 23

To a stirred solution of mesylate 109 (200 mg, 0.44 mmol) in DMF (4.4 mL) was added 2-piperazin-1-ylbenzoxazole (128.4 mg, 0.63 mmol) and triethylamine (0.198 mL, 1.42 mmol) at room temperature. The reaction mixture was heated to 70° C. overnight and then cooled down to room temperature. The reaction mixture was poured into NaHCO$_3$ (aq) solution and extracted with dichloromethane (50 mL×2). The combined organic layer was washed with H$_2$O and brine solution, dried over MgSO$_4$, filtered and concentrated by. The crude product was purified by flash chromatography (10% MeOH/CH$_2$Cl$_2$) to give 122 mg of the title compound. MH$^+$ 561

Example 24

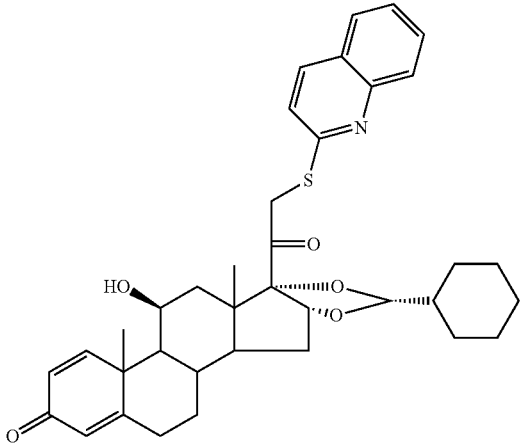 [SMILES: CC12C=CC(=O)C=C1CCC1C2[C@@H](O)CC2(C)C1C[C@H]1O[C@@H](C3CCCCC3)O[C@]12C(=O)CSc1ccc2ccccc2n1]

Example 24

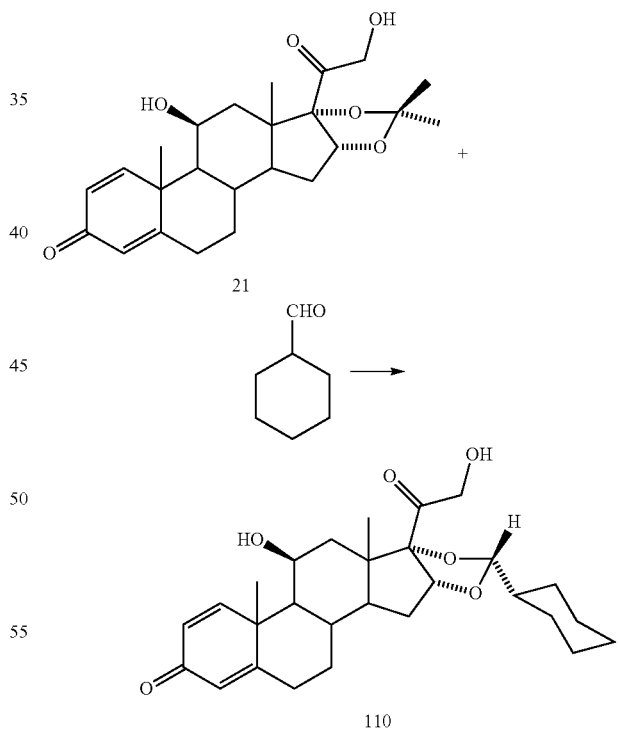

110

To a stirred suspension of desonide 21 (3 g, 7.20 mmol) in n-PrNO$_2$ (11 mL) was added 70% perchloric acid (4.39 mL, 21.6 mmol) and cyclohexanecarboxaldehyde (2.45 mL, 8.64 mmol) at 0° C. The white murky solution became clear. After 30 min at 0° C. the reaction mixture was stirred at room temperature for 3 days. The clear solution became light yellow murky. The precipitate was filtered and the filter cake was washed with n-PrNO₂ (20 mL×2). The filter cake was redissolved in dichloromethane and washed with sat. NaHCO₃ (aq) and H₂O. The organic layer was dried over MgSO₄, filtered and concentrated. The white solid was recrystallized with dichloromethane and diethyl ether to give white crystals of compound 110 (2.36 g).

Compound 110 was converted into the title compound (Example 26) using procedures of steps 1 and 2 of example 1. MW 614

Example 25

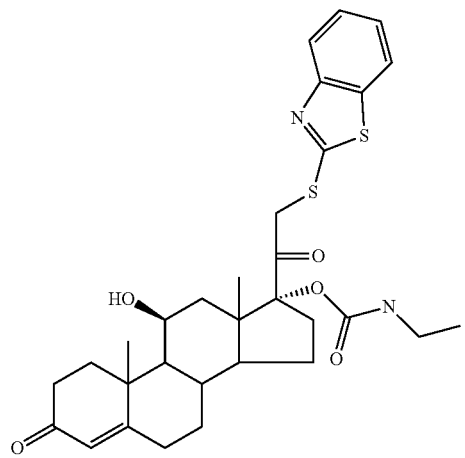 [SMILES: CCNC(=O)O[C@]1(C(=O)CSc2nc3ccccc3s2)CCC2C3CCC4=CC(=O)CCC4(C)C3[C@@H](O)CC21C]

Example 25

Step 1

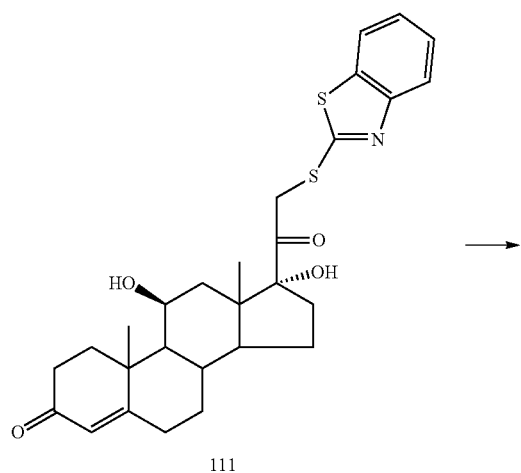
111

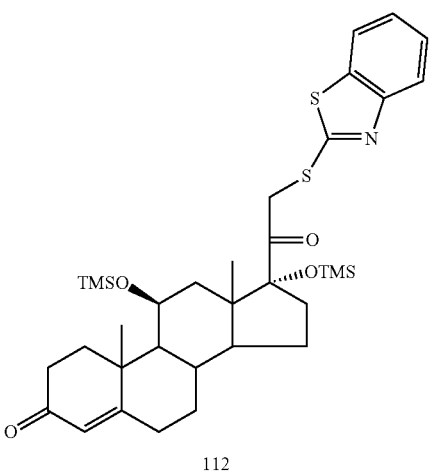
112

Compound 111 was prepared from mesylate 12 (see example 5) using procedure of step 2 of example 1.

Compound 111 (10.0 g, 19.54 mmol) and imidazole (26.60 g, 390.84 mmol) were dissolved in DMF (100 mL). TMSCl was then added dropwise, and solution was stirred at room temperature for twenty four hours. The reaction was then diluted with ethyl acetate and washed successively with water, saturated NH₄Cl, water, saturated NaHCO₃, water, and brine. Organic layer was collected and dried over anhydrous sodium sulfate. The filtrate was concentrated to afford the product 112 (11.87 g).

Step 2

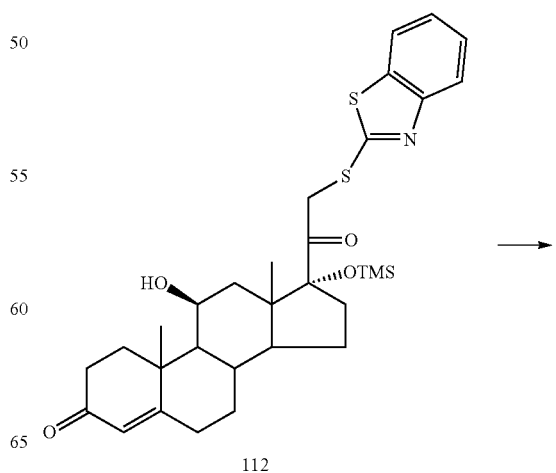
112

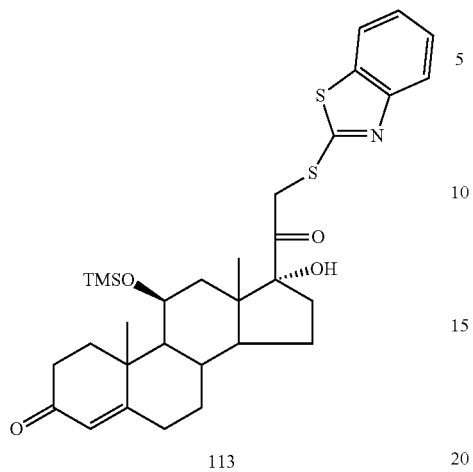

113

Compound 112 (11.87 g, 18.09 mmol) was dissolved in THF (150 mL) and cooled to 0° C. in an ice bath. To this solution, acetic acid (2.07 mL, 36.18 mmol) and TBAF (5.37 mL, 18.09 mmol) were added dropwise. After 4 h reaction was removed from ice bath and stirred at room temperature for 20 h. The solution was then taken into a separatory funnel and extracted successively with ethyl acetate, water, saturated NH₄Cl, water, saturated NaHCO₃, water, and brine. Organic layer was collected and dried over anhydrous sodium sulfate. The filtrate was concentrated to afford the product 113 (9.93 g).

Step 3

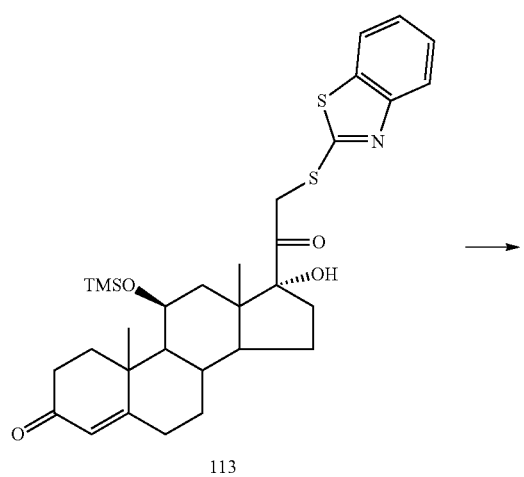

113

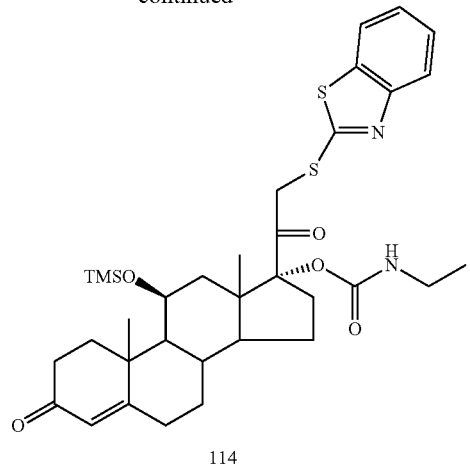

114

Compound 113 (0.500 g, 0.856 mmol) was dissolved in toluene (5 mL) and ethyl isocyanate (2.85 mL, 36.05 mmol) was slowly added. Solution was refluxed at 110° C. for 3 days. Additional ethyl isocyanate was then added (2.85 mL, 36.05 mmol), and the mixture was refluxed overnight. The solution was concentrated, and the residue was purified by flash chromatography (0-20% MeOH/CH₂Cl₂) to afford the product 114 (0.500 g).

Step 4

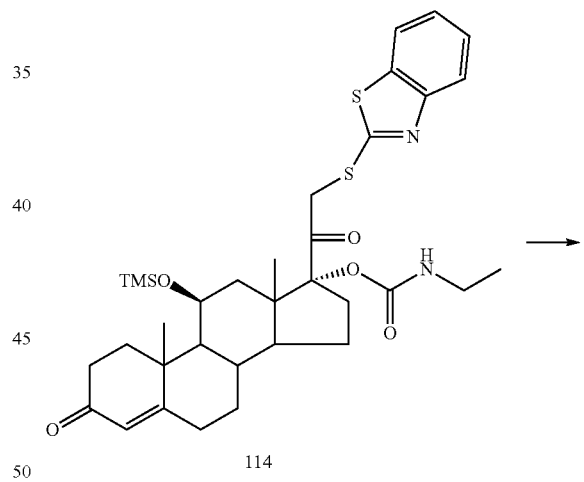

114

Example 25

Compound 114 (0.500 g, 0.763 mmol) was dissolved in 10 mL:2 mL:1 mL mixture of methanol, chloroform, and 6N HCl, respectively and stirred at room temperature for 3 h. Solution was then concentrated, dissolved in dichloromethane and washed with water, brine and dried over anhydrous sodium sulfate. The filtrate was concentrated, and the residue purified by flash chromatography (0-80% EtOAc/hexanes) to afford the title compound Example 25 (132 g). MH⁺ 583

The compounds shown in Table 1 are non-limiting examples of compounds of the invention which were synthesized using the procedures described herein (or procedures analogous thereto).

TABLE 1
| Structure | M + H |
|---|---|
| 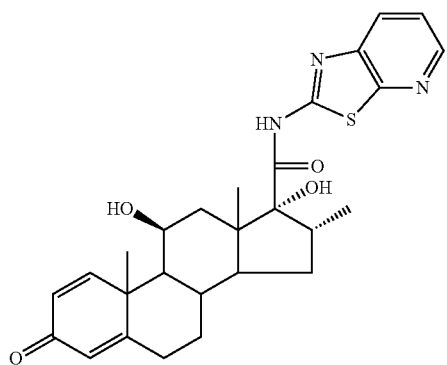 [SMILES: C[C@@H]1CC2C3CCC4=CC(=O)C=CC4(C)C3[C@@H](O)CC2(C)[C@@]1(O)C(=O)Nc1nc2cccnc2s1] | 494 |
| 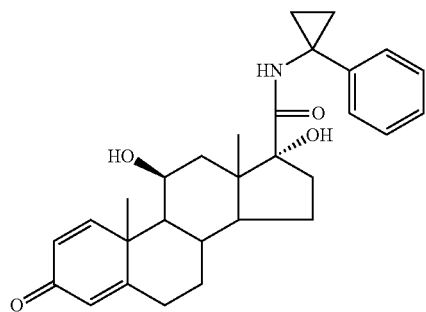 [SMILES: CC12C=CC(=O)C=C1CCC1C2[C@@H](O)CC2(C)C1CC[C@]2(O)C(=O)NC1(c2ccccc2)CC1] | 462 |
| 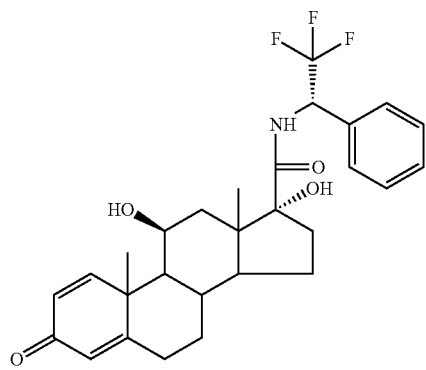 [SMILES: CC12C=CC(=O)C=C1CCC1C2[C@@H](O)CC2(C)C1CC[C@]2(O)C(=O)N[C@@H](c1ccccc1)C(F)(F)F] | 504 |
| 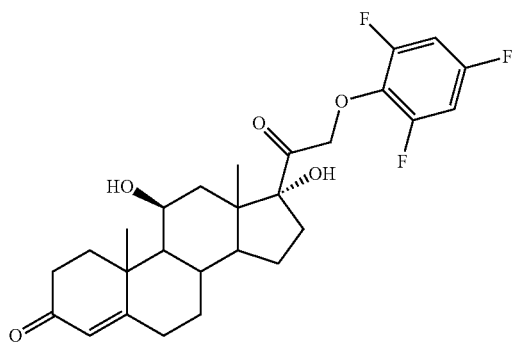 [SMILES: CC12CCC(=O)C=C1CCC1C2[C@@H](O)CC2(C)C1CC[C@]2(O)C(=O)COc1c(F)cc(F)cc1F] | 493 |

TABLE 1-continued

| Structure | M + H |
|---|---|
| (steroid with benzothiazole amide, Cl, HO, OH) | 527 |
| (steroid with N-benzyl amide, F, F, HO, OH) | 486 |
| (steroid with benzothiazole amide, F, F, HO, OH) | 529 |
| (steroid with pyridylmethyl ether, HO, OH) | 454 |

TABLE 1-continued
| Structure | M + H |
|---|---|
| 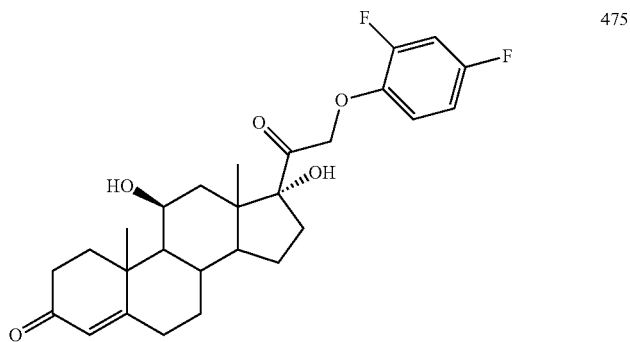 | 475 |
| 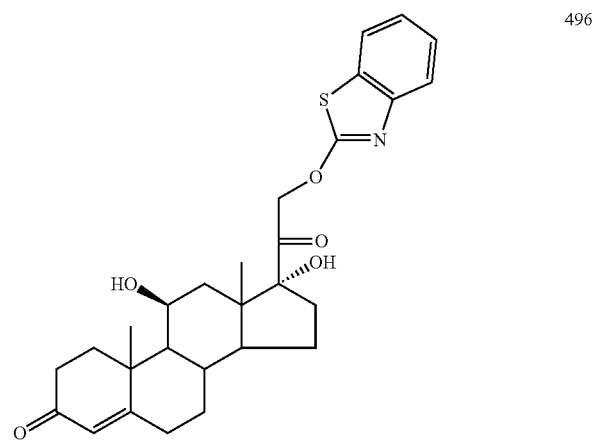 | 496 |
| 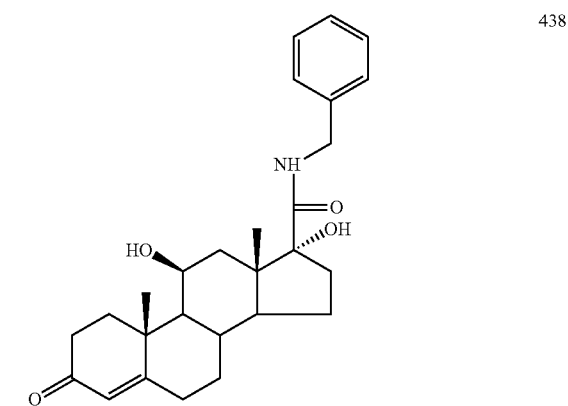 | 438 |
| 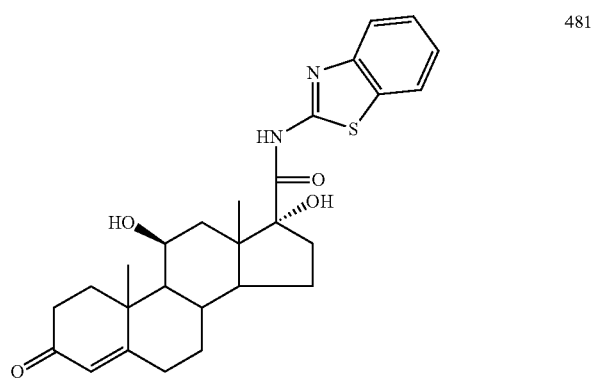 | 481 |

TABLE 1-continued
| Structure | M + H |
|---|---|
| 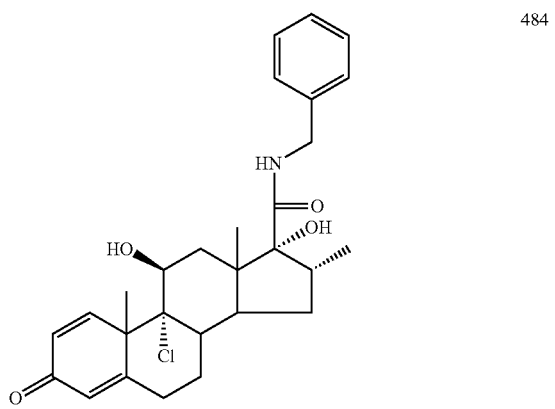 | 484 |
| 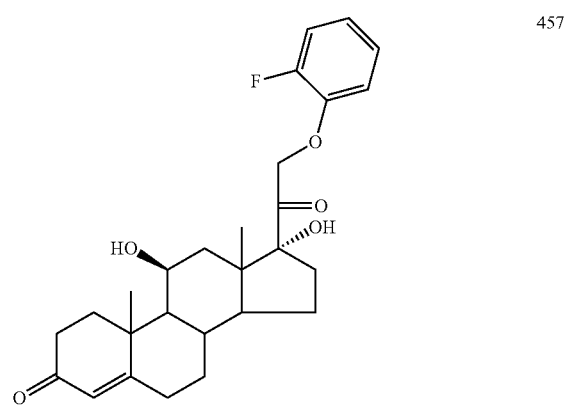 | 457 |
| 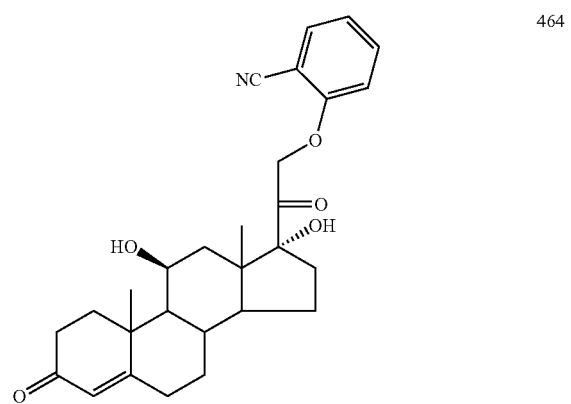 | 464 |
| 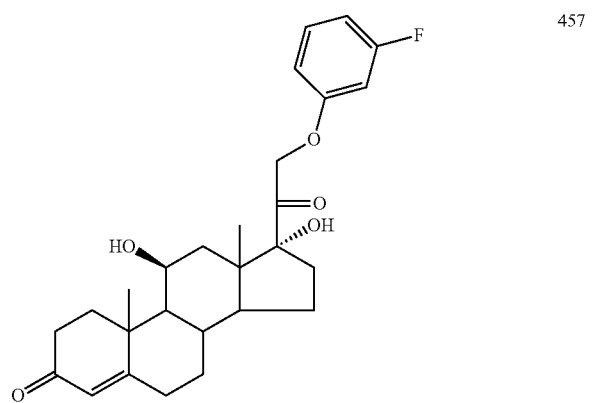 | 457 |

TABLE 1-continued
| Structure | M + H |
|---|---|
| 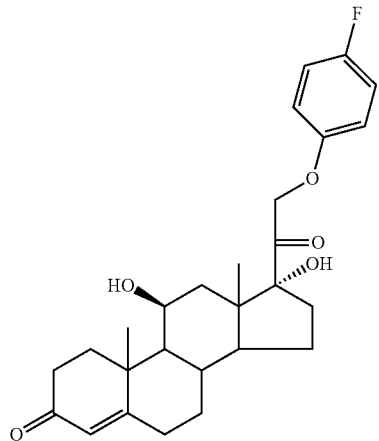 [SMILES: CC12CCC(=O)C=C1CCC1C2[C@@H](O)CC2(C)C1CC[C@]2(O)C(=O)COc1ccc(F)cc1] | 457 |
| 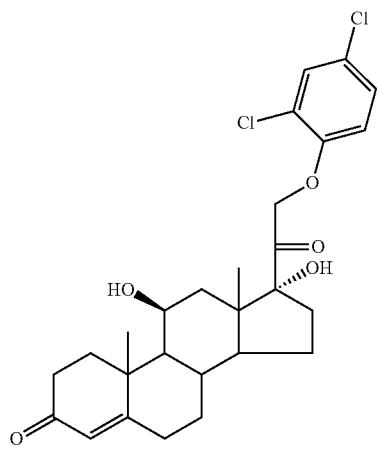 [SMILES: CC12CCC(=O)C=C1CCC1C2[C@@H](O)CC2(C)C1CC[C@]2(O)C(=O)COc1ccc(Cl)cc1Cl] | 507 |
| 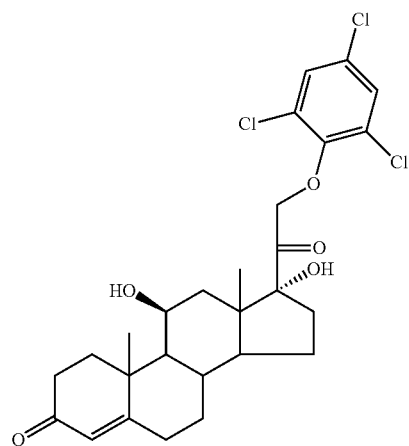 [SMILES: CC12CCC(=O)C=C1CCC1C2[C@@H](O)CC2(C)C1CC[C@]2(O)C(=O)COc1c(Cl)cc(Cl)cc1Cl] | 541 |

TABLE 1-continued
| Structure | M + H |
|---|---|
| 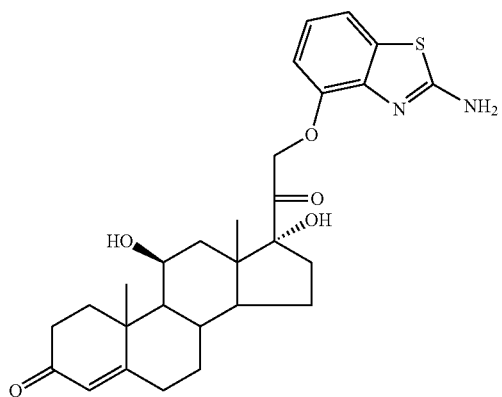 [SMILES: CC12CCC(=O)C=C1CCC1C2[C@@H](O)CC2(C)C1CC[C@]2(O)C(=O)COc1cccc2sc(N)nc12] | 511 |
| 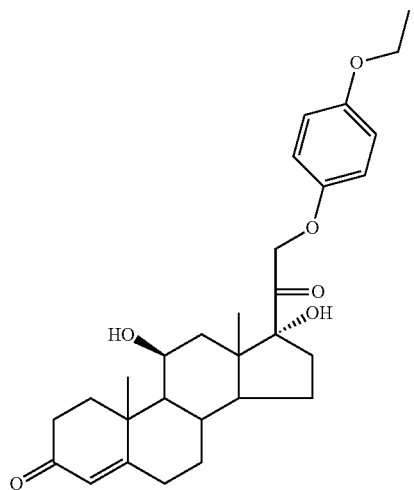 [SMILES: CCOc1ccc(OCC(=O)[C@@]2(O)CCC3C4CCC5=CC(=O)CCC5(C)C4[C@@H](O)CC32C)cc1] | 483 |
| 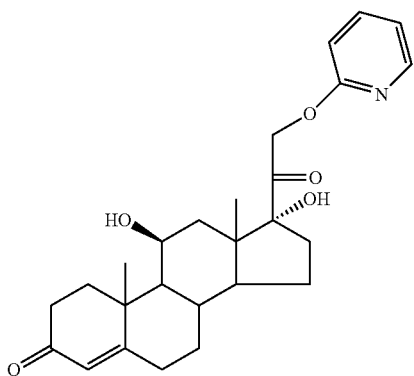 [SMILES: CC12CCC(=O)C=C1CCC1C2[C@@H](O)CC2(C)C1CC[C@]2(O)C(=O)COc1ccccn1] | 440 |

TABLE 1-continued
| Structure | M + H |
|---|---|
| 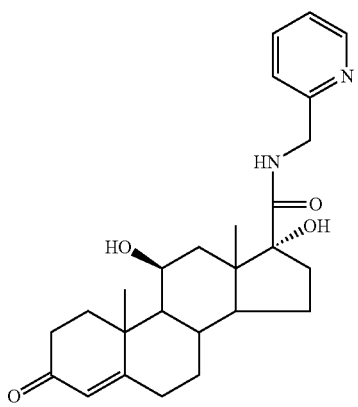 [SMILES: CC12CCC(=O)C=C1CCC1C2[C@@H](O)CC2(C)C1CC[C@]2(O)C(=O)NCc1ccccn1] | 439 |
| 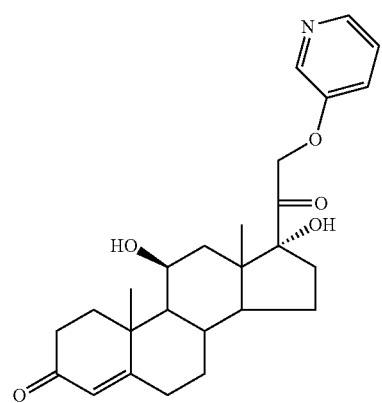 [SMILES: CC12CCC(=O)C=C1CCC1C2[C@@H](O)CC2(C)C1CC[C@]2(O)C(=O)COc1cccnc1] | 440 |
| 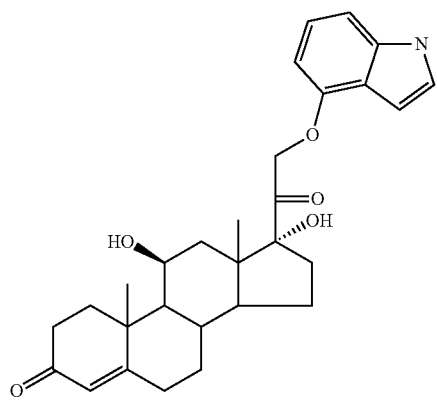 [SMILES: CC12CCC(=O)C=C1CCC1C2[C@@H](O)CC2(C)C1CC[C@]2(O)C(=O)COc1cccc2[nH]ccc12] | 478 |
| 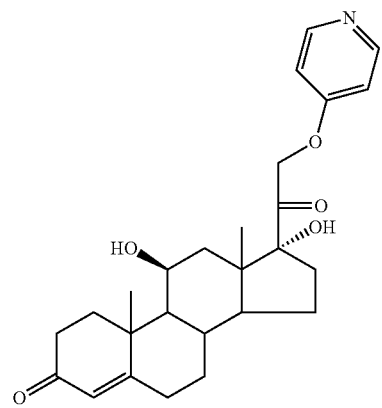 [SMILES: CC12CCC(=O)C=C1CCC1C2[C@@H](O)CC2(C)C1CC[C@]2(O)C(=O)COc1ccncc1] | 440 |

TABLE 1-continued
| Structure | M + H |
|---|---|
| 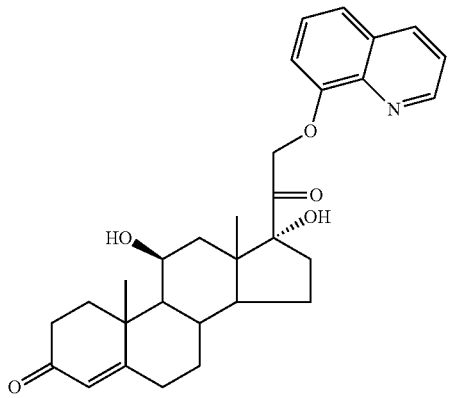 [SMILES: CC12CCC(=O)C=C1CCC1C2[C@@H](O)CC2(C)C1CC[C@]2(O)C(=O)COc1cccc2cccnc12] | 490 |
| 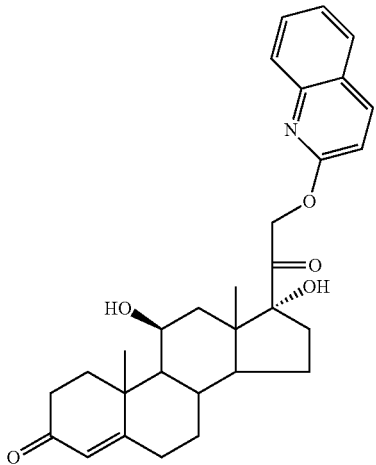 [SMILES: CC12CCC(=O)C=C1CCC1C2[C@@H](O)CC2(C)C1CC[C@]2(O)C(=O)COc1ccc2ccccc2n1] | 490 |
| 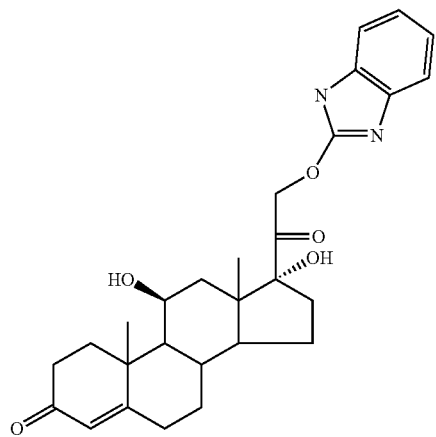 | 479 |

TABLE 1-continued
| Structure | M + H |
|---|---|
| 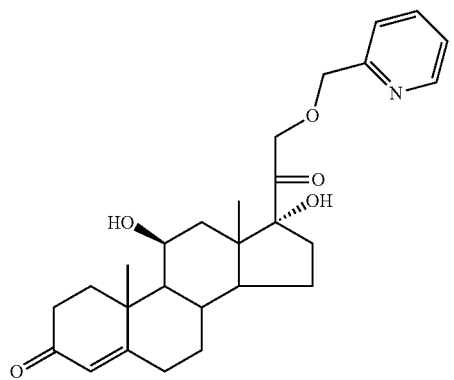 [SMILES: CC12CCC(=O)C=C1CCC1C2[C@@H](O)CC2(C)C1CC[C@]2(O)C(=O)COCc1ccccn1] | 454 |
| 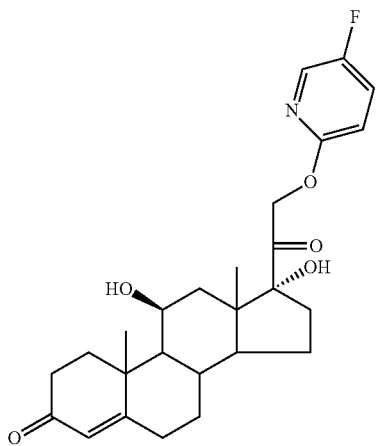 [SMILES: CC12CCC(=O)C=C1CCC1C2[C@@H](O)CC2(C)C1CC[C@]2(O)C(=O)COc1ccc(F)cn1] | 458 |
| 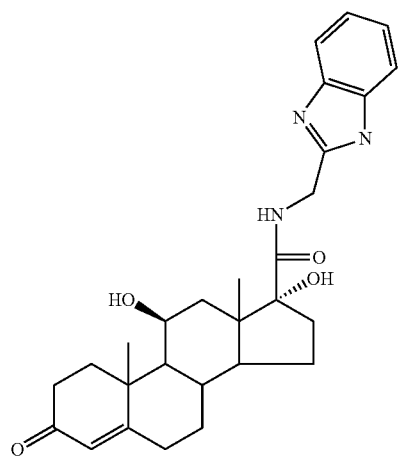 [SMILES: CC12CCC(=O)C=C1CCC1C2[C@@H](O)CC2(C)C1CC[C@]2(O)C(=O)NCc1nc2ccccc2[nH]1] | 478 |

TABLE 1-continued
| Structure | M + H |
|---|---|
| 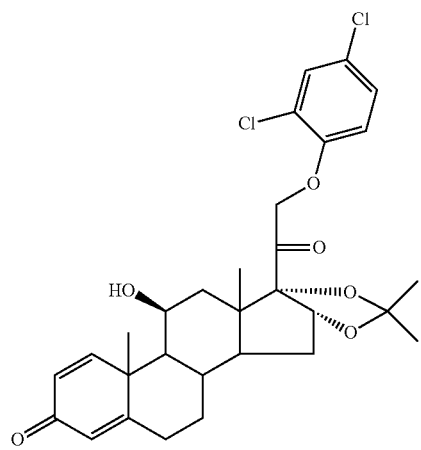 [SMILES: CC1(C)O[C@@H]2CC3C4CCC5=CC(=O)C=CC5(C)C4[C@@H](O)CC3(C)[C@]2(C(=O)COc2ccc(Cl)cc2Cl)O1] | 561 |
| 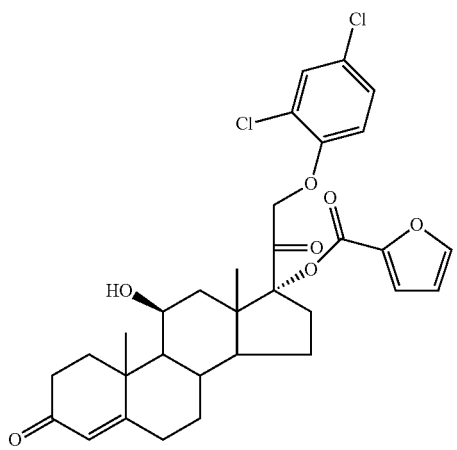 [SMILES: CC12CCC(=O)C=C1CCC1C2[C@@H](O)CC2(C)C1CC[C@]2(OC(=O)c1ccco1)C(=O)COc1ccc(Cl)cc1Cl] | 601 |
| 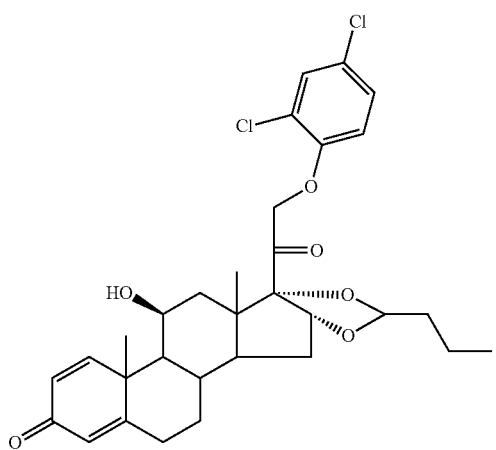 | 575 |

TABLE 1-continued
| Structure | M + H |
|---|---|
| 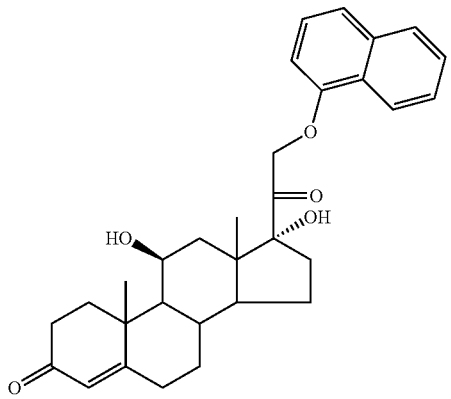 | 489 |
| 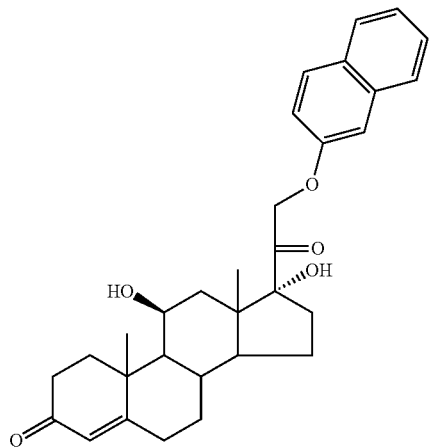 | 489 |
| 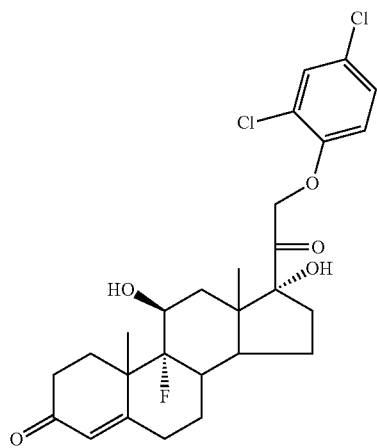 | 525 |

TABLE 1-continued
| Structure | M + H |
|---|---|
| 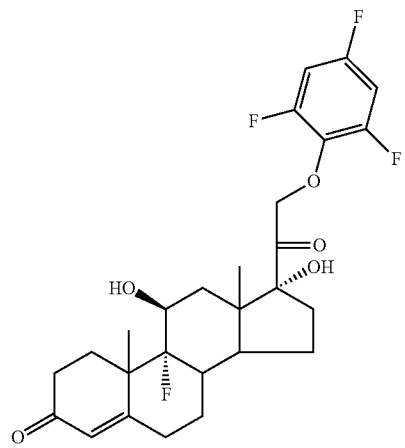 | 511 |
| 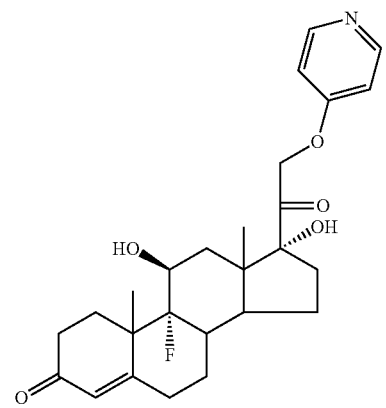 | 458 |
| 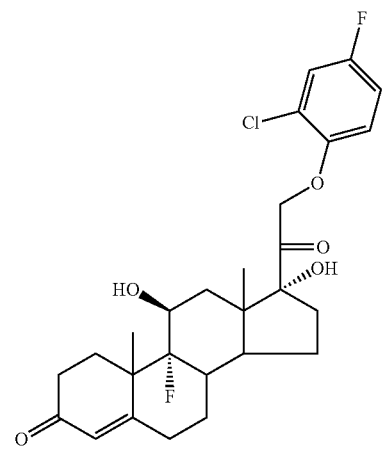 | 509 |

TABLE 1-continued
| Structure | M + H |
|---|---|
| 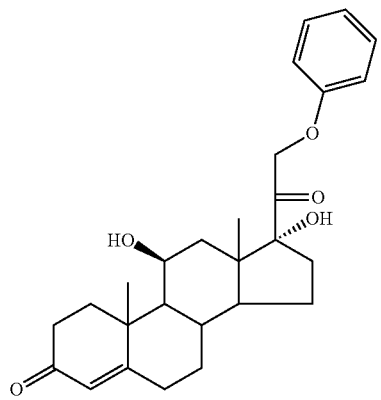 [SMILES: CC12CCC(=O)C=C1CCC1C2[C@@H](O)CC2(C)C1CC[C@]2(O)C(=O)COc1ccccc1] | 439 |
| 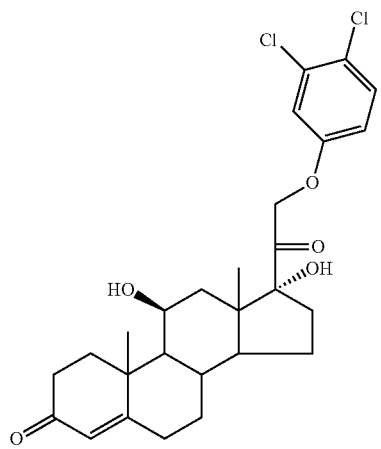 [SMILES: CC12CCC(=O)C=C1CCC1C2[C@@H](O)CC2(C)C1CC[C@]2(O)C(=O)COc1ccc(Cl)c(Cl)c1] | 507 |
| 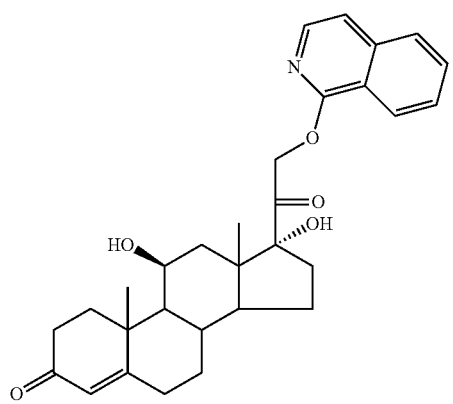 [SMILES: CC12CCC(=O)C=C1CCC1C2[C@@H](O)CC2(C)C1CC[C@]2(O)C(=O)COc1nccc2ccccc12] | 490 |

TABLE 1-continued
| Structure | M + H |
|---|---|
| 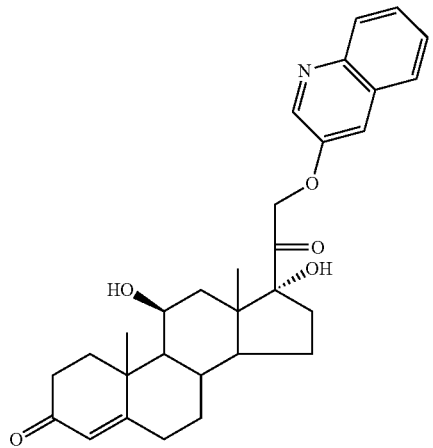 | 490 |
| 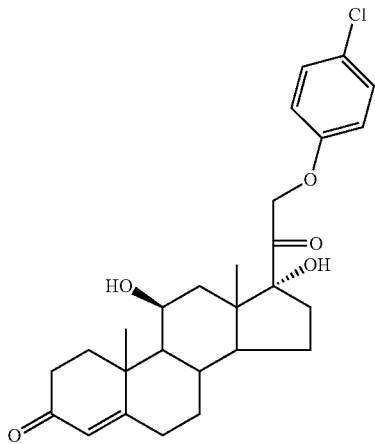 [SMILES: CC12CCC(=O)C=C1CCC1C2[C@@H](O)CC2(C)C1CC[C@]2(O)C(=O)COc1ccc(Cl)cc1] | 473 |
| 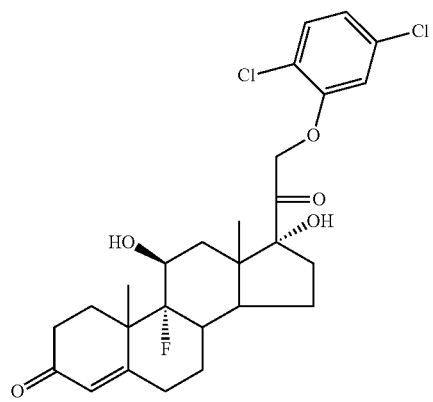 | 525 |

171
172
TABLE 1-continued
| Structure | M + H |
|---|---|
| 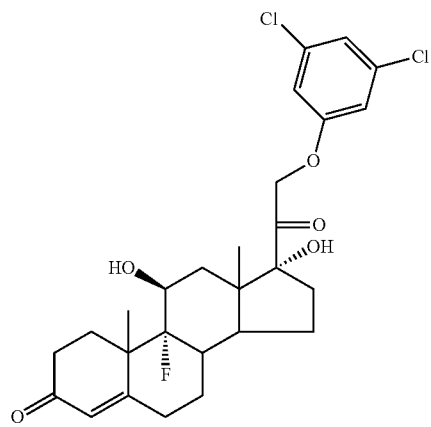 | 525 |
| 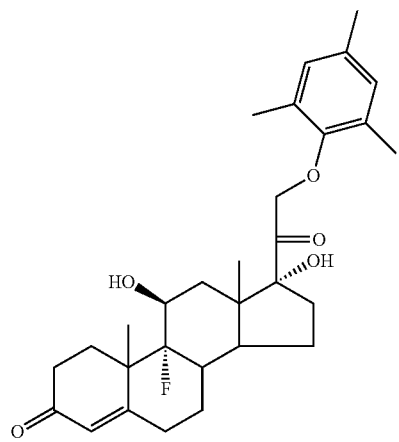 | 499 |
| 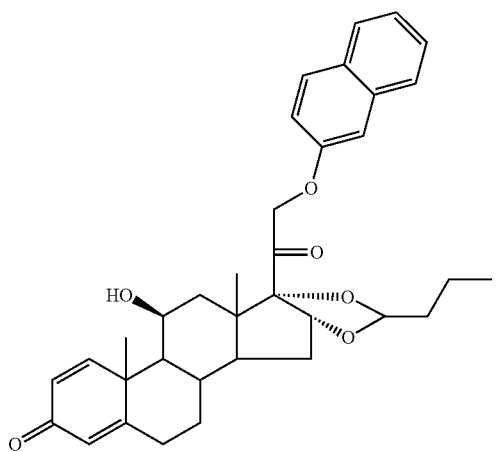 | 557 |

TABLE 1-continued
| Structure | M + H |
|---|---|
| 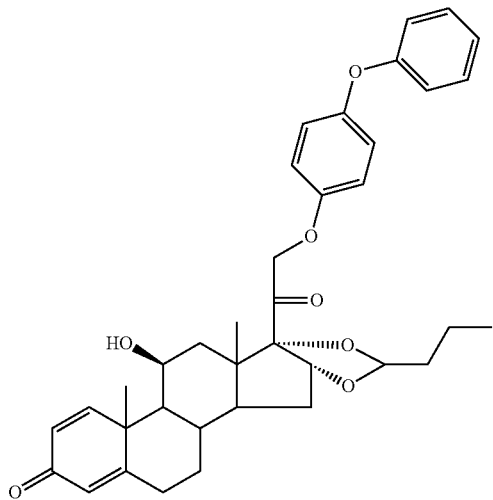 | 599 |
| 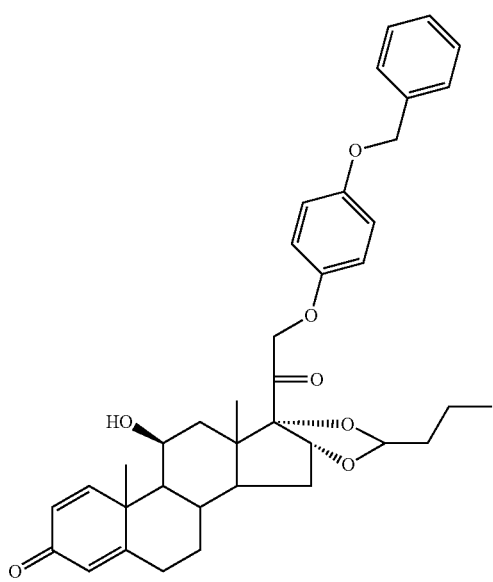 | 613 |
| 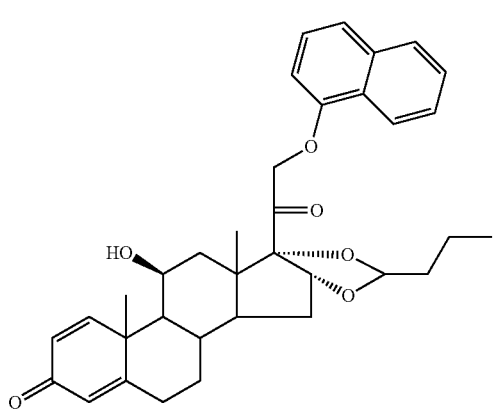 | 557 |

TABLE 1-continued
| Structure | M + H |
|---|---|
| 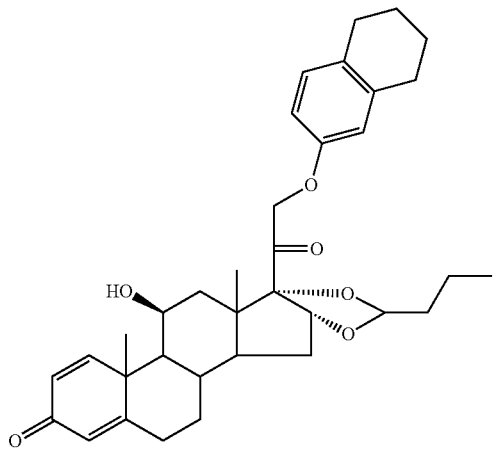 | 561 |
| 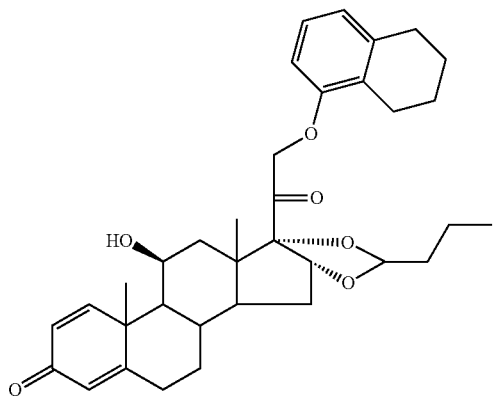 | 561 |
| 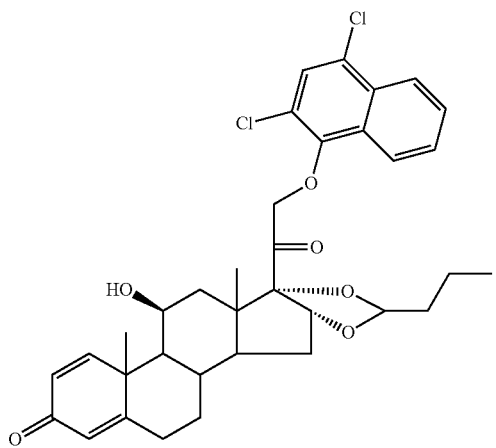 | 625 |

TABLE 1-continued
| Structure | M + H |
|---|---|
| 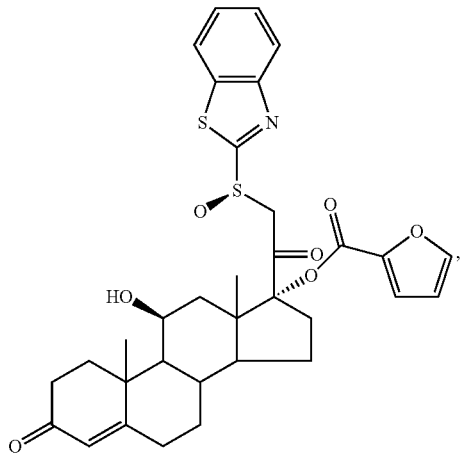 | 622 |
| 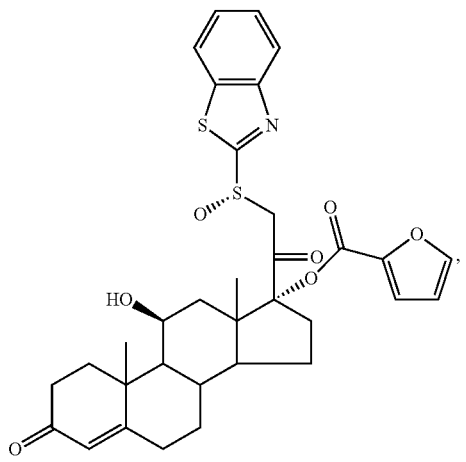 | 622 |
| 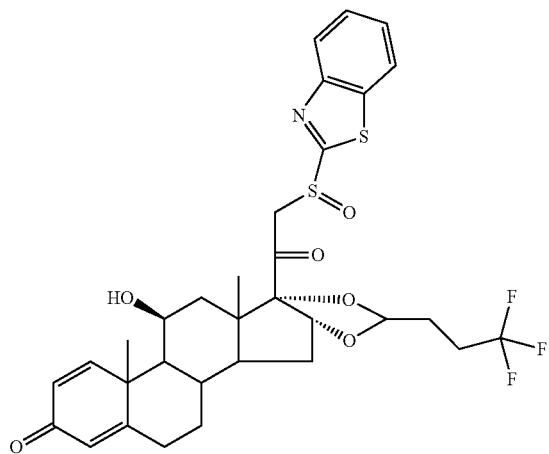 | 650 |

TABLE 1-continued
| Structure | M + H |
|---|---|
| 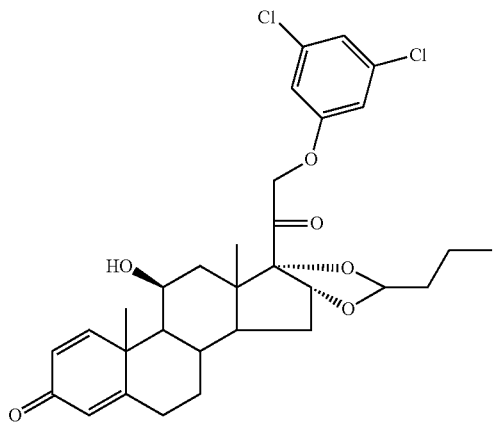 | 575 |
| 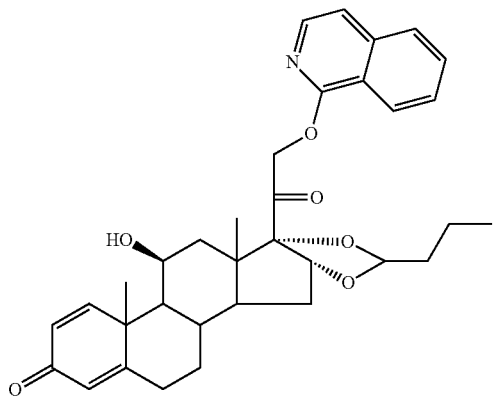 | 558 |
| 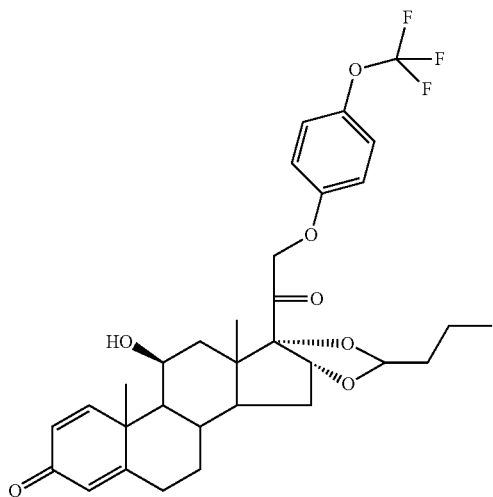 | 591 |

TABLE 1-continued
| Structure | M + H |
|---|---|
| 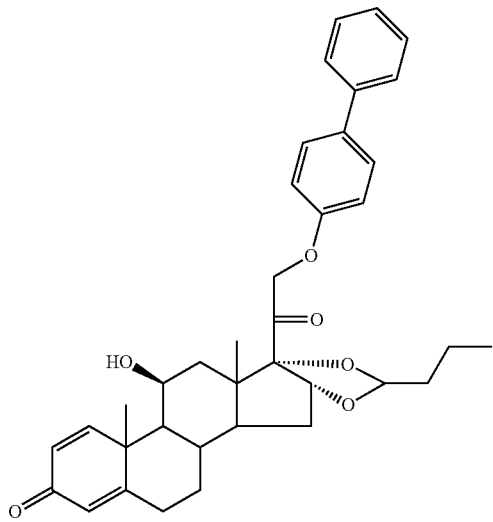 | 583 |
| 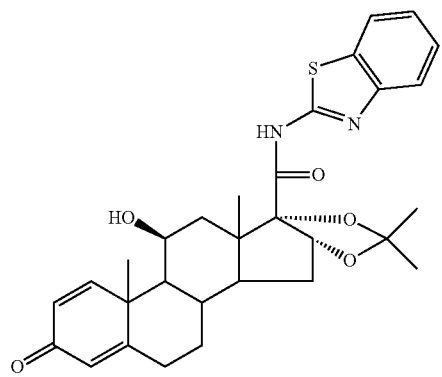 [SMILES: CC1(C)O[C@@H]2CC3C4CCC5=CC(=O)C=CC5(C)C4[C@@H](O)CC3(C)[C@]2(C(=O)Nc2nc3ccccc3s2)O1] | 535 |
| 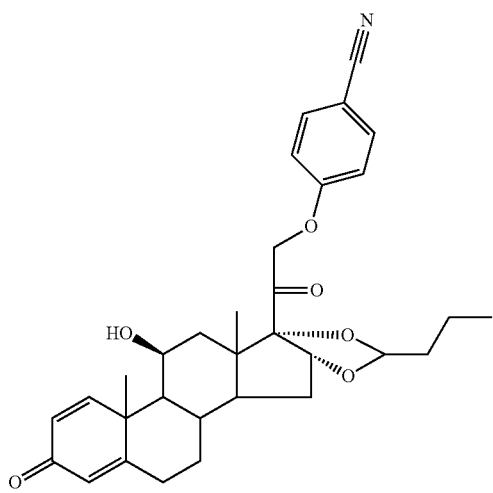 | 532 |

TABLE 1-continued
| Structure | M + H |
|---|---|
| 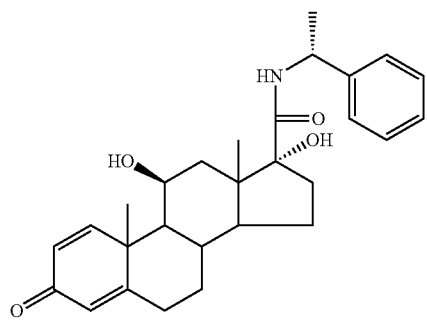 [SMILES: C[C@@H](NC(=O)[C@@]1(O)CCC2C3CCC4=CC(=O)C=CC4(C)C3[C@@H](O)CC21C)c1ccccc1] | 450 |
| 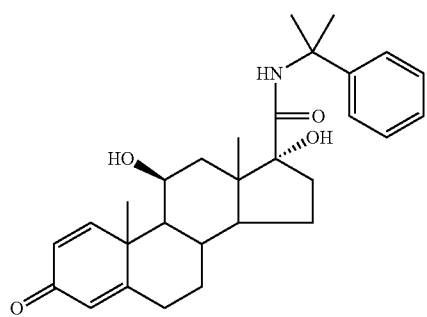 [SMILES: CC(C)(NC(=O)[C@@]1(O)CCC2C3CCC4=CC(=O)C=CC4(C)C3[C@@H](O)CC21C)c1ccccc1] | 464 |
| 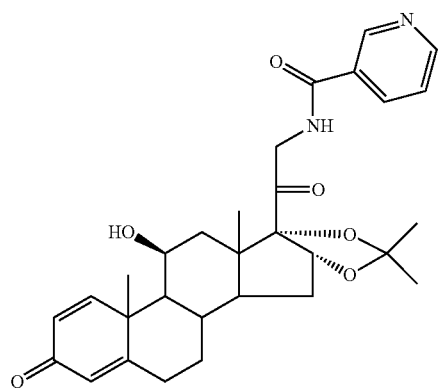 [SMILES: CC1(C)O[C@@H]2CC3C4CCC5=CC(=O)C=CC5(C)C4[C@@H](O)CC3(C)[C@]2(C(=O)CNC(=O)c2cccnc2)O1] | 521 |
| 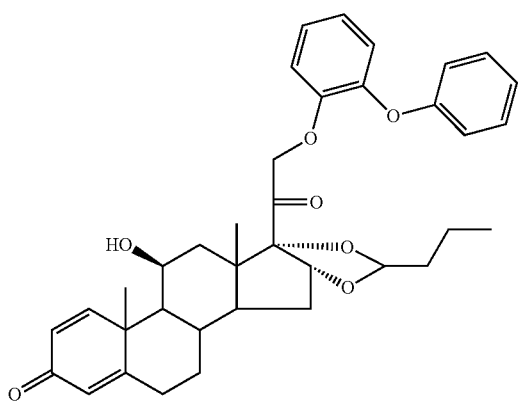 | 599 |

TABLE 1-continued
| Structure | M + H |
|---|---|
| 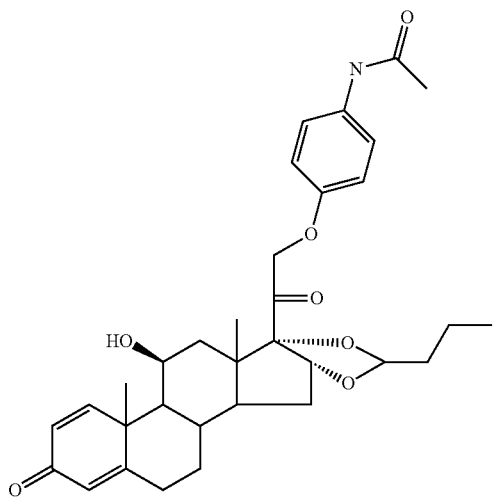 | 564 |
| 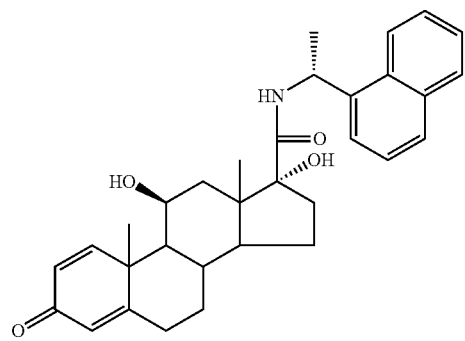 [SMILES: C[C@@H](NC(=O)[C@@]1(O)CCC2C3CCC4=CC(=O)C=CC4(C)C3[C@@H](O)CC21C)c1cccc2ccccc12] | 500 |
| 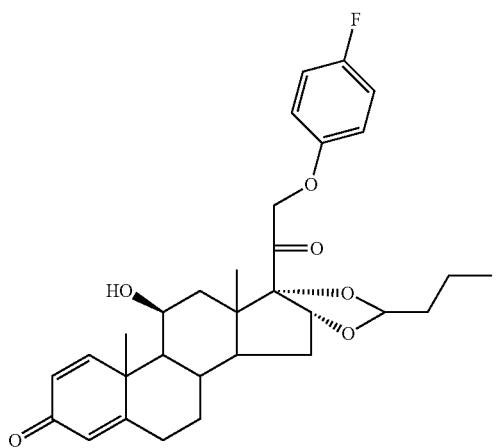 | 525 |

TABLE 1-continued
| Structure | M + H |
|---|---|
| 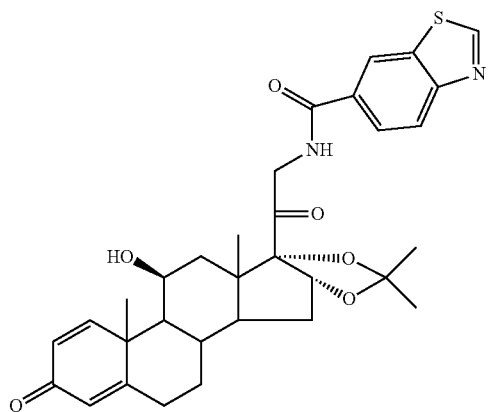 [SMILES: CC1(C)O[C@@H]2CC3C4CCC5=CC(=O)C=CC5(C)C4[C@@H](O)CC3(C)[C@]2(C(=O)CNC(=O)c2ccc3ncsc3c2)O1] | 577 |
| 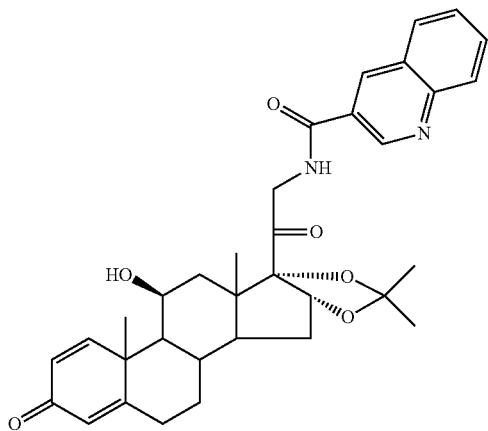 [SMILES: CC1(C)O[C@@H]2CC3C4CCC5=CC(=O)C=CC5(C)C4[C@@H](O)CC3(C)[C@]2(C(=O)CNC(=O)c2cnc3ccccc3c2)O1] | 571 |
| 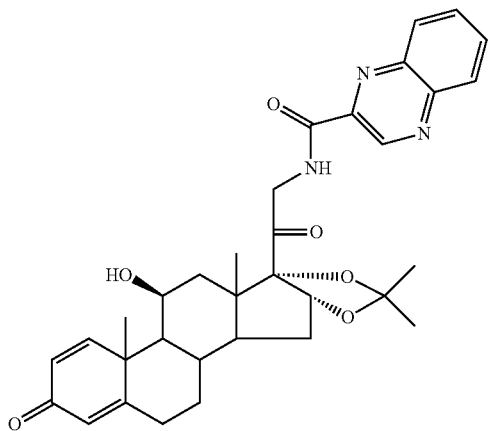 [SMILES: CC1(C)O[C@@H]2CC3C4CCC5=CC(=O)C=CC5(C)C4[C@@H](O)CC3(C)[C@]2(C(=O)CNC(=O)c2cnc3ccccc3n2)O1] | 572 |

TABLE 1-continued
| Structure | M + H |
|---|---|
| 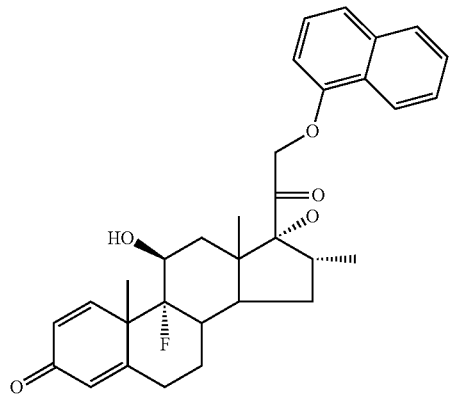 | 519 |
| | 519 |
| 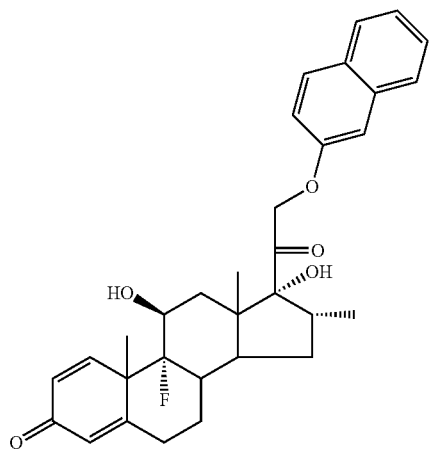 | 450 |
| 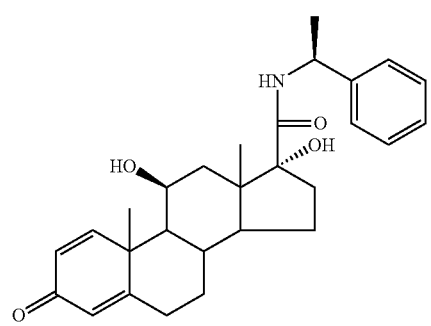 [SMILES: C[C@H](NC(=O)[C@@]1(O)CCC2C3CCC4=CC(=O)C=CC4(C)C3[C@@H](O)CC21C)c1ccccc1] | |

TABLE 1-continued
| Structure | M + H |
|---|---|
| 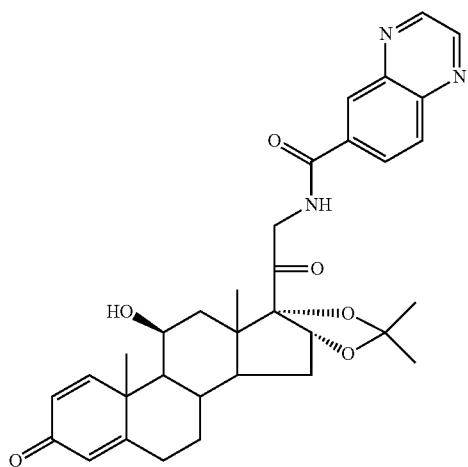 [SMILES: CC1(C)O[C@@H]2CC3C4CCC5=CC(=O)C=CC5(C)C4[C@@H](O)CC3(C)[C@]2(C(=O)CNC(=O)c2ccc3nccnc3c2)O1] | 572 |
| 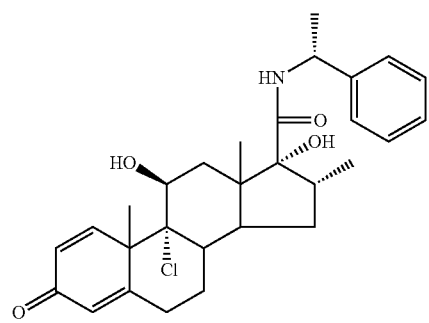 | 498 |
| 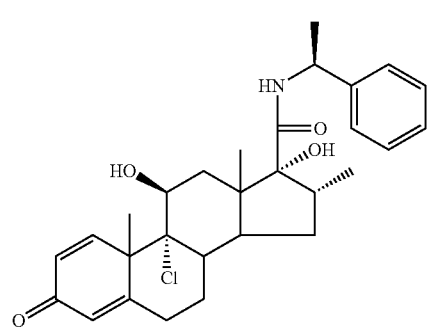 | 498 |
| 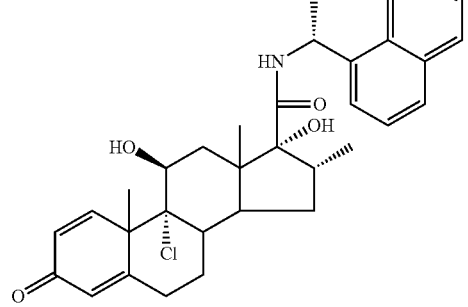 | 548 |

US 8,524,697 B2
193                                                                                             194
TABLE 1-continued
| Structure | M + H |
|---|---|
545
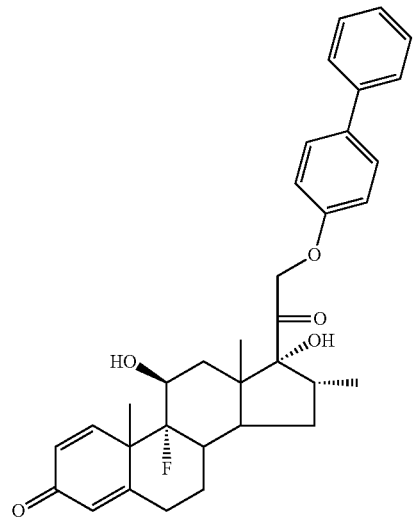
575
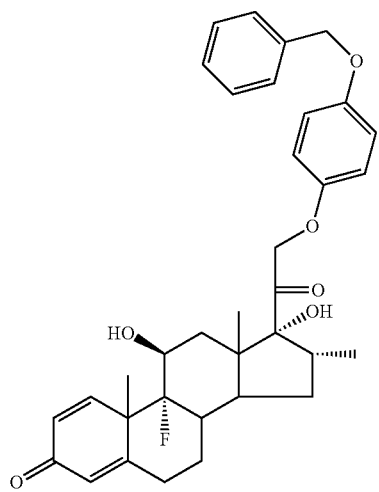
523
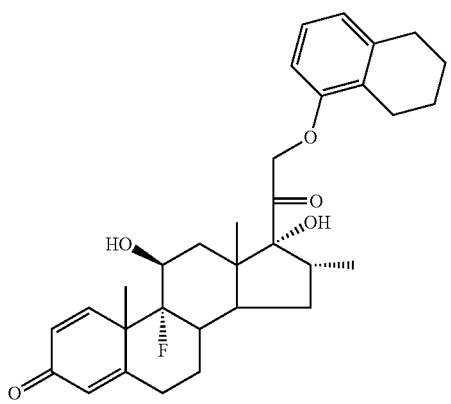

TABLE 1-continued
| Structure | M + H |
|---|---|
| 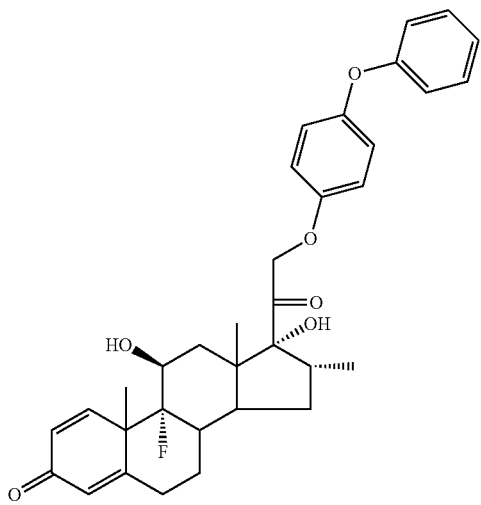 | 561 |
| 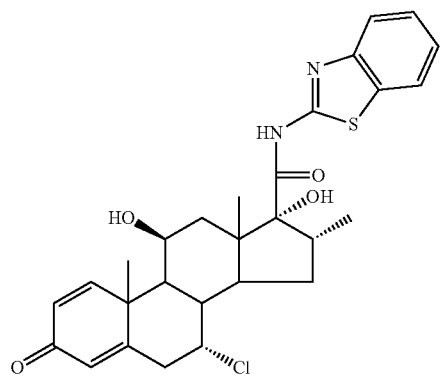 [SMILES: C[C@@H]1CC2C3C([C@@H](O)CC2(C)[C@@]1(O)C(=O)Nc1nc2ccccc2s1)C1(C)C=CC(=O)C=C1C[C@H]3Cl] | 527 |
| 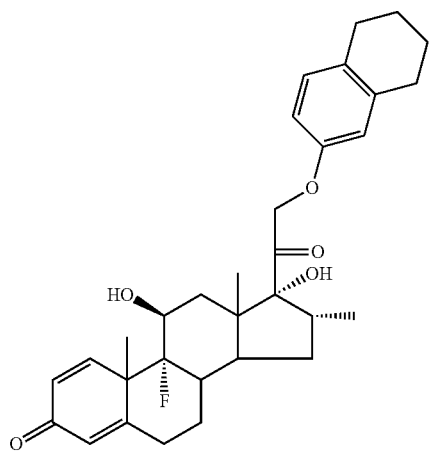 | 523 |

TABLE 1-continued

| Structure | M + H |
|---|---|
| 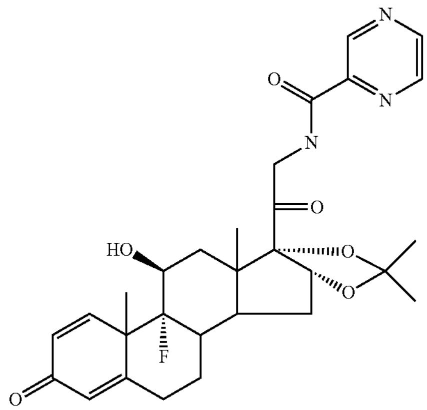 | 540 |
| 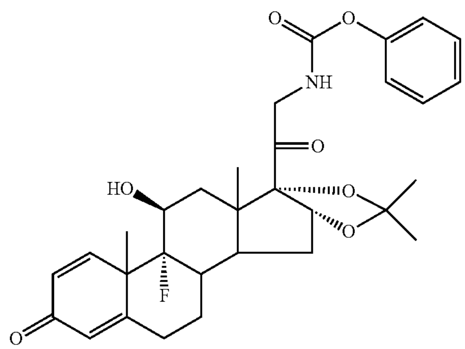 | 554 |
| 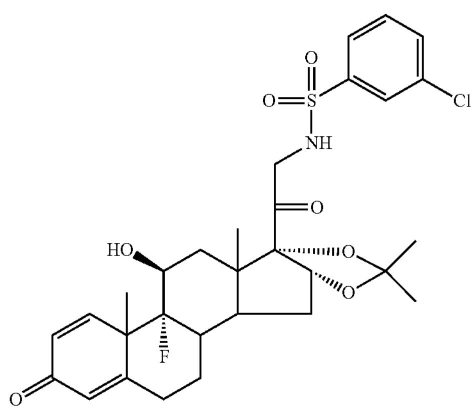 | 608 |
| 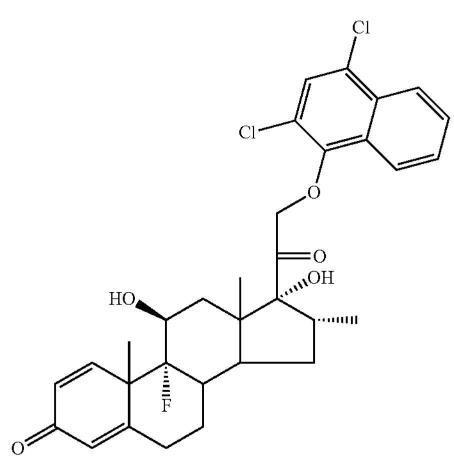 | 587 |

TABLE 1-continued
| Structure | M + H |
|---|---|
| 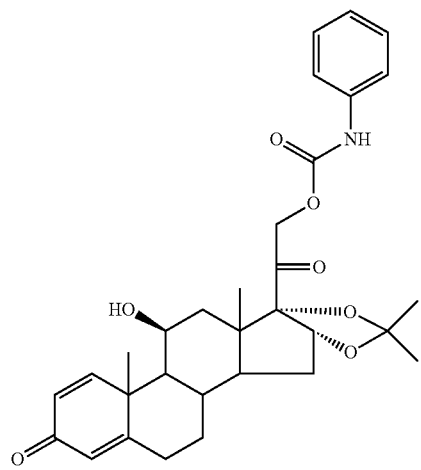 [SMILES: CC1(C)O[C@@H]2CC3C4CCC5=CC(=O)C=CC5(C)C4[C@@H](O)CC3(C)[C@]2(C(=O)COC(=O)Nc2ccccc2)O1] | 536 |
| 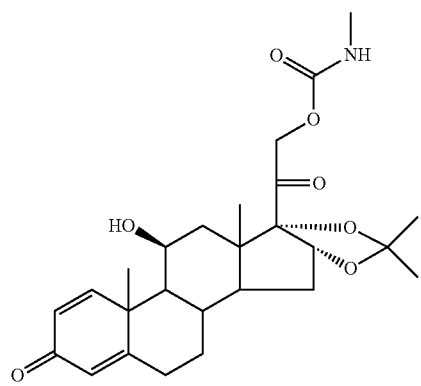 [SMILES: CNC(=O)OCC(=O)[C@@]12OC(C)(C)O[C@@H]1CC1C3CCC4=CC(=O)C=CC4(C)C3[C@@H](O)CC12C] | 474 |
| 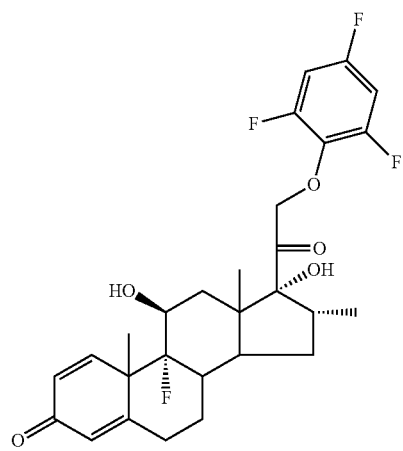 | 523 |

TABLE 1-continued
| Structure | M + H |
|---|---|
| 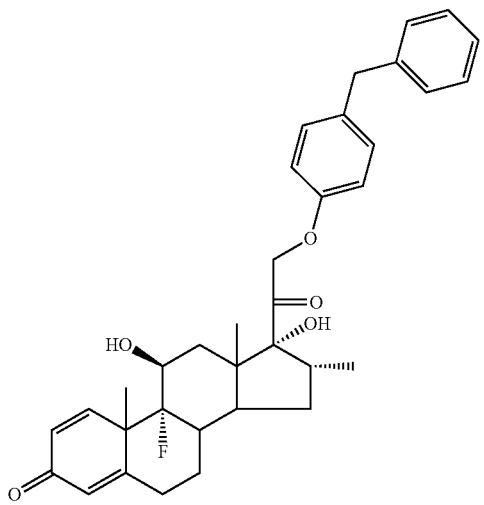 | 559 |
| 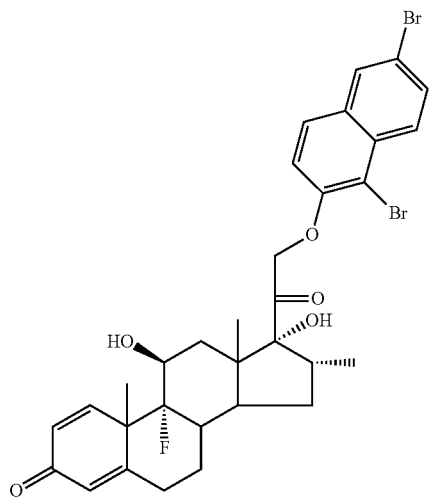 | 675 |
| 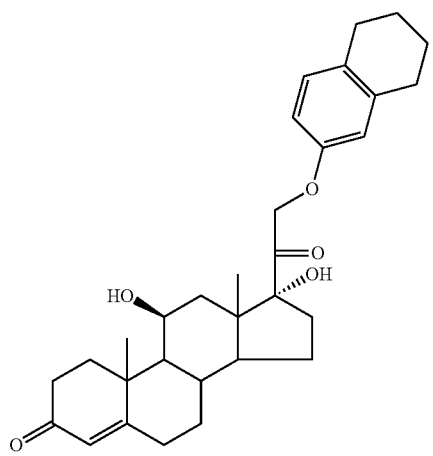 [SMILES: CC12CCC(=O)C=C1CCC1C2[C@@H](O)CC2(C)C1CC[C@]2(O)C(=O)COc1ccc2c(c1)CCCC2] | 493 |

TABLE 1-continued
| Structure | M + H |
|---|---|
| 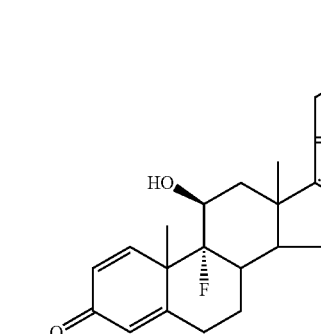 | 537 |
| 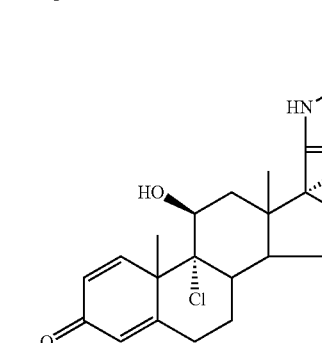 | 499 |
| 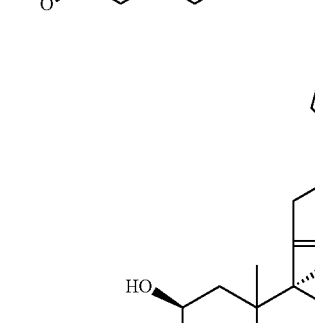 | 501 |
| 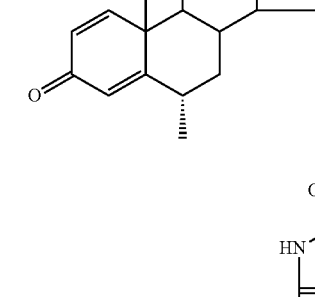 | 486 |

TABLE 1-continued
| Structure | M + H |
|---|---|
| 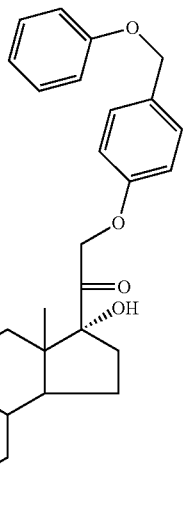 | 557 |
| 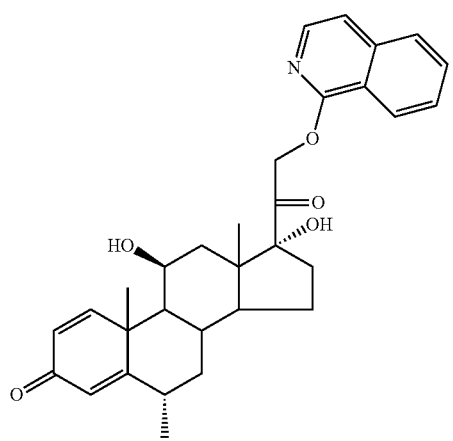 | 502 |
| 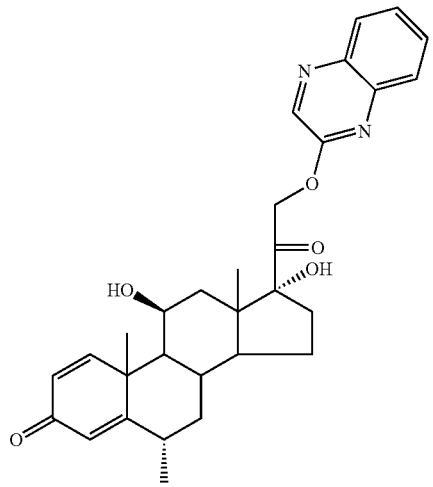 [SMILES: C[C@H]1CC2C([C@@H](O)CC3(C)C2CC[C@]3(O)C(=O)COc2cnc3ccccc3n2)C2(C)C=CC(=O)C=C12] | 503 |

TABLE 1-continued

| Structure | M + H |
|---|---|
| (structure) | 541 |
| (structure) | 537 |
| (structure) | 543 |

TABLE 1-continued
| Structure | M + H |
|---|---|
| 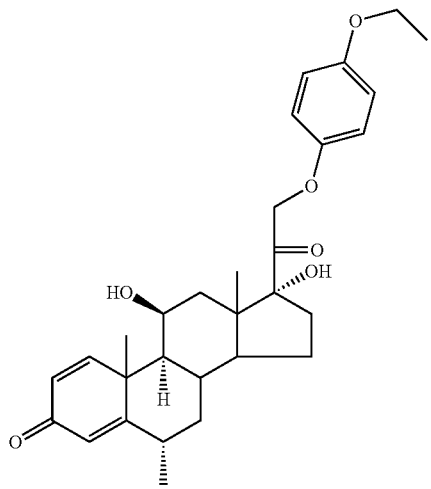 | 495 |
| 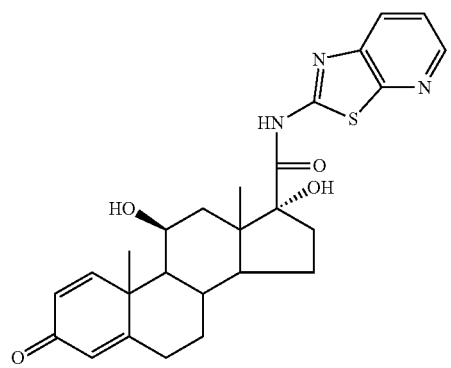 [SMILES: CC12C=CC(=O)C=C1CCC1C2[C@@H](O)CC2(C)C1CC[C@]2(O)C(=O)Nc1nc2cccnc2s1] | 480 |
| 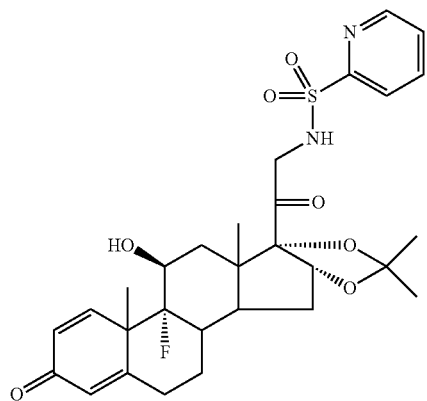 | 575 |

TABLE 1-continued
| Structure | M + H |
|---|---|
| 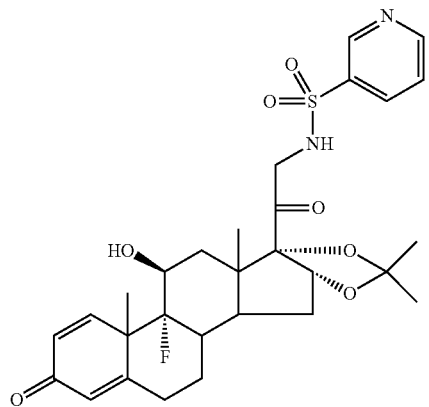 | 575 |
| 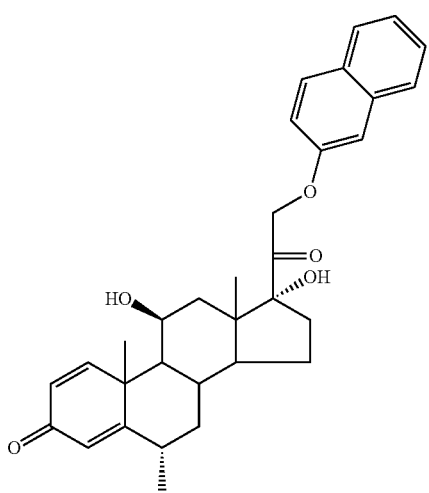 [SMILES: C[C@H]1CC2C([C@@H](O)CC3(C)C2CC[C@]3(O)C(=O)COc2ccc3ccccc3c2)C2(C)C=CC(=O)C=C12] | 501 |
| 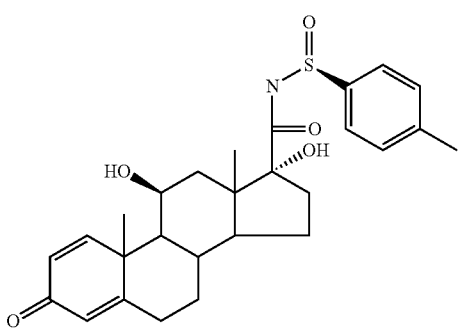 [SMILES: Cc1ccc([S@](=O)NC(=O)[C@@]2(O)CCC3C4CCC5=CC(=O)C=CC5(C)C4[C@@H](O)CC32C)cc1] | 484 |
| 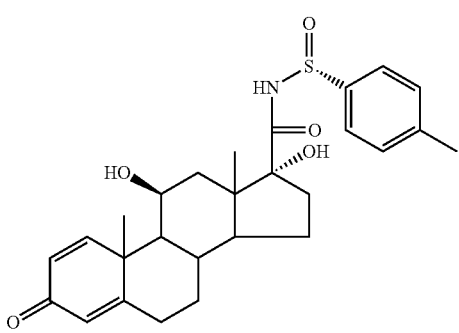 [SMILES: Cc1ccc([S@@](=O)NC(=O)[C@@]2(O)CCC3C4CCC5=CC(=O)C=CC5(C)C4[C@@H](O)CC32C)cc1] | 484 |

TABLE 1-continued

| Structure | M + H |
|---|---|
| [steroid with 2-(3,5-dichlorophenoxy)acetyl group, 11-OH, 17-OH, 6-methyl] | 519 |
| [steroid with C(=O)NH-(pyridin-2-yl) group, 11-OH, 17-OH] | 426 |
| [steroid with C(=O)NH-(thiazolo[5,4-b]pyridin-2-yl), 11-OH, 17-OH, 16-methyl, 9-Cl] | 528 |
| [steroid with 2-(quinolin-8-yloxy)acetyl group, 11-OH, 17-OH, 6-methyl] | 502 |

TABLE 1-continued

| Structure | M + H |
|---|---|
| 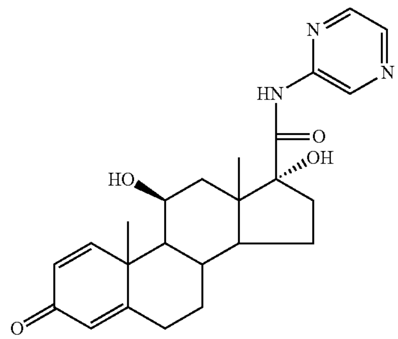 [SMILES: CC12C=CC(=O)C=C1CCC1C2[C@@H](O)CC2(C)C1CC[C@]2(O)C(=O)Nc1cnccn1] | 424 |
| 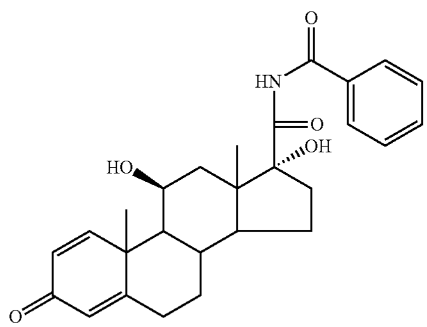 [SMILES: CC12C=CC(=O)C=C1CCC1C2[C@@H](O)CC2(C)C1CC[C@]2(O)C(=O)NC(=O)c1ccccc1] | 450 |
| 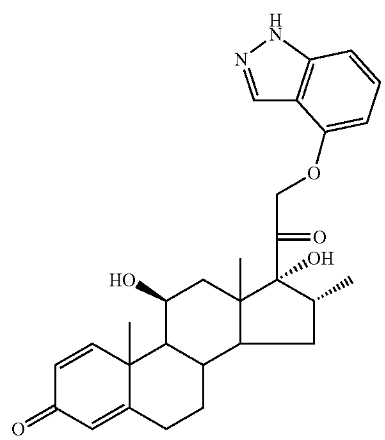 [SMILES: C[C@@H]1CC2C3CCC4=CC(=O)C=CC4(C)C3[C@@H](O)CC2(C)[C@@]1(O)C(=O)COc1cccc2[nH]ncc12] | 491 |
| 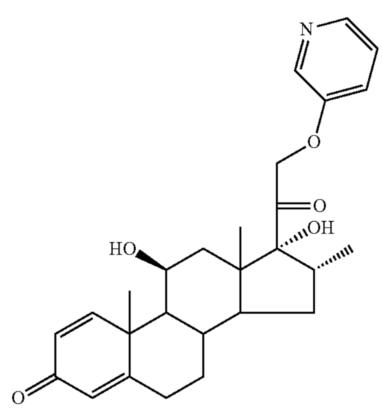 [SMILES: C[C@@H]1CC2C3CCC4=CC(=O)C=CC4(C)C3[C@@H](O)CC2(C)[C@@]1(O)C(=O)COc1cccnc1] | 452 |

TABLE 1-continued
| Structure | M + H |
|---|---|
| 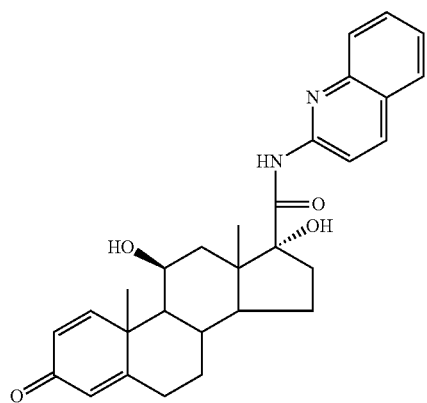 [SMILES: CC12C=CC(=O)C=C1CCC1C2[C@@H](O)CC2(C)C1CC[C@]2(O)C(=O)Nc1ccc2ccccc2n1] | 473 |
| 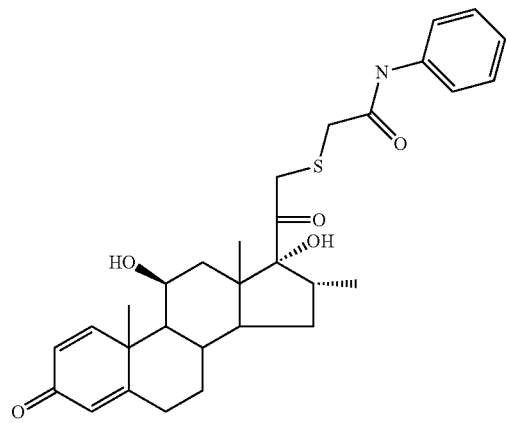 [SMILES: C[C@@H]1CC2C3CCC4=CC(=O)C=CC4(C)C3[C@@H](O)CC2(C)[C@@]1(O)C(=O)CSCC(=O)Nc1ccccc1] | 524 |
| 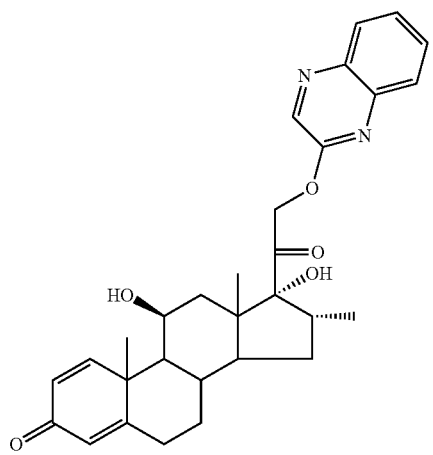 | 503 |

TABLE 1-continued
| Structure | M + H |
|---|---|
| 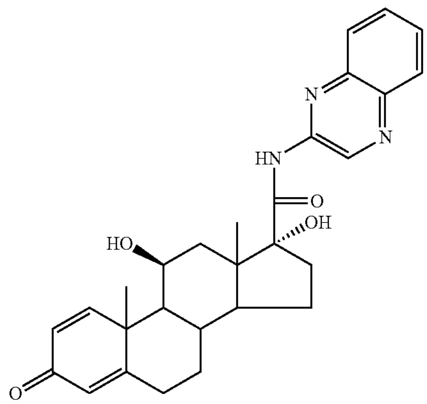 [SMILES: CC12C=CC(=O)C=C1CCC1C2[C@@H](O)CC2(C)C1CC[C@]2(O)C(=O)Nc1cnc2ccccc2n1] | 474 |
| 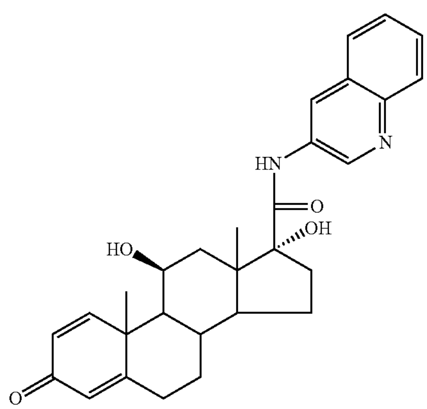 [SMILES: CC12C=CC(=O)C=C1CCC1C2[C@@H](O)CC2(C)C1CC[C@]2(O)C(=O)Nc1cnc2ccccc2c1] | 473 |
| 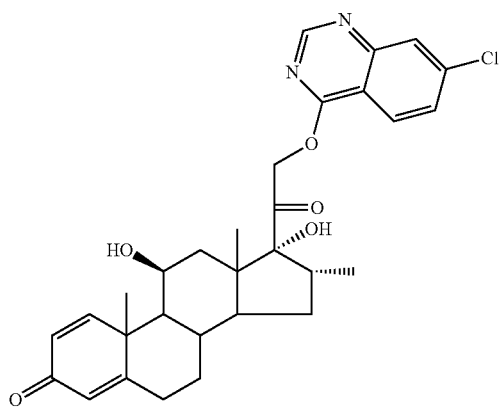 [SMILES: C[C@@H]1CC2C3CCC4=CC(=O)C=CC4(C)C3[C@@H](O)CC2(C)[C@@]1(O)C(=O)COc1ncnc2cc(Cl)ccc12] | 537 |

TABLE 1-continued
| Structure | M + H |
|---|---|
| 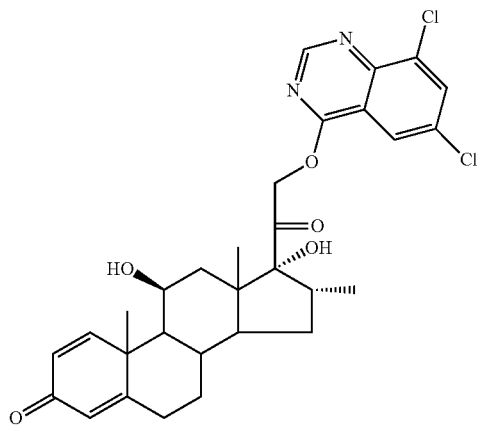 [SMILES: C[C@@H]1CC2C3CCC4=CC(=O)C=CC4(C)C3[C@@H](O)CC2(C)[C@@]1(O)C(=O)COc1ncnc2c(Cl)cc(Cl)cc12] | 571 |
| 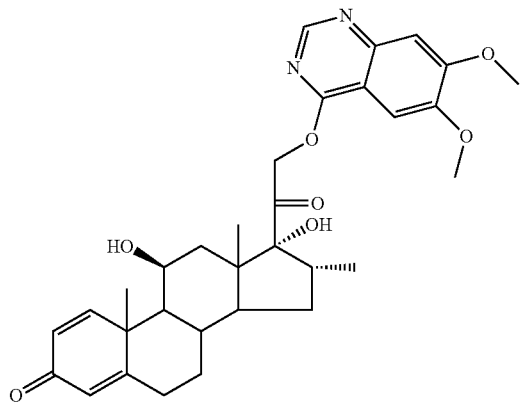 [SMILES: COc1cc2ncnc(OCC(=O)[C@@]3(O)[C@H](C)CC4C5CCC6=CC(=O)C=CC6(C)C5[C@@H](O)CC43C)c2cc1OC] | 563 |
| 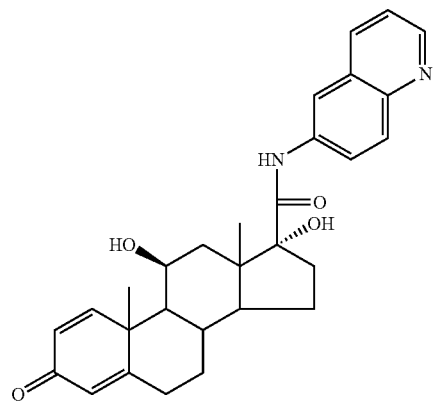 [SMILES: CC12C=CC(=O)C=C1CCC1C2[C@@H](O)CC2(C)C1CC[C@]2(O)C(=O)Nc1ccc2ncccc2c1] | 473 |

TABLE 1-continued
| Structure | M + H |
|---|---|
| 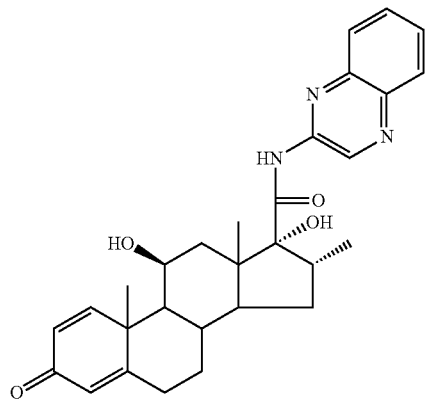 [SMILES: C[C@@H]1CC2C3CCC4=CC(=O)C=CC4(C)C3[C@@H](O)CC2(C)[C@@]1(O)C(=O)Nc1cnc2ccccc2n1] | 488 |
| 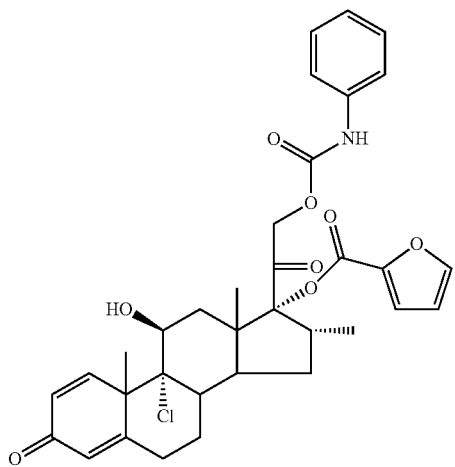 | 622 |
| 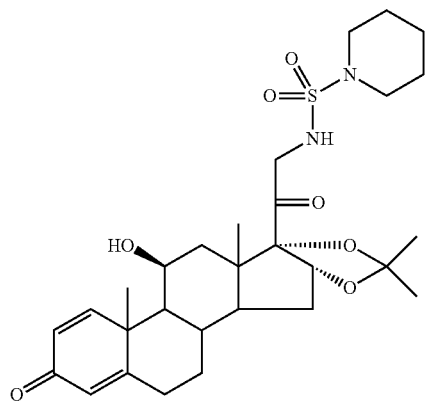 [SMILES: CC1(C)O[C@@H]2CC3C4CCC5=CC(=O)C=CC5(C)C4[C@@H](O)CC3(C)[C@]2(C(=O)CNS(=O)(=O)N2CCCCC2)O1] | 563 |

TABLE 1-continued
| Structure | M + H |
|---|---|
| 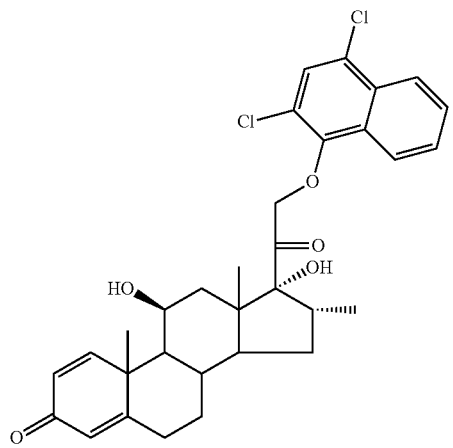 [SMILES: C[C@@H]1CC2C3CCC4=CC(=O)C=CC4(C)C3[C@@H](O)CC2(C)[C@@]1(O)C(=O)COc1c(Cl)cc(Cl)c2ccccc12] | 569 |
| 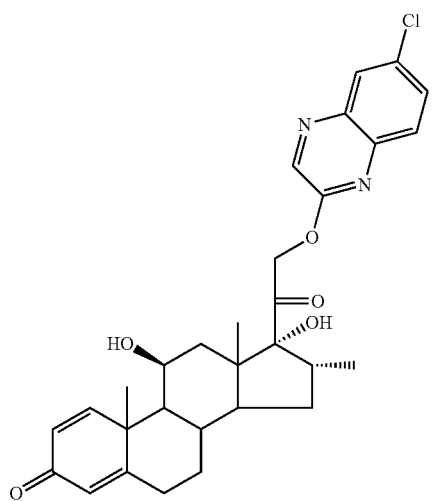 [SMILES: C[C@@H]1CC2C3CCC4=CC(=O)C=CC4(C)C3[C@@H](O)CC2(C)[C@@]1(O)C(=O)COc1cnc2cc(Cl)ccc2n1] | 537 |
| 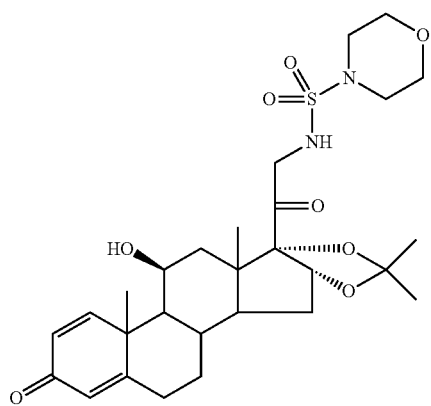 [SMILES: CC1(C)O[C@@H]2CC3C4CCC5=CC(=O)C=CC5(C)C4[C@@H](O)CC3(C)[C@]2(C(=O)CNS(=O)(=O)N2CCOCC2)O1] | 565 |

TABLE 1-continued
| Structure | M + H |
|---|---|
| 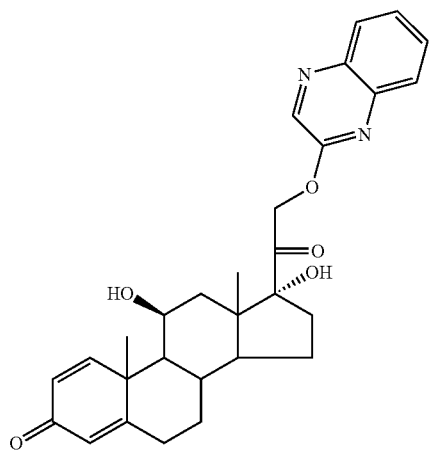 [SMILES: CC12C=CC(=O)C=C1CCC1C2[C@@H](O)CC2(C)C1CC[C@]2(O)C(=O)COc1cnc2ccccc2n1] | 489 |
| 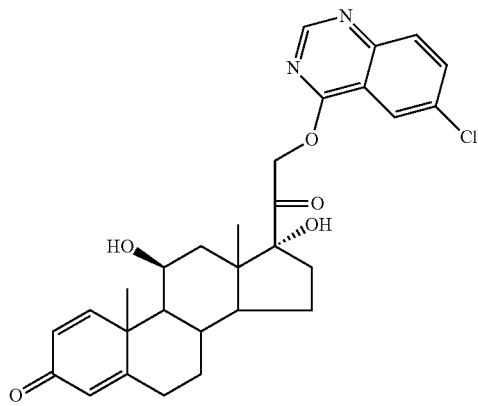 [SMILES: CC12C=CC(=O)C=C1CCC1C2[C@@H](O)CC2(C)C1CC[C@]2(O)C(=O)COc1ncnc2ccc(Cl)cc12] | 523 |
| 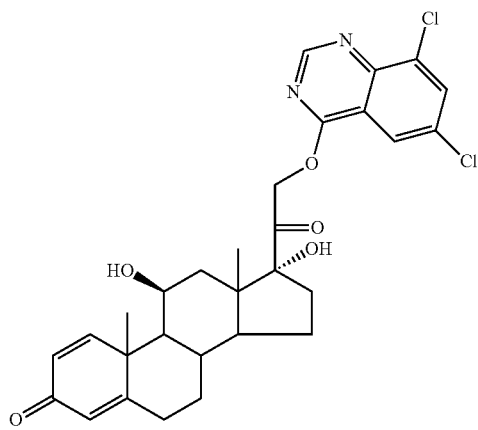 [SMILES: CC12C=CC(=O)C=C1CCC1C2[C@@H](O)CC2(C)C1CC[C@]2(O)C(=O)COc1ncnc2c(Cl)cc(Cl)cc12] | 557 |

TABLE 1-continued

| Structure | M + H |
|---|---|
| 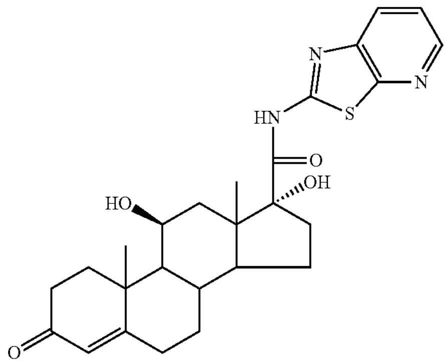 [SMILES: CC12CCC(=O)C=C1CCC1C2[C@@H](O)CC2(C)C1CC[C@]2(O)C(=O)Nc1nc2cccnc2s1] | 482 |
| 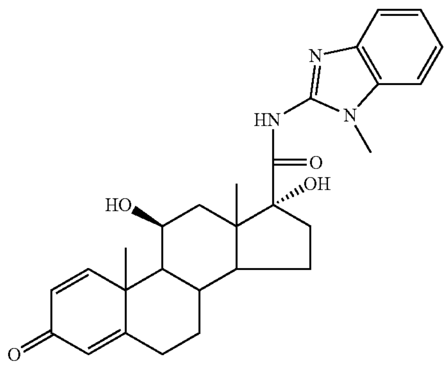 [SMILES: Cn1c(NC(=O)[C@@]2(O)CCC3C4CCC5=CC(=O)C=CC5(C)C4[C@@H](O)CC32C)nc2ccccc21] | 476 |
| 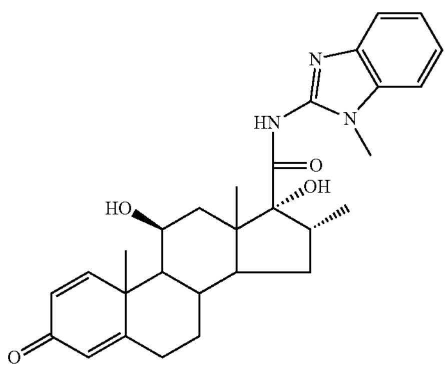 [SMILES: C[C@@H]1CC2C3CCC4=CC(=O)C=CC4(C)C3[C@@H](O)CC2(C)[C@@]1(O)C(=O)Nc1nc2ccccc2n1C] | 490 |
| 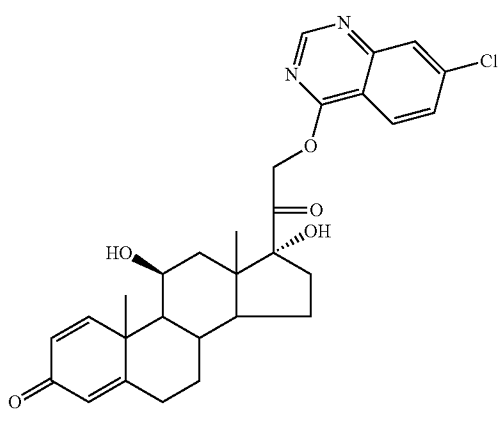 [SMILES: CC12C=CC(=O)C=C1CCC1C2[C@@H](O)CC2(C)C1CC[C@]2(O)C(=O)COc1ncnc2cc(Cl)ccc12] | 523 |

TABLE 1-continued
| Structure | M + H |
|---|---|
| 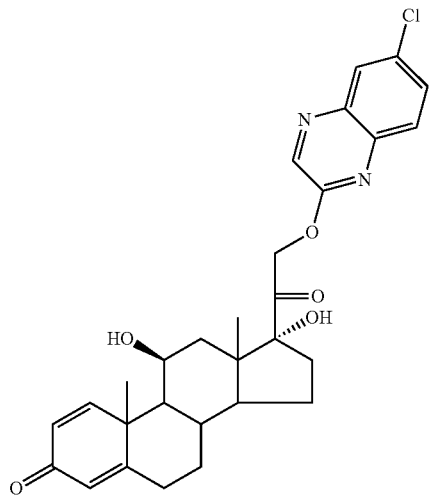 [SMILES: CC12C=CC(=O)C=C1CCC1C2[C@@H](O)CC2(C)C1CC[C@]2(O)C(=O)COc1cnc2cc(Cl)ccc2n1] | 523 |
| 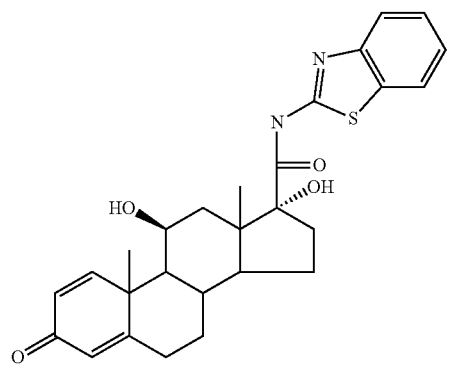 [SMILES: CC12C=CC(=O)C=C1CCC1C2[C@@H](O)CC2(C)C1CC[C@]2(O)C(=O)Nc1nc2ccccc2s1] | 479 |
| 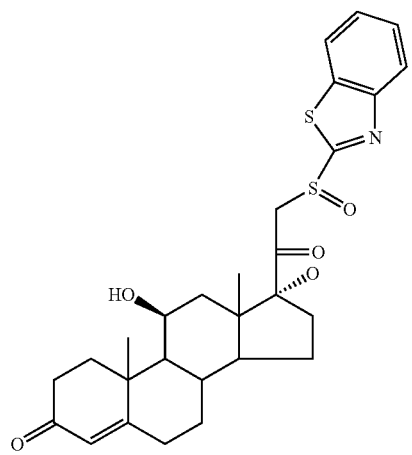 [SMILES: CC12CCC(=O)C=C1CCC1C2[C@@H](O)CC2(C)C1CC[C@]2(O)C(=O)CS(=O)c1nc2ccccc2s1] | 528 |

TABLE 1-continued

| Structure | M + H |
|---|---|
| 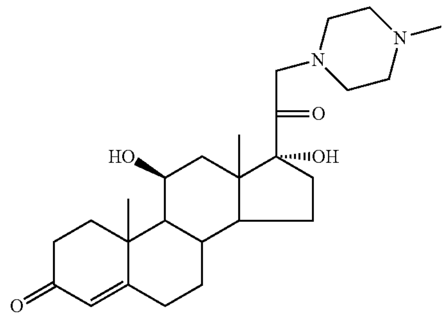 [SMILES: CN1CCN(CC(=O)[C@@]2(O)CCC3C4CCC5=CC(=O)CCC5(C)C4[C@@H](O)CC32C)CC1] | 445 |
| 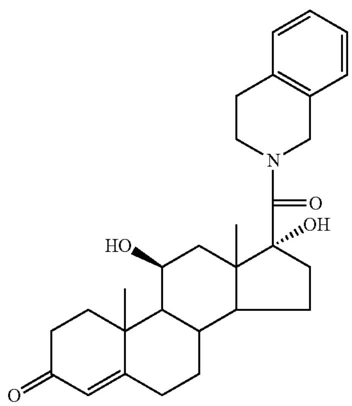 [SMILES: CC12CCC(=O)C=C1CCC1C2[C@@H](O)CC2(C)C1CC[C@]2(O)C(=O)N1CCc2ccccc2C1] | 464 |
| 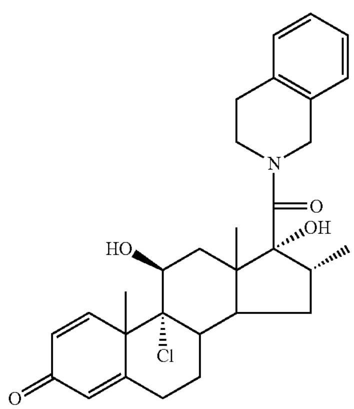 | 510 |
| 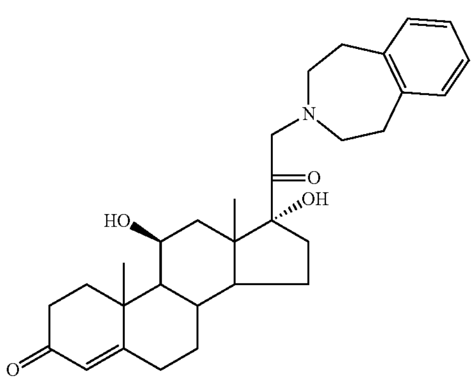 [SMILES: CC12CCC(=O)C=C1CCC1C2[C@@H](O)CC2(C)C1CC[C@]2(O)C(=O)CN1CCc2ccccc2CC1] | 492 |

TABLE 1-continued
| Structure | M + H |
|---|---|
| 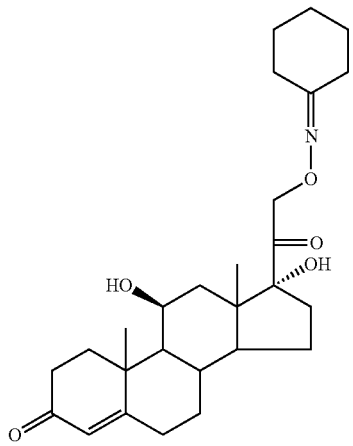 [SMILES: CC12CCC(=O)C=C1CCC1C2[C@@H](O)CC2(C)C1CC[C@]2(O)C(=O)CON=C1CCCCC1] | 458 |
| 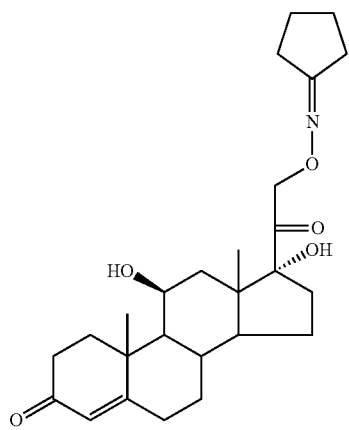 [SMILES: CC12CCC(=O)C=C1CCC1C2[C@@H](O)CC2(C)C1CC[C@]2(O)C(=O)CON=C1CCCC1] | 444 |
| 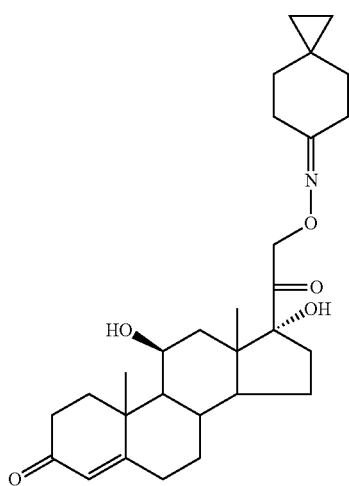 [SMILES: CC12CCC(=O)C=C1CCC1C2[C@@H](O)CC2(C)C1CC[C@]2(O)C(=O)CON=C1CCC2(CC1)CC2] | 484 |

TABLE 1-continued
| Structure | M + H |
|---|---|
| 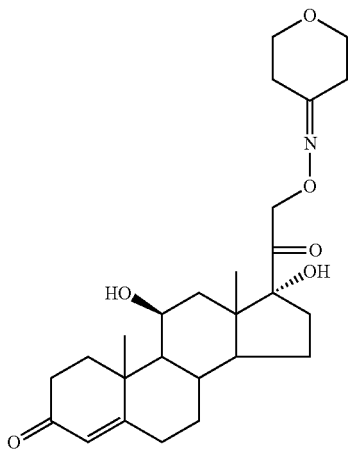 [SMILES: CC12CCC(=O)C=C1CCC1C2[C@@H](O)CC2(C)C1CC[C@]2(O)C(=O)CON=C1CCOCC1] | 460 |
| 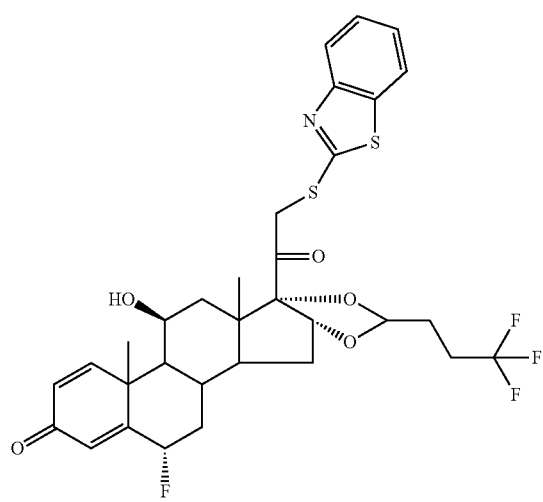 | 652 |
| 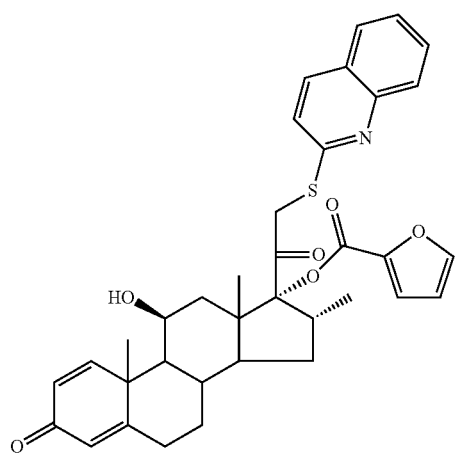 [SMILES: C[C@@H]1CC2C3CCC4=CC(=O)C=CC4(C)C3[C@@H](O)CC2(C)[C@@]1(OC(=O)c1ccco1)C(=O)CSc1ccc2ccccc2n1] | 612 |

TABLE 1-continued
| Structure | M + H |
|---|---|
| 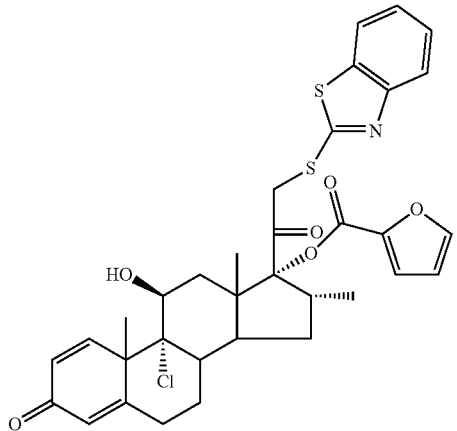 | 652 |
| 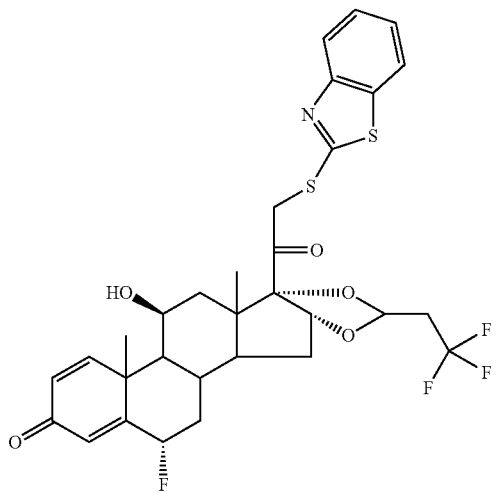 | 638 |
| 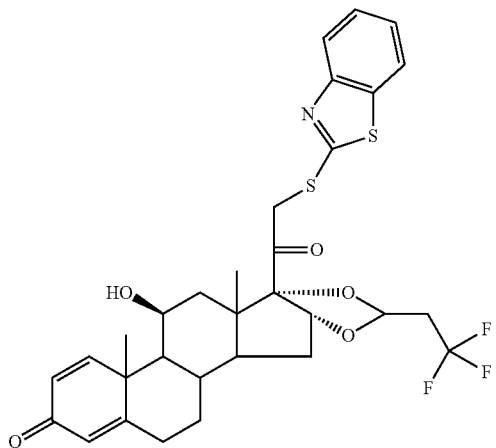 | 620 |

TABLE 1-continued
| Structure | M + H |
|---|---|
| 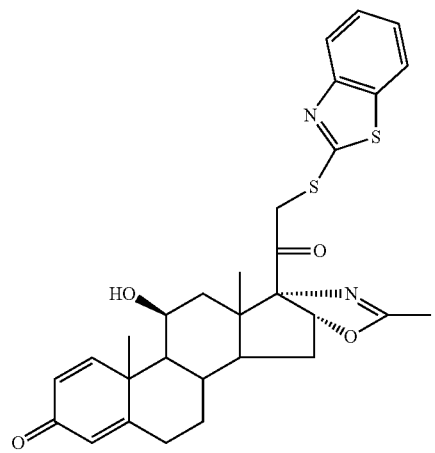 [SMILES: CC1=N[C@]2(C(=O)CSc3nc4ccccc4s3)[C@@H](CC3C4CCC5=CC(=O)C=CC5(C)C4[C@@H](O)CC32C)O1] | 549 |
| 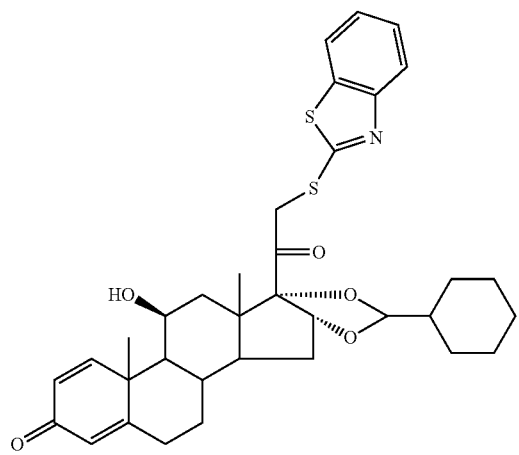 | 620 |
| 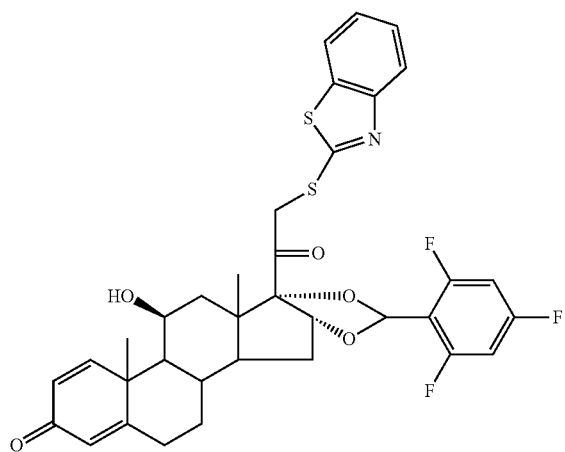 | 668 |

TABLE 1-continued
| Structure | M + H |
|---|---|
| 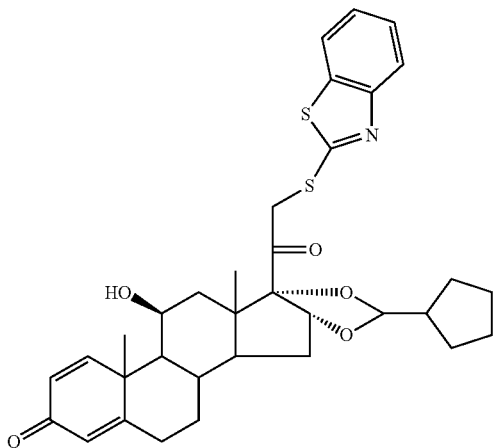 | 606 |
| 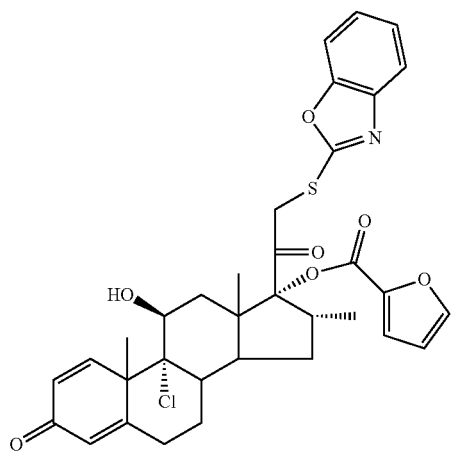 | 636 |
| 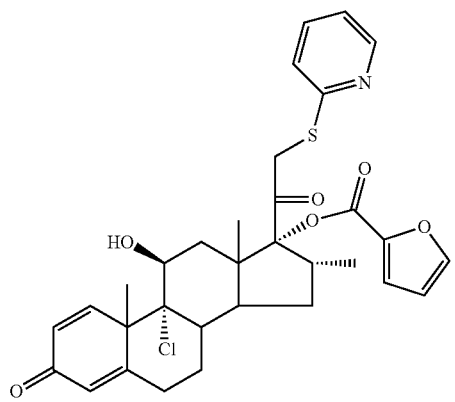 | 596 |

TABLE 1-continued
| Structure | M + H |
|---|---|
| 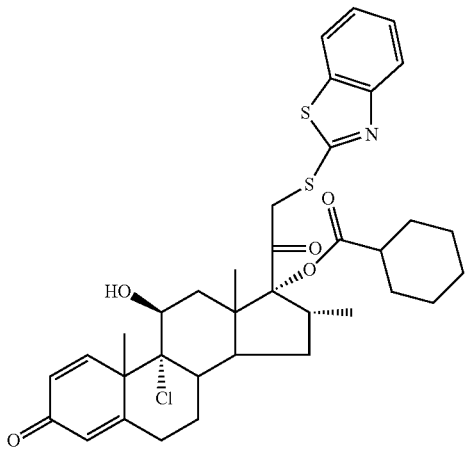 | 668 |
| 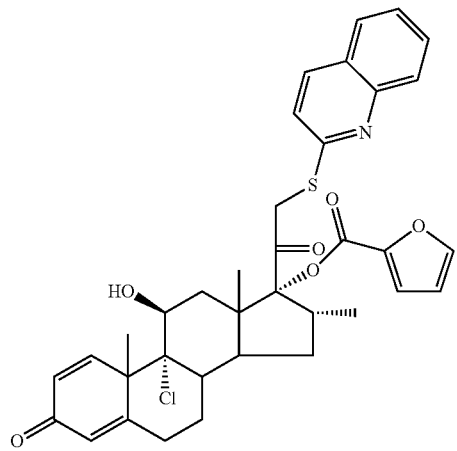 | 646 |
| 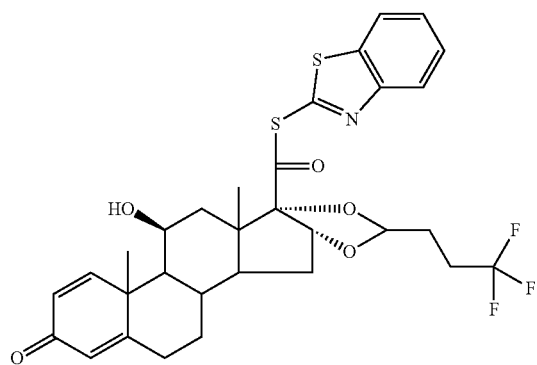 | 620 |

247
248
TABLE 1-continued
| Structure | M + H |
|---|---|
| 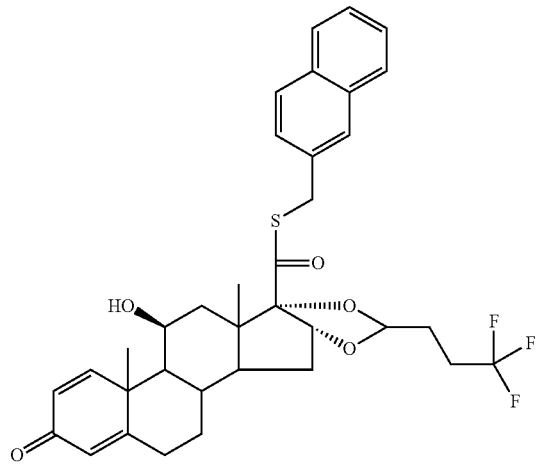 | 627 |
| 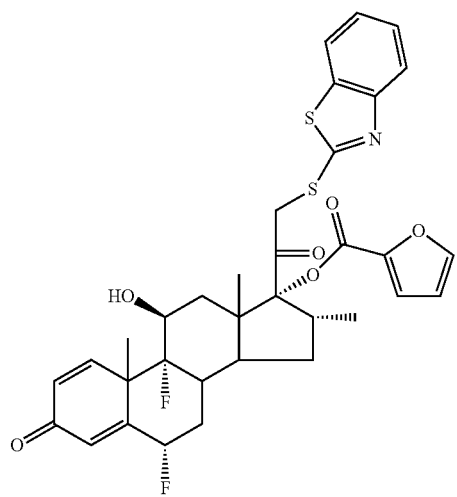 | 654 |
| 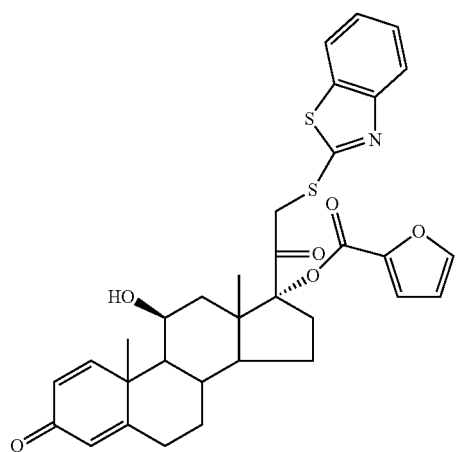 [SMILES: CC12C=CC(=O)C=C1CCC1C2[C@@H](O)CC2(C)C1CC[C@]2(OC(=O)c1ccco1)C(=O)CSc1nc2ccccc2s1] | 604 |

TABLE 1-continued
| Structure | M + H |
|---|---|
| 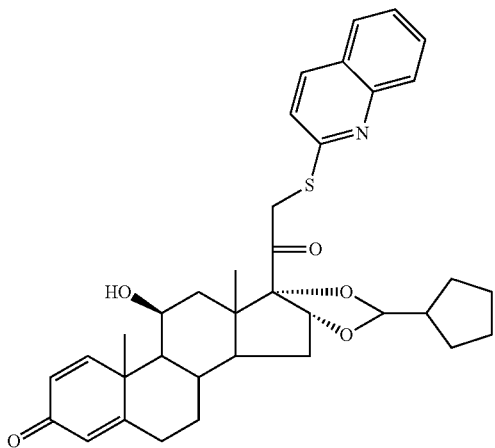 | 600 |
| 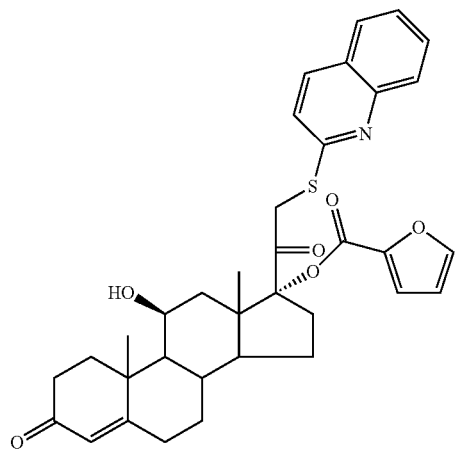 [SMILES: CC12CCC(=O)C=C1CCC1C2[C@@H](O)CC2(C)C1CC[C@]2(OC(=O)c1ccco1)C(=O)CSc1ccc2ccccc2n1] | 600 |
| 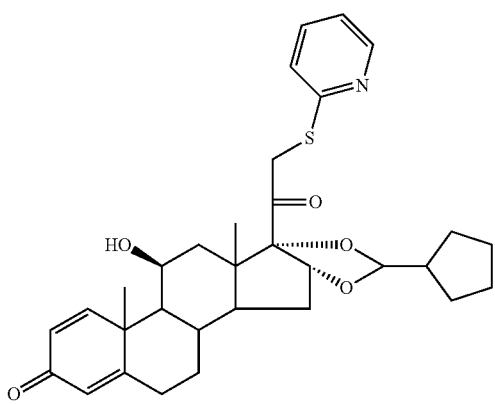 | 550 |

TABLE 1-continued
| Structure | M + H |
|---|---|
| 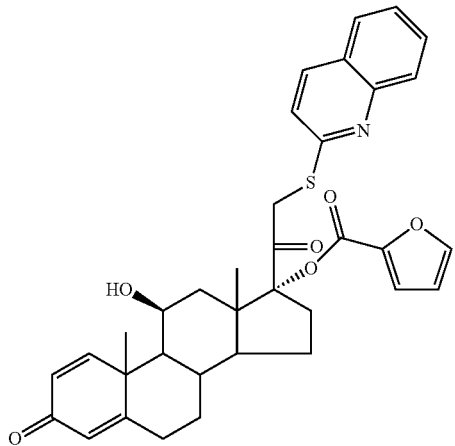 [SMILES: CC12C=CC(=O)C=C1CCC1C2[C@@H](O)CC2(C)C1CC[C@]2(OC(=O)c1ccco1)C(=O)CSc1ccc2ccccc2n1] | 598 |
| 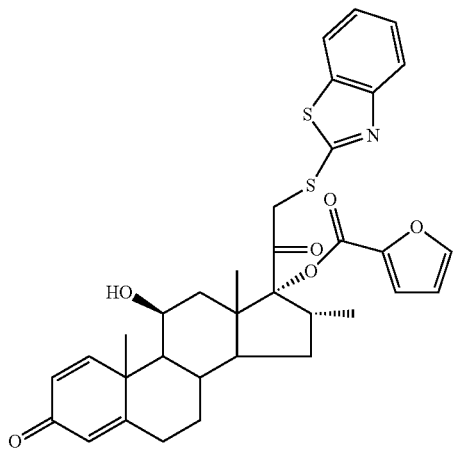 [SMILES: C[C@@H]1CC2C3CCC4=CC(=O)C=CC4(C)C3[C@@H](O)CC2(C)[C@@]1(OC(=O)c1ccco1)C(=O)CSc1nc2ccccc2s1] | 618 |
| 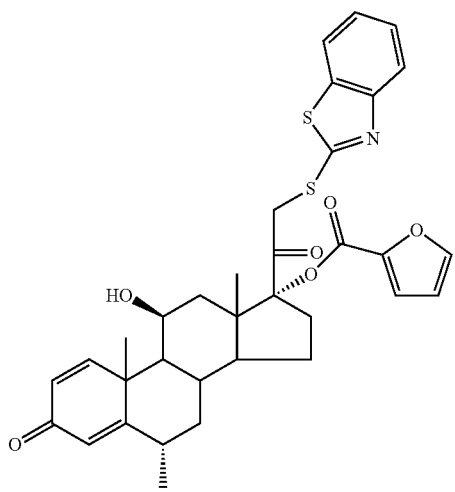 [SMILES: C[C@H]1CC2C([C@@H](O)CC3(C)C2CC[C@]3(OC(=O)c2ccco2)C(=O)CSc2nc3ccccc3s2)C2(C)C=CC(=O)C=C12] | 618 |

TABLE 1-continued
| Structure | M + H |
|---|---|
| 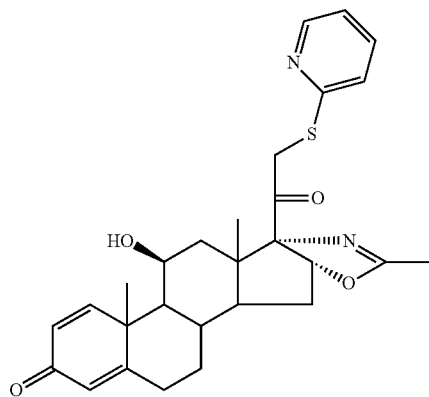 [SMILES: CC1=N[C@]2(C(=O)CSc3ccccn3)[C@@H](CC3C4CCC5=CC(=O)C=CC5(C)C4[C@@H](O)CC32C)O1] | 493 |
| 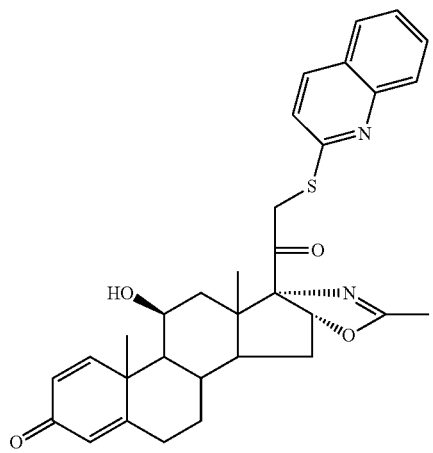 [SMILES: CC1=N[C@]2(C(=O)CSc3ccc4ccccc4n3)[C@@H](CC3C4CCC5=CC(=O)C=CC5(C)C4[C@@H](O)CC32C)O1] | 543 |
| 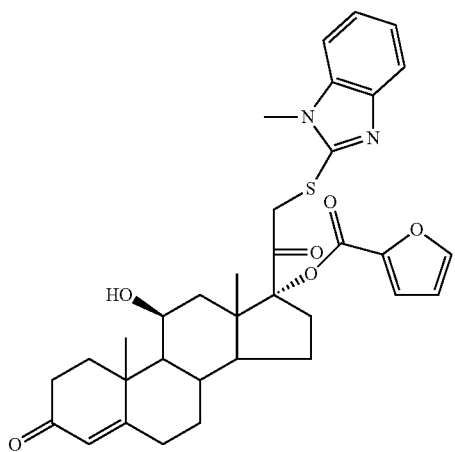 | 603 |

TABLE 1-continued
| Structure | M + H |
|---|---|
| 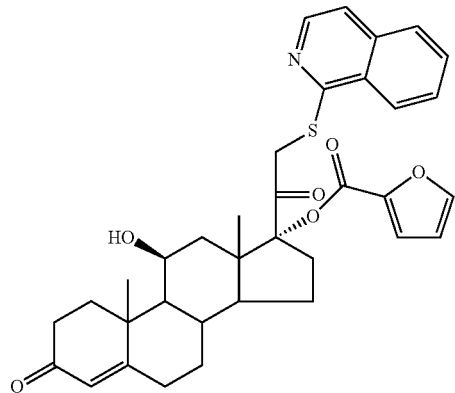 [SMILES: CC12CCC(=O)C=C1CCC1C2[C@@H](O)CC2(C)C1CC[C@]2(OC(=O)c1ccco1)C(=O)CSc1nccc2ccccc12] | 600 |
| 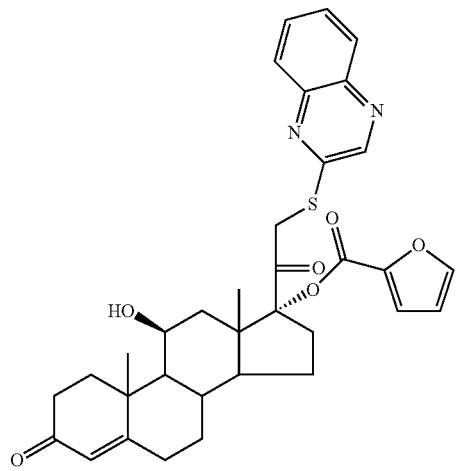 [SMILES: CC12CCC(=O)C=C1CCC1C2[C@@H](O)CC2(C)C1CC[C@]2(OC(=O)c1ccco1)C(=O)CSc1cnc2ccccc2n1] | 601 |
| 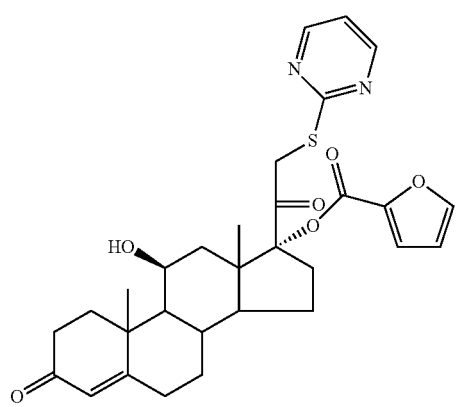 [SMILES: CC12CCC(=O)C=C1CCC1C2[C@@H](O)CC2(C)C1CC[C@]2(OC(=O)c1ccco1)C(=O)CSc1ncccn1] | 551 |

TABLE 1-continued
| Structure | M + H |
|---|---|
| 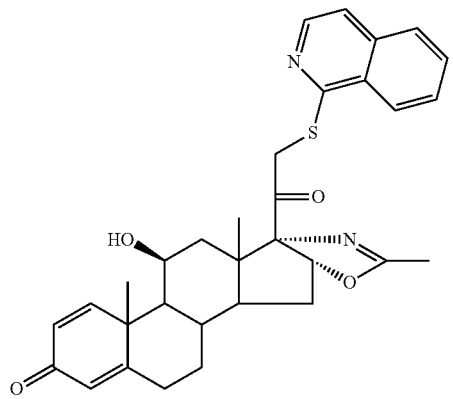 [SMILES: CC1=N[C@]2(C(=O)CSc3nccc4ccccc34)[C@@H](CC3C4CCC5=CC(=O)C=CC5(C)C4[C@@H](O)CC32C)O1] | 543 |
| 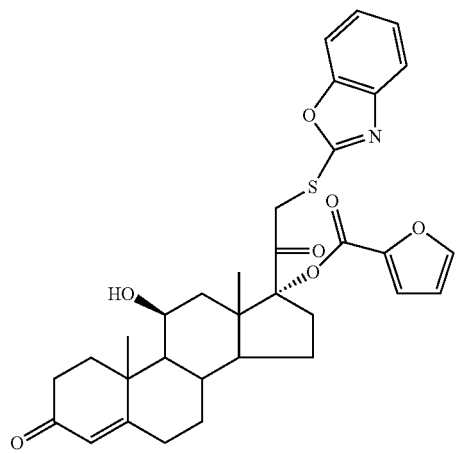 [SMILES: CC12CCC(=O)C=C1CCC1C2[C@@H](O)CC2(C)C1CC[C@]2(OC(=O)c1ccco1)C(=O)CSc1nc2ccccc2o1] | 590 |
| 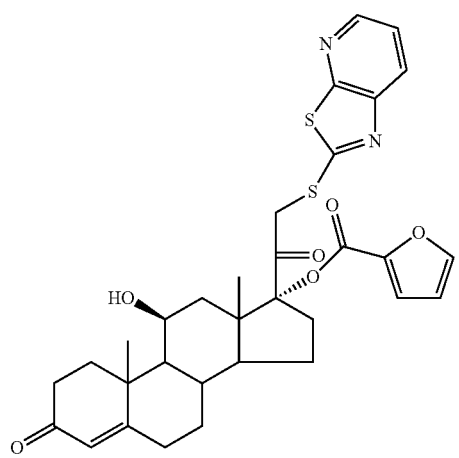 [SMILES: CC12CCC(=O)C=C1CCC1C2[C@@H](O)CC2(C)C1CC[C@]2(OC(=O)c1ccco1)C(=O)CSc1nc2cccnc2s1] | 607 |

TABLE 1-continued
| Structure | M + H |
|---|---|
| 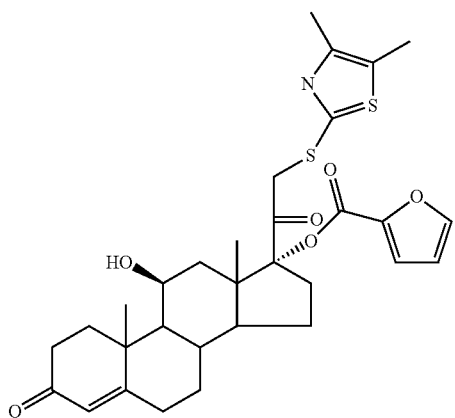 | 584 |
| 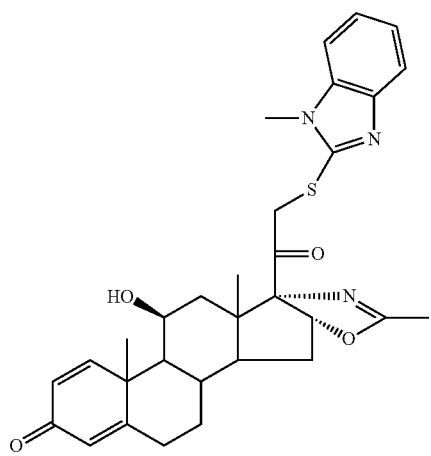 [SMILES: CC1=N[C@]2(C(=O)CSc3nc4ccccc4n3C)[C@@H](CC3C4CCC5=CC(=O)C=CC5(C)C4[C@@H](O)CC32C)O1] | 546 |
| 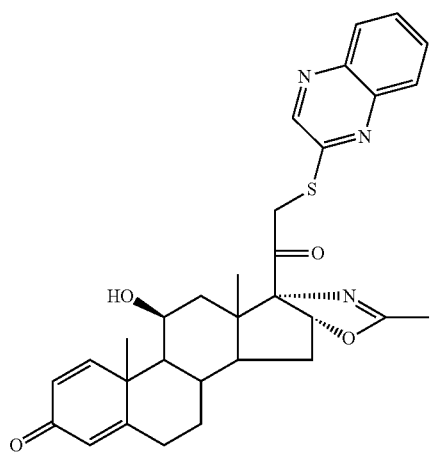 | 544 |

TABLE 1-continued
| Structure | M + H |
|---|---|
| 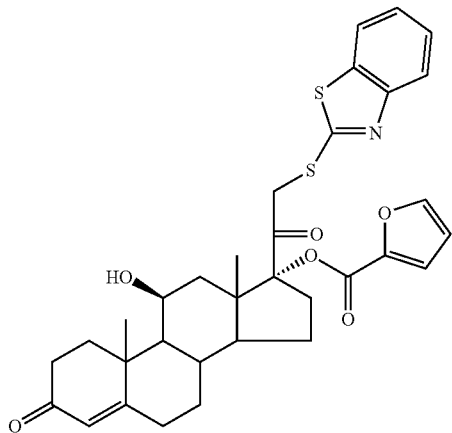 [SMILES: CC12CCC(=O)C=C1CCC1C2[C@@H](O)CC2(C)C1CC[C@]2(OC(=O)c1ccco1)C(=O)CSc1nc2ccccc2s1] | 606 |
| 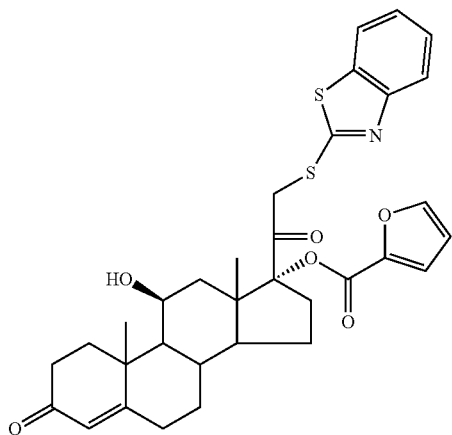 [SMILES: CC12CCC(=O)C=C1CCC1C2[C@@H](O)CC2(C)C1CC[C@]2(OC(=O)c1ccco1)C(=O)CSc1nc2ccccc2s1] | 606 |
| 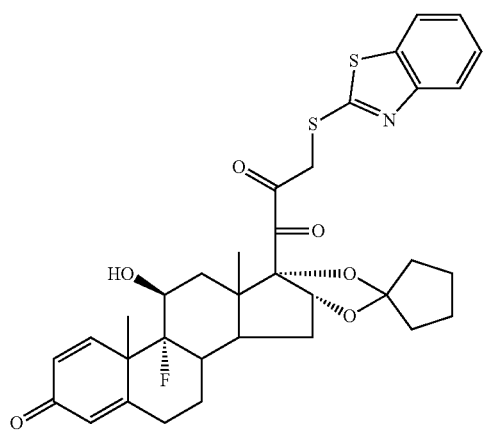 | 610 |

TABLE 1-continued
| Structure | M + H |
|---|---|
| 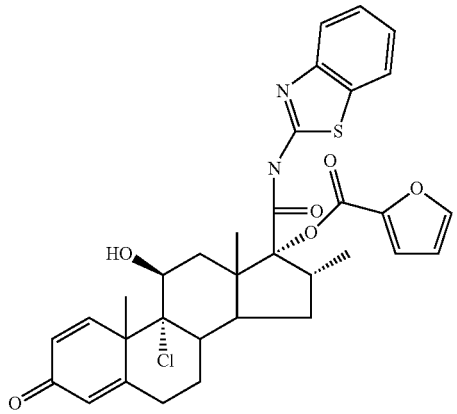 | 621 |
| 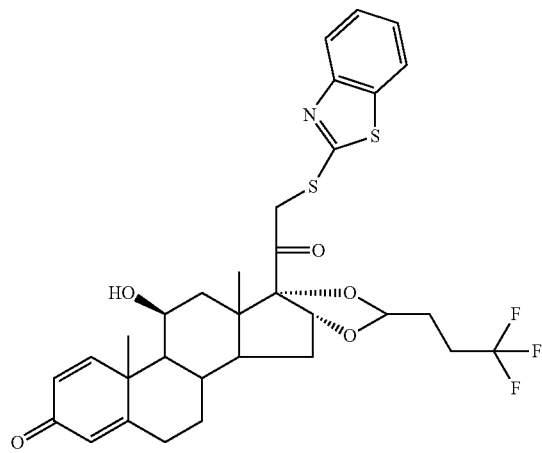 | 634 |
| 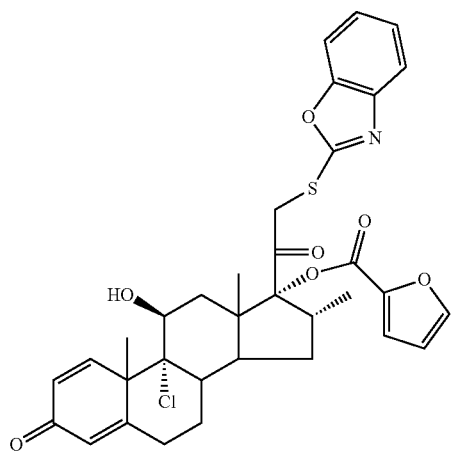 | 636 |

TABLE 1-continued
| Structure | M + H |
|---|---|
| 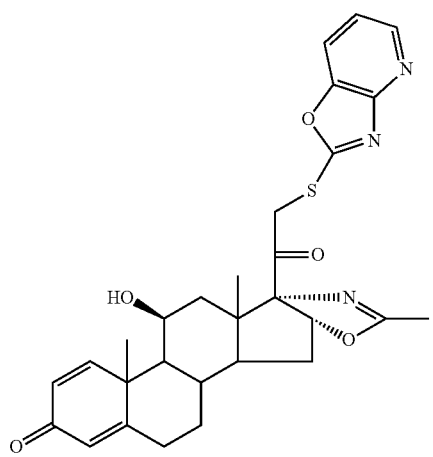 [SMILES: CC1=N[C@]2(C(=O)CSc3nc4ncccc4o3)[C@@H](CC3C4CCC5=CC(=O)C=CC5(C)C4[C@@H](O)CC32C)O1] | 537 |
| 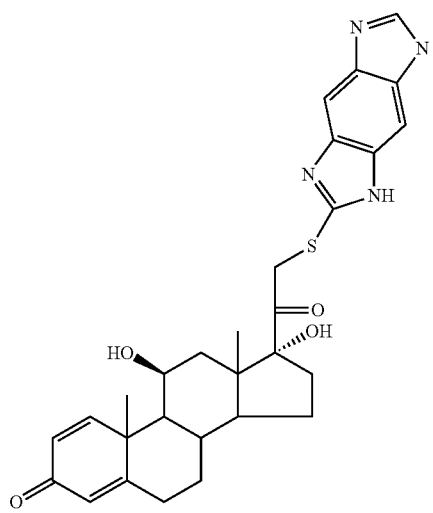 [SMILES: CC12C=CC(=O)C=C1CCC1C2[C@@H](O)CC2(C)C1CC[C@]2(O)C(=O)CSc1nc2cc3nc[nH]c3cc2[nH]1] | 533 |
| 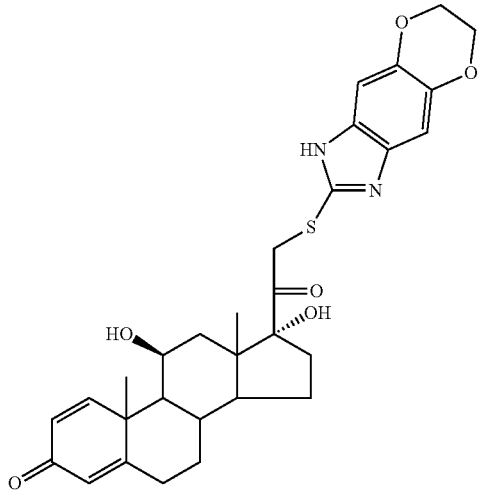 [SMILES: CC12C=CC(=O)C=C1CCC1C2[C@@H](O)CC2(C)C1CC[C@]2(O)C(=O)CSc1nc2cc3c(cc2[nH]1)OCCO3] | 551 |

TABLE 1-continued
| Structure | M + H |
|---|---|
| 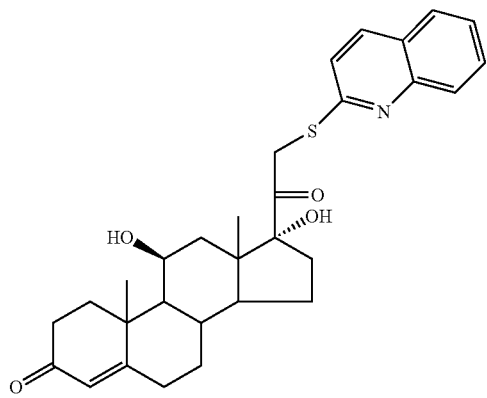 [SMILES: CC12CCC(=O)C=C1CCC1C2[C@@H](O)CC2(C)C1CC[C@]2(O)C(=O)CSc1ccc2ccccc2n1] | 506 |
| 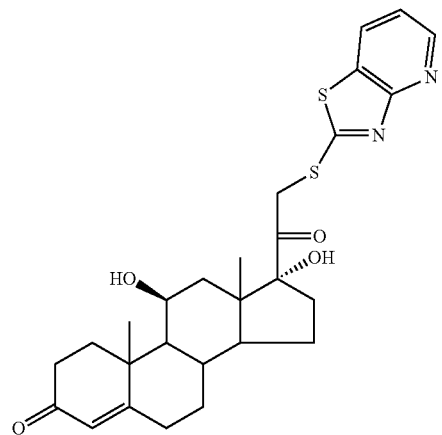 | 513 |
| 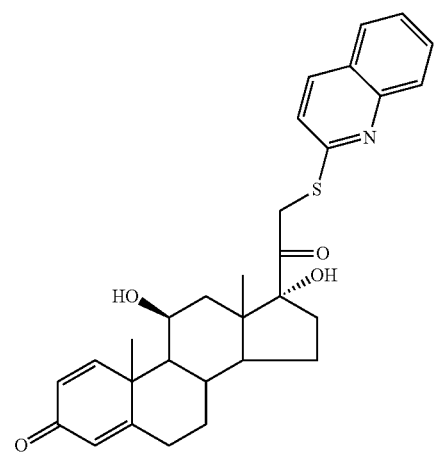 [SMILES: CC12C=CC(=O)C=C1CCC1C2[C@@H](O)CC2(C)C1CC[C@]2(O)C(=O)CSc1ccc2ccccc2n1] | 504 |

TABLE 1-continued
| Structure | M + H |
|---|---|
| 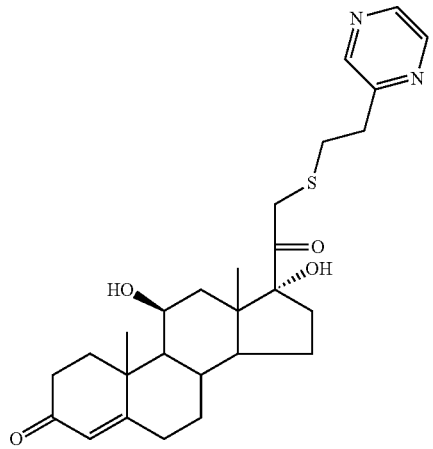 | 485 |
| 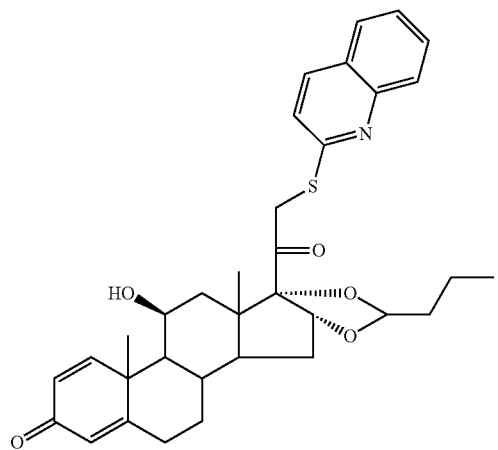 | 574 |
| 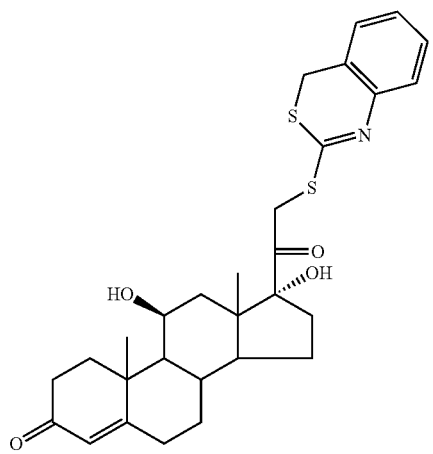 [SMILES: CC12CCC(=O)C=C1CCC1C2[C@@H](O)CC2(C)C1CC[C@]2(O)C(=O)CSC1=Nc2ccccc2CS1] | 526 |

TABLE 1-continued
| Structure | M + H |
|---|---|
| 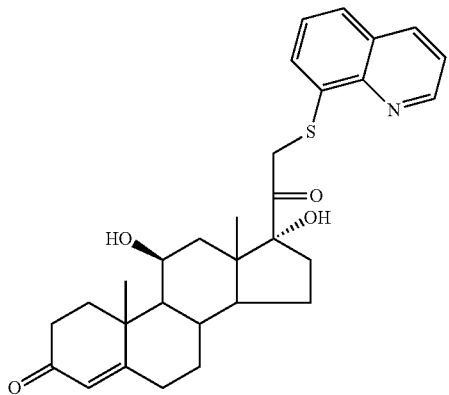 | 506 |
| 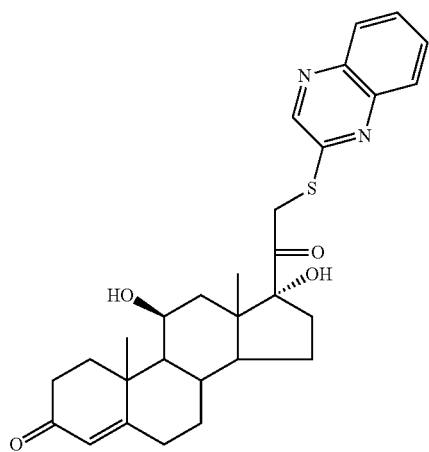 [SMILES: CC12CCC(=O)C=C1CCC1C2[C@@H](O)CC2(C)C1CC[C@]2(O)C(=O)CSc1cnc2ccccc2n1] | 507 |
| 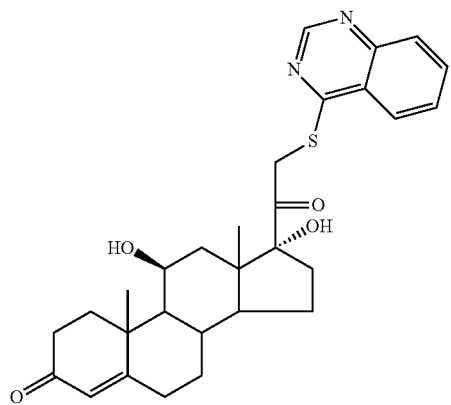 [SMILES: CC12CCC(=O)C=C1CCC1C2[C@@H](O)CC2(C)C1CC[C@]2(O)C(=O)CSc1ncnc2ccccc12] | 507 |

TABLE 1-continued
| Structure | M + H |
|---|---|
| 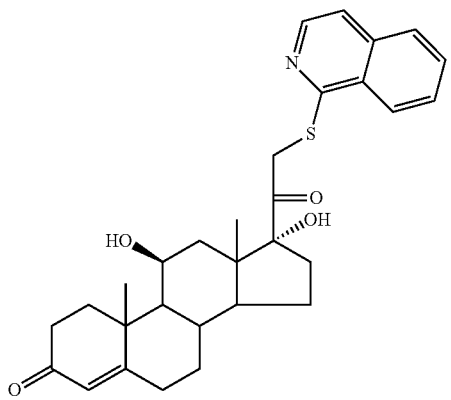 | 506 |
| 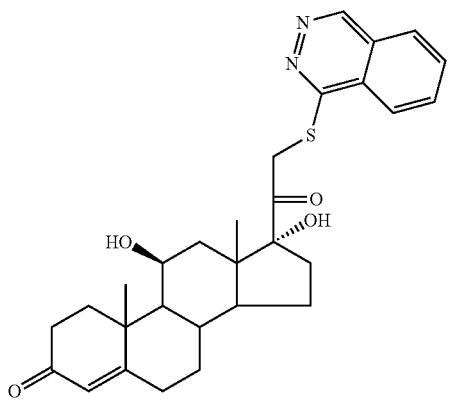 [SMILES: CC12CCC(=O)C=C1CCC1C2[C@@H](O)CC2(C)C1CC[C@]2(O)C(=O)CSc1nncc2ccccc12] | 507 |
| 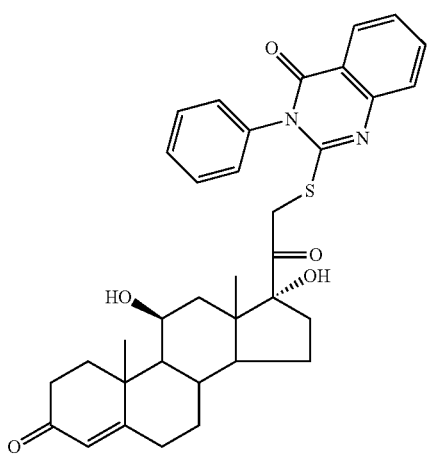 [SMILES: CC12CCC(=O)C=C1CCC1C2[C@@H](O)CC2(C)C1CC[C@]2(O)C(=O)CSc1nc2ccccc2c(=O)n1-c1ccccc1] | 599 |

TABLE 1-continued
| Structure | M + H |
|---|---|
| 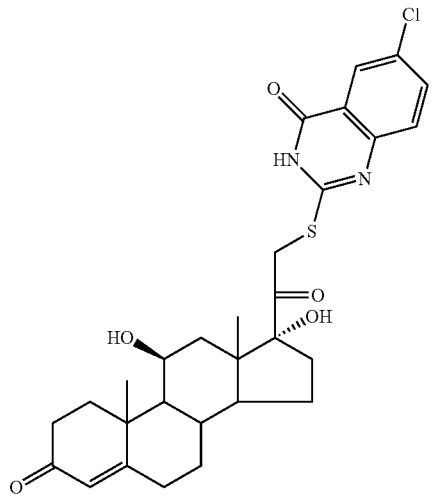 [SMILES: CC12CCC(=O)C=C1CCC1C2[C@@H](O)CC2(C)C1CC[C@]2(O)C(=O)CSc1nc2ccc(Cl)cc2c(=O)[nH]1] | 557 |
| 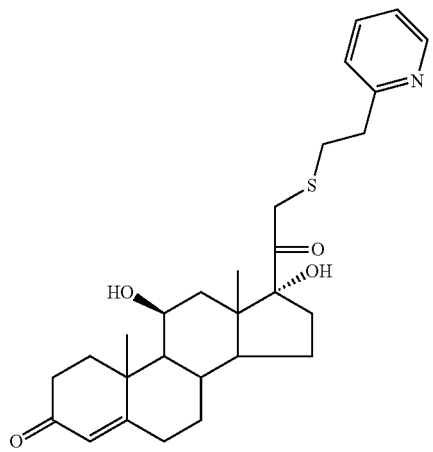 [SMILES: CC12CCC(=O)C=C1CCC1C2[C@@H](O)CC2(C)C1CC[C@]2(O)C(=O)CSCCc1ccccn1] | 484 |
| 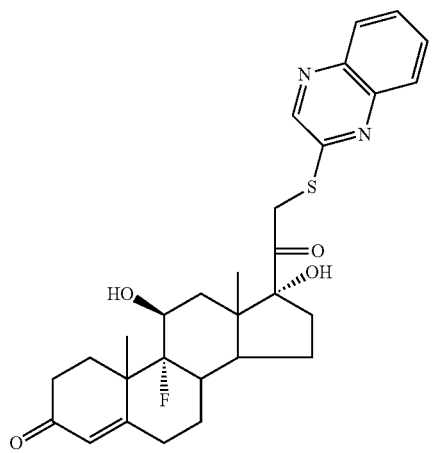 | 525 |

TABLE 1-continued
| Structure | M + H |
|---|---|
| 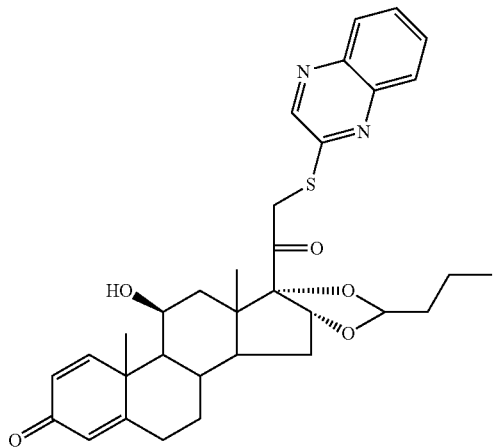 | 575 |
| 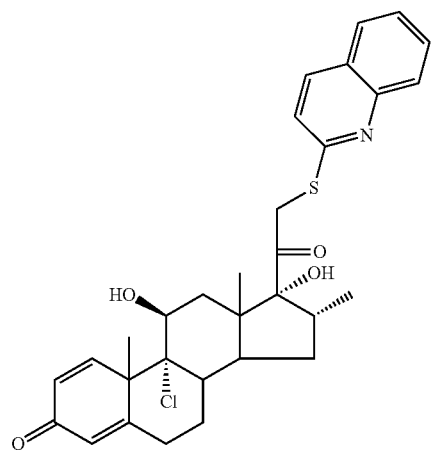 | 552 |
| 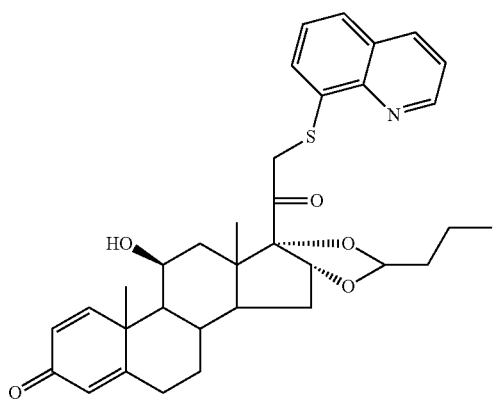 | 574 |

TABLE 1-continued
| Structure | M + H |
|---|---|
| 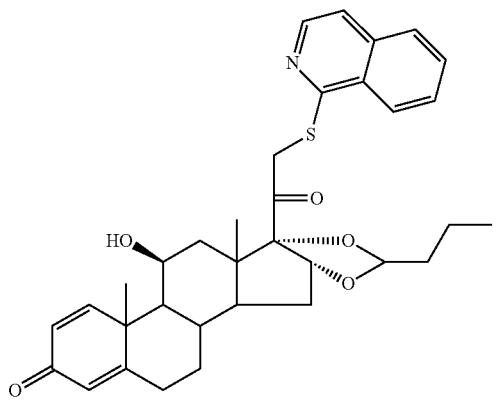 | 574 |
| 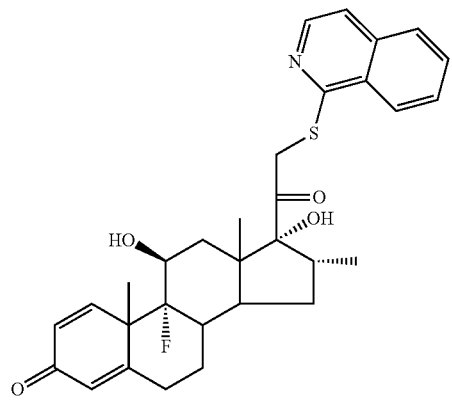 | 536 |
| 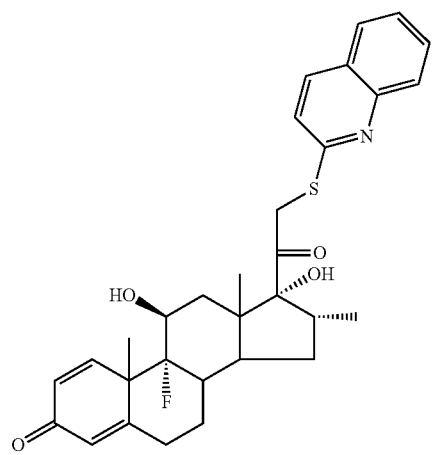 | 536 |

TABLE 1-continued
| Structure | M + H |
|---|---|
| 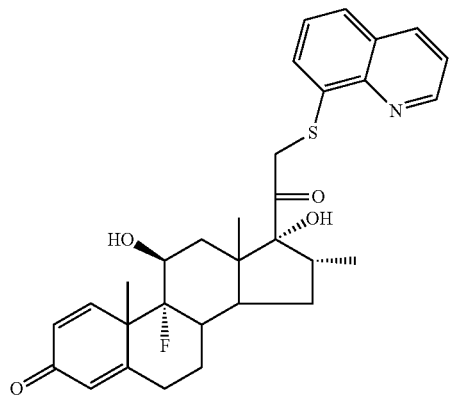 | 536 |
| 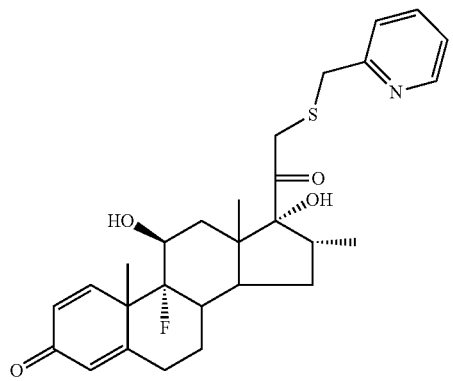 | 500 |
| 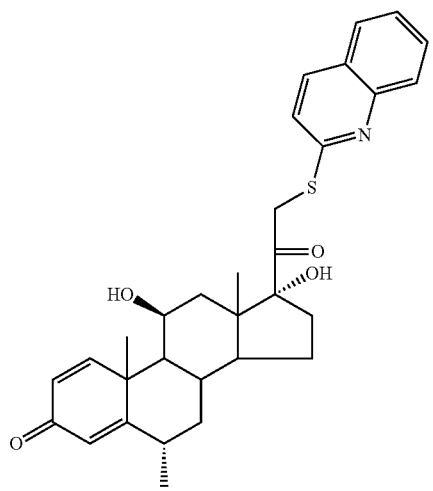 [SMILES: C[C@H]1CC2C([C@@H](O)CC3(C)C2CC[C@]3(O)C(=O)CSc2ccc3ccccc3n2)C2(C)C=CC(=O)C=C12] | 518 |

TABLE 1-continued
| Structure | M + H |
|---|---|
| 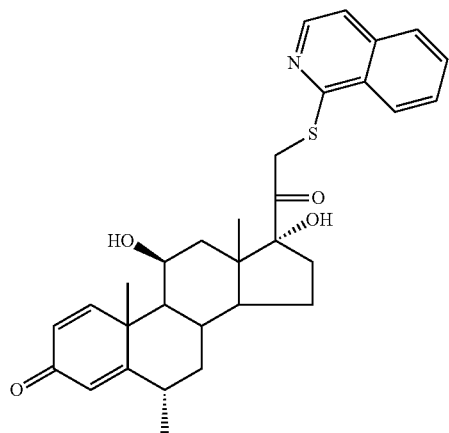 [SMILES: C[C@H]1CC2C([C@@H](O)CC3(C)C2CC[C@]3(O)C(=O)CSc2nccc3ccccc23)C2(C)C=CC(=O)C=C12] | 518 |
| 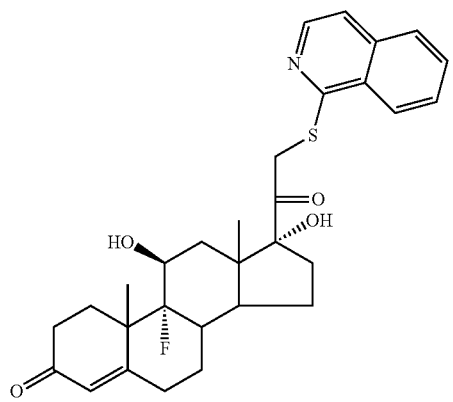 | 524 |
| 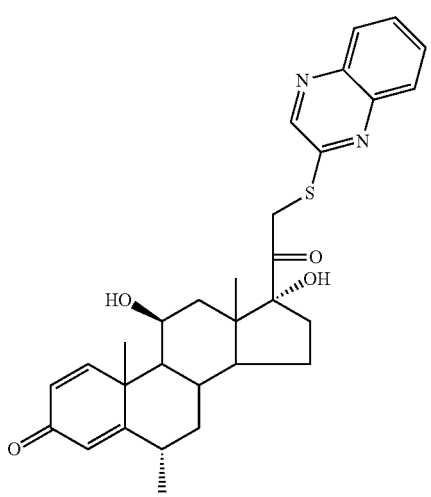 [SMILES: C[C@H]1CC2C([C@@H](O)CC3(C)C2CC[C@]3(O)C(=O)CSc2cnc3ccccc3n2)C2(C)C=CC(=O)C=C12] | 519 |

TABLE 1-continued
| Structure | M + H |
|---|---|
| 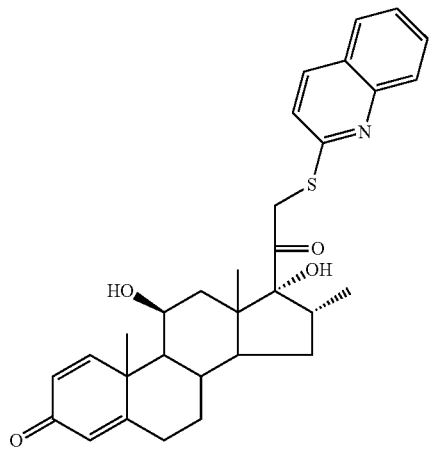 [SMILES: C[C@@H]1CC2C3CCC4=CC(=O)C=CC4(C)C3[C@@H](O)CC2(C)[C@@]1(O)C(=O)CSc1ccc2ccccc2n1] | 518 |
| 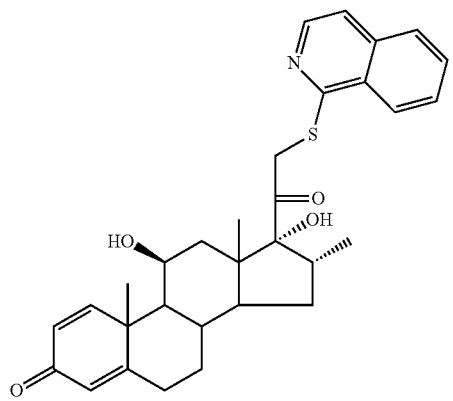 [SMILES: C[C@@H]1CC2C3CCC4=CC(=O)C=CC4(C)C3[C@@H](O)CC2(C)[C@@]1(O)C(=O)CSc1nccc2ccccc12] | 518 |
| 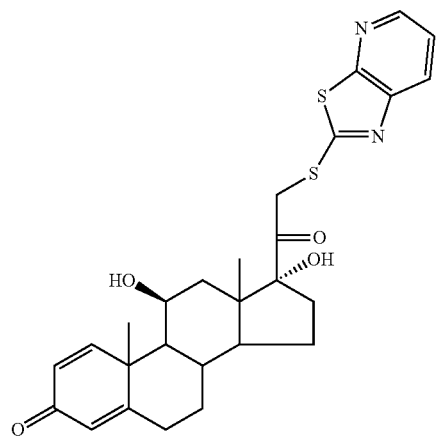 [SMILES: CC12C=CC(=O)C=C1CCC1C2[C@@H](O)CC2(C)C1CC[C@]2(O)C(=O)CSc1nc2cccnc2s1] | 511 |

TABLE 1-continued
| Structure | M + H |
|---|---|
| 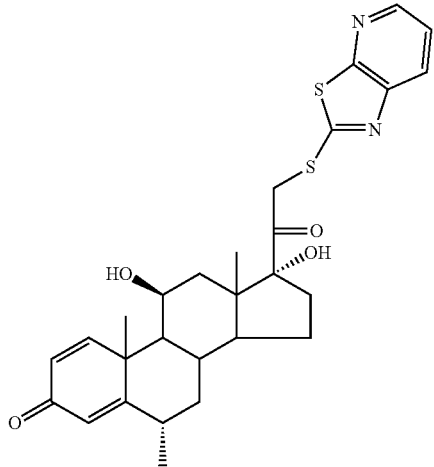 [SMILES: C[C@H]1CC2C([C@@H](O)CC3(C)C2CC[C@]3(O)C(=O)CSc2nc3cccnc3s2)C2(C)C=CC(=O)C=C12] | 525 |
| 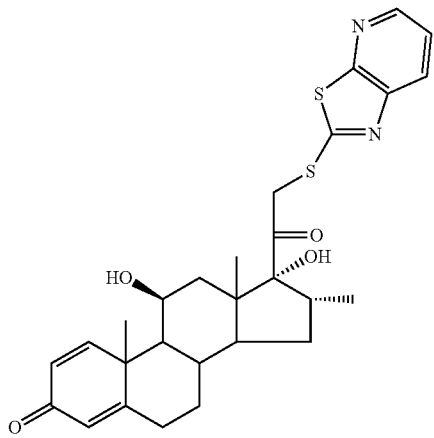 [SMILES: C[C@@H]1CC2C3CCC4=CC(=O)C=CC4(C)C3[C@@H](O)CC2(C)[C@@]1(O)C(=O)CSc1nc2cccnc2s1] | 525 |
| 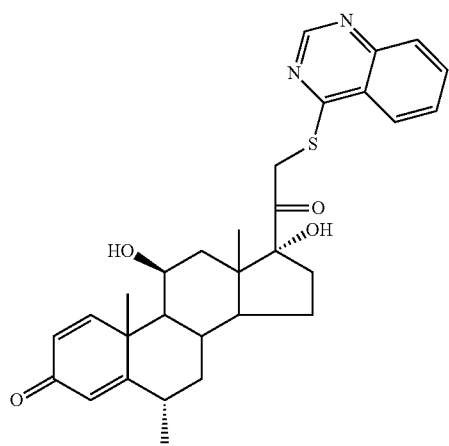 [SMILES: C[C@H]1CC2C([C@@H](O)CC3(C)C2CC[C@]3(O)C(=O)CSc2ncnc3ccccc23)C2(C)C=CC(=O)C=C12] | 519 |

TABLE 1-continued
| Structure | M + H |
|---|---|
| 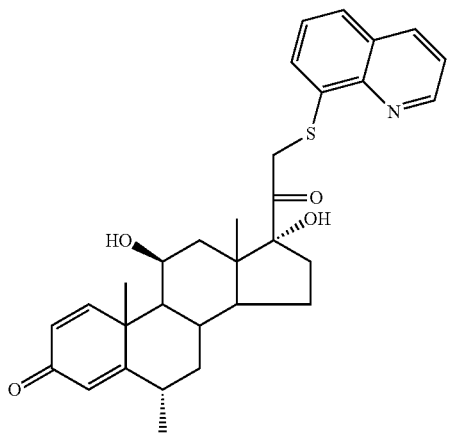 [SMILES: C[C@H]1CC2C([C@@H](O)CC3(C)C2CC[C@]3(O)C(=O)CSc2cccc3cccnc23)C2(C)C=CC(=O)C=C12] | 518 |
| 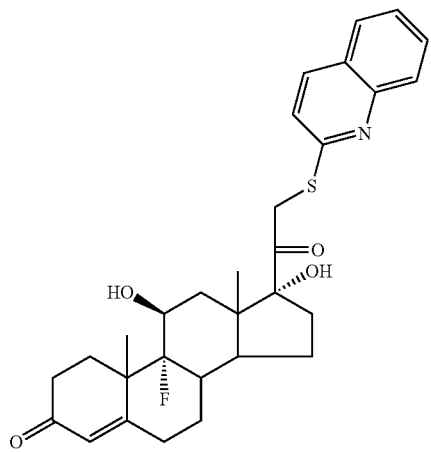 | 524 |
| 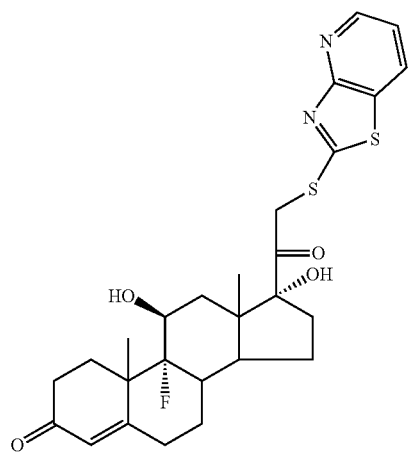 | 531 |

TABLE 1-continued
| Structure | M + H |
|---|---|
| 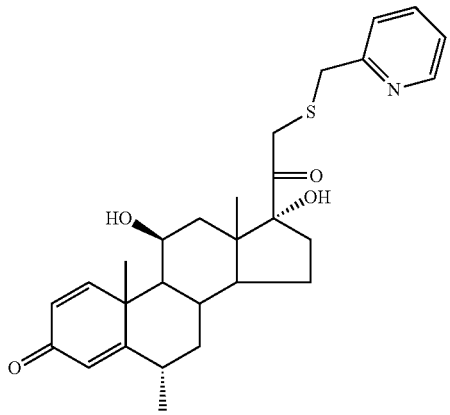 [SMILES: C[C@H]1CC2C([C@@H](O)CC3(C)C2CC[C@]3(O)C(=O)CSCc2ccccn2)C2(C)C=CC(=O)C=C12] | 482 |
| 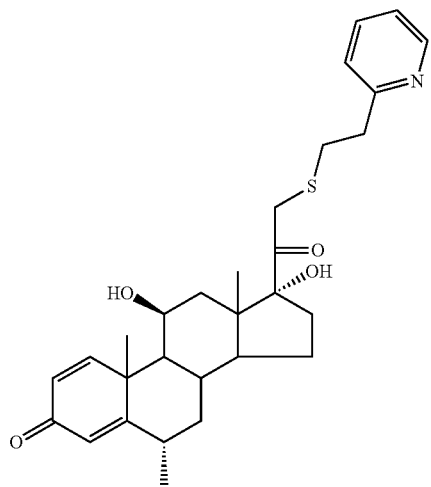 [SMILES: C[C@H]1CC2C([C@@H](O)CC3(C)C2CC[C@]3(O)C(=O)CSCCc2ccccn2)C2(C)C=CC(=O)C=C12] | 496 |
| 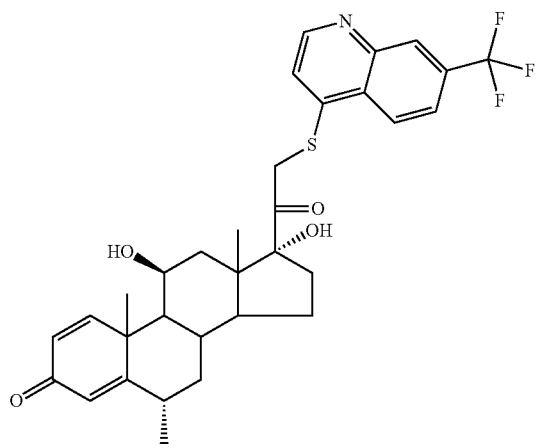 [SMILES: C[C@H]1CC2C([C@@H](O)CC3(C)C2CC[C@]3(O)C(=O)CSc2ccnc3cc(C(F)(F)F)ccc23)C2(C)C=CC(=O)C=C12] | 586 |

TABLE 1-continued
| Structure | M + H |
|---|---|
| 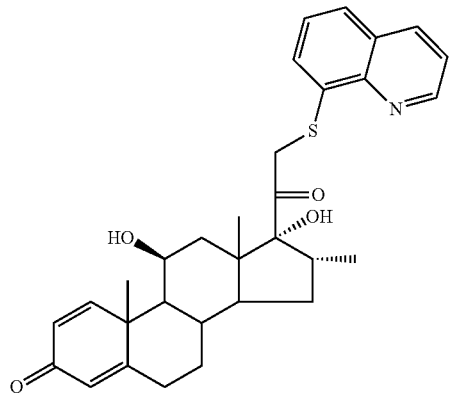 [SMILES: C[C@@H]1CC2C3CCC4=CC(=O)C=CC4(C)C3[C@@H](O)CC2(C)[C@@]1(O)C(=O)CSc1cccc2cccnc12] | 518 |
| 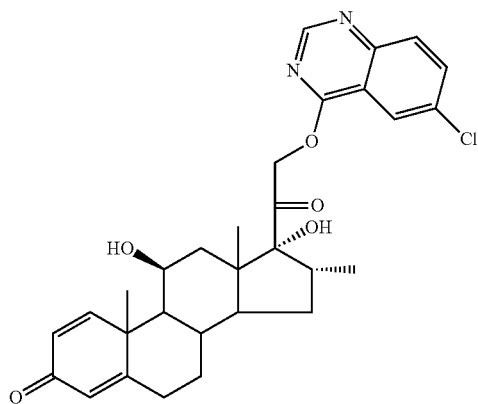 [SMILES: C[C@@H]1CC2C3CCC4=CC(=O)C=CC4(C)C3[C@@H](O)CC2(C)[C@@]1(O)C(=O)COc1ncnc2ccc(Cl)cc12] | 537 |
| 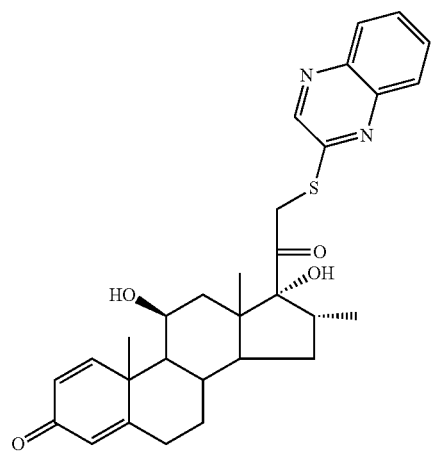 [SMILES: C[C@@H]1CC2C3CCC4=CC(=O)C=CC4(C)C3[C@@H](O)CC2(C)[C@@]1(O)C(=O)CSc1cnc2ccccc2n1] | 519 |

TABLE 1-continued
| Structure | M + H |
|---|---|
| 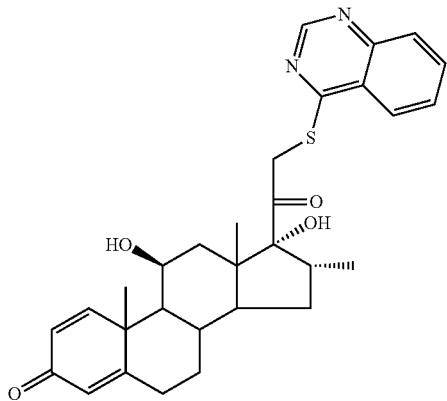 [SMILES: C[C@@H]1CC2C3CCC4=CC(=O)C=CC4(C)C3[C@@H](O)CC2(C)[C@@]1(O)C(=O)CSc1ncnc2ccccc12] | 519 |
| 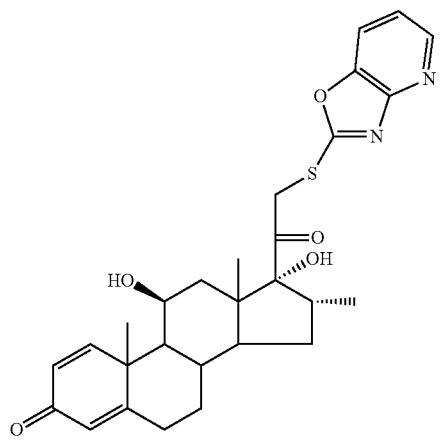 [SMILES: C[C@@H]1CC2C3CCC4=CC(=O)C=CC4(C)C3[C@@H](O)CC2(C)[C@@]1(O)C(=O)CSc1nc2ncccc2o1] | 509 |
| 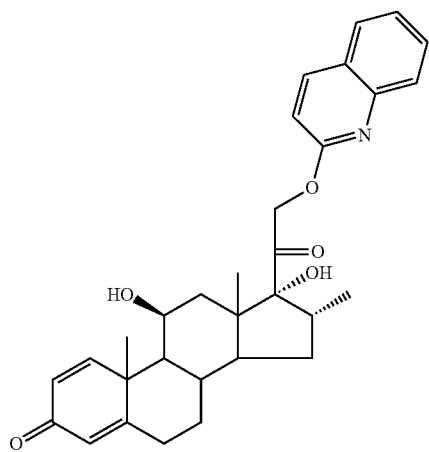 [SMILES: C[C@@H]1CC2C3CCC4=CC(=O)C=CC4(C)C3[C@@H](O)CC2(C)[C@@]1(O)C(=O)COc1ccc2ccccc2n1] | 502 |

TABLE 1-continued
| Structure | M + H |
|---|---|
| 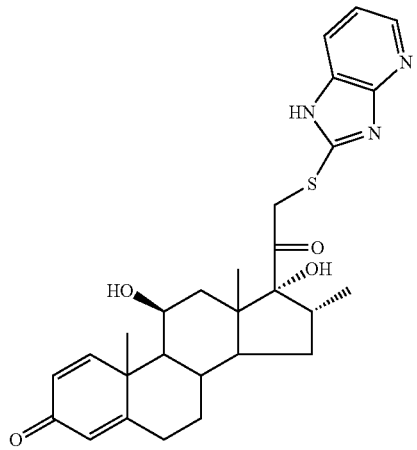 [SMILES: C[C@@H]1CC2C3CCC4=CC(=O)C=CC4(C)C3[C@@H](O)CC2(C)[C@@]1(O)C(=O)CSc1nc2ncccc2[nH]1] | 508 |
| 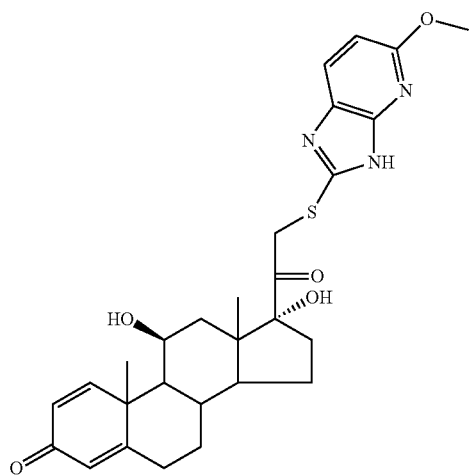 [SMILES: COc1ccc2nc(SCC(=O)[C@@]3(O)CCC4C5CCC6=CC(=O)C=CC6(C)C5[C@@H](O)CC43C)[nH]c2n1] | 524 |
| 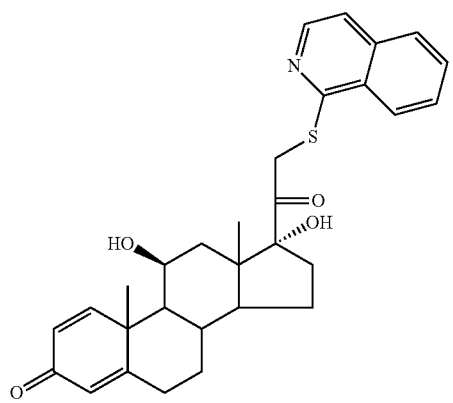 [SMILES: CC12C=CC(=O)C=C1CCC1C2[C@@H](O)CC2(C)C1CC[C@]2(O)C(=O)CSc1nccc2ccccc12] | 504 |

TABLE 1-continued
| Structure | M + H |
|---|---|
| 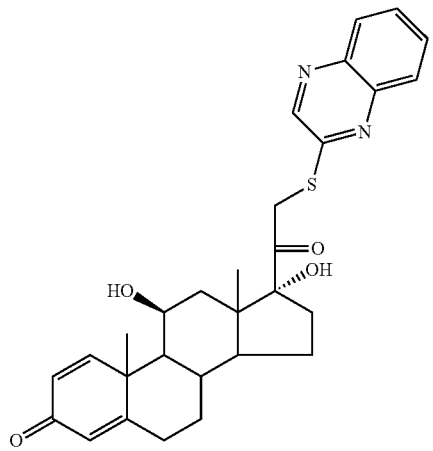 | 505 |
| 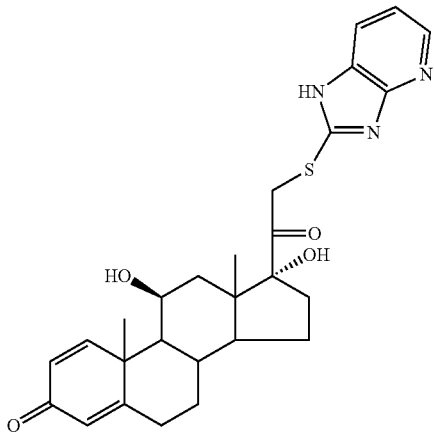 [SMILES: CC12C=CC(=O)C=C1CCC1C2[C@@H](O)CC2(C)C1CC[C@]2(O)C(=O)CSc1nc2ncccc2[nH]1] | 494 |
| 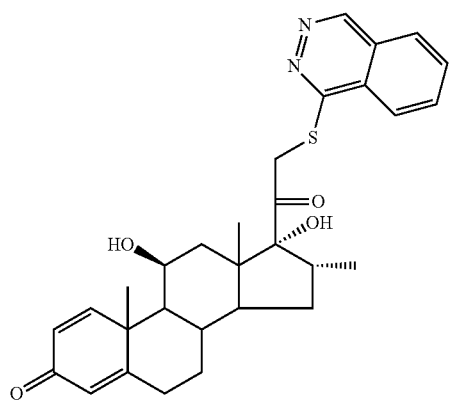 [SMILES: C[C@@H]1CC2C3CCC4=CC(=O)C=CC4(C)C3[C@@H](O)CC2(C)[C@@]1(O)C(=O)CSc1nncc2ccccc12] | 519 |

TABLE 1-continued
| Structure | M + H |
|---|---|
| 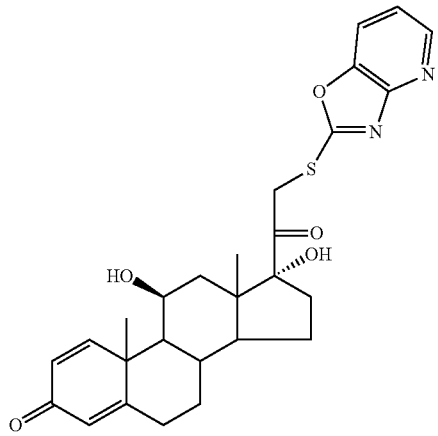 [SMILES: CC12C=CC(=O)C=C1CCC1C2[C@@H](O)CC2(C)C1CC[C@]2(O)C(=O)CSc1nc2ncccc2o1] | 495 |
| 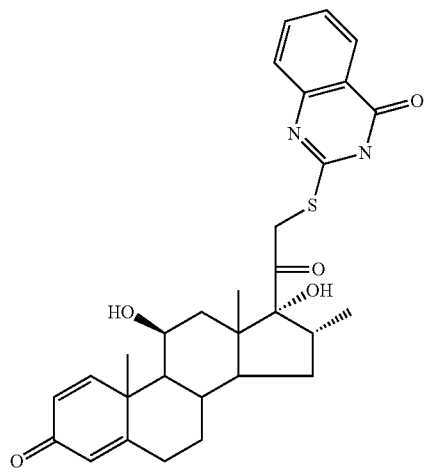 [SMILES: C[C@@H]1CC2C3CCC4=CC(=O)C=CC4(C)C3[C@@H](O)CC2(C)[C@@]1(O)C(=O)CSc1nc2ccccc2c(=O)[nH]1] | 535 |
| 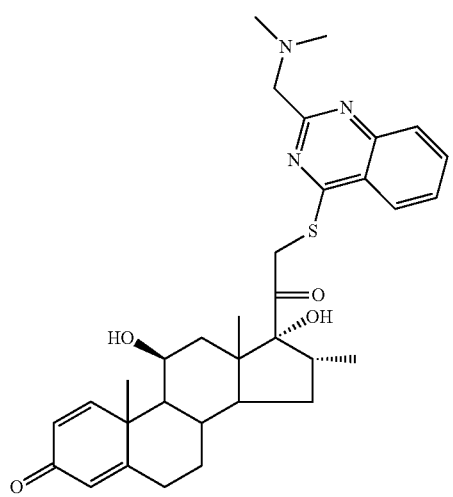 [SMILES: C[C@@H]1CC2C3CCC4=CC(=O)C=CC4(C)C3[C@@H](O)CC2(C)[C@@]1(O)C(=O)CSc1nc(CN(C)C)nc2ccccc12] | 576 |

TABLE 1-continued
| Structure | M + H |
|---|---|
| 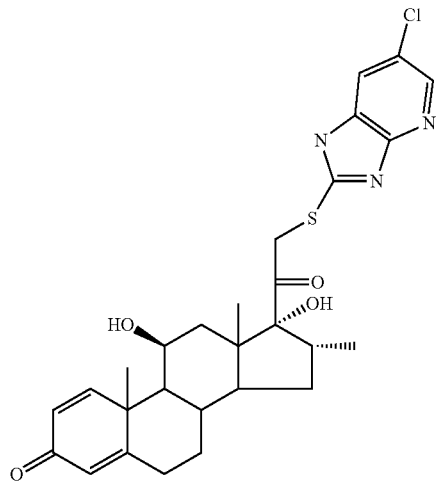 [SMILES: C[C@@H]1CC2C3CCC4=CC(=O)C=CC4(C)C3[C@@H](O)CC2(C)[C@@]1(O)C(=O)CSc1nc2ncc(Cl)cc2[nH]1] | 542 |
| 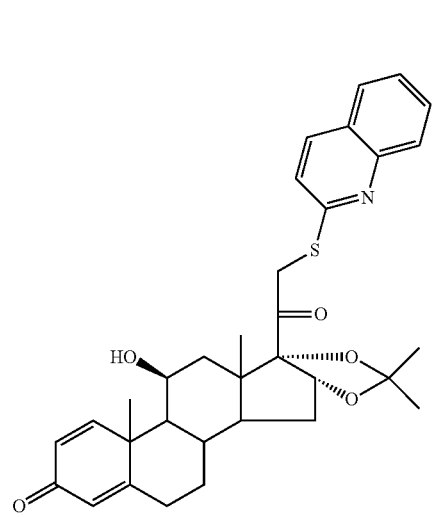 [SMILES: CC1(C)O[C@@H]2CC3C4CCC5=CC(=O)C=CC5(C)C4[C@@H](O)CC3(C)[C@]2(C(=O)CSc2ccc3ccccc3n2)O1] | 560 |
| 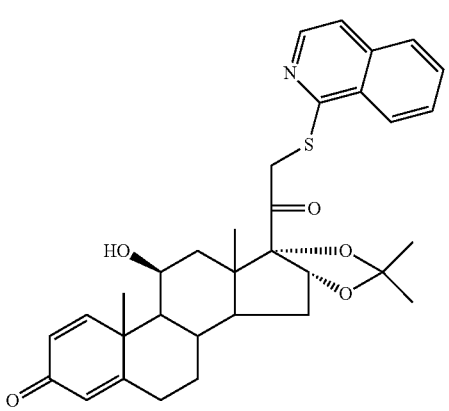 [SMILES: CC1(C)O[C@@H]2CC3C4CCC5=CC(=O)C=CC5(C)C4[C@@H](O)CC3(C)[C@]2(C(=O)CSc2nccc3ccccc23)O1] | 560 |

TABLE 1-continued
| Structure | M + H |
|---|---|
| 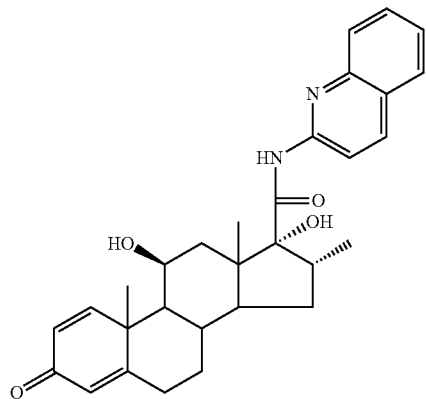 [SMILES: C[C@@H]1CC2C3CCC4=CC(=O)C=CC4(C)C3[C@@H](O)CC2(C)[C@@]1(O)C(=O)Nc1ccc2ccccc2n1] | 487 |
| 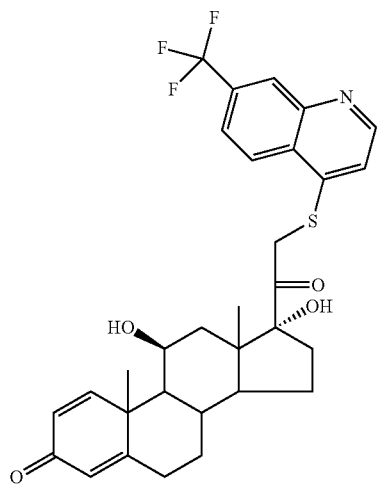 [SMILES: CC12C=CC(=O)C=C1CCC1C2[C@@H](O)CC2(C)C1CC[C@]2(O)C(=O)CSc1ccnc2cc(C(F)(F)F)ccc12] | 572 |
| 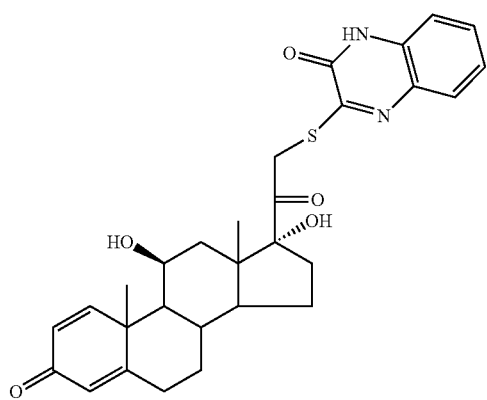 [SMILES: CC12C=CC(=O)C=C1CCC1C2[C@@H](O)CC2(C)C1CC[C@]2(O)C(=O)CSc1nc2ccccc2[nH]c1=O] | 521 |

TABLE 1-continued
| Structure | M + H |
|---|---|
| 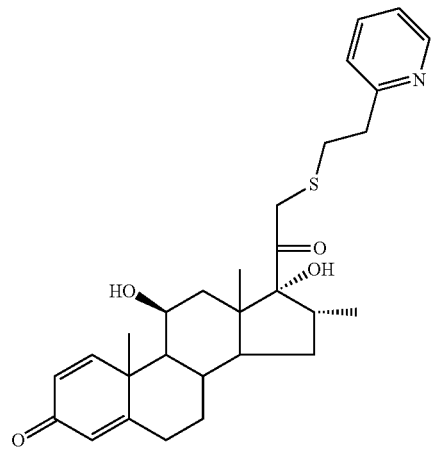 [SMILES: C[C@@H]1CC2C3CCC4=CC(=O)C=CC4(C)C3[C@@H](O)CC2(C)[C@@]1(O)C(=O)CSCCc1ccccn1] | 496 |
| 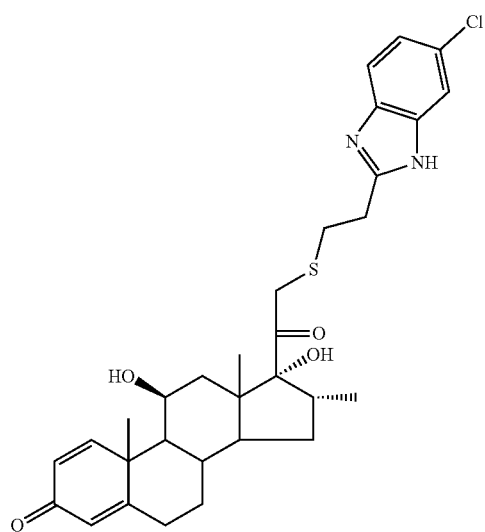 [SMILES: C[C@@H]1CC2C3CCC4=CC(=O)C=CC4(C)C3[C@@H](O)CC2(C)[C@@]1(O)C(=O)CSCCc1nc2ccc(Cl)cc2[nH]1] | 569 |
| 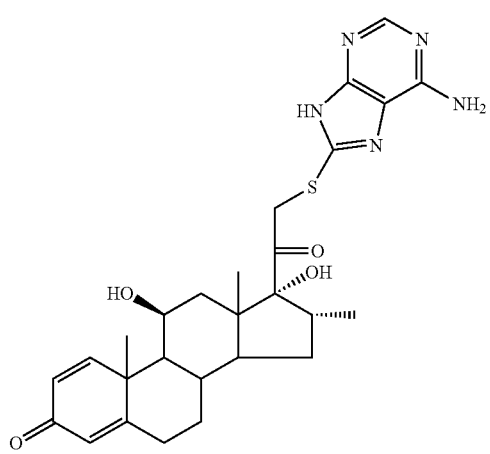 [SMILES: C[C@@H]1CC2C3CCC4=CC(=O)C=CC4(C)C3[C@@H](O)CC2(C)[C@@]1(O)C(=O)CSc1nc2c(N)ncnc2[nH]1] | 524 |

TABLE 1-continued
| Structure | M + H |
|---|---|
| 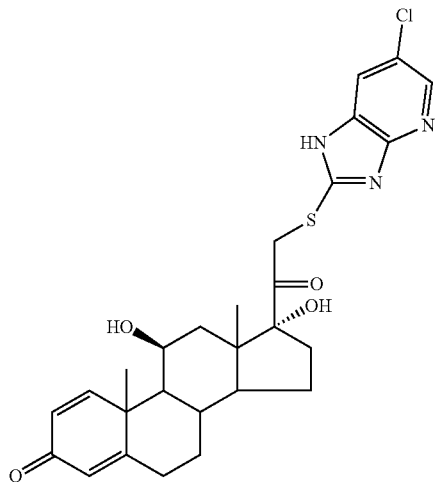 [SMILES: CC12C=CC(=O)C=C1CCC1C2[C@@H](O)CC2(C)C1CC[C@]2(O)C(=O)CSc1nc2ncc(Cl)cc2[nH]1] | 528 |
| 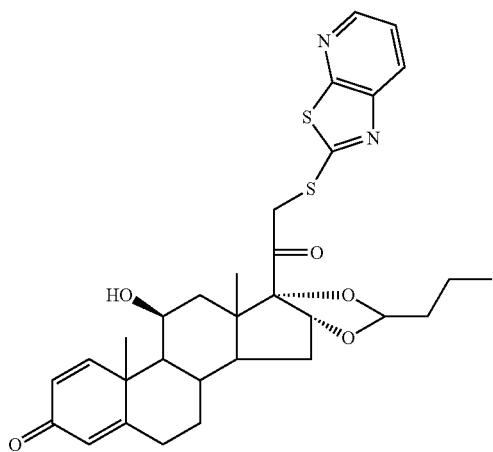 | 581 |
| 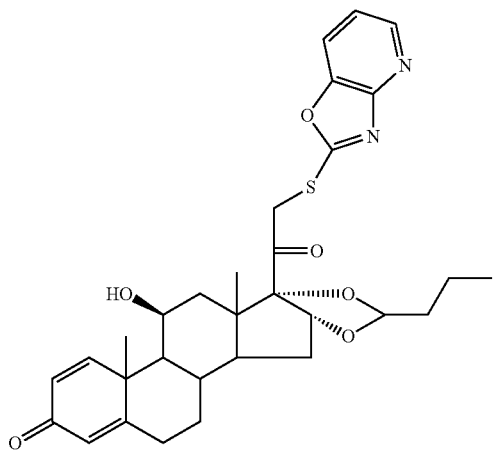 | 565 |

TABLE 1-continued
| Structure | M + H |
|---|---|
| 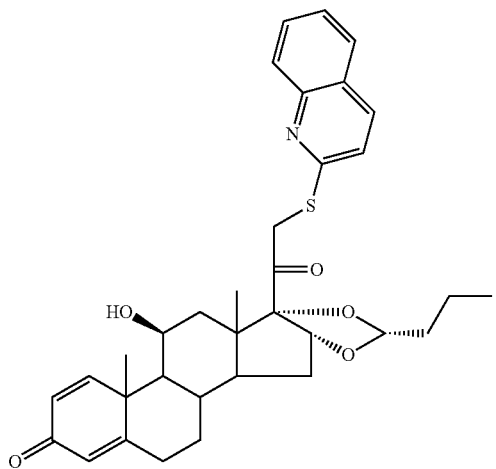 [SMILES: CCC[C@@H]1O[C@@H]2CC3C4CCC5=CC(=O)C=CC5(C)C4[C@@H](O)CC3(C)[C@]2(C(=O)CSc2ccc3ccccc3n2)O1] | 574 |
| 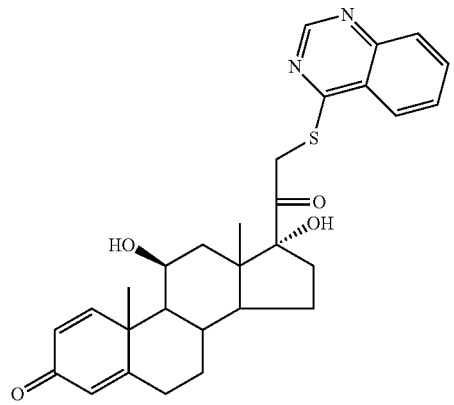 [SMILES: CC12C=CC(=O)C=C1CCC1C2[C@@H](O)CC2(C)C1CC[C@]2(O)C(=O)CSc1ncnc2ccccc12] | 505 |
| 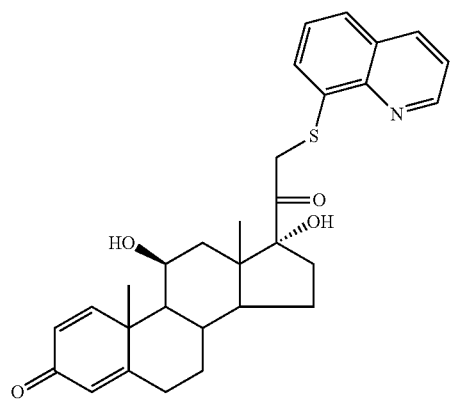 [SMILES: CC12C=CC(=O)C=C1CCC1C2[C@@H](O)CC2(C)C1CC[C@]2(O)C(=O)CSc1cccc2cccnc12] | 504 |

TABLE 1-continued
| Structure | M + H |
|---|---|
| 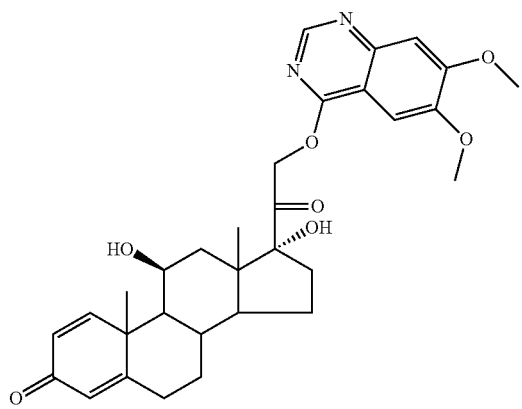 [SMILES: COc1cc2ncnc(OCC(=O)[C@@]3(O)CCC4C5CCC6=CC(=O)C=CC6(C)C5[C@@H](O)CC43C)c2cc1OC] | 549 |
| 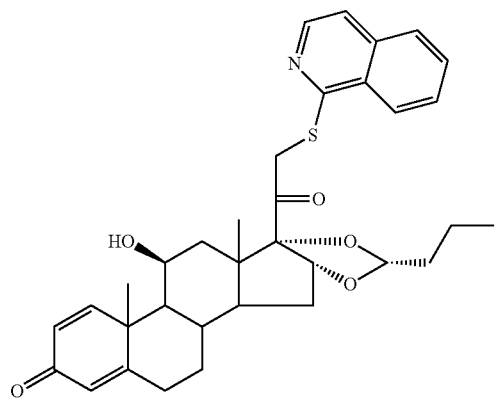 | 574 |
| 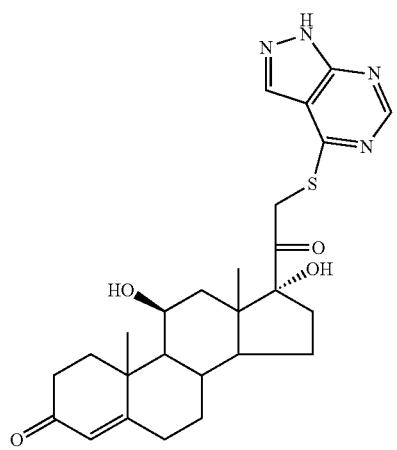 [SMILES: CC12CCC(=O)C=C1CCC1C2[C@@H](O)CC2(C)C1CC[C@]2(O)C(=O)CSc1ncnc2[nH]ncc12] | 497 |

TABLE 1-continued
| Structure | M + H |
|---|---|
| 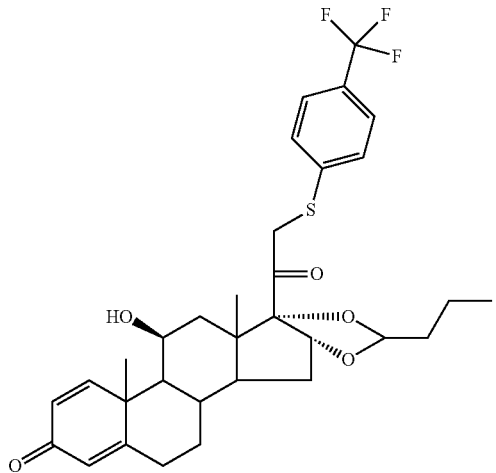 | 591 |
| 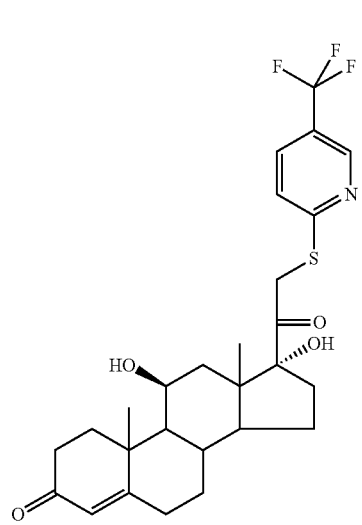 [SMILES: CC12CCC(=O)C=C1CCC1C2[C@@H](O)CC2(C)C1CC[C@]2(O)C(=O)CSc1ccc(C(F)(F)F)cn1] | 524 |
| 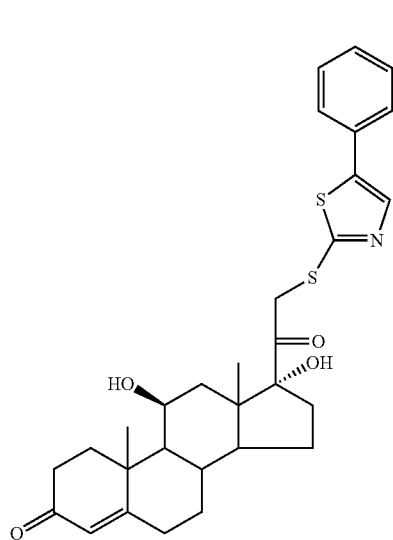 [SMILES: CC12CCC(=O)C=C1CCC1C2[C@@H](O)CC2(C)C1CC[C@]2(O)C(=O)CSc1ncc(-c2ccccc2)s1] | 538 |

TABLE 1-continued
| Structure | M + H |
|---|---|
| 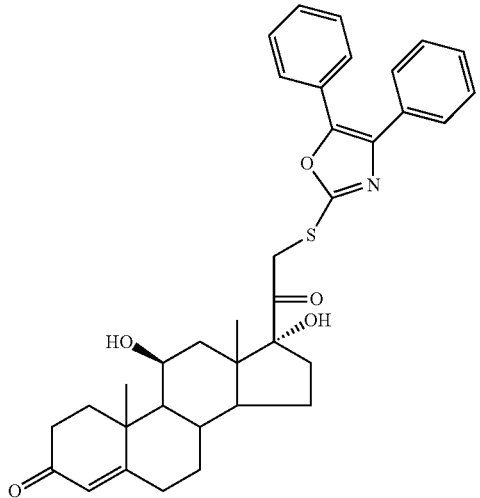 [SMILES: CC12CCC(=O)C=C1CCC1C2[C@@H](O)CC2(C)C1CC[C@]2(O)C(=O)CSc1nc(-c2ccccc2)c(-c2ccccc2)o1] | 598 |
| 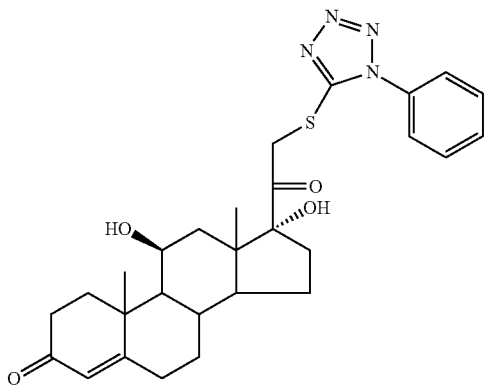 [SMILES: CC12CCC(=O)C=C1CCC1C2[C@@H](O)CC2(C)C1CC[C@]2(O)C(=O)CSc1nnnn1-c1ccccc1] | 523 |
| 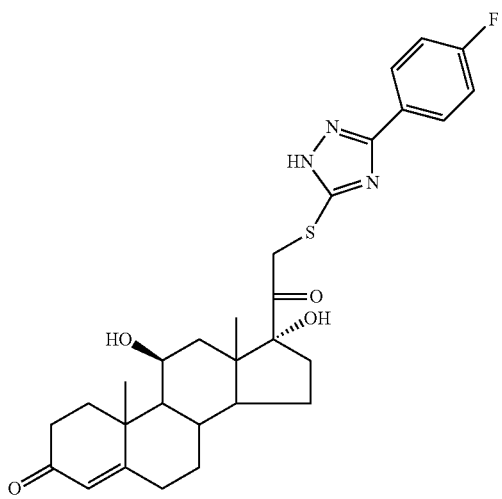 [SMILES: CC12CCC(=O)C=C1CCC1C2[C@@H](O)CC2(C)C1CC[C@]2(O)C(=O)CSc1nc(-c2ccc(F)cc2)n[nH]1] | 540 |

TABLE 1-continued
| Structure | M + H |
|---|---|
| 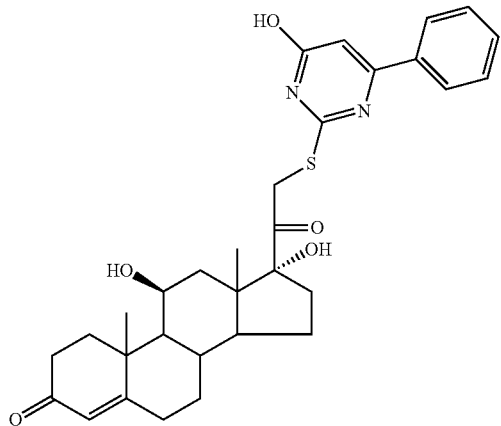 [SMILES: CC12CCC(=O)C=C1CCC1C2[C@@H](O)CC2(C)C1CC[C@]2(O)C(=O)CSc1nc(O)cc(-c2ccccc2)n1] | 549 |
| 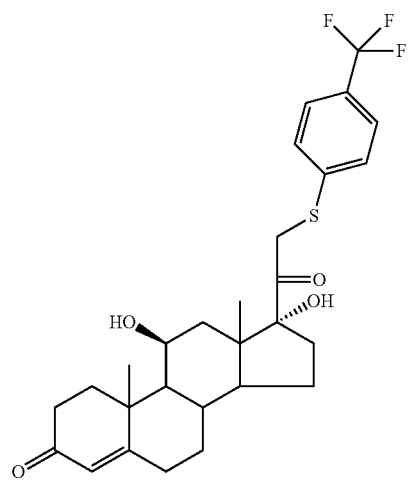 [SMILES: CC12CCC(=O)C=C1CCC1C2[C@@H](O)CC2(C)C1CC[C@]2(O)C(=O)CSc1ccc(C(F)(F)F)cc1] | 523 |
| 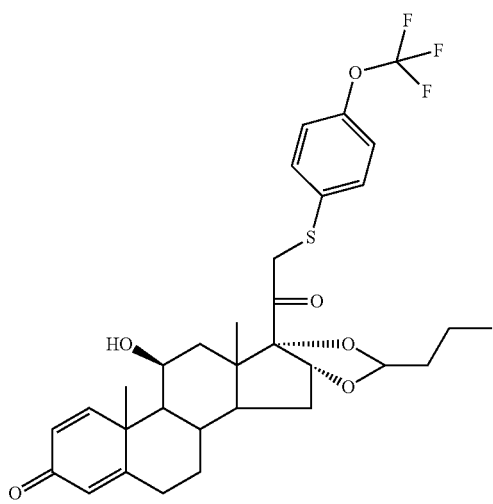 | 607 |

TABLE 1-continued
| Structure | M + H |
|---|---|
| 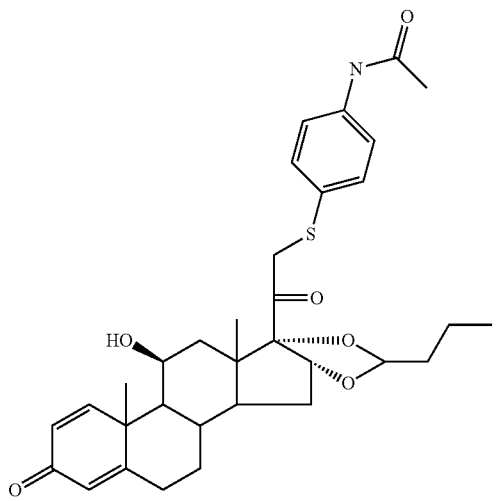 | 580 |
| 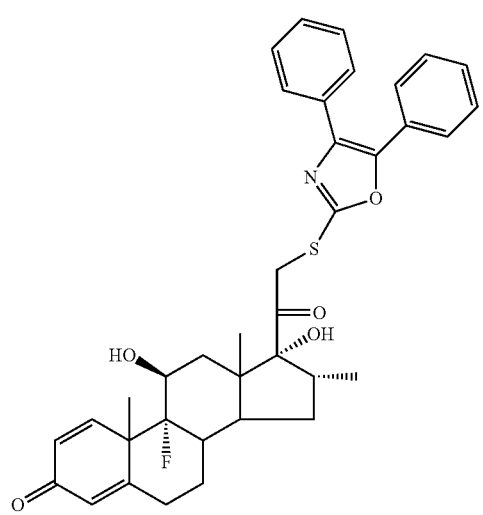 | 628 |
| 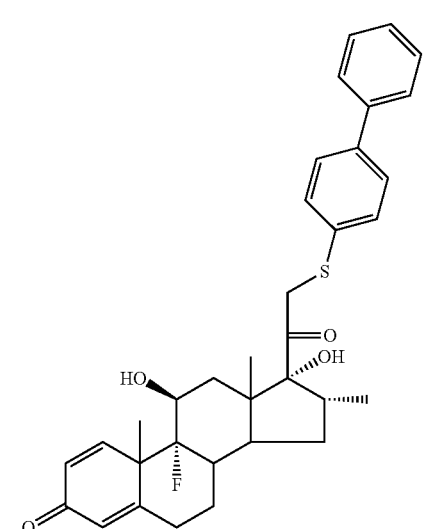 | 561 |

TABLE 1-continued
| Structure | M + H |
|---|---|
| 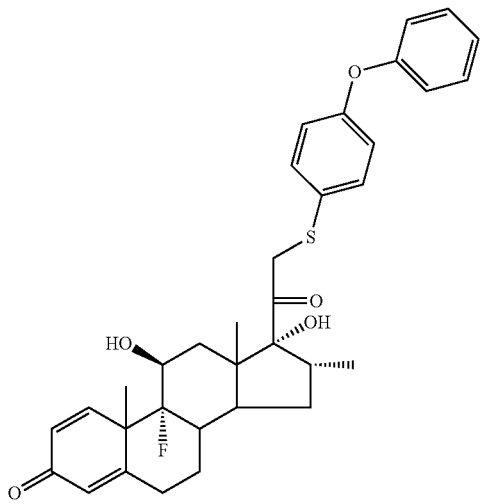 | 577 |
| 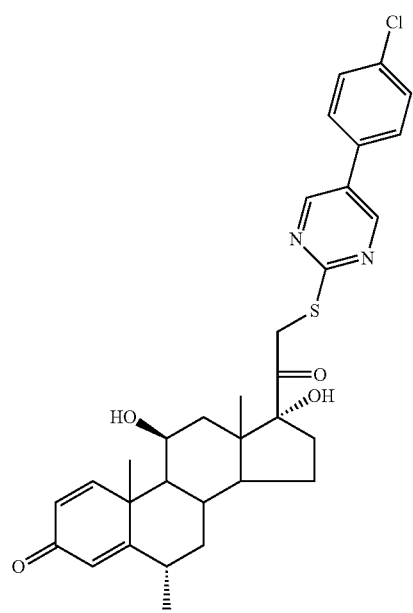 [SMILES: C[C@H]1CC2C([C@@H](O)CC3(C)C2CC[C@]3(O)C(=O)CSc2ncc(-c3ccc(Cl)cc3)cn2)C2(C)C=CC(=O)C=C12] | 579 |
| 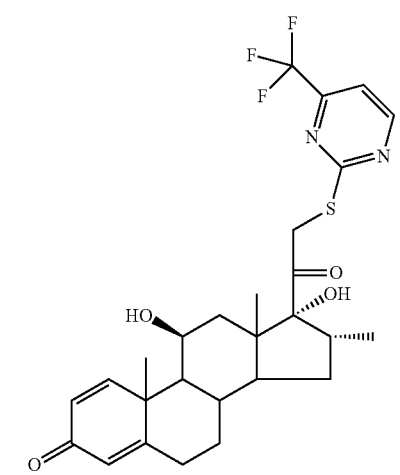 [SMILES: C[C@@H]1CC2C3CCC4=CC(=O)C=CC4(C)C3[C@@H](O)CC2(C)[C@@]1(O)C(=O)CSc1nccc(C(F)(F)F)n1] | 537 |

TABLE 1-continued
| Structure | M + H |
|---|---|
| 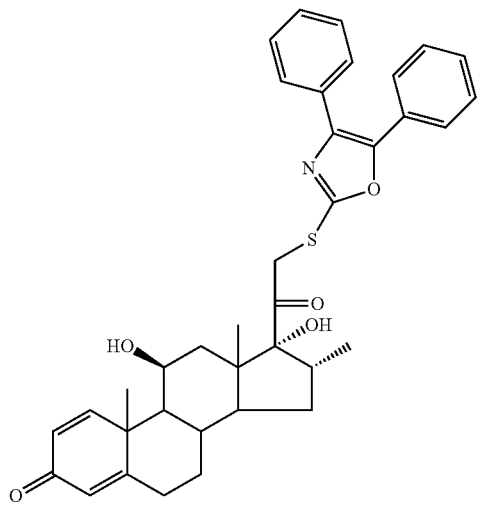 [SMILES: C[C@@H]1CC2C3CCC4=CC(=O)C=CC4(C)C3[C@@H](O)CC2(C)[C@@]1(O)C(=O)CSc1nc(-c2ccccc2)c(-c2ccccc2)o1] | 610 |
| 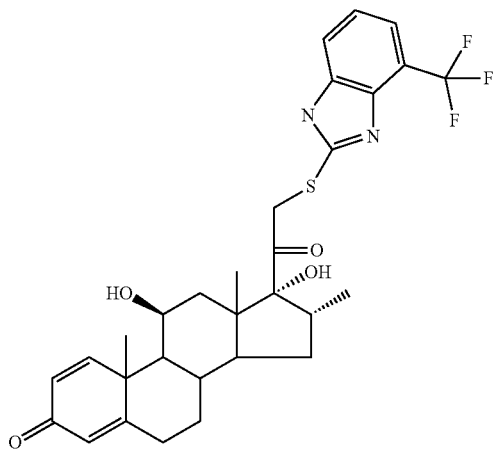 [SMILES: C[C@@H]1CC2C3CCC4=CC(=O)C=CC4(C)C3[C@@H](O)CC2(C)[C@@]1(O)C(=O)CSc1nc2c(C(F)(F)F)cccc2[nH]1] | 575 |
| 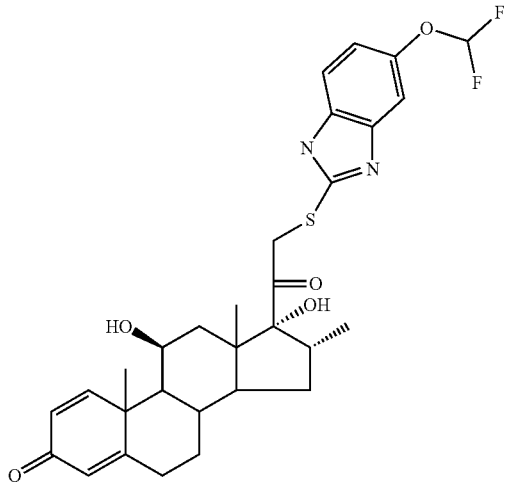 [SMILES: C[C@@H]1CC2C3CCC4=CC(=O)C=CC4(C)C3[C@@H](O)CC2(C)[C@@]1(O)C(=O)CSc1nc2cc(OC(F)F)ccc2[nH]1] | 573 |

TABLE 1-continued
| Structure | M + H |
|---|---|
| 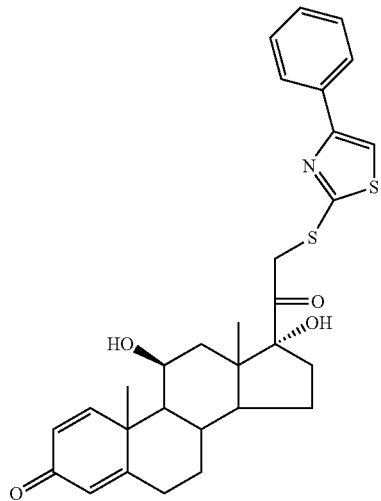 [SMILES: CC12C=CC(=O)C=C1CCC1C2[C@@H](O)CC2(C)C1CC[C@]2(O)C(=O)CSc1nc(-c2ccccc2)cs1] | 536 |
| 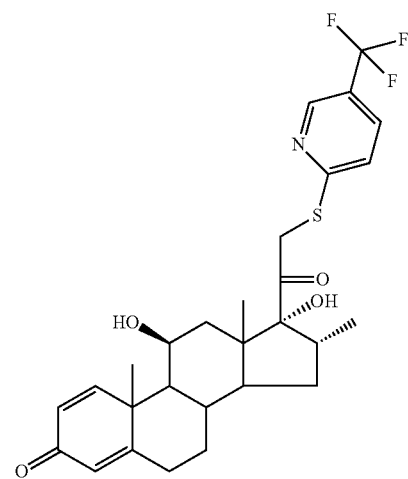 [SMILES: C[C@@H]1CC2C3CCC4=CC(=O)C=CC4(C)C3[C@@H](O)CC2(C)[C@@]1(O)C(=O)CSc1ccc(C(F)(F)F)cn1] | 536 |
| 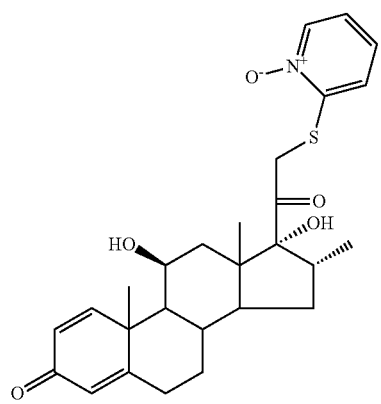 [SMILES: C[C@@H]1CC2C3CCC4=CC(=O)C=CC4(C)C3[C@@H](O)CC2(C)[C@@]1(O)C(=O)CSc1cccc[n+]1[O-]] | 484 |

TABLE 1-continued
| Structure | M + H |
|---|---|
| 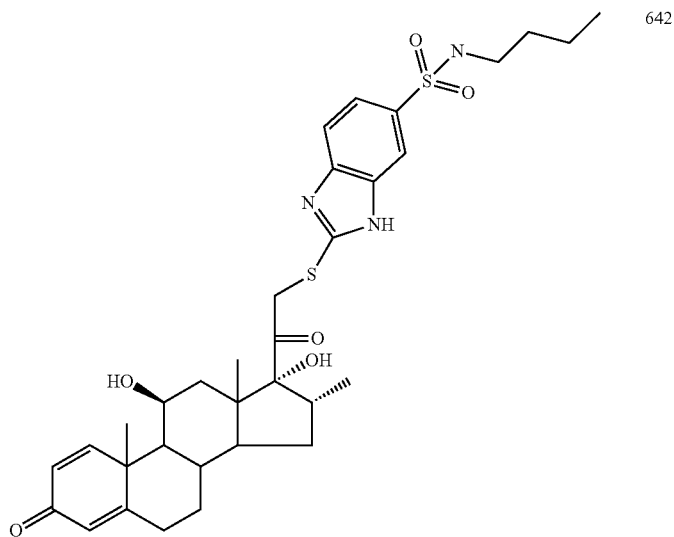 | 642 |
| 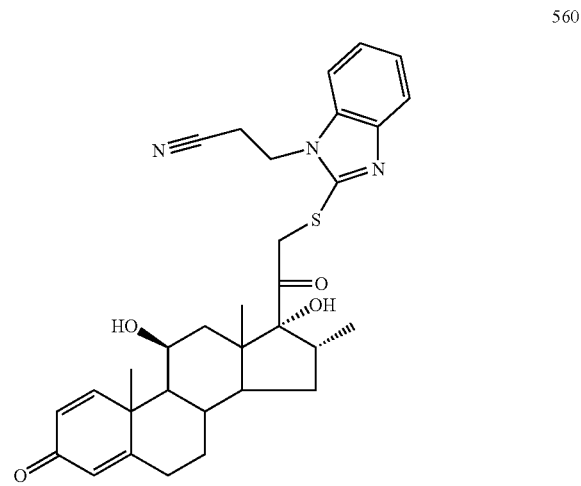 | 560 |
| 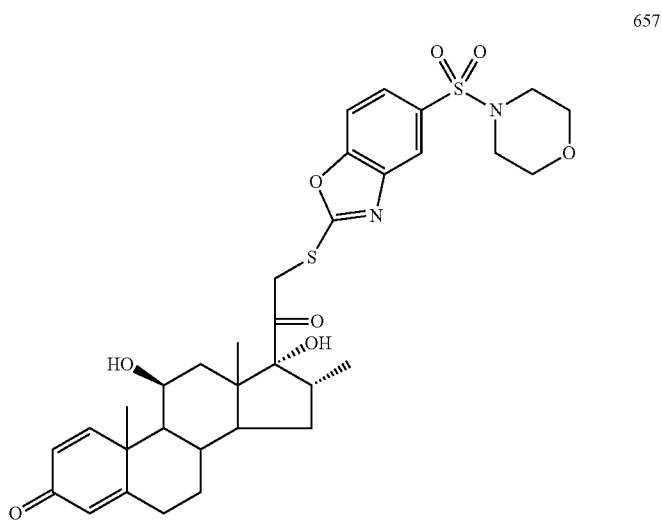 | 657 |

TABLE 1-continued
| Structure | M + H |
|---|---|
| 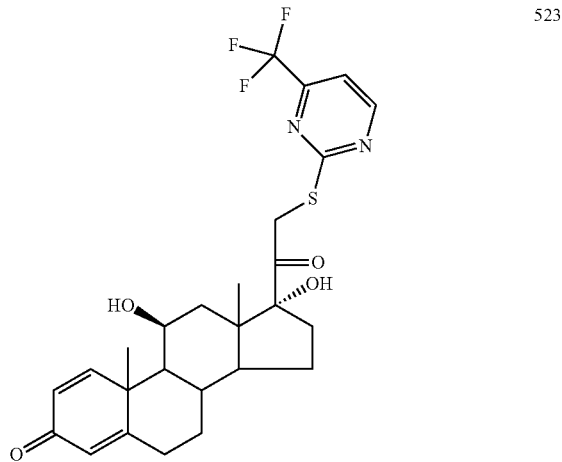 | 523 |
| 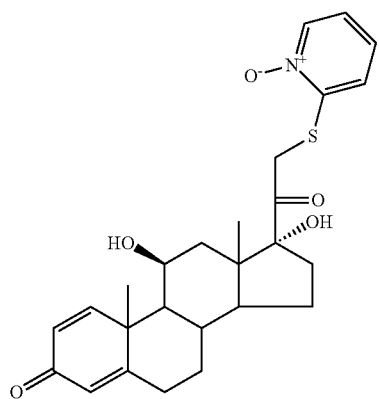 [SMILES: CC12C=CC(=O)C=C1CCC1C2[C@@H](O)CC2(C)C1CC[C@]2(O)C(=O)CSc1cccc[n+]1[O-]] | 470 |
| 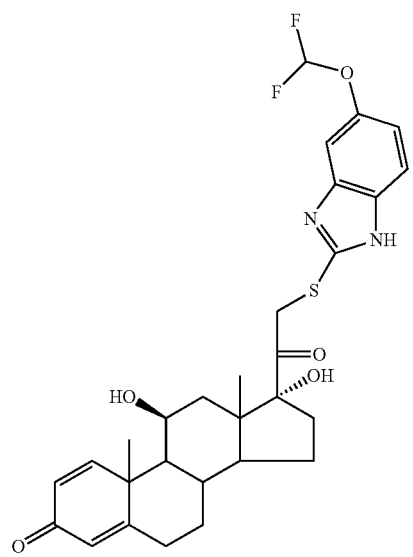 [SMILES: CC12C=CC(=O)C=C1CCC1C2[C@@H](O)CC2(C)C1CC[C@]2(O)C(=O)CSc1nc2cc(OC(F)F)ccc2[nH]1] | 559 |

TABLE 1-continued
| Structure | M + H |
|---|---|
| 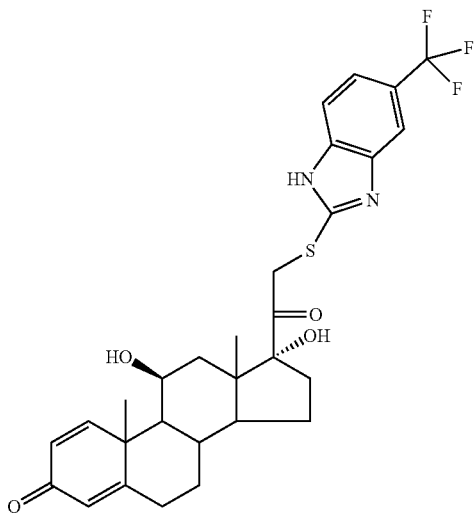 [SMILES: CC12C=CC(=O)C=C1CCC1C2[C@@H](O)CC2(C)C1CC[C@]2(O)C(=O)CSc1nc2cc(C(F)(F)F)ccc2[nH]1] | 561 |
| 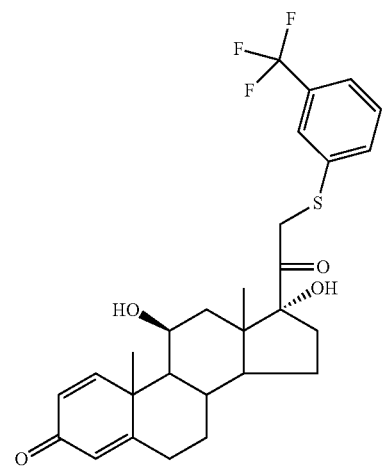 [SMILES: CC12C=CC(=O)C=C1CCC1C2[C@@H](O)CC2(C)C1CC[C@]2(O)C(=O)CSc1cccc(C(F)(F)F)c1] | 521 |
| 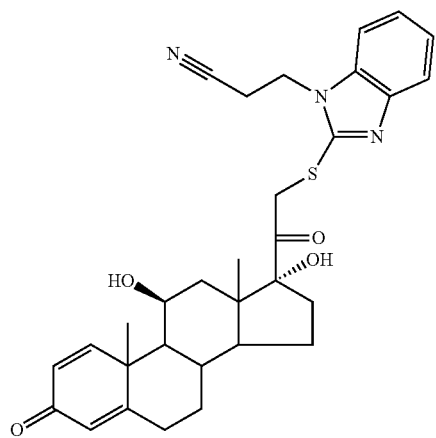 [SMILES: CC12C=CC(=O)C=C1CCC1C2[C@@H](O)CC2(C)C1CC[C@]2(O)C(=O)CSc1nc2ccccc2n1CCC#N] | 546 |

TABLE 1-continued
| Structure | M + H |
|---|---|
| 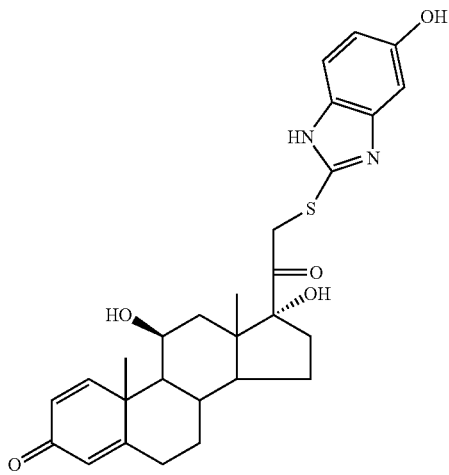 [SMILES: CC12C=CC(=O)C=C1CCC1C2[C@@H](O)CC2(C)C1CC[C@]2(O)C(=O)CSc1nc2cc(O)ccc2[nH]1] | 509 |
| 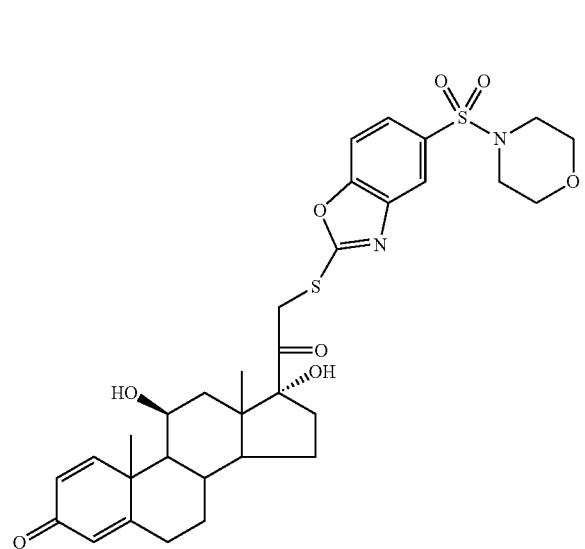 [SMILES: CC12C=CC(=O)C=C1CCC1C2[C@@H](O)CC2(C)C1CC[C@]2(O)C(=O)CSc1nc2cc(S(=O)(=O)N3CCOCC3)ccc2o1] | 643 |
| 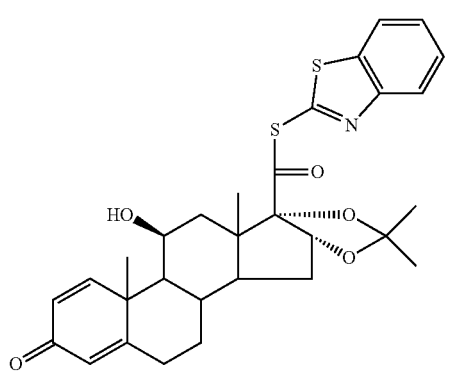 [SMILES: CC1(C)O[C@@H]2CC3C4CCC5=CC(=O)C=CC5(C)C4[C@@H](O)CC3(C)[C@]2(C(=O)Sc2nc3ccccc3s2)O1] | 552 |

TABLE 1-continued
| Structure | M + H |
|---|---|
| 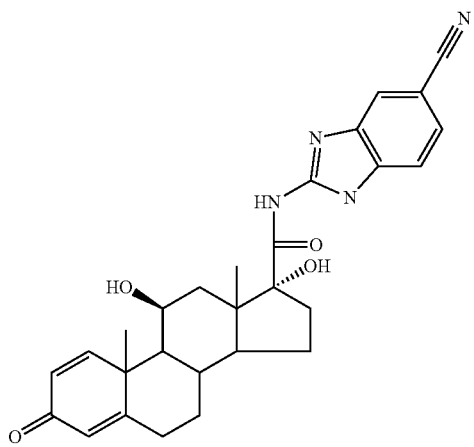 [SMILES: CC12C=CC(=O)C=C1CCC1C2[C@@H](O)CC2(C)C1CC[C@]2(O)C(=O)Nc1nc2cc(C#N)ccc2[nH]1] | 487 |
| 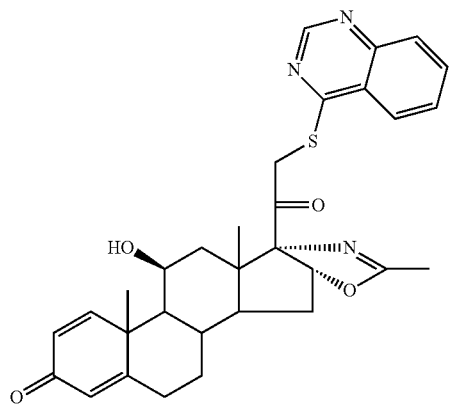 [SMILES: CC1=N[C@]2(C(=O)CSc3ncnc4ccccc34)[C@@H](CC3C4CCC5=CC(=O)C=CC5(C)C4[C@@H](O)CC32C)O1] | 544 |
| 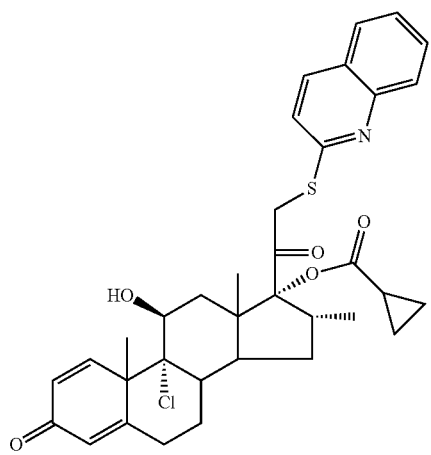 | 620 |

TABLE 1-continued
| Structure | M + H |
|---|---|
| 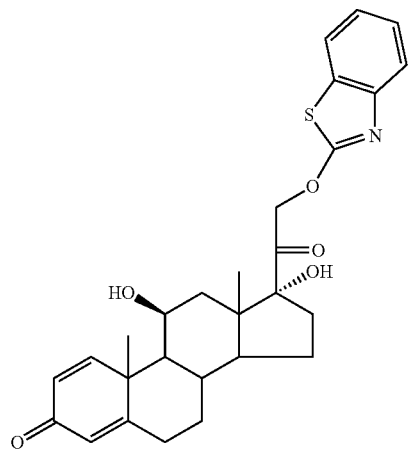 [SMILES: CC12C=CC(=O)C=C1CCC1C2[C@@H](O)CC2(C)C1CC[C@]2(O)C(=O)COc1nc2ccccc2s1] | 494 |
| 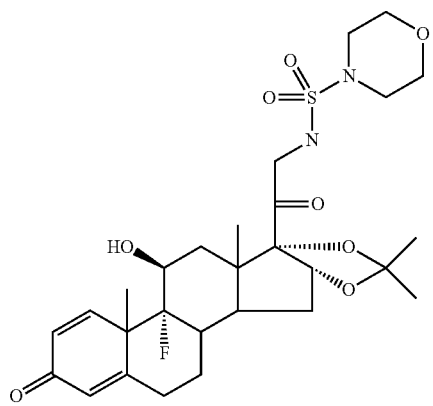 | 583 |
| 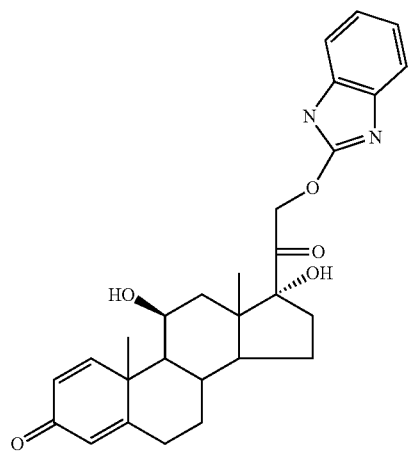 [SMILES: CC12C=CC(=O)C=C1CCC1C2[C@@H](O)CC2(C)C1CC[C@]2(O)C(=O)COc1nc2ccccc2[nH]1] | 477 |

TABLE 1-continued
| Structure | M + H |
|---|---|
| 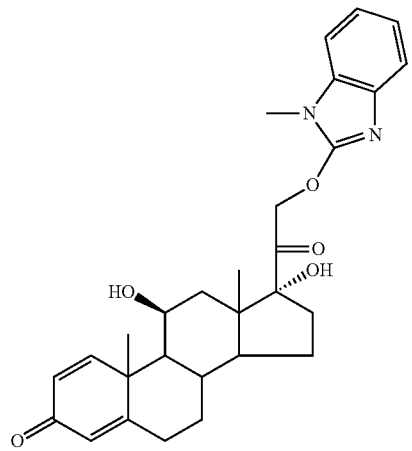 [SMILES: Cn1c(OCC(=O)[C@@]2(O)CCC3C4CCC5=CC(=O)C=CC5(C)C4[C@@H](O)CC32C)nc2ccccc21] | 491 |
| 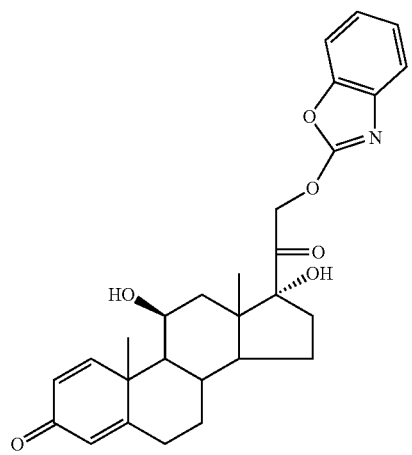 [SMILES: CC12C=CC(=O)C=C1CCC1C2[C@@H](O)CC2(C)C1CC[C@]2(O)C(=O)COc1nc2ccccc2o1] | 478 |
| 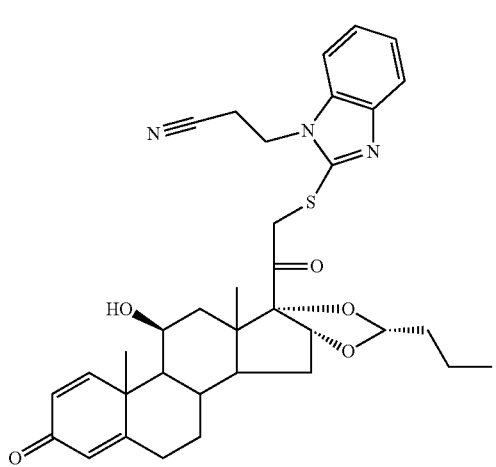 [SMILES: CCC[C@@H]1O[C@@H]2CC3C4CCC5=CC(=O)C=CC5(C)C4[C@@H](O)CC3(C)[C@]2(C(=O)CSc2nc3ccccc3n2CCC#N)O1] | 616 |

TABLE 1-continued
| Structure | M + H |
|---|---|
| 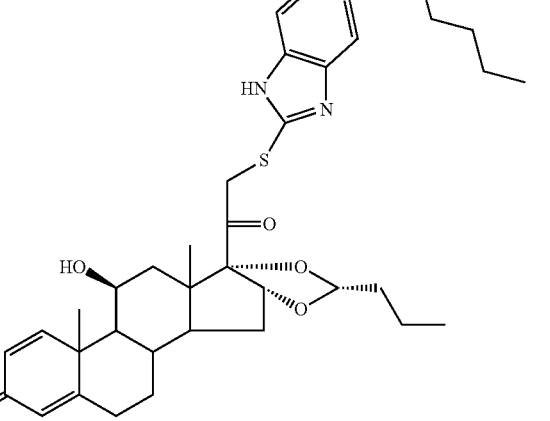 | 698 |
| 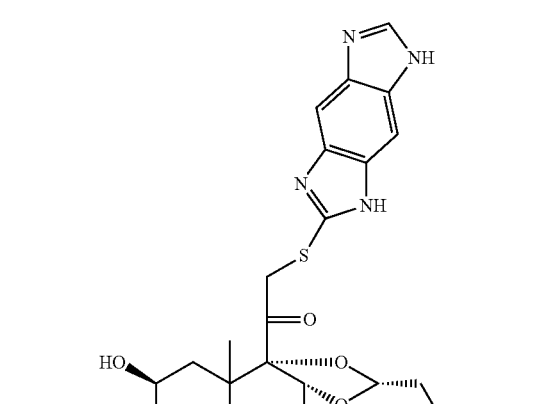 | 603 |
| 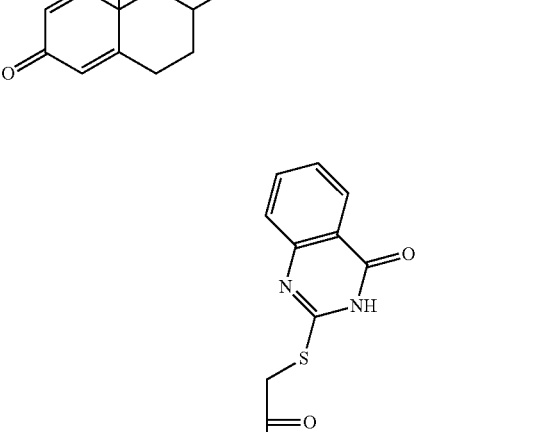 | 591 |

TABLE 1-continued
| Structure | M + H |
|---|---|
| 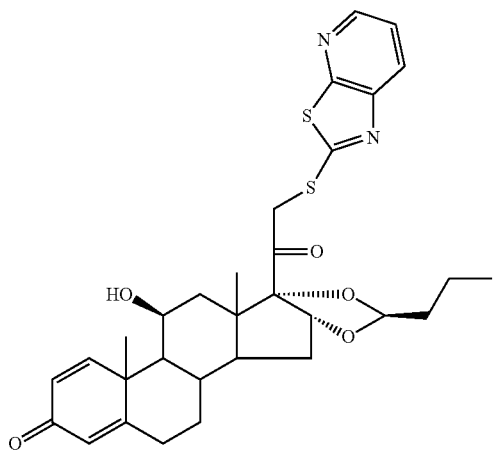 [SMILES: CCC[C@H]1O[C@@H]2CC3C4CCC5=CC(=O)C=CC5(C)C4[C@@H](O)CC3(C)[C@]2(C(=O)CSc2nc3cccnc3s2)O1] | 581 |
| 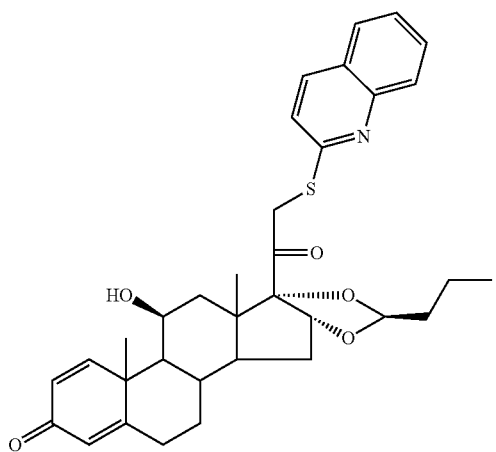 | 574 |
| 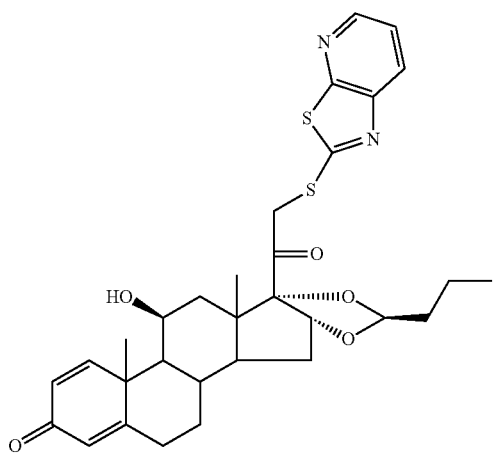 [SMILES: CCC[C@H]1O[C@@H]2CC3C4CCC5=CC(=O)C=CC5(C)C4[C@@H](O)CC3(C)[C@]2(C(=O)CSc2nc3cccnc3s2)O1] | 581 |

TABLE 1-continued
| Structure | M + H |
|---|---|
| 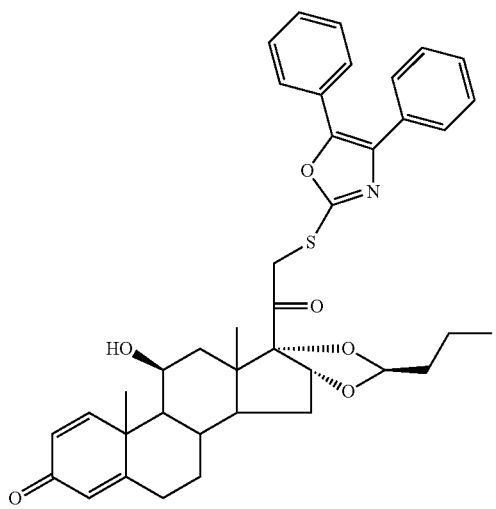 [SMILES: CCC[C@H]1O[C@@H]2CC3C4CCC5=CC(=O)C=CC5(C)C4[C@@H](O)CC3(C)[C@]2(C(=O)CSc2nc(-c3ccccc3)c(-c3ccccc3)o2)O1] | 666 |
| 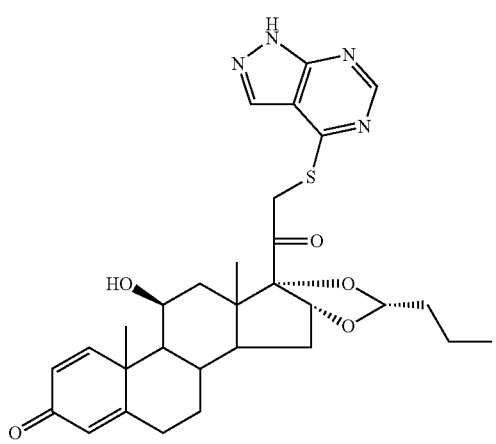 [SMILES: CCC[C@@H]1O[C@@H]2CC3C4CCC5=CC(=O)C=CC5(C)C4[C@@H](O)CC3(C)[C@]2(C(=O)CSc2ncnc3[nH]ncc23)O1] | 565 |
| 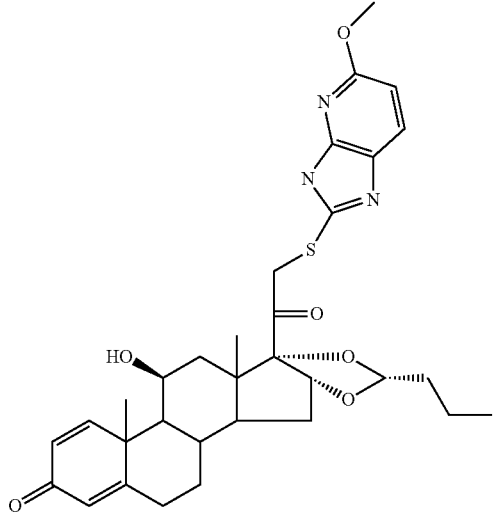 [SMILES: CCC[C@@H]1O[C@@H]2CC3C4CCC5=CC(=O)C=CC5(C)C4[C@@H](O)CC3(C)[C@]2(C(=O)CSc2nc3ccc(OC)nc3[nH]2)O1] | 594 |

TABLE 1-continued
| Structure | M + H |
|---|---|
| 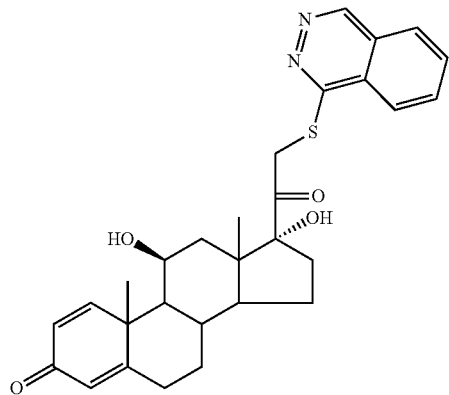 | 505 |
| 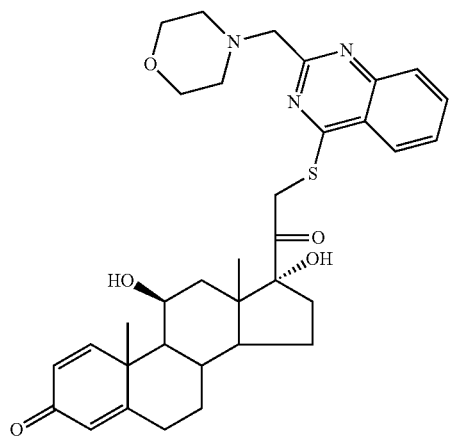 [SMILES: CC12C=CC(=O)C=C1CCC1C2[C@@H](O)CC2(C)C1CC[C@]2(O)C(=O)CSc1nc(CN2CCOCC2)nc2ccccc12] | 604 |
| 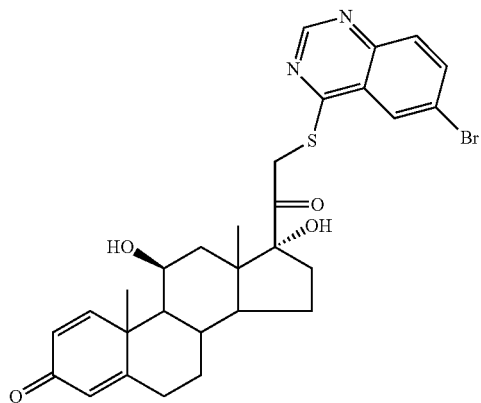 [SMILES: CC12C=CC(=O)C=C1CCC1C2[C@@H](O)CC2(C)C1CC[C@]2(O)C(=O)CSc1ncnc2ccc(Br)cc12] | 583 |

TABLE 1-continued
| Structure | M + H |
|---|---|
| 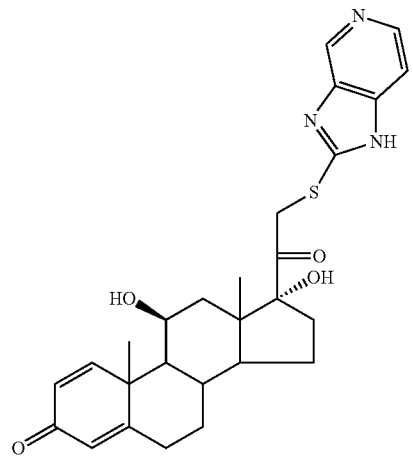 [SMILES: CC12C=CC(=O)C=C1CCC1C2[C@@H](O)CC2(C)C1CC[C@]2(O)C(=O)CSc1nc2cnccc2[nH]1] | 494 |
| 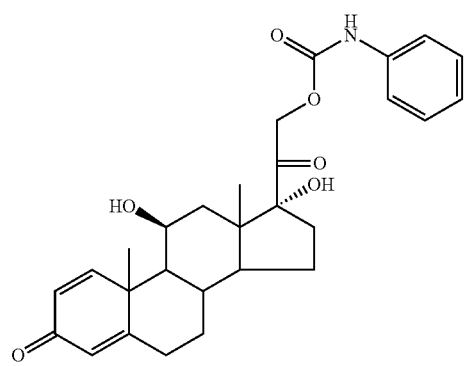 [SMILES: CC12C=CC(=O)C=C1CCC1C2[C@@H](O)CC2(C)C1CC[C@]2(O)C(=O)COC(=O)Nc1ccccc1] | 480 |
| 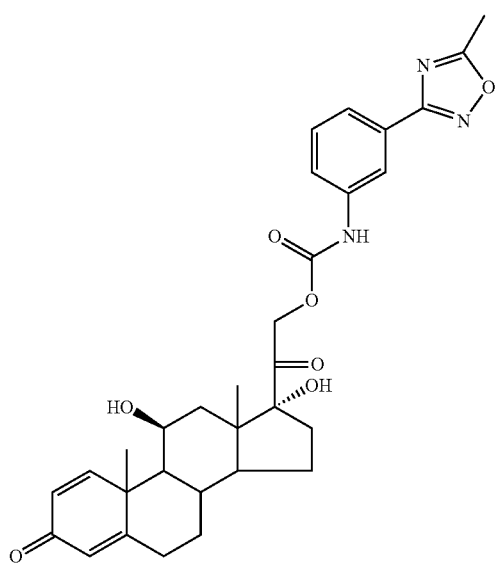 [SMILES: Cc1nc(-c2cccc(NC(=O)OCC(=O)[C@@]3(O)CCC4C5CCC6=CC(=O)C=CC6(C)C5[C@@H](O)CC43C)c2)no1] | 562 |

TABLE 1-continued
| Structure | M + H |
|---|---|
| 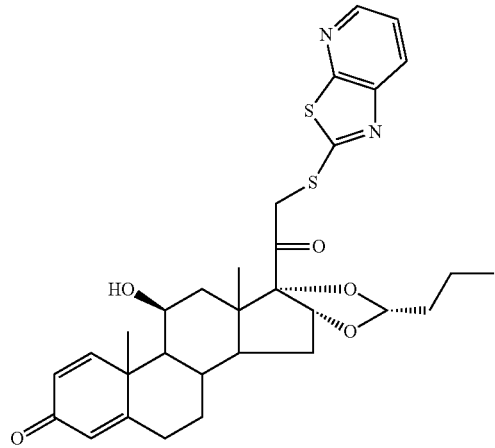 | 581 |
| 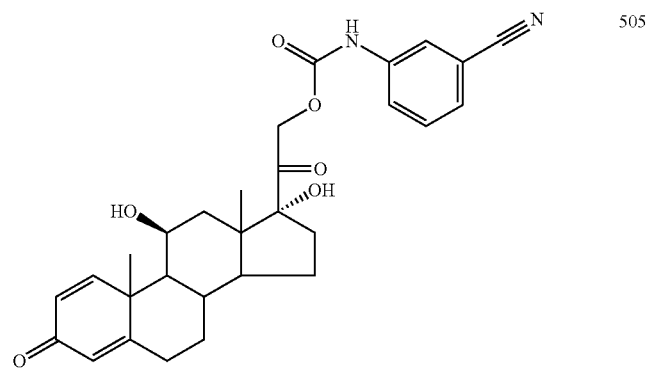 | 505 |
| 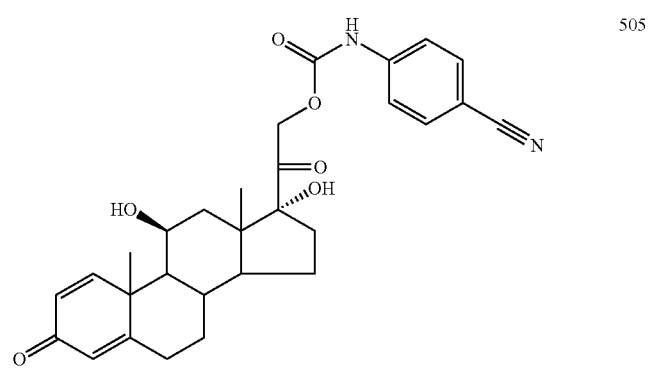 | 505 |
| 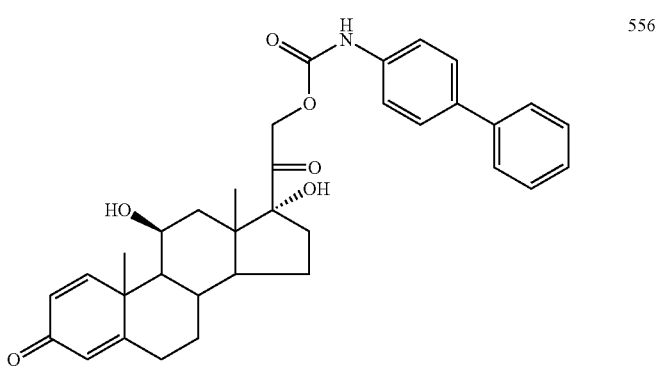 | 556 |

TABLE 1-continued
| Structure | M + H |
|---|---|
| 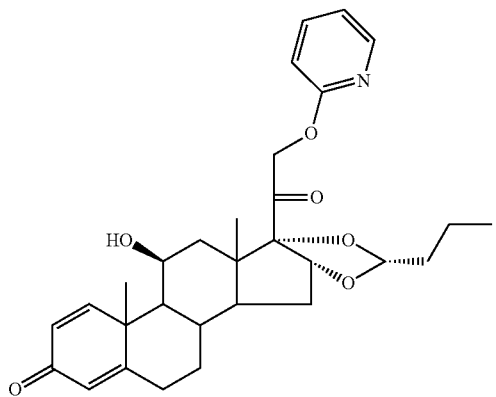 [SMILES: CCC[C@@H]1O[C@@H]2CC3C4CCC5=CC(=O)C=CC5(C)C4[C@@H](O)CC3(C)[C@]2(C(=O)COc2ccccn2)O1] | 508 |
| 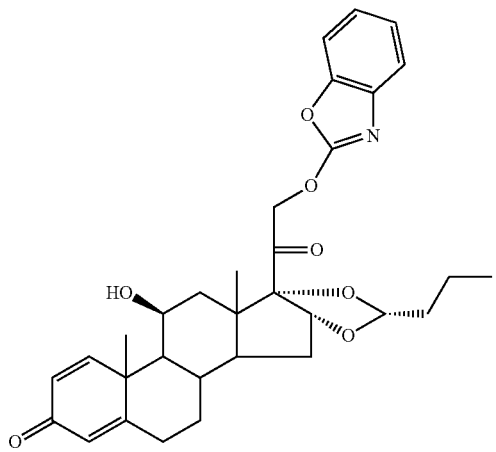 [SMILES: CCC[C@@H]1O[C@@H]2CC3C4CCC5=CC(=O)C=CC5(C)C4[C@@H](O)CC3(C)[C@]2(C(=O)COc2nc3ccccc3o2)O1] | 548 |
| 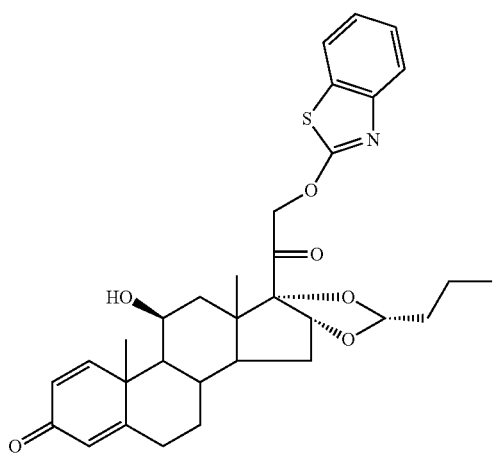 [SMILES: CCC[C@@H]1O[C@@H]2CC3C4CCC5=CC(=O)C=CC5(C)C4[C@@H](O)CC3(C)[C@]2(C(=O)COc2nc3ccccc3s2)O1] | 564 |

TABLE 1-continued
| Structure | M + H |
|---|---|
| 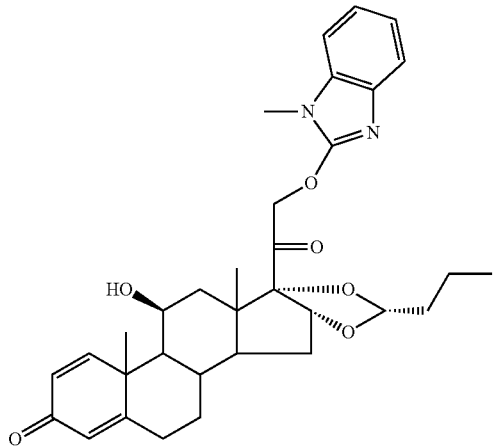 [SMILES: CCC[C@@H]1O[C@@H]2CC3C4CCC5=CC(=O)C=CC5(C)C4[C@@H](O)CC3(C)[C@]2(C(=O)COc2nc3ccccc3n2C)O1] | 561 |
| 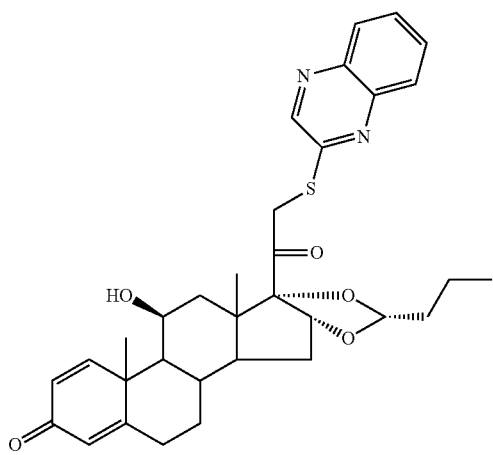 [SMILES: CCC[C@@H]1O[C@@H]2CC3C4CCC5=CC(=O)C=CC5(C)C4[C@@H](O)CC3(C)[C@]2(C(=O)CSc2cnc3ccccc3n2)O1] | 575 |
| 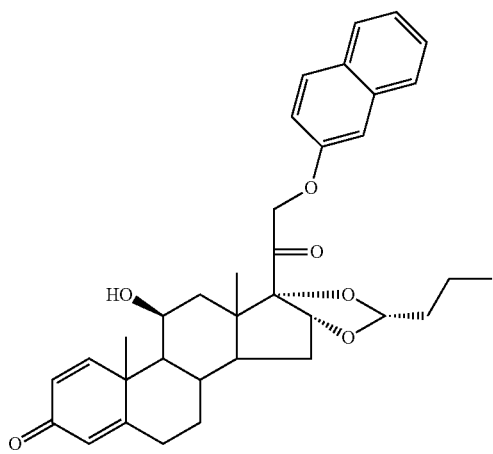 [SMILES: CCC[C@@H]1O[C@@H]2CC3C4CCC5=CC(=O)C=CC5(C)C4[C@@H](O)CC3(C)[C@]2(C(=O)COc2ccc3ccccc3c2)O1] | 557 |

TABLE 1-continued
| Structure | M + H |
|---|---|
| 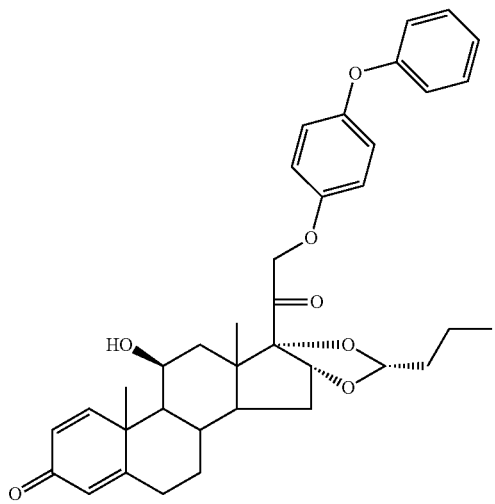 [SMILES: CCC[C@@H]1O[C@@H]2CC3C4CCC5=CC(=O)C=CC5(C)C4[C@@H](O)CC3(C)[C@]2(C(=O)COc2ccc(Oc3ccccc3)cc2)O1] | 599 |
| 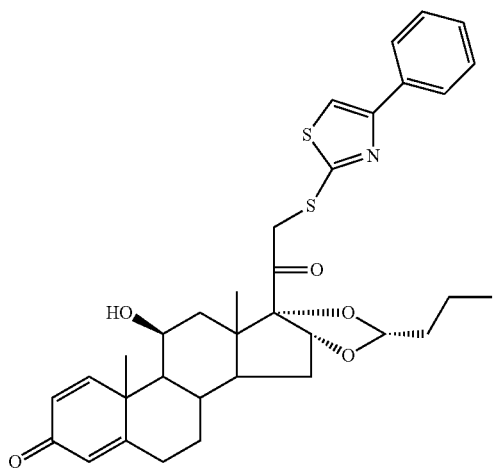 [SMILES: CCC[C@@H]1O[C@@H]2CC3C4CCC5=CC(=O)C=CC5(C)C4[C@@H](O)CC3(C)[C@]2(C(=O)CSc2nc(-c3ccccc3)cs2)O1] | 606 |
| 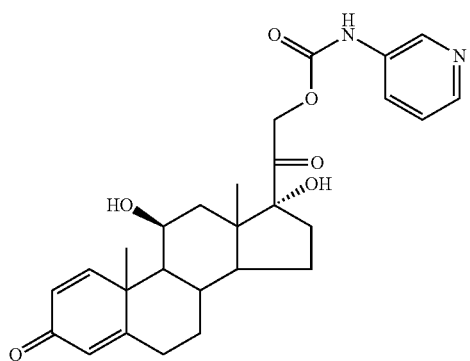 [SMILES: CC12C=CC(=O)C=C1CCC1C2[C@@H](O)CC2(C)C1CC[C@]2(O)C(=O)COC(=O)Nc1cccnc1] | 481 |

TABLE 1-continued
| Structure | M + H |
|---|---|
| 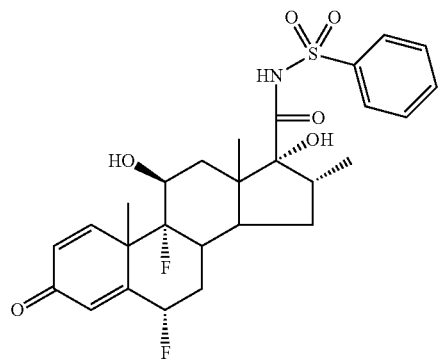 | 536 |
| 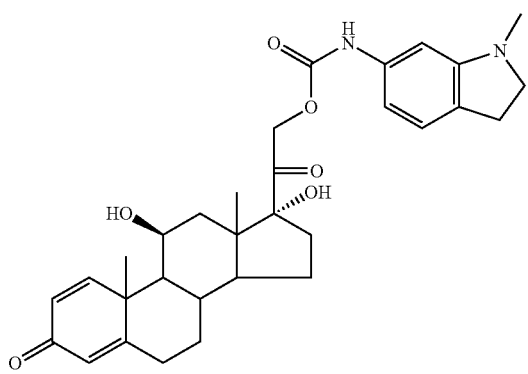 [SMILES: CN1CCc2ccc(NC(=O)OCC(=O)[C@@]3(O)CCC4C5CCC6=CC(=O)C=CC6(C)C5[C@@H](O)CC43C)cc21] | 533 |
| 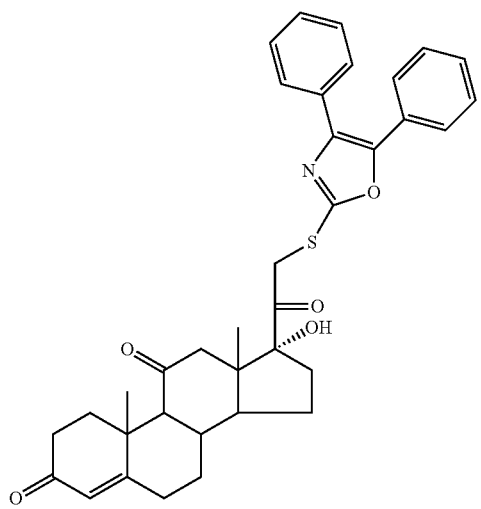 [SMILES: CC12CCC(=O)C=C1CCC1C2C(=O)CC2(C)C1CC[C@]2(O)C(=O)CSc1nc(-c2ccccc2)c(-c2ccccc2)o1] | 596 |

TABLE 1-continued
| Structure | M + H |
|---|---|
| 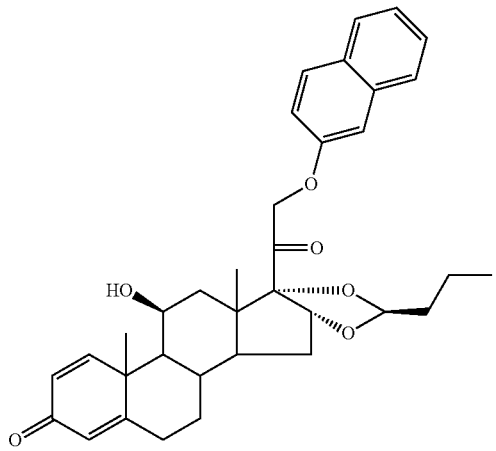 [SMILES: CCC[C@H]1O[C@@H]2CC3C4CCC5=CC(=O)C=CC5(C)C4[C@@H](O)CC3(C)[C@]2(C(=O)COc2ccc3ccccc3c2)O1] | 557 |
| 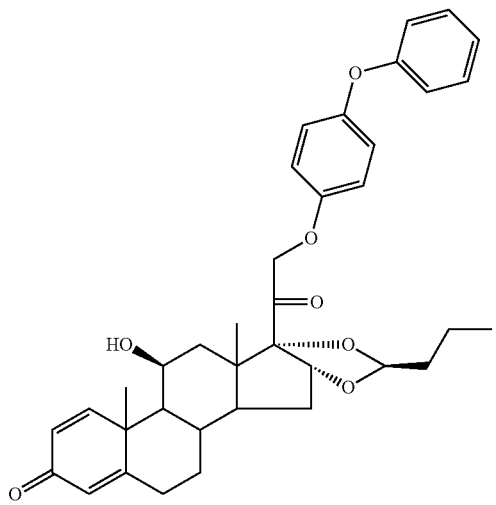 [SMILES: CCC[C@H]1O[C@@H]2CC3C4CCC5=CC(=O)C=CC5(C)C4[C@@H](O)CC3(C)[C@]2(C(=O)COc2ccc(Oc3ccccc3)cc2)O1] | 599 |
| 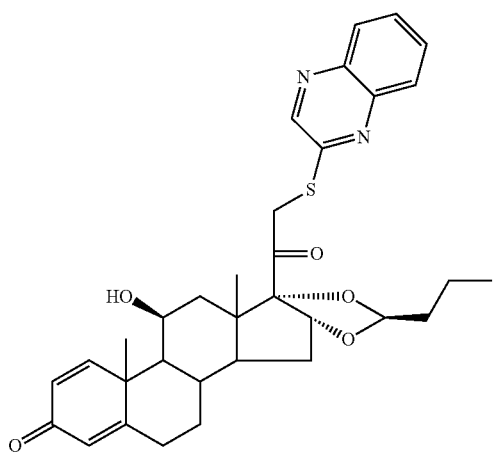 [SMILES: CCC[C@H]1O[C@@H]2CC3C4CCC5=CC(=O)C=CC5(C)C4[C@@H](O)CC3(C)[C@]2(C(=O)CSc2cnc3ccccc3n2)O1] | 575 |

TABLE 1-continued
| Structure | M + H |
|---|---|
| 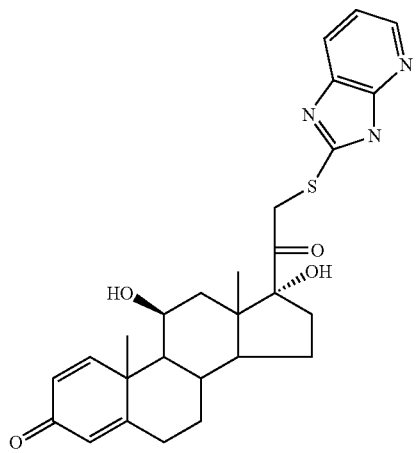 [SMILES: CC12C=CC(=O)C=C1CCC1C2[C@@H](O)CC2(C)C1CC[C@]2(O)C(=O)CSc1nc2cccnc2[nH]1] | 494 |
| 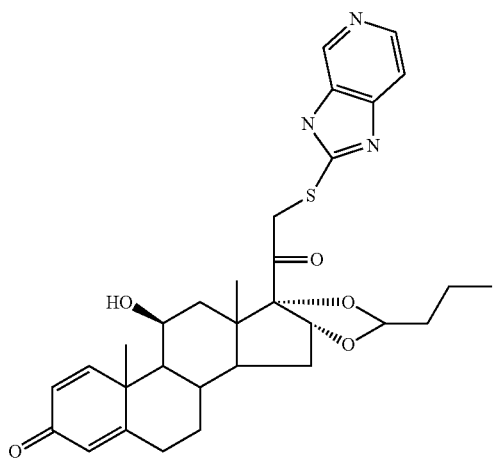 | 564 |
| 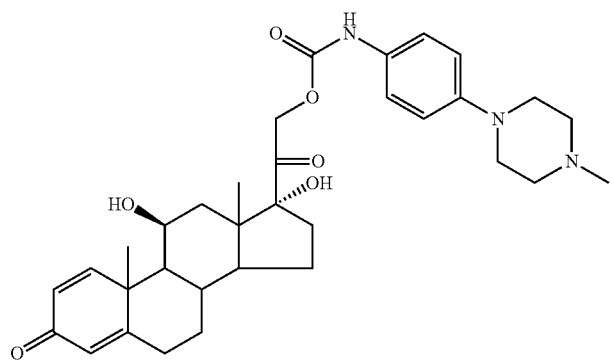 [SMILES: CN1CCN(c2ccc(NC(=O)OCC(=O)[C@@]3(O)CCC4C5CCC6=CC(=O)C=CC6(C)C5[C@@H](O)CC43C)cc2)CC1] | 578 |

TABLE 1-continued
| Structure | M + H |
|---|---|
| 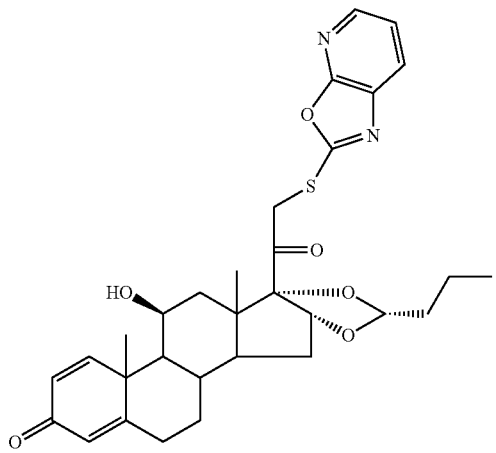 | 565 |
| 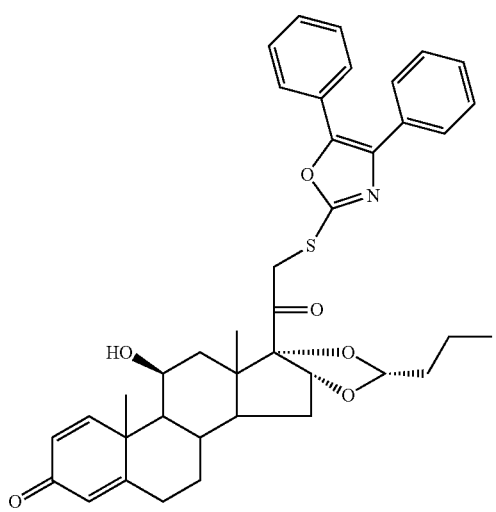 [SMILES: CCC[C@@H]1O[C@@H]2CC3C4CCC5=CC(=O)C=CC5(C)C4[C@@H](O)CC3(C)[C@]2(C(=O)CSc2nc(-c3ccccc3)c(-c3ccccc3)o2)O1] | 666 |
| 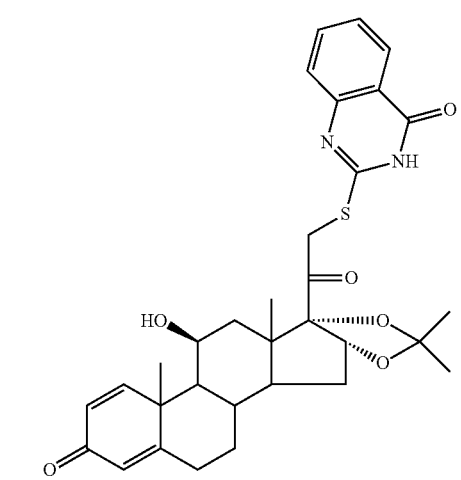 [SMILES: CC1(C)O[C@@H]2CC3C4CCC5=CC(=O)C=CC5(C)C4[C@@H](O)CC3(C)[C@]2(C(=O)CSc2nc3ccccc3c(=O)[nH]2)O1] | 577 |

TABLE 1-continued
| Structure | M + H |
|---|---|
| 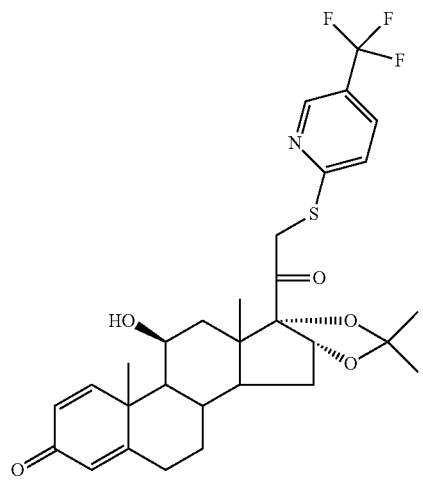 [SMILES: CC1(C)O[C@@H]2CC3C4CCC5=CC(=O)C=CC5(C)C4[C@@H](O)CC3(C)[C@]2(C(=O)CSc2ccc(C(F)(F)F)cn2)O1] | 578 |
| 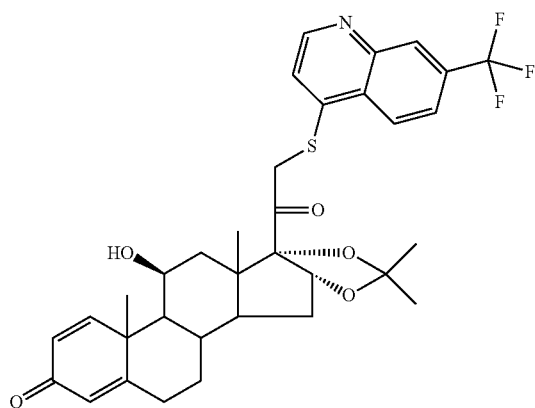 [SMILES: CC1(C)O[C@@H]2CC3C4CCC5=CC(=O)C=CC5(C)C4[C@@H](O)CC3(C)[C@]2(C(=O)CSc2ccnc3cc(C(F)(F)F)ccc23)O1] | 628 |
| 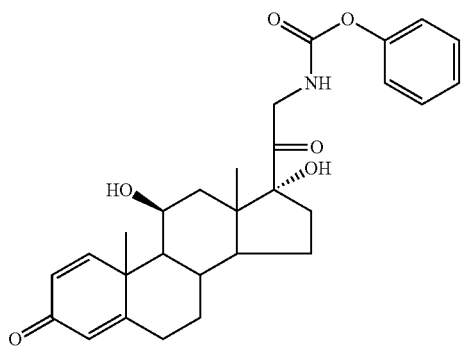 [SMILES: CC12C=CC(=O)C=C1CCC1C2[C@@H](O)CC2(C)C1CC[C@]2(O)C(=O)CNC(=O)Oc1ccccc1] | 480 |

TABLE 1-continued
| Structure | M + H |
|---|---|
| 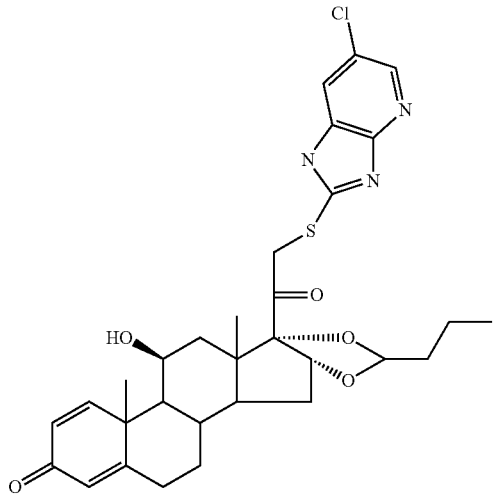 | 598 |
| 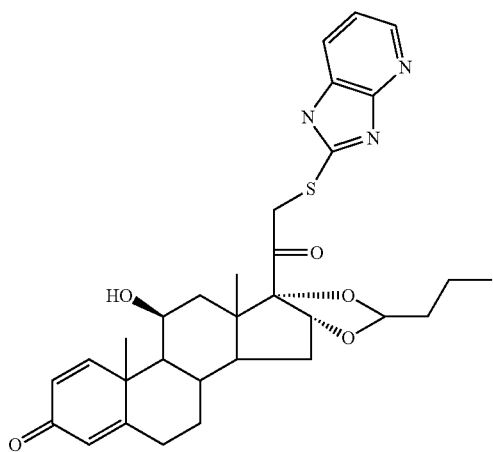 | 564 |
| 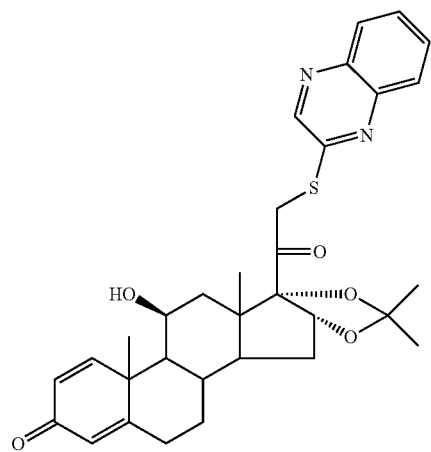 [SMILES: CC1(C)O[C@@H]2CC3C4CCC5=CC(=O)C=CC5(C)C4[C@@H](O)CC3(C)[C@]2(C(=O)CSc2cnc3ccccc3n2)O1] | 561 |

TABLE 1-continued
| Structure | M + H |
|---|---|
| 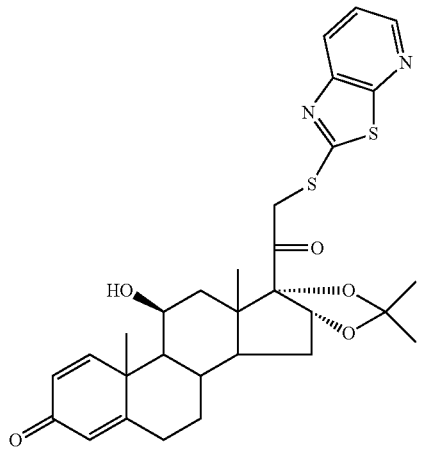 [SMILES: CC1(C)O[C@@H]2CC3C4CCC5=CC(=O)C=CC5(C)C4[C@@H](O)CC3(C)[C@]2(C(=O)CSc2nc3cccnc3s2)O1] | 567 |
| 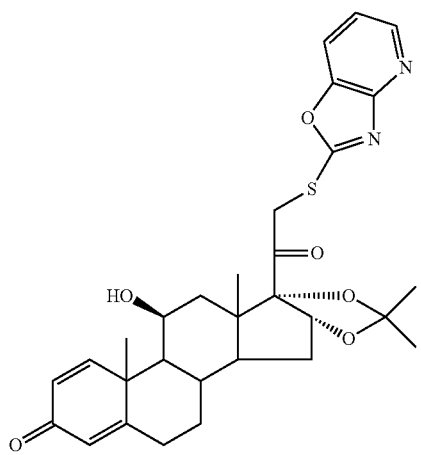 [SMILES: CC1(C)O[C@@H]2CC3C4CCC5=CC(=O)C=CC5(C)C4[C@@H](O)CC3(C)[C@]2(C(=O)CSc2nc3ncccc3o2)O1] | 551 |
| 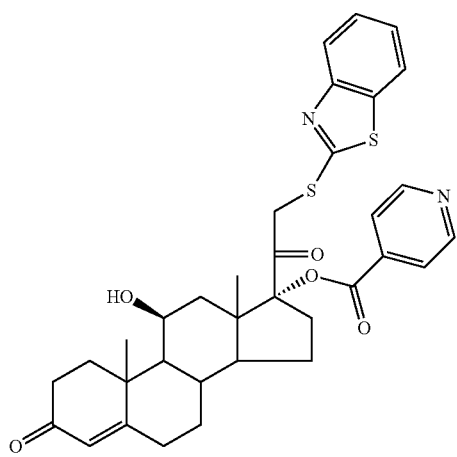 [SMILES: CC12CCC(=O)C=C1CCC1C2[C@@H](O)CC2(C)C1CC[C@]2(OC(=O)c1ccncc1)C(=O)CSc1nc2ccccc2s1] | 617 |

TABLE 1-continued
| Structure | M + H |
|---|---|
| 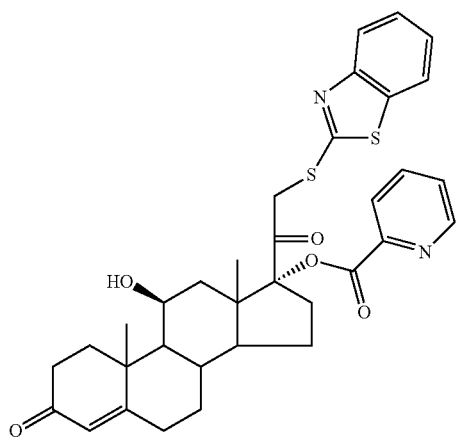 [SMILES: CC12CCC(=O)C=C1CCC1C2[C@@H](O)CC2(C)C1CC[C@]2(OC(=O)c1ccccn1)C(=O)CSc1nc2ccccc2s1] | 617 |
| 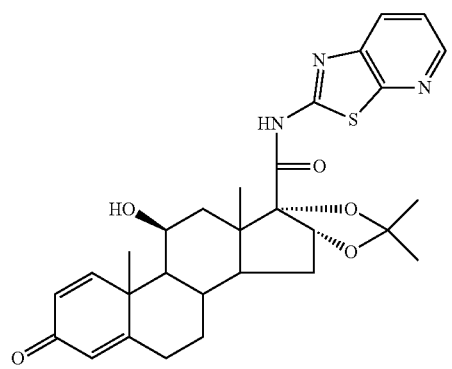 [SMILES: CC1(C)O[C@@H]2CC3C4CCC5=CC(=O)C=CC5(C)C4[C@@H](O)CC3(C)[C@]2(C(=O)Nc2nc3cccnc3s2)O1] | 536 |
| 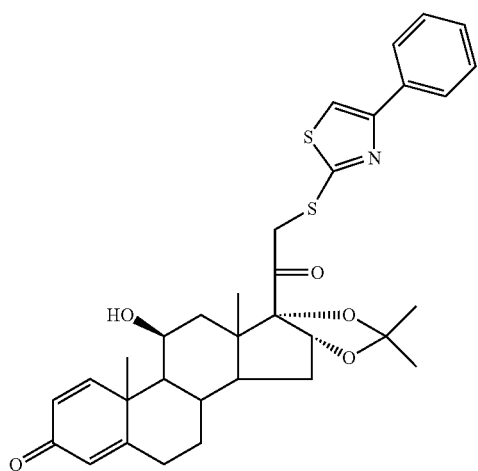 [SMILES: CC1(C)O[C@@H]2CC3C4CCC5=CC(=O)C=CC5(C)C4[C@@H](O)CC3(C)[C@]2(C(=O)CSc2nc(-c3ccccc3)cs2)O1] | 592 |

TABLE 1-continued
| Structure | M + H |
|---|---|
| 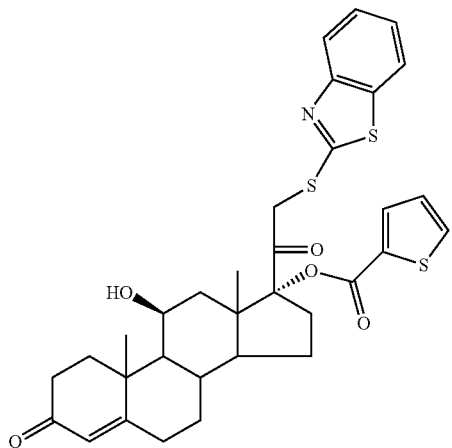 [SMILES: CC12CCC(=O)C=C1CCC1C2[C@@H](O)CC2(C)C1CC[C@]2(OC(=O)c1cccs1)C(=O)CSc1nc2ccccc2s1] | 622 |
| 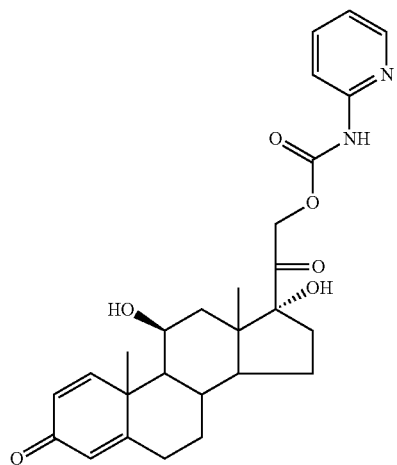 [SMILES: CC12C=CC(=O)C=C1CCC1C2[C@@H](O)CC2(C)C1CC[C@]2(O)C(=O)COC(=O)Nc1ccccn1] | 481 |
| 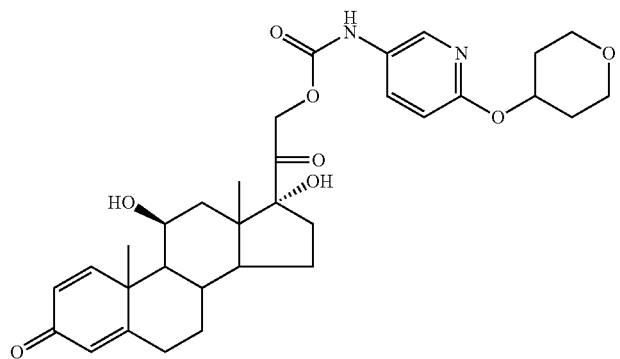 [SMILES: CC12C=CC(=O)C=C1CCC1C2[C@@H](O)CC2(C)C1CC[C@]2(O)C(=O)COC(=O)Nc1ccc(OC2CCOCC2)nc1] | 581 |

TABLE 1-continued
| Structure | M + H |
|---|---|
| 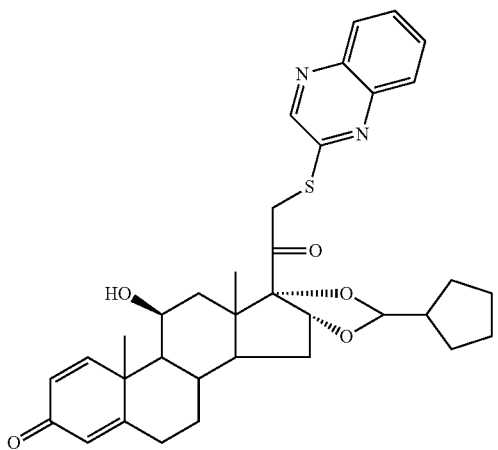 | 601 |
| 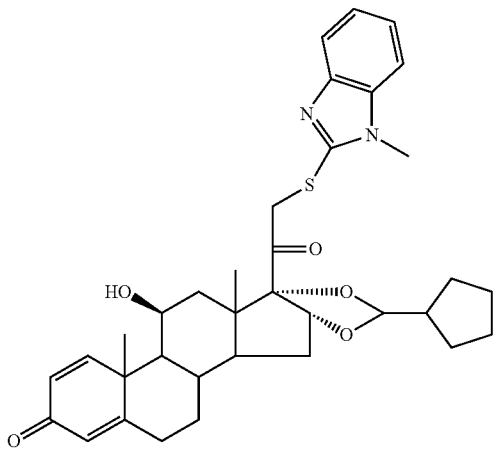 | 603 |
| 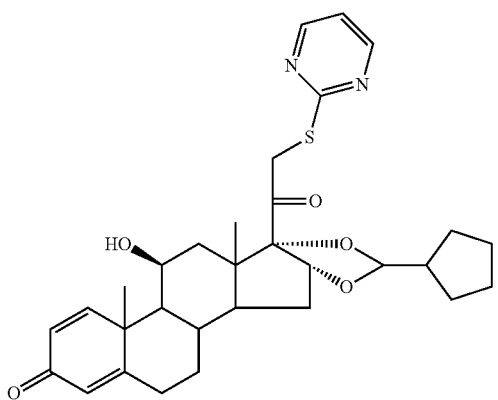 | 551 |

TABLE 1-continued
| Structure | M + H |
|---|---|
| 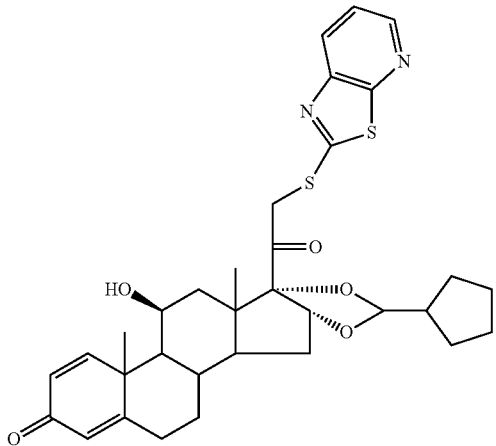 | 607 |
| 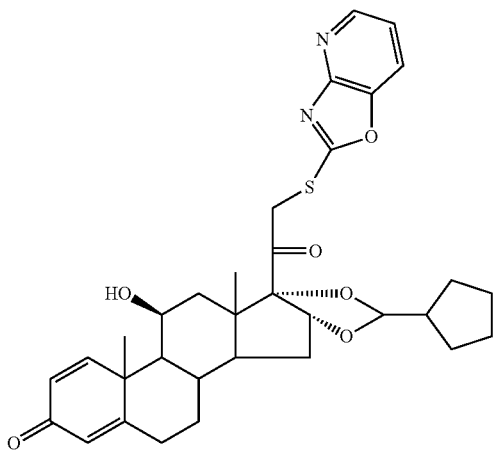 | 591 |
| 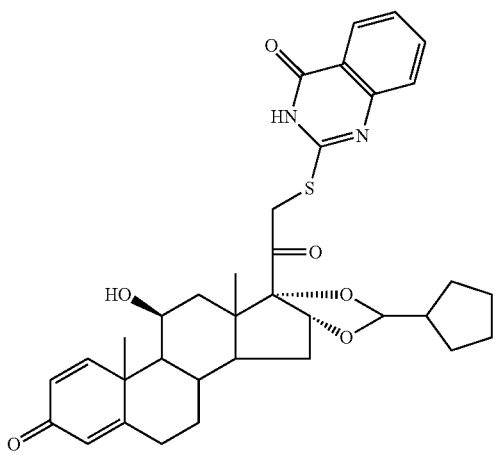 | 617 |

TABLE 1-continued
| Structure | M + H |
|---|---|
| 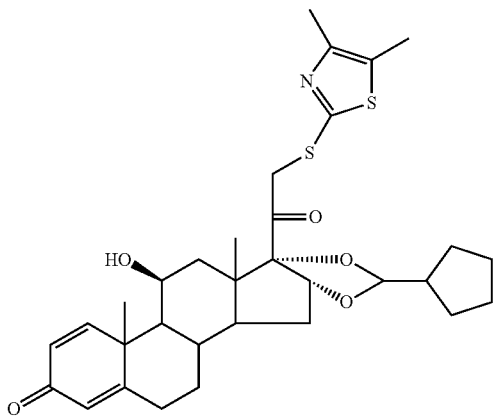 | 584 |
| 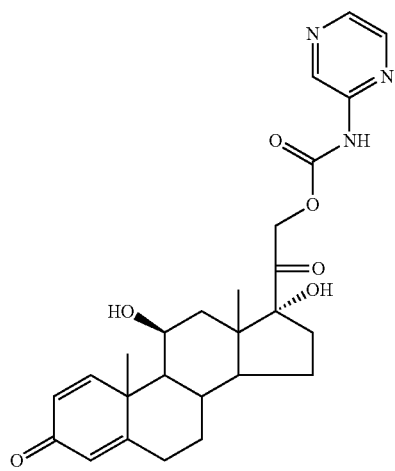 [SMILES: CC12C=CC(=O)C=C1CCC1C2[C@@H](O)CC2(C)C1CC[C@]2(O)C(=O)COC(=O)Nc1cnccn1] | 482 |
| 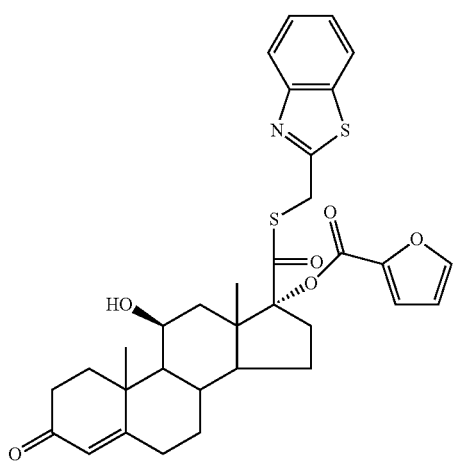 | 606 |

TABLE 1-continued
| Structure | M + H |
|---|---|
| 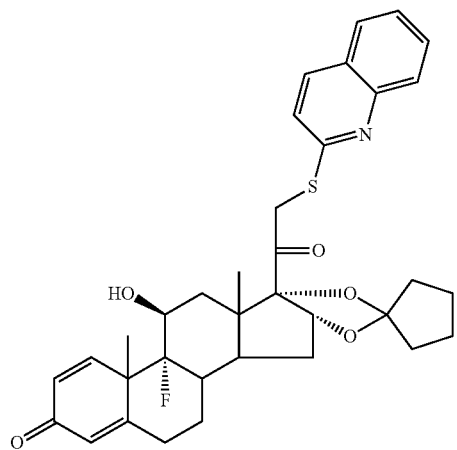 | 604 |
| 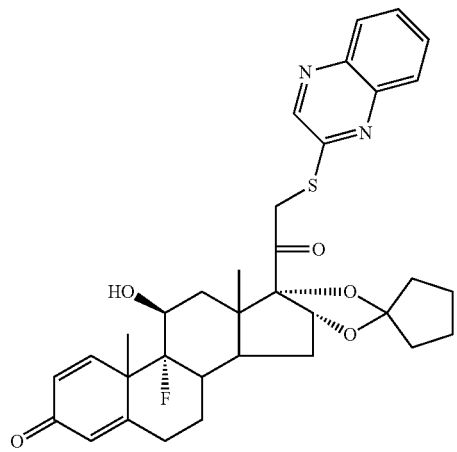 | 605 |
| 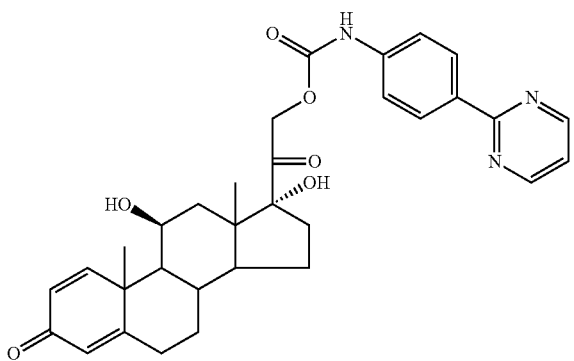 [SMILES: CC12C=CC(=O)C=C1CCC1C2[C@@H](O)CC2(C)C1CC[C@]2(O)C(=O)COC(=O)Nc1ccc(-c2ncccn2)cc1] | 558 |

TABLE 1-continued

| Structure | M + H |
|---|---|
| 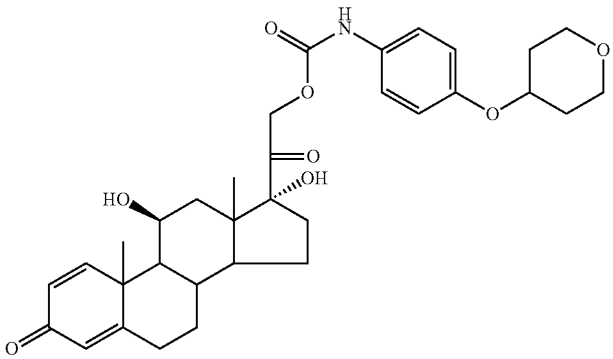 [SMILES: CC12C=CC(=O)C=C1CCC1C2[C@@H](O)CC2(C)C1CC[C@]2(O)C(=O)COC(=O)Nc1ccc(OC2CCOCC2)cc1] | 580 |
| 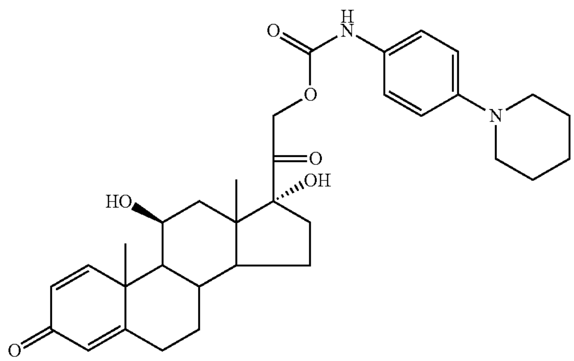 [SMILES: CC12C=CC(=O)C=C1CCC1C2[C@@H](O)CC2(C)C1CC[C@]2(O)C(=O)COC(=O)Nc1ccc(N2CCCCC2)cc1] | 563 |
| 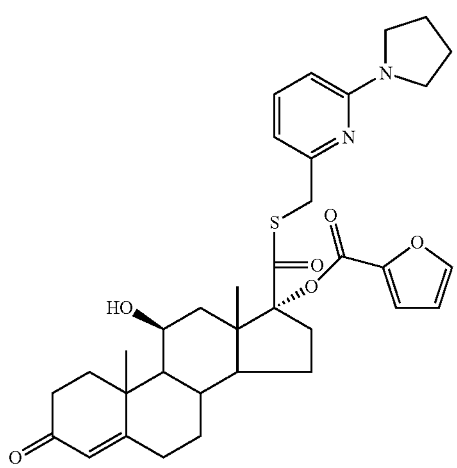 [SMILES: CC12CCC(=O)C=C1CCC1C2[C@@H](O)CC2(C)C1CC[C@]2(OC(=O)c1ccco1)C(=O)SCc1cccc(N2CCCC2)n1] | 619 |
| 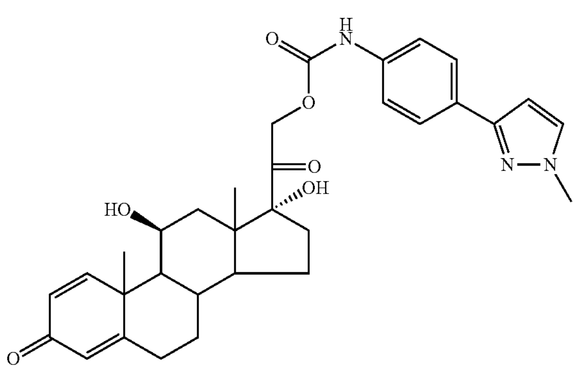 [SMILES: Cn1ccc(-c2ccc(NC(=O)OCC(=O)[C@@]3(O)CCC4C5CCC6=CC(=O)C=CC6(C)C5[C@@H](O)CC43C)cc2)n1] | 560 |

TABLE 1-continued
| Structure | M + H |
|---|---|
| 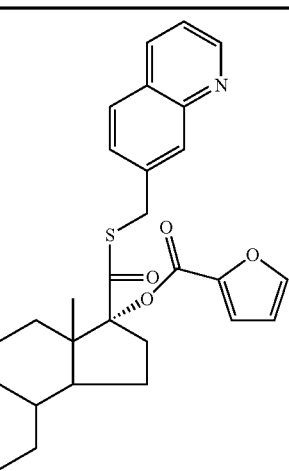 | 600 |
| 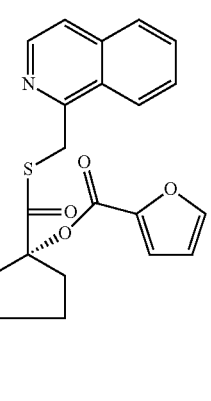 | 600 |
| 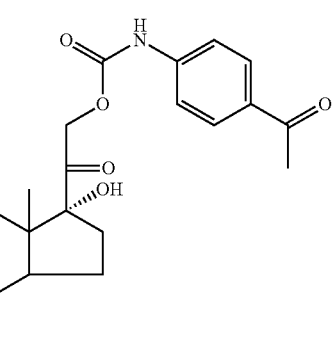 | 522 |
| 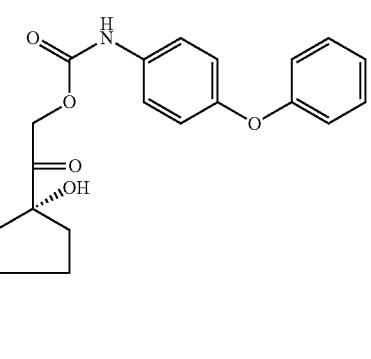 | 572 |

TABLE 1-continued
| Structure | M + H |
|---|---|
| 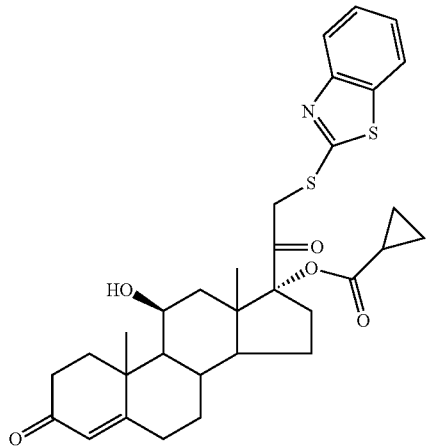 [SMILES: CC12CCC(=O)C=C1CCC1C2[C@@H](O)CC2(C)C1CC[C@]2(OC(=O)C1CC1)C(=O)CSc1nc2ccccc2s1] | 580 |
| 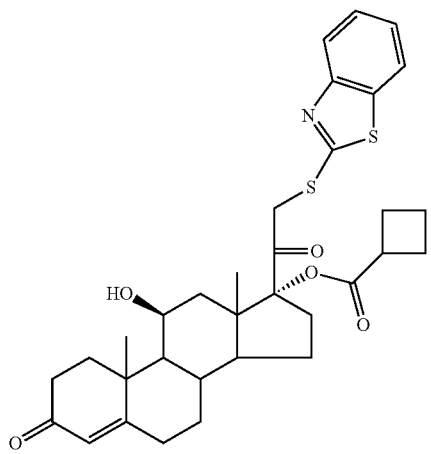 [SMILES: CC12CCC(=O)C=C1CCC1C2[C@@H](O)CC2(C)C1CC[C@]2(OC(=O)C1CCC1)C(=O)CSc1nc2ccccc2s1] | 594 |
| 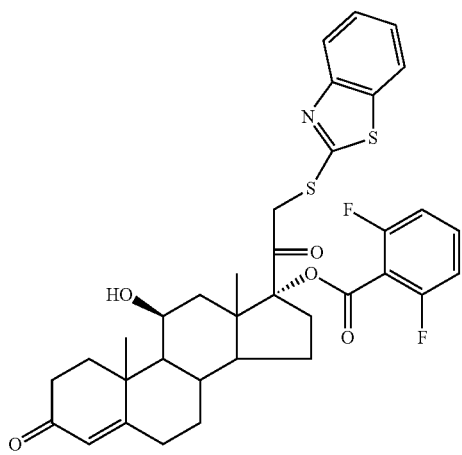 [SMILES: CC12CCC(=O)C=C1CCC1C2[C@@H](O)CC2(C)C1CC[C@]2(OC(=O)c1c(F)cccc1F)C(=O)CSc1nc2ccccc2s1] | 652 |

TABLE 1-continued
| Structure | M + H |
|---|---|
| 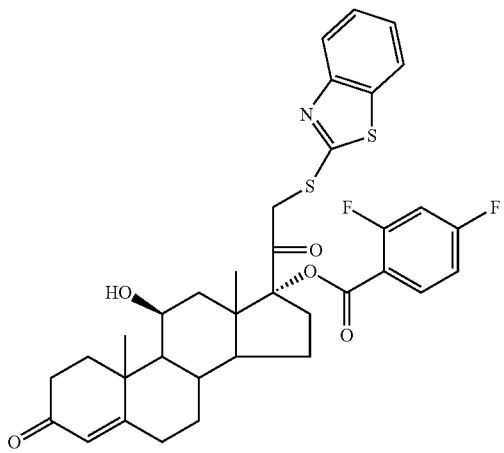 [SMILES: CC12CCC(=O)C=C1CCC1C2[C@@H](O)CC2(C)C1CC[C@]2(OC(=O)c1ccc(F)cc1F)C(=O)CSc1nc2ccccc2s1] | 652 |
| 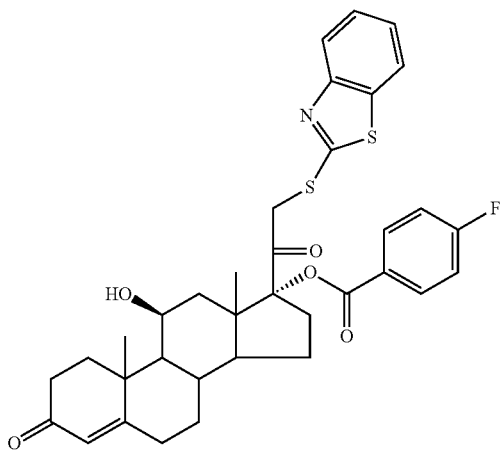 [SMILES: CC12CCC(=O)C=C1CCC1C2[C@@H](O)CC2(C)C1CC[C@]2(OC(=O)c1ccc(F)cc1)C(=O)CSc1nc2ccccc2s1] | 634 |
| 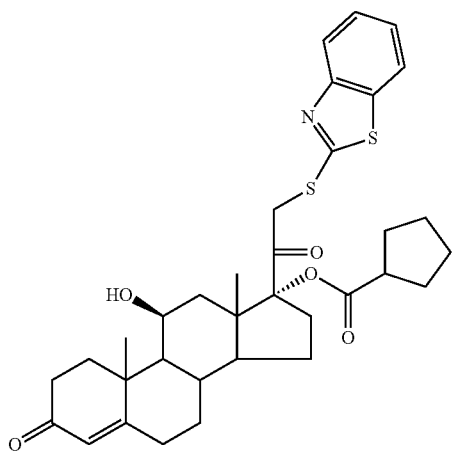 [SMILES: CC12CCC(=O)C=C1CCC1C2[C@@H](O)CC2(C)C1CC[C@]2(OC(=O)C1CCCC1)C(=O)CSc1nc2ccccc2s1] | 608 |

TABLE 1-continued
| Structure | M + H |
|---|---|
| 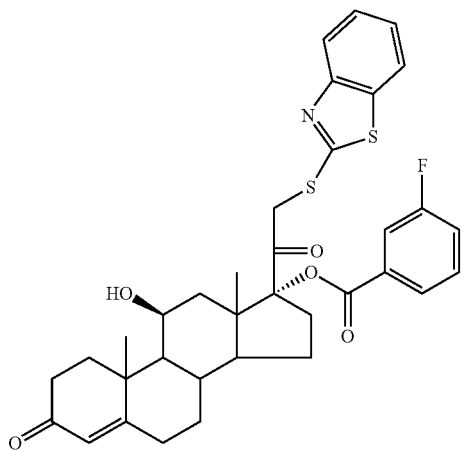 [SMILES: CC12CCC(=O)C=C1CCC1C2[C@@H](O)CC2(C)C1CC[C@]2(OC(=O)c1cccc(F)c1)C(=O)CSc1nc2ccccc2s1] | 634 |
| 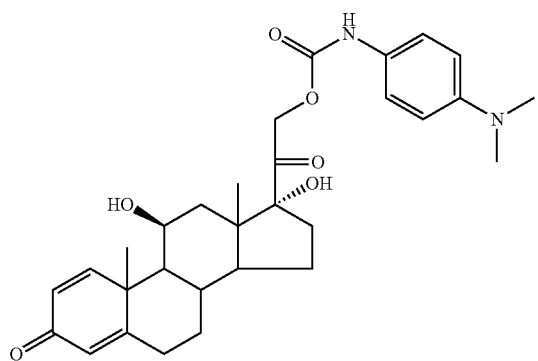 [SMILES: CN(C)c1ccc(NC(=O)OCC(=O)[C@@]2(O)CCC3C4CCC5=CC(=O)C=CC5(C)C4[C@@H](O)CC32C)cc1] | 523 |
| 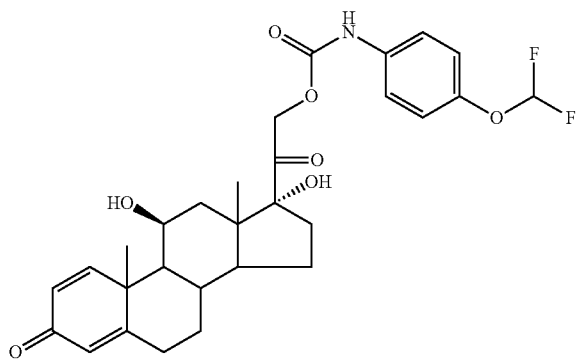 [SMILES: CC12C=CC(=O)C=C1CCC1C2[C@@H](O)CC2(C)C1CC[C@]2(O)C(=O)COC(=O)Nc1ccc(OC(F)F)cc1] | 546 |

TABLE 1-continued
| Structure | M + H |
|---|---|
| 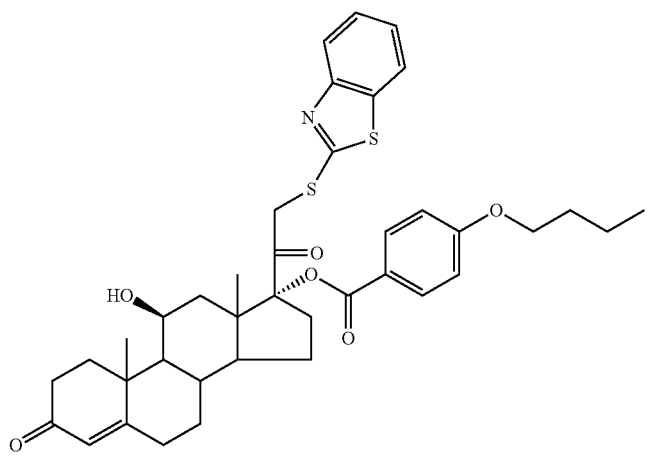 [SMILES: CCCCOc1ccc(C(=O)O[C@]2(C(=O)CSc3nc4ccccc4s3)CCC3C4CCC5=CC(=O)CCC5(C)C4[C@@H](O)CC32C)cc1] | 688 |
| 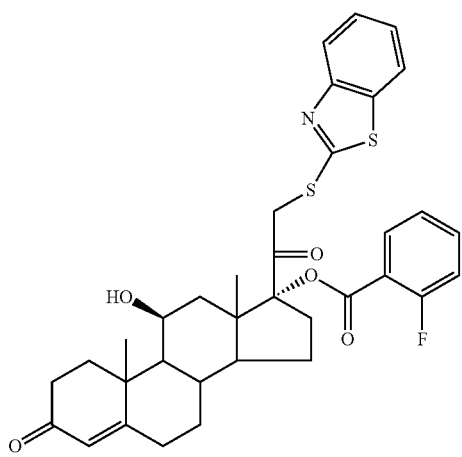 [SMILES: CC12CCC(=O)C=C1CCC1C2[C@@H](O)CC2(C)C1CC[C@]2(OC(=O)c1ccccc1F)C(=O)CSc1nc2ccccc2s1] | 634 |
| 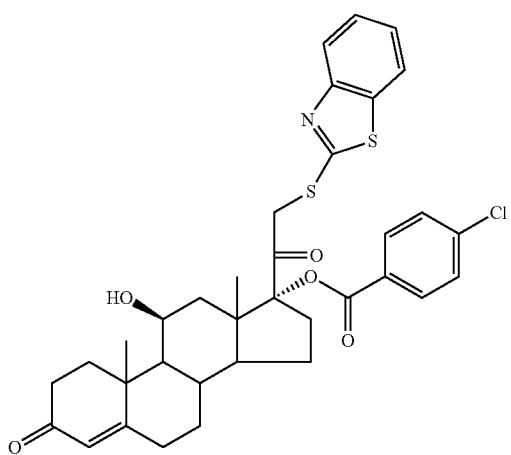 [SMILES: CC12CCC(=O)C=C1CCC1C2[C@@H](O)CC2(C)C1CC[C@]2(OC(=O)c1ccc(Cl)cc1)C(=O)CSc1nc2ccccc2s1] | 650 |

TABLE 1-continued
| Structure | M + H |
|---|---|
| 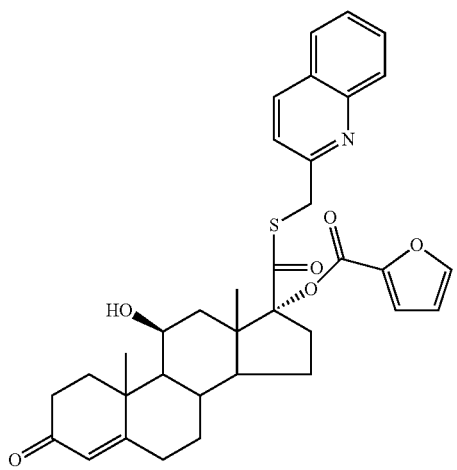 [SMILES: CC12CCC(=O)C=C1CCC1C2[C@@H](O)CC2(C)C1CC[C@]2(OC(=O)c1ccco1)C(=O)SCc1ccc2ccccc2n1] | 600 |
| 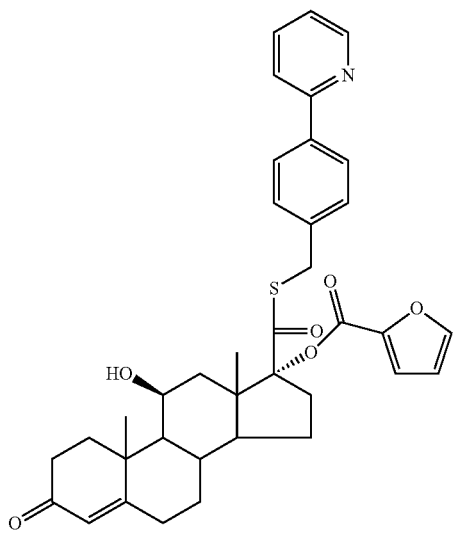 [SMILES: CC12CCC(=O)C=C1CCC1C2[C@@H](O)CC2(C)C1CC[C@]2(OC(=O)c1ccco1)C(=O)SCc1ccc(-c2ccccn2)cc1] | 626 |
| 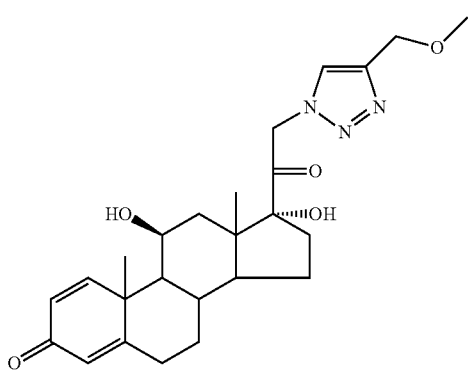 [SMILES: COCc1cn(CC(=O)[C@@]2(O)CCC3C4CCC5=CC(=O)C=CC5(C)C4[C@@H](O)CC32C)nn1] | 456 |

TABLE 1-continued
| Structure | M + H |
|---|---|
| 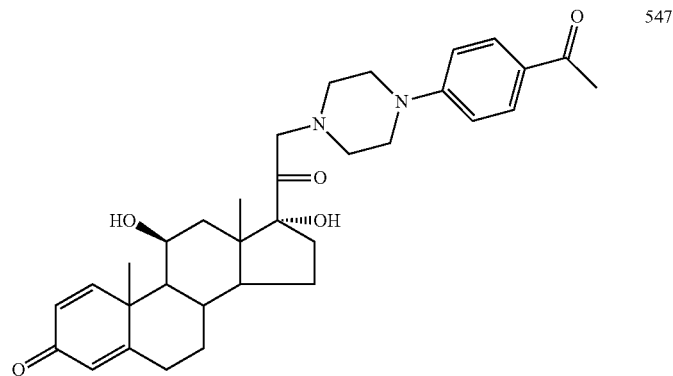 | 547 |
| 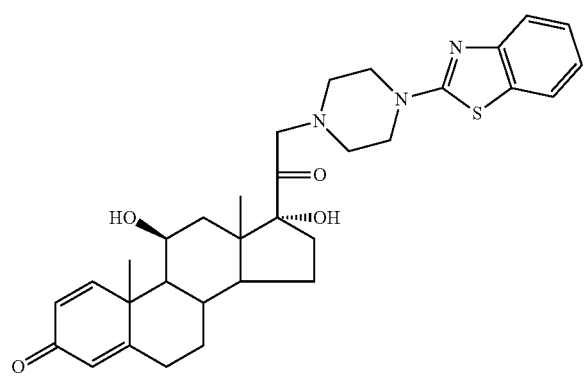 [SMILES: CC12C=CC(=O)C=C1CCC1C2[C@@H](O)CC2(C)C1CC[C@]2(O)C(=O)CN1CCN(c2nc3ccccc3s2)CC1] | 562 |
| 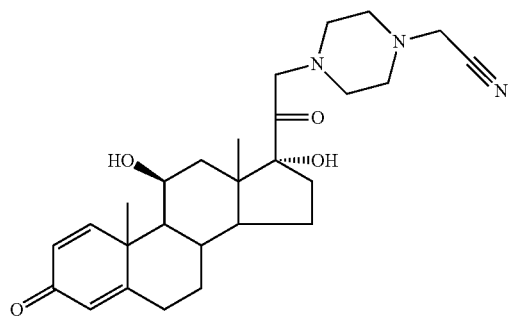 [SMILES: CC12C=CC(=O)C=C1CCC1C2[C@@H](O)CC2(C)C1CC[C@]2(O)C(=O)CN1CCN(CC#N)CC1] | 467 |
| 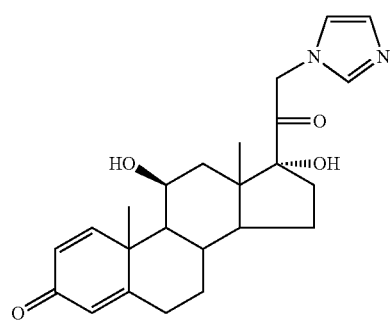 [SMILES: CC12C=CC(=O)C=C1CCC1C2[C@@H](O)CC2(C)C1CC[C@]2(O)C(=O)Cn1ccnc1] | 411 |

TABLE 1-continued
| Structure | M + H |
|---|---|
| 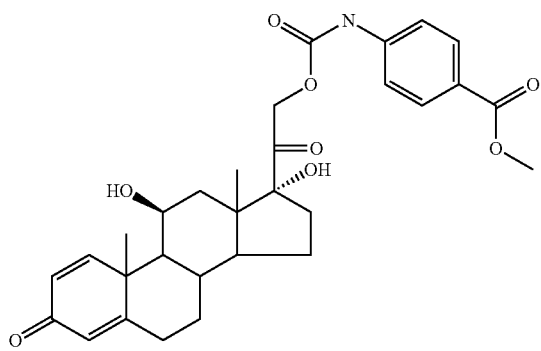 [SMILES: COC(=O)c1ccc(NC(=O)OCC(=O)[C@@]2(O)CCC3C4CCC5=CC(=O)C=CC5(C)C4[C@@H](O)CC32C)cc1] | 538 |
| 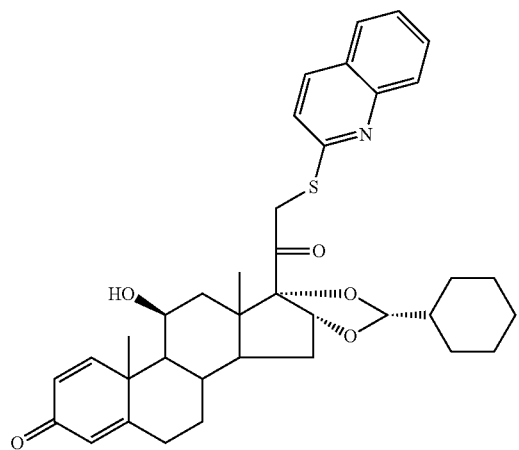 [SMILES: CC12C=CC(=O)C=C1CCC1C2[C@@H](O)CC2(C)C1C[C@H]1O[C@@H](C3CCCCC3)O[C@]12C(=O)CSc1ccc2ccccc2n1] | 614 |
| 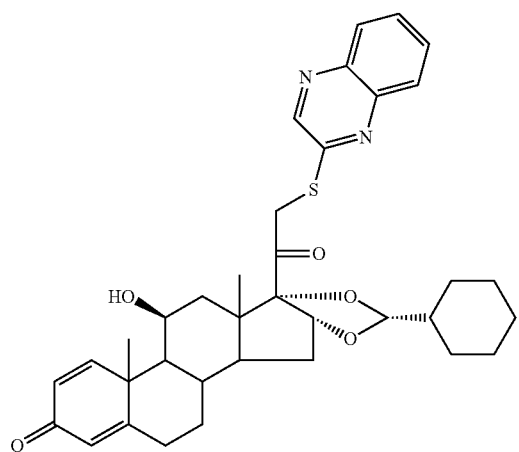 [SMILES: CC12C=CC(=O)C=C1CCC1C2[C@@H](O)CC2(C)C1C[C@H]1O[C@@H](C3CCCCC3)O[C@]12C(=O)CSc1cnc2ccccc2n1] | 615 |

TABLE 1-continued
| Structure | M + H |
|---|---|
| 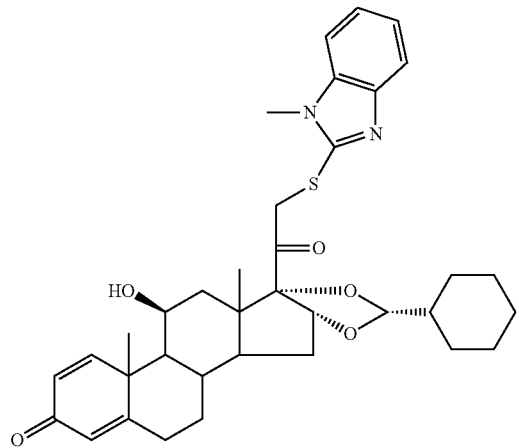 [SMILES: Cn1c(SCC(=O)[C@@]23O[C@H](C4CCCCC4)O[C@@H]2CC2C4CCC5=CC(=O)C=CC5(C)C4[C@@H](O)CC23C)nc2ccccc21] | 617 |
| 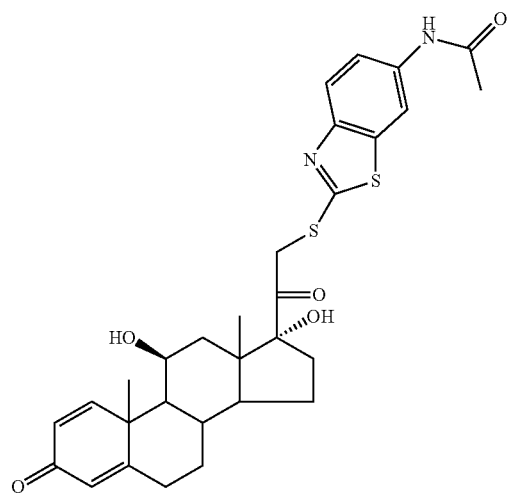 [SMILES: CC(=O)Nc1ccc2nc(SCC(=O)[C@@]3(O)CCC4C5CCC6=CC(=O)C=CC6(C)C5[C@@H](O)CC43C)sc2c1] | 567 |
| 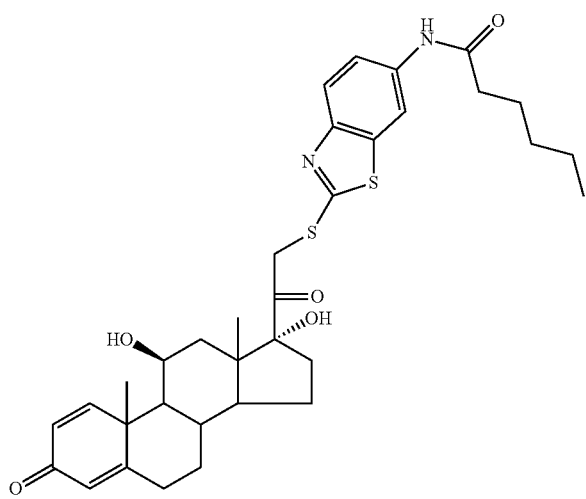 [SMILES: CCCCCC(=O)Nc1ccc2nc(SCC(=O)[C@@]3(O)CCC4C5CCC6=CC(=O)C=CC6(C)C5[C@@H](O)CC43C)sc2c1] | 623 |

TABLE 1-continued
| Structure | M + H |
|---|---|
| 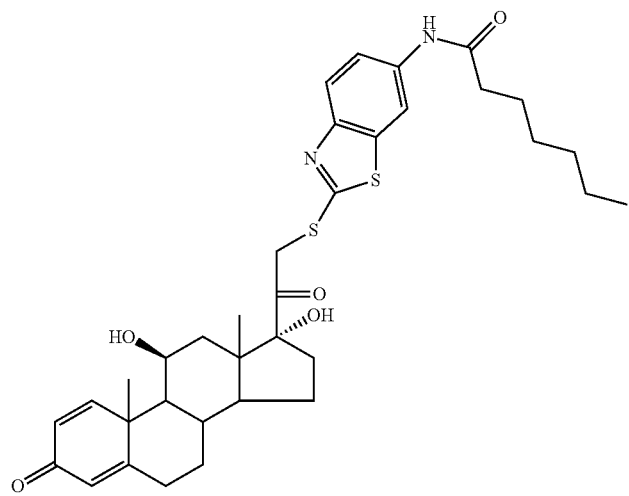 [SMILES: CCCCCCC(=O)Nc1ccc2nc(SCC(=O)[C@@]3(O)CCC4C5CCC6=CC(=O)C=CC6(C)C5[C@@H](O)CC43C)sc2c1] | 637 |
| 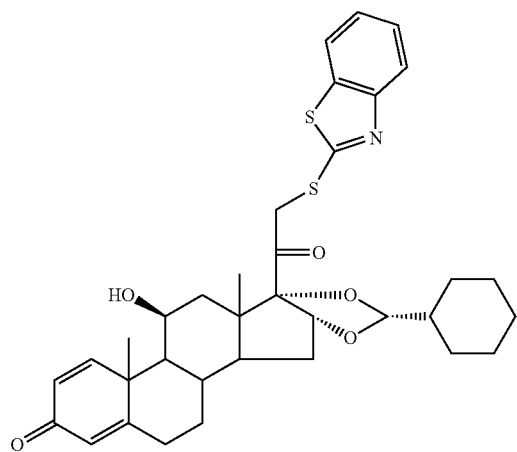 [SMILES: CC12C=CC(=O)C=C1CCC1C2[C@@H](O)CC2(C)C1C[C@H]1O[C@@H](C3CCCCC3)O[C@]12C(=O)CSc1nc2ccccc2s1] | 620 |
| 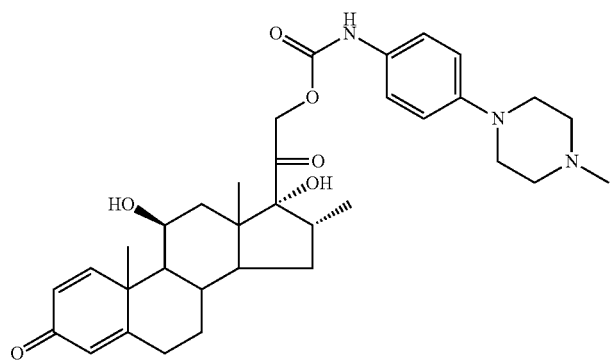 [SMILES: C[C@@H]1CC2C3CCC4=CC(=O)C=CC4(C)C3[C@@H](O)CC2(C)[C@@]1(O)C(=O)COC(=O)Nc1ccc(N2CCN(C)CC2)cc1] | 592 |

TABLE 1-continued
| Structure | M + H |
|---|---|
| 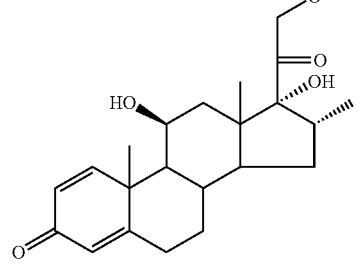 | 495 |
| 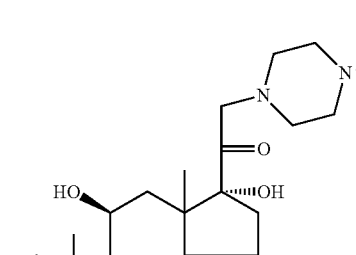 | 546 |
| 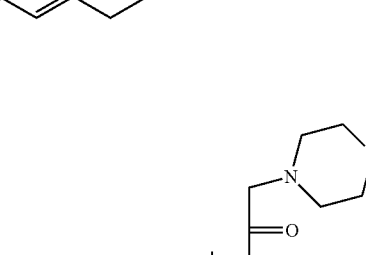 | 506 |
| 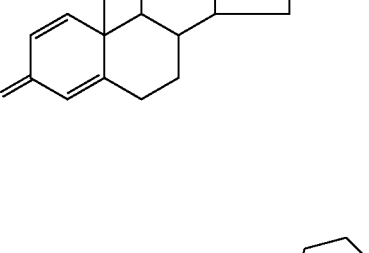 | 507 |

TABLE 1-continued

| Structure | M + H |
|---|---|
| 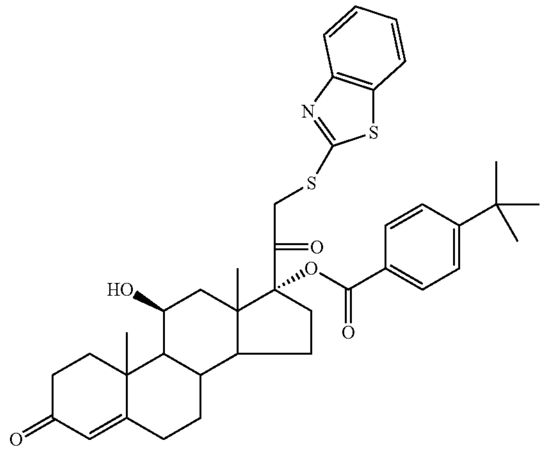 [SMILES: CC(C)(C)c1ccc(C(=O)O[C@]2(C(=O)CSc3nc4ccccc4s3)CCC3C4CCC5=CC(=O)CCC5(C)C4[C@@H](O)CC32C)cc1] | 672 |
| 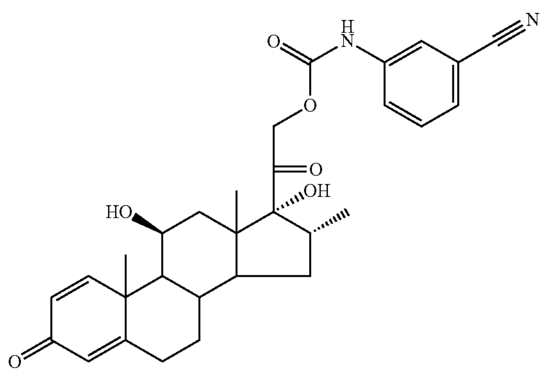 [SMILES: C[C@@H]1CC2C3CCC4=CC(=O)C=CC4(C)C3[C@@H](O)CC2(C)[C@@]1(O)C(=O)COC(=O)Nc1cccc(C#N)c1] | 519 |
| 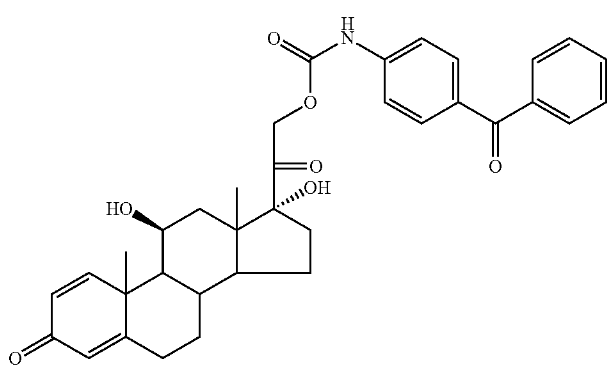 [SMILES: CC12C=CC(=O)C=C1CCC1C2[C@@H](O)CC2(C)C1CC[C@]2(O)C(=O)COC(=O)Nc1ccc(C(=O)c2ccccc2)cc1] | 584 |
| 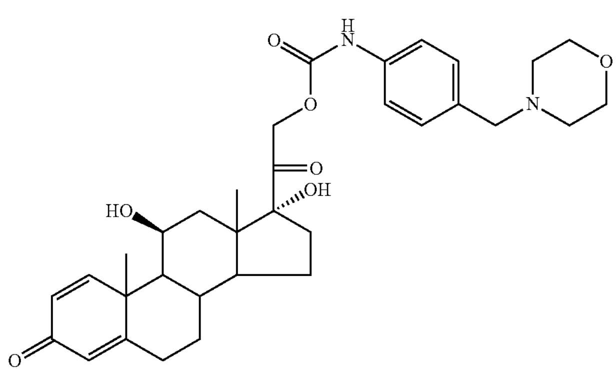 [SMILES: CC12C=CC(=O)C=C1CCC1C2[C@@H](O)CC2(C)C1CC[C@]2(O)C(=O)COC(=O)Nc1ccc(CN2CCOCC2)cc1] | 579 |

TABLE 1-continued

| Structure | M + H |
|---|---|
| (structure) | 573 |
| (structure) | 590 |
| (structure) | 443 |
| (structure) | 634 |

TABLE 1-continued
| Structure | M + H |
|---|---|
| 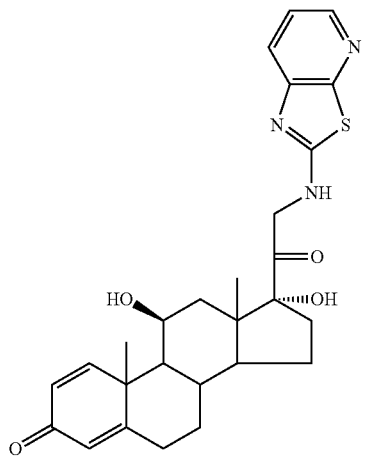 [SMILES: CC12C=CC(=O)C=C1CCC1C2[C@@H](O)CC2(C)C1CC[C@]2(O)C(=O)CNc1nc2cccnc2s1] | 494 |
| 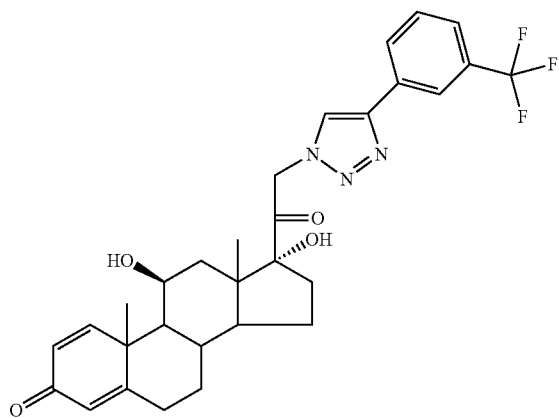 [SMILES: CC12C=CC(=O)C=C1CCC1C2[C@@H](O)CC2(C)C1CC[C@]2(O)C(=O)Cn1cc(-c2cccc(C(F)(F)F)c2)nn1] | 556 |
| 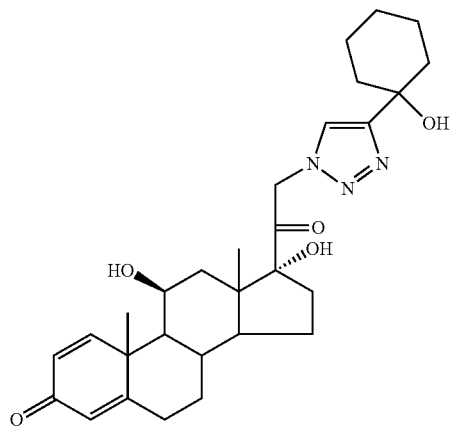 [SMILES: CC12C=CC(=O)C=C1CCC1C2[C@@H](O)CC2(C)C1CC[C@]2(O)C(=O)Cn1cc(C2(O)CCCCC2)nn1] | 510 |

TABLE 1-continued
| Structure | M + H |
|---|---|
| 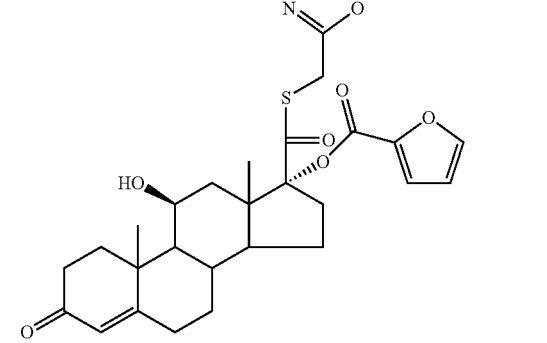 | 591 |
| 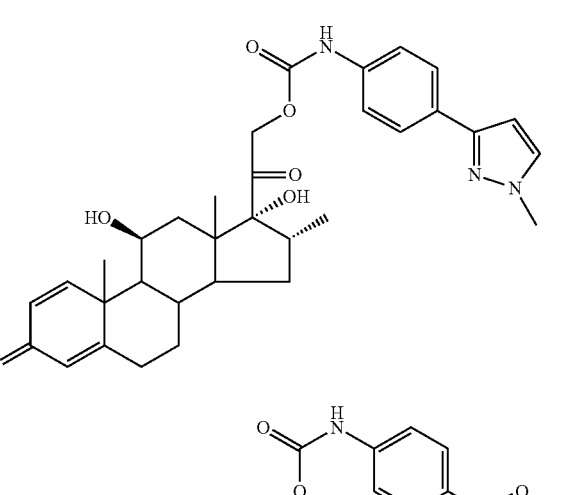 | 574 |
| 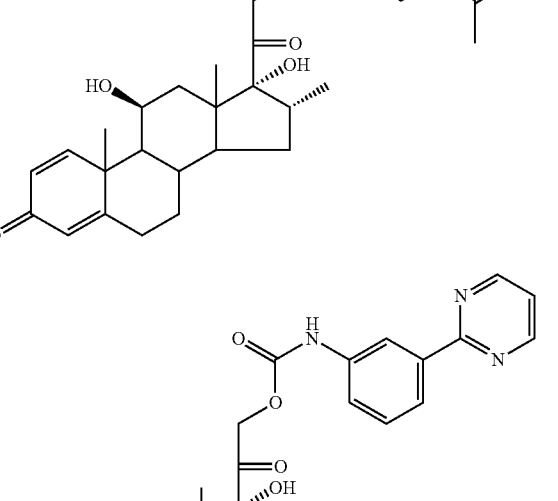 | 536 |
| 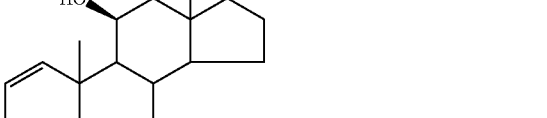 | 558 |

TABLE 1-continued
| Structure | M + H |
|---|---|
| 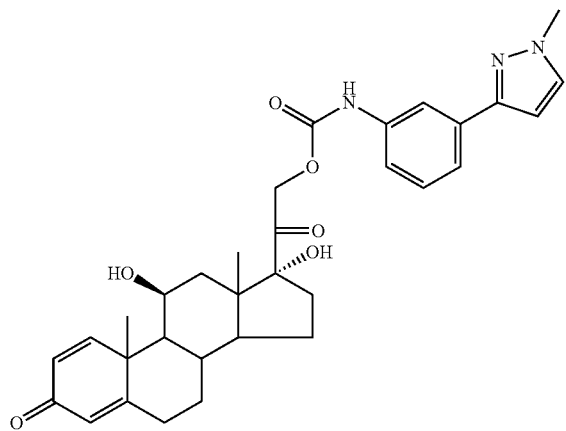 [SMILES: Cn1ccc(-c2cccc(NC(=O)OCC(=O)[C@@]3(O)CCC4C5CCC6=CC(=O)C=CC6(C)C5[C@@H](O)CC43C)c2)n1] | 560 |
| 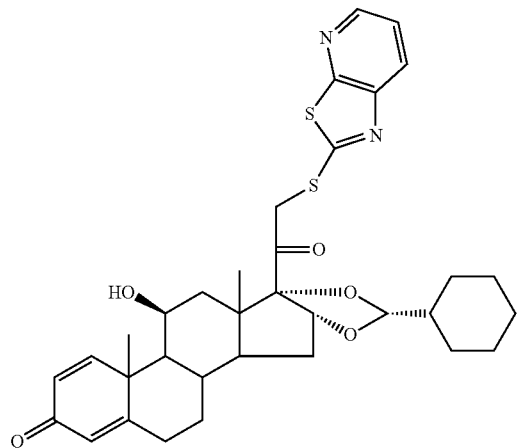 [SMILES: CC12C=CC(=O)C=C1CCC1C2[C@@H](O)CC2(C)C1C[C@H]1O[C@@H](C3CCCCC3)O[C@]12C(=O)CSc1nc2cccnc2s1] | 621 |
| 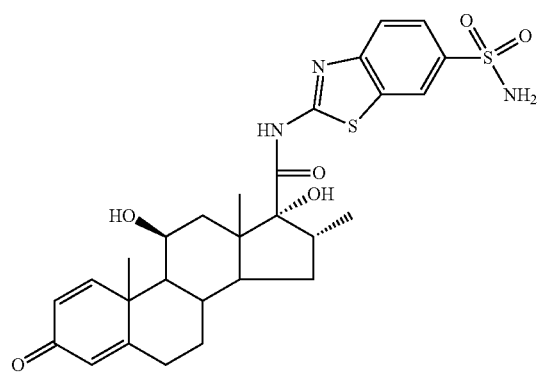 [SMILES: C[C@@H]1CC2C3CCC4=CC(=O)C=CC4(C)C3[C@@H](O)CC2(C)[C@@]1(O)C(=O)Nc1nc2ccc(S(N)(=O)=O)cc2s1] | 572 |

TABLE 1-continued
| Structure | M + H |
|---|---|
| 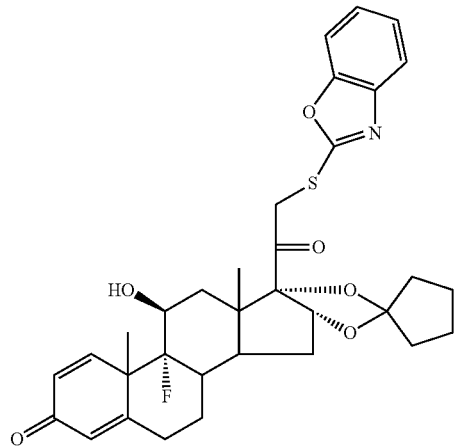 | 594 |
| 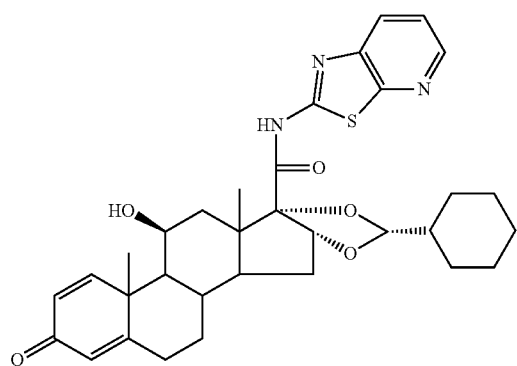 [SMILES: CC12C=CC(=O)C=C1CCC1C2[C@@H](O)CC2(C)C1C[C@H]1O[C@@H](C3CCCCC3)O[C@]12C(=O)Nc1nc2cccnc2s1] | 590 |
| 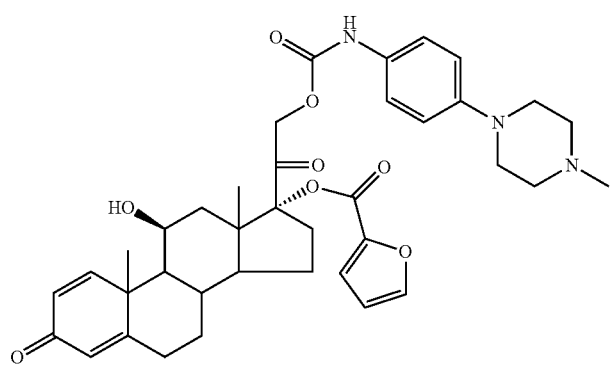 [SMILES: CN1CCN(c2ccc(NC(=O)OCC(=O)[C@@]3(OC(=O)c4ccco4)CCC4C5CCC6=CC(=O)C=CC6(C)C5[C@@H](O)CC43C)cc2)CC1] | 672 |

TABLE 1-continued
| Structure | M + H |
|---|---|
| 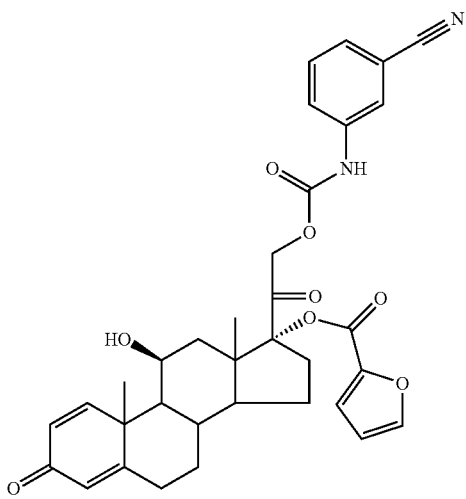 [SMILES: CC12C=CC(=O)C=C1CCC1C2[C@@H](O)CC2(C)C1CC[C@]2(OC(=O)c1ccco1)C(=O)COC(=O)Nc1cccc(C#N)c1] | 599 |
| 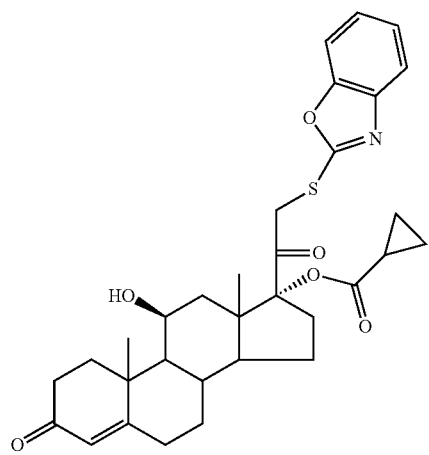 [SMILES: CC12CCC(=O)C=C1CCC1C2[C@@H](O)CC2(C)C1CC[C@]2(OC(=O)C1CC1)C(=O)CSc1nc2ccccc2o1] | 564 |
| 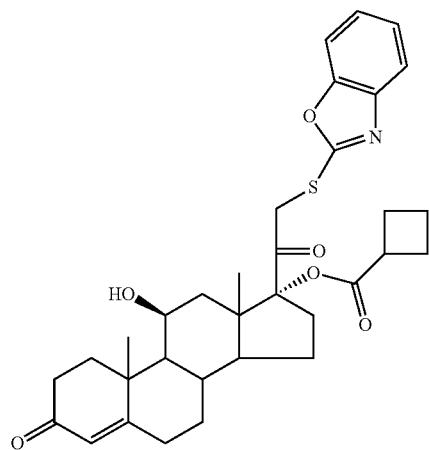 [SMILES: CC12CCC(=O)C=C1CCC1C2[C@@H](O)CC2(C)C1CC[C@]2(OC(=O)C1CCC1)C(=O)CSc1nc2ccccc2o1] | 578 |

TABLE 1-continued
| Structure | M + H |
|---|---|
| 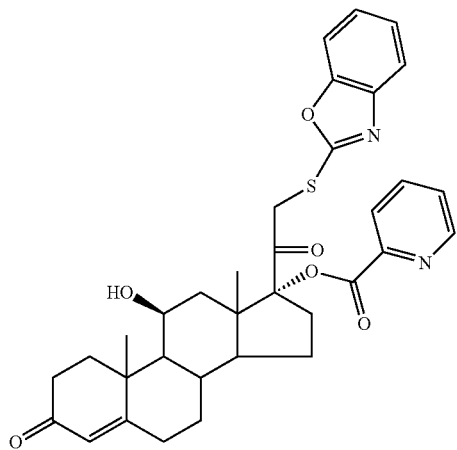 [SMILES: CC12CCC(=O)C=C1CCC1C2[C@@H](O)CC2(C)C1CC[C@]2(OC(=O)c1ccccn1)C(=O)CSc1nc2ccccc2o1] | 601 |
| 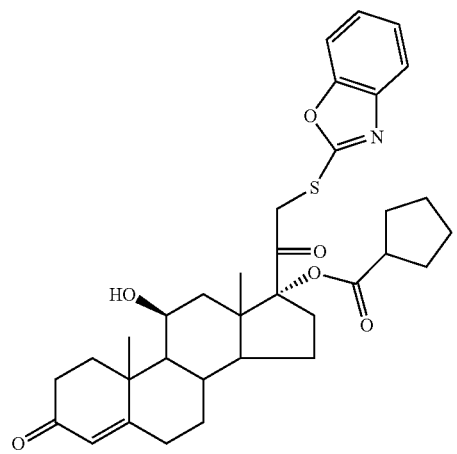 [SMILES: CC12CCC(=O)C=C1CCC1C2[C@@H](O)CC2(C)C1CC[C@]2(OC(=O)C1CCCC1)C(=O)CSc1nc2ccccc2o1] | 592 |
| 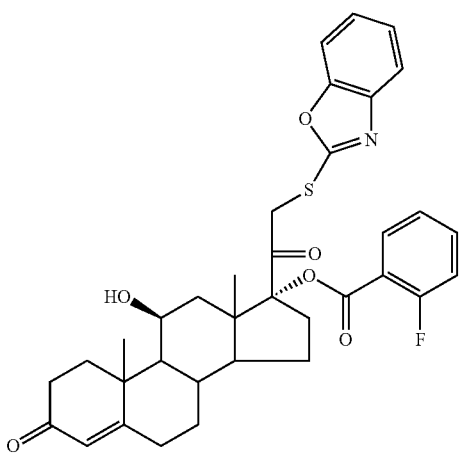 [SMILES: CC12CCC(=O)C=C1CCC1C2[C@@H](O)CC2(C)C1CC[C@]2(OC(=O)c1ccccc1F)C(=O)CSc1nc2ccccc2o1] | 618 |

TABLE 1-continued
| Structure | M + H |
|---|---|
| 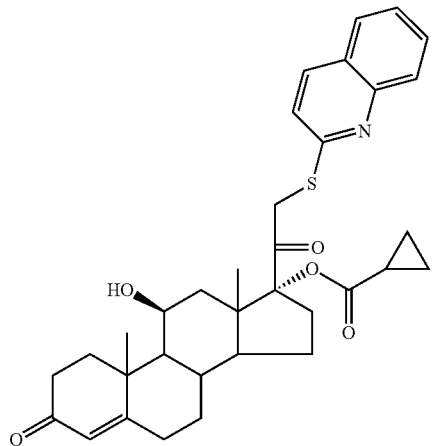 [SMILES: CC12CCC(=O)C=C1CCC1C2[C@@H](O)CC2(C)C1CC[C@]2(OC(=O)C1CC1)C(=O)CSc1ccc2ccccc2n1] | 574 |
| 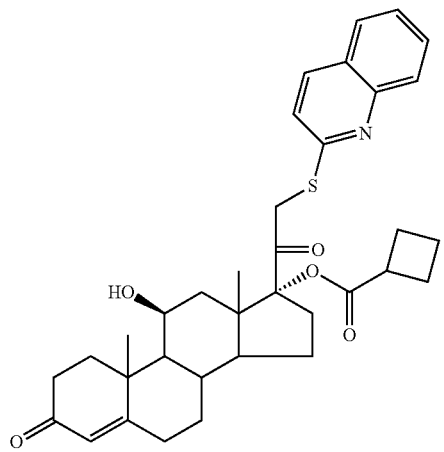 [SMILES: CC12CCC(=O)C=C1CCC1C2[C@@H](O)CC2(C)C1CC[C@]2(OC(=O)C1CCC1)C(=O)CSc1ccc2ccccc2n1] | 588 |
| 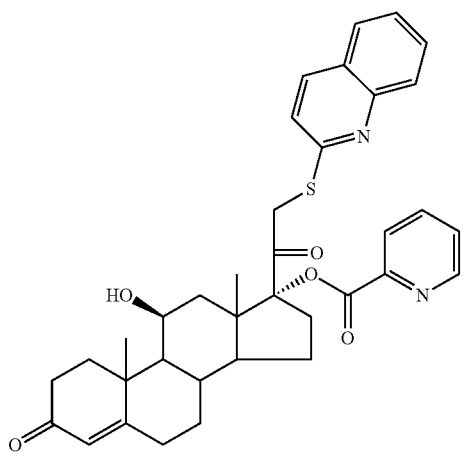 [SMILES: CC12CCC(=O)C=C1CCC1C2[C@@H](O)CC2(C)C1CC[C@]2(OC(=O)c1ccccn1)C(=O)CSc1ccc2ccccc2n1] | 611 |

TABLE 1-continued
| Structure | M + H |
|---|---|
| 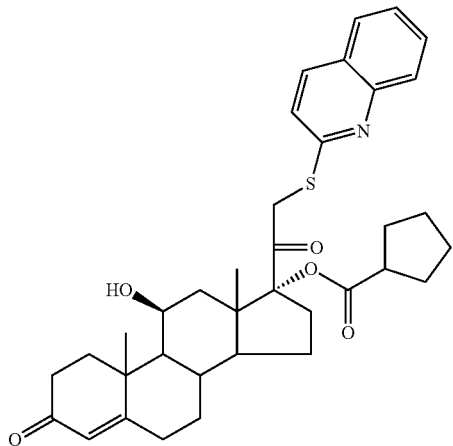 [SMILES: CC12CCC(=O)C=C1CCC1C2[C@@H](O)CC2(C)C1CC[C@]2(OC(=O)C1CCCC1)C(=O)CSc1ccc2ccccc2n1] | 602 |
| 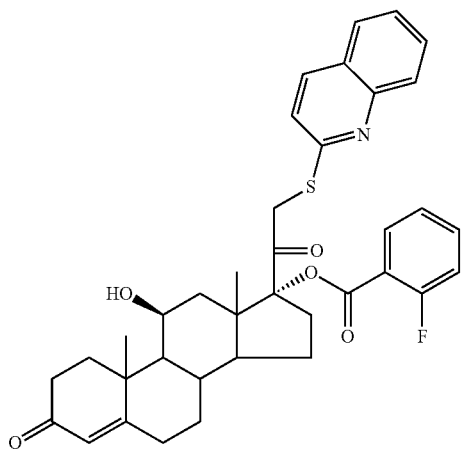 [SMILES: CC12CCC(=O)C=C1CCC1C2[C@@H](O)CC2(C)C1CC[C@]2(OC(=O)c1ccccc1F)C(=O)CSc1ccc2ccccc2n1] | 628 |
| 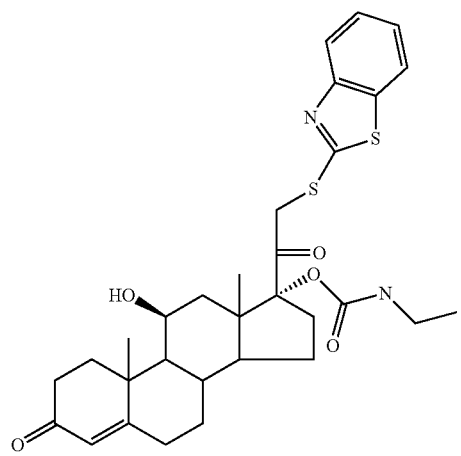 [SMILES: CCNC(=O)O[C@]1(C(=O)CSc2nc3ccccc3s2)CCC2C3CCC4=CC(=O)CCC4(C)C3[C@@H](O)CC21C] | 583 |

TABLE 1-continued
| Structure | M + H |
|---|---|
| 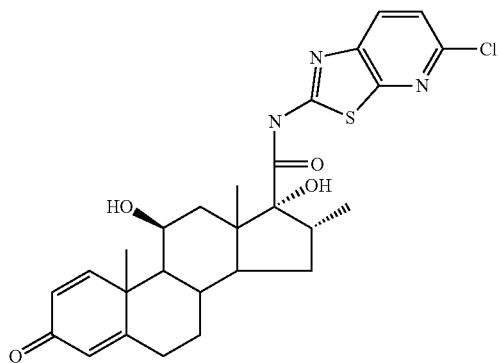 [SMILES: C[C@@H]1CC2C3CCC4=CC(=O)C=CC4(C)C3[C@@H](O)CC2(C)[C@@]1(O)C(=O)Nc1nc2ccc(Cl)nc2s1] | 528 |
| 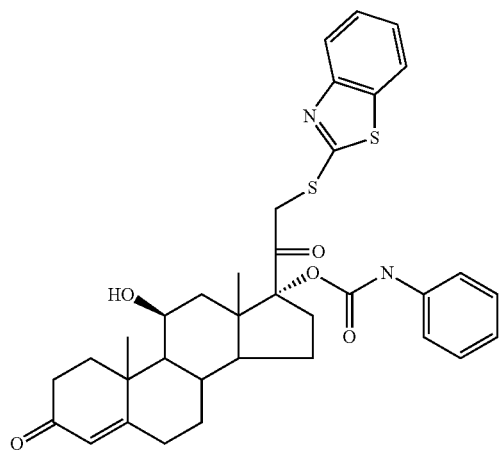 [SMILES: CC12CCC(=O)C=C1CCC1C2[C@@H](O)CC2(C)C1CC[C@]2(OC(=O)Nc1ccccc1)C(=O)CSc1nc2ccccc2s1] | 631 |
| 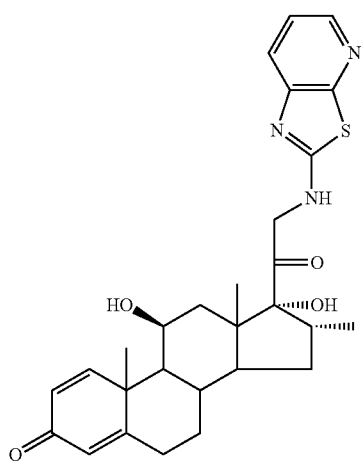 [SMILES: C[C@@H]1CC2C3CCC4=CC(=O)C=CC4(C)C3[C@@H](O)CC2(C)[C@@]1(O)C(=O)CNc1nc2cccnc2s1] | 508 |

TABLE 1-continued
| Structure | M + H |
|---|---|
| 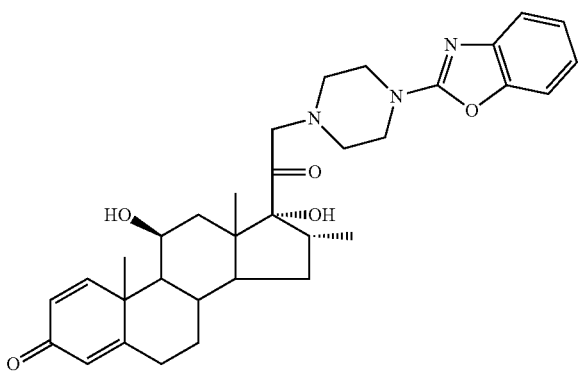 [SMILES: C[C@@H]1CC2C3CCC4=CC(=O)C=CC4(C)C3[C@@H](O)CC2(C)[C@@]1(O)C(=O)CN1CCN(c2nc3ccccc3o2)CC1] | 560 |
| 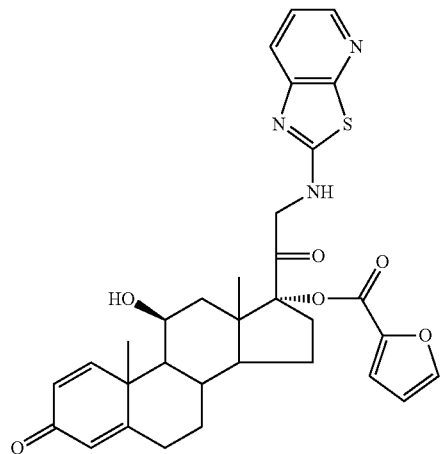 [SMILES: CC12C=CC(=O)C=C1CCC1C2[C@@H](O)CC2(C)C1CC[C@]2(OC(=O)c1ccco1)C(=O)CNc1nc2cccnc2s1] | 588 |
| 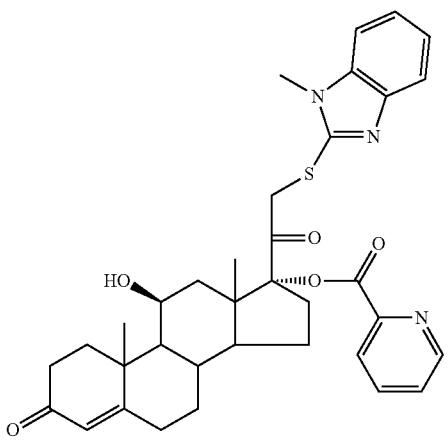 [SMILES: Cn1c(SCC(=O)[C@@]2(OC(=O)c3ccccn3)CCC3C4CCC5=CC(=O)CCC5(C)C4[C@@H](O)CC32C)nc2ccccc21] | 614 |

TABLE 1-continued
| Structure | M + H |
|---|---|
| 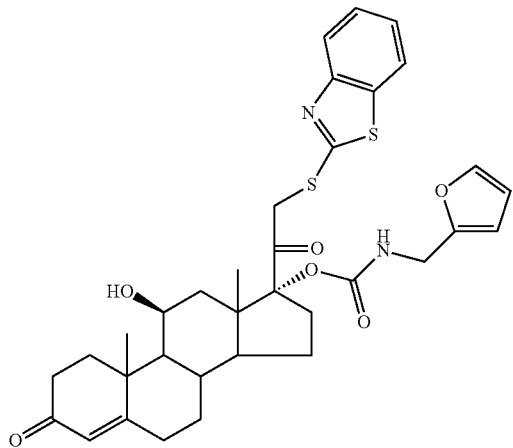 [SMILES: CC12CCC(=O)C=C1CCC1C2[C@@H](O)CC2(C)C1CC[C@]2(OC(=O)NCc1ccco1)C(=O)CSc1nc2ccccc2s1] | 635 |
| 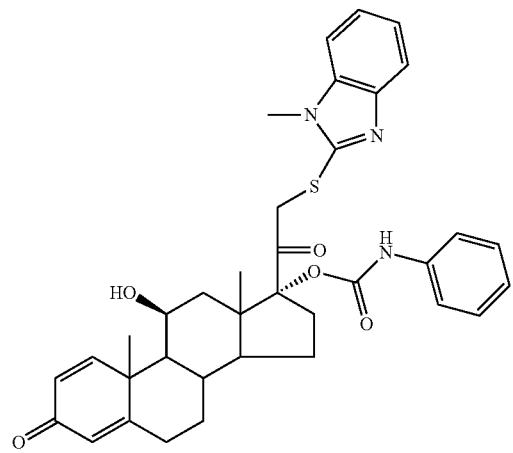 [SMILES: Cn1c(SCC(=O)[C@@]2(OC(=O)Nc3ccccc3)CCC3C4CCC5=CC(=O)C=CC5(C)C4[C@@H](O)CC32C)nc2ccccc21] | 626 |
| 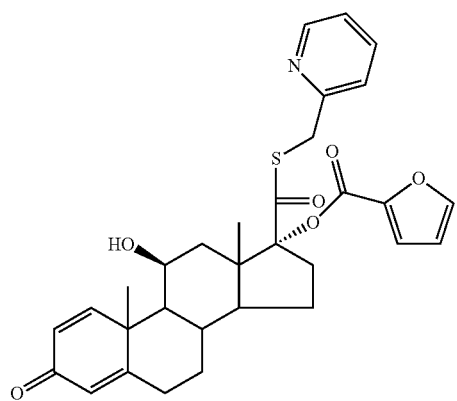 [SMILES: CC12C=CC(=O)C=C1CCC1C2[C@@H](O)CC2(C)C1CC[C@]2(OC(=O)c1ccco1)C(=O)SCc1ccccn1] | 548 |

TABLE 1-continued
| Structure | M + H |
|---|---|
| 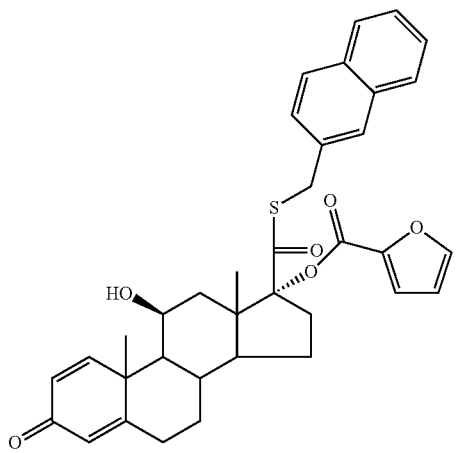 [SMILES: CC12C=CC(=O)C=C1CCC1C2[C@@H](O)CC2(C)C1CC[C@]2(OC(=O)c1ccco1)C(=O)SCc1ccc2ccccc2c1] | 597 |
| 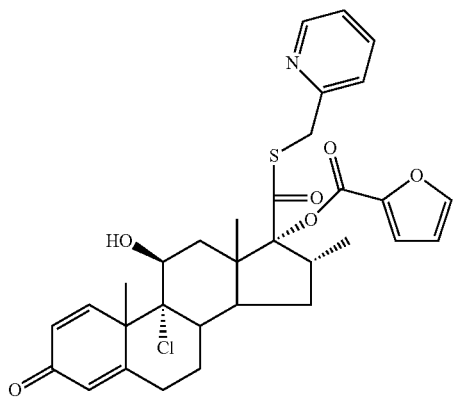 | 596 |
| 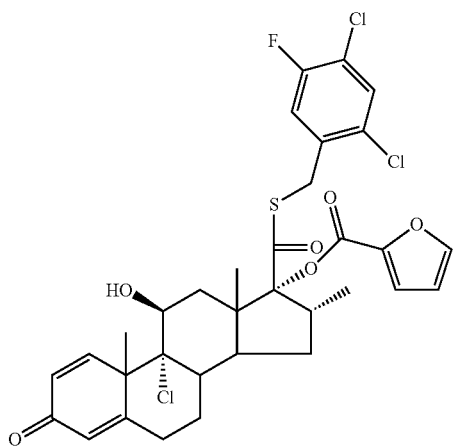 | 681 |

TABLE 1-continued
| Structure | M + H |
|---|---|
| 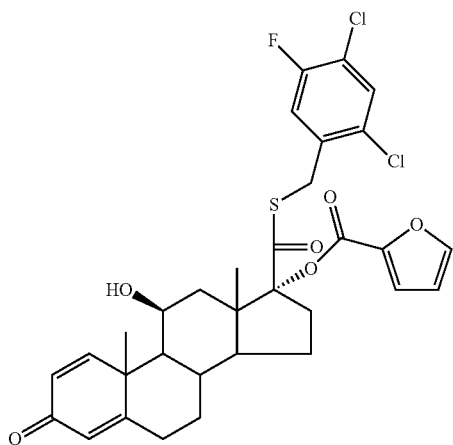 [SMILES: CC12C=CC(=O)C=C1CCC1C2[C@@H](O)CC2(C)C1CC[C@]2(OC(=O)c1ccco1)C(=O)SCc1cc(F)c(Cl)cc1Cl] | 633 |
| 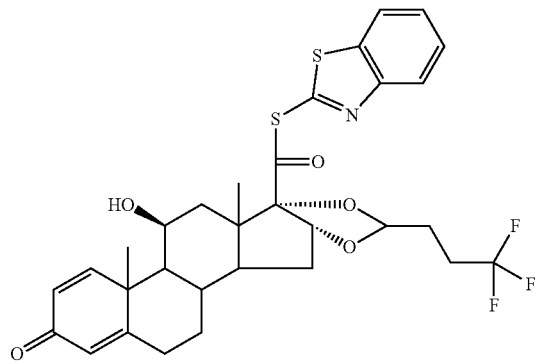 | 620 |
| 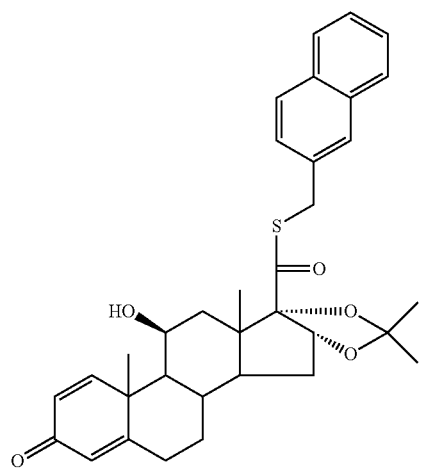 [SMILES: CC1(C)O[C@@H]2CC3C4CCC5=CC(=O)C=CC5(C)C4[C@@H](O)CC3(C)[C@]2(C(=O)SCc2ccc3ccccc3c2)O1] | 559 |

TABLE 1-continued
| Structure | M + H |
|---|---|
| 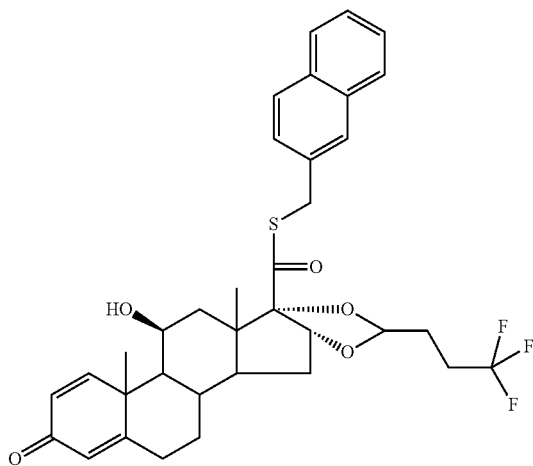 | 627 |
| 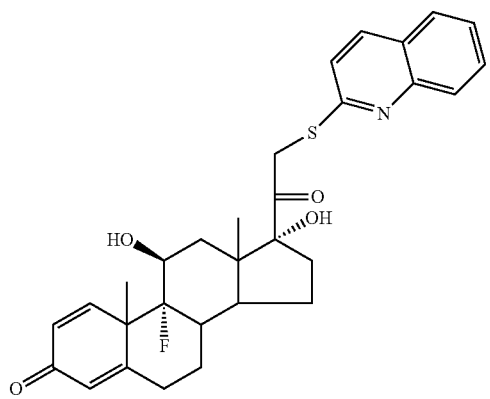 | 622 |
| 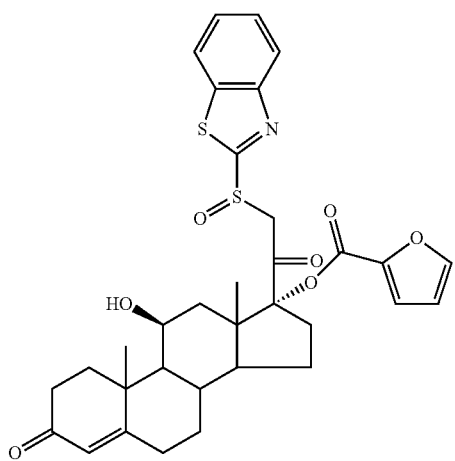 [SMILES: CC12CCC(=O)C=C1CCC1C2[C@@H](O)CC2(C)C1CC[C@]2(OC(=O)c1ccco1)C(=O)CS(=O)c1nc2ccccc2s1] | |

TABLE 1-continued
| Structure | M + H |
|---|---|
| 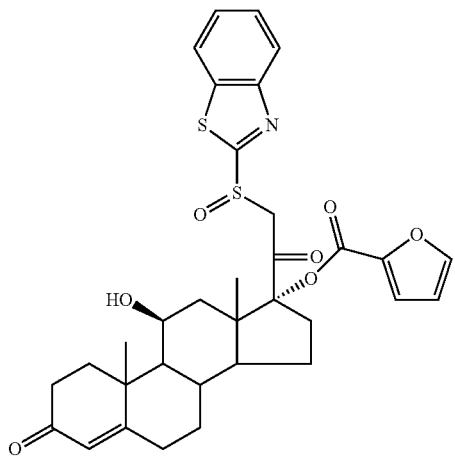 [SMILES: CC12CCC(=O)C=C1CCC1C2[C@@H](O)CC2(C)C1CC[C@]2(OC(=O)c1ccco1)C(=O)CS(=O)c1nc2ccccc2s1] | 622 |
| 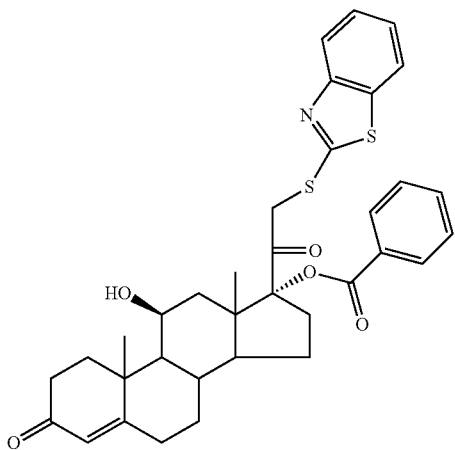 [SMILES: CC12CCC(=O)C=C1CCC1C2[C@@H](O)CC2(C)C1CC[C@]2(OC(=O)c1ccccc1)C(=O)CSc1nc2ccccc2s1] | 616 |
| 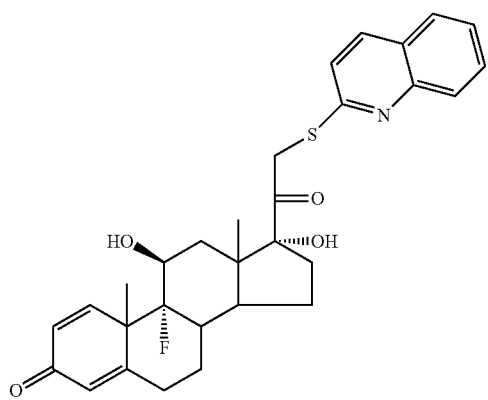 | 522 |

TABLE 1-continued
| Structure | M + H |
|---|---|
| 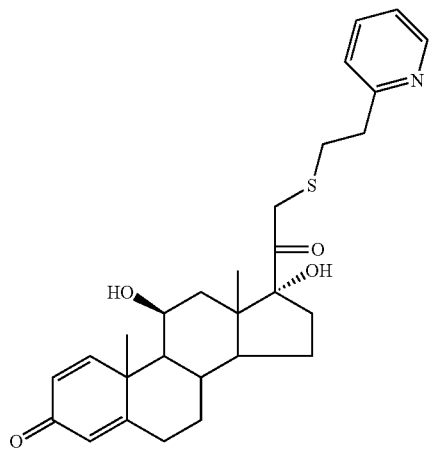 | 482 |
| 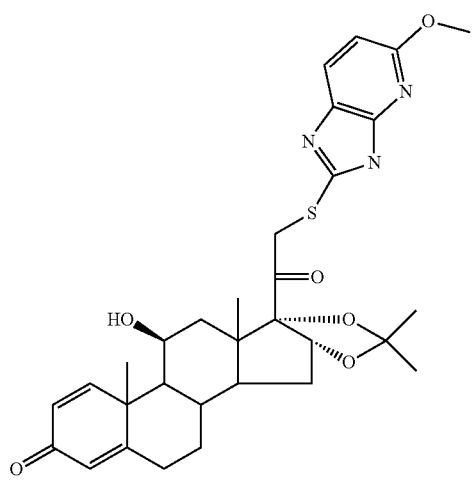 [SMILES: COc1ccc2nc(SCC(=O)[C@@]34OC(C)(C)O[C@@H]3CC3C5CCC6=CC(=O)C=CC6(C)C5[C@@H](O)CC34C)[nH]c2n1] | 580 |

TABLE 1-continued

| Structure | M + H |
|---|---|
| (structure) | 543 |
| (structure) | 604 |
| (structure) | 652 |

As discussed above, C-11-keto analogs of the compounds of the invention are also contemplated, which are expected to generate the corresponding C-11 hydroxy compound in vivo by metabolic conversion. Conversion of 11-keto group into 11-beta-hydroxy group in vivo can be mediated by 11-beta-hydroxysteroid dehydrogenase type 1 enzyme, the action of which on cortisone in humans has been extensively discussed in the literature. See, for example, WO 199707789 and references therein. Non-limiting examples of C-11-keto prodrugs of the invention, made by procedures known in the art and/or analogous to those described herein, are shown in Table 2.
TABLE 2
| C-11 keto ananlog (structure) | M + H |
|---|---|
| 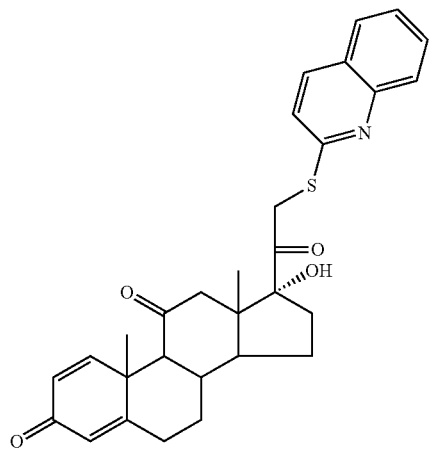 [SMILES: CC12C=CC(=O)C=C1CCC1C2C(=O)CC2(C)C1CC[C@]2(O)C(=O)CSc1ccc2ccccc2n1] | 502 |
| 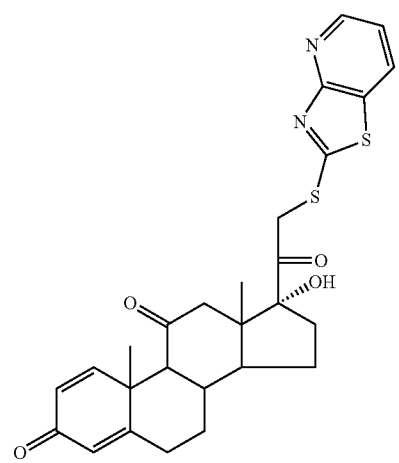 [SMILES: CC12C=CC(=O)C=C1CCC1C2C(=O)CC2(C)C1CC[C@]2(O)C(=O)CSc1nc2ncccc2s1] | 509 |
| 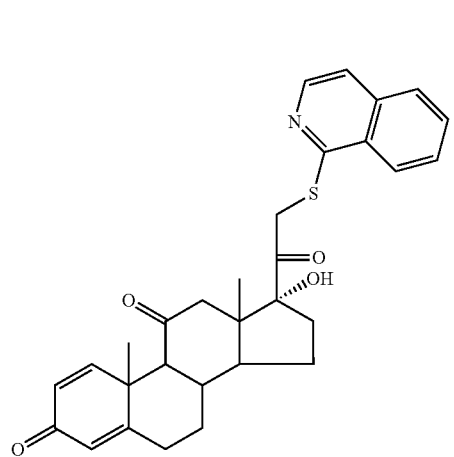 [SMILES: CC12C=CC(=O)C=C1CCC1C2C(=O)CC2(C)C1CC[C@]2(O)C(=O)CSc1nccc2ccccc12] | 502 |
TABLE 2-continued
| C-11 keto ananlog (structure) | M + H |
|---|---|
| 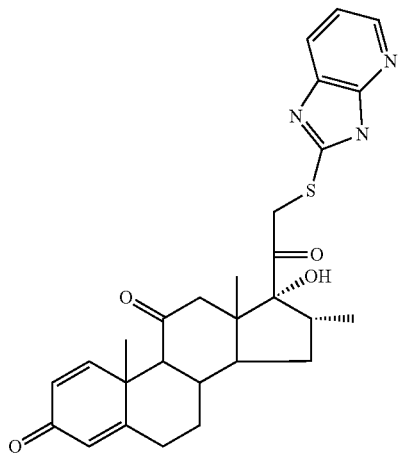 [SMILES: C[C@@H]1CC2C3CCC4=CC(=O)C=CC4(C)C3C(=O)CC2(C)[C@@]1(O)C(=O)CSc1nc2cccnc2[nH]1] | 506 |
| 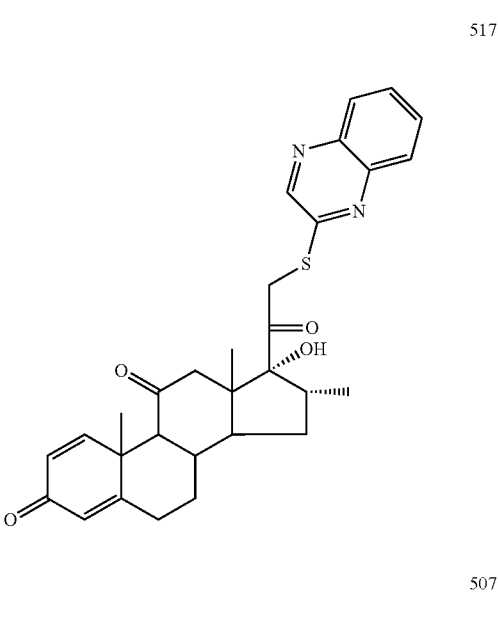 | 517 |
| 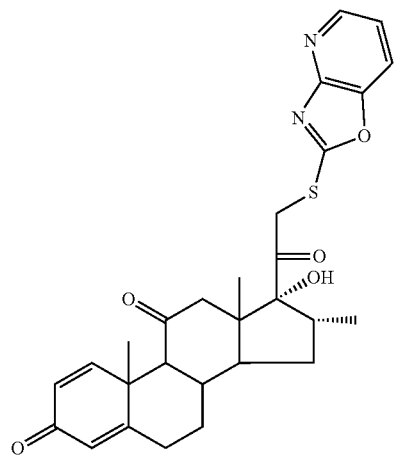 [SMILES: C[C@@H]1CC2C3CCC4=CC(=O)C=CC4(C)C3C(=O)CC2(C)[C@@]1(O)C(=O)CSc1nc2ncccc2o1] | 507 |

451
TABLE 2-continued
| Table 2 C-11 keto ananlog (structure) | M + H |
| --- | --- |
| 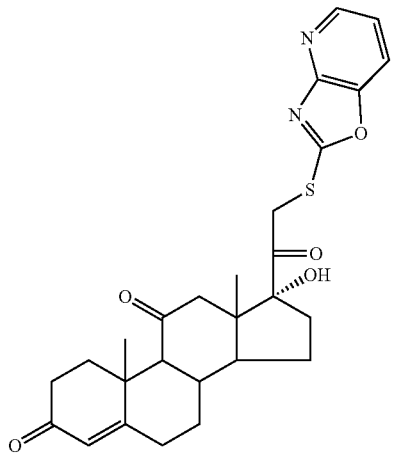 [SMILES: CC12CCC(=O)C=C1CCC1C2C(=O)CC2(C)C1CC[C@]2(O)C(=O)CSc1nc2ncccc2o1] | 495 |
| 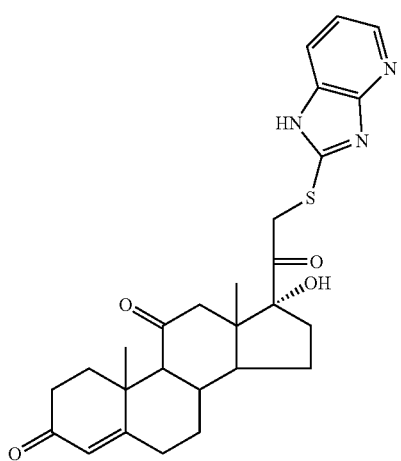 [SMILES: CC12CCC(=O)C=C1CCC1C2C(=O)CC2(C)C1CC[C@]2(O)C(=O)CSc1nc2ncccc2[nH]1] | 494 |
| 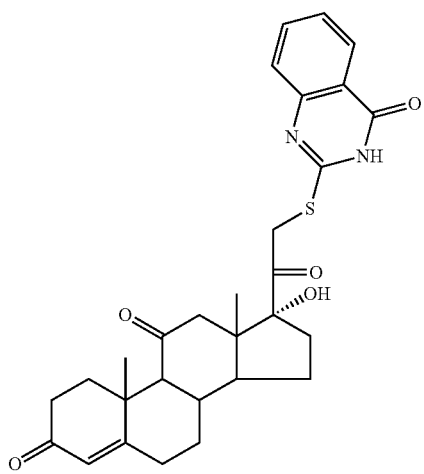 [SMILES: CC12CCC(=O)C=C1CCC1C2C(=O)CC2(C)C1CC[C@]2(O)C(=O)CSc1nc2ccccc2c(=O)[nH]1] | 521 |
452
TABLE 2-continued
| Table 2 C-11 keto ananlog (structure) | M + H |
| --- | --- |
| 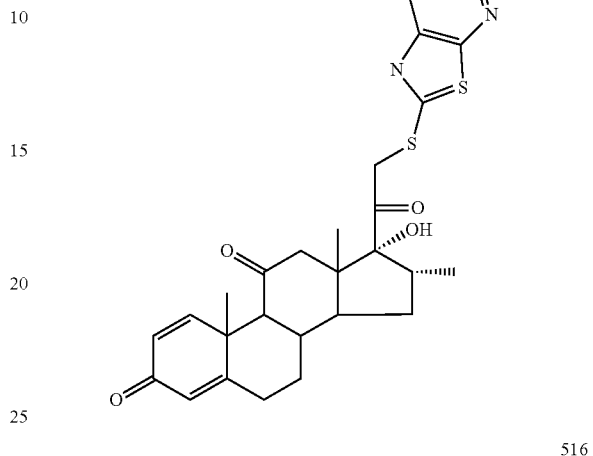 | 523 |
| 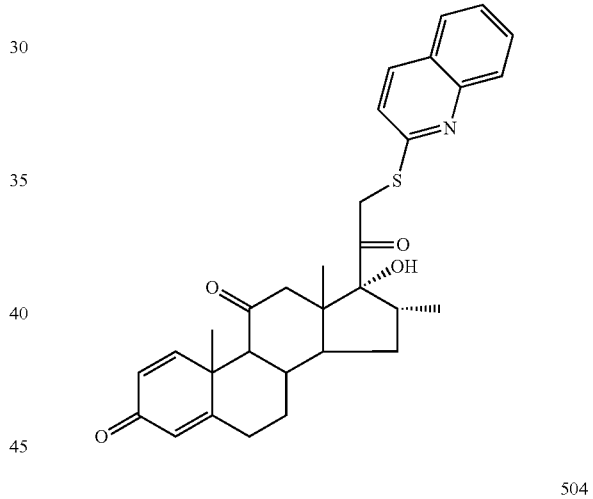 | 516 |
| 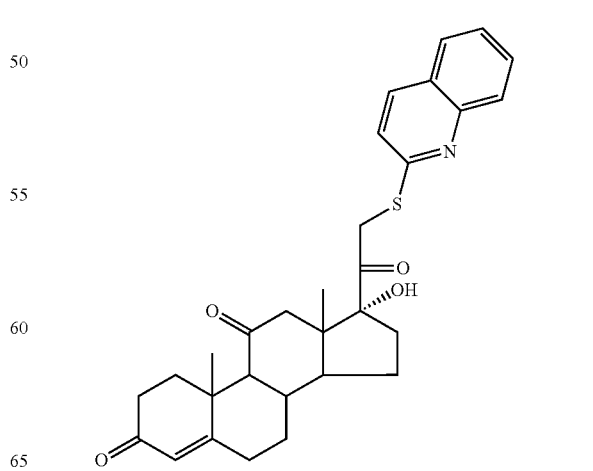 | 504 |

TABLE 2-continued
Table 2
C-11 keto ananlog (structure) | M + H
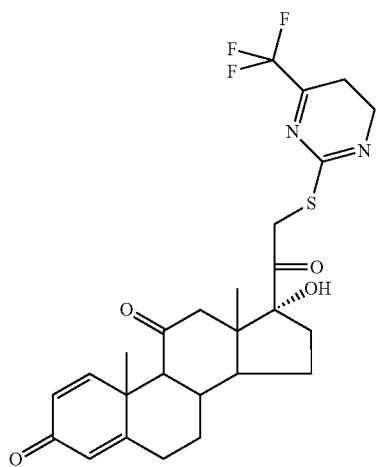 [SMILES: CC12C=CC(=O)C=C1CCC1C2C(=O)CC2(C)C1CC[C@]2(O)C(=O)CSC1=NCCC(C(F)(F)F)=N1] 521
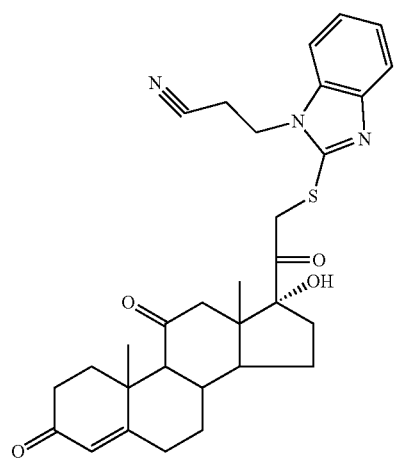 [SMILES: CC12CCC(=O)C=C1CCC1C2C(=O)CC2(C)C1CC[C@]2(O)C(=O)CSc1nc2ccccc2n1CCC#N] 546
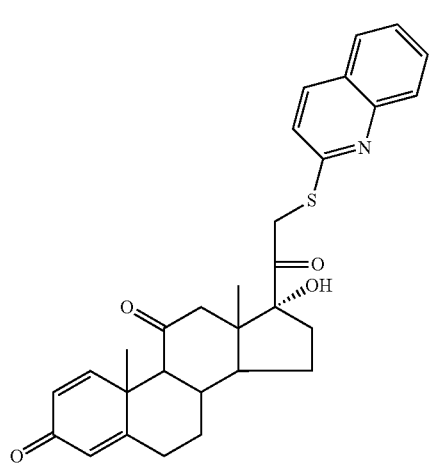 [SMILES: CC12C=CC(=O)C=C1CCC1C2C(=O)CC2(C)C1CC[C@]2(O)C(=O)CSc1ccc2ccccc2n1] 504
TABLE 2-continued
Table 2
C-11 keto ananlog (structure) | M + H
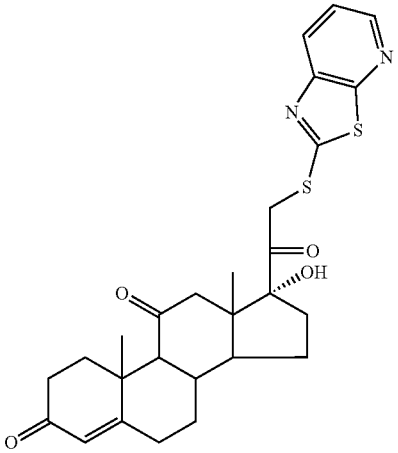 [SMILES: CC12CCC(=O)C=C1CCC1C2C(=O)CC2(C)C1CC[C@]2(O)C(=O)CSc1nc2cccnc2s1] 511
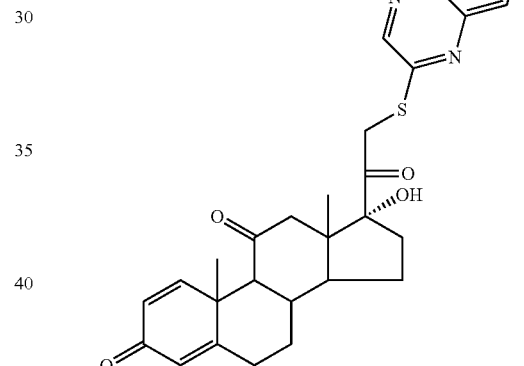 505
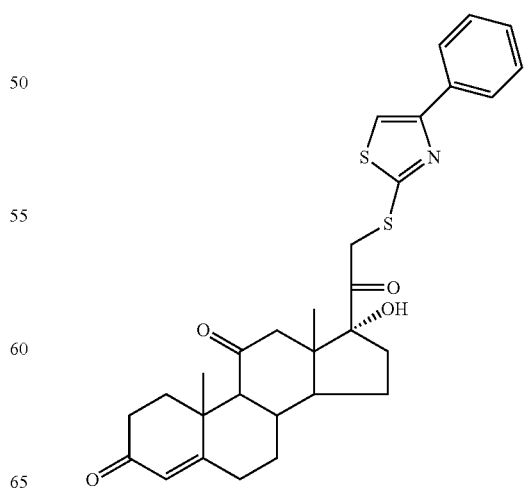 536

TABLE 2-continued

Table 2
C-11 keto ananlog (structure)    M + H

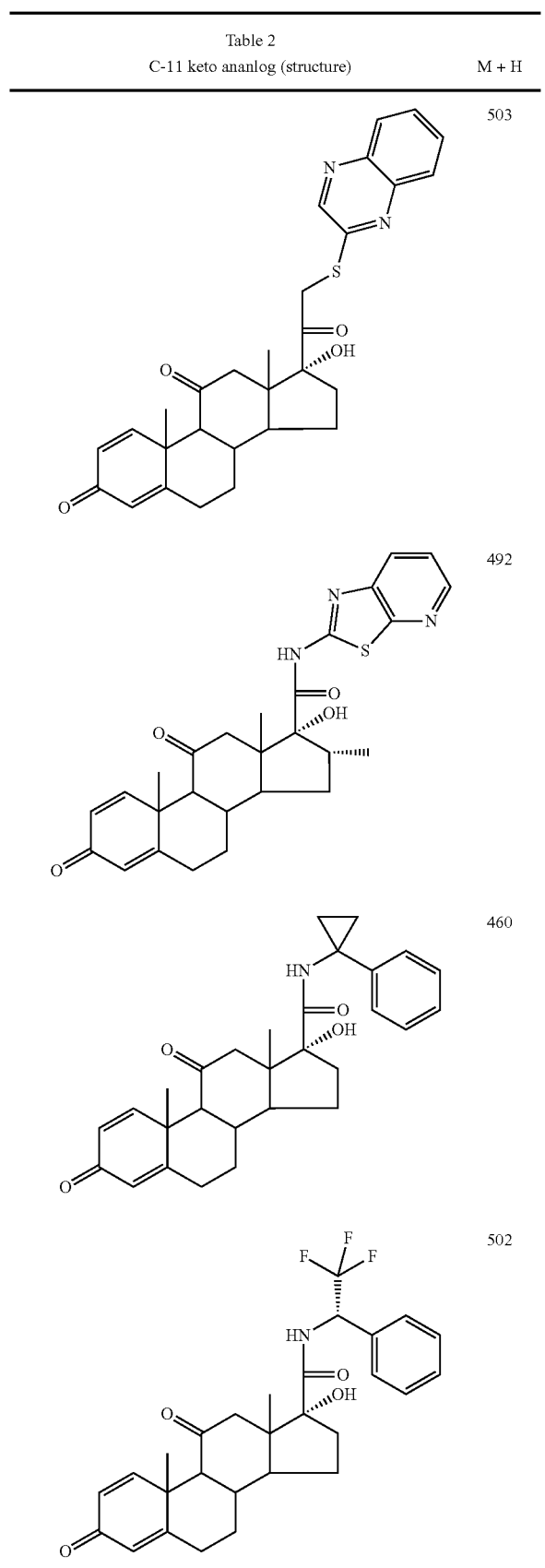

503

492

460

502

TABLE 2-continued

Table 2
C-11 keto ananlog (structure)    M + H

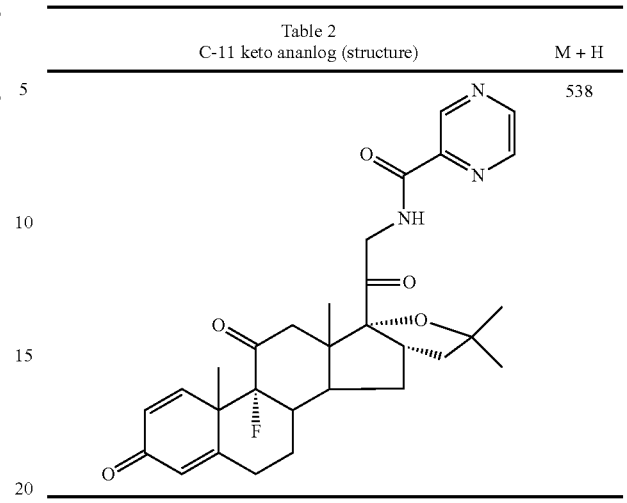

538

Assays

Glucocorticoid Receptor Binding Assay

Glucocorticoid receptor competitor assay kits were obtained under license from Invitrogen (product #P2893) and the protocol followed. The assay is a competition binding assay, used to measure the affinity of test compound for the human glucocorticoid receptor. Affinity is measured based on the ability of test compounds to displace a fluorescent glucocorticoid. The presence of effective competitors prevents the formation of a fluorescent-labeled glucocorticoid to bind to the glucocorticoid receptor complex, resulting in a decrease of the polarization value. The shift in polarization value in the presence of test compounds is used to determine the relative affinity of test compounds for the glucocorticoid receptor. Exemplary compounds of the invention that were tested in the assay exhibited $IC_{50}$ values in the range of from about 2.3 nM to about 6100 nM. Preferred compounds of the invention that were tested exhibited $IC_{50}$ values in the range of from about 2.3 nM to about 16.1 nM. A more preferred compound that was tested exhibited an $IC_{50}$ of about 2.34 nM.

Glucocorticoid Transrepression Assay

Human Lung epithelial cell line NCI-H292 cells were dissociated from stock flask using 0.05% trypsin/0.53 mM EDTA. Cells were suspended in complete medium and counted. Cells were plated in 96-well flat-bottom plates at 20K cells/well in 0.2 ml/well. Plates were incubated for 24-48 hours until cells were between 75-90% confluent. Medium was aspirated and replaced with medium containing various concentrations of steroids or antagonists. After 1 hour incubation at 37°, INFα (10 ng/ml final concentration in 0.2 ml) was added and the cells incubated overnight. Control wells with and without TNF were included on each plate, as well as wells with TNF in addition to a maximum (10 μM) concentration of dexamethasone.

The cell culture medium was sampled and IL-6 and IL-8 cytokine production was measured using the MSD Multi-Spot immunoassay.

Exemplary compounds of the invention that were tested in this assay exhibited $IC_{50}$ values in the range of from about 0.36 nM to about 3700 nM. Preferred compounds of the invention that were tested exhibited $IC_{50}$ values in this assay in the range of from about 0.36 nM to about 58 nM. One compound that was tested in this assay exhibited an $IC_{50}$ of about 0.36 nM.

GRE-Transactivation Assay

HeLa cells were stably transfected with a human glucocorticoid response element coupled with a luciferase reporter gene.

Cells were plated in 96 well Packard View Plates (black sides/clear bottom) at 20 K cells/0.2 ml complete medium. Plates were incubated overnight at 37°/5% $CO_2$. Medium was aspirated and replaced with 150 µl medium containing 5% charcoal-treated FBS and cells incubated overnight again. Test compounds were prepared in 5% charcoal-treated FBS medium. Medium was aspirated from plates and replaced with 100 µl of test compounds or controls. Plates were returned to incubator for exactly 24 hours. To measure induced luciferase, 100 µl of Steady-Glo luciferase assay substrate (Promega) was added to each well. Plates were sealed and mixed on a plate shaker for 5 minutes. Plate bottom opaque seals were added and the plates were allowed to stand for 60 minutes. Luminescence was measured on a Top-Count instrument (Perkin-Elmer).

Compositions and Methods

The compounds of the invention are beneficial, inter alia, their ability to bind glucocorticoid receptor and to illicit a response via that receptor. Hence, the compounds of the invention are useful wherever glucocorticoid agonists are useful. Such uses include, but are not limited to, the treatment of any diseases, conditions, or disorders for which steroids (or other glucocorticoid agonists) are believed useful, including a wide range of immune, autoimmune, and/or inflammatory diseases and conditions. Ex vivo use, e.g., as test instruments, is also contemplated. In some embodiments, the compounds of the invention possess the advantage of having little or no systemic activity. Therefore, in some embodiments, the compounds of the invention may be safer than those known glucocorticoids which have poor side effect profiles.

Non-limiting examples of inflammatory, immune, autoimmune and other diseases or conditions in which the compounds of the invention are useful include skin diseases such as eczema, posriasis, allergic dermatitis, atopic dermatitis, neurodermatitis, pruritis, and hypersensitivity reactions; inflammatory conditions of the nose, throat, or lungs such as asthma (including allergen-induced asthmatic reactions), rhinitis (including hayfever), allergic rhinitis, rhinosinusitis, sinusitis, nasal polyps, chronic bronchitis, chronic obstructive pulmonary disease, interstitial lung disease, and fibrosis; inflammatory bowel conditions such as ulcerative colitis and Chron's disease; and autoimmune diseases such as rheumatoid arthritis. Treatment of inflammation associated with CNS or peripheral nervous system disorders is also contemplated. Non-limiting examples include CNS trauma (e.g., brain trauma). Treatment of multiple sclerosis is also contemplated. Compounds of the invention may also be useful in treatment or prophylaxis of diseases and conditions of the eye, non-limiting examples of which include treatment of conjunctiva and allergic and nonallergic conjunctivitis.

Those skilled in the art will appreciate that, in some embodiments, the compounds and compositions of the invention are useful for both treatment and prophylaxis conditions and/or symptoms thereof described herein.

In another embodiment, the present invention provides for the use (and/or preparation) of a compound of the invention, or a pharmaceutically acceptable salt, solvate, ester, prodrug, tautomer, or isomer thereof, or the manufacture of a medicament for the treatment or prophylaxis of patients for the various diseases, conditions, and/or disorders described herein, including immune, autoimmune, and/or inflammatory diseases and/or conditions.

In another embodiment, the compounds of the invention may be used in acute treatment a wide range of immune, autoimmune, and inflammatory diseases and conditions, such as those listed above. In some embodiments, the compounds of the invention exhibit diminished side effect profiles in respect of one or more side effects associated with standard long-term steroidal treatments. Side effects associated with standard steroidal treatments include, for example, interference with carbohydrate metabolism, calcium resorption, suppression of endogenous corticosteroids, and suppression of the pituitary gland, adrenal cortex, and thymus. In such embodiments, compounds of the invention are useful for long-term treatment (as well as short- and medium-term treatment) of a wide range of chronic immune, autoimmune, and inflammatory diseases and conditions.

In another embodiment, the present invention provides a method for the treatment of neonatal sepsis, ALS, multiple sclerosis, type I diabetes, viral induced infections of the upper and lower airways, viral meningitis, and life-threatening diseases such as chronic meningeoencephalitis, neonatal enteroviral disease, polio, and myocarditis. The compounds and compositions of the present invention may also be used prophylactically to prevent exacerbations of symptoms associated with such diseases.

In another embodiment, the present invention provides a method for the treatment of viral related disorders. In one embodiment, the viral disorder is associated with the common cold. Compounds and compositions of the present invention may be utilized also in preventing exacerbation of disorders of the upper and lower airways. With respect to upper airway disorders, for example, the congestion and nasal blockage associated with allergic rhinitis, sinusitis, fungal induced sinusitis, bacterial based sinusitis, polyposis and the like. Examples with regard to disorders of the lower airways include administration of compositions of the present invention to prevent the need for the use of rescue medications for disorders of the lower airways, for example, asthma, chronic obstructive pulmonary disorder, allergic asthma, and emphysema. The compounds and compositions of the present invention may be useful also for the treatment and prevention of the nasal (stuffiness/congestion, rhinorrhea, nasal itching, sneezing) and non-nasal (itchy/burning eyes, tearing/watery eyes, redness of the eyes, itching of the ears/palate) symptoms of seasonal and perennial In another embodiment, the present invention provides a method for the treatment of a patient with an immune, autoimmune, or an inflammatory disease or condition, which method comprises administering to a patient in need thereof an effective amount of a compound of the invention or a pharmaceutically acceptable salt, solvate, ester, prodrug, tautomers, or isomers thereof. The present invention also provides the use of a compound of the invention, (or a pharmaceutically acceptable salt, solvate, ester, prodrug, tautomers, or isomers thereof), for the treatment of patients with immune, autoimmune, and/or inflammatory diseases and conditions.

In another embodiment, the present invention provides a method for the treatment of corticosteroid-responsive diseases of the airway passage ways and lungs. Such diseases include those allergic, non-allergic and/or inflammatory diseases of the upper or lower airway passages or of the lungs which are treatable by administering corticosteroids. Typical corticosteroid-responsive diseases include allergic and non-allergic rhinitis, nasal polyps, chronic obstructive pulmonary disease (COPD), and non-malignant proliferative and inflammatory diseases of the airways passages and lungs.

In another embodiment, the present invention provides a method for the treatment of allergic and non-allergic rhinitis as well as non-malignant proliferative and/or inflammatory disease of the airway passages and lungs. Exemplary allergic or inflammatory conditions of the upper and lower airway passages which can be treated or relieved according to various embodiments of the present invention include nasal symptoms associated with allergic rhinitis, such as seasonal allergic rhinitis, intermittent allergic rhinitis, persistent allergic rhinitis and/or perennial allergic rhinitis as well as congestion in moderate to severe seasonal allergic rhinitis patients. Other conditions that may be treated or prevented include corticosteroid responsive diseases, nasal polyps, asthma, chronic obstructive pulmonary disease (COPD), rhinovirus, rhinosinusitis including acute rhinosinusitis and chronic rhinosinusitis, congestion, total nasal symptoms (stuffiness/congestion, rhinorrhea, nasal itching, sneezing) and non-nasal symptoms (itchy/burning eyes, tearing/watery eyes, redness of the eyes, itching of the ears/palate) and nasal blockage associated with sinusitis, fungal induced sinusitis, bacterial based sinusitis.

The term "allergic rhinitis" as used herein means any allergic reaction of the nasal mucosa and includes hay fever (seasonal allergic rhinitis) and perennial rhinitis (non-seasonal allergic rhinitis) which are characterized by seasonal or perennial sneezing, rhinorrhea, nasal congestion, pruritis and eye itching, redness and tearing.

The term "non-allergic rhinitis" as used herein means eosinophilic nonallergic rhinitis which is found in patients with negative skin tests and those who have numerous eosinophils in their nasal secretions.

The term "asthma" as used herein includes any asthmatic condition marked by recurrent attacks of paroxysmal dyspnea (i.e., "reversible obstructive airway passage disease") with wheezing due to spasmodic contraction of the bronchi (so called "bronchospasm"). Asthmatic conditions which may be treated or even prevented in accordance with this invention include allergic asthma and bronchial allergy characterized by manifestations in sensitized persons provoked by a variety of factors including exercise, especially vigorous exercise ("exercise-induced bronchospasm"), irritant particles (pollen, dust, cotton, cat dander) as well as mild to moderate asthma, chronic asthma, severe chronic asthma, severe and unstable asthma, nocturnal asthma, and psychologic stresses. The invention is particularly useful in preventing the onset of asthma in mammals e.g., humans afflicted with reversible obstructive disease of the lower airway passages and lungs as well as exercise-induced bronchospasm.

The term "non-malignant prolifertive and/or inflammatory disease" as used herein in reference to the pulmonary system means one or more of (1) alveolitis, such as extrinsic allergic alveolitis, and drug toxicity such as caused by, e.g. cytotoxic and/or alkylating agents; (2) vasculitis such as Wegener's granulomatosis, allergic granulomatosis, pulmonary hemangiomatosis and idiopathic pulmonary fibrosis, chronic eosinophilic pneumonia, eosinophilic granuloma and sarcoidoses.

The compounds of the invention may be formulated for administration in any way known to those of skill in the art, and the invention therefore also provides within its scope pharmaceutical compositions comprising a compound of the invention (or a pharmaceutically acceptable salt, solvate, ester, prodrug, tautomers, or isomers thereof) together, if desirable, in admixture with one or more pharmaceutically acceptable diluents, excipients, and/or carriers. Further, in one embodiment, the present invention provides a process for the preparation of such pharmaceutical compositions comprising mixing the ingredients.

The compounds of the invention may, for example, be formulated for oral, buccal, sublingual, parenteral, local, or rectal administration. Local administration includes, but is not limited to, insufflation, inhalation, and dermal. Examples of various types of preparation for local administration include ointments, lotions, creams, gels, foams, preparations for delivery by transdermal patches, powders, sprays, aerosols, capsules, or cartridges for use in an inhaler or insufflator or drops (e.g., eye or nose drops), solutions or suspensions for nebulization, suppositories, pessaries, retention enemas, and chewable or suckable or fast dissolving tablets or pellets (e.g., for the treatment of aphthous ulcers) or liposome or microencapsulation preparations. Compositions for topical administration, e.g., to the lung, include dry powder compositions and spray compositions.

Dry powder compositions for topical delivery to the lung may, for example, be presented in capsules and cartridges for use in an inhaler or insufflator of, for example, gelatine. Formulations generally contain a powder mix for inhalation of a compound (or compounds) of the invention and a suitable powder base such as lactose or starch. Each capsule or cartridge may generally contain between 20 micrograms to 10 milligrams of a compound (or compounds) of the invention. Other amounts of such compounds are also included within the scope of the invention and may be readily determined by those of ordinary skill in the art, such as a pharmacist or attending physician. Alternatively, compounds of the invention may be administered without excipients. Packaging of the formulation may be suitable for unit dose or multi-dose delivery. In the case of multi-dose delivery, the formulation can be pre-metered (e.g., as in Diskus, see GB 2242134 or Diskhaler, see GB2178965, 2129691, and 2169265) or metered in use (e.g., as in Turbuhaler, see EP69715). An example of a unit-dose device is Rotahaler (see GB2064336).

Spray compositions may, for example, be formulated as aqueous solutions or as suspensions or as aerosols delivered from pressurized packs, such as a metered dose inhaler, with the use of a suitable liquefied propellant. Aerosol compositions suitable for inhalation can be either a suspension or a solution and generally contain a compound of the invention and a suitable propellant such as a fluorocarbon or a hydrogen-containing chlorofluorocarbon or other suitable propellants or mixtures of any of the foregoing, The aerosol composition may optionally contain additional formulation excipients well known in the art such as surfactants, e.g., oleic acid or lecithin and cosolvents, e.g., ethanol. One example formulation is excipient free and consists essentially of (e.g., consists of) a compound of the invention (optionally together with another active ingredient) and a propellant selected from 1,1,1,2-tetrafuloroethane, 1,1,1,2,3,3,3-heptafuloro-n-propand and mixtures thereof. Another example formulation comprises particulate compound of the invention, a propellant selected from 1,1,1,2-tetrafluoroethane, 1,1,1,2,3,3,3-heptafluoro-n-propane, and mixtures thereof and a suspending agent which is soluble in the propellant, e.g., an oligolactic acid or derivative thereof, as described, for example, in WO94/21229. A preferred propellant is 1,1,1,2-tetrafluoroethane. Pressurized formulations will generally be retained in a canister (e.g., an aluminium canister) closed with a valve (e.g., a metering valve) and fitted into an actuator provided with a mouthpiece.

Medicaments for administration by inhalation are also contemplated. As will be appreciated by those of ordinary skill in the art, such medicaments desirably have controlled particle size. The optimum particle sizes for inhalation into the bronchial system are well known to those skilled in the art and typically range from 1-10 micrometers, preferably 2-5 micrometers. Particles having a size above 20 micrometers are generally not preferred for reaching small airways. To achieve these or other desired particle sizes the particles of a compound of the invention as produced may be reduced in size by conventional means, e.g., by microencapsulation. The desired fraction may be separated by any suitable means such as by air classification or by sieving. Preferably, the particles will be crystalline. Crystalline particles may be prepared for example by a process which comprises mixing in a continuous flow cell, in the presence of ultrasonic radiation, a flowing solution of a compound of the invention in a liquid solvent with a flowing liquid antisolvent for said compound (e.g., as described in PCT/GB99/04368). Alternatively, crystalline particles may be prepared by a process comprising admitting a stream of solution of the substance in a liquid solvent and a stream of liquid antisolvent for the substance tangentially into a cylindrical mixing chamber having an axial outlet port such that the streams are thereby intimately mixed through formulation of a vortex which causes precipitation of crystalline particles of the substance (e.g., as described in International Patent Application PCT/GB00/04327). When an excipient such as lactose is employed, generally, the particle size of the excipient will be much greater than the inhaled compound of the invention. When the excipient is lactose it will typically be present as milled lactose, wherein not more than about 85% of lactose particles will have a MMD of 60-90 micrometers and not less than about 15% will have a MMD of less than 15 micrometers.

Formulations for administration topically to the nose are also contemplated. Such formulations include pressurized arosol formulations and aqueous formulations administered to the nose by pressurized pump.

Aqueous formulations for administration to the lung or nose may be provided with conventional excipients such as buffering agents, tonicity modifying agents and the like. Aqueous formulations may also be administered to the nose by nebulisation or other means known in the art.

Other non-limiting examples of modes of administration include which are contemplated include: ointments, creams and gels, which may, for example, be formulated with an aqueous or oily base with the addition of suitable thickening and/or gelling agent and/or solvents. Such bases may, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions are also contemplated. Lotions may be formulated with an aqueous or oily base and will in general also contain one or more emulsifying agents, stabilizing agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilizing agents, suspending agents or preservatives.

If appropriate, the formulations of the invention may be buffered by the addition of suitable buffering agents.

The proportion of the active compound of the invention in compositions according to the invention depends on the precise type of formulation to be prepared but will generally be within the range of from 0.001 to 50% by weight. Generally, however for most types of preparations the proportion used will be within the range of from 0.005 to 1% and preferably 0.01 to 0.5%. However, in powders for inhalation or insufflation, the proportion used will usually be within the range of from 0.1 to 50%.

Aerosol formulations are contemplated. In some embodiments, aerosol formulations are preferably arranged so that each metered dose or "puff" of aerosol contains 1 micrograms to 2000 micrograms, eg 20 micrograms to 2000 micrograms, alternatively about 20 micrograms to about 1500 micrograms of a compound of the invention. Administration may be once daily or several times daily, for example 2, 3, 4 or 8 times, giving for example 1, 2 or 3 doses each time. Preferably the compound of the invention is delivered once or twice daily. The overall daily dose with an aerosol will typically be within the range 10 micrograms to 10 milligrams, eg 100 micrograms to 10 milligrams, alternatively, 200 micrograms to 2000 micrograms, alternatively about 1500 micrograms.

Topical preparations may be administered by one or more applications per day to the affected area; over skin areas occlusive dressings may advantageously be used. Continuous or prolonged delivery may be achieved, e.g., by an adhesive reservoir system.

For internal administration the compounds according to the invention may, for example, be formulated in conventional manner for oral, parenteral or rectal administration. Formulations for oral administration include syrups, elixirs, powders, granules, tablets and capsules which typically contain conventional excipients such as binding agents, fillers, lubricants, disintegrants, wetting agents, suspending agents, emulsifying agents, preservatives, buffer salts, flavouring, colouring and/or sweetening agents as appropriate. Dosage unit forms are, however, preferred as described herein.

Preferred forms of preparation for internal administration are dosage unit forms, i.e., tablets and capsules. Such dosage unit forms contain from 0.1 mg to 20 mg preferably from 2.5 to 10 mg of the compounds of the invention.

The compounds according to the invention may, in general, may be given by internal administration in cases where systemic adreno-cortical therapy is indicated.

In general terms, preparations for internal administration may contain from 0.05 to 10% of the active ingredient, depending upon the type of preparation involved. The daily dose may vary from 0.1 mg to 60 mg, e.g. 5-30 mg, dependent on the condition being treated, and the duration of treatment desired.

Slow release or enteric coated formulations may be advantageous, particularly for the treatment of inflammatory bowel disorders.

In some embodiments, administration may be accomplished utilizing inhalation devices. Non-limiting examples of such devices include, but are not limited to, nebulizers, metered pump-spray devices, soft mist inhalers, and pressurized metered dosing inhalers. A single pressurized metered dose inhaler may be adapted for oral or nasal inhalation routes simply by switching between an actuator that is designed for nasal delivery and an actuator designed for oral delivery.

Solutions may be administered intranasally by inserting an appropriate device (such as a nasal spray bottle and actuator used to deliver NASONEX® Nasal Spray) into each nostril. Active drug, which would include at least one compound of the invention, is then expelled from the nasal spray device. Efficacy can be generally assessed in a double blind fashion by a reduction in nasal and non-nasal symptoms (e.g., sneezing, itching, congestion, and discharge). Other objective measurements (e.g., nasal peak flow and resistance) can be used as supportive indices of efficacy. Any suitable pump spray may be used, such as pump sprays used for NASONEX® as sold by Schering-Plough or AFRIN as sold by Schering-Plough.

Pressurized metered-dose inhalers ("MDI") contain propellants, for example, chlorofluorocarbon propellants, for example, CFC-11, CFC-12, hydrofluorocarbon propellants, for example, HFC-134A, HFC-227 or combinations thereof, to produce a precise quantity of an aerosol of the medicament contained with the device, which is administered by inhaling the aerosol nasally, treating the nasal mucosa and/or the sinus cavities.

A suitable MDI formulation will include a propellant such as 1,1,1,2,3,3,3 heptafluoropropane; an excipient, including but not limited to alcohols, MIGLYOL® 812, MIGLYOL® 840, PEG-400, menthol, lauroglycol, VERTREL®_245, TRANSCUTOL®, LABRAFAC® Hydro WL 1219, perfluorocyclobutane, eucalyptus oil, short chain fatty adds, and combinations thereof; a steroid and optionally a surfactant. MDI's may be prepared by conventional processes such as cold filling or pressure filling.

A "soft-mist" inhaler is a mult-dose, metered aerosol delivery device typically used to deliver aqueous based solution medicaments to the lungs via oral inhalation. The aerosol plume that they create is both slow in velocity and lasts for approximately 6× that of a typical pMDI (e.g. typically 1-2 sec. vs. milliseconds). An example of such a device would be Boehringer Ingelheim's (BI) RESPIMAT® which is currently used to deliver ipatropium bromide to the lungs.

In some embodiments, medicament formulations of the present invention may also be administered utilizing a nebulizer device. Typical commercial nebulizer devices produce dispersions of droplets in gas streams by one of two methods. Jet nebulizers use a compressed air supply to draw liquid up a tube and through an orifice by venturi action and introduce it into a flowing gas stream as droplets suspended therein, after which the fluid is caused to impact one or more stationary baffles to remove excessively large droplets, Ultrasonic nebulizers use an electrically driven transducer to subject a fluid to high-frequency oscillations, producing a cloud of droplets which can be entrained in a moving gas stream; these devices are less preferred for delivering suspensions. For instance, from about 2 to about 4 mL of the mometasone furoate solution may be placed in a plastic nebulizer container and the patient would inhale for 1-30 minutes. The total dosage placed in such a container may be determined by those skilled in the art. A non-limiting example would be in the range of 5 to about 100 mcg.

Also contemplated are hand-held nebulizers which atomize a liquid with a squeeze bulb air supply, but the more widely used equipment incorporates an electrically powered compressor or connects to a cylinder of compressed gas. Although the various devices which are commercially available vary considerably in their delivery efficiency for a given medicament since their respective outputs of respirable droplets are far from identical, any may be used for delivery of the medicaments of the present invention when a prescriber specifies an exact amount of medicament formulation which is to be charged to each particular device.

As noted herein, in some embodiments, the present invention provides compositions comprising at least one compound of the invention (optionally together with one or more additional active ingredients), formulated for nasal spray administration. Suitable nasal spray formulations can include, inter alia, water, auxiliaries and/or one or more of the excipients, such as: suspending agents, e.g., microcrystalline cellulose, sodium carboxymethylcellulose, hydroxypropylmethyl cellulose; humectants, e.g. glycerin and propylene glycol; acids, bases or buffer substances for adjusting the pH, e.g., citric acid, sodium citrate, phosphoric acid, sodium phosphate as well as mixtures of citrate and phosphate buffers; surfactants, e.g. polysorbate 80; and antimicrobial preservatives, e.g., benzalkonium chloride, phenylethyl alcohol and potassium sorbate.

Depending on the intended application, it may be desirable to incorporate up to about 5 percent by weight, more typically about 0.5 to about 5 weight percent, of an additional rheology-modifying agent, such as a polymer or other material. Useful materials include, without limitation thereto, sodium carboxymethyl cellulose, algin, carrageenans, carbomers, galactomannans, hydroxypropyl methylcellulose, hydroxypropyl cellulose, polyethylene glycols, polyvinyl alcohol, polyvinylpyrrolidone, sodium carboxymethyl chitin, sodium carboxymethyl dextran, sodium carboxymethyl starch and xanthan gum. Combinations of any two or more of the foregoing are also useful.

Mixtures of microcrystalline cellulose and an alkali metal carboxyalkylcellulose are commercially available, a non-limiting example of which includes one being sold by FMC Corporation, Philadelphia, Pa. U.S.A. as AVICEL® RC-591. This material contains approximately 89 weight percent microcrystalline cellulose and approximately 11 weight percent sodium carboxymethylcellulose, and is known for use as a suspending agent in preparing various pharmaceutical suspensions and emulsions. The compositions of the present invention may contain at least about 1.0 to about 10 weight percent, or from about 1 to about 4 weight percent of the mixture of the cellulose/carboxyalkylcellulose compound mixture.

A closely related mixture is available from the same source as AVICEL® RC-581, having the same bulk chemical composition as the RC-591, and this material is also useful in the invention. Microcrystalline cellulose and alkali metal carboxyalkylcellulose are commercially available separately, and can be mixed in desired proportions for use in the invention, with the amount of microcrystalline cellulose may be between about 85 and about 95 weight percent of the mixture for both separately mixed and co-processed mixtures.

When the compositions of the invention are intended for application to sensitive mucosal membranes, it may be desirable to adjust the pH to a relatively neutral value, using an acid or base, unless the natural pH already is suitable. In general, pH values about 3 to about 8 are preferred for tissue compatibility; the exact values chosen should also promote chemical and physical stability of the composition. In some instances, buffering agents will be included to assist with maintenance of selected pH values; typical buffers are well known in the art and include, without limitation thereto, phosphate, citrate and borate salt systems.

The compositions may contain any of a number of optional components, such as humectants, preservatives, antioxidants, chelating agents and aromatic substances. Humectants, which are hygroscopic materials such as glycerin, a polyethylene or other glycol, a polysaccharide and the like act to inhibit water loss from the composition and may add moisturizing qualities. Useful aromatic substances include camphor, menthol, eucalyptol and the like, flavors and fragrances. Preservatives are typically incorporated to establish and maintain a freedom from pathogenic organisms; representative components include benzyl alcohol, methylparaben, propylparaben, butylparaben, chlorobutanol, phenethyl alcohol (which also is a fragrance additive), phenyl mercuric acetate and benzalkonium chloride.

Pharmaceutical compositions comprising one (or more) compound(s) of the invention for use in combination with one or more other therapeutically active agent(s) are also contemplated. Non-limiting examples of such additional therapeutically active agents include, for example, beta$_2$ adrenoreceptor agonists, anti-histamines, anti-allergic agents, and anticholinergic agents. Additional agents are also described below. Such combinations may be administered simultaneously or sequentially (with a compound of the invention being administered either before or after the other active ingredient(s)) in separate or combined pharmaceutical formulations. For simultaneous administration, the invention thus provides, in another embodiment, pharmaceutical compositions comprising a compound of the invention (or a physiologically acceptable salt, solvate, prodrug, ester, tautomer, or isomer thereof) together with one or more other therapeutically active agent, for example, a beta$_2$ adrenoreceptor agonist, an antihistamine or an anti-allergic agent. The selection of the additional active agents is made on the basis of the intended use.

Compositions comprising long-acting beta$_2$ adrenoreceptor agonists (sometimes referred to as LABAs) are contemplated as being within the scope of the invention. Use of LABAs capable of providing a therapeutic effect over 24 hours is also contemplated. In another non-limiting embodiment, the present invention provides pharmaceutical compositions suitable for once-per-day administration comprising a compound of the invention (or a salt, solvate, ester, prodrug, tautomer, or isomer thereof) in combination with a long acting beta$_2$ adrenoreceptor agonist.

Non-limiting examples of beta$_2$-adrenoreceptor agonists include salmeterol (eg as racemate or a single enantiomer such as the R-enantiomer), salbutamol, formoterol, salmefamol, fenoterol, indacaterol, or terbutaline and salts thereof, for example the xinofoate salt of salmeterol, the sulphate salt or free base of salbutamol or the fumarate salt of formoterol. Long acting beta$_2$ adrenoreceptor agonists, such as salmeterol or formoterol or indacaterol, are preferred. Preferred long acting beta$_2$-adrenoreceptor agonists include those described in WO 266422A.

Additional active agents include antihistamines. Non-limiting examples of anti-histamines useful in combination with the compounds of the present invention include methapyrilene, loratadine, acrivastine, astemizole, cetirizine, mizolastine, fexofenadine, azelastine, levocabastine, olopatadine, levocetirizine, and desloratadine.

Additional active agents include histamine H$_1$ receptor antagonists. Examples of Histamine H$_1$ receptor antagonists (herein also antihistamines) include, but are not limited to, Astemizole, Azatadine, Azelastine, Acrivastine, Brompheniramine, Chlorpheniramine, Clemastine, Cyclizine, Carebastine, Cyproheptadine, Carbinoxamine, Desloratadine, Doxylamine, Diphenhydramine, Cetirizine, Dimenhydrinate, Dimethindene, Ebastine, Epinastine, Efletirizine, Fexofenadine, Hydroxyzine, Ketotifen, Loratadine, Levocabastine, Levocetirizine, Mizolastine, Mequitazine, Mianserine, Noberastine, Meclizine, Norastemizole, Picumast, Pyrilamine, Promethazine, Terfenadine, Tripelennamine, Temelastine, Trimeprazine, Triprolidine and mixtures of any two or more of the foregoing. Preferred Histamine H$_1$ receptors are desloratadine, loratadine, fexofenadine and ceterazine.

Desloratadine is also termed Descarboethoxyloratidine and DCL. DCL is a non-sedating antihistamine, whose technical name is 8-chloro-6,11-dihydro-11-(4-piperidylidene)-5H-benzo[5,6]cyclohepta[1,2]pyridine. This compound is described in Quercia, et al., Hosp. Formul., 28: 137-53 (1993), in U.S. Pat. No. 4,659,716, and in WO 96/20708. The use of Desloratadine for the treatment of congestion is disclosed in U.S. Pat. No. 6,432,972. DCL is an antagonist of the H$_1$ histamine receptor protein. The H$_1$ receptors are those that mediate the response antagonized by conventional antihistamines. H$_1$ receptors are present, for example, in the ileum, the skin, and the bronchial smooth muscle of man and other mammals. The amount of DCL which can be employed in a unit (i.e. single) dosage form of the present compositions can range from about 2.5 to about 45 mg, also from about 2.5 to about 20 mg, also from about 5 to about 10 mg. Preferred dosage amounts include 2.5 mg, 5.0 mg, 10.0 mg and 20.0 mg.

Loratadine is a non-sedating antihistamine whose technical name is 11-(4-piperidylidene)-5H-benzo-[5,6]-cyclohepta-[1,2-b]-pyridine. The compound is described in U.S. Pat. No. 4,282,233. Loratadine is a potent tricyclic and antihistaminic drug of slow release, with a selective antagonist of peripheral H$_1$ receptors activity.

Fexofenadine reportedly is a non-sedating antihistamine, whose technical name is 4-[1-hydroxy-4-(4-hydroxy-diphenylmethyl)-1-piperidinyl)butyl]-α,α-dimethyl-benzene acetic acid. Preferably the pharmaceutically acceptable salt is the hydrochloride, also known as fexofenadine hydrochloride. The amount of fexofenadine which can be employed in a unit dosage form of the present composition can range from about 40 to 200 mg, also from about 60 to about 180 milligrams, also about 120 milligrams.

Cetirizine hydrochloride reportedly is an H$_1$ receptor antagonist. The chemical name is (±)-[2-[4-[(4-chlorophenyl)phenylmethyl]-1-piperazinyl]ethoxy]acetic acid, dihydrochloride. Cetirizine hydrochloride is a racemic compound with an empirical formula of $C_{21}H_{25}ClN_2O_3 \cdot 2HCl$. Cetirizine hydrochloride is a white, crystalline powder and is water soluble. Cetirizine hydrochloride is available from Pfizer Inc., New York, N.Y., under the trade name ZYRTEC®. The amount of Cetirizine which can be employed in a unit dosage form of the present composition can range from about 0 to 40 mg, also from about 5 to about 10 milligrams. The levo isomer of Cetirizine may also be combined with Pleconaril in the formulations of the present invention. Another form of Cetirizine for use in the present invention is Cetirizine dinitrate.

Additional active agents include expectorants. Examples of expectorants suitable for use are known in the art and include, but are not limited to, ambroxol, guaiafenesin, terpin hydrate, and potassium quaicolsulfonate. Ambroxol is a bromhexine metabolite, chemically identified as trans-4(2-amino-3,5-dibromobenzil, amine) cyclohexane hydrochloride, which has been widely used during more than two decades as an expectorant agent or stimulating pulmonary surfactant factor. The compound is described in U.S. Pat. No. 3,536,712. Guaiafenesin is an expectorant, whose technical name is 3-(2-methoxyphenoxy)-1,2-propanediol. The compound is described in U.S. Pat. No. 4,390,732. Terpin hydrate is an expectorant, whose technical name is 4-hydroxy-α,α,4-trimethylcyclohexane-methanol. Potassium guaicolsulfonate is an expectorant, whose technical name is 3-Hydroxy-4-methoxybenzenesulfonic acid mix with mono-potassium 4-hydroxy-3-methoxybenzenesulfonate.

Additional active agents include decongestants. Examples of suitable decongestants for use include both oral and nasal decongestants. Examples of nasal decongestants useful in the present invention include, without being limited to, the sympathomimetic amine nasal decongestants. Those currently approved for topical use in the United States include, without limitation, levmetamfetamine (also known as 1-desoxyephedrine), ephedrine, ephedrine hydrochloride, ephedrine sulfate, naphazoline hydrochloride, oxymetazoline and pharmaceutically acceptable salts thereof, oxymetazoline hydrochloride, phenylephrine hydrochloride, and propylhexedrine. Oral decongestants for use in the present invention include, without limitation, phenylpropanolamine, phenylephrine and pseudoephedrine as well as pharmaceutically acceptable salts thereof. Pseudoephedrine and its acid additional salts, e.g., those of HCl or $H_2SO_4$, are recognized by those skilled in the art as a sympathomimetic therapeutic agent that is safe and effective for treating nasal congestion. They are commonly administered orally concomitantly with an antihistamine for treatment of nasal congestion associated with allergic rhinitis. When used in the present invention as a nasal decongestant it is preferred to use pseudoephedrine in amounts of equivalent to about 120 mg pseudoephedrine sulfate dosed one to 4 times daily. However, lesser amounts of pseudoephedrine sulfate may be used.

Additional active agents include histamine $H_3$ receptor antagonists. Examples of Histamine $H_3$ receptor antagonists suitable for use in the present invention include, but are not limited to, thioperamide, impromidine, Burimamide, Clobenpropit, Impentamine, Mifetidine, S-sopromidine, R-sopromidine, 3-(imidazol-4-yl)-propylguanidine (SKF-91486), 3->(4-chlorophenyl)methyl-5->2-(1H-imidazol-4-yl)ethyl 1,2,3-oxadiazole (GR-175737), 4-(1-cyclohexylpentanoyl-4-piperidyl) 1H-imidazole (GT-2016), 2-{>2->4(5)-imidazolylethylthio}-5-nitropyridine (UCL-1199) Clozapine, SCH497079 and SCH539858. Additional examples are disclosed and claimed in U.S. Pat. No. 6,720,328 and United States Patent Application Publication No. 20040097483A1, both assigned to Schering Corp., and both of which are hereby incorporated by reference. Other preferred compositions may further include both $H_1$ and $H_3$ receptors antagonists as is disclosed in U.S. Pat. No. 5,869,479, also assigned to Schering Corp., which is hereby incorporated by reference, Other compounds can readily be evaluated to determine activity at $H_3$ receptors by known methods, including the guinea pig brain membrane assay and the guinea pig neuronal ileum contraction assay, both of which are described in U.S. Pat. No. 5,352,707. Another useful assay utilizes rat brain membranes and is described by West et al., "Identification of Two $H_3$-Histamine Receptor Subtypes," Molecular Pharmacology, Vol. 38, pages 610-613 (1990).

Additional active agents include anti-cholinergic agents. Examples of anti-cholinergic agents for use in the present invention include, but are not limited to, Tiotropium, Oxitropium, Ipratropium, Methantheline, Propantheline, Dicyclomine, Scopolamine, Methscopolamine, Telenzepine, Benztropine, QNX-hemioxalate, Hexahydro-sila-difenidol hydrochloride and Pirenzepine. In one embodiment, such compositions comprising at least one compound of the invention and at least one anti-cholinergic agent (and optionally other active agents) are zadministered either orally or nasally in amounts that are known to, or determined by, those of skill in the art.

Additional active agents include antibiotics. Non-limiting examples include macrolides, cephalosporin, and antibacterials. Specific examples of suitable antibiotics include, but are not limited to, Tetracycline, Chlortetracycline, Bacitracin, Neomycin, Polymyxin, Gramicidin, Oxytetracycline, Chloramphenicol, Florfenicol, Gentamycin, Erythromycin, Clarithromycin, Azithromycin, Tulathromycin, Cefuroxime, Ceftibuten, Ceftiofur, Cefadroxil, Amoxicillin, Peniccilins, Amoxicillin with clavulanic acid or an other suitable beta-lactamase inhibitor, Sulfonamides, Sulfacetamide, Sulfamethizole, Sulfisoxazole; Nitrofurazone, and Sodium propionate. The therapeutic amounts of compositions which may be administered are known to one of skill in the art.

Additional active agents include $P2Y_2$ receptor agonsts. Non-limiting examples of $P2Y_2$ receptor agonists for use in the present invention include, but are not limited to, diquafosol tetrasodium. Diquafosol tetrasodium is a $P2Y_2$ receptor agonist that activates receptors on the ocular surface and inner lining of the eyelid to stimulate the release of water, salt, mucin and lipids—the key components of natural tears. Mucin is made in specialized cells and acts to lubricate surfaces. Lipids in the eye are oily substances that form the outer-most layer of the tear film and are responsible for the prevention of excess tear fluid evaporation. In preclinical testing, diquafosol reportedly increased the secretions of natural tear components. Diquafosol is available from Inspire. $P2Y_2$ receptor agonists are a class of compounds that are being developed for the treatment of a variety of conditions in which mucociliary clearance (MCC) is impaired, including chronic bronchitis and cystic fibrosis (CF). Other mucolytic agents may include N-Acetylcysteine and endogenous ligand compound UTP. These compositions may be administered by routes known to those of skill in the art, including orally and nasally.

Additional active agents include Leukotriene$_4$ antagonists and/or inhibitors. Non-limiting examples of Leukotriene$_4$ antagonists and/or inhibitors suitable for use in the present invention include, but are not limited to Zileuton, Docebenone, Piripost, ICI-D2318, MK-591, MK-886, sodium 1-(((R)-(3-(2-(6,7-difluoro-2-quinolinyl)ethynyl)phenyl)-3-(2-(2-hydroxy-2-propyl)phenyl)thio)methyl)cyclopropaneacetate (also referred to herein for convenience as "compound LAcetate"); 1-(((R)-(3-(2-(2,3-dichlorothieno[3,2-b]pyridin-5-yl)-(E)-ethenyl)phenyl)-3-(2-(1-hydroxy-1-methylethyl)phenyl)propyl)thio)-methyl)cyclopropaneacetic acid (also referred to herein for convenience as "compound LAcid"), Pranlukast, Zafirlukast, and Montelukast and the compound [2-[[2-(4-tert-butyl-2-thiazolyl)-5-benzofuranyl] oxymethyl]phenyl]acetic acid (also referred to herein for convenience as "compound FK011" or "FR150011"). Preferred are montelukast, pranlukast, zafirlukast, compounds "FK011", "LAcetate", and "LAcid". Compositions containing these constituents may be administered either orally or nasally as set forth below in amounts that are known to one of skill in the art.

Additional active agents include leukotriene $D_4$ antagonists. Non-limiting examples of suitable leukotriene $D_4$ antagonists include montelukast, which is a Leukotriene $D_4$ antagonist capable of antagonizing the receptors for the cysteinyl leukotrienes. The technical name of Montelukast is [R-(E)]-1-[[[1-[3-[2-(7-chloro-2-quinolinyl)ethenyl]phenyl]-3-[2-(1-hydroxy-1-methylethyl)phenyl]propyl]thio] methyl]-cyclopropaneacetic acid. This compound is described in EP 480,717. A preferred pharmaceutically acceptable salt of Montelukast is the monosodium salt, also known as Montelukast sodium. The amount of Montelukast which can be employed in a unit dosage form of the present invention can range from about one to 100 milligrams, also from about 5 to about 20 milligrams, preferably about 10 milligrams.

Additional non-limiting examples of suitable leukotriene D4 antagonists include the compound 1-(((R)-(3-(2-(6,7-difluoro-2-quinolinyl)ethenyl)phenyl)-3-(2-(2-hydroxy-2-propyl)phenyl)thio)methylcyclopropaneacetic acid, described in WO 97/28797 and U.S. Pat. No. 5,270,324. A pharmaceutically acceptable salt of this compound is the sodium salt, also known as sodium 1-MR)-(3-(2-(6,7-difluoro-2-quinolinyl) ethenyl)phenyl)-3-(2-(2-hydroxy-2-propyl)phenyl)thio)-methylcyclopropaneacetate.

Additional non-limiting examples of suitable leukotriene D4 antagonists include the compound 1-((((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)-thio)methyl)

cyclopropaneacetic acid, described in WO 97/28797 and U.S. Pat. No. 5,472,964. A pharmaceutically acceptable salt of this compound is the sodium salt, also known as sodium 1-(((1 (R)-3(3-(2-(2,3-dichlorothieno[3,2-b]pyridin-5-yl)-(E)-ethenyl)phenyl)-3-(2-(1-hydroxy-1-methylethyl)phenyl) propyl)-thio)methyl)cyclopropaneacetate.

Additional non-limiting examples of suitable leukotriene D4 antagonists include the compound pranlukast, described in WO 97/28797 and EP 173,516. The technical name for this compound is N-[4-oxo-2-(1H-tetrazol-5-yl)-4H-1-benzopyran-8-yl]-p-(4-phenylbutoxy)benzamide. The amount of Pranlukast which can be employed in a unit dosage form can range from about 100 to about 700 mg, preferably from about 112 to about 675 mg; also from about 225 mg to about 450 mg; also from about 225 to about 300 mg.

Additional non-limiting examples of suitable leukotriene D4 antagonists include the compound, described in WO 97/28797 and EP 199,543. The technical name for this compound is cyclopentyl-3-[2-methoxy-4-[(o-tolylsulfonyl)carbamoyl]benzyl]-1-methylindole-5-carbamate.

Additional non-limiting examples of suitable leukotriene D4 antagonists include the compound [2-[[2-(4-tert-butyl-2-thiazolyl)-5-benzofuranyl]oxymethyl]phenyl]acetic acid, described in U.S. Pat. No. 5,296,495 and Japanese Patent JP 08325265A. An alternative name for this compound is 2-[[[2-[4-(1,1-dimethylethyl)-2-thiazolyl]-5-benzofuranyl]oxy] methyl]-benzeneacetic acid. The code number for this compound is FK011 or FR150011.

Additional active agents include pharmaceutically acceptable zinc salts, including those water soluble salts reported to have beneficial effects against the common cold. Typically such preparations comprise an aqueous or saline solution with a concentration of ionic zinc below that which causes irritation to mucus membranes. Generally the ionic zinc in such solutions is present substantially as unchelated zinc and is in the form of free ionic solution. Zinc ionic solutions for use in the present invention will typically contain substantially unchelated zinc ions in a concentration of from about 0.004 to about 0.12% (w/vol). Preferably the substantially unchelated ionic zinc compound can comprise a mineral acid salt of zinc selected from the group consisting of zinc sulfate, zinc chloride, and zinc acetate. These compositions may be administered either orally or nasally in amounts that are known to, or readily determined by, those of skill in the art.

Additional active agents include SYK kinase analogs. SYK kinase analogs are a class of molecules which work by blocking SYK kinase. Compound R112, available from Rigel Pharmaceuticals, Inc, is an example of an SYK kinase analog. A recent study reportedly showed a greater than 20% relative improvement for R112 over placebo (an absolute difference of 9% over placebo) and up to 38% improvement for R112 from baseline measurements (prior to drug initiation) of symptoms associated with chronic nasal congestion (e.g. stuffy nose) over a placebo.

Additional active agents include 5-lipoxygenase inhibitors. As used herein, the term "5-lipoxygenase inhibitor" (also referred to as a "5-LO inhibitor") includes any agent, or compound that inhibits, restrains, retards or otherwise interacts with the enzymatic action of 5-lipoxygenase. Examples of 5-lipoxygenase inhibitors include, but not limited to, zileuton, docebenone, piripost, and the like. As used herein, the associated term "5-lipoxygenase activating protein antagonist" or "FLAP antagonist" includes any agent or compound that inhibits, retrains, retards or otherwise interacts with the action or activity of 5-lipoxygenase activating protein, examples of which include, but not limited, "FLAP antagonists" MK-591 and MK-886.

Additional active agents include those known to relieve oropharyngeal discomfort, including, for example, sore throats, cold or canker sores, and painful gums. Such active agents include topical anesthetics such as phenol, hexylresorcinol, salicyl alcohol, benzyl alcohol, dyclonine, dibucaine, benzocaine, buticaine, cetylpyridinium chloride, diperidon, clove oil, menthol, camphor, eugenol and others. Medicaments of the invention intended for application to the skin may similarly include a therapeutic agent for relieving skin discomfort including, but not limited to, lidocaine, benzocaine, tetracaine, dibucaine, pramoxine, diphenhydramine, and benzyl alcohol.

Additional active agents useful in combination with compound(s) of the invention include salicylates, such as aspirin, NSAIDs (non-steroidal anti-inflammatory agents such as indomethacin, sulindac, mefenamic, meclofenamic, tolfenamic, tolmetin, ketorolac, dicofenac, ibuprofen, naproxen, fenoprofen, ketoprofen, flurbirofin, or oxaprozin), TNF inhibitors such as etanercept or infliximab, IL-1 receptor antagonists, cytotoxic or immunosuppressive drugs such as methotrexate, leflunomide, azathiorpine, or cyclosporine, a gold compound, hydroxychloroquine or sulfasalazine, penicillamine, darbufelone, and p38 kinase inhibitors, sodium cromoglycate, nedocromil sodium, $PDE_4$ inhibitors, leukotriene antagonists, iNOS inhibitors, tryptase and elastase inhibitors, beta-2 integrin antagonists, adenosine 2a agonists; antiinfective agents such as antibiotics, antivirals; anticholinergic compounds, such as ipratropium (e.g., as the bromide), tiotropium (e.g., as the bromide), glycopyrronium (e.g., as the bromide), atropine, and oxitropium, or salts or other forms of any of the foregoing.

Additional active agents suitable for use in combination with one or more compounds of the invention include those useful for addressing one or more side effects associated with the use of steroids. Non-limiting examples include one or more inhibitors of osteoclast-mediated bone resportion. Suitable osteoclast-mediated bone resportion inhibitors include bisphosphonates (also called diphosphonates), such as Pamidronate (APD, Aredia®), Risedronate (Actonel®), Neridronate, Olpadronate, Alendronate (Fosamax®), Ibandronate (Boniva®), Risedronate (Actonel®), and Zoledronate (Zometa®).

Additional active agents suitable for use in combination with one or more compounds of the invention are described in WO03/035668, which are incorporated herein by reference.

The combinations referred to herein may conveniently be presented for use in the form of a pharmaceutical formulation and thus pharmaceutical formulations comprising a combination as defined above together with a pharmaceutically acceptable diluent or carrier represent additional embodiments of the present invention. Appropriate doses of known therapeutic agents will be readily appreciated by those skilled in the art.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

Therefore, we claim:

1. A compound, or a pharmaceutically acceptable salt, ester, or isomer thereof, of Formula (IV):

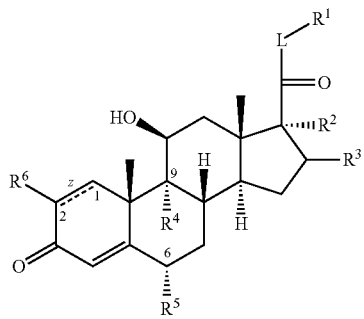

wherein L, $R^1$, $R^2$, $R^3$, $R^4$, $R^5$, and $R^6$ are selected independently of each other and wherein:

L is —$CH_2$—S—;

$R^1$ is a benzofused heteroaryl-,
  wherein said $R^1$ group is unsubstituted or optionally substituted with from 1 to 5 substituents, which may be the same or different, each independently selected from halogen, hydroxy, —CN, oxo, oxide, alkyl, haloalkyl, haloalkoxy-, hydroxyalkyl-, heteroalkyl, cyanoalkyl-, alkoxy, optionally substituted aryl, optionally substituted —O-aryl, optionally substituted —O-alkyl-aryl, optionally substituted heteroaryl, optionally substituted arylalkyl-, optionally substituted arylalkoxy, —N($R^7$)$_2$, -alkylN($R^7$)$_2$, —NC(O)$R^7$, —$CO_2R^7$, —$SO_2R^7$, and —$SO_2N(R^7)_2$, wherein said optional substituents are present from 1 to 4 times and may be the same or different, each independently selected from alkyl, halogen, haloalkyl, hydroxyl, —CN, and —N($R^{11}$)$_2$;
  and wherein the benzo portion of each said benzofused $R^1$ group is optionally further fused to another ring selected from heteroaryl, cycloalkyl, cycloalkenyl, heterocycloalkyl, and heterocycloalkenyl, $R^2$ is —$OR^8$;

$R^3$ is selected from hydrogen, hydroxy, and straight or branched alkyl, $R^4$ is selected from H and halogen;

$R^5$ is selected from H, halogen, and alkyl;

z (the dotted line) represents a single or double bond, with the proviso that when z is a single bond, $R^6$ is H;

$R^6$ is selected from H and halogen;

each $R^7$ is independently selected from hydrogen, alkyl, haloalkyl, aryl, and heteroaryl, or, when two groups $R^7$ are attached to the same nitrogen atom, two groups $R^7$ are taken together with the nitrogen atom to which they are attached to form a 3- to 7-membered heterocycloalkyl group;

$R^8$ selected from haloalkyl, aryl, heteroaryl, arylalkyl, heteroarylalkyl, —C(O)NHR$^9$, and —C(O)$R^{11}$;

$R^9$ is selected from alkyl, haloalkyl, aryl, heteroaryl, cycloalkyl, and heterocycloalkyl, each unsubstituted or optionally substituted with from 1 to 4 substituents independently selected from the group consisting of alkyl, halogen, haloalkyl, hydroxy, —N($R^7$)$_2$, and —CN;

$R^{10}$ is selected from hydrogen and alkyl; and $R^{11}$ is selected from haloalkyl, aryl, heteroaryl, cycloalkyl, heterocycloalkyl, and heterocycloalkenyl, each unsubstituted or optionally substituted with from 1 to 4 substituents independently selected from the group consisting of alkyl, halogen, haloalkyl, hydroxy, —N($R^7$)$_2$, and —CN.

2. A compound according to claim 1, or a pharmaceutically acceptable salt, ester, or isomer thereof, selected from:

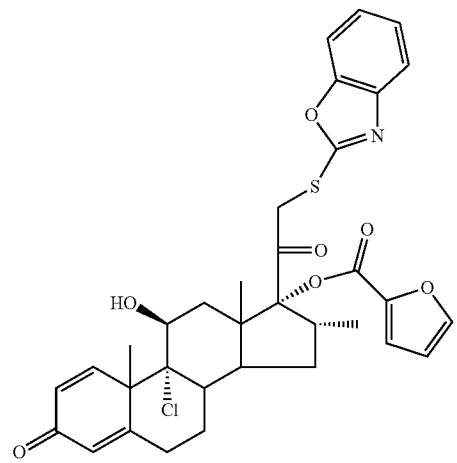

,

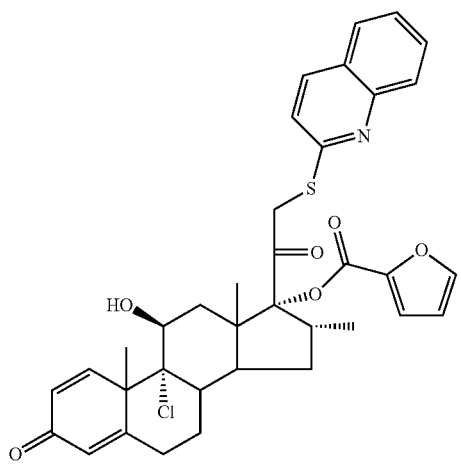

,

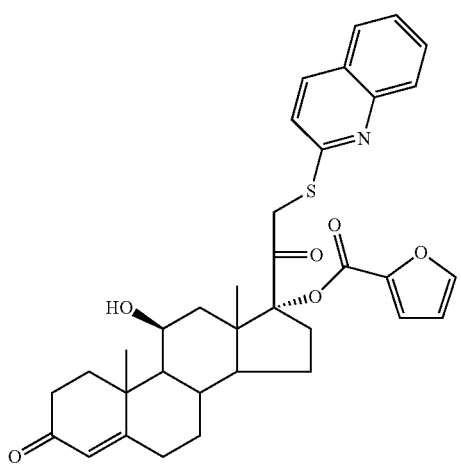

,

473
-continued
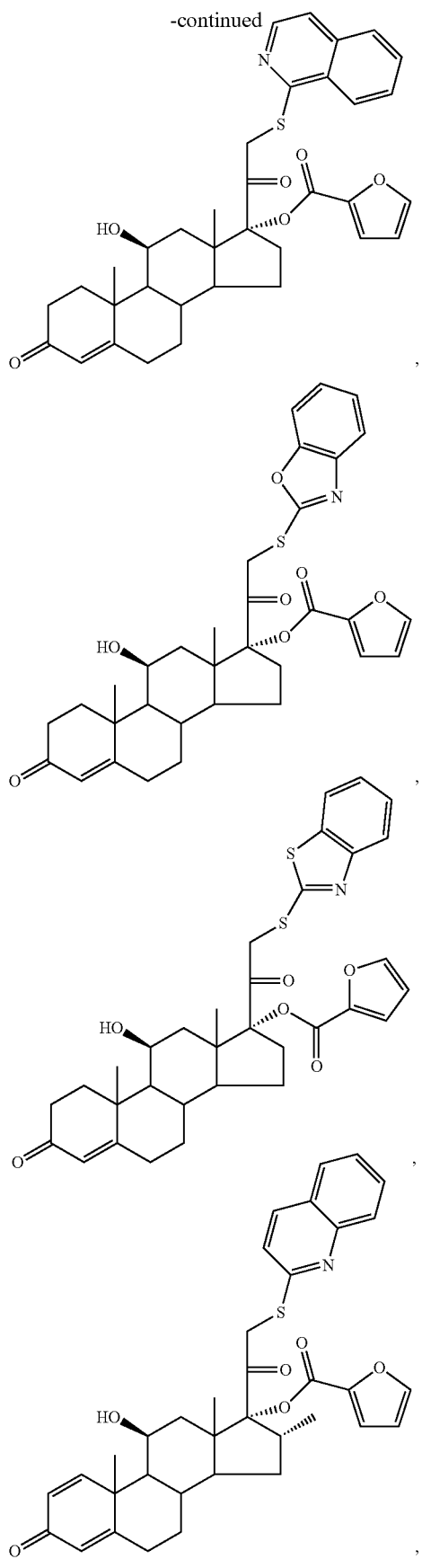
474
-continued
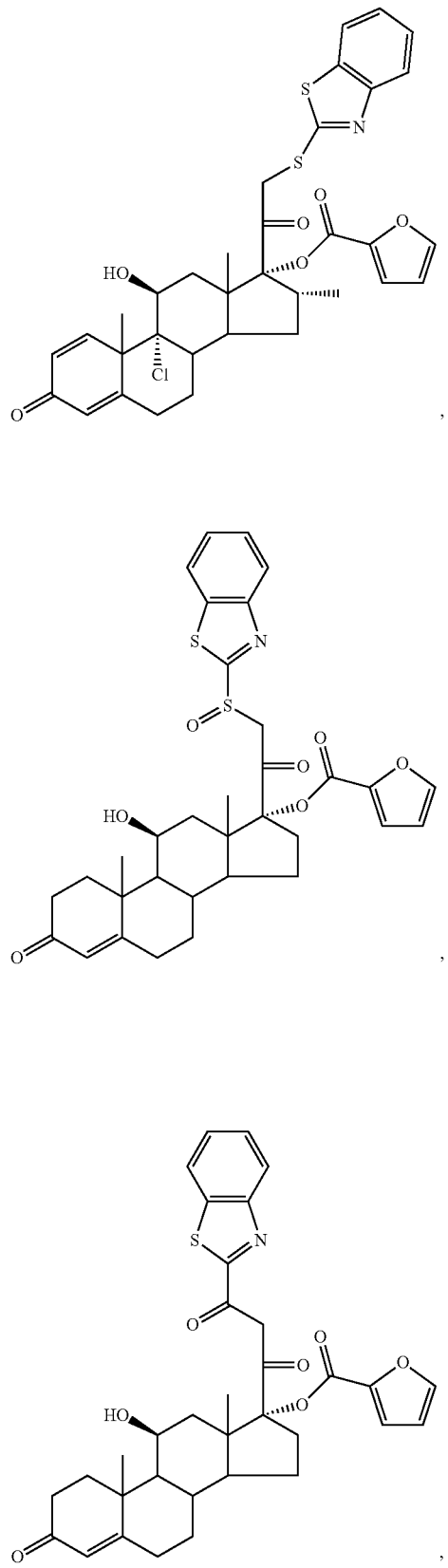

475
-continued
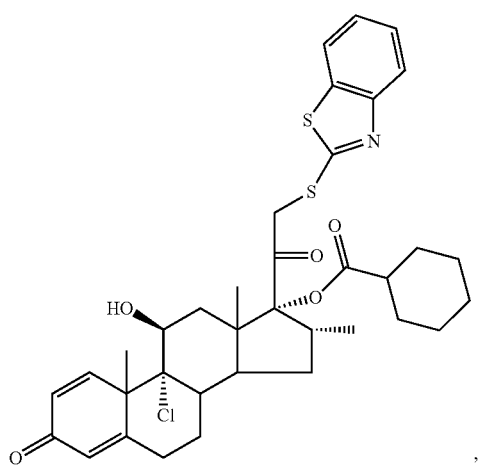
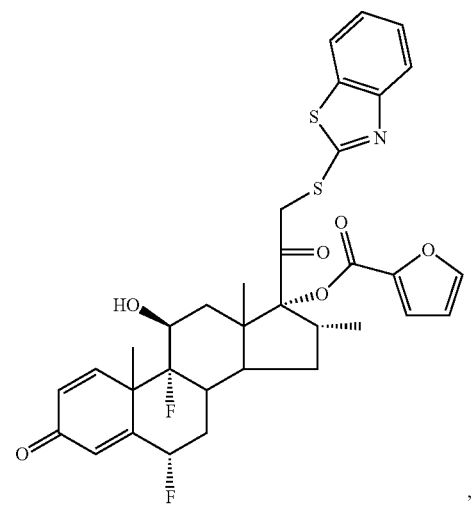
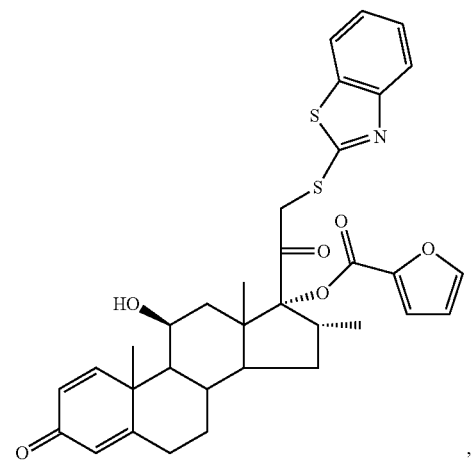
476
-continued
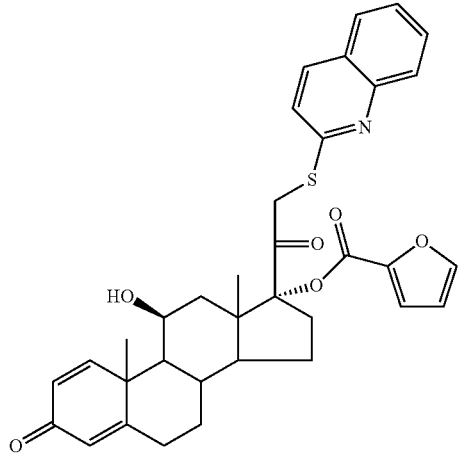
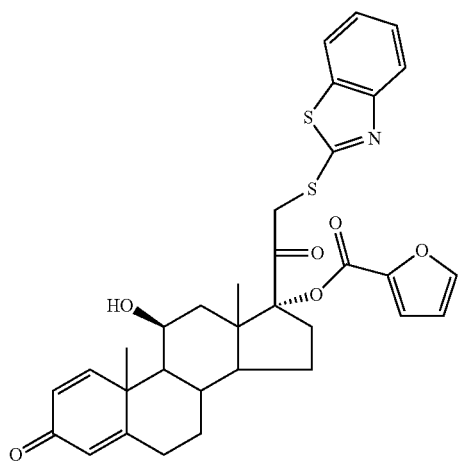
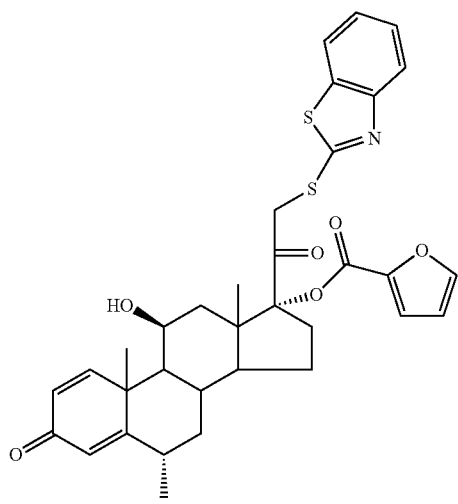

477
-continued
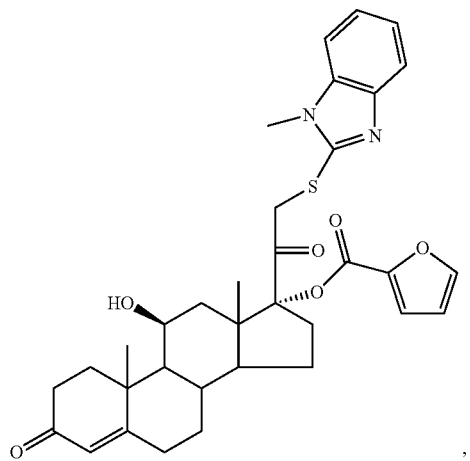
,
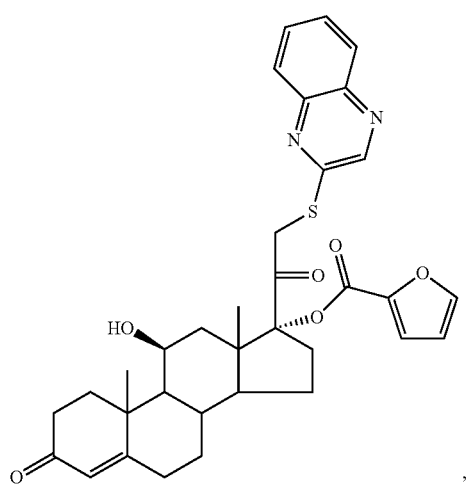
,
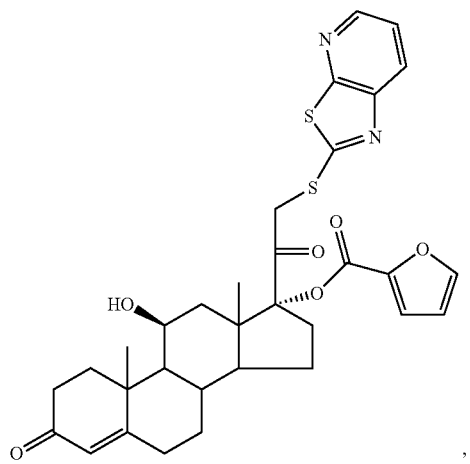
,
478
-continued
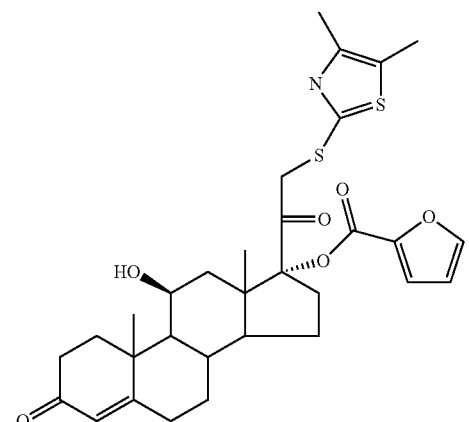
,
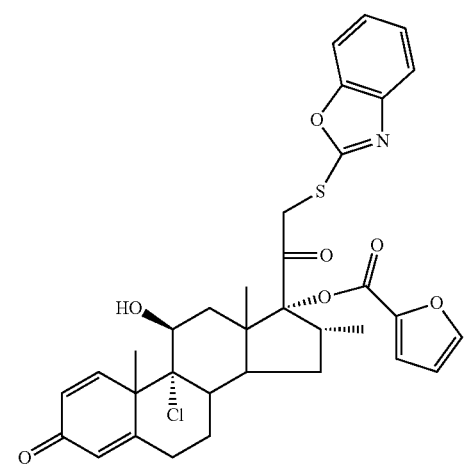
,
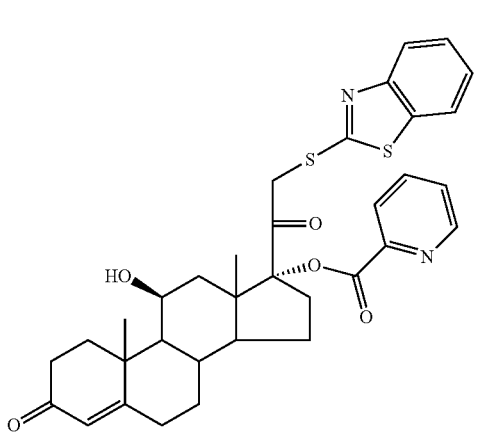
, 479
-continued
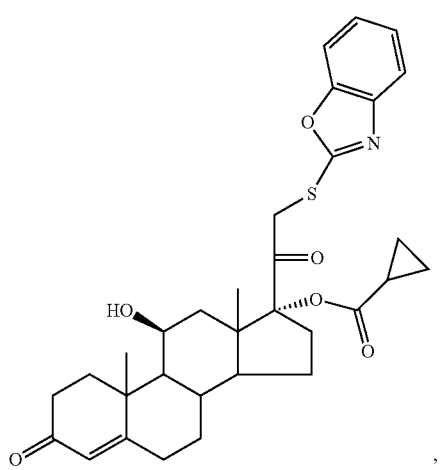
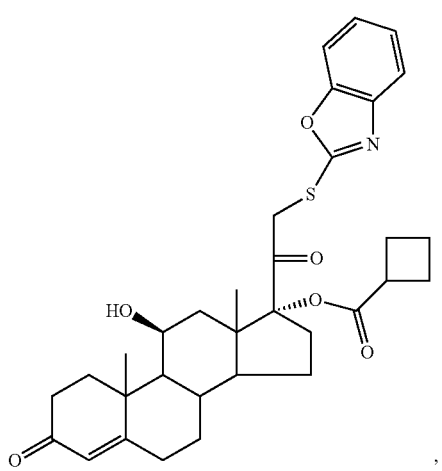
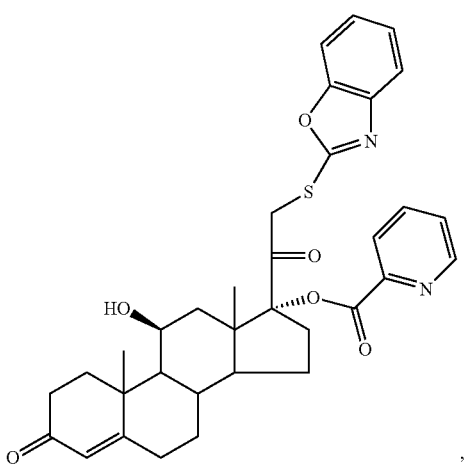
480
-continued
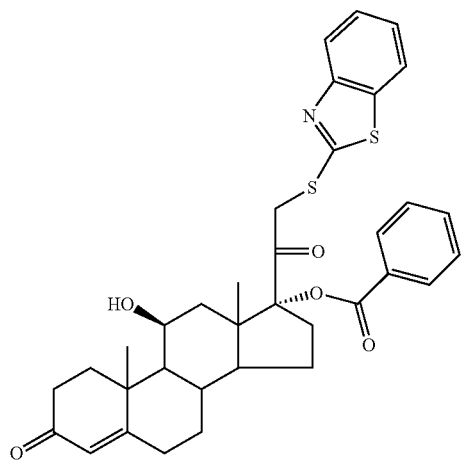
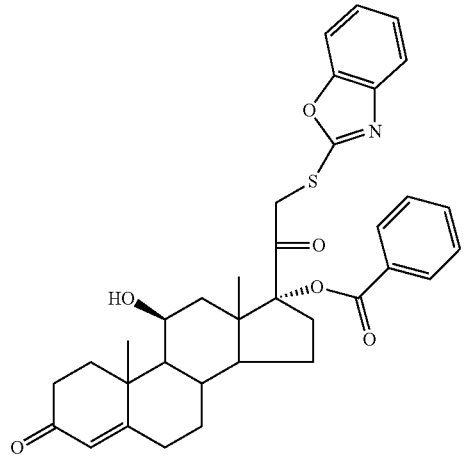
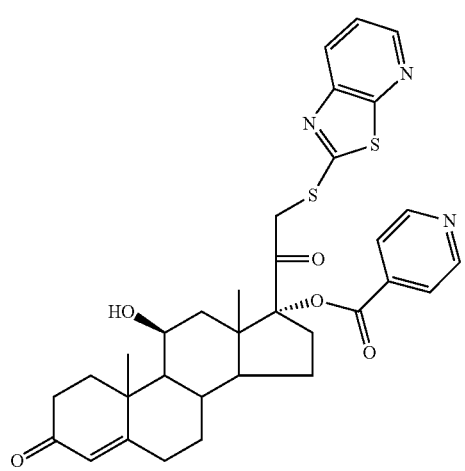

481
-continued
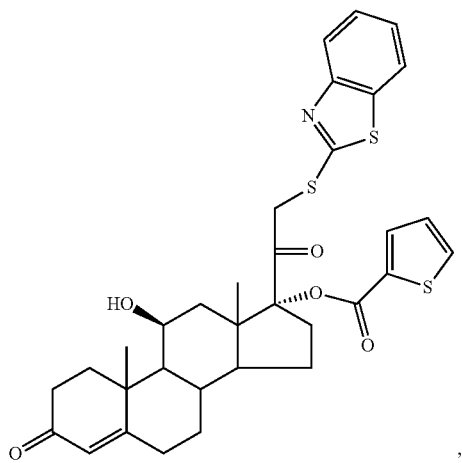 [SMILES: CC12CCC(=O)C=C1CCC1C2[C@@H](O)CC2(C)C1CC[C@]2(OC(=O)c1cccs1)C(=O)CSc1nc2ccccc2s1]
,
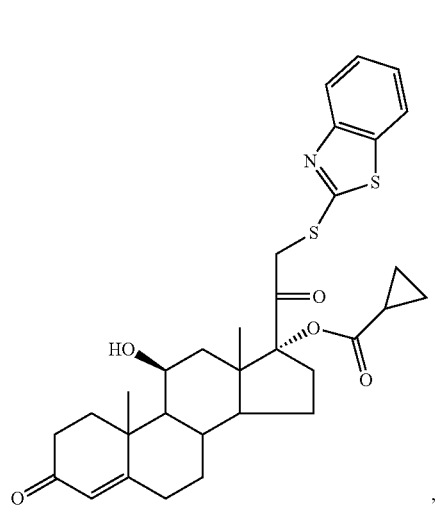
,
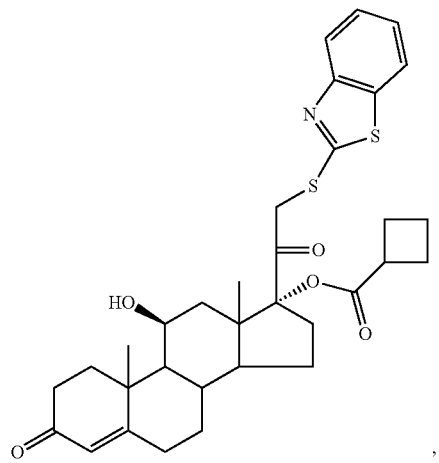
,
482
-continued
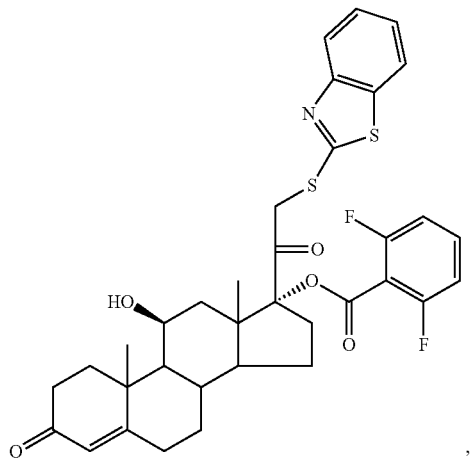
,
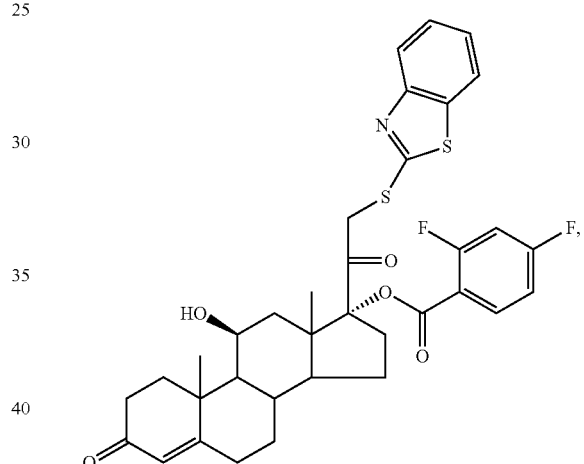
,
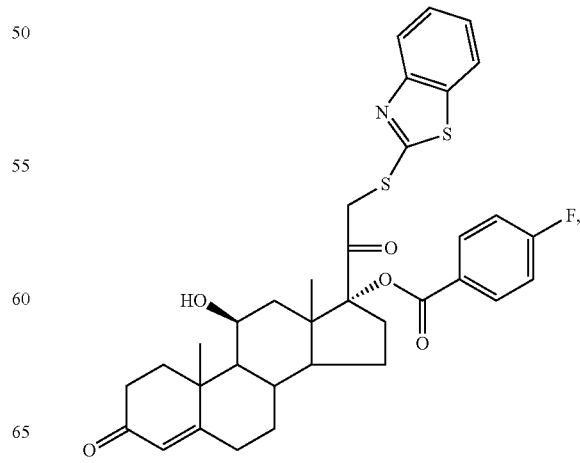
,

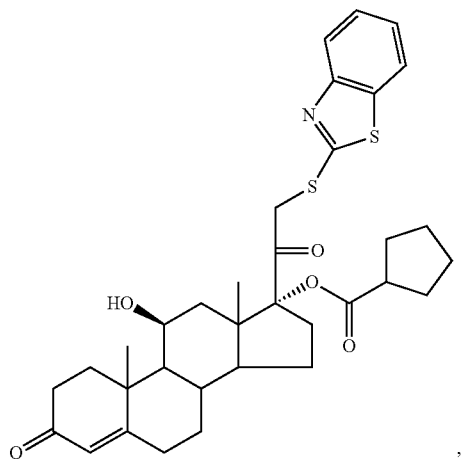
,
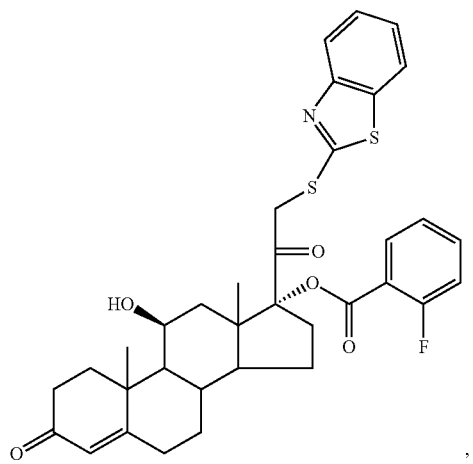
,
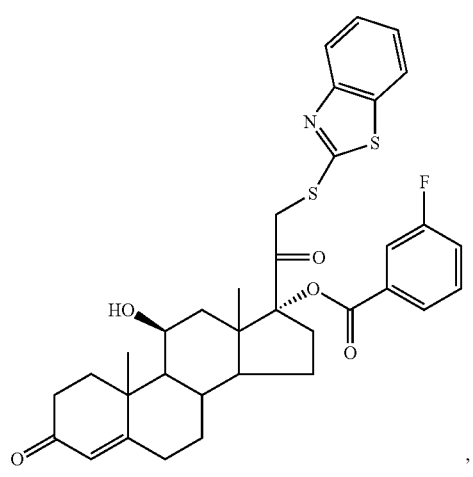
,
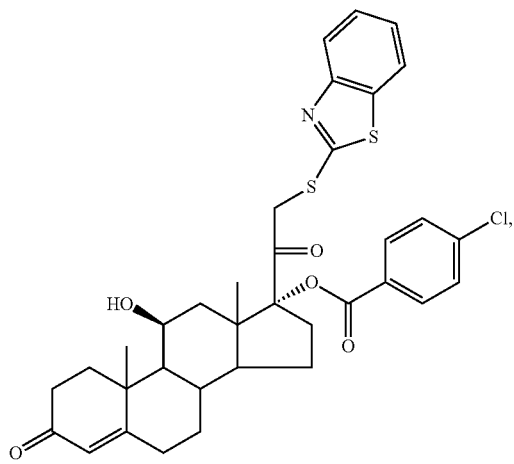
,
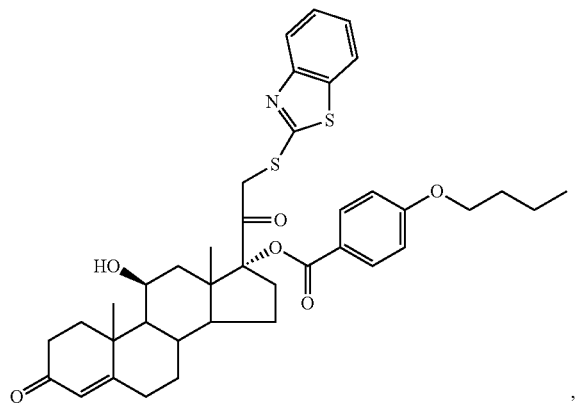
,
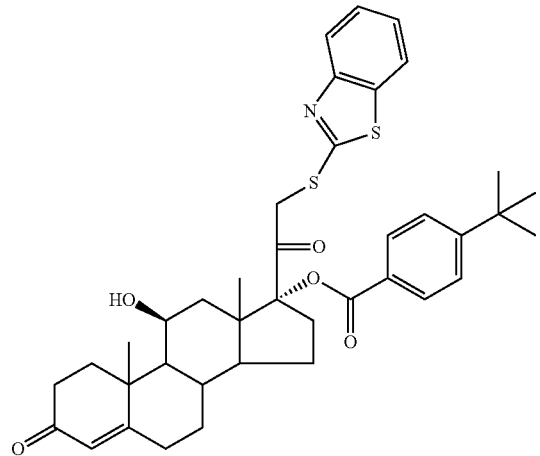
, 485
-continued
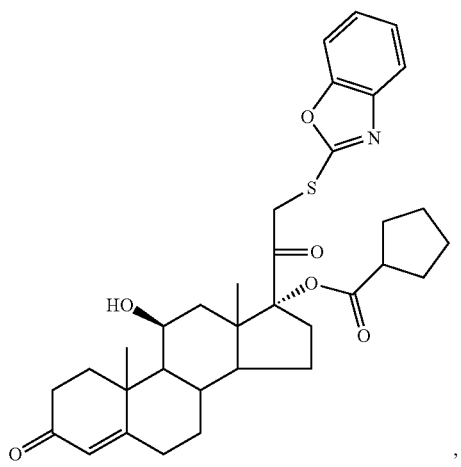
,
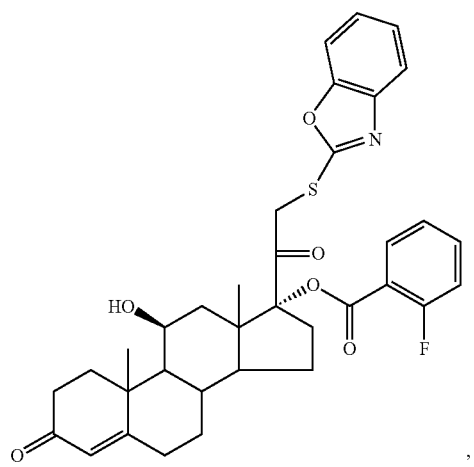
,
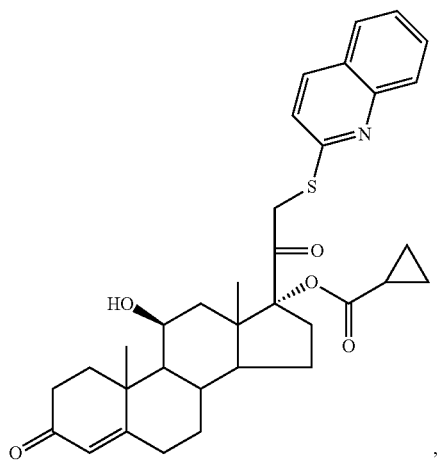
,
486
-continued
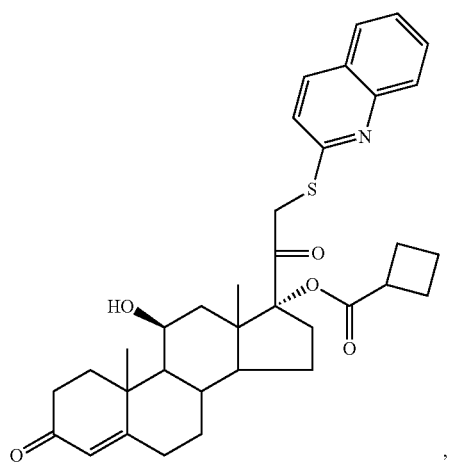
,
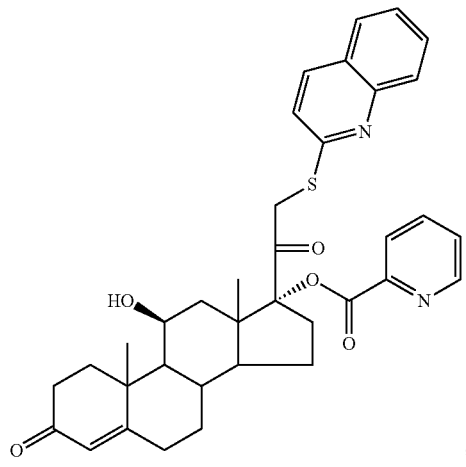
,
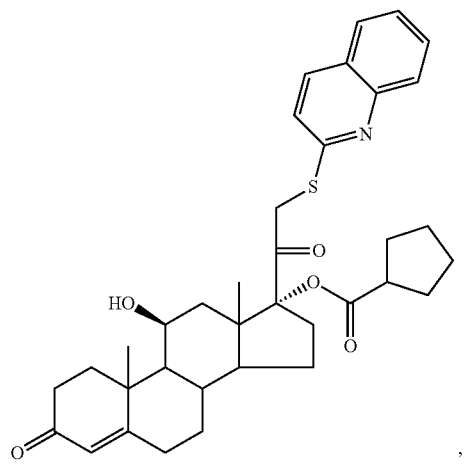
, 487
-continued
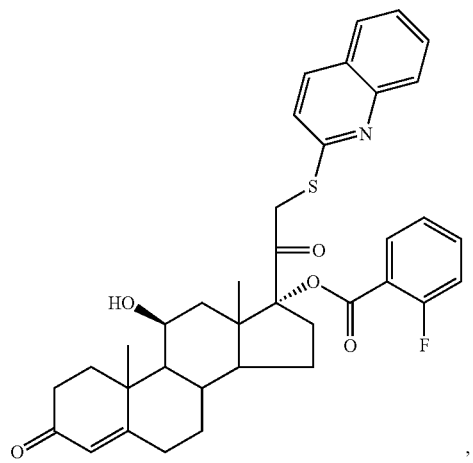
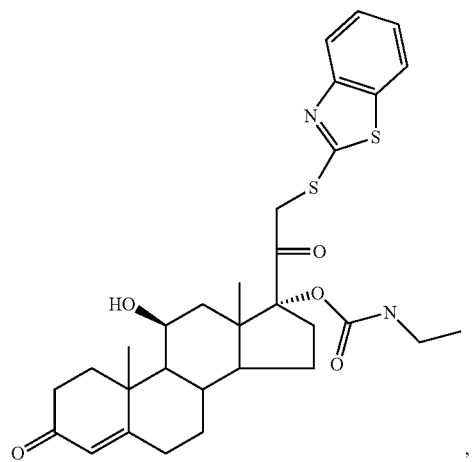
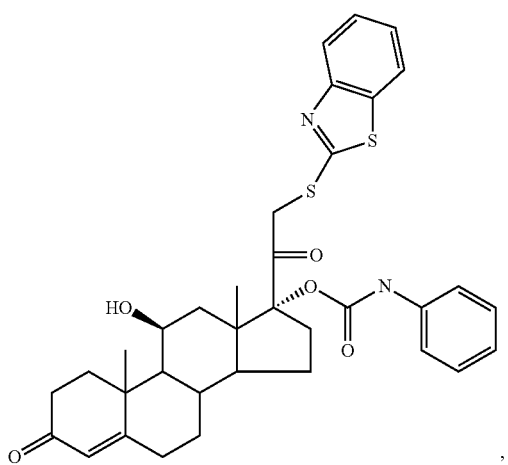
488
-continued
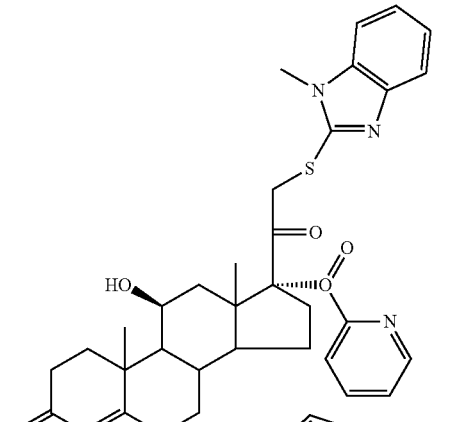
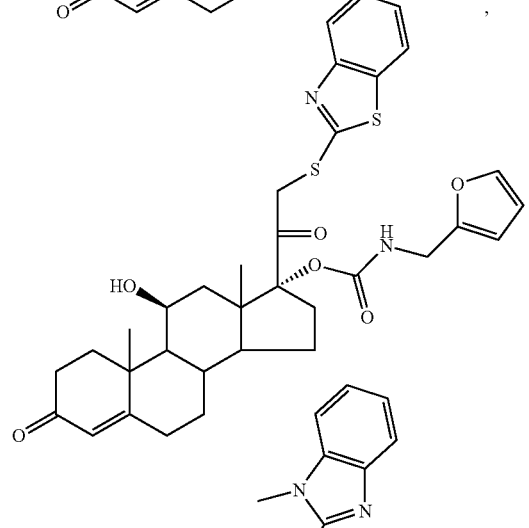
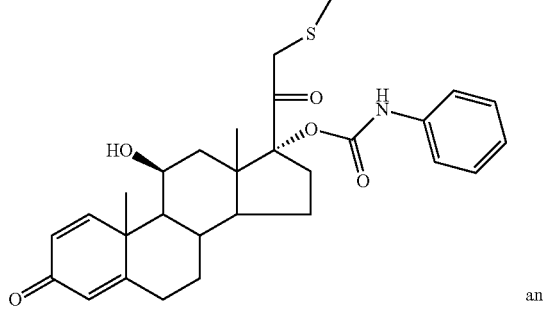
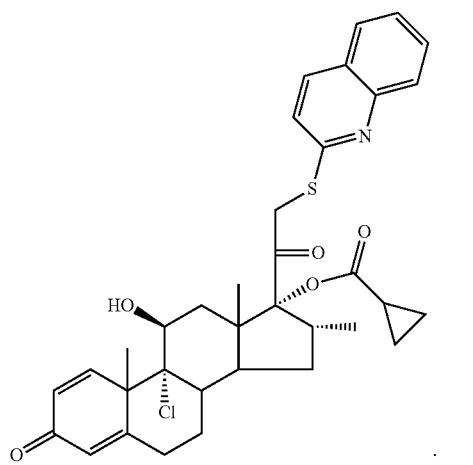
and 3. A compound according to claim 2, or a pharmaceutically acceptable salt, ester, or isomer thereof, selected from:
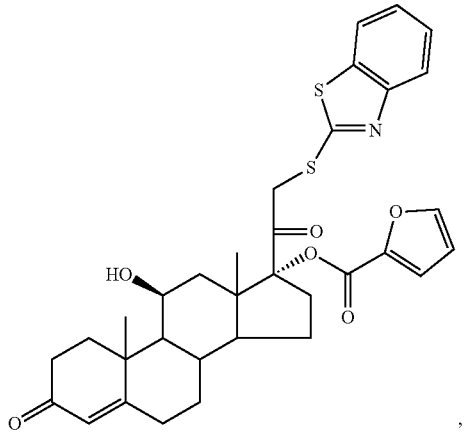 [SMILES: CC12CCC(=O)C=C1CCC1C2[C@@H](O)CC2(C)C1CC[C@]2(OC(=O)c1ccco1)C(=O)CSc1nc2ccccc2s1]
,
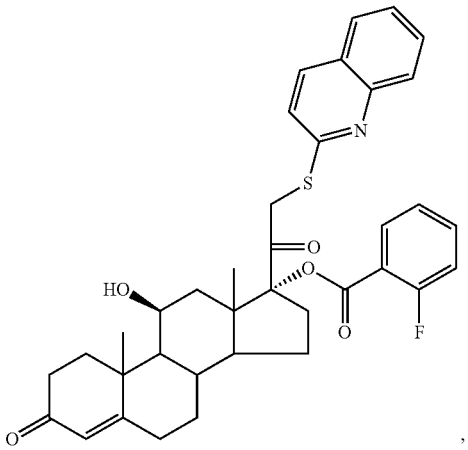
,
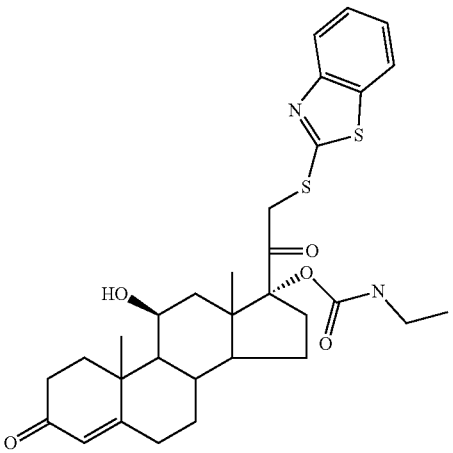
, and
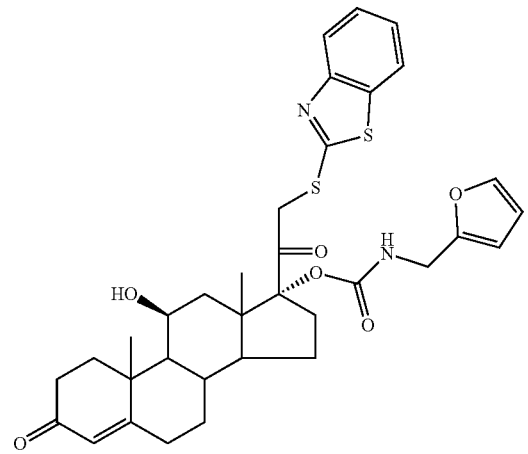 [SMILES: CC12CCC(=O)C=C1CCC1C2[C@@H](O)CC2(C)C1CC[C@]2(OC(=O)NCc1ccco1)C(=O)CSc1nc2ccccc2s1]
.
4. A compound or a pharmaceutically acceptable salt, ester, or isomer thereof of structure:
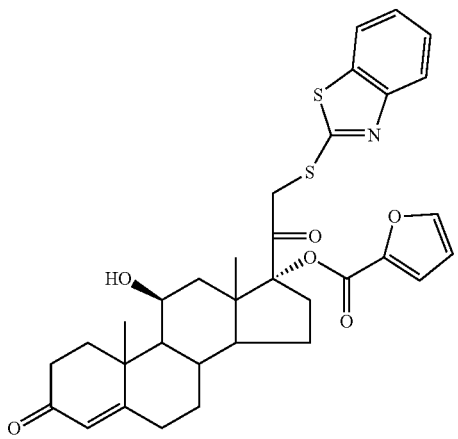
.
5. A compound or a pharmaceutically acceptable salt, ester, or isomer therof of stucture:
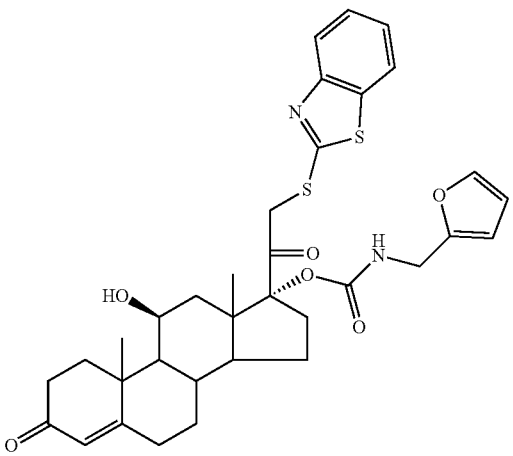
.

6. A compound or a pharmaceutically acceptable salt, ester, or isomer thereof of structure:
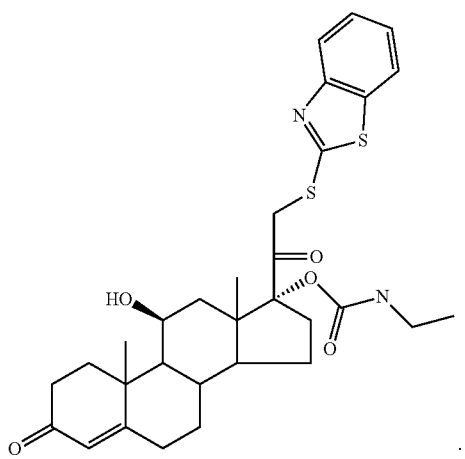 [SMILES: CCNC(=O)O[C@]1(C(=O)CSc2nc3ccccc3s2)CCC2C3CCC4=CC(=O)CCC4(C)C3[C@@H](O)CC21C]
7. A compound or a pharmaceutically acceptable salt, ester, or isomer thereof of structure:
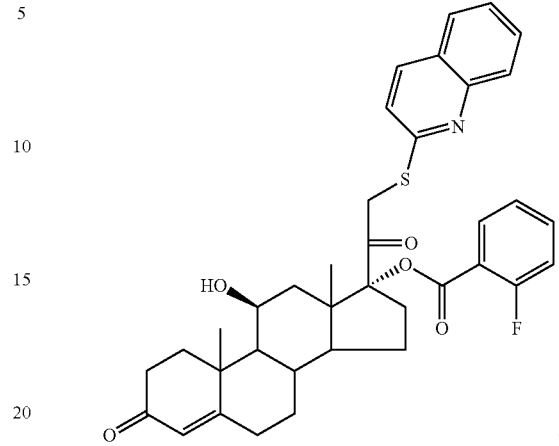
* * * * *

UNITED STATES PATENT AND TRADEMARK OFFICE
CERTIFICATE OF CORRECTION

| | | |
|---|---|---|
| PATENT NO. | : 8,524,697 B2 | Page 1 of 1 |
| APPLICATION NO. | : 12/736063 | |
| DATED | : September 3, 2013 | |
| INVENTOR(S) | : Anthes et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 265 days.

Signed and Sealed this
Twenty-fourth Day of February, 2015

Michelle K. Lee
*Deputy Director of the United States Patent and Trademark Office*